US010364245B2

(12) United States Patent
Capaldi et al.

(10) Patent No.: US 10,364,245 B2
(45) Date of Patent: Jul. 30, 2019

(54) KINASE INHIBITORS

(71) Applicant: CHIESI FARMACEUTICI S.p.A., Parma (IT)

(72) Inventors: Carmelida Capaldi, Parma (IT); Elisabetta Armani, Parma (IT); Christopher Hurley, Saffron Walden (GB); Barbara Giuseppina Avitabile-Woo, Saffron Walden (GB); Roberta Lanaro, Saffron Walden (GB); Neil Stuart Jennings, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/987,277

(22) Filed: May 23, 2018

(65) Prior Publication Data

US 2018/0354945 A1 Dec. 13, 2018

(30) Foreign Application Priority Data

Jun. 7, 2017 (EP) .................................... 17174686

(51) Int. Cl.
*C07D 471/04* (2006.01)
*A61P 11/00* (2006.01)

(52) U.S. Cl.
CPC ............ *C07D 471/04* (2013.01); *A61P 11/00* (2018.01)

(58) Field of Classification Search
CPC .................................................... C07D 471/04
See application file for complete search history.

(56) References Cited

U.S. PATENT DOCUMENTS

| | | | | |
|---|---|---|---|---|
| 8,835,431 B2 * | 9/2014 | Van Niel | C07D 471/04 | 514/233.2 |
| 8,907,094 B2 * | 12/2014 | Van Niel | C07D 401/12 | 546/119 |
| 8,916,708 B2 * | 12/2014 | Woo | C07D 401/12 | 546/112 |
| 9,029,373 B2 * | 5/2015 | Van Niel | C07D 471/04 | 514/233.2 |
| 9,139,584 B2 * | 9/2015 | Van Niel | C07D 401/12 | |
| 9,145,413 B2 * | 9/2015 | Van Niel | C07D 401/12 | |
| 9,315,503 B2 * | 4/2016 | Van Niel | C07D 401/12 | |
| 9,359,354 B2 * | 6/2016 | Woo | C07D 471/10 | |
| 9,440,974 B2 * | 9/2016 | Alcaraz | C07C 53/06 | |
| 9,458,154 B2 * | 10/2016 | Finch | C07D 403/12 | |
| 9,527,846 B2 * | 12/2016 | Van Niel | C07D 401/12 | |
| 9,573,949 B2 * | 2/2017 | Alcaraz | C07D 519/00 | |
| 9,758,521 B2 * | 9/2017 | Capaldi | C07D 471/04 | |
| 2013/0143914 A1 * | 6/2013 | Woo | C07D 471/04 | 514/303 |

FOREIGN PATENT DOCUMENTS

WO 2014/194956 12/2014

OTHER PUBLICATIONS

European Search Report in Application No. 17174686.0 dated Aug. 10, 2017, citing document AO therein, 6 pages.
International Search Report in Application No. PCT/EP2018/064575 dated Aug. 21, 2018.
Written Opinion of the International Searching Authority in Application No. PCT/EP2018/064575 dated Aug. 21, 2018.

* cited by examiner

*Primary Examiner* — Alexander R Pagano
(74) *Attorney, Agent, or Firm* — Oblon, McClelland, Maier & Neustadt, L.L.P.

(57) ABSTRACT

Compounds of formula (I) defined herein are p38 MAPK inhibitors and are useful as anti-inflammatory agents in the treatment of, inter alia, diseases of the respiratory tract.

19 Claims, No Drawings

KINASE INHIBITORS

CROSS REFERENCES TO RELATED APPLICATIONS

This application claims priority to European Patent Application No. 17174686.0 filed on Jun. 7, 2017, which is incorporated herein by reference in its entirety.

BACKGROUND OF THE INVENTION

Field of the Invention

The present invention relates to compounds and compositions that are p38 MAPK inhibitors and which are useful as anti-inflammatory agents in the treatment of, inter alia, diseases of the respiratory tract.

Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAPK) and RK, are responsible for phosphorylating (see Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (see Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNFα) and interleukin-(IL)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (see e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (see Badger et al., J. Pharm. Exp. Thera., 1996, 279, 1453-1461; Griswold et al, Pharmacol. Comm., 1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1β, IL-6, IL-4, IL-5 and IL-13 (see Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (see Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety). It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733, which is incorporated herein by reference in its entirety), J Hynes et al. (Current Topics in Medicinal Chemistry, 2005, 5, 967-985, which is incorporated herein by reference in its entirety), C. Dominguez et al (Expert Opinions on Therapeutics Patents, 2005, 15, 801-816, which is incorporated herein by reference in its entirety), and L. H. Pettus & R. P. Wurtz (Current Topics in Medicinal Chemistry, 2008, 8, 1452-1467, which is incorporated herein by reference in its entirety). P38 kinase inhibitors are known in the art, for example WO 2014/195400 and WO 2013/083604, which are incorporated herein by reference in their entireties.

However, there remains a need for more potent anti-inflammatory agents to be used in the treatment of diseases of the respiratory tract.

SUMMARY OF THE INVENTION

Accordingly, it is one object of the present invention to provide novel anti-inflammatory agents to be used in the treatment of diseases of the respiratory tract.

It is another object of the present invention to provide novel potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

It is another object of the present invention to provide novel pharmaceutical compositions which contain such an anti-inflammatory agent.

It is another object of the present invention to provide novel devices which contain such a composition.

It is another object of the present invention to provide novel methods of treating a disease of the respiratory tract by administering such an anti-inflammatory agent.

These and other objects, which will become apparent during the following detailed description, have been achieved by the inventors' discovery that the compounds of formula (I) described below are inhibitors of p38 mitogen activated protein kinase ("p38 MAPK," "p38 kinase," or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma; therefore are particularly suited for pulmonary delivery, by inhalation by nose or mouth.

DETAILED DESCRIPTION OF THE PREFERRED EMBODIMENTS

According to the present invention there is provided a compound of formula (I)

(I)

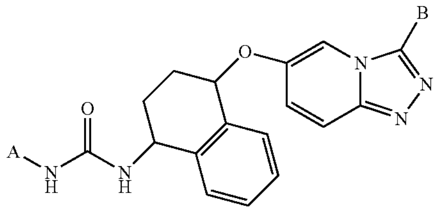

wherein:

A is selected from the group consisting of (Ia)-(Id)

(Ia)

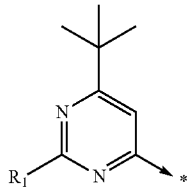

(Ib)

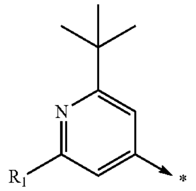

(Ic)

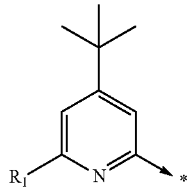

(Id)

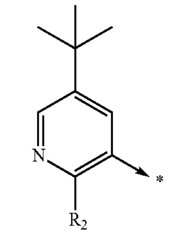

B is selected from the group consisting of (IIa)-(IIi)

(IIa)

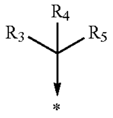

(IIb)

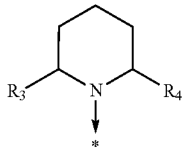

-continued (IIc)

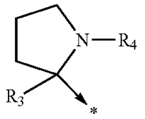

(IId)

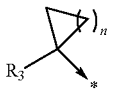

(IIe)

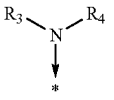

(IIf)

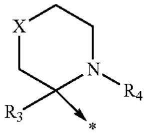

(IIg)

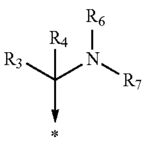

(IIh)

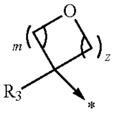

(IIi)

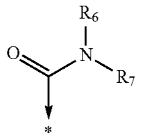

$R_1$ is H or is selected from the group consisting of —CN, linear or branched $(C_1-C_4)$alkyl-, $(R_8)(R_9)NC(O)$—; $R_{12}O$—$(C_1-C_4)$alkylen-; $(R_8)(R_9)N$—$(C_1-C_4)$alkylen-; $(C_1-C_4)$alkyl-C(O)O—$(C_1-C_4)$alkylen-; $(R_8)C(O)O$—; $(C_1-C_4)$alkyl-$S(O)_2NH$—; $(C_1-C_4)$alkyl-S—; $(R_8)(R_9)N$—; $(R_8)(R_9)N$—$(C_1-C_4)$alkylen-C(O)NH—$(C_1-C_4)$alkylen-; optionally substituted $(C_3-C_7)$heterocycloalkyl-C(O)NH—$(C_1-C_4)$alkylen-; $(C_1-C_4)$alkyl-OC(O)—; $(R_8)(R_9)N$—$(C_1-C_4)$alkylen-O—$(C_1-C_4)$alkylen-;

$R_2$ is H or selected from a group consisting of linear or branched $(C_1-C_4)$alkyl- and $(C_1-C_4)$alkyl-O—;

$R_3$ is H or linear or branched $(C_1-C_4)$alkyl-;

$R_4$ is H or linear or branched $(C_1-C_4)$alkyl-;

$R_5$ is H or selected from a group consisting of linear or branched $(C_1-C_4)$alkyl-, $R_{12}O$—$(C_1-C_4)$alkylen- and $R_{12}O$—;

$R_6$ is H or linear or branched $(C_1-C_4)$alkyl-;

$R_7$ is H or linear or branched $(C_1-C_4)$alkyl-;

or $R^6$ and $R^7$ may form together with the nitrogen atom to which they are attached an optionally substituted 4-7 membered saturated heterocyclic monocyclic ring system, optionally containing a further oxygen or nitrogen heteroatom;

X is selected from a group consisting of —$CH_2$—, $(R_3)N$— and —O—;

$R_8$ is H or selected from a group consisting of linear or branched —$(C_1-C_4)$alkyl- and $R_{12}O$—$(C_1-C_4)$alkylen-;

$R_9$ is H or is selected from a group consisting of linear or branched $(C_1-C_4)$alkyl-, optionally substituted $(C_3-C_7)$heterocycloalkyl-, optionally substituted $(C_3-C_7)$cycloalkyl-, $R_{12}O$—$(C_1-C_4)$alkylen-, $(R_{10})(R_{11})N$—$(C_1-C_4)$alkylen- and $(R_{10})(R_{11})N$—$(C_1-C_4)$alkylen-O—$(C_1-C_4)$alkylen-, wherein said $(C_1-C_4)$alkylen- in $(C_3-C_7)$cycloalkyl-, $R_{12}O$—$(C_1-C_4)$alkylen-, $(R_{10})(R_{11})N$—$(C_1-C_4)$alkylen- and $(R_{10})(R_{11})N$—$(C_1-C_4)$alkylen-O—$(C_1-C_4)$alkylen can be optionally substituted with one or more groups selected from linear or branched $(C_1-C_4)$alkyl-, spiro-$(C_1-C_6)$cycloalkyl and spiro-$(C_1-C_6)$heterocycloalkyl;

or $R^8$ and $R^9$ may form together with the nitrogen atom to which they are attached an optionally substituted 4-7 membered saturated heterocyclic monocyclic ring system, optionally containing a further oxygen or nitrogen heteroatom;

$R_{10}$ is H or is selected from a group consisting of linear or branched $(C_1-C_4)$alkyl-, $R_{12}O$—$(C_1-C_4)$alkylen-, $(C_3-C_7)$cycloalkyl- and $(C_3-C_7)$heterocycloalkyl-;

$R_{11}$ is H or is selected from a group consisting of linear or branched $(C_1-C_4)$alkyl-, and $R_{12}O$—$(C_1-C_4)$alkylen-;

or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom;

n is an integer from 1 to 4;

m is an integer from 1 to 2;

z is an integer from 1 to 2;

and wherein for "optionally substituted" is intended a substitution by one or more groups selected from linear or branched $(C_1-C_4)$alkyl-, halo, $R_{12}O$—$(C_1-C_4)$alkylen-, $R_{12}O$—, oxo, $(C_1-C_4)$alkyl$(C_1-C_4)$alkyl)N—;

$R_{12}$ is H or linear or branched $(C_1-C_4)$alkyl-;

with the proviso that when A is (Ib) then $R_1$ is not H, $CH_3$ or CN.

Compounds of the present invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and re-crystallization techniques). Where appropriate such isomers may be prepared by the application of adaptation of known methods (e.g. asymmetric synthesis).

All preferred groups or embodiments described herebelow for compounds of formula (I) may be combined among each other and apply as well to compounds of formula (Ia) mutatis mutandis.

In one embodiment, the invention is directed to compounds of formula (I)

(I)

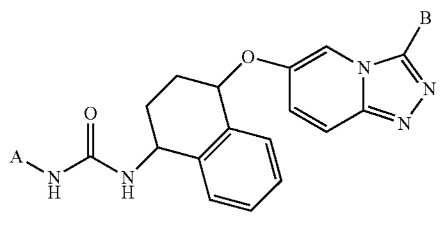

wherein:

A is selected from the group consisting of (Ia)-(Id)

(Ia)

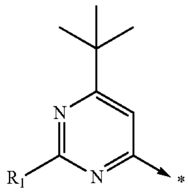

(Ib)

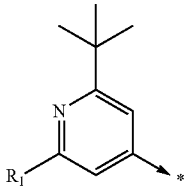

(Ic)

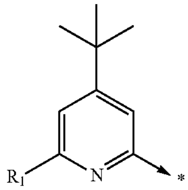

(Id)

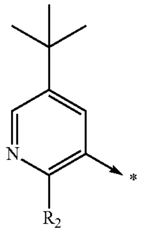

B is selected from the group consisting of (IIa)-(IIe) and (IIg)-(IIi)

(IIa)

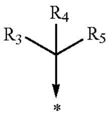

(IIb)

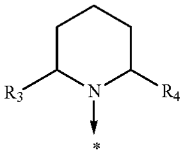

(IIc)

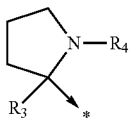

(IId)

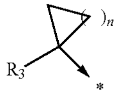

-continued (IIe)

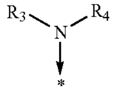

(IIg)

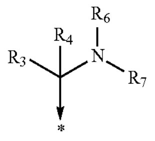

(IIh)

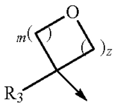

(IIi)

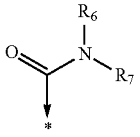

$R_1$ is H or is selected from the group consisting of —CN, linear or branched ($C_1$-$C_4$)alkyl, ($R_8$)($R_9$)NC(O)—; $R_{12}$O—($C_1$-$C_4$)alkylen-; ($R_8$)($R_9$)N—($C_1$-$C_4$)alkylen-; ($C_1$-$C_4$)alkyl-S(O)$_2$NH—; ($C_1$-$C_4$)alkyl-S—; ($C_1$-$C_4$)alkyl-OC(O)—; ($R_8$)($R_9$)N—($C_1$-$C_4$)alkylen-O—($C_1$-$C_4$)alkylen-; $R_2$ is H or selected from a group consisting of linear or branched ($C_1$-$C_4$)alkyl- and ($C_1$-$C_4$)alkyl-O—; $R_3$ is H or linear or branched ($C_1$-$C_4$)alkyl-; $R_4$ is H, or linear or branched ($C_1$-$C_4$)alkyl-; $R_5$ is H or selected from a group consisting of linear or branched ($C_1$-$C_4$)alkyl-, $R_{12}$O—($C_1$-$C_4$)alkylen- and $R_{12}$O—; $R^6$ and $R^7$ may form together with the nitrogen atom to which they are attached an optionally substituted 4-7 membered saturated heterocyclic monocyclic ring system, optionally containing a further oxygen or nitrogen heteroatom; $R_8$ is H or selected from a group consisting of linear or branched —($C_1$-$C_4$)alkyl-; $R_9$ is selected from a group consisting of linear or branched ($C_1$-$C_4$)alkyl-, optionally substituted ($C_3$-$C_7$)cycloalkyl-, $R_{12}$O—($C_1$-$C_4$)alkylen-, ($R_{10}$)($R_{11}$)N—($C_1$-$C_4$)alkylen- wherein said ($C_1$-$C_4$)alkylen- in ($R_{10}$)($R_{11}$)N—($C_1$-$C_4$)alkylen- can be optionally substituted with one or more groups selected from linear or branched ($C_1$-$C_4$)alkyl-, spiro-($C_1$-$C_6$)cycloalkyl and spiro-($C_1$-$C_6$)heterocycloalkyl; or $R^8$ and $R^9$ may form together with the nitrogen atom to which they are attached an optionally substituted 4-7 membered saturated heterocyclic monocyclic ring system, optionally containing a further oxygen or nitrogen heteroatom; $R_{10}$ is selected from a group consisting of linear or branched ($C_1$-$C_4$)alkyl-, ($C_3$-$C_7$)cycloalkyl-; $R_{11}$ is selected from a group consisting of linear or branched ($C_1$-$C_4$)alkyl-, and $R_{12}$O—($C_1$-$C_4$)alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; n is 3; m is 1; z is 1; and wherein "optionally substituted" means a substitution by one or more groups selected from linear or branched ($C_1$-$C_4$)alkyl-, halo, $R_{12}$O—($C_1$-$C_4$)alkylen-, $R_{12}$O—, oxo, ($C_1$-$C_4$)alkyl($C_1$-$C_4$)alkyl)N—; $R_{12}$ is H or linear or branched ($C_1$-$C_4$)alkyl-; with the proviso that when A is (Ib) then $R_1$ is not H, $CH_3$ or CN.

In another embodiment, the invention is directed to compounds of formula (I) wherein A is group (Ia)

(Ia)

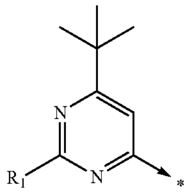

B is selected from the group consisting of (IIa) and (IIe)

(IIa)

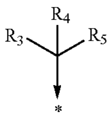

(IIe)

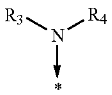

$R_1$ is H or is selected from the group consisting of $(R_8)(R_9)NC(O)$—; $R_3$ is linear or branched $(C_1$-$C_4)$alkyl-; $R_4$ is H, or linear or branched $(C_1$-$C_4)$alkyl-; $R_5$ linear or branched $(C_1$-$C_4)$alkyl-, $R_{12}O$—$(C_1$-$C_4)$alkylen- and $R_{12}O$—; $R_8$ is H; $R_9$ $(R_{10})(R_{11})N$—$(C_1$-$C_4)$alkylen- wherein said $(C_1$-$C_4)$alkylen- in $(R_{10})(R_{11})N$—$(C_1$-$C_4)$alkylen- can be optionally substituted with one or more groups selected from linear or branched $(C_1$-$C_4)$alkyl-; $R_{10}$ linear or branched $(C_1$-$C_4)$alkyl-; $R_{11}$ linear or branched $(C_1$-$C_4)$ alkyl-, and $R_{12}O$—$(C_1$-$C_4)$alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; $R_{12}$ is H or linear or branched $(C_1$-$C_4)$alkyl-; and wherein for "optionally substituted" is intended a substitution by one or more groups selected from linear or branched $(C_1$-$C_4)$alkyl-, halo, $R_{12}O$—$(C_1$-$C_4)$alkylen-, $R_{12}O$—, oxo, $(C_1$-$C_4)$alkyl$(C_1$-$C_4)$ alkyl)N—; with the proviso that when A is (Ib) then $R_1$ is not H, $CH_3$ or CN.

In another embodiment, the invention is directed to compounds of formula (I) wherein A is group (Ib)

(Ib)

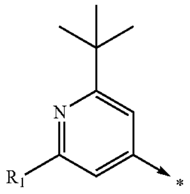

B is selected from the group consisting of (IIa) and (IIe)

(IIa)

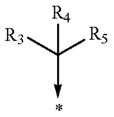

(IIe)

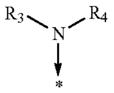

$R_1$ is H or is selected from the group consisting of $(R_8)(R_9)NC(O)$—; $R_3$ is linear or branched $(C_1$-$C_4)$alkyl-; $R_4$ is H, or linear or branched $(C_1$-$C_4)$alkyl-; $R_5$ linear or branched $(C_1$-$C_4)$alkyl-, $R_{12}O$—$(C_1$-$C_4)$alkylen- and $R_{12}O$—; $R_8$ is H; $R_9$ $(R_{10})(R_{11})N$—$(C_1$-$C_4)$alkylen- wherein said $(C_1$-$C_4)$alkylen- in $(R_{10})(R_{11})N$—$(C_1$-$C_4)$alkylen- can be optionally substituted with one or more groups selected from linear or branched $(C_1$-$C_4)$alkyl-; $R_{10}$ linear or branched $(C_1$-$C_4)$alkyl-; $R_{11}$ linear or branched $(C_1$-$C_4)$ alkyl-, and $R_{12}O$—$(C_1$-$C_4)$alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; $R_{12}$ is H or linear or branched $(C_1$-$C_4)$alkyl-; and wherein for "optionally substituted" is intended a substitution by one or more groups selected from linear or branched $(C_1$-$C_4)$alkyl-, halo, $R_{12}O$—$(C_1$-$C_4)$alkylen-, $R_{12}O$—, oxo, $(C_1$-$C_4)$alkyl$(C_1$-$C_4)$ alkyl)N—; with the proviso that when A is (Ib) then $R_1$ is not H, $CH_3$ or CN.

In one embodiment, the invention is directed to compounds of formula (I) wherein A is (Ia)

(Ia)

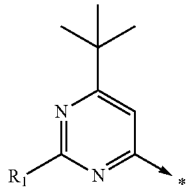

B is selected from the group consisting of (IIa)-(IIe) and (IIg)-(IIi)

(IIa)

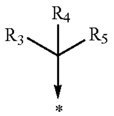

(IIb)

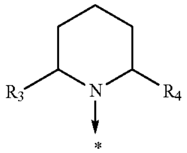

-continued (IIc)

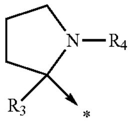

(IId)

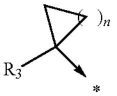

(IIe)

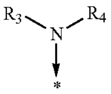

(IIg)

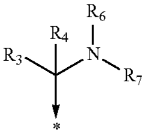

(IIh)

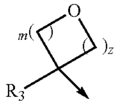

(IIi)

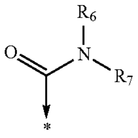

$R_1$ is H or linear or branched ($C_1$-$C_4$)alkyl, ($R_8$)($R_9$)NC(O)—; $R_{12}$O—($C_1$-$C_4$)alkylen-; ($R_8$)($R_9$)N—($C_1$-$C_4$)alkylen-; ($C_1$-$C_4$)alkyl-S(O)$_2$NH—; ($C_1$-$C_4$)alkyl-S—; ($C_1$-$C_4$)alkyl-OC(O)—; ($R_8$)($R_9$)N—($C_1$-$C_4$)alkylen-O—($C_1$-$C_4$)alkylen-; $R_3$ is H or linear or branched ($C_1$-$C_4$)alkyl-; $R_4$ is H, or linear or branched ($C_1$-$C_4$)alkyl-; $R_5$ is H or selected from a group consisting of linear or branched ($C_1$-$C_4$)alkyl-, $R_{12}$O—($C_1$-$C_4$)alkylen- and $R_{12}$O—; $R^6$ and $R^7$ may form together with the nitrogen atom to which they are attached an optionally substituted 4-7 membered saturated heterocyclic monocyclic ring system, optionally containing a further oxygen or nitrogen heteroatom; $R_8$ is H or selected from a group consisting of linear or branched —($C_1$-$C_4$)alkyl-; $R_9$ is selected from a group consisting of linear or branched ($C_1$-$C_4$)alkyl-, optionally substituted ($C_3$-$C_7$)cycloalkyl-, $R_{12}$O—($C_1$-$C_4$)alkylen-, ($R_{10}$)($R_{11}$)N—($C_1$-$C_4$)alkylen- wherein said ($C_1$-$C_4$)alkylen- in ($R_{10}$)($R_{11}$)N—($C_1$-$C_4$)alkylen- can be optionally substituted with one or more groups selected from linear or branched ($C_1$-$C_4$)alkyl-, spiro-($C_1$-$C_6$)cycloalkyl and spiro-($C_1$-$C_6$)heterocycloalkyl; or $R^8$ and $R^9$ may form together with the nitrogen atom to which they are attached an optionally substituted 4-7 membered saturated heterocyclic monocyclic ring system, optionally containing a further oxygen or nitrogen heteroatom; $R_{10}$ is selected from a group consisting of linear or branched ($C_1$-$C_4$)alkyl-, ($C_3$-$C_7$)cycloalkyl-; $R_{11}$ is selected from a group consisting of linear or branched ($C_1$-$C_4$)alkyl-, and $R_{12}$O—($C_1$-$C_4$)alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; n is 3; m is 1; z is 1; and wherein for "optionally substituted" is intended a substitution by one or more groups selected from linear or branched ($C_1$-$C_4$)alkyl-, halo, $R_{12}$O—($C_1$-$C_4$)alkylen-, $R_{12}$O—, oxo, ($C_1$-$C_4$)alkyl($C_1$-$C_4$)alkyl)N—;

$R_{12}$ is H or linear or branched ($C_1$-$C_4$)alkyl-.

In one embodiment, the invention is directed to compounds of formula (I) wherein A is (Ib)

(Ib)

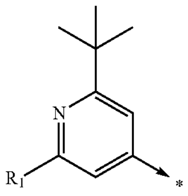

B is selected from the group consisting of (IIa), (IIc) and (IIe)

(IIa)

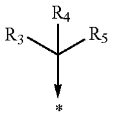

(IIc)

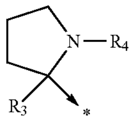

(IIe)

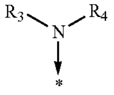

$R_1$ is H or is selected from the group consisting of ($R_8$)($R_9$)NC(O)—; $R_{12}$O—($C_1$-$C_4$)alkylen-; ($C_1$-$C_4$)alkyl-S(O)$_2$NH—; $R_3$ is linear or branched ($C_1$-$C_4$)alkyl-; $R_4$ is H, or linear or branched ($C_1$-$C_4$)alkyl-; $R_5$ is selected from a group consisting of linear or branched ($C_1$-$C_4$)alkyl-, $R_{12}$O—($C_1$-$C_4$)alkylen- and $R_{12}$O—; $R_8$ is H; $R_9$ is selected from a group consisting of $R_{12}$O—($C_1$-$C_4$)alkylen-, ($R_{10}$)($R_{11}$)N—($C_1$-$C_4$)alkylen- wherein said ($C_1$-$C_4$)alkylen- in ($R_{10}$)($R_{11}$)N—($C_1$-$C_4$)alkylen- can be optionally substituted with one or more groups selected from linear or branched ($C_1$-$C_4$)alkyl-; $R_{10}$ is selected from a group consisting of linear or branched ($C_1$-$C_4$)alkyl-; $R_{11}$ is selected from a group consisting of linear or branched ($C_1$-$C_4$)alkyl-, and $R_{12}$O—($C_1$-$C_4$)alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; and wherein for "optionally substituted" is intended a substitution by one or more $R_{12}$O; $R_{12}$ is H or linear or branched ($C_1$-$C_4$)alkyl- with the proviso that when A is (Ib) then $R_1$ is not H, $CH_3$ or CN.

In one embodiment, the invention is directed to compounds of formula (I) wherein A is selected from the group consisting of (Ic) and (Id)

(Ic)

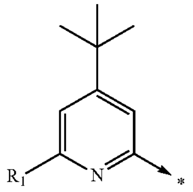

(Id)

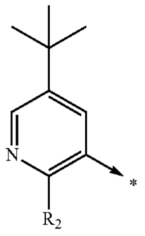

B is selected from the group consisting of (IIa) and (IIc)

(IIa)

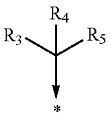

(IIc)

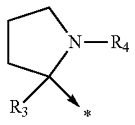

$R_1$ is H or is selected from the group consisting of —CN, $(R_8)(R_9)NC(O)$—; $R_2$ is selected from a group consisting of linear or branched $(C_1$-$C_4)$alkyl- and $(C_1$-$C_4)$alkyl-O—; $R_3$ is H or linear or branched $(C_1$-$C_4)$alkyl-; $R_4$ is linear or branched $(C_1$-$C_4)$alkyl-; $R_5$ is linear or branched $(C_1$-$C_4)$alkyl-, $R_8$ is H, $R_9$ is $(R_{10})(R_{11})N$—$(C_1$-$C_4)$alkylen-, $R_{10}$ linear or branched $(C_1$-$C_4)$alkyl-; $R_{11}$ is linear or branched $(C_1$-$C_4)$alkyl- or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom.

In one embodiment, the invention is directed to compounds of formula (I) wherein A is selected from the group consisting of (Ia)-(Id)

(Ia)

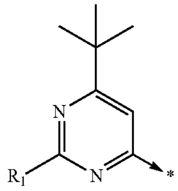

-continued (Ib)

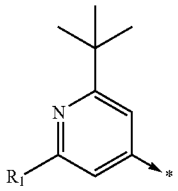

(Ic)

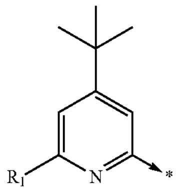

B is (IIa)

(IIa)

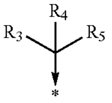

$R_1$ is selected from the group consisting of $(R_8)(R_9)NC(O)$—; $(R_8)(R_9)N$—$(C_1$-$C_4)$alkylen-; $(R_8)(R_9)N$—$(C_1$-$C_4)$alkylen-O—$(C_1$-$C_4)$alkylen-; $R_3$ is linear or branched $(C_1$-$C_4)$alkyl-;

$R_4$ is H, or linear or branched $(C_1$-$C_4)$alkyl-; $R_5$ is selected from a group consisting of linear or branched $(C_1$-$C_4)$alkyl-, $R_{12}O$—$(C_1$-$C_4)$alkylen- and $R_{12}O$—; $R_8$ is H or selected from a group consisting of linear or branched —$(C_1$-$C_4)$alkyl-; $R_9$ is selected from a group consisting of optionally substituted $(C_3$-$C_7)$cycloalkyl-, $R_{12}O$—$(C_1$-$C_4)$alkylen-, $(R_{10})(R_{11})N$—$(C_1$-$C_4)$alkylen- wherein said $(C_1$-$C_4)$alkylen- in $(R_{10})(R_{11})N$—$(C_1$-$C_4)$alkylen- can be optionally substituted with one or more groups selected from linear or branched $(C_1$-$C_4)$alkyl-, spiro-$(C_1$-$C_6)$cycloalkyl and spiro-$(C_1$-$C_6)$heterocycloalkyl;

or $R^8$ and $R^9$ may form together with the nitrogen atom to which they are attached an optionally substituted 4-7 membered saturated heterocyclic monocyclic ring system, optionally containing a further oxygen or nitrogen heteroatom; $R_{10}$ is selected from a group consisting of linear or branched $(C_1$-$C_4)$alkyl-; $(C_3$-$C_7)$cycloalkyl-; $R_{11}$ is selected from a group consisting of linear or branched $(C_1$-$C_4)$alkyl-, and $R_{12}O$—$(C_1$-$C_4)$alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom;

and wherein for "optionally substituted" is intended a substitution by one or more groups selected from linear or branched $(C_1$-$C_4)$alkyl-, halo, $R_{12}O$—$(C_1$-$C_4)$alkylen-, $R_{12}O$—, oxo, $(C_1$-$C_4)$alkyl$(C_1$-$C_4)$alkyl)N—; $R_{12}$ is H or linear or branched $(C_1$-$C_4)$alkyl-.

In one embodiment, the invention is directed to compounds of formula (I) wherein A is selected from the group consisting of (Ia)-(Id)

(Ia)

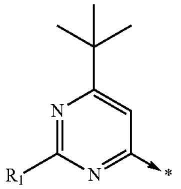

(Ib)

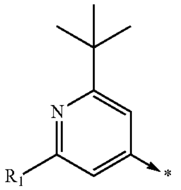

(Ic)

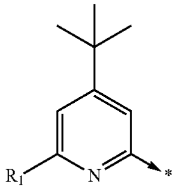

(Id)

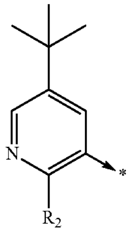

B is selected from the group consisting of (IIb) and (IIc)

(IIb)

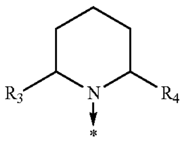

(IIc)

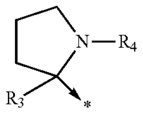

$R_1$ is H or is selected from the group consisting of —CN, linear or branched ($C_1$-$C_4$)alkyl, ($R_8$)($R_9$)NC(O)—; $R_{12}$O—($C_1$-$C_4$)alkylen-; ($C_1$-$C_4$)alkyl-S(O)$_2$NH—; ($C_1$-$C_4$)alkyl-S—; ($C_1$-$C_4$)alkyl-OC(O)—; $R_2$ is selected from a group consisting of linear or branched ($C_1$-$C_4$)alkyl- and ($C_1$-$C_4$) alkyl-O—; $R_3$ is H or linear or branched ($C_1$-$C_4$)alkyl-; $R_4$ is linear or branched ($C_1$-$C_4$)alkyl-; $R_2$ is H; $R_9$ is selected from a group consisting of linear or branched ($C_1$-$C_4$)alkyl-, $R_{12}$O—($C_1$-$C_4$)alkylen-, ($R_{10}$)($R_{11}$)N—($C_1$-$C_4$)alkylen-; $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; $R_{12}$ is H; with the proviso that when A is (Ib) then $R_1$ is not H, $CH_3$ or CN.

In one embodiment, the invention is directed to compounds of formula (I) wherein A is selected from the group consisting of (Ia) and (Ib)

(Ia)

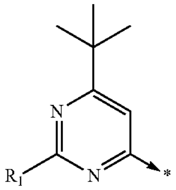

(Ib)

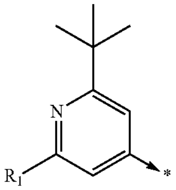

B is selected from the group consisting of (IId), (IIe), (IIg), (IIh) and (IIi)

(IId)

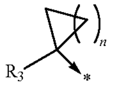

(IIe)

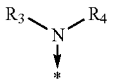

(IIg)

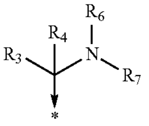

(IIh)

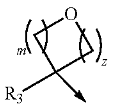

(IIi)

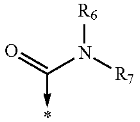

$R_1$ is selected from the group consisting of ($R_8$)($R_9$)NC(O)—; $R_3$ is linear or branched ($C_1$-$C_4$)alkyl-; $R_4$ is linear or branched ($C_1$-$C_4$)alkyl-; $R^6$ and $R^7$ may form together with the nitrogen atom to which they are attached an optionally substituted 4-7 membered saturated heterocyclic monocyclic ring system, optionally containing a further oxygen or nitrogen heteroatom; $R_8$ is H; $R_9$ is selected from a group consisting of $R_{12}$O—($C_1$-$C_4$)alkylen-, ($R_{10}$)($R_{11}$)N—($C_1$-$C_4$)alkylen- wherein said ($C_1$-$C_4$)alkylen- in ($R_{10}$)($R_{11}$)N—($C_1$-$C_4$)alkylen- can be optionally substituted with one or more groups selected from linear or branched ($C_1$-$C_4$)alkyl-; $R_{10}$ is selected from a group consisting of linear or branched ($C_1$-$C_4$)alkyl-; $R_{11}$ is selected from a group consisting of linear or branched ($C_1$-$C_4$)alkyl-, and $R_{12}$O—($C_1$-$C_4$)alkylen-; or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom; n is 3; m is 1; z is 1; and wherein for "optionally substituted" is intended a substitution by one or more groups selected from linear or branched ($C_1$-$C_4$)alkyl-; $R_{12}$ is H.

In one embodiment, a compound of formula (I) is selected from 4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(dimethylamino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(3-methoxyazetidin-1-yl)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

6-(tert-butyl)-4-(3-((1S,4R)-4-((3-(tert-butyl)-[1,2,4]triazolo[4,3-a]pyridin-6-yl)oxy]-1,2,3,4-tetrahydronaphthalen-1-yl}ureido)-N-(2-(4-hydroxypiperidin-1-yl)ethyl)picolinamide;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

4-(tert-Butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy]-1,2,3,4-tetrahydronaphthalen-1-yl)ureido)-N-(2-morpholinoethyl)pyrimidine-2-carboxamide;

1-(6-(tert-butyl)-2-(hydroxymethyl)pyrimidin-4-yl)-3-((1S,4R)-4-((3-(2-methoxypropan-2-yl)-[1,2,4]triazolo[4,3-a]pyridine-6-yl)oxy)-1,2,3,4-tetrahydronaphthalene-1-yl)urea;

1-(6-(tert-Butyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-((dimethylamino)methyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

4-(tert-Butyl)-N-(2-(dimethylamino)ethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

4-(tert-Butyl)-N-(2-(dimethylamino)ethyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-Butyl)-2-(morpholinomethyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-Butyl)-N-(2-(dimethylamino)ethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-Butyl)-2-(hydroxymethyl)pyrimidin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea;

N-((4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-2-(dimethylamino)acetamide;

4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

(4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methyl acetate;

1-(6-(tert-butyl)-2-(hydroxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

4-(tert-butyl)-N-(2-(dimethylamino)ethyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

N-(4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methanesulfonamide;

1-(6-(tert-butyl)-2-(4-methylpiperazin-1-yl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

4-(tert-butyl)-N-(2-(dimethylamino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-((S)-2-methylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide;

1-(5-(tert-butyl)-2-methoxypyridin-3-yl)-3-((1S,4R)-4-((3-((S)-1-methylpyrrolidin-2-yl)-[1,2,4]triazolo[4,3-a]pyridin-6-yl)oxy)-1,2,3,4-tetrahydronaphthalen-1-yl)urea hydrochloride salt;

Ethyl 4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylate;

4-(tert-butyl)-N-(2-(dimethylamino)ethyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpyrimidine-2-carboxamide;

1-(4-(tert-butyl)-6-cyanopyridin-2-yl)-3-((1S,4R)-4-((3-((R)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-methylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-ethylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-isopropylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-(methoxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(4-(tert-butyl)pyridin-2-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-butyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea;

1-(6-(tert-butyl)pyrimidin-4-yl)-3-((1S,4R)-4-((3-((S)-1-methylpyrrolidin-2-yl)-[1,2,4]triazolo[4,3-a]pyridine-6-yl)oxy)-1,2,3,4-tetrahydronaphthalene-1-yl)urea hydrochloride;

1-(6-(tert-butyl)pyrimidin-4-yl)-3-((1S,4R)-4-((3-((S)-1-isopropylpyrrolidin-2-yl)-[1,2,4]triazolo[4,3-a]pyridine-6-yl)oxy)-1,2,3,4-tetrahydronaphthalene-1-yl)urea hydrochloride;

1-(6-(tert-butyl)-2-(methylthio)pyrimidin-4-yl)-3-((1S,4R)-4-((3-((S)-1-[1,2,4]triazolo[4,3-a]pyridine-6-yl)oxy)-1,2,3,4-tetrahydronaphthalen-1-yl)urea;

1-(6-(tert-butyl)-2-(methylthio)pyrimidin-4-yl)-3-((1S,4R)-4-((3-((S)-1,2-dimethylpyrrolidin-2-yl)-[1,2,4]triazolo[4,3-a]pyridine-6-yl)oxy)-1,2,3,4-tetrahydronaphthalen-1-yl)urea;

1-(2-(tert-Butyl)-5-methylpyridin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(2-(tert-Butyl)-6-(hydroxymethyl)pyridin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(5-(tert-butyl)-2-methoxypyridin-3-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpicolinamide;

4-(tert-butyl)-N-(2-(dimethylamino)ethyl)-6-(3-((1S,4R)-4-((3-(methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalene-1-yl)ureido)pyrimidin-2-carboxamide;

1-(2-(tert-butyl)-6-((2-morpholinoethoxy)methyl)pyrimidin-4-yl)-3-((1S,4R)-4-((3-(2-methoxypropan-2-yl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

4-(tert-butyl)-N-(2-(dimethylamino)ethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide;

6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)picolinamide;

6-(tert-Butyl)-N-(2-(dimethylamino)ethyl)-4-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)picolinamide;

1-(6-(tert-Butyl)-2-((2-morpholinoethoxy)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-N-(2-hydroxyethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-morpholinoethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-N-(2-(dimethylamino)ethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-methoxyethyl)(methyl)amino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)pyrimidine-2-carboxamide;

1-(6-(tert-butyl)-2-(3,3-difluoroazetidine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylazetidin-3-yl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)-N-methylpyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1s,3R)-3-(hydroxymethyl)cyclobutyl)pyrimidine-2-carboxamide;

4-(tert-butyl)-N-(1-methylazetidin-3-yl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

N-(2-(bis(2-methoxyethyl)amino)ethyl)-4-(tert-butyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

1-(2-((bis(2-methoxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

1-(2-((bis(2-hydroxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

1-(6-(tert-butyl)-2-(((2-hydroxyethyl)(methyl)amino)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

N-(2-(1,4-oxazepan-4-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-(dimethylamino)ethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide;

N-(2-(bis(2-methoxyethyl)amino)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((R)-3-hydroxypyrrolidin-1-yl)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-(dimethylamino)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-morpholinoethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-3-morpholinopropanamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-N-(2-((2-methoxyethyl)(methyl)amino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(methyl(oxetan-3-yl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-hydroxypiperidin-1-yl)ethyl)pyrimidine-2-carboxamide;

4-(tert-butyl)-6-(3-((1S,4R)-4-((3-(1-methylcyclobutyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

(S)—N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylpyrrolidine-2-carboxamide;

N-(3-(1,4-Oxazepan-4-yl)propyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide partial formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-(dimethylamino)-2-methylpropan-2-yl)pyrimidine-2-carboxamide;

1-(6-(tert-Butyl)-2-((3-oxopiperazin-1-yl)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea partial formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)-N-methylpyrimidine-2-carboxamide;

1-(6-(tert-butyl)-2-(4-(2-hydroxyethyl)piperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-(dimethylamino)propyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methylpiperazin-1-yl)ethyl)pyrimidine-2-carboxamide;

N-(2-(bis(2-hydroxyethyl)amino)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

N-(2-(1,4-oxazepan-4-yl)ethyl)-4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-hydroxyethyl)(methyl)amino)ethyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

4-(tert-butyl)-N-(2-((2-hydroxyethyl)(methyl)amino)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylazetidine-3-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-3-(dimethylamino)propanamide;

1-(6-(tert-butyl)-2-(4-methylpiperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N—((R)-1-methylpyrrolidin-3-yl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(2-(dimethylamino)ethoxy)ethyl)pyrimidine-2-carboxamide;

4-(tert-butyl)-N-(2-morpholinoethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(3-morpholinopropyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-butyl)-2-(4-methyl-1,4-diazepane-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylpiperidin-4-yl)pyrimidine-2-carboxamide;

1-(6-(tert-Butyl)-2-((4-methyl-2-oxopiperazin-1-yl)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N—((S)-1-methylpyrrolidin-3-yl)pyrimidine-2-carboxamide;

4-(tert-butyl)-N-(2-((2-methoxyethyl)(methyl)amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(3-methoxyazetidin-1-yl)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide;

N-(2-(azetidin-1-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

1-(6-(tert-butyl)-2-((2-morpholinoethoxy)methyl)pyrimidin-4-yl)-3-((1S,4R)-4-((3-(2-methoxypropan-2-yl)-[1,2,4]triazolo[4,3-a]pyridin-6-yl)oxy)-1,2,3,4-tetrahydronaphthalen-1-yl)urea;

4-(tert-butyl)-N-(2-((2-hydroxyethyl)(amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-N-(2-(dimethylamino)-2-ethylbutyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)-2-methylpropyl)pyrimidine-2-carboxamide;

4-(tert-butyl)-N-((1-(dimethylamino)cyclopropyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((4-(dimethylamino)tetrahydro-2H-pyran-4-yl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-butyl)-N-(2-(ethyl(methyl)amino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((1-(dimethylamino)cyclohexyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((1-(dimethylamino)cyclopentyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-butyl)-N-(2-(ethyl(methyl)amino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-Butyl)-N-((1-(dimethylamino)cyclobutyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclopropyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((4-(dimethylamino)tetrahydro-2H-pyran-4-yl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclohexyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclobutyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclopentyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(cyclopropyl(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1S,2S)-2-(dimethylamino)cyclohexyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-N-(2-(3-methoxyazetidin-1-yl)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-ethylbutyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide;

4-(tert-butyl)-N-(2-(3-methoxyazetidin-1-yl)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-methyl-2-(4-methylpiperazin-1-yl)propyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(3-methoxyazetidin-1-yl)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(dimethylamino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(ethyl(methyl)amino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)-2-methylpropyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)-2-methylpropyl)pyrimidine-2-carboxamide;

4-(tert-butyl)-N-(2-((2-methoxyethyl)(methyl)amino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(dimethylamino)ethyl)-6-(3-((1S,4R)-4-((3-(2-ethoxypropan-2-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-((2-hydroxyethyl)(methyl)amino)ethyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

N-(2-(1,4-oxazepan-4-yl)ethyl)-4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide formate salt;

6-(tert-butyl)-N-(2-(dimethylamino)ethyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)picolinamide;

N-(2-(1,4-oxazepan-4-yl)ethyl)-6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)picolinamide;

6-(tert-butyl)-N-(2-(dimethylamino)ethyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)picolinamide 6-(tert-butyl)-N-(2-(dimethylamino)-2-methylpropyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)picolinamide;

6-(tert-butyl)-N-(2-(dimethylamino)-2-methylpropyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)picolinamide;

1-(2-(tert-butyl)-6-(hydroxymethyl)pyridin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea;

6-(tert-Butyl)-N-(2-(dimethylamino)ethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt;

6-(tert-Butyl)-N-(2-hydroxyethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt;

6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide formate salt;

6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)picolinamide formate salt;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methoxypiperidin-1-yl)ethyl)picolinamide;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)picolinamide formate salt;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(ethyl(methyl)amino)ethyl)picolinamide formate salt;

6-(tert-butyl)-N-(2-(dimethylamino)ethyl)-4-(3-((1S,4R)-4-((3-(tert-pentyl)-[1,2,4]triazolo[4,3-a]pyridin-6-yl)oxy)-1,2,3,4-tetrahydronaphthalen-1-yl)ureido)picolinamide;

6-(tert-butyl)-N-(2-(dimethylamino)ethyl)-4-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)picolinamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)picolinamide formate salt;

N-(2-(1,4-oxazepan-4-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)picolinamide formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)picolinamide formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(-(2-(4-hydroxypiperidin-1-yl)ethyl)picolinamide formate salt;

N-(6-(tert-butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)methanesulfonamide;

N-(6-(tert-butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)ethanesulfonamide;

4-(tert-butyl)-N-(2-(dimethylamino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-hydroxyethyl)(methyl)amino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide and pharmaceutically acceptable salts thereof.

Chemical Names of the compounds were generated with Chem Draw version 15.1 using the embedded Name to Structure tool, Copyright of Perkin Elmer Informatics, Inc.

As mentioned above the compounds of the invention are p38 MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of formula (I) for the prevention and/or treatment of any disease or condition which benefit from inhibition of the p38 enzyme.

In a further aspect, the present invention provides the use of compounds (I) for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of formula (I)

The compounds of the present invention are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, health, sex, diet, time of administration, route of administration, rate of excretion, drug combination and the severity of the particular disease undergoing treatment. Optimum dose levels and frequency of dosing will be determined by clinical trial, as is required in the pharmaceutical art. The daily dose range for oral administration will lie within the range of from about 0.001 mg to about 100 mg per kg body weight of a human, often 0.01 mg to about 50 mg per kg, for example 0.1 to 10 mg per kg, in single or divided doses. The daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases. For the purpose of the invention, inhaled administration is preferred.

The compounds of the present invention may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

However, for the treatment of an inflammatory disease of the respiratory tract, the compounds of the invention may also be formulated for inhalation, for example as a nasal spray, or dry powder or aerosol inhalers. For delivery by inhalation, the active compound is preferably in the form of microparticles which may be prepared by a variety of techniques, including spray-drying, freeze-drying and micronization. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known, and include CFC-12, HFA-134a, HFA-227, HCFC-22 and HFA-152.

In a preferred embodiment of the invention, a composition of the invention is in dry powder form, for delivery using a dry powder inhaler (DPI).

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

Compound of the invention 24 mg/canister
Lecithin, NF Liq. Conc. 1.2 mg/canister
Trichlorofluoromethane, NF 4.025 g/canister
Dichlorodifluoromethane, NF 12.15 g/canister.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety). Additionally, the compounds of the invention may be delivered in multi-chamber devices thus allowing for delivery of combination agents.

Other compounds may be combined with compounds of the invention for the prevention and treatment of inflammatory diseases, in particular respiratory diseases. The present invention also provides pharmaceutical compositions comprising a therapeutically effective amount of a compound of formula (I) and one or more other therapeutic agents. Examples of suitable therapeutic agents for a combination therapy with the compounds of the invention include: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, EP-101; (5) dual pharmacology M3-anticholinergic/β2-adrenoreceptor agonists such as GSK961081, AZD2115 and LAS 190792; (6) leukotriene modulators, for example leukotriene antagonists such as montelukast, zafirlukast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonuclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289, which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412, which are incorporated herein by reference in their entireties; (20) A2b antagonists such as those described in WO2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP 1052264 and EP 1241176, which are incorporated herein by reference in their entireties; (26) CXCR2 or IL-8 antagonists such as SCH 527123 or GSK 656933; (27) IL-R signalling modulators such as kineret and ACZ 885; and (28) MCP-1 antagonists such as ABN-912.

The invention present is also directed to a kit comprising the pharmaceutical compositions of compounds of formula (I) alone or in combination with or in admixture with one or more pharmaceutically acceptable carriers and/or excipients and a device which may be a single- or multi-dose dry powder inhaler, a metered dose inhaler or a nebulizer.

The present invention also provides a process for the preparation of compounds of formula (I). In the following reaction schemes, unless otherwise indicated, the groups mentioned assume the same meaning as those reported for compounds of formula (I). The skilled person may introduce, where appropriate, suitable variations to the conditions specifically described in the examples in order to adapt the synthetic routes to the provision of further compounds of the invention. Such variations may include use of appropriate starting materials to generate different compounds, changes in the solvent and temperature of reactions, replacements of reactants with analogous chemical role, introduction or removal of protection/de-protection stages of functional groups sensitive to reaction conditions and reagents, as well as introduction or removal of specific synthetic steps oriented to further functionalization of the chemical scaffold. The process described is particularly advantageous as it is susceptible of being properly modulated, through any proper variant known to the skilled person, so as to obtain any of the desired compounds of the invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent de-protection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known (see, for a reference, T. W. Green; Protective Groups in Organic Synthesis (Wiley, N.Y. 1981) which is incorporated herein by reference in its entirety).

Likewise, selective protection and de-protection of any of the said groups, for instance including carbonyl, hydroxyl or amino groups, may be accomplished according to well-known methods.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

Thus, the present invention also provides pharmaceutically acceptable salts of the compound of formula (I).

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example, compounds of the invention of formula (Ia) may be prepared according to the routes illustrated in Scheme 1:

Scheme 1

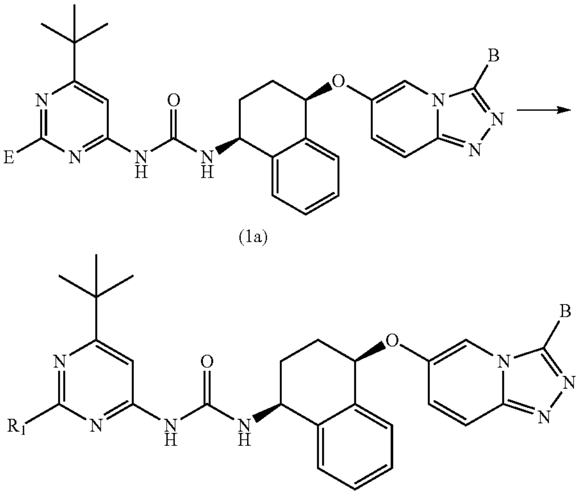

(1a)

(Ia)

wherein E is a known suitable chemical group selected such that it can facilitate a suitable transformation to give compounds of formula (Ia): for example E may include esters or a hydroxymethyl group. Compounds of formula (Ia) may be prepared by derivatization of compounds of formula (1a) by known reactions. For example, compounds of formula (Ia) may be prepared from compounds of formula (1a) by reaction with an appropriate amine or amide in a suitable solvent such as methanol or ethanol at a range of temperatures, preferably between RT and 90° C.

Compounds of formula (1a) may be prepared according to the routes illustrated in Scheme 2:

Scheme 2

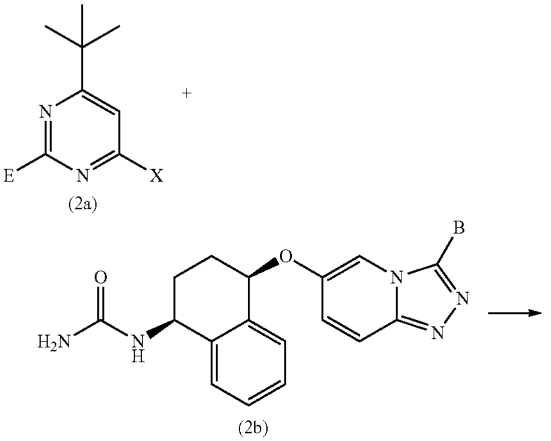

(2a)

(2b)

-continued

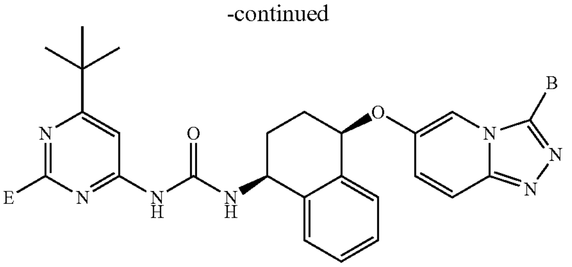

(1a)

Compounds of formula (1a) may be prepared from compounds of formula (2b) by reaction with a compound of formula (2a) wherein X is a suitable known chemical group selected such that it can facilitate a suitable coupling reaction such as metal catalzsed cross coupling: for example, X may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Alternatively, compounds of formula (Ia) may be prepared according to the routes illustrated in Scheme 3:

Scheme 3

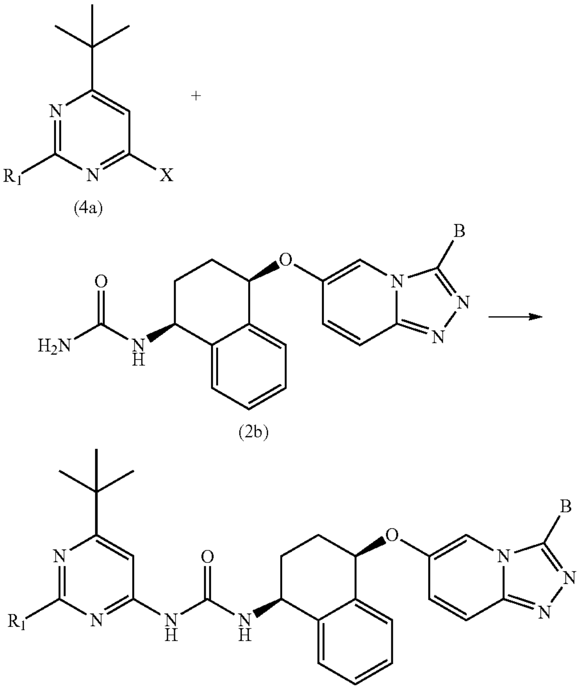

(4a)

(2b)

(Ia)

Compounds of formula (Ia) may be prepared from compounds of formula (2b) by reaction with a compound of formula (4a) wherein X is a suitable chemical group selected such that it can facilitate a suitable coupling reaction such as metal catalyzed cross coupling: for example X may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Compounds of formula (2a) and (4a) are either known or may be prepared according to the route illustrated in Scheme 4:

Scheme 4

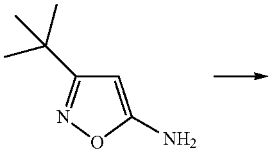

(3c)

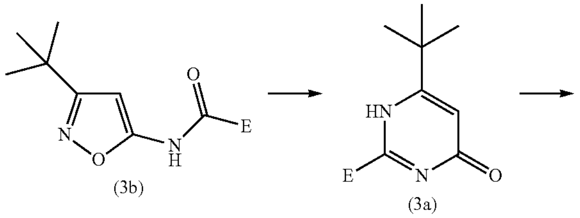

(3b) (3a)

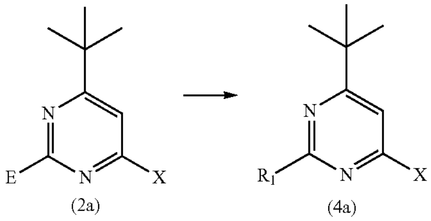

(2a) (4a)

Compounds of formula (4a) may be prepared from compounds of formula (2a) using a reducing agent such as sodium borohydride in a suitable solvent such as EtOH at a range of temperatures preferably between 0° C. to room temperature. Compounds of formula (2a) may be prepared from compounds of formula (3a) by reaction with neat $POCl_3$ or $SOCl_2$ or in a suitable solvent such as DMF, toluene or acetonitrile in a range of temperatures, preferably between RT and 100° C. Compounds of formula (3a) may be prepared from compounds of formula (3b) by hydrogenation in the presence of hydrogen gas in the presence of a suitable catalyst such as palladium on carbon or platinum on carbon in a suitable solvent such as ethanol or methanol at a range of temperatures, preferably between RT and 60° C. Compounds of formula (3b) may be synthesized from the commercially available compound (3c) by reaction with the relevant acid chloride in a suitable solvent such as pyridine, DCM, toluene, acetonitrile or 2-methyltetrahydrofuran in the presence of a suitable base such as pyridine, TEA or potassium carbonate, at a range of temperatures, preferably between 0° C. and RT.

Compounds of formula (4a) may be also prepared according to the routes illustrated in Scheme 5:

Scheme 5

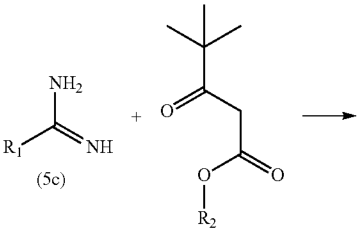

(5c) (5b)

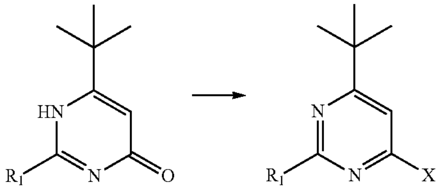

(5a) (4a)

Compounds of formula (4a) may be prepared from compounds of formula (5a) by reaction with neat $POCl_3$ or $SOCl_2$ or in a suitable solvent such as DMF, toluene or acetonitrile at a range of temperatures, preferably between RT and 100° C. Compounds of formula (5a) may be prepared from compounds of formula (5c) by condensation with compounds (5b) in the presence of a suitable base such as sodium methoxide, sodium ethoxide, potassium tert-butoxide or sodium carbonate in a suitable solvent such as methanol, ethanol or $H_2O$ at a range of temperatures, preferably between RT and 90° C.

Alternatively, compounds of formula (Ia) may be prepared according to the routes illustrated in Scheme 6:

Scheme 6

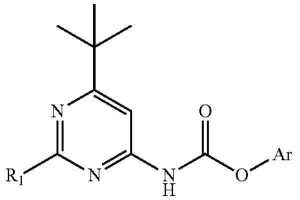

(6a1)

+

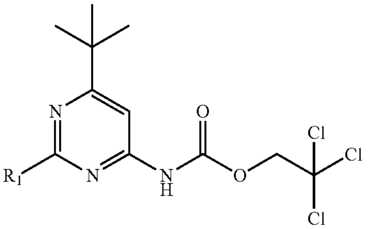

(6a2)

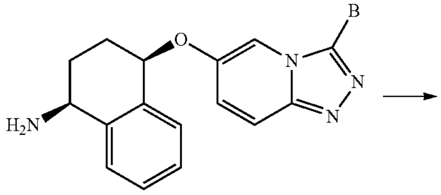

(6b)

-continued

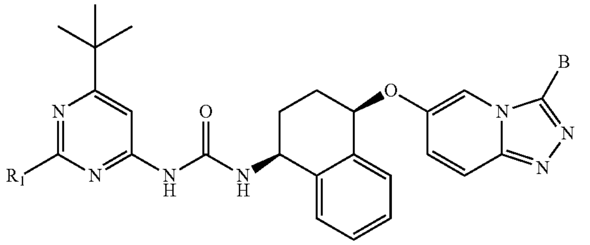

(Ia)

Compounds of formula (Ia) may be prepared from compounds of formula (6b) by reaction with a compound of formula (6a1) wherein Ar is a suitable aryl group such as phenyl or 4-nitrophenyl in a suitable solvent such as EtOAc, DCM, 1,4-dioxane, DMF, 2-methyl THF, THF or acetonitrile, in the presence of a base such as diisopropylethylamine, sodium bicarbonate or sodium hydroxide at a range of temperatures, preferably between RT and 100° C. Alternatively, compounds of formula (Ia) may be prepared from compounds of formula (6b) by reaction with a compound of formula (6a2) in a suitable solvent such as dimethyl sulfoxide, 1,4-dioxane, DMF, 2-methyl THF, THF or acetonitrile, in the presence of a base such as diisopropylethylamine or TEA at a range of temperatures, preferably between RT and 100° C.

Compounds of formula (6a1) are either known in the literature or may be prepared from amines of formula (6c) according to known procedures (e.g. US 2011/0311474, and J. Med. Chem., 2012, 55, 2869-2881, which are incorporated herein by reference in their entireties).

(6c)

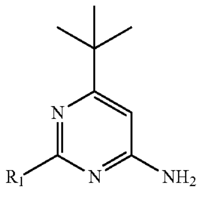

Compounds of formula (6a2) are either known or may be prepared according to the route illustrated in Scheme 7:

Scheme 7

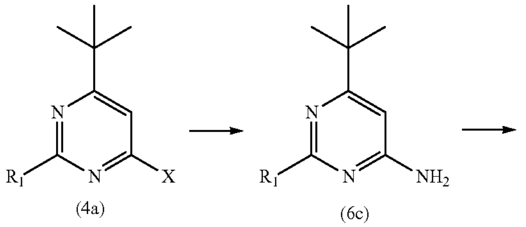

(4a) (6c)

-continued

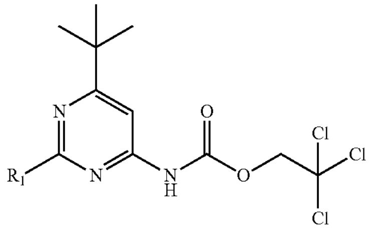

(6a2)

Compounds of formula (6a2) may be prepared from compounds of formula (6c) by reaction with 2,2,2-trichloroethyl chloroformate in a suitable solvent such as DCM, THF, 2-methyltetrahydrofuran or acetonitrile at a range of temperatures, preferably between RT and 100° C. Microwave conditions may also be applied to increase the range of temperatures, preferably between RT and 150° C.

Compounds of formula (6c) are either known or may be prepared from compounds of formula (4a) by reaction with ammonia hydroxide solution or a solution of $NH_3$ in MeOH or 1,4-dioxane, in a suitable solvent such as IPA, MeOH or 1,4-dioxane. Microwave conditions may also be applied to increase the range of temperatures, preferably between RT and 180° C.

Compounds of formula (2b) may be prepared according to the route illustrated in Scheme 8:

Scheme 8

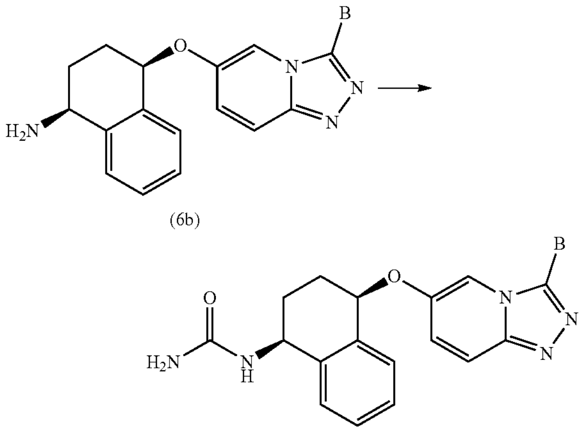

(6b)

(2b)

Compounds of formula (2b) may be prepared from compounds of formula (6b) by reaction with phosgene or triphosgene in a suitable solvent such as DCM or THF in the presence of a suitable base such as TEA or DIPEA at a range of temperatures, preferably between 0° C. and RT, followed by adding the mixture to a solution of ammonia in a suitable solvent such as methanol or water. Alternatively, compounds of formula (2b) may be prepared from compounds of formula (6b) by reaction with (trimethylsilyl)isocyanate in a suitable solvent such as DCM or THF or in a mixture of solvents, such as DCM/MeOH.

Compounds of formula (6b) may be prepared according to the route illustrated in Scheme 9.

Scheme 9

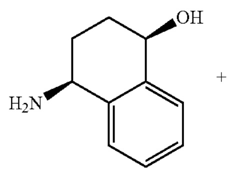

(9a)

Compounds of formula (6b) may be prepared from compounds of formula (9b) by reaction with compound (9a), wherein G is a known suitable chemical group selected such that it can facilitate a suitable coupling reaction such as nucleophilic displacement or metal catalysed cross coupling: for example G may include halogen such as fluorine. Examples of the coupling conditions may include using a base such as sodium hydride or potassium tert-butoxide and 18-crown-6 in a suitable solvent such as N,N-dimethylformamide or 2-methyl-THF at a range of temperatures, preferably between RT and 150° C.

Compounds of formula (9b) may be prepared according to the route in Scheme 10:

Scheme 10

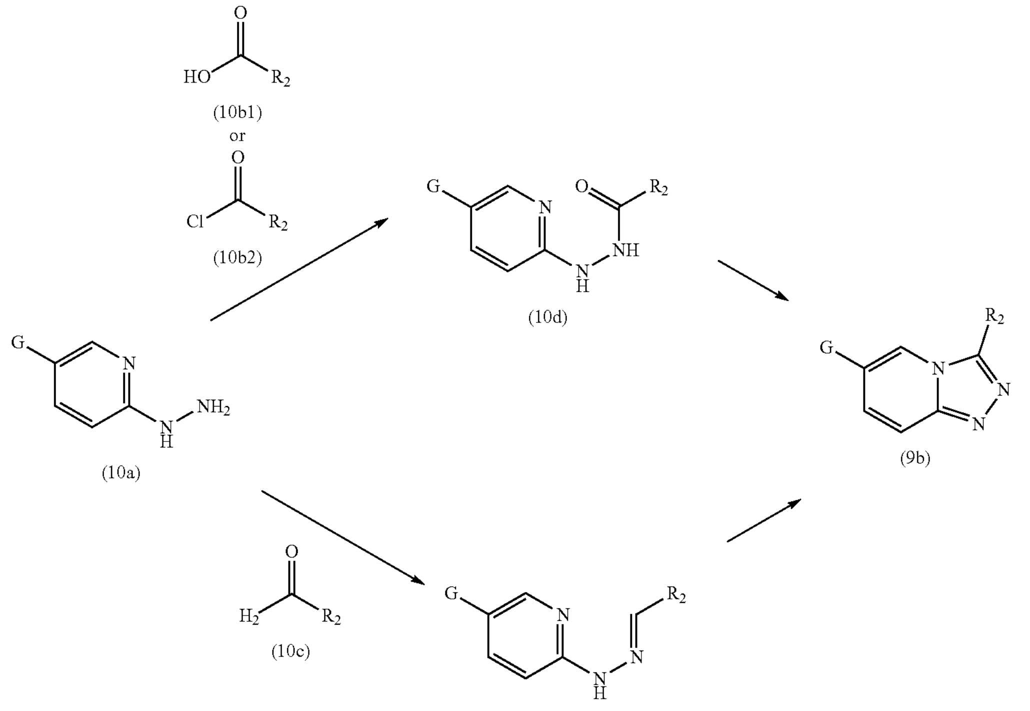

(10b1)
or
(10b2)
(10a)
(10d)
(9b)
(10c)
(10e)

-continued

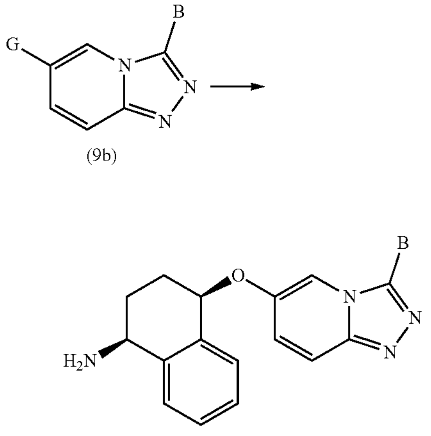

(9b)
(6b)

Compounds of formula (9b) may be prepared from compounds of formula (10e) as above reported using a suitable oxidant such as chloramine T, lead tetracetate or phenyl iodine(III) diacetate, in a suitable solvent such as dichloromethane or ethanol at a range of temperatures, preferably between RT and 100° C.

Compounds of formula (10e) may be prepared from compounds of formula (10a) by reaction with an aldehyde of formula (10c) in a suitable solvent such as ethanol or tetrahydrofuran at a range of temperatures, preferably between RT and 80° C.

Compounds of formula (10a) and (10c) are commercially available, known or may be prepared by known methods.

Alternatively, compounds of formula (9b) may be prepared from compounds of formula (10d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between RT and 120° C.

Compounds of formula (10d) may be prepared from compounds of formula (10a) by reaction with a compound of formula (10b1) using a suitable acylating/dehydrating agent such as triphenylphosphine/trichloroacetonitrile/HOBt/2-(7-aza-1H-benzotriazole-1-yl)-1,1,3,3-tetramethyl-uronium hexafluorophosphate or 1-ethyl-3-(3-dimethylaminopropyl)carbodiimide in the presence of a base such as diisopropylethylamine, in a suitable solvent such as dichloromethane or acetonitrile, at a range of temperatures, preferably between RT and 150° C.

Alternatively, compounds of formula (10d) may be prepared from compounds of formula (10a) by reaction with a compound of formula (10b2) in the presence of a base such as diisopropylethylamine, in a suitable solvent such as dichloromethane or THF at a range of temperatures preferably between −10° C. and the boiling point of the solvent.

Compounds of formulae (10b1) and (10b2) are commercially available, known or may be prepared by adapting appropriate methods.

Compound (9a) is disclosed in WO 014/195402, which is incorporated herein by reference in its entirety.

Compounds of formula (Ib) may be prepared according to the route illustrated in Scheme 11:

Scheme 11

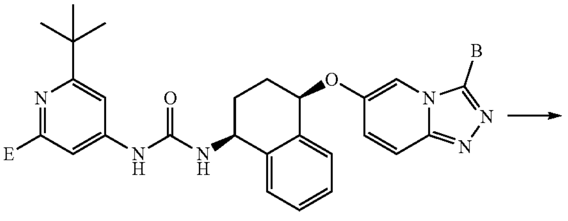

(11a)

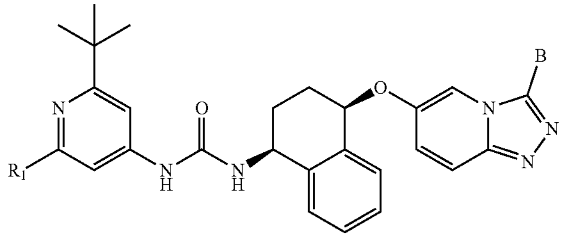

(Ib)

wherein E is a known suitable chemical group selected such that it can facilitate a suitable transformation to give compounds of formula (Ib): for example E may include esters or a hydroxymethyl group. Compounds of formula (Ib) may be prepared by derivatisation of compounds of formula (11a) by known reactions. For example, compounds of formula (Ib) may be prepared from compounds of formula (11a) by reaction with an appropriate amine or amide in a suitable solvent such as methanol or ethanol at a range of temperatures, preferably between RT and 90° C.

Compounds of formula (11a) may be prepared according to the route illustrated in Scheme 12:

Scheme 12

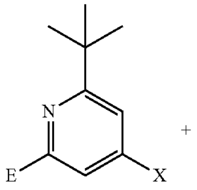

(12a)

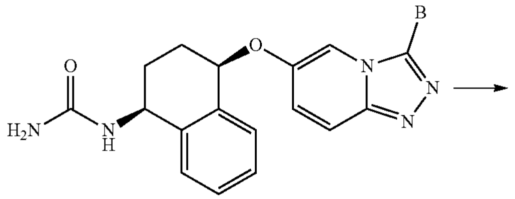

(2b)

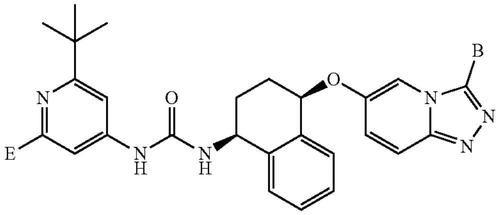

(11a)

Compounds of formula (11a) may be prepared from compounds of formula (2b) by reaction with a compound of formula (12a) wherein X is a suitable chemical group known to those skilled in the art selected such that it can facilitate a suitable coupling reaction such as metal catalysed cross coupling: for example X may include halogen or a suitable leaving group such as mesylate or triflate. Examples of the coupling conditions may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Alternatively, compounds of formula (Ib) may be prepared according to the route illustrated in Scheme 13:

Scheme 13

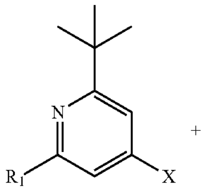

(14a)

-continued

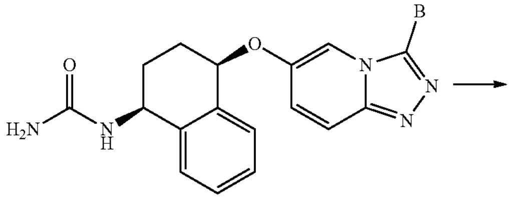

(2b)

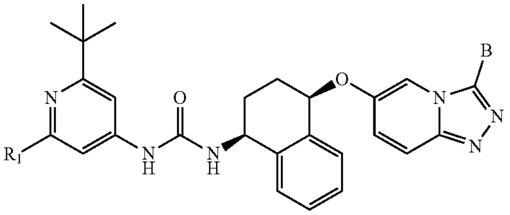

(Ib)

Compounds of formula (Ib) may be prepared from compounds of formula (2b) by reaction with a compound of formula (14a) wherein X is a known suitable group selected such that it can facilitate a suitable coupling reaction such as metal catalysed cross coupling: for example, X may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Compounds of formula (12a) and (14a) may be prepared according to the route illustrated in Scheme 14:

Scheme 14

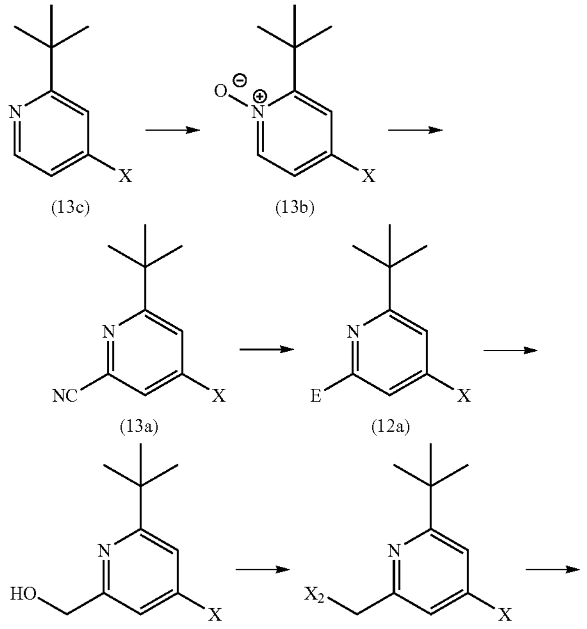

(13c) (13b)

(13a) (12a)

(14c) (14b)

-continued

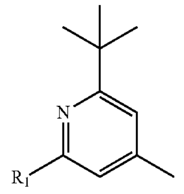

(14a)

Compounds of formula (14a) can be prepared from compounds of formula (14b) using an alcohol such as 4-(2-hydroxyethyl)morpholine with a base such as sodium hydride in a suitable solvent such as THF preferably between RT and 130° C. Compounds of formula (14b) can be prepared from compounds of formula (14c) using a suitable activating reagent such methylsulfonic anhydride with a suitable base such as trimethylamine in a solvent such as DCM preferably between −10° C. and RT. Compounds of formula (14c) and be prepared from compounds of formula (12a) when E is a known suitable group, for example ester by reduction using a suitable reducing agent such as sodium borohydride in a suitable solvent such as a mixture of THF/EtOH, preferably between 0° C. and RT. Compounds of formula (12a) may be prepared from compounds of formula (13a) by reaction with aqueous $H_2SO_4$ or aqueous HCl in a suitable solvent such as methanol or ethanol a range of temperatures, preferably between RT and 130° C. Compounds of formula (13a) may be prepared from compounds of formula (13b) by reaction with trimethylsilyl cyanide or zinc cyanide according to known procedures (e.g. J. Med. Chem., 2013, 56, 9874-9896, WO 2013/102145, and WO 2013/026866, which are incorporated herein by reference in their entireties). Compounds of formula (13b) may be synthesized from the commercially available compounds (13c) by oxidation of the pyridine with a suitable oxidant, such as m-CPBA, oxone or dimethyldioxirane in a suitable solvent such as DCM, acetone or cyclohexanone at a range of temperatures, preferably between 0° C. and RT.

Compounds of formula (14a) may be also prepared according to the route illustrated in Scheme 15:

Scheme 15

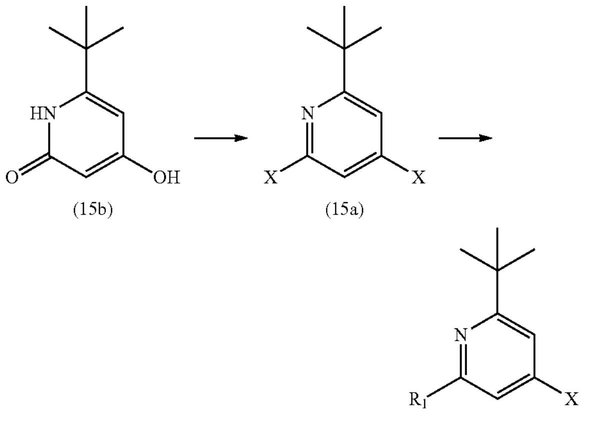

(15b) (15a)

(14a)

Compounds of formula (14a) may be prepared from compounds of formula (15a) by reaction with the relevant $R_1$ compounds, such as methanesulfonamide and ethanesulfonamide and where X is a known suitable chemical group selected such that it can facilitate a suitable metal catalysed cross coupling: for example X may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C. Compounds of formula (15a) may be prepared from compounds of formula (15b) by reaction with neat $POCl_3$ or $SOCl_2$ in a suitable solvent such as DMF, toluene, N,N-dimethylbenzenamine or DCM at a range of temperatures, preferably between RT and 130° C.

Compounds of formula (Ic) may be prepared according to the route illustrated in Scheme 16:

Scheme 16

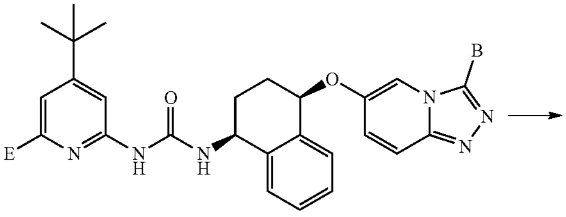

(16a)

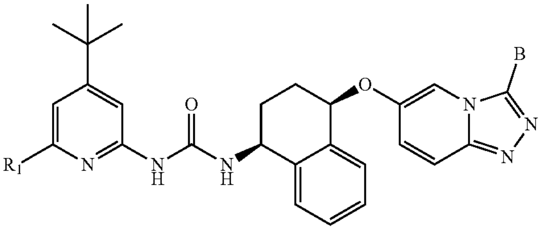

(Ic)

wherein E is a known suitable chemical group selected such that it can facilitate a suitable transformation to give compounds of formula (Ic): for example E may include esters or a hydroxymethyl group. Compounds of formula (Ic) may be prepared by derivatisation of compounds of formula (16a) by known reactions. For example, compounds of formula (Ic) may be prepared from compounds of formula (16a) by reaction with an appropriate amine or amide in a suitable solvent such as methanol or ethanol at a range of temperatures, preferably between RT and 90° C.

Compounds of formula (16a) may be prepared according to the route illustrated in Scheme 17:

Scheme 17

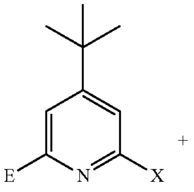

(17a)

-continued

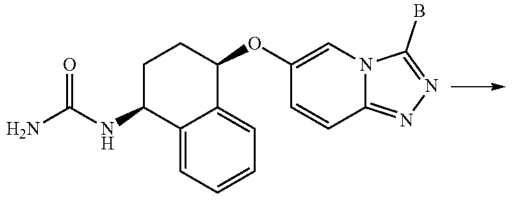

(2b)

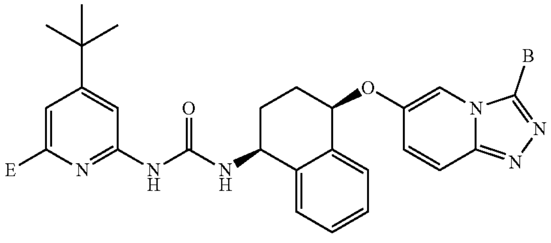

(16a)

Compounds of formula (16a) may be prepared from compounds of formula (2b) by reaction with a compound of formula (17a) wherein X is a known suitable chemical group selected such that it can facilitate a suitable coupling reaction such as metal catalysed cross coupling: for example X may include halogen or a suitable leaving group such as mesylate or triflate. Examples of the coupling conditions used may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Alternatively, compounds of formula (Ic) may be prepared according to the route illustrated in Scheme 18:

Scheme 18

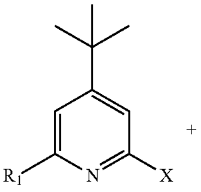

(17b)

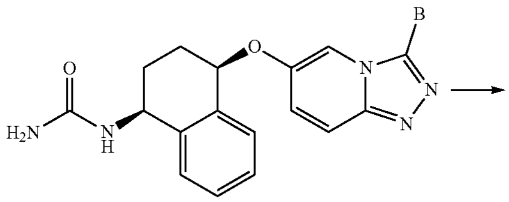

(2b)

-continued

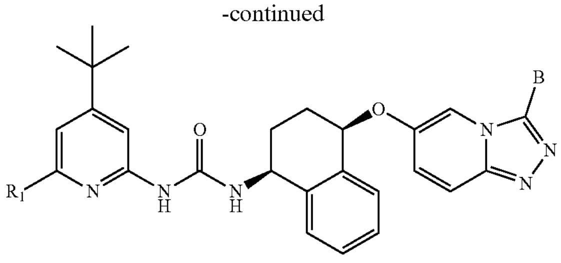

(Ic)

Compounds of formula (Ic) may be prepared from compounds of formula (2b) by reaction with a compound of formula (17b) wherein X is a suitable chemical group selected such that it can facilitate a suitable known coupling reaction such as metal catalysed cross coupling: for example X may include halogen or a suitable leaving group such as mesylate or triflate. Examples of the coupling conditions may include a catalyst such as palladium acetate or $Pd_2(dba)_3$, a ligand such as xantphos or X-phos in a suitable solvent such as 1,4-dioxane, 2-methyl THF, THF or toluene, in the presence of a base such as cesium carbonate, potassium carbonate, potassium tert-butoxide or potassium phosphate at a range of temperatures, preferably between RT and 110° C.

Compounds of formula (17a) and (17b) are either known or may be prepared according to the route illustrated in Scheme 19:

Compounds of formula (17b) can be prepared from compounds of formula (17a) wherein E is a suitable known chemical group selected such that it can facilitate a suitable transformation for example E may include esters or a hydroxymethyl group. Compounds of formula (17b) may be prepared by derivatization of compounds of formula (17a) by reactions for example, by reaction with an appropriate amine in a suitable solvent such as methanol or ethanol at a range of temperatures, preferably between RT and 90° C. Compounds of formula (17a) may be prepared from compounds of formula (18a) by reaction with aqueous $H_2SO_4$ or aqueous HCl in a suitable solvent such as methanol or ethanol a range of temperatures, preferably between RT and 130° C. Compounds of formula (18a) may be prepared from compounds of formula (18b1) by reaction with trimethylsilyl cyanide or zinc cyanide according to known procedures (e.g. J. Med. Chem., 2013, 56, 9874-9896, WO 2013/102145, and WO 2013/026866, which are incorporated herein by reference in their entireties). Compounds of formula (18b1) may be synthesized from compounds of formula (18c1) by oxidation of the pyridine with a suitable oxidant, such as m-CPBA, oxone or dimethyldioxirane in a suitable solvent such as DCM, acetone or cyclohexanone at a range of temperatures, preferably between 0° C. and RT. Compounds of formula (18c1) may be synthesized from commercially available compounds of formula (18d) by reaction with neat $POCl_3$ or $SOCl_2$ in a suitable solvent such as DMF, toluene, N,N-dimethylbenzenamine or DCM at a range of temperatures, preferably between RT and 130° C.

Scheme 19

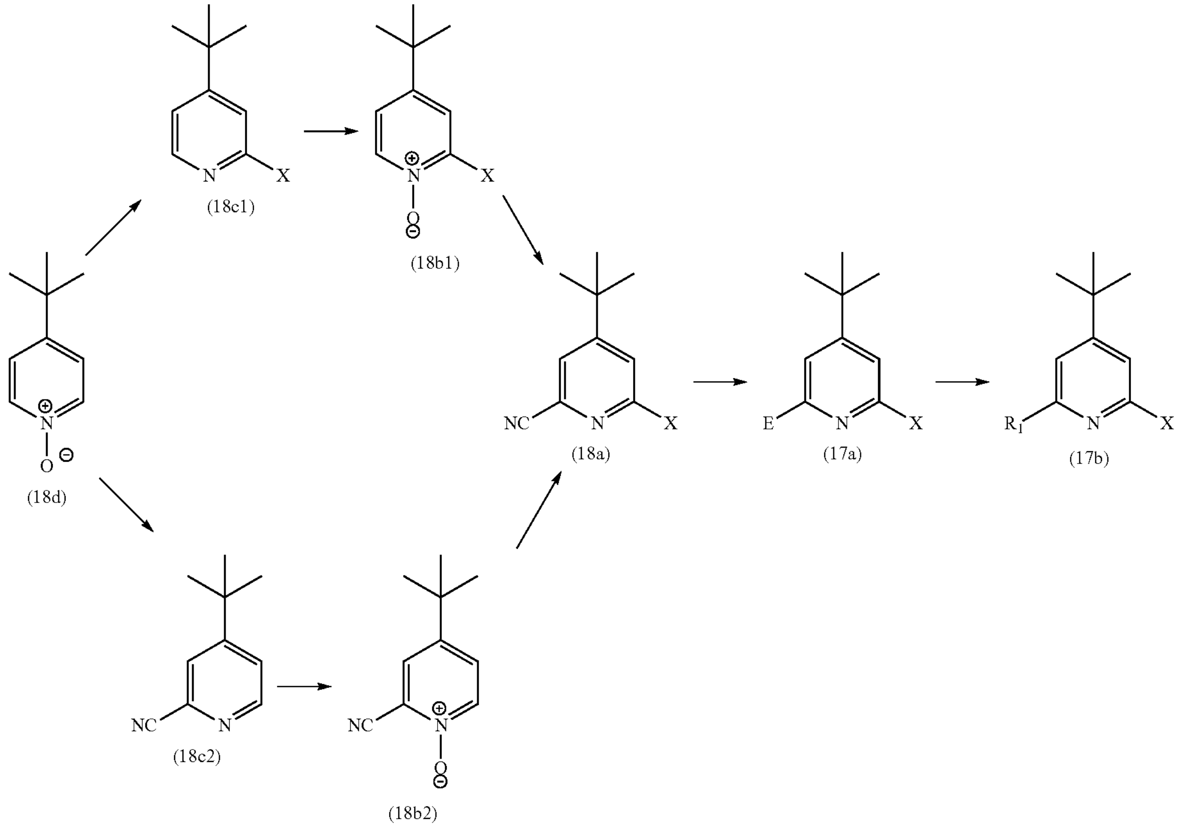

(18c1) (18b1) (18d) (18a) (17a) (17b) (18c2) (18b2)

Alternatively, compounds of formula (18a) may be prepared from compounds of formula (18b2) by reaction with neat $POCl_3$ or $SOCl_2$ in a suitable solvent such as DMF, toluene, N,N-dimethylbenzenamine or DCM at a range of temperatures, preferably between RT and 130° C. Compounds of formula (18b2) may be synthesised from compounds of formula (18c2) by oxidation of the pyridine with a suitable oxidant, such as m-CPBA, oxone or dimethyldioxirane in a suitable solvent such as DCM, acetone or cyclohexanone at a range of temperatures, preferably between 0° C. and RT. Compounds of formula (18c2) may be prepared from compounds of formula (18d) by reaction with trimethylsilyl cyanide or zinc cyanide according to known procedures (e.g. J. Med. Chem., 2013, 56, 9874-9896, WO 2013/102145, and WO 2013/026866, which are incorporated herein by reference in their entireties).

Alternatively compounds of formula (Ic) may be prepared according to the route illustrated in Scheme 20:

Scheme 20

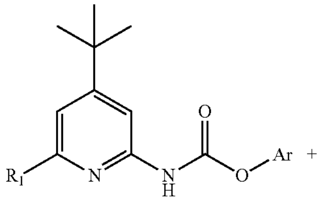

(19a)

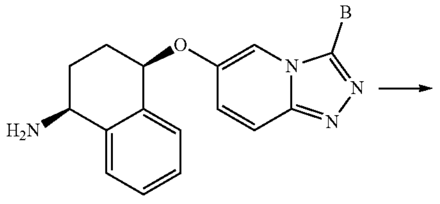

(2b)

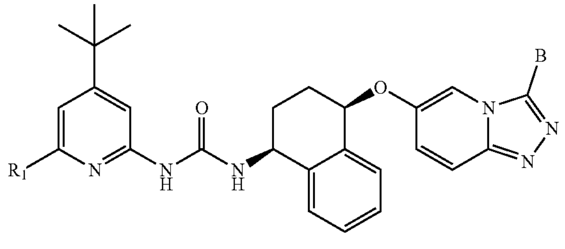

(Ic)

Compounds of formula (Ic) may be prepared from compounds of formula (2b) by reaction with a compound of formula (19a) wherein Ar is a suitable aryl group such as phenyl or 4-nitrophenyl in a suitable solvent such as EtOAc, DCM, 1,4-dioxane, DMF, 2-methyl THF, THF or acetonitrile, in the presence of a base such as diisopropylethylamine, sodium bicarbonate or sodium hydroxide at a range of temperatures, preferably between RT and 100° C.

Compounds of formula (19a) may be prepared from amines of formula (19b) according to known procedures (e.g. Tetrahedron Letters, 2014, 55, 1540-1543, WO 2006/074025, and WO 2014/186313, which are incorporated herein by reference in their entireties).

(19b)

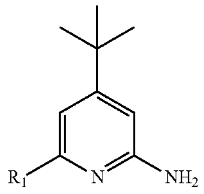

Compounds of formula (Id) may be prepared according to the route illustrated in Scheme 21:

Scheme 21

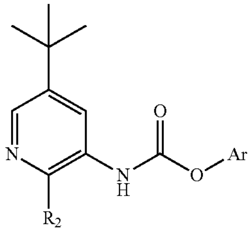

(20a1)

+

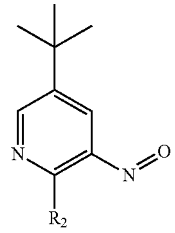

(20a2)

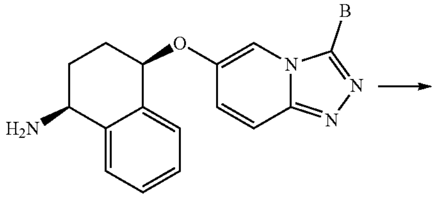

(2b)

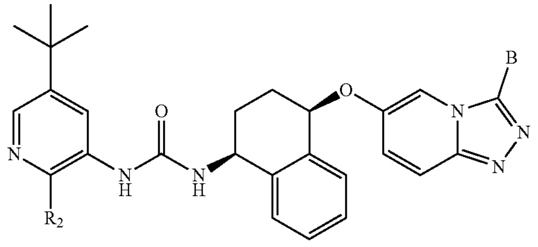

(Id)

Compounds of formula (Id) may be prepared from compounds of formula (2b) by reaction with a compound of formula (20a1) wherein Ar is a suitable aryl group such as phenyl or 4-nitrophenyl in a suitable solvent such as EtOAc, DCM, 1,4-dioxane, DMF, 2-methyl THF, THF or acetonitrile, in the presence of a base such as diisopropylethylamine, sodium bicarbonate or sodium hydroxide at a range of temperatures, preferably between RT and 100° C. Alternatively, compounds of formula (Id) may be prepared from compounds of formula (2b) by reaction with a compound of formula (20a2) in a suitable solvent such as dimethyl sulfoxide, 1,4-dioxane, DMF, 2-methyl THF, THF or acetonitrile, in the presence of a base such as diisopropylethylamine or TEA at a range of temperatures, preferably between RT and 100° C.

Compounds of formula (20a1) and (20a2) may be prepared from amines of formula (20b) according to known procedures (e.g. WO 2009/127949 and WO 2016/100652, which are incorporated herein by reference in their entireties).

(20b)

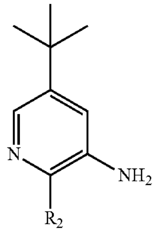

All the other specific syntheses are described in the experimental session.

Other features of the invention will become apparent in the course of the following descriptions of exemplary embodiments which are given for illustration of the invention and are not intended to be limiting thereof.

EXAMPLES

Abbreviations used in the experimental section:
aq.=aqueous;
DCM=dichloromethane;
DIPEA=diisopropylethylamine;
DMF=N,N-dimethylformamide;
DMSO=dimethyl sulfoxide;
EDC=1-ethyl-3-(3'-dimethylaminopropyl)carbodiimide hydrochloride;
EtOAc=ethyl acetate;
EtOH=ethanol;
$Et_2O$=diethyl ether;
FCC=flash column chromatography;
h=hour;
$H_2O$=water;
HOBt=1-hydroxy-benzotriazole;
HPLC=high performance liquid chromatography;
IMS=industrial methylated spirit;
LCMS=liquid chromatography mass spectrometry;
mCPBA=meta-chloroperbenzoic acid;
MDAP=mass-directed auto-purification;
MeCN=acetonitrile;
MeOH=methanol;
min=minutes;
NaOH=sodium hydroxide;
$NH_3$=ammonia;
NMR=nuclear magnetic resonance;
$PPh_3$=triphenylphosphine;
RT=room temperature;
Rt=retention time;
sat.=saturated;
SCX-2=strong cation exchange chromatography;
SFC=supercritical fluid chromatography;
TEA=trimethylamine;
TFA=trifluoroacetic acid; and
THF=Tetrahydrofuran.

In the procedures that follow, after each starting material, reference to an Intermediate/Example number is usually provided. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Stereochemical assignments of compounds are based on comparisons with data reported in WO 2008/043019, which is incorporated herein by reference in its entirety, for key intermediates. All reactions were carried out under anhydrous conditions and an atmosphere of nitrogen or argon unless specified otherwise.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography (FCC), 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d. Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or a C18-reverse-phase column (19×250 mm, XBridge OBD, with 5 μm particle size), eluting with gradients from 100-0 to 0-100% water/acetonitrile (containing 0.1% $NH_4OH$); or a ChiralPak IC column (10×250 mm i.d., with 5 μm particle size), unless otherwise indicated. Fractions containing the required product (identified by LCMS analysis) were pooled, the organic solvent removed by evaporation, and the remaining aqueous residue lyophilized, to give the final product. Products purified by preparative HPLC were isolated as free base, formate or TFA salts, unless otherwise stated.

The Liquid Chromatography Mass Spectroscopy (LCMS) Systems Used are:

Method 1

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |

-continued

| Gradient - Time | flow mL/min | % A | % B |
|---|---|---|---|
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 2

Acquity i-Class (quaternary pump/PDA detector)+Quattro Micro Mass Spectrometer with an ACQUITY UPLC BEH $C_{18}$ 1.7 μm, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 3

Waters micromass ZQ2000 quadrupole mass spectrometer with an Acquity BEH C18 1.7 um 100×2.1 mm, Acquity BEH Shield RP18 1.7 um 100×2.1 mm, Acquity UPLC BEH Phenyl 1.7 μm, 100×2.1 mm or Acquity HSST3 1.8 um 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 4

Acquity H-Class (quaternary pump/PDA detector)+QDa Mass Spectrometer, Acquity UPLC BEH C18 1.7μ, 50×2.1 mm at 50° C. or at 40° C. or Acquity UPLC CSH C18 1.7μ, 50×2.1 mm at 40° C. Elution with A: water+0.1% formic acid; B: acetonitrile+0.1% formic acid. Gradient:

| Gradient - Time | flow mL/min | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-450 nm. MS ionization method—Electrospray (positive and negative ion).

Method 5

Acquity H-Class (quaternary pump/PDA detector)+QDa Mass Spectrometer, Acquity UPLC BEH C18 1.7μ, 50×2.1 mm at 50° C. or XBridge BEH C18 2.5μ, 50×2.1 mm at 40° C. or at 50° C. Elution with A: water+0.1% aqueous ammonia; B: acetonitrile+0.1% aqueous ammonia. Gradient:

| Gradient - Time | flow mL/min | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-450 nm. MS ionization method—Electrospray (positive and negative ion).

Example 1. 4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)-pyrimidine-2-carboxamide

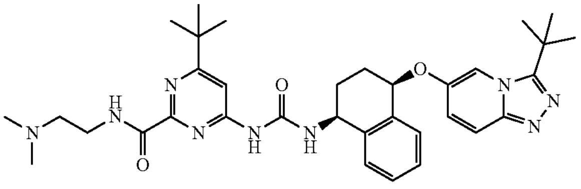 [SMILES: CN(C)CCNC(=O)c1nc(NC(=O)N[C@H]2CC[C@@H](Oc3ccc4nnc(C(C)(C)C)n4c3)c3ccccc32)cc(C(C)(C)C)n1]

a. 3-(tert-Butyl)isoxazol-5-amine (Intermediate 1a)

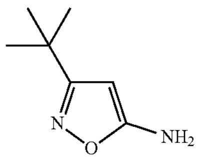

A solution of sodium hydroxide (250 g, 6.25 mol) in water (1250 ml) was added with pivaloylacetonitrile (CAS: 59997-51-2, 250 g, 2.0 mol) followed by hydroxylamine hydrochloride (150 g, 2.16 mol). The mixture was heated to 60° C. during which time it became homogeneous and then began to deposit a solid. After 3 h the mixture was cooled to RT and the solid removed by filtration, washed well with water and dried at 45° C. under vacuum to give the title compound (245.1 g, 88%). The aqueous filtrate was extracted with DCM (2×100 ml) and the combined DCM layers were dried ($Na_2SO_4$) and evaporated. (10.9 g, 4%).

$^1H$ NMR (300 MHz, $CDCl_3$) 1.28 (9H, s), 4.31 (2H, br s), 5.03 (1H, s).

b. Ethyl 2-((3-(tert-butyl)isoxazol-5-yl)amino)-2-oxoacetate (Intermediate 1b)

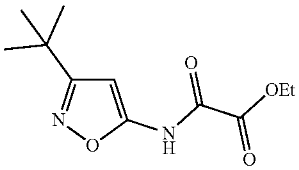 [SMILES: CCOC(=O)C(=O)Nc1cc(C(C)(C)C)no1]

A solution of Intermediate 1a (125 g, 892.9 mmol) and pyridine (77.6 g, 79.3 mL, 982.1 mmol) in ethyl acetate (1250 ml) was cooled in ice and treated dropwise, over ca. 30 min with ethyl chlorooxoacetate (134 g, 109.7 mL, 982.1 mmol), keeping the internal temperature ca. 15-20° C. The ice bath was removed and stirring continued for 1 h. The mixture was transferred to a separating funnel and washed with water, 1M HCl solution, brine, dried ($Na_2SO_4$) and evaporated. The residue was triturated with iso-hexane to afford the title compound (205.7 g, 96%).

$^1H$ NMR (300 MHz, $CDCl_3$) 1.34 (9H, s), 1.44 (3H, t, J=7.1 Hz), 4.45 (2H, q, J=7.1 Hz), 6.41 (1H, s), 9.53 (1H, br s).

c. Ethyl 6-(tert-butyl)-4-oxo-1,4-dihydropyrimidine-2-carboxylate (Intermediate 1c)

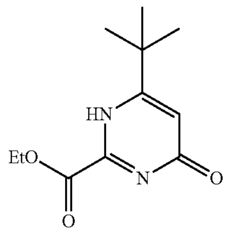 [SMILES: CCOC(=O)c1nc(=O)cc(C(C)(C)C)[nH]1]

A solution of Intermediate 1b (144 g, 600 mmol) and 1-methyl-1-cyclohexene (172.8 g, 1.8 mol) in IMS (720 ml) was treated, under an inert atmosphere, with 10% palladium on carbon (14 g, dry weight). The mixture was heated to reflux and stirred for ca. 6 h. The flask was evacuated/purged with nitrogen and the mixture filtered through Celite®. The filtrate was evaporated to afford the title compound (135.3 g, >100%).

$^1H$ NMR (300 MHz, $CDCl_3$) 1.29 (9H, s), 1.45 (3H, t, J=7.1 Hz), 4.49 (2H, q, J=7.1 Hz), 6.57 (1H, s), 11.23 (1H, br s).

d. Ethyl 4-(tert-butyl)-6-chloropyrimidine-2-carboxylate (Intermediate 1d)

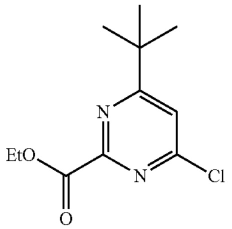 [SMILES: CCOC(=O)c1nc(Cl)cc(C(C)(C)C)n1]

A solution of Intermediate 1c (321 g, 1.42 mol) in $POCl_3$ (350 ml) was heated to 55° C. (block temperature) and stirred for 1 h. The solution was evaporated and the residue stirred with ice water, adding ice periodically, until any residual $POCl_3$ was destroyed. The mixture was carefully basified by adding solid $K_2CO_3$ in portions and then DCM was added and the layers were separated and the aqueous phase further extracted with DCM (×2). The combined organic layers were dried ($Na_2SO_4$) and evaporated. The residue was dissolved in DCM and treated with silica gel and filtered. The filtrate was evaporated to afford the title compound (333 g, 96%).

$^1H$ NMR (300 MHz, $CDCl_3$): 1.39 (9H, s), 1.44 (3H, t, J=7.2 Hz), 4.50 (2H, q, J=7.2 Hz), 7.46 (1H, s).

e. N'-(5-Fluoropyridin-2-yl)pivalohydrazide (Intermediate 1e)

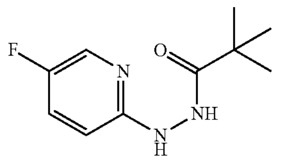

A solution of (5-fluoro-pyridin-2-yl) hydrazine (WO2014/195402, 12.7 g, 100 mmol) and DIPEA (19.3 g, 150 mmol) in DCM (150 ml) was cooled in ice and treated dropwise with pivaloyl chloride (14.5 g, 120 mmol) over ca. 15 mins. The mixture was stirred cold for ca. 30 mins. The reaction mixture was evaporated and the residue partitioned between EtOAc and water. The two phases were separated and the organic layer extracted with an aqueous 1M HCl solution. The HCl layer was washed with $Et_2O$ and then basified with solid $K_2CO_3$ extracting into EtOAc. The organic layer was dried ($Na_2SO_4$) and evaporated to give the title compound (15.5 g, 73%).

$^1H$ NMR (300 MHz, $CDCl_3$): 1.29 (9H, s), 6.63 (1H, dd, J=9.0, 3.5 Hz), 6.7 (1H, br d), 7.22-7.35 (1H, m), 7.84 (1H, br d), 8.04 (1H, d, J=2.9 Hz)

f. 3-(tert-Butyl)-6-fluoro-[1,2,4]triazolo[4,3-a]pyridine (Intermediate 1f)

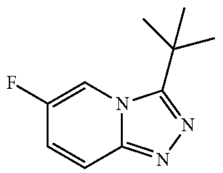

A solution of Intermediate 1e (15.5 g, 73.4 mmol) in 2-methyl THF (300 ml) was treated with triethylamine (29.7 g, 294 mmol), triphenylphosphine (38.5 g, 147 mmol) and finally with hexachloroethane (CAS: 67-72-1, 34.8 g, 147 mmol). The reaction mixture was stirred and the internal temperature maintained ca. 30° C. by external cooling. After 1 h the RM was washed with water and then extracted with 1M HCl solution. The HCl layer was washed with $Et_2O$ and basified with solid $K_2CO_3$ extracting into DCM (×3). The combined DCM layers were dried ($Na_2SO_4$) and evaporated under reduced pressure to give the title compound (12.7 g, 90%).

$^1H$ NMR (300 MHz, $CDCl_3$): 1.60 (9H, s), 7.16 (1H, ddd, J=10, 7.3, 2.2 Hz), 7.77 (1H, ddd, J=10, 5.2, 0.8 Hz), 8.10 (1H, ddd, J=4, 2.1, 0.8 Hz).

g. (1S,4R)-4-((3-(tert-Butyl)-[1,2,4]triazolo[4,3-a]pyridin-6-yl)oxy)-1,2,3,4-tetrahydronaphthalen-1-amine (Intermediate 1g)

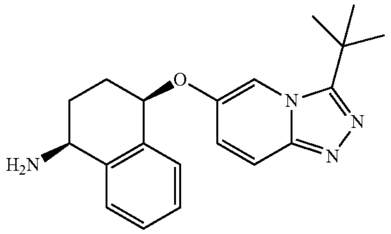 [SMILES: CC(C)(C)c1nnc2ccc(O[C@@H]3CC[C@H](N)c4ccccc43)cn12]

A solution of Intermediate 1f (12.7 g, 65.8 mmol) in 2-methyl THF (200 ml) was treated with (1R, 4S)-4-amino-1,2,3,4-tetrahydronaphthalen-1-ol (WO2014/195402, which is incorporated herein by reference in its entirety, 10.7 g, 65.8 mmol) and 18-crown-6 (1.77 g, 6.6 mmol) and the mixture was cooled to 0-5° C. and treated with KOtBu (8.47 g, 75.7 mmol). The flask was evacuated and purged with nitrogen (×3) and stirred at RT under nitrogen. After ca. 2 h the reaction was quenched with water and the aqueous phase extracted with 2-methyl THF. The combined organic layers were extracted with 10% citric acid solution and the citric acid layer basified with solid $K_2CO_3$ extracting into DCM. The DCM layer was dried ($Na_2SO_4$) and evaporated. The residue was purified by silica gel plug filtration eluting with DCM followed by 10% 2M $NH_3$ in MeOH/DCM to afford the title compound (14.9 g, 86%).

$^1$H NMR (300 MHz, $CDCl_3$): 1.56 (9H, s), 1.68 (2H, br s), 1.87-2.13 (3H, m), 2.32-2.44 (1H, m), 3.63-3.77 (1H, m), 4.00 (1H, dd, J=8.1, 5.1 Hz), 5.22 (1H, t, J=4.5 Hz), 7.13 (1H, dd, J=10, 2 Hz), 7.22-7.43 (3H, m), 7.60 (1H, br d, J=7.7 Hz), 7.69-7.77 (2H, m).

h. 1-((1S,4R)-4-((3-(tert-Butyl)-[1,2,4]triazolo[4,3-a]pyridin-6-yl)oxy)-1,2,3,4-tetrahydronaphthalen-1-yl)urea (Intermediate 1h)

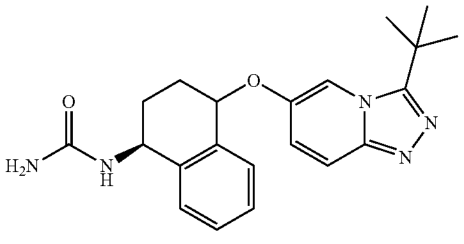 [SMILES: CC(C)(C)c1nnc2ccc(OC3CC[C@H](NC(N)=O)c4ccccc43)cn12]

A solution of Intermediate 1g (3.0 g, 8.9 mmol) and trimethylsilyl isocyanate (2.05 g, 17.9 mmol) in DCM (40 ml) was stirred at RT for 18 h and then treated MeOH (5 ml). The solution was evaporated and the residue purified by silica gel plug filtration eluting with 5% 2M $NH_3$ in MeOH/DCM to give the title compound (3.38 g, 100%).

$^1$H NMR (300 MHz, $CDCl_3$): 1.51 (9H, s), 2.00-2.18 (3H, m), 2.25-2.38 (1H, m), 4.99-5.13 (3H, m), 5.15-5.24 (1H, m), 6.28 (1H, br d, J=9.0 Hz), 7.00 (1H, dd, J=9.9, 2.0 Hz), 7.19-7.37 (3H, m), 7.47-7.55 (2H, m), 7.70 (1H br d, J=1.3 Hz).

i. Ethyl 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxylate (Intermediate 1i)

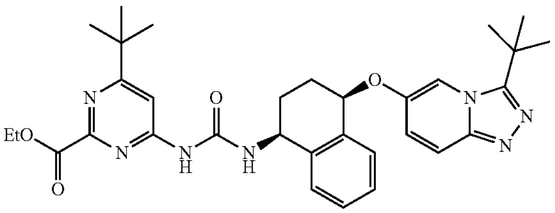 [SMILES: CCOC(=O)c1nc(NC(=O)N[C@H]2CC[C@@H](Oc3ccc4nnc(C(C)(C)C)n4c3)c3ccccc32)cc(C(C)(C)C)n1]

A solution of Intermediate 1h (5.7 g, 15.0 mmol) in dioxane (125 ml) was treated with Intermediate 1d (3.65 g, 15.0 mmol), $Pd(OAc)_2$ (170 mg, 0.75 mmol), XantPhos (870 mg, 1.5 mmol) and $Cs_2CO_3$ (6.8 g, 21.0 mmol). The reaction mixture was purged with nitrogen and then heated at 95° C. for 18 h. The reaction mixture was cooled at RT and filtered through a pad of Celite® and the filtrate evaporated. The residue was purified by silica gel plug filtration, eluting with EtOAc followed by 10% IMS/EtOAc to afford the title compound (4.8 g, 55%).

$^1$H NMR (300 MHz, $CDCl_3$): 1.14 (3H, t, J=7.1 Hz), 1.36 (9H, s), 1.57 (9H, s), 2.11-2.51 (4H, m), 4.14-4.36 (2H, m), 5.18-5.33 (2H, br m), 7.13 (1H, dd, J=10.0, 2.1 Hz), 7.20-7.42 (4H, m), 7.58 (1H, br d, J=7.6 Hz), 7.79 (1H, d, J=1.3 Hz), 7.87 (1H, d, J=10.0 Hz), 9.81 (1H, br s), 10.12 (1H, br s).

j. Example 1

A solution of Intermediate 1i (2.8 g, 4.79 mmol) and N,N-dimethylethylenediamine (2.1 g, 23.9 mmol) in MeOH (30 ml) was heated to 55° C. and stirred for 18 h. The RM was evaporated and the residue partitioned between water and EtOAc. The two phases were separated and the organic layer extracted into 10% citric acid solution. The citric acid layer was washed with $Et_2O$ and basified with solid $K_2CO_3$ extracting into DCM. The DCM layer was dried ($Na_2SO_4$) and evaporated to give the title compound (2.8 g, 93%).

LCMS (Method 3): Rt 3.29 min, m/z 628.3 [$MH^+$]. $^1$H NMR (300 MHz, $CDCl_3$): 1.31 (9H, s), 1.53 (9H, s), 1.91-2.28 (10H, m), 2.39 (2H, t, J=6.6 Hz), 3.28-3.40 (2H, m, peak partially obscured by solvent), 4.95-5.04 (1H, m), 5.64 (1H, t, J=3.8 Hz), 7.28-7.47 (5H, m), 7.73-7.76 (2H, m), 8.15 (1H, d, J=1.3 Hz), 8.25 (1H, br s), 8.58 (1H, t, J=5.7 Hz), 9.90 (1H, br s).

Example 2. 4-(tert-Butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide

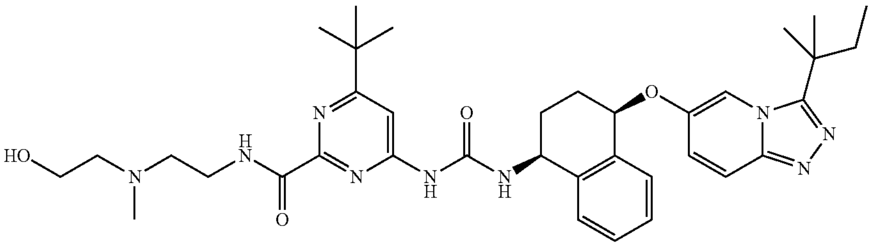 [SMILES: CCC(C)(C)c1nnc2ccc(O[C@@H]3CC[C@H](NC(=O)Nc4cc(C(C)(C)C)nc(C(=O)NCCN(C)CCO)n4)c4ccccc43)cn12]

a. N'-(5-Fluoropyridin-2-yl)-2,2-dimethylbutanehydrazide (Intermediate 2a)

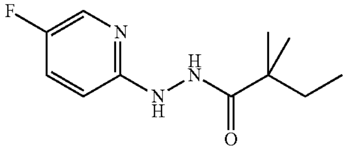 [SMILES: CCC(C)(C)C(=O)NNc1ccc(F)cn1]

A solution of (5-fluoro-pyridin-2-yl)-hydrazine (WO 2014/195402, which is incorporated herein by reference in its entirety, 40.6 g, 320 mmol) and HOBt (4.34 g, 32 mmol) in DCM (440 ml) was cooled down to 0° C. and then treated with 2,2-dimethylbutanoic acid (40 mL, 320 mmol). EDC (76.7 g, 400 mmol) was added slowly to the reaction, which was left to stir at 0° C. for 30 minutes and then 90 minutes at RT. The reaction mixture was diluted with DCM (100 mL) and washed with brine (100 mL). The organic phase was dried with $Na_2SO_4$. The solvent was removed under reduced pressure and the residue was triturated with $Et_2O$, filtered and dried to give the title compound (57.7 g, 80%).

$^1H$ NMR (300 MHz, $CDCl_3$): 0.89 (3H, t, J=7.7 Hz), 1.24 (6H, s), 1.63 (2H, q, J=7.7 Hz), 6.66 (1H, dd, J=9.0, 3.5 Hz), 6.71 (1H, d, J=3.6 Hz), 7.26-7.32 (1H, m), 7.58 (1H, br s), 8.03 (1H, d, J=2.9 Hz).

b. 6-Fluoro-3-(pentan-3-yl)-[1,2,4]triazolo[4,3-a]pyridine (Intermediate 2b)

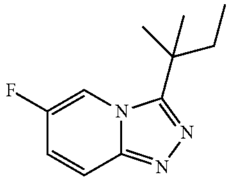

Hexachloroethane (108.8 g, 459.5 mmol) was portionwise added to a cooled solution of Intermediate 2a (48.5 g, 229.8 mmol), triphenylphosphine (120.5 g, 459.5 mmol) and TEA (125 g, 919.2 mmol) in 2-methyltetrahydrofuran (1000 ml) at 0° C., while stirring. The reaction mixture was stirred at 0° C. for 30 minutes and then at RT for 2 h (maintaining the reaction temperature <30° C.). The reaction mixture was filtered and the solvent was removed under reduced pressure. The residue was taken up in DCM (150 mL) and washed with aqueous 6M HCl solution. The aqueous phase was washed with $Et_2O$ and then basified with solid $K_2CO_3$. The resulting aqueous phase was extracted with DCM and the organic phase was dried with $Na_2SO_4$ and the solvent was removed under reduced pressure to afford the title compound (46 g, 96%).

$^1H$ NMR (300 MHz, $CDCl_3$): 0.76 (3H, t, J=8.9 Hz), 1.59 (6H, s), 1.93 (2H, q, J=9.0 Hz), 7.16 (1H, ddd, J=9.7, 7.4, 2.2 Hz), 7.77 (1H, ddd, J=9.9, 5.2, 0.9 Hz), 8.06-8.10 (1H, m).

c. (1S,4R)-4-((3-(tert-Pentyl)-[1,2,4]triazolo[4,3-a]pyridin-6-yl)oxy)-1,2,3,4-tetrahydronaphthalen-1-amine (Intermediate 2c)

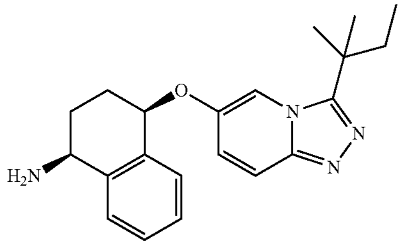 [SMILES: CCC(C)(C)c1nnc2ccc(O[C@@H]3CC[C@H](N)c4ccccc43)cn12]

A stirred solution of Intermediate 2b (13.1 g, 63.3 mmol), (1R,4S)-4-amino-1,2,3,4-tetrahydro-naphthalen-1-ol (WO 2014/195402, which is incorporated herein by reference in its entirety, 10.3 g, 63.3 mmol) and 18-crown-6 (1.67 g, 6.3 mmol) in 2-methyltetrahydrofuran (300 ml) at 0° C. under nitrogen was added with potassium tert-butoxide (8.20 g, 72.8 mmol). The reaction mixture was evacuated and purged with argon (×3), warmed at RT and stirred for 4 h. The reaction mixture was partitioned between 2-methyltetrahydrofuran and $H_2O$ and the two phases were separated. The organic phase was extracted with aqueous 10% citric acid solution. The aqueous phase was washed with $Et_2O$ and then basified with solid $K_2CO_3$. The resulting aqueous phase was extracted with DCM. The organic phase was dried with $Na_2SO_4$ and the solvent was removed under reduced pressure. Purification by FCC, eluting with 0-5% 2N $NH_3$ in MeOH/DCM afforded the title compound (19.6 g, 88%).

$^1H$ NMR (300 MHz, $CDCl_3$): 0.74 (3H, t, J=7.6 Hz), 1.54 (3H, s), 1.55 (3H, s), 1.63 (2H, br s), 1.82-2.14 (5H, m), 2.30-2.43 (1H, m), 3.97-4.05 (1H, m), 5.18-5.24 (1H, t, J=4.2 Hz), 7.08-7.16 (1H, dd, J=10.0, 2.6 Hz), 7.22-7.33 (2H, m), 7.34-7.43 (1H, dd, J=7.8, 2.2 Hz), 7.60 (1H, d, J=7.6 Hz), 7.70 (1H, s), 7.73 (1H, d, J=9.9 Hz).

d. 1-((1S,4R)-4-((3-(Pentan-3-yl)-[1,2,4]triazolo[4,3-a]pyridin-6-yl)oxy)-1,2,3,4-tetrahydronaphthalen-1-yl)urea (Intermediate 2d)

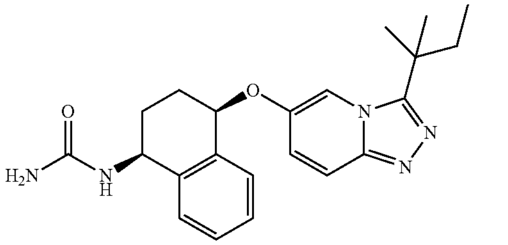 [SMILES: CCC(C)(C)c1nnc2ccc(O[C@@H]3CC[C@H](NC(N)=O)c4ccccc43)cn12]

A solution of Intermediate 2c (5.0 g, 14.3 mmol) in DCM (50 ml) was treated with (trimethylsilyl)isocyanate (3.3 g, 28.6 mmol) at 0° C. The reaction mixture was warmed at RT and stirred for 15 minutes. Methanol (0.5 ml) was added and the reaction mixture was stirred for 15 minutes. The solvents were removed under reduced pressure and the residue was taken up in DCM and applied directly to a pad of silica gel eluting with DCM followed by 5% MeOH/DCM. Evaporation under reduced pressure of the relevant fractions afforded the title compound (5.6 g, 100%).

$^1$H NMR (400 MHz, $CDCl_3$): 0.71 (3H, t, J=7.6 Hz), 1.49 (3H, s), 1.50 (3H, s), 1.87 (2H, q, J=7.5 Hz), 1.99-2.18 (3H, m), 2.23-2.38 (1H, m), 5.07 (3H, bm), 5.18 (1H, t, J=5.1 Hz), 6.21 (1H, d, J=9.2 Hz), 7.00 (1H, dd, J=10.3, 2.1 Hz), 7.21-7.35 (3H, m), 7.48-7.53 (2H, m), plus one proton not observed.

e. Ethyl 4-(tert-butyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxylate (Intermediate 2e)

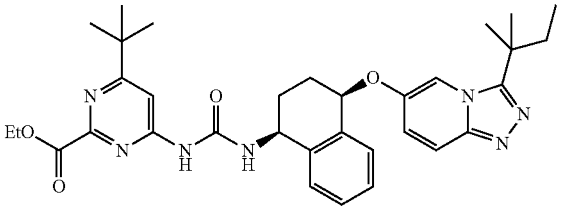 [SMILES: CCOC(=O)c1nc(NC(=O)N[C@H]2CC[C@@H](Oc3ccc4nnc(C(C)(C)CC)n4c3)c3ccccc32)cc(C(C)(C)C)n1]

A solution of Intermediate 2d (5.6 g, 14.2 mmol), Intermediate 1d (3.46 g, 14.2 mmol), XantPhos (0.82 g, 1.42 mmol) in dioxane (100 ml) was treated with $Cs_2CO_3$ (6.5 g, 19.9 mmol) and $Pd(OAc)_2$ (0.16 g, 0.71 mmol). The reaction mixture was evacuated and purged with argon (×3) and then heated at 95° C. for 18 hours. The reaction mixture was cooled at RT and then filtered through a pad of Celite®. The solvents were removed under reduced pressure. Purification by FCC, eluting with 0-10% IMS/EtOAc afforded the title compound (4.48 g, 52%).

$^1$H NMR (300 MHz, $CDCl_3$): 0.74 (3H, t, J=7.4 Hz), 1.13 (3H, t, J=7.4 Hz), 1.36 (9H, s), 1.55 (6H, s), 1.90 (2H, q, J=7.2 Hz), 2.10-2.29 (3H, m), 2.31-2.44 (1H, m), 4.15-4.33 (2H, m), 5.17-5.30 (2H, m), 7.09 (1H, br s), 7.11 (1H, dd, J=9.9, 1.9 Hz), 7.27-7.39 (3H, m), 7.57 (1H, d, J=7.6 Hz), 7.77 (1H, d, J=1.8 Hz), 7.83 (1H, d, J=9.5 Hz), 9.43 (1H, br s), 9.79 (1H, br s).

f. Example 2

A solution of Intermediate 2e (4.4 g, 7.34 mmol) in IMS (100 ml) was treated with N-(2-hydroxyethyl)-N-methylethylenediamine (CAS: 5753-50-4, 2.35 g, 22 mmol). The reaction mixture was heated at 55° C. for 18 h. The reaction mixture was cooled at RT and the solvent was removed under reduced pressure. The residue was dissolved in EtOAc and extracted with aqueous 10% citric acid solution. The aqueous phase was washed with $Et_2O$ and then it was basified with solid $K_2CO_3$. The aqueous phase was extracted with DCM and the organic phase was dried with $Na_2SO_4$. The solvent was removed under reduced pressure. Purification by FCC, eluting with 0-10% 2N $NH_3$ in MeOH/DCM, followed by crystallization with acetonitrile afforded the title compound (2.74 g, 55%).

LCMS (Method 3): Rt 3.37 min, m/z 672 [$MH^+$]. $^1$H NMR (400 MHz, $d_6$-DMSO): 0.63 (3H, t, J=8.8 Hz), 1.31 (9H, s), 1.49 (6H, s), 1.89-2.15 (5H, m), 2.16-2.21 (1H, m), 2.23 (3H, s), 2.46 (2H, t, J=6.9 Hz), 2.52 (2H, t, J=6.9 Hz, partially obscured by the solvent peak), 3.33-3.37 (2H, m, partially obscured by the water peak), 3.47 (2H, q, J=6.0 Hz), 4.35 (1H, t, J=6.0 Hz), 4.96-5.03 (1H, m), 5.62 (1H, t, J=4.0 Hz), 7.26-7.39 (3H, m), 7.42 (2H, d, J=8.1 Hz), 7.72 (1H, br s), 7.75 (1H, d, J=9.8 Hz), 8.10 (1H, d, J=1.4 Hz), 8.27 (1H, br s), 8.6 (1H, t, J=5.5 Hz), 9.92 (1H, s).

Example 3. 4-(tert-Butyl)-N-(2-(dimethylamino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide

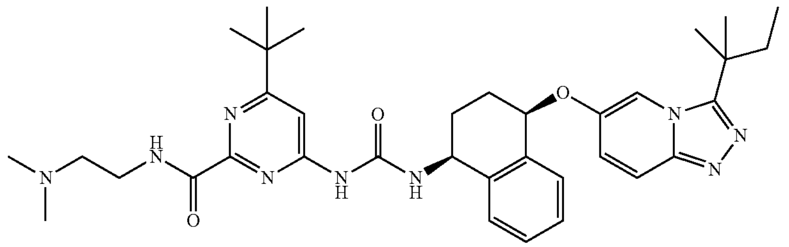 [SMILES: CCC(C)(C)c1nnc2ccc(O[C@@H]3CC[C@H](NC(=O)Nc4cc(C(C)(C)C)nc(C(=O)NCCN(C)C)n4)c4ccccc43)cn12]

A solution of Intermediate 2e (6.36 g, 10.6 mmol) in MeOH (120 ml) was treated with N,N-dimethylethylene diamine (9.36 g, 106 mmol). The reaction mixture was heated at 55° C. for 18 h. The reaction mixture was cooled at RT and the solvent was removed under reduced pressure. The residue was partitioned between DCM and $H_2O$ and the two phases were separated. The aqueous phase was back extracted with DCM and the organic phase was dried with $Na_2SO_4$. The solvent was removed under reduced pressure and the residue was dissolved in MeCN (15-20 mL) and left to stir at RT for 3 h and then filtered and desiccated for 18 h to afford the title compound (5.0 g, 74%).

LCMS (Method 3): Rt 3.35 min, m/z 642 [$MH^+$]. $^1H$ NMR (400 MHz, d-$_6$-DMSO): 0.63 (3H, t, J=5.9 Hz), 1.31 (9H, s), 1.49 (6H, s), 1.87-2.13 (6H, m), 2.17 (6H, s), 2.40 (2H, t, J=7.8 Hz), 3.34 (2H, m, partially obscured by the water peak), 4.99 (1H, m), 5.62 (1H, t, J=3.9 Hz), 7.26-7.39 (3H, m), 7.42 (2H, d, J=7.2 Hz), 7.71-7.76 (2H, m), 8.10 (1H, d, J=1.4 Hz), 8.27 (1H, br s), 8.58 (1H, t, J=6.3 Hz), 9.90 (1H, s).

Example 4. 4-(tert-Butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide

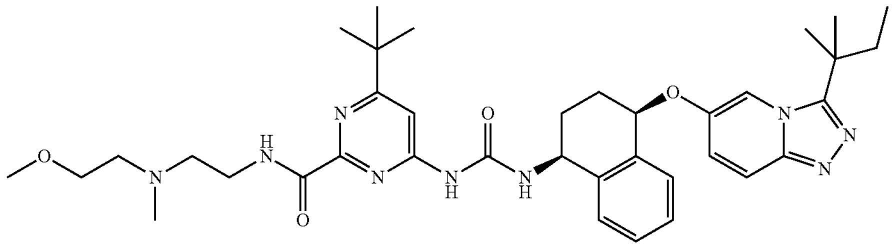 [SMILES: CCC(C)(C)c1nnc2ccc(O[C@@H]3CC[C@H](NC(=O)Nc4cc(C(C)(C)C)nc(C(=O)NCCN(C)CCOC)n4)c4ccccc43)cn12]

A solution of Intermediate 2e (5.00 g, 8.34 mmol) in MeOH (120 ml) was treated with N1-(2-methoxyethyl)-N1-methyl-1,2-ethanediamine (CAS: 14165-17-4, 4.41 g, 33.35 mmol). The reaction mixture was heated at 55° C. for 18 hours. The residue was partitioned between DCM and $H_2O$ and the two phases were separated. The aqueous phase was back extracted with DCM and the organic phase was dried with $Na_2SO_4$. The solvent was removed under reduced pressure. Purification by FCC, eluting with 0-10% 2N $NH_3$ in MeOH/DCM, followed by crystallization with acetonitrile afforded the title compound (4.08 g, 71%).

LCMS (Method 3): Rt 3.49 min, m/z 686 [$MH^+$]. $^1H$ NMR (400 MHz, d-$_6$-DMSO): 0.63 (3H, t, J=7.5 Hz), 1.31 (9H, s), 1.49 (6H, s), 1.85-2.14 (5H, m), 2.17-2.22 (1H, m), 2.23 (3H, s), 2.51-2.57 (4H, m, partially obscured by the solvent peak), 3.21 (3H, s), 3.33-3.37 (2H, m, partially obscured by the water peak), 3.41 (2H, t, J=5.8 Hz), 5.00 (1H, m), 5.62 (1H, t, J=4.2 Hz), 7.26-7.39 (3H, m), 7.39-7.44 (2H, d, J=7.9 Hz), 7.71 (1H, br s), 7.74 (1H, d, J=8.9 Hz), 8.10 (1H, d, J=1.8 Hz), 8.3 (1H, br s), 8.58 (1H, t, J=5.4 Hz), 9.93 (1H, s).

Example 5. 4-(tert-Butyl)-N-(2-(dimethylamino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide

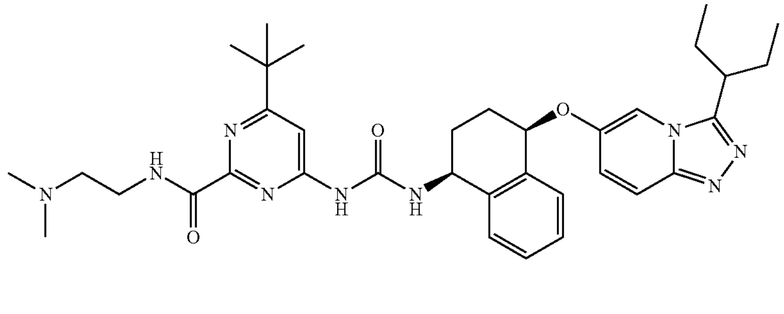 [SMILES: CCC(CC)c1nnc2ccc(O[C@@H]3CC[C@H](NC(=O)Nc4cc(C(C)(C)C)nc(C(=O)NCCN(C)C)n4)c4ccccc43)cn12]

a. 2-Ethyl-N'-(5-fluoropyridin-2-yl)butane hydrazide (Intermediate 5a)

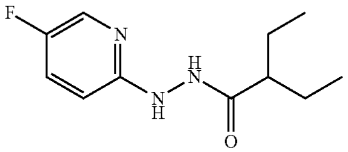 [SMILES: CCC(CC)C(=O)NNc1ccc(F)cn1]

A solution of (5-fluoro-pyridin-2-yl)-hydrazine (WO 2014/195402, which is incorporated herein by reference in its entirety, 12.7 g, 100 mmol), HOBt (1.53 g, 10 mmol) and EDC (19.15 g, 100 mmol) in DCM (250 ml) was treated with 2-ethylbutyric acid (11.6 g, 100 mmol). The reaction mixture was stirred at RT for 1 h maintaining the reaction temperature <25° C. The volatiles were removed under reduced pressure and the residue was partitioned between EtOAc and $H_2O$. The organic phase was extracted with aqueous 1M HCl solution. The aqueous phase was washed with $Et_2O$ and then it was basified with solid $K_2CO_3$. The aqueous phase was extracted with DCM and the organic phase was dried with $Na_2SO_4$. The solvent was removed under reduced pressure to give the title compound (17.3 g, 77%).

$^1$H NMR (300 MHz, $CDCl_3$): 0.93 (6H, t, J=7.4 Hz), 1.49-1.72 (4H, m), 1.95-2.05 (1H, m), 6.66 (1H, dd, J=9.0, 3.5 Hz), 6.94 (1H, d, J=3.9 Hz), 7.24-7.31 (1H, m), 7.83 (1H, d, J=3.3 Hz), 8.02 (1H, d, J=2.9 Hz).

b. 6-Fluoro-3-(pentan-3-yl)-[1,2,4]triazolo[4,3-a] pyridine (Intermediate 5b)

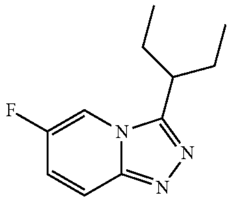

Hexachloroethane (36.4 g, 153.8 mmol) was portionwise added to a stirred solution of Intermediate 5a (17.3 g, 76.9 mmol), triphenylphosphine (40.3 g, 153.8 mmol) and TEA (31.1 g, 307.6 mmol) in 2-methyltetrahydrofuran (300 ml). The reaction mixture was stirred at RT for 1 h maintaining the reaction temperature <30° C. The reaction mixture was partitioned between 2-methyltetrahydrofuran and $H_2O$ and the two phases were separated. The organic phase was extracted with an aqueous 1M HCl solution. The aqueous phase was washed with $Et_2O$ and then basified with solid $K_2CO_3$. The resulting aqueous phase was extracted with DCM and the organic phase was dried with $Na_2SO_4$ and the solvent was removed under reduced pressure. Trituration with $Et_2O$/petrol (v/v 1:1) afforded the title compound (12.7 g, 80%).

$^1$H NMR (300 MHz, $CDCl_3$): 0.89 (6H, t, J=7.4 Hz), 1.86-2.07 (4H, m), 2.92-3.01 (1H, m), 7.17 (1H, ddd, J=9.8, 7.5, 2.2 Hz), 7.76 (1H, ddd, J=10.0, 5.0, 0.8 Hz), 7.85-7.88 (1H, m).

c. (1S,4R)-4-((3-(Pentan-3-yl)-[1,2,4]triazolo[4,3-a] pyridin-6-yl)oxy)-1,2,3,4-tetrahydronaphthalen-1-amine (Intermediate 5c)

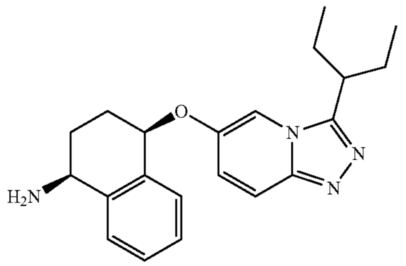 [SMILES: CCC(CC)c1nnc2ccc(O[C@@H]3CC[C@H](N)c4ccccc43)cn12]

A stirred solution of Intermediate 5b (12.7 g, 61.3 mmol), (1R,4S)-4-amino-1,2,3,4-tetrahydro-naphthalen-1-ol (WO 2014/195402, which is incorporated herein by reference in its entirety, 10.0 g, 61.3 mmol) and 18-crown-6 (1.62 g, 6.1 mmol) in 2-methyltetrahydrofuran (250 ml) at 0° C. under nitrogen was added potassium tert-butoxide (7.90 g, 70.6 mmol). The reaction mixture was evacuated and purged with argon (×3), warmed at RT and stirred for 3 h. The reaction mixture was partitioned between 2-methyltetrahydrofuran and $H_2O$ and the two phases were separated. The organic phase was extracted with aqueous 10% citric acid solution. The aqueous phase was washed with $Et_2O$ and then basified with solid $K_2CO_3$. The resulting aqueous phase was extracted with DCM. The organic phase was dried with $Na_2SO_4$ and the solvent was removed under reduced pressure. Purification by FCC, eluting with 0-5% 2N $NH_3$ in MeOH/DCM afforded the title compound (15.06 g, 70%).

$^1$H NMR (300 MHz, $CDCl_3$): 0.85 (3H, t, J=7.4 Hz), 0.89 (3H, t, J=7.4 Hz), 1.82-2.12 (7H, m), 2.33-2.42 (1H, m), 2.89-2.98 (1H, m), 3.98-4.03 (1H, m), 5.24 (1H, t, J=7.4 Hz), 7.12 (1H, dd, J=9.8, 2.1 Hz), 7.24-7.42 (3H, m), 7.50 (1H, d, J=1.3 Hz), 7.60 (1H, d, J=7.8 Hz), 7.70 (1H, dd, J=9.9, 0.8 Hz), plus two protons not observed.

d. 1-((1S,4R)-4-((3-(Pentan-3-yl)-[1,2,4]triazolo[4,3-a]pyridin-6-yl)oxy)-1,2,3,4-tetrahydronaphthalen-1-yl)urea (Intermediate 5d)

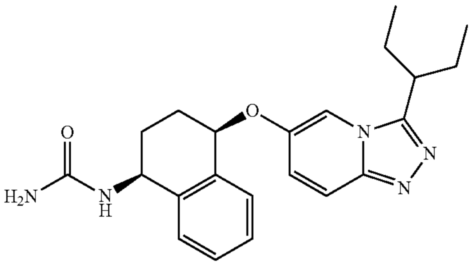 [SMILES: CCC(CC)c1nnc2ccc(O[C@@H]3CC[C@H](NC(N)=O)c4ccccc43)cn12]

A stirred solution of triphosgene (8.54 g, 28.8 mmol) in DCM (140 ml) at −10° C. was slowly added with a solution of Intermediate 5c (9.15 g, 26.1 mmol) and TEA (10.5 g, 104.4 mmol). The reaction mixture was stirred at 0° C. for 1 h and then added to a solution of $NH_3$ in MeOH (7M, 75 ml, 522 mmol) pre-cooled at 0° C. The resulting mixture was stirred at 0° C. for 30 minutes and then the volatiles were removed under reduced pressure. The residue was dissolved in DCM and $H_2O$ and the two phases were separated. The aqueous phase was extracted with DCM (×2), the combined organic phases were dried with $MgSO_4$ and the solvent was removed under reduced pressure. The crude was purified by FCC, eluting with 0-10% 2N $NH_3$ in MeOH/DCM and the residue was partitioned between DCM and a saturated aqueous $NaHCO_3$ solution. The two phases were separated and the organic phase was washed with saturated aqueous $NaHCO_3$ solution. The organic phase was dried with $MgSO_4$ and the solvent was removed under reduced pressure to give the title compound (10.9 g, quant.).

$^1$H NMR (300 MHz, $CDCl_3$): 0.81 (3H, t, J=7.4 Hz), 0.84 (3H, t, J=7.4 Hz), 1.75-2.15 (7H, m), 2.25-2.33 (1H, m), 2.87-2.94 (1H, m), 5.01-5.22 (4H, m), 6.48 (1H, d, J=8.7 Hz), 6.98-7.02 (1H, m), 7.21-7.33 (3H, m), 7.48-7.53 (3H, m).

e. Ethyl 4-(tert-butyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxylate (Intermediate 5e)

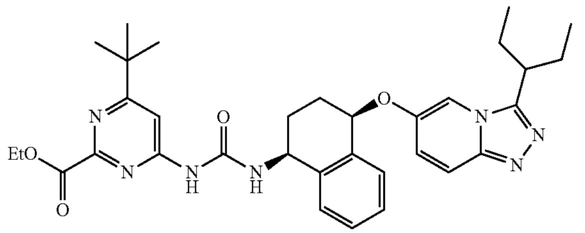

A solution of Intermediate 5d (10.9 g, 26.0 mmol), Intermediate 1d (6.60 g, 27.3 mmol), XantPhos (3.10 g, 5.4 mmol) in dioxane (150 ml) was treated with $Cs_2CO_3$ (12.7 g, 39.0 mmol) and $Pd(OAc)_2$ (0.58 g, 2.6 mmol). The reaction mixture was evacuated and purged with argon (×3) and then heated at 100° C. for 90 minutes. The reaction mixture was cooled to RT and stirred overnight. The mixture was diluted with DCM and EtOH and filtered through a pad of Celite®. The solvents were removed under reduced pressure. Purification by FCC, eluting with 0-10% IMS/DCM afforded the title compound (8.83 g, 57%).

$^1$H NMR (300 MHz, $CDCl_3$): 0.85 (3H, t, J=7.4 Hz), 0.88 (3H, t, J=7.4 Hz), 1.13 (3H, t, J=7.1 Hz), 1.36 (9H, s), 1.76-2.06 (5H, m), 2.17-2.40 (3H, m), 2.91-3.01 (1H, m), 4.15-4.33 (2H, m), 5.23-5.28 (2H, m), 7.12 (1H, dd, J=9.9, 2.0 Hz), 7.20 (1H, br s), 7.28-7.38 (3H, m), 7.54-7.59 (2H, m), 7.83 (1H, dd, J=9.8, 0.8 Hz), 9.75 (2H, br s).

f. Example 5

A solution of Intermediate 5e (3.80 g, 6.34 mmol) in methanol (40 ml) was treated with N,N-dimethylethylenediamine (1.40 g, 15.9 mmol). The reaction mixture was heated at 55° C. for 18 h. The reaction mixture was cooled at RT and the solvent was removed under reduced pressure. The residue was dissolved in EtOAc and extracted with aqueous 10% citric acid solution. The aqueous phase was washed with $Et_2O$ and then it was basified with solid $K_2CO_3$. The aqueous phase was extracted with DCM and the organic phase was dried with $Na_2SO_4$. The solvent was removed under reduced pressure. Purification by FCC, eluting with 0-5% 2N $NH_3$ in MeOH/DCM, followed by crystallisation with acetonitrile afforded the title compound (1.82 g, 45%).

LCMS (Method 3): Rt 3.37 min, m/z 642 [$MH^+$]. $^1$H NMR (400 MHz, $d_6$-DMSO): 0.77 (3H, t, J=7.4 Hz), 0.80 (3H, t, J=7.4 Hz), 1.31 (9H, s), 1.75-2.26 (14H, m), 2.39 (2H, t, J=6.6 Hz), 3.34-3.38 (2H, m, partially obscured by the solvent peak), 4.98-5.04 (1H, m), 5.57 (1H, t, J=4.0 Hz), 7.25-7.43 (5H, m), 7.70 (1H, dd, J=9.8, 0.5 Hz), 7.74 (1H, br s), 8.25 (1H, br s), 8.28 (1H, d, J=1.3 Hz), 8.55 (1H, t, J=5.8 Hz), 9.89 (1H, s), plus one proton obscured by the solvent peak.

Example 6. 4-(tert-Butyl)-N-(2-(3-methoxyazetidin-1-yl)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide

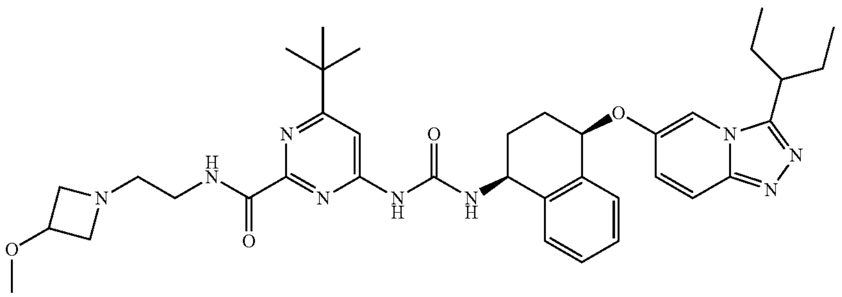 [SMILES: CCC(CC)c1nnc2ccc(O[C@@H]3CC[C@H](NC(=O)Nc4cc(C(C)(C)C)nc(C(=O)NCCN5CC(OC)C5)n4)c4ccccc43)cn12]

A solution of Intermediate 5e (4.40 g, 7.34 mmol) in ethanol (20 ml) was treated with 2-(3-methoxyazetidin-1-yl)ethan-1-amine (CAS: 911300-65-7, 2.50 g, 19.2 mmol). The reaction mixture was heated at 70° C. for 6 h. The reaction mixture was cooled at RT and the solvent was removed under reduced pressure. Purification by FCC, eluting with 0-10% 2N $NH_3$ in MeOH/DCM, afforded the title compound (4.49 g, 89%).

LCMS (Method 3): Rt 3.48 min, m/z 684 [$MH^+$]. $^1$H NMR (400 MHz, $d_6$-DMSO): 0.78 (3H, t, J=7.4 Hz), 0.80 (3H, t, J=7.4 Hz), 1.32 (9H, s), 1.76-2.25 (8H, m), 2.54 (2H, t, J=6.4 Hz), 2.80-2.83 (2H, m), 3.12 (3H, s), 3.24 (2H, q, J=6.2 Hz), 3.50-3.54 (2H, m), 3.93 (1H, quintet, J=5.8 Hz), 4.99-5.04 (1H, m), 5.57 (1H, t, J=3.8 Hz), 7.25-7.43 (5H, m), 7.69-7.73 (2H, m), 8.24-8.34 (2H, br s), 8.56 (1H, t, J=5.9 Hz), 9.90 (1H, s), plus one proton obscured by the solvent peak.

Example 7. 4-(tert-Butyl)-N-(2-(dimethylamino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido) pyrimidine-2-carboxamide

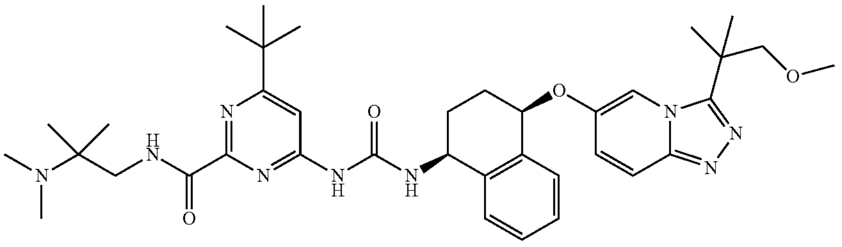

a. N'-(5-fluoropyridin-2-yl)-3-methoxy-2,2-dimethylpropanehydrazide (Intermediate 7a)

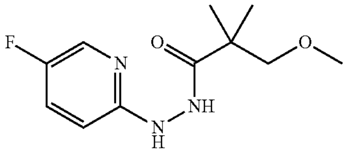 [SMILES: COCC(C)(C)C(=O)NNc1ccc(F)cn1]

A solution of 3-methoxy-2,2-dimethyl-propanoic acid (CAS: 64241-78-7, 4.9 g, 37.1 mmol), 5-fluoro-2-pyridyl) hydrazine (WO 2014/195402, which is incorporated herein by reference in its entirety, 4.71 g, 37.1 mmol) and HOBt Hydrate (0.57 g, 3.7 mmol) in DCM (100 ml) was treated with EDC.HCl (7.11 g, 37.1 mmol). The reaction mixture was placed in water bath and stirred for 2 h. The reaction mixture was evaporated under reduced pressure and the residue was partitioned between 2-methyltetrahydrofuran and $H_2O$. The two phases were separated and the organic phase was extracted with aqueous 1M HCl solution. The aqueous phase was washed with $Et_2O$ and basified with solid $K_2CO_3$. The resulting aqueous phase was extracted with DCM and the organic phase was dried with $NaSO_4$ and the solvent was removed under reduced pressure. Trituration with $Et_2O$/Petrol afforded the title compound (6.9 g, 77%).

$^1$H NMR (300 MHz, $CDCl_3$): 1.23 (6H, s), 3.40 (2H, s), 3.46 (3H, s), 6.58-6.54 (2H, m), 7.24-7.31 (1H, m), 8.03 (1H, d, J=2.9 Hz), 8.68 (1H, d, J=3.1H)

b. (4-(tert-Butyl)-6-chloropyrimidin-2-yl)methyl acetate (Intermediate 7b)

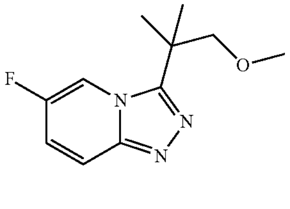 [SMILES: COCC(C)(C)c1nnc2ccc(F)cn12]

A solution of Intermediate 7a (6.9 g, 28.6 mmol), triphenylphosphine (15.0 g, 57.3 mmol) and TEA (11.6 g, 114.5 mmol) in 2-methyltetrahydrofuran (200 ml) was treated with hexachloroethane (13.6 g, 57.3 mmol). The reaction mixture was stirred at RT (maintaining the reaction temperature <30° C.). The reaction mixture was partitioned between 2-methyltetrahydrofuran and $H_2O$ and the two phases were separated. The organic phase was extracted with an aqueous 1M HCl solution. The aqueous phase was washed with $Et_2O$ and then basified with solid $K_2CO_3$. The resulting aqueous phase was extracted with DCM and the organic phase was dried with $Na_2SO_4$ and the solvent was removed under reduced pressure. Trituration with $Et_2O$/petrol (v/v 1:1) afforded the title compound (5.88 g, 92%).

$^1$H NMR (300 MHz, $CDCl_3$): 1.62 (6H, s), 3.33 (3H, s), 3.59 (2H, s), 7.17 (1H, ddd, J=9.6, 7.2, 2.2 Hz), 7.71 (1H, ddd, J=10.0, 5.2, 0.8 Hz), 8.57 (1H, ddd, J=4.89, 2.2, 0.8 Hz).

c. (1S,4R)-4-((3-(1-methoxy-2-methylpropan-2-yl)-[1,2,4]triazolo[4,3-a]pyridin-6-yl)oxy)-1,2,3,4-tetrahydronaphthalen-1-amine (Intermediate 7c)

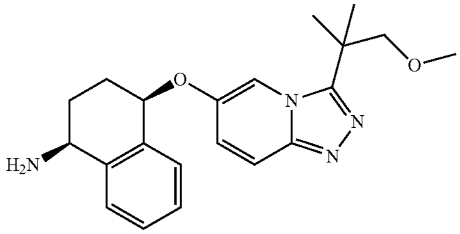 [SMILES: COCC(C)(C)c1nnc2ccc(O[C@@H]3CC[C@H](N)c4ccccc43)cn12]

A stirred solution of Intermediate 7b (5.8 g, 26.0 mmol), (1R,4S)-4-amino-1,2,3,4-tetrahydro-naphthalen-1-ol (WO 2014/195402, which is incorporated herein by reference in its entirety, 4.24 g, 26.0 mmol) and 18-crown-6 (0.7 g, 2.6 mmol) in 2-methyltetrahydrofuran (150 ml) at 0° C. under nitrogen was added with potassium tert-butoxide (3.35 g, 29.9 mmol). The reaction mixture was evacuated and purged with argon (×3), warmed to RT and stirred for 3 h. The reaction mixture was partitioned between 2-methyltetrahydrofuran and $H_2O$ and the two phases were separated. The organic phase was extracted with aqueous 10% citric acid solution. The aqueous phase was washed with $Et_2O$ and then basified with solid $K_2CO_3$. The resulting aqueous phase was extracted with EtOAc. The organic phase was dried with $Na_2SO_4$ and the solvent was removed under reduced pressure. The residue was applied to a plug of silica, eluting with 0-5% 2N $NH_3$ in MeOH/DCM to afford the title compound (7.42 g, 81%).

$^1$H NMR (300 MHz, $CDCl_3$): 1.61 (6H, s), 1.91-2.12 (3H, m), 2.30-2.38 (1H, m), 3.31 (3H, s), 3.56 (2H, s), 3.96-4.01 (1H, m), 5.19 (1H, t, J=4.5 Hz), 7.08 (1H, dd, J=9.8, 2.1 Hz), 7.25-7.41 (3H, m), 7.60 (1H, d, J=7.7 Hz), 7.67 (1H, dd, J=9.9, 0.8 Hz), 8.27 (1H, dd, J=2.0, 0.6 Hz) plus two protons not observed.

d. 1-((1S,4R)-4-((3-(1-Methoxy-2-methylpropan-2-yl)-[1,2,4]triazolo[4,3-a]pyridin-6-yl)oxy)-1,2,3,4-tetrahydronaphthalen-1-yl)urea (Intermediate 7d)

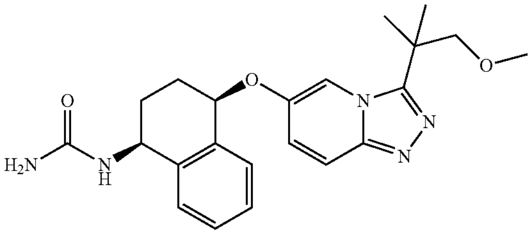 [SMILES: COCC(C)(C)c1nnc2ccc(O[C@@H]3CC[C@H](NC(N)=O)c4ccccc43)cn12]

A solution of Intermediate 7c (5.00 g, 13.7 mmol) in DCM (50 ml) was treated with (trimethylsilyl)isocyanate (3.14 g, 27.4 mmol) at 0° C. The reaction mixture was warmed at RT and stirred overnight. A further aliquot of (trimethylsilyl)isocyanate (0.39 g, 3.4 mmol) was added and the reaction mixture was stirred at RT for 5 h. The reaction mixture was treated with methanol and the solvents were removed under reduced pressure. The residue was applied to a plug of silica, eluting with 0-5% 2N $NH_3$ in MeOH/DCM to afford the title compound (5.7 g, >100%, contains DCM).

$^1$H NMR (300 MHz, $CDCl_3$): 1.55 (6H, s), 2.03-2.18 (3H, m), 2.27-2.35 (1H, m), 3.29 (3H, s), 3.55 (2H, s), 4.97-5.18 (4H, m), 6.20 (1H, d, J=8.8 Hz), 6.97 (1H, dd, J=9.8, 2.1 Hz), 7.23-7.36 (3H, m), 7.45-7.51 (2H, m), 8.30 (1H, d, J=1.6 Hz)

e. Ethyl 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxylate (Intermediate 7e)

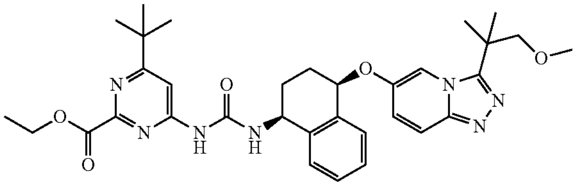 [SMILES: CCOC(=O)c1nc(NC(=O)N[C@H]2CC[C@@H](Oc3ccc4nnc(C(C)(C)COC)n4c3)c3ccccc32)cc(C(C)(C)C)n1]

A solution of Intermediate 7d (5.59 g, 13.7 mmol) in dioxane (150 ml) was treated with Intermediate id (3.31 g, 13.7 mmol), $Pd(OAc)_2$ (0.15 g, 0.7 mmol), XantPhos (0.79 g, 1.4 mmol) and $Cs_2CO_3$ (6.2 g, 19.1 mmol). The reaction mixture was evacuated and purged with nitrogen (×3) and then heated at 95° C. overnight. The reaction mixture was cooled to RT and filtered through a pad of Celite® and the solvent was removed under reduced pressure. The residue was applied to a plug of silica, eluting with EtOAc followed by 10% IMS/EtOAc to afford the title compound (5.60 g, 67%).

$^1$H NMR (300 MHz, $CDCl_3$): 1.10 (3H, t, J=7.1 Hz), 1.35 (9H, s), 1.61 (6H, s), 2.11-2.43 (4H, m), 3.32 (3H, s), 3.59 (2H, s), 4.15-4.33 (2H, m), 5.21-5.26 (2H, m), 7.05 (1H, dd, J=9.9, 2.1 Hz), 7.16 (1H, br s), 7.28-7.42 (3H, m), 7.54-7.58 (1H, m), 7.83 (1H, d, J=9.9 Hz), 8.36 (1H, d, J=1.6 Hz), 9.58 (1H, br s), 9.78 (1H, br s).

f. Example 7

A solution of Intermediate 7e (5.6 g, 9.1 mmol) in methanol (50 ml) was treated with (2-amino-1,1-dimethyl-ethyl)dimethylamine (CAS: 76936-44-2, 2.11 g, 18.2 mmol). The reaction mixture was heated at 55° C. for overnight. The reaction mixture was cooled to RT and the solvent was removed under reduced pressure. The residue was purified by FCC, eluting with 0-10% 2N $NH_3$ in MeOH/DCM. The resulting foam was crystallized from acetonitrile to give the title compound (3.7 g, 59%).

LCMS (Method 3): Rt 3.37 min, m/z 686 [$MH^+$]. $^1$H NMR (400 MHz, d-$_6$-DMSO): 0.98 (6H, s), 1.30 (9H, s), 1.52 (6H, s), 1.91-2.25 (10H, m), 3.23 (5H, s), 3.66 (2H, s), 4.97-5.02 (1H, m), 5.54 (1H, t, J=4.0 Hz), 7.29-7.45 (5H, m), 7.73 (1H, dd, J=9.8, 0.4 Hz), 7.78 (1H, br s), 8.16 (1H, br s), 8.28 (1H, d, J=1.3 Hz), 8.51 (1H, t, J=5.2 Hz), 9.89 (1H, s).

Example 8. 4-(tert-Butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide

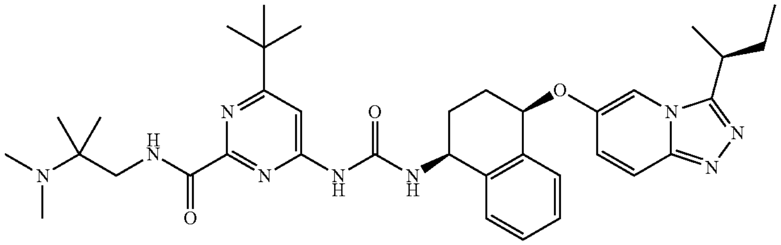 [SMILES: CC[C@H](C)c1nnc2ccc(O[C@@H]3CC[C@H](NC(=O)Nc4cc(C(C)(C)C)nc(C(=O)NCC(C)(C)N(C)C)n4)c4ccccc43)cn12]

a. (S)—N'-(5-Fluoropyridin-2-yl)-2-methylbutane-hydrazide (Intermediate 8a)

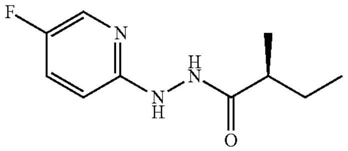

A solution of (5-fluoro-pyridin-2-yl)-hydrazine (WO 2014/195402, which is incorporated herein by reference in its entirety, 6.22 g, 49.0 mmol), HOBt (665 mg, 4.9 mmol) and (S)-(+)-2-methylbutyric acid (5.00 g, 49.0 mmol) in DCM (50 ml) was treated with EDC (11.7 g, 61.25 mmol). The reaction mixture was stirred at RT overnight, partitioned between DCM and $H_2O$ and the two phases were separated. The aqueous phase was extracted with DCM (×3) and the combined organic phases were washed with brine, dried with $Na_2SO_4$ and the solvent was removed under reduced pressure. Titration with $Et_2O$ afforded a first crop of the title compound (5.38 g). The solvent of the filtrate was removed under reduced pressure. Purification by FCC, eluting with 0-8% MeOH/DCM afforded a second crop of the title compound (2.91 g). The two batches were unified to give the title compound (8.29 g, 80%).

$^1$H NMR (300 MHz, $CDCl_3$): 0.96 (3H, t, J=7.4 Hz), 1.21 (3H, d, J=6.9 Hz), 1.43-1.78 (2H, m), 2.24 (1H, q, J=7.3 Hz), 6.66 (1H, dd, J=9.0, 3.5 Hz), 6.71 (1H, d, J=3.6 Hz), 7.26-7.32 (1H, m), 7.58 (1H, br s), 8.03 (1H, d, J=2.9 Hz).

b. (S)-3-(sec-Butyl)-6-fluoro-[1,2,4]triazolo[4,3-a]pyridine (Intermediate 8b)

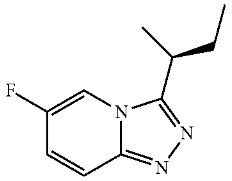

Hexachloroethane (18.6 g, 78.4 mmol) was portionwise added to a stirred solution of Intermediate 8a (8.29 g, 39.2 mmol), triphenylphosphine (20.56 g, 78.4 mmol) and TEA (22 ml, 156.8 mmol) in 2-methyltetrahydrofuran (200 ml). The reaction mixture was stirred at RT for 3 hours. The solvent was removed under reduced pressure and the residue was loaded to an SCX-2 cartridge (70 g). The cartridge was washed with MeCN/MeOH (v/v 1:1) and then the product was eluted with 2N $NH_3$ in MeOH. The solvent of the first wash was removed under reduced pressure and the residue was loaded to another SCX-2 cartridge (70 g). The cartridge was washed with MeCN/MeOH (v/v 1:1) and then the product was eluted with 2N $NH_3$ in MeOH. The two basic elutions were unified together and the solvent was removed under reduced pressure to afford the title compound (7.17 g, 95%).

$^1$H NMR (300 MHz, $CDCl_3$): 0.97 (3H, t, J=7.4 Hz), 1.51 (3H, d, J=7.0 Hz), 1.77-2.12 (2H, m), 3.13 (1H, sextet, J=7.0 Hz), 7.17 (1H, ddd, J=10.0, 7.5, 2.2 Hz), 7.76 (1H, ddd, J=10.0, 5.0, 0.9 Hz), 7.83-7.86 (1H, m).

c. (1S,4R)-4-((3-((S)-sec-Butyl)-[1,2,4]triazolo[4,3-a]pyridin-6-yl)oxy)-1,2,3,4-tetrahydronaphthalen-1-amine (Intermediate 8c)

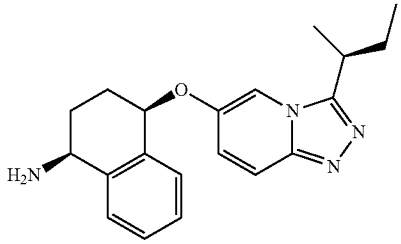 [SMILES: CC[C@H](C)c1nnc2ccc(O[C@@H]3CC[C@H](N)c4ccccc43)cn12]

A stirred solution of Intermediate 8b (6.00 g, 31.05 mmol), (1R,4S)-4-amino-1,2,3,4-tetrahydro-naphthalen-1-ol (WO 2014/195402, which is incorporated herein by reference in its entirety, 5.07 g, 31.05 mmol) and 18-crown-6 (4.10 g, 15.5 mmol) in 2-methyltetrahydrofuran was evacuated and purged with argon (×3). Potassium tert-butoxide (4.53 g, 40.36 mmol) was added and the reaction mixture was evacuated and purged with argon (×3). The reaction mixture was stirred at RT overnight. The reaction mixture was partitioned between 2-methyltetrahydrofuran and $H_2O$ and the two phases were separated. The aqueous phase was extracted with DCM (×3) and the organic phases were washed with brine. The combined organic phases were dried with $Na_2SO_4$ and the solvent was removed under reduced pressure. Purification by FCC, eluting with 0-10% 2N $NH_3$ in MeOH/DCM afforded the title compound (7.13 g, 68%, ratio cis/trans 96:4).

$^1$H NMR (400 MHz, $CDCl_3$): 0.97 (3H, t, J=7.4 Hz), 1.45 (3H, d, J=7.0 Hz), 1.78-2.12 (5H, m), 2.34-2.42 (1H, m), 3.09 (1H, sextet, J=7.0 Hz), 3.99-4.02 (1H, m), 5.24 (1H, t, J=4.6 Hz), 7.12 (1H, dd, J=9.9, 2.1 Hz), 7.25-7.33 (2H, m), 7.37-7.41 (1H, m), 7.48 (1H, d, J=1.5 Hz), 7.60 (1H, d, J=7.8 Hz), 7.70 (1H, dd, J=9.8, 0.5 Hz), plus two protons not observed.

d. 1-((1S,4R)-4-((3-((S)-sec-Butyl)-[1,2,4]triazolo[4,3-a]pyridin-6-yl)oxy)-1,2,3,4-tetrahydronaphthalen-1-yl)urea (Intermediate 8d)

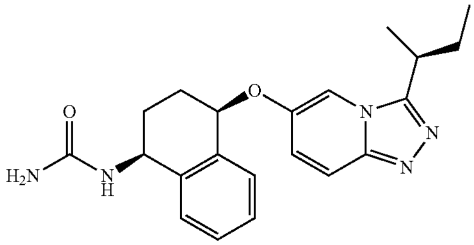 [SMILES: CC[C@H](C)c1nnc2ccc(O[C@@H]3CC[C@H](NC(N)=O)c4ccccc43)cn12]

A solution of Intermediate 8c (7.13 g, 21.2 mmol) in DCM (120 ml) was treated with (trimethylsilyl)isocyanate (4.88 g, 42.38 mmol) at 0° C. The reaction mixture was warmed at RT and stirred for 15 minutes. Methanol (15 ml) was added and the reaction mixture was stirred for 1 hour. The solvents were removed under reduced pressure and the residue was partitioned between DCM and $H_2O$. The two phases were separated and the aqueous phase was extracted with DCM (×3). The organic phases were combined and the solvent was removed under reduced pressure. Purification by FCC, eluting with 0-10% MeOH/DCM afforded the title compound (5.48 g, 68%).

$^1$H NMR (400 MHz, $CDCl_3$): 0.81 (3H, t, J=7.4 Hz), 0.84 (3H, t, J=7.4 Hz), 1.75-2.15 (5H, m), 2.25-2.33 (1H, m), 2.87-2.94 (1H, m), 5.01-5.22 (4H, m), 6.48 (1H, d, J=8.7 Hz), 6.98-7.02 (1H, m), 7.21-7.33 (3H, m), 7.48-7.53 (3H, m).

e. Ethyl 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)pyrimidine-2-carboxylate (Intermediate 8e)

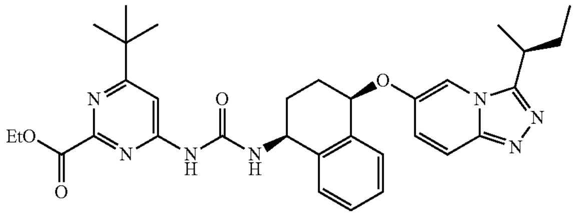 [SMILES: CCOC(=O)c1nc(NC(=O)N[C@H]2CC[C@@H](Oc3ccc4nnc([C@@H](C)CC)n4c3)c3ccccc32)cc(C(C)(C)C)n1]

A solution of Intermediate 8d (5.48 g, 14.43 mmol), Intermediate 1d (3.50 g, 14.43 mmol), XantPhos (833 mg, 1.44 mmol) in dioxane (100 ml) was treated with $Cs_2CO_3$ (6.58 g, 20.20 mmol) and $Pd(OAc)_2$ (161 mg, 0.72 mmol). The reaction mixture was evacuated and purged with argon (×3) and then heated at 90° C. for 70 hours. The reaction mixture was cooled at RT, diluted with EtOAc and filtered through a pad of Celite®. The solvents were removed under reduced pressure. Purification by FCC, eluting with 0-10% 2N $NH_3$ in MeOH/DCM afforded the title compound (3.61 g, 43%).

$^1$H NMR (400 MHz, $CDCl_3$): 0.96 (3H, t, J=7.4 Hz), 1.13 (3H, t, J=7.1 Hz), 1.36 (9H, s), 1.44 (3H, d, J=7.0 Hz), 1.77-1.87 (1H, m), 1.99-2.27 (4H, m), 2.36-2.42 (1H, m), 3.11 (1H, sextet, J=6.9 Hz), 4.15-4.32 (2H, m), 5.23-5.29 (2H, m), 7.12 (1H, dd, J=9.9, 2.0 Hz), 7.24 (1H, br s), 7.28-7.38 (3H, m), 7.52 (1H, d, J=1.4 Hz), 7.58 (1H, d, J=7.4 Hz), 7.83 (1H, d, J=9.8 Hz), 9.84 (1H, br s), 9.94 (1H, s).

f. Example 8

A solution of Intermediate 8e (4.38 g, 7.48 mmol) in methanol (50 ml) was treated with (2-amino-1,1-dimethylethyl)dimethylamine (CAS: 76936-44-2, 2.95 g, 25.38 mmol). The reaction mixture was heated at 60° C. for 18 hours. The reaction mixture was cooled at RT and the solvent was removed under reduced pressure. The residue was partitioned between DCM and $H_2O$ and the two phases were separated. The aqueous phase was extracted with DCM (×3) and the solvent was removed under reduced pressure. The crude was crystallized from acetonitrile, followed by a further purification by FCC, eluting with 0-10% 2N $NH_3$ in MeOH/DCM. The resulting foam was crystallised from acetonitrile to give the title compound (3.75 g, 76%).

LCMS (Method 3): Rt 3.39 min, m/z 656 [$MH^+$]. $^1$H NMR (400 MHz, $d_6$-DMSO): 0.87 (3H, t, J=7.4 Hz), 0.98 (6H, s), 1.31 (9H, s), 1.34 (3H, d, J=6.9 Hz), 1.75 (1H, quintet, J=7.1 Hz), 1.87-2.26 (11H, m), 3.23 (2H, d, J=5.3 Hz), 3.44 (1H, q, J=6.9 Hz), 4.98-5.03 (1H, m), 5.57 (1H, t, J=4.0 Hz), 7.25-7.44 (5H, m), 7.70 (1H, dd, J=9.8, 0.6 Hz), 7.78 (1H, br s), 8.20 (1H, br s), 8.24 (1H, d, J=1.3 Hz), 8.52 (1H, d, J=5.1 Hz), 8.89 (1H, s).

Example 9. 6-(tert-Butyl)-4-(3-((1S,4R)-4-((3-(tert-butyl)-[1,2,4]triazolo[4,3-a]pyridin-6-yl)oxy]-1,2,3,4-tetrahydronaphthalen-1-yl}ureido)-N-(2-(4-hydroxypiperidin-1-yl)ethyl)picolinamide

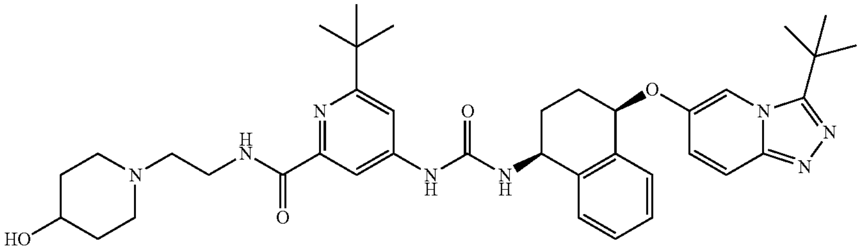 [SMILES: CC(C)(C)c1cc(NC(=O)N[C@H]2CC[C@@H](Oc3ccc4nnc(C(C)(C)C)n4c3)c3ccccc32)cc(C(=O)NCCN2CCC(O)CC2)n1]

a. 2-(tert-Butyl)-4-chloropyridine (Intermediate 9a)

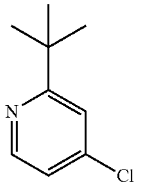

A suspension of copper cyanide (9.99 g, 111.0 mmol) in THF (500 mL) at or below −60° C. was dropwise added with tert-butyl magnesium chloride (1N in THF, 213 mL, 213 mmol) then left at −70° C. for 20 minutes before 2-bromo-4-chloropyridine (18.65 g, 97.3 mmol) was dropwise added at or slightly below −60° C. This solution was stirred at −70° C. for 20 minutes before the cold bath was removed and the reaction mixture was left to warm to RT over 2 hours. The mixture was diluted with saturated sodium bicarbonate solution and an equal volume of $Et_2O$ was added. The resulting emulsion was filtered through Celite®, separated and the aqueous layer was partitioned with $Et_2O$. The combined organic layers were dried over $MgSO_4$ and the solvent was removed under reduced pressure. Purification by FCC eluting with 0-20% EtOAc in cyclohexane afforded the title compound (15.86 g, 48%).

$^1H$ NMR (300 MHz, $CDCl_3$): 1.36 (9H, s), 7.11 (1H, dd, J=1.9, 5.3 Hz), 7.34 (1H, d, J=1.9 Hz), 8.46 (1H, d, J=5.3 Hz).

b. 2-(tert-Butyl)-4-chloropyrimidine 1-oxide (Intermediate 9b)

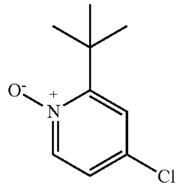

A stirred solution of Intermediate 9a (24.0 g, 142 mmol) in DCM (500 mL) was added with meta-chloroperbenzoic acid (73.7 g, 426 mmol) and left at RT for 24 hours. The reaction mixture was partitioned between saturated sodium bicarbonate solution and DCM. The two phases were separated and the aqueous phase was extracted with DCM (×2). The combined organic layers were dried over solid $MgSO_4$ and the solvent was removed under reduced pressure. Purification by FCC eluting 0-100% EtOAc/cyclohexane afforded the title compound (22.85 g, 86%).

LCMS (Method 4): Rt=1.16 min, m/z 186 [$M+H^+$].

c. 6-(tert-Butyl)-4-chloropicolinonitrile (Intermediate 9c)

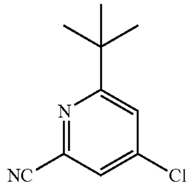

A solution of Intermediate 9b (22.80 g, 122.5 mmol) in DCM (40 mL) was treated with trimethylsilyl cyanide (19.98 g, 202 mmol) followed by a solution of dimethyl carbamic chloride (26.6 g, 248.6 mmol) in DCM (10 mL) exotherming to a vigorous boil. The reaction was allowed to cool to RT and was partitioned between saturated sodium bicarbonate and DCM. The organic layer was washed with 10% citric acid solution. The acidic layer was basified with 10% potassium carbonate solution and partitioned into DCM. This DCM layer was dried over solid $Na_2SO_4$ and the solvent was removed under reduced pressure. Purification by FCC 0-25% EtOAc/cyclohexane afforded the title compound (8.00 g, 33%).

$^1H$ NMR (300 MHz, $CDCl_3$): 1.36 (9H, s), 7.51 (1H, d, J=1.7 Hz), 7.54 (1H, d, J=1.7 Hz).

d. Ethyl 6-(tert-butyl)-4-chloropicolinate (Intermediate 9d)

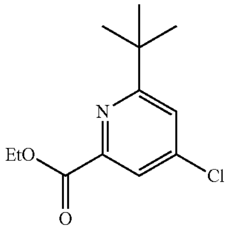 [SMILES: CCOC(=O)c1cc(Cl)cc(C(C)(C)C)n1]

A stirred solution of Intermediate 9c (8.0 g, 41.2 mmol) in sulphuric acid (80%, 28.5 g, 247.0 mmol) was heated at 130° C. for 0.5 hours then allowed to cool to RT. Ethanol (360 mL) was cautiously added and the reaction mixture was heated at reflux for 5.5 hours. The solvent was removed under reduced pressure and the residue was partitioned between saturated brine and EtOAc. The two phases were separated and the aqueous phase was extracted with EtOAc (×2). The combined organic layers were washed with saturated sodium bicarbonate solution, dried over solid $MgSO_4$ and the solvent was removed under reduced pressure to afford the title compound (8.0 g, 80%).

$^1H$ NMR (300 MHz, $CDCl_3$): 1.39 (9H, s), 1.42 (3H, t, J=7.1 Hz), 4.44 (2H, q, J=7.1 Hz), 7.49 (1H, d, J=1.8 Hz), 7.88 (1H, d, J=1.7 Hz).

e. Ethyl 6-(tert-butyl)-4-(3-((1S,4R)-4-((3-(tert-butyl)-[1,2,4]triazolo[4,3-a]pyradin-6-yl)oxy)-1,2,3,4-tetrahydronaphthalen-1-yl)ureido)picolinate (Intermediate 9e)

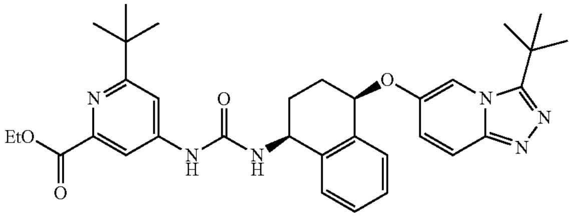 [SMILES: CCOC(=O)c1cc(NC(=O)N[C@H]2CC[C@@H](Oc3ccc4nnc(C(C)(C)C)n4c3)c3ccccc32)cc(C(C)(C)C)n1]

A solution of Intermediate 1h (2.71 g, 6.62 mmol), Intermediate 9d (1.59 g, 6.62 mmol), $Pd(OAc)_2$ (150 mg, 0.66 mmol), Xantphos (770 mg. 1.32 mmol) and $Cs_2CO_3$ (3.24 g, 9.93 mmol) in dioxan (40 mL) was degassed by bubbling argon through the mixture under sonication for 10 minutes. The reaction mixture was stirred at 100° C. for 6 hours then filtered through Celite® washing well with DCM and EtOH. The solvent was removed under reduced pressure and the crude mixture was purified by FCC eluting with 0-10% EtOH/DCM to afford the title compound (2.90 g, 75%).

LCMS (Method 4): Rt=1.50 min, m/z 585 [$M+H^+$], m/z 607 [$M+Na^+$].

e. Example 9

Intermediate 9e (2.90 g, 4.96 mmol) and 1-(2-aminoethyl)-4-piperidinol (2.24 g, 15.55 mmol) in ethanol (10 mL) were warmed to 70° C. for 24 hours then allowed to cool to RT. The solvent was removed under reduced pressure and the mixture was partitioned between water and DCM (×3). The combined organic layers were dried over solid $MgSO_4$ and the solvent was removed under reduced pressure. Purification by FCC eluting 0-10% (2M $NH_3$ in MeOH) DCM produced the title compound (1.90 g, 90% pure). This product was suspended in boiling MeCN (30 mL) and MeOH (25 mL) was added at boiling to obtain a complete solution. This mixture was left at RT for 2 days and the title compound was collected (1.33 g, 39%).

LCMS (Method 3): Rt 3.34 min, m/z 683 [M+H$^+$], sample assessed as ca. 99.2%. $^1$H NMR (400 MHz, $d_6$DMSO): 1.34 (9H, s), 1.36-1.48 (2H, m), 1.52 (9H, s), 1.66-1.78 (2H, m), 1.90-2.24 (6H, m), 2.48 (2H, t, J=6.3 Hz, partially obscured by the solvent peak), 2.70-2.81 (2H, m), 3.38 (2H, q, J=6.1 Hz), 3.42-3.52 (1H, m), 4.57 (1H, d, J=3.8 Hz), 4.93 (1H, q, J=8.2 Hz), 5.63 (1H, t, J=3.4 Hz), 6.91 (1H, d, J=8.6 Hz), 7.28 (1H, dd, J=2.0, 9.9 Hz), 7.31 (1H, dd, J=1.5, 7.2 Hz), 7.34-7.45 (3H, m), 7.68 (1H, d, J=1.9 Hz), 7.76 (1H, d, J=9.8 Hz), 7.90 (1H, d, J=1.9 Hz), 8.14 (1H, s), 8.69 (1H, t, J=5.3 Hz), 9.09 (1H, s).

Example 10. 6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)picolinamide

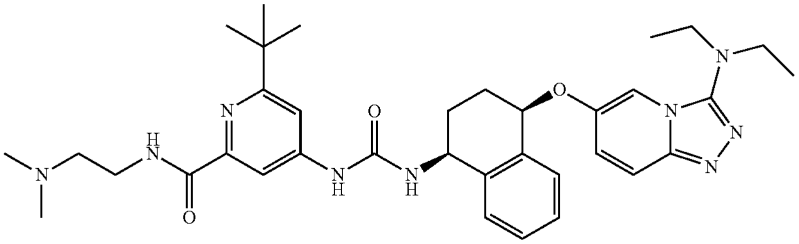 [SMILES: CCN(CC)c1nnc2ccc(O[C@@H]3CC[C@H](NC(=O)Nc4cc(C(=O)NCCN(C)C)nc(C(C)(C)C)c4)c4ccccc43)cn12]

a. N,N-Diethyl-2-(5-fluoropyridin-2-yl)hydrazine-1-carboxamide (Intermediate 10a)

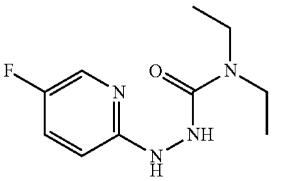 [SMILES: CCN(CC)C(=O)NNc1ccc(F)cn1]

A solution of (5-fluoro-pyridin-2-yl)hydrazine (12.7 g, 100 mmol) and DIPEA (19.4 g, 150 mmol) in DCM (150 ml) was treated with diethylcarbamoyl chloride (13.5 g, 100 mmol) and the mixture was stirred at RT for 18 h. The RM was evaporated and the residue partitioned between EtOAc and 5% citric acid solution. The organic layer was washed with water, brine, dried ($Na_2SO_4$) and evaporated. The residue was triturated with $Et_2O$ to give the title compound (14.6 g, 65%).

$^1$H NMR (300 MHz, $CDCl_3$): 1.20 (6H, t, J=7.1 Hz), 3.33 (4H, q, J=7.1 Hz), 6.39 (1H, br s), 6.51 (1H, br s), 6.74 (1H, dd, J=9.0, 3.6 Hz), 7.22-7.33 (1H, m), 8.02 (1H, d, J=2.9 Hz).

b. N,N-Diethyl-6-fluoro-[1,2,4]triazolo[4,3-a]pyridin-3-amine (Intermediate 10b)

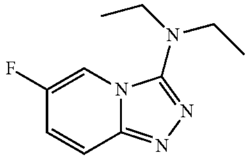

A solution of Intermediate 10a (14.6 g, 64.6 mmol) in 2-methyl THF (250 ml) was treated with TEA (26.1 g, 258.4 mmol), $PPh_3$ (33.8 g, 129.2 mmol) and finally with hexachloroethane (30.6 g, 129.2 mmol). The reaction mixture was stirred and the internal temperature kept ca. 30° C. by external cooling. After 2 h the RM was washed with water and then extracted with 1M HCl solution. The HCl layer was washed with $Et_2O$ and basified with solid $K_2CO_3$ extracting into DCM (×3). The combined DCM layers were dried ($Na_2SO_4$) and evaporated under reduced pressure. The residue was purified by FCC eluting with 0-5% MeOH/EtOAc to give the title compound (5.68 g, 42%).

$^1$H NMR (300 MHz, $CDCl_3$): 1.12 (6H, t, J=7.1 Hz), 3.29 (4H, q, J=7.1 Hz), 7.11 (1H, ddd, J=9.9, 7.6, 2.3 Hz), 7.64 (1H, ddd, J=9.9, 4.8, 0.9 Hz), 7.76 (1H, ddd, J=3.2, 2.3, 0.9 Hz).

c. 6-(((1R,4S)-4-Amino-1,2,3,4-tetrahydronaphthalen-1-yl)oxy)-N,N-diethyl-[1,2,4]triazolo[4,3-a]pyridin-3-amine (Intermediate 10c)

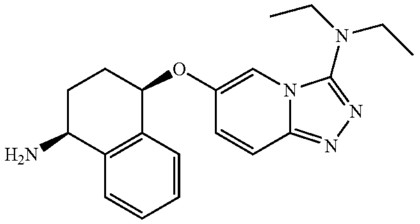 [SMILES: CCN(CC)c1nnc2ccc(O[C@@H]3CC[C@H](N)c4ccccc43)cn12]

A solution of Intermediate 10b (5.6 g, 26.9 mmol) in 2-methyl THF (100 ml) was treated with (1R, 4S)-4-amino-1,2,3,4-tetrahydronaphthalen-1-ol (WO 2014/195402, which is incorporated herein by reference in its entirety, 4.39 g, 26.9 mmol) and 18-crown-6 (710 mg, 2.7 mmol). The mixture was cooled to 0° C. and treated with KOtBu (3.50 g, 31.0 mmol). The flask was evacuated and purged with nitrogen and the RM was stirred at RT under nitrogen for ca. 18 h. The reaction was quenched with water and the aqueous phase extracted with 2-methyl THF (×3). The combined organic layers were extracted with 10% citric acid solution and the citric acid layer basified with solid $K_2CO_3$ extracting into DCM. The DCM layer was dried with $Na_2SO_4$ and the solvent was removed under reduced pressure. The residue was purified by silica gel FCC eluting with 0-10% 2M $NH_3$ in MeOH/DCM to afford the title compound (5.18 g, 55%). $^1$H NMR (300 MHz, $CDCl_3$): 1.56 (6H, t, J=7.1 Hz), 1.64 (2H, br s), 1.84-2.14 (3H, m), 2.28-2.42 (1H, m), 3.27 (4H, q, J=7.1 Hz), 3.98 (1H, dd, J=8.4, 5.1 Hz), 5.22 (1H, t, J=4.5 Hz), 7.05 (1H, dd, J=9.9, 2.1 Hz), 7.22-7.47 (4H, m), 7.55-7.64 (2H, m).

d. 1-((1S,4R)-4-((3-(Diethylamino)-[1,2,4]triazolo[4,3-a]pyridin-6-yl)oxy)-1,2,3,4-tetrahydronaphthalen-1-yl)urea (Intermediate 10d)

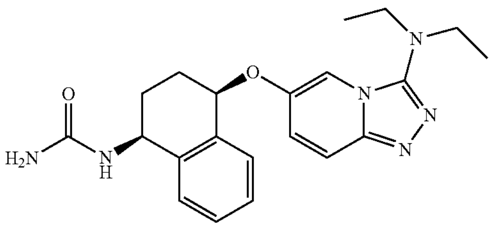 [SMILES: CCN(CC)c1nnc2ccc(O[C@@H]3CC[C@H](NC(N)=O)c4ccccc43)cn12]

A solution of Intermediate 10c (5.18 g, 14.8 mmol) and trimethylsilylisocyanate (3.39 g, 29.5 mmol) in DCM (50 ml) was stirred at RT for 15 mins and then treated with MeOH (0.5 ml) and stirring continued for 15 mins. The solution was evaporated and the residue partitioned between water and EtOAc. The organic layer was dried ($Na_2SO_4$) and evaporated. The residue was purified by FCC eluting with 0-10% 2M $NH_3$ in MeOH/DCM to afford the title compound (5.26 g, 91%).

$^1$H NMR (300 MHz, $CDCl_3$): 1.06 (6H, t, J=7.1 Hz), 1.93-2.18 (3H, m), 2.23-2.37 (1H, m), 3.21 (4H, q, J=7.1 Hz), 4.98-5.11 (3H, m), 5.15-5.25 (1H, m), 6.27 (1H, br d, J=9.0 Hz), 6.93 (1H, dd, J=9.8, 2.1 Hz), 7.20-7.54 (6H, m).

e. Ethyl 6-(tert-butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)picolinate (Intermediate 10e)

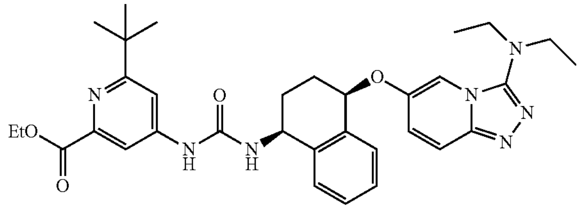 [SMILES: CCOC(=O)c1cc(NC(=O)N[C@H]2CC[C@@H](Oc3ccc4nnc(N(CC)CC)n4c3)c3ccccc32)cc(C(C)(C)C)n1]

A solution of Intermediate 10d (2.6 g, 6.6 mmol) in dioxane (50 ml) was treated with Intermediate 9d (1.75 g, 7.3 mmol), $Pd(OAc)_2$ (74 mg, 0.33 mmol), XantPhos (380 mg, 0.66 mmol) and $Cs_2CO_3$ (3.0 g, 9.2 mmol). The mixture was purged with nitrogen and then heated at 95° C. for 18 hours. The RM was cooled at RT and filtered through a pad of Celite® and the filtrate evaporated. Purification by silica gel plug filtration, eluting with EtOAc followed by 10% IMS/EtOAc followed by FCC eluting with 0-5% 2M NH3 in MeOH/DCM afforded the title compound (1.23 g, 31%).

$^1$H NMR (300 MHz, $CDCl_3$): 1.06 (6H, t, J=7.1 Hz), 1.35-1.45 (12H, m), 2.06-2.42 (4H, m), 3.25 (4H, q, J=7.1 Hz), 4.38 (2H, q, J=7.1 Hz), 5.18-5.31 (2H, br m), 6.93 (1H, dd, J=9.9, 2.1 Hz), 7.19-7.38 (4H, m), 7.45 (1H, d, J=1.4 Hz), 7.56 (1H, br d, J=7.5 Hz), 7.96 (1H, d, J=1.9 Hz), 8.08-8.19 (2H, m), 9.32 (1H, br s).

f. Example 10

A solution of Intermediate 10e (1.23 g, 2.05 mmol) and N,N-dimethylethylenediamine (900 mg, 23.9 mmol) in MeOH (25 ml) was heated to 55° C. and stirred for 18 h. The RM was evaporated and the residue partitioned between water and EtOAc and the organic layer extracted into 10% citric acid solution. The citric acid layer was washed with $Et_2O$ and basified with solid $K_2CO_3$ extracting into DCM. The DCM layer was dried ($Na_2SO_4$) and evaporated and the residue dissolved in warm MeCN (10 ml) and the solution cooled to RT. The mixture was filtered and the solid washed with MeCN and dried to afford the title compound (1.19 g, 90%).

LCMS (Method 3): Rt 3.34 min, m/z 642 [$MH^+$]. $^1$H NMR (400 MHz, $d_6$-DMSO): 1.02 (6H, t, J=7.1 Hz), 1.33 (9H, s), 1.89-2.20 (4H, m), 2.21 (6H, s), 2.43 (2H, t, J=6.6 Hz), 3.24 (4H, q, J=7.1 Hz), 3.39 (2H, q, J=6.5 Hz), 4.88-4.98 (1H, m), 5.55 (1H, t, J=3.9 Hz), 6.93 (1H, d, J=8.6 Hz), 7.19 (1H, dd, J=9.8, 2.1 Hz), 7.27-7.44 (4H, m), 7.64 (1H, dd, J=9.8, 0.5 Hz), 7.68 (1H, d, J=1.9 Hz), 7.72 (1H, d, J=1.5 Hz), 7.90 (1H, d, J=1.9 Hz), 8.58 (1H, t, J=5.8 Hz), 9.06 (1H, br s).

Example 11. 4-(tert-Butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide

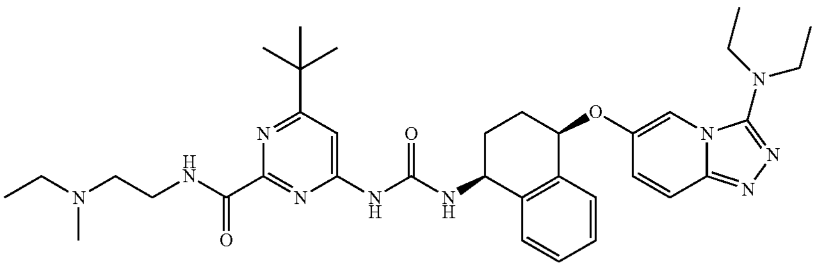 [SMILES: CCN(C)CCNC(=O)c1nc(NC(=O)N[C@H]2CC[C@@H](Oc3ccc4nnc(N(CC)CC)n4c3)c3ccccc32)cc(C(C)(C)C)n1]

a. Ethyl 4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)pyrimidine-2-carboxylate (Intermediate 11a)

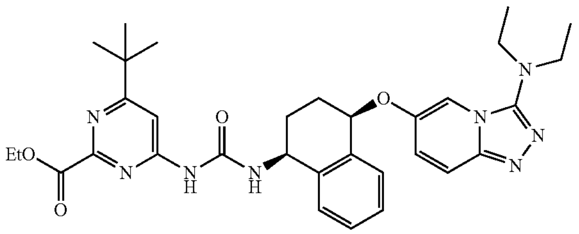 [SMILES: CCOC(=O)c1nc(NC(=O)N[C@H]2CC[C@@H](Oc3ccc4nnc(N(CC)CC)n4c3)c3ccccc32)cc(C(C)(C)C)n1]

A solution of Intermediate 10d (2.50 g, 6.33 mmol), Intermediate id (1.54 g, 6.33 mmol), XantPhos (366 mg, 0.63 mmol) in dioxane (25 ml) was treated with $Cs_2CO_3$ (2.90 g, 8.86 mmol) and $Pd(OAc)_2$ (72 mg, 0.32 mmol). The reaction mixture was evacuated and purged with nitrogen (×3) and then heated at 90° C. overnight. The reaction mixture was cooled at RT, diluted with IMS and filtered through a pad of Celite®. The solvents were removed under reduced pressure. The crude was loaded on a silica pad, which was subsequently eluted with DCM, EtOAc and IMS to afford the title compound (8.83 g, 57%).

$^1$H NMR (300 MHz, $CDCl_3$): 1.06-1.13 (9H, m), 1.36 (9H, s), 2.13-2.43 (4H, m), 3.28 (4H, q, J=9.5 Hz), 4.11-4.30 (2H, m), 5.21-5.28 (2H, m), 6.97 (1H, br s), 7.03 (1H, dd, J=13.0, 2.9 Hz), 7.30-7.40 (3H, m), 7.47-7.57 (2H, m), 7.64 (1H, dd, J=13.0, 1.0 Hz), 8.56 (1H, br s), 9.79 (1H, br s).

b. Example 11

A solution of Intermediate 11a (120 mg, 0.20 mmol) in methanol (2.5 ml) was treated with (2-aminoethyl)(ethyl)methylamine (CAS: 70111-47-6, 82 mg, 0.80 mmol). The reaction mixture was heated at 55° C. for 6 hours. The reaction mixture was cooled at RT and the solvent was removed under reduced pressure. Purification by MDAP (basic) afforded the title compound (74 mg, 56%).

LCMS (Method 3): Rt 3.32 min, m/z 658 [$MH^+$]. $^1$H NMR (400 MHz, d-$_6$-DMSO): 0.97-1.03 (9H, m), 1.31 (9H, s), 1.90-2.27 (7H, m), 2.39 (2H, q, J=7.1 Hz), 2.45-2.49 (2H, m, partially obscured by the solvent peak), 3.23 (4H, q, J=7.1 Hz), 3.32-3.37 (2H, m, partially obscured by the water peak), 4.97-5.03 (1H, m), 5.54 (1H, t, J=4.0 Hz), 7.23-7.43 (5H, m), 7.63 (1H, dd, J=9.8, 0.7 Hz), 7.71-7.72 (1H, m), 8.33 (1H, br s), 8.60 (1H, d, J=5.6 Hz), 8.55 (1H, t, J=5.8 Hz), 9.92 (1H, s).

Example 12. N-(2-(1,4-Oxazepan-4-yl)ethyl)-4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide

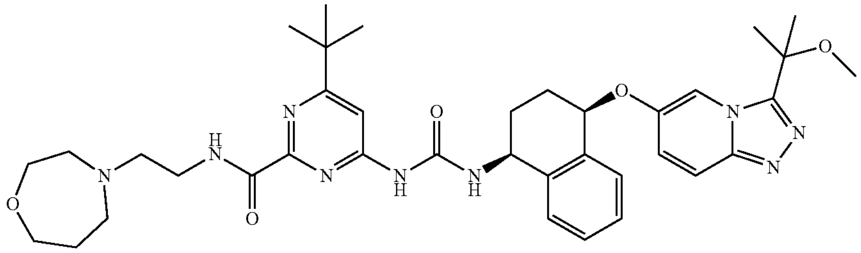 [SMILES: COC(C)(C)c1nnc2ccc(O[C@@H]3CC[C@H](NC(=O)Nc4cc(C(C)(C)C)nc(C(=O)NCCN5CCCOCC5)n4)c4ccccc43)cn12]

a. N'-(5-Fluoropyridin-2-yl)-2-methoxy-2-methylpropanehydrazine (Intermediate 12a)

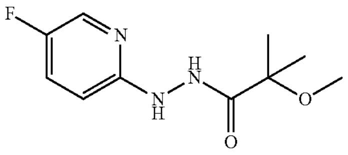 [SMILES: COC(C)(C)C(=O)NNc1ccc(F)cn1]

A solution of 2-methoxy-2-methylpropanoic acid (4.0 g, 33.4 mmol) and (5-fluoro-2-pyridyl)hydrazine (4.3 g, 33.4 mmol) in DCM (100 ml) was treated with HOBt (4.66 g, 33.9 mmol) and EDC (7.8 g, 40.7 mmol). The reaction mixture was stirred at 20° C. for 20 hours then diluted with DCM and washed with water. The organic phase was dried over solid $MgSO_4$ and the solvent was removed under reduced pressure. Purification by FCC, eluting with 0-100% EtOAc in cyclohexane afforded the title compound (7.20 g, 74%).

$^1$H NMR (300 MHz, $CDCl_3$): 1.44 (6H, s), 3.36 (3H, s), 6.22 (1H, d, J=3.5 Hz), 6.50 (1H, t, J=4.0 Hz), 7.28 (1H, dt, J=2.9, 8.0 Hz), 8.04 (1H, d, J=2.9 Hz), 8.64 (1H, s).

b. 6-Fluoro-3-(2-methoxypropan-2-yl)-[1,2,4]triazolo[4,3-a]pyridine (Intermediate 12b)

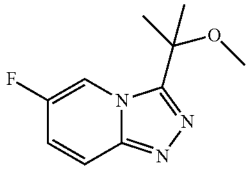

A solution of Intermediate 12a (7.20 g, 31.7 mmol) in 2-methyltetrahydrofuran (140 mL) was treated with triphenylphosphine (8.30 g, 63.4 mmol) and triethylamine (12.80 g, 126.8 mmol) and cooled to 0° C. before hexachloroethane (15.0 g, 63.40 mmol) was added. The reaction mixture was allowed to warm to 20° C. overnight and then the reaction mixture was filtered, washing the solid with diethyl ether. The filtrate was washed with water, dried over solid $MgSO_4$ and the solvent removed under reduced pressure. Purification by FCC eluting 0 to 7% MeOH in DCM gave a pale brown solid which was triturated with diethyl ether/cyclohexane (1:1, 8 mL) to afford the title compound (4.16 g, 62%).

$^1$H NMR (300 MHz, $CDCl_3$): 1.79 (6H, s), 3.10 (3H, s), 7.21 (1H, dt, J=2.3, 7.4 Hz), 7.77 (1H, dq, J=0.8, 5.0 Hz), 8.46 (1H, dq, J=0.8, 2.3 Hz). LCMS (Method 4): Rt=0.93 min, m/z 210 [M+H$^+$], m/z 232 [M+Na$^+$].

c. (1S,4R)-4-((3-(2-Methoxypropan-2-yl)-[1,2,4]triazolo[4,3-a]pyridine-6-yl)oxy)-1,2,3,4-tetrahydronaphthalen-1-amine (Intermediate 12c)

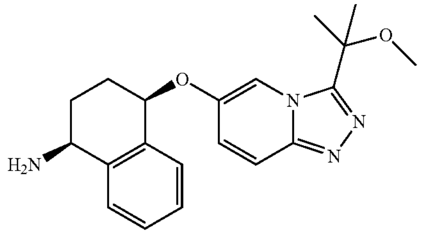 [SMILES: COC(C)(C)c1nnc2ccc(O[C@@H]3CC[C@H](N)c4ccccc43)cn12]

A solution of Intermediate 12b (4.16 g, 19.90 mmol), (1R,4S)-4-amino-1,2,3,4-tetrahydronaphthalen-1-ol (WO 2014/195402, which is incorporated herein by reference in its entirety, 3.24 g, 19.90 mmol) and 18-crown-6 ether (2.62 g, 9.95 mmol) in 2-methyltetrahydrofuran (50 mL) was degassed for 10 minutes under sonication bubbling argon through the mixture, then cooled to 0° C. and potassium tert-butoxide (2.67 g, 23.88 mmol) was added. The reaction mixture was allowed to warm to 20° C. overnight with stirring. The reaction mixture was partitioned with DCM and water and the two phases were separated. The aqueous phase was extracted with DCM, combined organic layers were dried over solid $MgSO_4$ and the solvent removed under reduced pressure. Purification by FCC eluting 0 to 10% (2N $NH_3$ in MeOH) in DCM afforded the title compound (5.52 g, 78%).

$^1$H NMR (300 MHz, $CDCl_3$): 1.65 (2H, s), 1.77 (6H, d, J=5.90 Hz), 1.87-1.99 (1H, m), 2.00-2.14 (2H, m), 2.32-2.45 (1H, m), 3.05 (3H, s), 3.99 (1H, dd, J=5.1, 8.3 Hz), 5.24 (1H, t, J=4.3 Hz), 7.14 (1H, dd, J=2.2, 9.9 Hz), 7.22-7.34 (2H, m), 7.38 (1H, dt, J=1.6, 7.4 Hz), 7.60 (1H, d, J=7.8 Hz), 7.71 (1H, dd, J=0.7, 9.9 Hz), 8.10 (1H, d, J=1.5 Hz). LCMS (Method 4): Rt=0.77 min, m/z 353 [M+H$^+$], m/z 375 [M+Na$^+$].

d. 1-((1S,4R)-4-((3-(2-Methoxypropan-2-yl)-[1,2,4]triazolo[4,3-a]pyridine-6-yl)oxy)-1,2,3,4-tetrahydronaphthalen-1-yl)urea (Intermediate 12d)

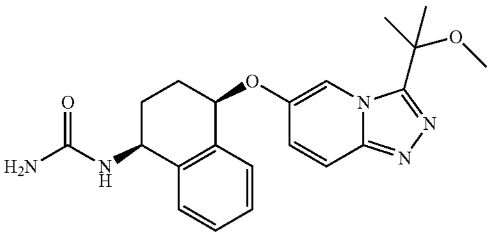 [SMILES: COC(C)(C)c1nnc2ccc(O[C@@H]3CC[C@H](NC(N)=O)c4ccccc43)cn12]

A solution of Intermediate 12c (1.59 g, 4.51 mmol) and trimethylsilyl isocyanate (1.22 mL, 9.02 mmol) in DCM (20 mL) was stirred at RT for 2 hours prior to adding few drops of MeOH. The resulting solution was stirred at RT for 18 hours. The reaction solvents were removed under reduced pressure and the residues were partitioned between water and DCM and the two phases were separated. The aqueous phase was extracted with DCM (×2) and the combined organic layers were dried over solid $MgSO_4$. The solvent was removed under reduced pressure and purification by FCC eluting 0 to 10% (2N $NH_3$ in MeOH) in DCM afforded the title compound (780 mg, 44%).

$^1$H NMR (300 MHz, $CDCl_3$): 1.54 (3H, s), 1.77 (3H, s), 2.04-2.18 (3H, m), 2.32-2.46 (1H, m), 3.00 (3H, s), 4.85 (2H, s), 5.06 (1H, q, J=5.9 Hz), 5.34 (1H, q, J=3.5 Hz), 5.85 (1H, d, J=8.4 Hz), 7.08 (1H, dd, J=2.8, 9.9 Hz), 7.19-7.34 (3H, m), 7.47 (1H, d, J=7.3 Hz), 7.60 (1H, dd, J=0.6, 9.9 Hz), 7.86 (1H, d, J=1.6 Hz). LCMS (Method 4): Rt=1.00 min, m/z 396 [M+H$^+$], m/z 418 [M+Na$^+$].

e. Ethyl 4-(tert-butyl)-6-(3-((1S,4R)-4-((3-(2-methoxypropan-2yl)-[1,2,4]triazolo[4,3-a]pyridine-6-yl)oxy)-1,2,3,4-tetrahydronaphthalen-1-yl)ureido) pyrimidine-2-carboxylate (Intermediate 12e)

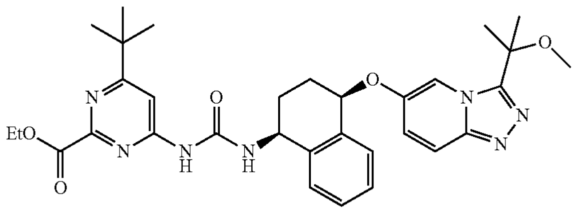 [SMILES: CCOC(=O)c1nc(NC(=O)N[C@H]2CC[C@@H](Oc3ccc4nnc(C(C)(C)OC)n4c3)c3ccccc32)cc(C(C)(C)C)n1]

A solution of Intermediate 12d (780 mg, 1.97 mmol), Intermediate 1d (480 mg, 1.97 mmol), palladium(II)acetate (22 mg, 0.1 mmol), Xantphos (116 mg, 0.2 mmol) and cesium carbonate (900 mg, 2.76 mmol) in dioxan (30 mL) was degassed by bubbling argon through the mixture for 5 minutes under sonication then warmed to 95° C. for 20 hours. The reaction mixture was filtered through a pad of Celite® washing with DCM and EtOH. The liquor was evaporated to dryness under reduced pressure and purification by FCC eluting 0 to 10% EtOH in DCM afforded the title compound (940 mg, 79%).

$^1$H NMR (300 MHz, $CDCl_3$): 1.11 (3H, t, J=7.1 Hz), 1.36 (9H, s), 1.77 (3H, s), 1.81 (3H, s), 2.13-2.30 (3H, m), 2.33-2.46 (1H, m), 3.09 (3H, s), 4.07-4.33 (2H, m), 5.17-5.31 (2H, m), 7.12 (2H, dd, J=2.2, 9.9 Hz), 7.26-7.42 (3H, m), 7.55 (1H, d, J=7.7 Hz), 7.78 (1H, d, J=9.9 Hz), 8.13 (1H, d, J=1.6 Hz), 8.97 (1H, s), 9.62 (1H, br s). LCMS (Method 4): Rt=1.47 min, m/z 602 [M+H$^+$], m/z 624 [M+Na$^+$].

f. Example 12

Intermediate 12e (940 mg, 1.56 mmol) and 2-(1,4-oxazepan-4-yl)ethan-1-amine (CAS: 878155-50-1, 790 mg, 5.46 mmol) in methanol (30 mL) were warmed to 55° C. for 18 hours then allowed to cool to RT. The solvent was removed under reduced pressure. Purification by FCC eluting 0-5% (2M $NH_3$ in MeOH)/DCM produced the title compound (726 mg, 66%).

LCMS (Method 3): Rt 3.29 min, m/z 700 [M+H$^+$]. $^1$H NMR (400 MHz, $d_6$DMSO): 1.32 (9H, s), 1.69 (6H, s), 1.76-1.82 (2H, m), 1.88-2.35 (4H, m), 2.60-2.72 (6H, m), 2.98 (3H, s), 3.33-3.41 (2H, m, partially obscured by the water peak), 3.60 (2H, t, J=4.5 Hz), 3.68 (2H, t, J=6.0 Hz), 5.00 (1H, q, J=9.0 Hz), 5.49 (1H, t, J=3.7 Hz), 7.26-7.48 (5H, m), 7.72 (1H, s), 7.81 (1H, d, J=9.9 Hz), 8.14 (1H, s), 8.29 (1H, br s), 8.66 (1H, t, J=5.6 Hz), 9.93 (1H, s).

Intermediate AA. (4-(tert-Butyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidin-2-yl)methyl methanesulfonate

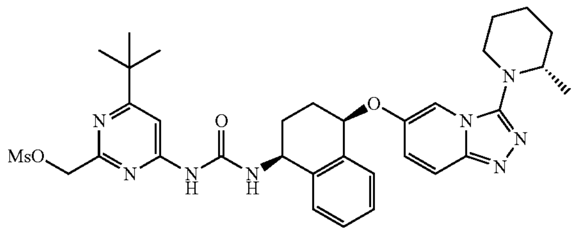 [SMILES: C[C@H]1CCCCN1c1nnc2ccc(O[C@@H]3CC[C@H](NC(=O)Nc4cc(C(C)(C)C)nc(COS(C)(=O)=O)n4)c4ccccc43)cn12]

a. 1-((1S,4R)-4-((3-((S)-2-Methylpiperidin-1-yl)-[1,2,4]triazolo[4,3-a]pyridin-6-yl)oxy)-1,2,3,4-tetrahydronaphthalen-1-yl)urea (Intermediate AAa)

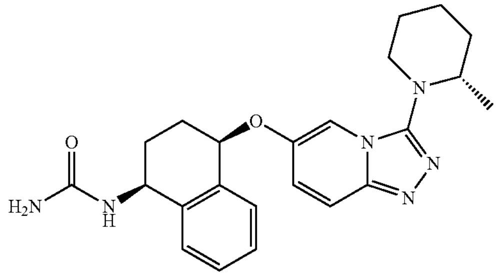 [SMILES: C[C@H]1CCCCN1c1nnc2ccc(O[C@@H]3CC[C@H](NC(N)=O)c4ccccc43)cn12]

A solution of triphosgene (4.32 g, 14.57 mmol) in DCM (80 ml) was cooled to −10° C. and treated portionwise with a solution of (1S,4R)-4-[3-((S)-2-methyl-piperidin-1-yl)-[1,2,4]triazolo[4,3-a]pyridin-6-yloxy]-1,2,3,4-tetrahydronaphthalen-1-ylamine (WO2014/194956, 5.0 g, 13.25 mmol) and trimethylamine (5.35 g, 52.98 mmol) in DCM (80 ml) maintaining the temperature between −5 and −10° C. The resulting mixture was stirred at −10° C. for 1 hour and then added to a solution of 2M $NH_3$ in MeOH (300 ml) pre-cooled to −10° C. The resulting mixture was allowed to reach RT over ca. 1.5 hours and then evaporated under reduced pressure. The residue was partitioned between DCM and $H_2O$ and the two phases were separated. The aqueous phase was further extracted with DCM. The combined organic layers were washed with brine, passed through a phase separator and evaporated under reduced pressure. The crude mixture was purified by FCC, eluting with 0-10% 2M $NH_3$ in MeOH/DCM to afford the title compound (4.18 g, 75%).

$^1$H NMR (300 MHz, $CDCl_3$): 0.94 (3H, br d, J=6.0 Hz), 1.40-2.36 (10H, br m), 2.93-3.16 (2H, br m), 3.27-3.42 (1H, br m), 4.72 (2H, br s), 5.00-5.13 (1H, br m), 5.29 (1H, br s), 5.53 (1H, br d, J=8.3 Hz), 6.98 (1H, br d, J=9.8 Hz), 7.21-7.56 (6H, br m).

b. (4-(tert-Butyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidin-2-yl)methyl acetate (Intermediate AAb)

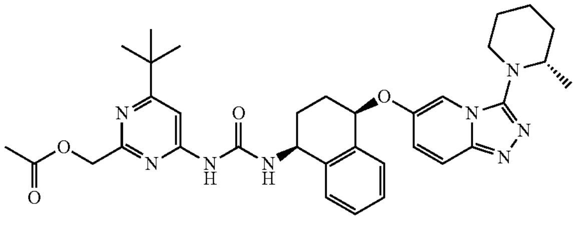 [SMILES: CC(=O)OCc1nc(NC(=O)N[C@H]2CC[C@@H](Oc3ccc4nnc(N5CCCC[C@@H]5C)n4c3)c3ccccc32)cc(C(C)(C)C)n1]

A solution of Intermediate XX (220 mg, 0.91 mmol), Intermediate AAa (457 mg, 1.09 mmol), XantPhos (52 mg, 0.091 mmol) in dioxane (20 ml) was treated with $K_3PO_4$ (269 mg, 1.27 mmol) and $Pd(OAc)_2$ (10 mg, 0.045 mmol). The reaction mixture was degassed with argon for a few minutes and then evacuated and purged with argon (×3). The reaction mixture was heated at 90° C. for 3 hours. The reaction mixture was cooled at RT, diluted with EtOAc and filtered through a pad of Celite®. The filtrate was washed with water and brine (×2) and the organic phase was dried with $MgSO_4$ and the solvent was removed under reduced pressure. Purification by FCC, eluting with 0-10% 2N $NH_3$ in MeOH/DCM afforded the title compound (311 mg, 55%).

LCMS (Method 1): Rt 3.79 min, m/z 627 [$MH^+$].

c. 1-(6-(tert-Butyl)-2-(hydroxymethyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea (Intermediate AAc)

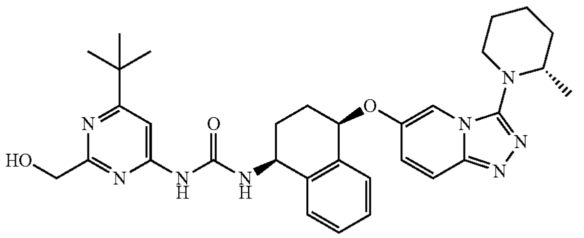 [SMILES: C[C@H]1CCCCN1c1nnc2ccc(O[C@@H]3CC[C@H](NC(=O)Nc4cc(C(C)(C)C)nc(CO)n4)c4ccccc43)cn12]

A solution of Intermediate AAb (297 mg, 0.47 mmol) in methanol (6 ml) and $H_2O$ (1 ml) was treated with $K_2CO_3$ (131 mg, 0.95 mmol). The reaction mixture was stirred at RT for 2 hours, partitioned between DCM and $H_2O$ and the two phases were separated. The organic phase was washed with brine, dried with $Na_2SO_4$ and the solvent was removed under reduced pressure to give the title compound (266 mg, 97%).

LCMS (Method 1): Rt 3.39 min, m/z 585 [$MH^+$].

c. Intermediate AA

A solution of Intermediate AAc (297 mg, 0.47 mmol) in DCM (1.5 ml) at 0° C. was treated with TEA (71 µl, 0.51 mmol) and mesyl chloride (17 µl, 0.22 mmol). The reaction mixture was stirred at 0° C. for 30 minutes and at RT for 40 minutes. Another aliquot of mesyl chloride (17 µl, 0.22 mmol) was added and the resulting mixture was stirred at RT for 50 minutes. The reaction mixture was partitioned between DCM and $H_2O$ and the two phases were separated. The aqueous phase was extracted with DCM and the combined organic phases were washed with brine, dried with $Na_2SO_4$ and the solvent was removed under reduced pressure to give the title compound (140 mg, quant.).

LCMS (Method 1): Rt 3.67 min, m/z 663 [$MH^+$].

Intermediate BB. Phenyl (6-(tert-butyl)pyrimidin-4-yl)carbamate

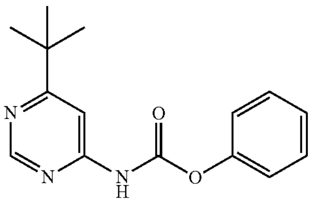 [SMILES: CC(C)(C)c1cc(NC(=O)Oc2ccccc2)ncn1]

A solution of 6-t-butyl-4-aminopyridine (400 mg, 2.64 mmol) in tetrahydrofuran (10 ml) at 0° C. was treated with TEA (810 µl, 5.81 mmol) and a slow addition of phenyl chloroformate (500 µl, 3.96 mmol). The reaction mixture was warmed at RT overnight. The reaction mixture was partitioned between EtOAc and a saturated aqueous $NaHCO_3$ solution and the two phases were separated. The aqueous phase was extracted with EtOAc and the combined organic phases were washed with brine, passed through a phase separator and the solvent was removed under reduced pressure. Purification by FCC, eluting with 0-40% EtOAc/cyclohexane gave the title compound (327 mg, 46%).

LCMS (Method 4): Rt 1.47 min, m/z 272 [$MH^+$].

Intermediate CC. Ethyl 4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxylate

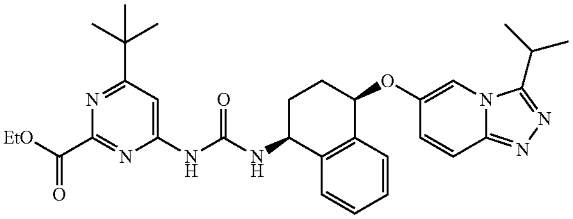 [SMILES: CCOC(=O)c1nc(NC(=O)N[C@H]2CC[C@@H](Oc3ccc4nnc(C(C)C)n4c3)c3ccccc32)cc(C(C)(C)C)n1]

a. 1-((1S,4R)-4-((3-Isopropyl-[1,2,4]triazolo[4,3-a]pyridin-6-yl)oxy)-1,2,3,4-tetrahydronaphthalen-1-yl)urea (Intermediate CCa)

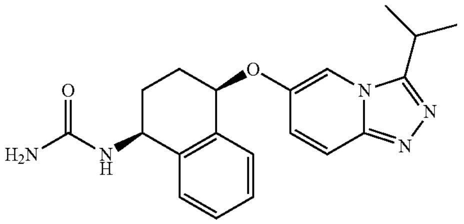 [SMILES: CC(C)c1nnc2ccc(O[C@@H]3CC[C@H](NC(N)=O)c4ccccc43)cn12]

A stirred solution of triphosgene (4.05 g, 13.7 mmol) in DCM (50 ml) at −10° C. was slowly added with a solution of (1S,4R)-4-((3-isopropyl-[1,2,4]triazolo[4,3-a]pyridin-6-yl)oxy)-1,2,3,4-tetrahydronaphthalen-1-amine (WO2013/083206, which is incorporated herein by reference in its entirety, 4.0 g, 12.4 mmol) and TEA (6.6 ml, 49.6 mmol) cooled at −10° C. The reaction mixture was stirred at 0° C. for 1 hour and then added to a solution of $NH_3$ in MeOH (2M, 160 ml) pre-cooled at 0° C. The resulting mixture was stirred at 0° C. for 1 hour and at RT for 72 hours. The solvents were removed under reduced pressure and the residue was dissolved in DCM and $H_2O$. The two phases were separated and the aqueous phase was extracted with DCM (×2). The combined organic phases were passed through a phase separator and the solvent was removed under reduced pressure. Purification by FCC, eluting with 0-10% 2N $NH_3$ in MeOH/DCM, followed by a trituration with $Et_2O$ afforded the title compound (2.77 g, 59%).

LCMS (Method 4): Rt 0.89 min, m/z 366 [$MH^+$].

b. Intermediate CC

A solution of Intermediate CCa (400 mg, 1.05 mmol), Intermediate 1d (255 mg, 1.05 mmol), XantPhos (64 mg, 0.11 mmol) in dioxane (20 ml) was treated with $Cs_2CO_3$ (479 mg, 1.47 mmol) and $Pd(OAc)_2$ (12 mg, 0.055 mmol). The reaction mixture was degassed for a few minutes with argon and then it was evacuated and purged with argon (×3). The reaction mixture was heated at 95° C. for 18 hours, cooled at RT, diluted with DCM and MeOH and filtered through a pad of Celite®. The solvents were removed under reduced pressure. Purification by FCC, eluting with 0-6% 2N $NH_3$ in MeOH/DCM afforded the title compound (415 mg, 69%, isolated as a mixture of ethyl and methyl esters (ratio ethyl/methyl 1:8)).

LCMS (Method 5): Ethyl ester: Rt 1.80 min, m/z 572 [$MH^+$]; methyl ester: Rt 1.74 min, m/z 558 [$MH^+$].

Intermediate DD. Ethyl 4-(tert-butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)pyrimidine-2-carboxylate

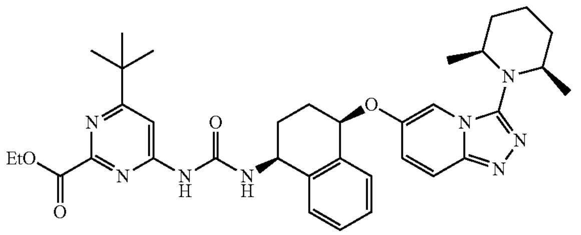 [SMILES: CCOC(=O)c1nc(NC(=O)N[C@H]2CC[C@@H](Oc3ccc4nnc(N5[C@H](C)CCC[C@@H]5C)n4c3)c3ccccc32)cc(C(C)(C)C)n1]

a. 1-((1S,4R)-4-((3-((2R,6S)-2,6-Dimethylpiperidin-1-yl)-[1,2,4]triazolo[4,3-a]pyridin-6-yl)oxy)-1,2,3,4-tetrahydronaphthalen-1-yl)urea (Intermediate DDa)

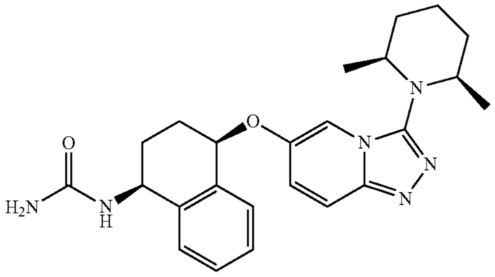 [SMILES: C[C@@H]1CCC[C@H](C)N1c1nnc2ccc(O[C@@H]3CC[C@H](NC(N)=O)c4ccccc43)cn12]

A stirred solution of triphosgene (2.92 g, 9.83 mmol) in DCM (50 ml) at −10° C. was slowly added with a solution of (1S,4R)-4-((3-((2S,6R)-2,6-dimethylpiperidin-1-yl)-[1,2,4]triazolo[4,3-a]pyridin-6-yl)oxy)-1,2,3,4-tetrahydronaphthalen-1-amine (WO2013/083604, 3.50 g, 8.94 mmol) and TEA (4.8 ml, 35.8 mmol) pre-cooled at −10° C. The reaction mixture was stirred at 0° C. for 1 hour and then added to a solution of $NH_3$ in MeOH (2M, 140 ml) pre-cooled at 0° C. The resulting mixture was stirred at 0° C. for 30 minutes and at RT for 72 hours. The solvents were removed under reduced pressure and the residue was dissolved in DCM and $H_2O$. The two phases were separated and the aqueous phase was extracted with DCM (×3). The combined organic phases were passed through a phase separator and the solvent was removed under reduced pressure. Purification by FCC, eluting with 0-10% 2N $NH_3$ in MeOH/DCM afforded the title compound (3.30 g, 85%).

LCMS (Method 4): Rt 1.11 min, m/z 435 [$MH^+$].

b. Intermediate DD

A solution of Intermediate DDa (450 mg, 1.04 mmol), Intermediate 1d (251 mg, 1.04 mmol), XantPhos (60 mg, 0.10 mmol) in dioxane (20 ml) was treated with $Cs_2CO_3$ (474 mg, 1.46 mmol) and $Pd(OAc)_2$ (12 mg, 0.052 mmol). The reaction mixture was degassed for a few minutes with argon and then it was evacuated and purged with argon (×3). The reaction mixture was heated at 95° C. for 18 hours, cooled at RT and other aliquots of XantPhos (60 mg, 0.10 mmol) and $Pd(OAc)_2$ (12 mg, 0.052 mmol) were added. The reaction mixture was degassed for a few minutes with argon and then it was evacuated and purged with argon (×3). The reaction mixture was heated at 95° C. for 5 hours, cooled at RT, diluted with DCM and MeOH and filtered through a pad of Celite®. The solvents were removed under reduced pressure. Purification by FCC, eluting with 0-5% 2N $NH_3$ in MeOH/DCM afforded the title compound (387 mg, 58%, isolated as a mixture of ethyl and methyl esters (ratio ethyl/methyl 1:2)).

LCMS (Method 5): Ethyl ester: Rt 2.13 min, m/z 641 [$MH^+$]; methyl ester: Rt 2.06 min, m/z 627 [$MH^+$].

Intermediate EE. (4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl methanesulfonate

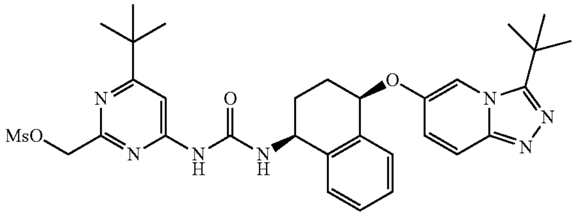 [SMILES: CC(C)(C)c1cc(NC(=O)N[C@H]2CC[C@@H](Oc3ccc4nnc(C(C)(C)C)n4c3)c3ccccc32)nc(COS(C)(=O)=O)n1]

a. (4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl acetate (Intermediate EEa)

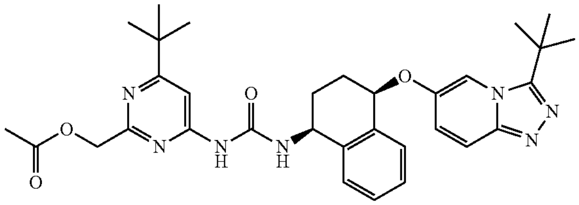 [SMILES: CC(=O)OCc1nc(NC(=O)N[C@H]2CC[C@@H](Oc3ccc4nnc(C(C)(C)C)n4c3)c3ccccc32)cc(C(C)(C)C)n1]

A solution of Intermediate XX (307 mg, 1.26 mmol), Intermediate 1h (500 mg, 1.26 mmol), XantPhos (73 mg, 0.126 mmol) in dioxane (25 ml) was treated with $Cs_2CO_3$ (573 mg, 1.77 mmol) and $Pd(OAc)_2$ (14 mg, 0.06 mmol). The reaction mixture was degassed with argon for a few minutes and then evacuated and purged with argon (×3). The reaction mixture was heated at 95° C. for 18 hours. The reaction mixture was cooled at RT, diluted with MeOH and filtered through a pad of Celite®. The solvent was removed under reduced pressure. Purification by FCC, eluting with 0-5% 2N $NH_3$ in MeOH/DCM afforded the title compound (525 mg, 71%).

LCMS (Method 5): Rt 2.04 min, m/z 586 [$MH^+$].

b. 1-(6-(tert-Butyl)-2-(hydroxymethyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea (Intermediate EEb)

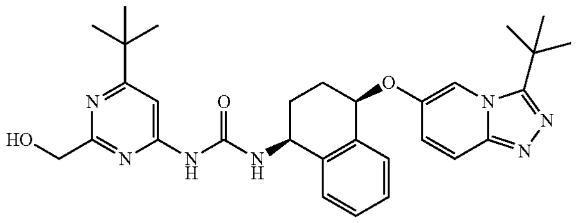 [SMILES: CC(C)(C)c1cc(NC(=O)N[C@H]2CC[C@@H](Oc3ccc4nnc(C(C)(C)C)n4c3)c3ccccc32)nc(CO)n1]

A solution of Intermediate EEa (525 mg, 0.90 mmol) in methanol (10 ml) and $H_2O$ (2 ml) was treated with $K_2CO_3$ (250 mg, 1.80 mmol). The reaction mixture was stirred at RT for 2 hours, partitioned between DCM and $H_2O$ and the two phases were separated. The aqueous phase was extracted with DCM (×3) and the combined organic phases were passed through a phase separator. The solvent was removed under reduced pressure to give the title compound (467 mg, 95%).

LCMS (Method 4): Rt 1.25 min, m/z 544 [$MH^+$].

c. Intermediate EE

A solution of Intermediate EEb (467 mg, 0.86 mmol) in DCM (8 ml) at 0° C. was treated with TEA (360 μl, 2.58 mmol) and mesyl chloride (137 μl, 1.77 mmol). The reaction mixture was stirred at 0° C. for 30 minutes and at RT for 50 minutes. The reaction mixture was partitioned between DCM and a saturated aqueous $Na_2CO_3$ solution and the two phases were separated. The aqueous phase was extracted with DCM (×2) and the combined organic phases were washed with brine, dried with $Na_2SO_4$ and the solvent was removed under reduced pressure to give the title compound (586 mg, quant.).

LCMS (Method 5): Rt 1.94 min, m/z 622 [$MH^+$].

Intermediate FF. Ethyl 4-(tert-butyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxylate

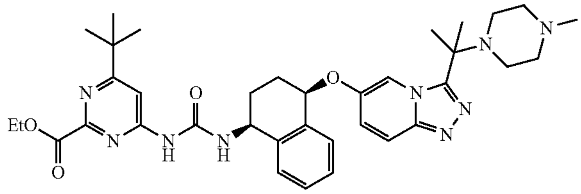 [SMILES: CCOC(=O)c1nc(NC(=O)N[C@H]2CC[C@@H](Oc3ccc4nnc(C(C)(C)N5CCN(C)CC5)n4c3)c3ccccc32)cc(C(C)(C)C)n1]

a. N'-(5-Fluoropyridin-2-yl)-2-methyl-2-(4-methylpiperazin-1-yl)propanehydrazide (Intermediate FFa)

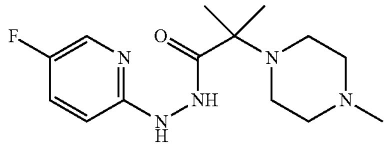 [SMILES: CN1CCN(C(C)(C)C(=O)NNc2ccc(F)cn2)CC1]

A solution of (5-fluoro-2-pyridyl) hydrazine (935 mg, 7.36 mmol) in DCM (25 ml) was treated with 2-methyl-2-(4-4-methylpiperazin-1-yl) propanoic acid dihydrobromide (2.5 g, 7.18 mmol), DIPEA (2.5 ml, 14.4 mmol), HOBt.x$H_2O$ (97 mg, 0.72 mmol) and finally EDC (1.7 g, 8.85 mmol). The mixture was stirred at RT overnight. The reaction mixture was washed with water and the aqueous phase was extracted with DCM (×3). The combined organic phases were passed through a phase separator and evaporated under reduced pressure. The crude mixture was purified by FCC, eluting with 0-8% 2M $NH_3$ in MeOH/DCM to afford the title compound (1.29 g, 61%).

$^1$H NMR (300 MHz, $CDCl_3$): 1.27 (6H, s), 2.32 (3H, s), 2.35-2.78 (8H, br m), 6.53 (1H, br d, J=4.0 Hz), 6.61 (1H, dd, J=8.9, 3.5 Hz), 7.22-7.32 (1H, m), 8.01 (1H, d, J=2.8 Hz), 9.09 (1H, br d, J=3.5 Hz).

b. 6-fluoro-3-(2-(4-methylpiperazin-1-yl)propan-2-yl)-[1,2,4]triazolo[4,3-a]pyridine (Intermediate FFb)

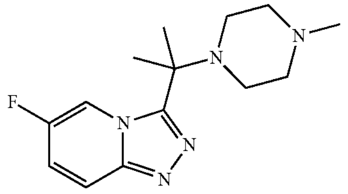 [SMILES: CN1CCN(C(C)(C)c2nnc3ccc(F)cn23)CC1]

A solution of Intermediate FFa (1.21 g, 4.10 mmol) in THF was treated with triethylamine (4.57 ml, 32.8 mmol) and triphenylphosphine (2.15 g, 8.20 mmol). The mixture was treated portionwise with hexachloroethane (1.94 g, 8.20 mmol) and stirred at RT for 5 hours. The reaction mixture was filtered and evaporated under reduced pressure. The residue was partitioned between DCM and an aqueous 1M HCl solution and the two phases were separated. The organic layer was further extracted with an aqueous 1M HCl solution (×3). The combined aqueous layers were washed with $Et_2O$ and then basified with solid $Na_2CO_3$ and extracted with DCM (×4). The combined DCM layers were passed through a phase separator and evaporated under reduced pressure to give the title compound (1.08 g, 95%).

$^1$H NMR (300 MHz, $CDCl_3$): 1.63 (6H, s), 2.29 (3H, s), 2.33-2.59 (8H, br m), 7.17 (1H, ddd, J=10.0, 10.0, 2.4 Hz), 7.73 (1H, ddd, J=10.0, 5.0, 0.8 Hz), 8.94 (1H, ddd, J=4.5, 2.5, 0.8 Hz).

c. (1S,4R)-4-((3-(2-(4-Methylpiperazin-1-yl)propan-2-yl)-[1,2,4]triazolo[4,3-a]pyridin-6-yl)oxy)-1,2,3,4-tetrahydronaphthalen-1-amine (Intermediate FFc)

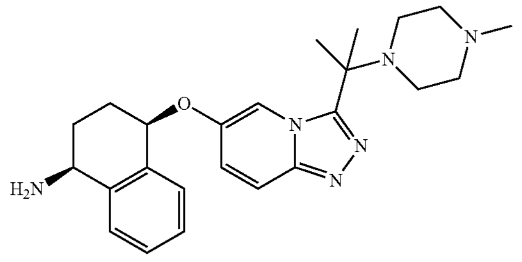 [SMILES: CN1CCN(C(C)(C)c2nnc3ccc(O[C@@H]4CC[C@H](N)c5ccccc54)cn23)CC1]

A solution of Intermediate FFb (225 mg, 0.81 mmol) in 2-methyltetrahydrofuran (5 ml) was treated with (1R, 4S)-4-amino-1,2,3,4-tetrahydronaphthalen-1-ol (WO 2014/195402, which is incorporated herein by reference in its entirety, 132 mg, 0.81 mmol) and 18-crown-6 (106 mg, 0.4 mmol) and the flask was evacuated and purged with argon. The mixture was treated with KO$^t$Bu (136 mg, 1.22 mmol) and stirred at RT overnight under argon. The reaction was quenched with water and the aqueous phase extracted with 2-methyltetrahydrofuran and DCM. The combined organic layers were dried ($Na_2SO_4$) and evaporated. The residue was purified by FCC, eluting with 0-10% 2M $NH_3$ in MeOH/DCM to afford the title compound (69 mg, 20%).

$^1$H NMR (300 MHz, $CDCl_3$): 1.63 (6H, s), 1.87-2.64 (16H, m), 3.63-3.77 (1H, m), 3.96-4.04 (1H, m), 5.22 (1H, t, J=4.1 Hz), 7.11 (1H, dd, J=10.0, 2.2 Hz), 7.21-7.31 (5H, m), 8.72 (1H, d, J=1.8 Hz).

d. 1-((1S,4R)-4-((3-(2-(4-Methylpiperazin-1-yl)propan-2-yl)-[1,2,4]triazolo[4,3-a]pyridin-6-yl)oxy)-1,2,3,4-tetrahydronaphthalen-1-yl)urea (Intermediate FFd)

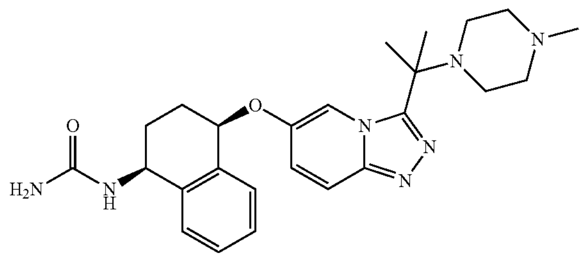 [SMILES: CN1CCN(C(C)(C)c2nnc3ccc(O[C@@H]4CC[C@H](NC(N)=O)c5ccccc54)cn23)CC1]

A stirred solution of triphosgene (831 mg, 2.80 mmol) in DCM (10 ml) at −10° C. was slowly added with a solution of Intermediate FFc (1.07 g, 2.54 mmol) and TEA (1.03 ml, 10.2 mmol). The reaction mixture was stirred at 0° C. for 1 hour and then added to a solution of $NH_3$ in MeOH (2M, 30 ml) pre-cooled at 0° C. The resulting mixture was stirred at 0° C. for 90 minutes and at RT for 1 hour. The volatiles were removed under reduced pressure and the residue was partitioned between DCM and $H_2O$. The two phases were separated and the aqueous phase was extracted with DCM (×3) and DCM with 5% of MeOH (×3). The combined organic phases were passed through a phase separator and the solvent was removed under reduced pressure. Purification by FCC, eluting with 0-10% 2N $NH_3$ in MeOH/DCM afforded the title compound (613 mg, 50%).

$^1$H NMR (300 MHz, $CDCl_3$): 1.59 (3H, s), 1.60 (3H, s), 2.06-2.61 (15H, m), 4.94 (2H, s), 5.07-5.14 (1H, m), 5.23 (1H, t, J=4.5 Hz), 6.15 (1H, d, J=8.6 Hz), 7.03 (1H, dd, J=9.8, 2.2 Hz), 7.29-7.41 (3H, m), 7.50-7.54 (2H, m), 8.75 (1H, d, J=1.8 Hz).

e. Intermediate FF

A solution of Intermediate FFd (613 mg, 1.28 mmol), Intermediate 1d (310 mg, 1.28 mmol), XantPhos (74 mg, 0.128 mmol) in dioxane (30 ml) was treated with $Cs_2CO_3$ (584 mg, 1.79 mmol) and $Pd(OAc)_2$ (14 mg, 0.064 mmol). The reaction mixture was degassed for a few minutes with argon and then evacuated and purged with argon (×3). The reaction mixture was heated at 95° C. for 24 hours. The reaction mixture was cooled at RT, diluted with DCM and filtered through a pad of Celite®. The solvents were removed under reduced pressure. Purification by FCC, eluting with 0-7% 2N $NH_3$ in MeOH/DCM afforded the title compound (580 mg, 68%).

$^1$H NMR (300 MHz, $CDCl_3$): 1.09 (3H, t, J=7.1 Hz), 1.36 (9H, s), 1.63 (3H, s), 1.64 (3H, s), 2.17-2.62 (15H, m), 4.09-4.33 (2H, m), 5.23-5.29 (2H, m), 7.00 (1H, s), 7.07 (1H, dd, J=9.9, 2.2 Hz), 7.32-7.45 (3H, m), 7.54-7.57 (1H, m), 7.75 (1H, d, J=9.9 Hz), 8.66 (1H, br s), 8.77 (1H, d, J=1.7 Hz), 9.80 (1H, br s).

Intermediate GG. (4-(tert-Butyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidin-2-yl)methyl acetate

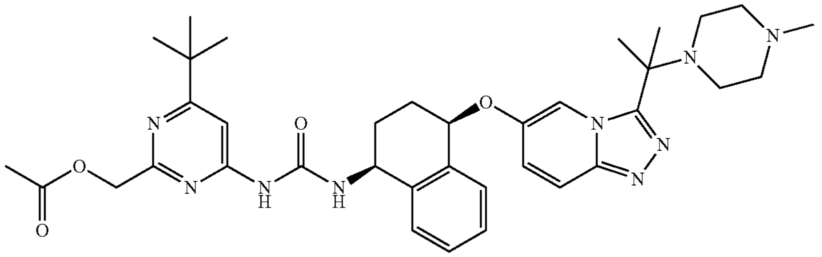 [SMILES: CC(=O)OCc1nc(NC(=O)N[C@H]2CC[C@@H](Oc3ccc4nnc(C(C)(C)N5CCN(C)CC5)n4c3)c3ccccc32)cc(C(C)(C)C)n1]

A solution of Intermediate FFd (110 mg, 0.24 mmol), Intermediate XX (58 mg, 0.24 mmol), XantPhos (14 mg, 0.024 mmol) in dioxane (3 ml) was treated with $Cs_2CO_3$ (110 mg, 0.34 mmol) and $Pd(OAc)_2$ (3 mg, 0.012 mmol). The reaction mixture was degassed for a few minutes with argon and then evacuated and purged with argon (×3). The reaction mixture was heated at 95° C. for 24 hours. The reaction mixture was cooled at RT, diluted with DCM and filtered through a pad of Celite®. The solvents were removed under reduced pressure. Purification by FCC, eluting with 0-7% 2N $NH_3$ in MeOH/DCM afforded the title compound (113 mg, 70%).

LCMS (Method 4): Rt 1.10 min, m/z 670 [$MH^+$].

Intermediate HH. Ethyl 4-(tert-butyl)-6-(3-((1S,4R)-4-((3-(2-ethoxypropan-2-yl)-[1,2,4]triazolo[4,3-a]pyridin-6-yl)oxy)-1,2,3,4-tetrahydronaphthalen-1-yl)ureido)pyrimidine-2-carboxylate

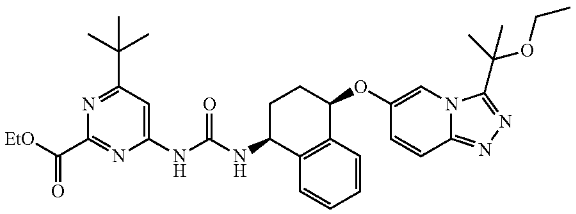 [SMILES: CCOC(=O)c1nc(NC(=O)N[C@H]2CC[C@@H](Oc3ccc4nnc(C(C)(C)OCC)n4c3)c3ccccc32)cc(C(C)(C)C)n1]

a. 2-Ethoxy-N'-(5-fluoropyridin-2-yl)-2-methylpropanehydrazide (Intermediate HHa)

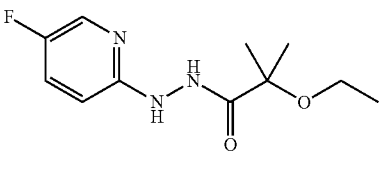 [SMILES: CCOC(C)(C)C(=O)NNc1ccc(F)cn1]

The title compound (8.97 g, 98%) was prepared starting from (5-fluoro-pyridin-2-yl)-hydrazine (WO 2014/195402, which is incorporated herein by reference in its entirety, 4.81 g, 37.8 mmol) and 2-ethoxy-2-methylpropanoic acid (5.00 g, 37.8 mmol) using the procedure described to make Intermediate 8a.

$^1H$ NMR (300 MHz, $CDCl_3$): 1.28 (3H, t, J=7.0 Hz), 1.45 (6H, s), 3.55 (2H, q, J=7.0 Hz), 6.62-6.66 (2H, m), 7.27-7.33 (1H, m), 8.03 (1H, d, J=2.9 Hz), 8.64 (1H, br s).

b. 3-(2-Ethoxypropan-2-yl)-6-fluoro-[1,2,4]triazolo[4,3-a]pyridine (Intermediate HHb)

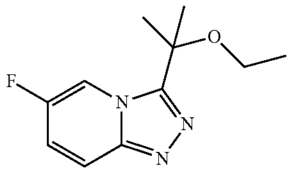 [SMILES: CCOC(C)(C)c1nnc2ccc(F)cn12]

The title compound (6.53 g, 79%, containing ~7% of $Ph_3P{=}O$ by NMR) was prepared starting from Intermediate HHa (8.97 g, 37.2 mmol) using the procedure described to make Intermediate 8b.

$^1H$ NMR (300 MHz, $CDCl_3$): 1.16 (3H, t, J=7.0 Hz), 1.80 (6H, s), 3.22 (1H, q, J=7.0 Hz), 7.21 (1H, ddd, J=9.9, 7.4, 2.3 Hz), 7.77 (1H, ddd, J=10.0, 5.0, 0.8 Hz), 8.51-8.53 (1H, m).

c. (1S,4R)-4-((3-(2-Ethoxypropan-2-yl)-[1,2,4]triazolo[4,3-a]pyridin-6-yl)oxy)-1,2,3,4-tetrahydronaphthalen-1-amine (Intermediate HHc)

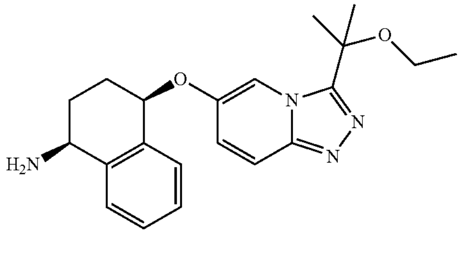 [SMILES: CCOC(C)(C)c1nnc2ccc(O[C@@H]3CC[C@H](N)c4ccccc43)cn12]

The title compound (950 mg, 58%) was prepared starting from Intermediate HHb (1.00 g, 4.48 mmol) using the procedure described to make Intermediate 8c.

$^1H$ NMR (300 MHz, $CDCl_3$): 1.14 (3H, t, J=7.0 Hz), 1.79 (3H, s), 1.80 (3H, s), 1.88-2.12 (3H, m), 2.30-2.39 (1H, m), 3.23 (2H, dq, J=7.0, 1.5 Hz), 3.96-4.00 (1H, m), 5.23 (1H, t, J=4.6 Hz), 7.14 (1H, dd, J=9.9, 2.2 Hz), 7.24-7.42 (3H, m), 7.61 (1H, d, J=7.7 Hz), 7.71 (1H, dd, J=9.9, 0.8 Hz), 8.21 (1H, d, J=1.4 Hz), plus two protons not observed.

d. 1-((1S,4R)-4-((3-(2-Ethoxypropan-2-yl)-[1,2,4]triazolo[4,3-a]pyridin-6-yl)oxy)-1,2,3,4-tetrahydronaphthalen-1-yl)urea (Intermediate HHd)

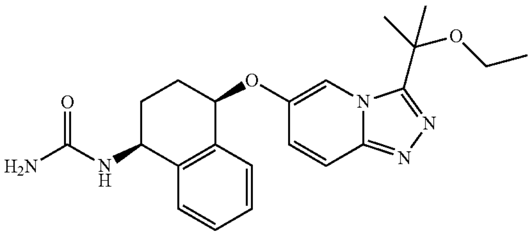 [SMILES: CCOC(C)(C)c1nnc2ccc(O[C@@H]3CC[C@H](NC(N)=O)c4ccccc43)cn12]

The title compound (1.08 g, quant.) was prepared starting from Intermediate HHc (950 mg, 2.59 mmol) using the procedure described to make Intermediate 8d.

$^1$H NMR (300 MHz, $CDCl_3$): 1.12 (3H, t, J=7.0 Hz), 1.65 (3H, s), 1.78 (3H, s), 2.07-2.18 (3H, m), 2.32-2.42 (1H, m), 3.13-3.24 (2H, m), 4.68 (2H, s), 5.04-5.12 (1H, m), 5.31-5.38 (2H, m), 7.10 (1H, dd, J=9.9, 2.2 Hz), 7.24-7.36 (3H, m), 7.46-7.50 (1H, m), 7.65 (1H, dd, J=9.9, 0.8 Hz), 8.01 (1H, d, J=1.4 Hz).

e. Intermediate HH

The title compound (189 mg, 50%) was prepared starting from Intermediate HHd (193 mg, 0.79 mmol) using the procedure described to make Intermediate 8e.

$^1$H NMR (300 MHz, $CDCl_3$): 1.09 (3H, t, J=7.1 Hz), 1.15 (3H, t, J=6.9 Hz), 1.36 (9H, s), 1.80 (3H, s), 1.81 (3H, s), 2.12-2.43 (4H, m), 3.20-3.29 (2H, m), 4.15-4.33 (2H, m), 5.21-5.28 (2H, m), 7.06 (1H, br s), 7.11 (1H, dd, J=9.9, 2.1 Hz), 7.28-7.41 (3H, m), 7.54-7.57 (1H, m), 7.77 (1H, dd, J=9.9, 0.5 Hz), 8.23 (1H, d, J=1.4 Hz), 8.97 (1H, br s), 9.71 (1H, br s).

Intermediate II. 1-(2-(Aminomethyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea

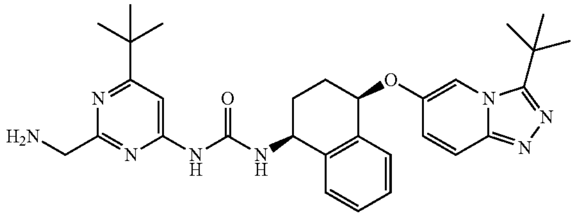 [SMILES: CC(C)(C)c1cc(NC(=O)N[C@H]2CC[C@@H](Oc3ccc4nnc(C(C)(C)C)n4c3)c3ccccc32)nc(CN)n1]

A solution of Intermediate EEb (170 mg, 0.31 mmol) in DCM (10 ml) was treated with TEA (90 μl, 0.62 mmol) and mesyl chloride (30 μl, 0.38 mmol). The reaction mixture was stirred at RT overnight. The reaction mixture was added with $NH_3$ in MeOH (2N, 10 ml) and the resulting mixture was stirred at RT for 20 hours and at 40° C. for 24 hours. Another aliquot of $NH_3$ in MeOH (2N, 10 ml) was added and the reaction mixture was stirred at 40° C. for 24 hours and then another aliquot of $NH_3$ in MeOH (2N, 10 ml) was added and the reaction mixture was stirred at 40° C. for 5 hours. The volatiles were removed under reduced pressure. Purification by FCC, eluting with 0-8% 2N $NH_3$ in MeOH/DCM afforded the title compound (154 mg, 92%).

LCMS (Method 4): Rt 1.05 min, m/z 543 [$MH^+$].

Intermediate JJ. Ethyl 4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxylate

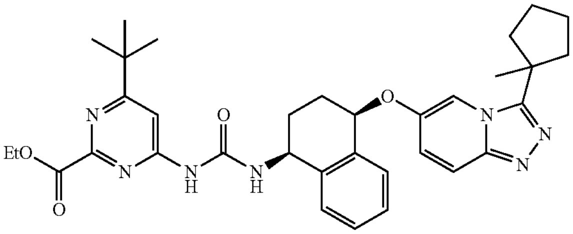 [SMILES: CCOC(=O)c1nc(NC(=O)N[C@H]2CC[C@@H](Oc3ccc4nnc(C5(C)CCCC5)n4c3)c3ccccc32)cc(C(C)(C)C)n1]

a. N'-(5-Fluoropyridin-2-yl)-1-methylcyclopentane-1-carbohydrazide (Intermediate JJa)

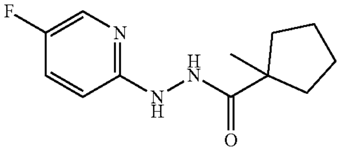 [SMILES: CC1(C(=O)NNc2ccc(F)cn2)CCCC1]

A solution of (5-fluoro-pyridin-2-yl)-hydrazine (WO 2014/195402, which is incorporated herein by reference in its entirety, 4.95 g, 39 mmol), HOBt (530 mg, 3.9 mmol) and EDC (8.23 g, 43 mmol) in DCM (60 ml) was treated with 1-methylcyclopentanecarboxylic acid (5.00 g, 39 mmol). The reaction mixture was stirred at RT for 18 hours. The reaction mixture was partitioned between DCM and $H_2O$. The organic phase was passed through a phases separator and the solvent was removed under reduced pressure. Purification by FCC, eluting with 0-100% EtOAc/DCM, followed by trituration with $Et_2O$ afforded the title compound (6.5 g, 70%).

$^1$H NMR (300 MHz, $CDCl_3$): 1.31 (3H, d, J=5.6 Hz), 1.47-1.51 (2H, m), 1.63-1.74 (1H, m), 1.99 (1H, br s), 2.04-2.14 (1H, m), 2.34 (1H, br s), 3.88-3.96 (1H, m), 4.40 (1H, dd, J=8.1, 3.5 Hz), 6.54 (1H, br s), 6.67 (1H, dd, J=9.0, 3.5 Hz), 7.24-7.30 (1H, m), 8.03 (1H, d, J=2.9 Hz), 8.71 (1H, br s).

b. 6-Fluoro-3-(1-methylcyclopentyl)-[1,2,4]triazolo[4,3-a]pyridine (Intermediate JJb)

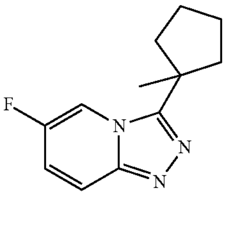 [SMILES: CC1(c2nnc3ccc(F)cn23)CCCC1]

Hexachloroethane (13 g, 54.8 mmol) was portionwise added at 0° C. to a stirred solution of Intermediate JJa (6.5 g, 27.4 mmol), triphenylphosphine (7.2 g, 54.8 mmol) and TEA (15.3 ml, 110 mmol) in 2-methyltetrahydrofuran (120 ml). The reaction mixture was warmed at RT and stirred for 3 hours. The reaction mixture was partitioned between 2-methyltetrahydrofuran and $H_2O$ and the two phases were separated. The organic phase was dried with $Na_2SO_4$ and the solvent was removed under reduced pressure. The residue was purified by FCC, eluting with 100% EtOAc. The residue was partitioned between EtOAc and an aqueous 6M HCl solution. The two phases were separated and the aqueous phase was washed with EtOAc (×2) and then basified with solid $K_2CO_3$. The resulting aqueous phase was extracted with DCM (×2), the combined organic phases were dried with $Na_2SO_4$ and the solvent was removed under reduced pressure to afford the title compound (4.8 g, 80%).

LCMS (Method 4): Rt 0.93 min, m/z 220 [$MH^+$].

c. (1S,4R)-4-((3-(1-Methylcyclopentyl)-[1,2,4]triazolo[4,3-a]pyridin-6-yl)oxy)-1,2,3,4-tetrahydronaphthalen-1-amine (Intermediate JJc)

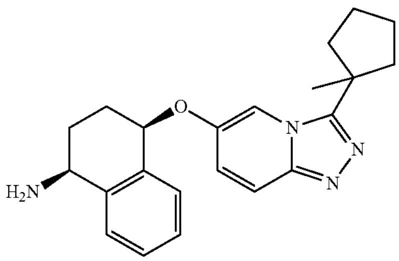 [SMILES: CC1(c2nnc3ccc(O[C@@H]4CC[C@H](N)c5ccccc54)cn23)CCCC1]

A stirred solution of Intermediate JJb (4.8 g, 21.9 mmol), (1R,4S)-4-amino-1,2,3,4-tetrahydro-naphthalen-1-ol (WO 2014/195402, which is incorporated herein by reference in its entirety, 3.57 g, 21.9 mmol) and 18-crown-6 (2.9 g, 11.0 mmol) in 2-methyltetrahydrofuran (50 ml) at 0° C. under nitrogen was added with potassium tert-butoxide (2.95 g, 26.3 mmol). The reaction mixture was evacuated and purged with nitrogen (×3), warmed at RT and stirred for 18 hours. The reaction mixture was partitioned between EtOAc and $H_2O$ and the two phases were separated. The organic phase was dried with $Na_2SO_4$ and the solvent was removed under reduced pressure. Purification by FCC, eluting with 0-10% 2N $NH_3$ in MeOH/DCM afforded the title compound (5.05 g, 64%).

LCMS (Method 4): Rt 0.83 min, m/z 363 [$MH^+$].

d. 1-((1S,4R)-4-((3-(1-Methylcyclopentyl)-[1,2,4]triazolo[4,3-a]pyridin-6-yl)oxy)-1,2,3,4-tetrahydronaphthalen-1-yl)urea (Intermediate JJd)

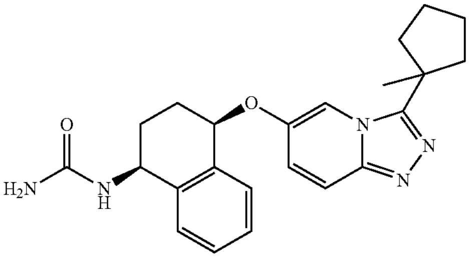 [SMILES: CC1(c2nnc3ccc(O[C@@H]4CC[C@H](NC(N)=O)c5ccccc54)cn23)CCCC1]

The title compound (4.0 g, 80%) was prepared starting from Intermediate JJc (4.0 g, 11 mmol) using the procedure described to make Intermediate 5d.

$^1H$ NMR (400 MHz, $CDCl_3$): 1.47 (3H, s), 1.73-1.94 (6H, m), 2.01-2.18 (3H, m), 2.27-2.35 (1H, m), 2.43-2.51 (2H, m), 4.50 (2H, s), 5.02-5.09 (2H, m), 5.19 (1H, t, J=3.9 Hz), 7.06 (1H, dd, J=9.9, 2.1 Hz), 7.27-7.40 (3H, m), 7.51 (1H, d, J=7.5 Hz), 7.63-7.67 (2H, m).

e. Intermediate JJ

The title compound (1.1 g, 60%) was prepared starting from Intermediate JJd (1.0 g, 2.5 mmol) and Intermediate 1d (600 mg, 2.5 mmol) using the procedure described to make Intermediate 5e.

LCMS (Method 4): Rt 1.53 min, m/z 612 [$MH^+$].

Intermediate KK. Ethyl 4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)pyrimidine-2-carboxylate

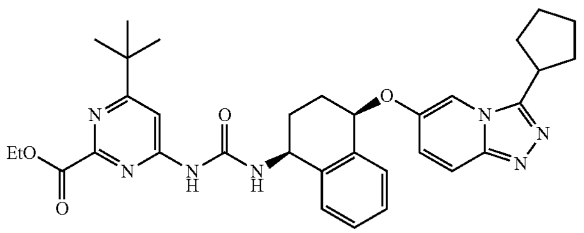 [SMILES: CCOC(=O)c1nc(NC(=O)N[C@H]2CC[C@@H](Oc3ccc4nnc(C5CCCC5)n4c3)c3ccccc32)cc(C(C)(C)C)n1]

The title compound (1.1 g) was prepared following the procedures outlined for Intermediate JJ starting from cyclopentanecarboxylic acid (CAS: 3400-45-1, 1.0 g, 2.5 mmol) and (5-fluoro-pyridin-2-yl)-hydrazine (600 mg, 2.5 mmol).

LCMS (Method 4): Rt 1.48 min, m/z 598 [$MH^+$].

Intermediate LL. Ethyl 4-(tert-butyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidine-2-carboxylate

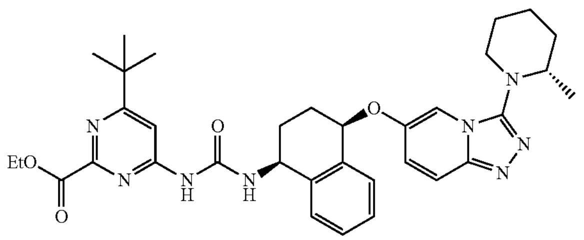 [SMILES: CCOC(=O)c1nc(NC(=O)N[C@H]2CC[C@@H](Oc3ccc4nnc(N5CCCC[C@@H]5C)n4c3)c3ccccc32)cc(C(C)(C)C)n1]

The title compound (413 mg, 53%) was prepared starting from Intermediate AAa (624 mg, 1.48 mmol) and Intermediate id (300 mg, 1.24 mmol) using the procedure described to make Intermediate 5e.

LCMS (Method 1): Rt 3.79 min, m/z 627 [$MH^+$].

Intermediate MM. 4-(tert-Butyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidine-2-carboxylic Acid

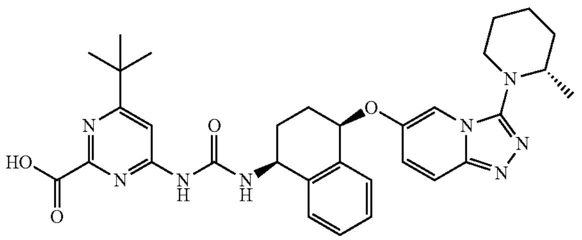 [SMILES: C[C@H]1CCCCN1c1nnc2ccc(O[C@@H]3CC[C@H](NC(=O)Nc4cc(C(C)(C)C)nc(C(=O)O)n4)c4ccccc43)cn12]

A solution of Intermediate LL (200 mg, 0.32 mmol) in THF (2 ml) was treated with LiOH (8.4 mg, 0.35 mmol) and water (0.2 ml) and the resulting mixture stirred at RT for 18 h. The mixture was partitioned between DCM and aqueous 1M HCl solution and the two phases were separated. The aqueous layer extracted with DCM (×2), the combined organic layers were passed through a phase separator and evaporated to afford the title compound (165 mg, 86%).

LCMS (Method 1): Rt 3.34 min, m/z 599 [$MH^+$].

Intermediate NN. 2,2,2-Trichloroethyl (6-(tert-butyl)-2-(methylcarbamoyl)pyrimidin-4-yl)carbamate

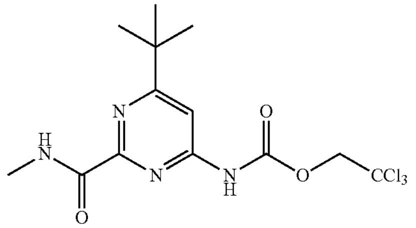

a. Ethyl 4-((tert-butoxycarbonyl)amino)-6-(tert-butyl)pyrimidine-2-carboxylate (Intermediate NNa)

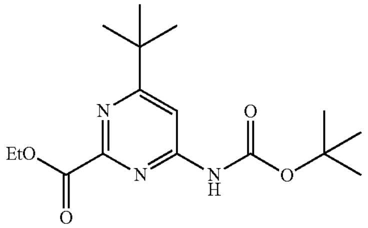 [SMILES: CCOC(=O)c1nc(NC(=O)OC(C)(C)C)cc(C(C)(C)C)n1]

A mixture of Intermediate 1d (1.0 g, 4.12 mmol), tert-butylcarbamate (579 mg, 4.94 mmol), XPhos (196 mg, 0.41 mmol), $Pd(OAc)_2$ (46 mg, 0.21 mmol) and $Cs_2CO_3$ (1.88 g, 5.77 mmol) was degassed with argon and refluxed for 2 h. The reaction mixture was cooled to RT, diluted with EtOAc, filtered through Celite® and the filtrate washed with water. The two phases were separated and the aqueous layer was extracted with EtOAc. The combined organic layers were washed with brine, dried with $Na_2SO_4$ and the solvent was removed under reduced pressure. The residue was purified by FCC eluting with 0-30% EtOAc in cyclohexane to afford the title compound (1.05 g, 79%).

$^1H$ NMR (300 MHz, $CDCl_3$): 1.39 (9H, s), 1.44 (3H, t, J=7.2 Hz), 1.53 (9H, s), 4.47 (2H, q, J=7.2 Hz), 7.53 (1H br s), 8.05 (1H, s).

b. tert-Butyl (6-(tert-butyl)-2-(methylcarbamoyl)pyrimidin-4-yl)carbamate (Intermediate NNb)

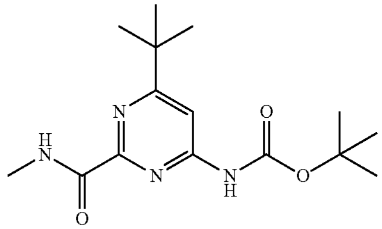 [SMILES: CNC(=O)c1nc(NC(=O)OC(C)(C)C)cc(C(C)(C)C)n1]

Intermediate NNa (500 mg, 1.55 mmol) was dissolved in 2M methylamine in THF (3.87 ml, 7.74 mmol) and the solution stirred at RT for 2.5 h. The RM was evaporated to leave the title compound (400 mg, 83%).

$^1H$ NMR (300 MHz, $CDCl_3$): 1.37 (9H, s), 1.52 (9H, s), 3.06 (3H, d, J=5.2 Hz), 7.69 (1H br s), 8.03 (1H, s), 8.05 (1H, br s).

c. 4-Amino-6-(tert-butyl)-N-methylpyrimidine-2-carboxamide (Intermediate NNc)

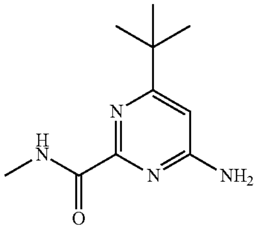

Intermediate NNb (400 mg, 1.29 mmol) was dissolved in 4M HCl in dioxan (5 ml) and the solution was stirred for 18 h. The reaction mixture was evaporated and the residue loaded onto a pre-conditioned SCX-2 cartridge. The cartridge was washed with DCM, DCM/MeOH (1:1) and MeOH and then the product was eluted with 2M $NH_3$ in MeOH. Evaporation of the last elution afforded the title compound (231 mg, 86%).

$^1H$ NMR (300 MHz, $CDCl_3$): 1.29 (9H, s), 3.02 (3H, d, J=5.2 Hz), 5.98 (2H br s), 6.42 (1H, s), 8.09 (1H, br s).

d. Intermediate NN

A solution of Intermediate NNc (100 mg, 0.48 mmol), 2,2,2-trichloroethyl chloroformate (165 µl, 1.20 mmol) and $Et_3N$ (67 µl, 0.48 mmol) in dioxan (2 ml) was heated to 150° C. for 1.5 h in the microwave. The reaction mixture was evaporated and purification by FCC eluting with 0-50% EtOAc in cyclohexane afforded the title compound (87 mg, 47%).

$^1H$ NMR (300 MHz, $CDCl_3$): 1.39 (9H, s), 3.07 (3H, d, J=5.2 Hz), 4.84 (2H, s), 8.05 (2H, br s), 8.13 (1H, br s)

Intermediate OO. Ethyl 6-(tert-butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)picolinate

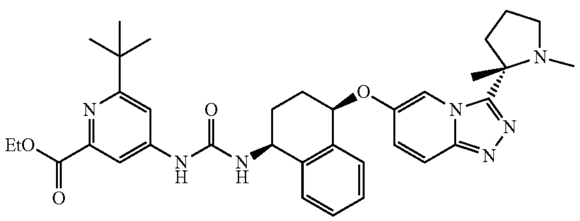 [SMILES: CCOC(=O)c1cc(NC(=O)N[C@H]2CC[C@@H](Oc3ccc4nnc([C@]5(C)CCCN5C)n4c3)c3ccccc32)cc(C(C)(C)C)n1]

a. 1-((1S,4R)-4-((3-((S)-1,2-Dimethylpyrrolidin-2-yl)-[1,2,4]triazolo[4,3-a]pyridin-6-yl)oxy)-1,2,3,4-tetrahydronaphthalen-1-yl)urea (Intermediate OOa)

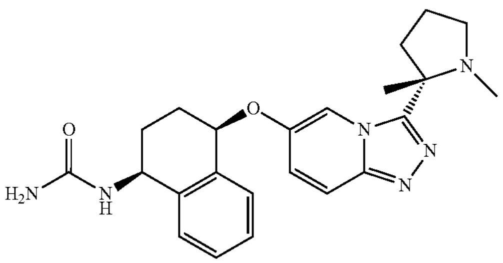 [SMILES: CN1CCC[C@@]1(C)c1nnc2ccc(O[C@@H]3CC[C@H](NC(N)=O)c4ccccc43)cn12]

A stirred solution of triphosgene (2.22 g, 7.49 mmol) in DCM (40 ml) at −10° C. was slowly added with a solution of (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 2.57 g, 6.81 mmol) and TEA (3.8 ml, 27.2 mmol). The reaction mixture was stirred at 0° C. for 1 hour and then added to a solution of $NH_3$ in MeOH (2M, 250 ml, 511 mmol) pre-cooled at 0° C. The resulting mixture was stirred at 0° C. for 30 minutes and then the volatiles were removed under reduced pressure. The residue was dissolved in DCM and $H_2O$ and the two phases were separated. The aqueous phase was extracted with DCM and the combined organic phases were washed with brine (×2), passed through a phase separator and the solvent was removed under reduced pressure. Purification by FCC, eluting with 0-10% 2N $NH_3$ in MeOH/DCM afforded the title compound (2.08 g, 73%).

LCMS (Method 1): Rt 0.36 min, m/z 443 [$MNa^+$].

b. Intermediate OO

The title compound (250 mg, 43%) was prepared starting from Intermediate OOa (90 mg, 0.90 mmol) and Intermediate 9d (270 mg, 1.1 mmol) using the procedure described to make Intermediate 5e.

LCMS (Method 1): Rt 2.72 mins, m/z 648 [$M+Na^+$].

Intermediate PP. 4-(tert-Butyl)-6-chloro-2-methylpyrimidine

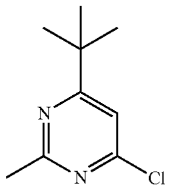

a. 6-(tert-Butyl)-2-methylpyrimidin-4(1H)-one (Intermediate PPa)

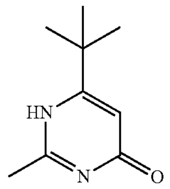

A solution of acetamidine hydrochloride (1.99 g, 21.1 mmol) and methyl pivaloylacetate (4.0 g, 25.3 mmol) in MeOH (100 ml) was treated with sodium methoxide (2.85 g, 52.7 mmol). The mixture was heated to 75° C. for 18 h. The reaction mixture was cooled to RT and evaporated under vacuum. The residue was partitioned between EtOAc and a saturated aqueous $NaHCO_3$ solution and the two phases were separated. The organic layer was washed with brine, dried with $Na_2SO_4$ and the solvent was removed under reduced pressure. The residue was triturated with acetone (2.34 g, 67%).

$^1H$ NMR (400 MHz, $d_6$-DMSO) 1.17 (9H, s), 2.26 (3H, s), 6.01 (1H, s), 12.20 (1H, br s).

b. Intermediate PP

A suspension of Intermediate PPa (2.33 g, 14.0 mmol) in $POCl_3$ (15 ml) was heated to 90° C. (block temperature) and stirred for 1.5 h. The volatiles were evaporated and the residue stirred with water (50 ml) and neutralised with 1M NaOH solution. The mixture was filtered and the solid washed with water and dried to afford the title compound (2.37 g, 87%).

$^1H$ NMR (400 MHz, $d_6$-DMSO): 1.28 (9H, s), 2.59 (3H, s), 7.48 (1H, s).

Intermediate QQ. 4-(tert-Butyl)-6-chloro-2-ethylpyrimidine

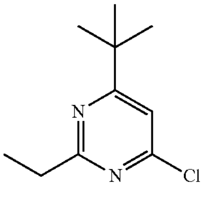

a. 6-(tert-Butyl)-2-ethylpyrimidin-4(1H)-one (Intermediate QQa)

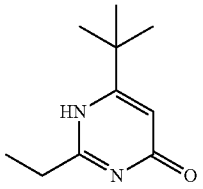

The title compound (3.15 g, 83%) was prepared starting from propanamidine hydrochloride (2.29 g, 21.1 mmol) using the procedure described to make Intermediate PPa. The product was purified by FCC eluting with 0-20% MeOH/DCM.

$^1$H NMR (400 MHz, $d_6$-DMSO): 1.17 (3H, t, J=7.6 Hz), 1.18 (9H, s), 2.53 (2H, q, J=7.6 Hz signal partially obscured by solvent signal), 6.01 (1H, s), 12.16 (1H, br s).

b. Intermediate QQ

The title compound (3.32 g, 96%) was prepared starting from Intermediate QQa (3.14 g, 17.4 mmol) using the procedure described to make Intermediate PP.

$^1$H NMR (400 MHz, $d_6$-DMSO): 1.26 (3H, t, J=7.6 Hz), 1.29 (9H, s), 2.86 (2H, q, J=7.6 Hz), 7.48 (1H, s).

Intermediate RR. 4-(tert-Butyl)-6-chloro-2-isopropylpyrimidine

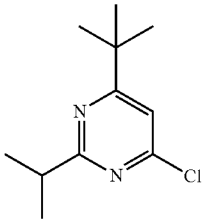

a. 6-(tert-Butyl)-2-isopropylpyrimidin-4(1H)-one (Intermediate RRa)

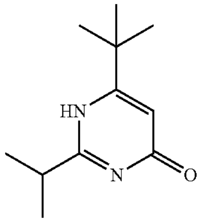

The title compound (2.98 g, 73%) was prepared starting from 2-methylpropanamidine hydrochloride, (2.58 g, 21.1 mmol) using the procedure described to make Intermediate PPa.

$^1$H NMR (400 MHz, $d_6$-DMSO): 1.16-1.20 (15H, m), 2.79 (1H, septet, J=6.9 Hz), 6.00 (1H, s), 12.12 (1H, br s).

b. Intermediate RR

The title compound (3.09 g, 95%) was prepared starting from Intermediate RRa (2.97 g, 15.3 mmol) using the procedure described to make Intermediate PP.

$^1$H NMR (400 MHz, $d_6$-DMSO): 1.26 (6H, d, J=6.9 Hz), 1.29 (9H, s), 3.09 (1H, septet, J=6.9 Hz), 7.47 (1H, s).

Intermediate SS. 4-(tert-butyl)-6-Chloro-2-(methoxymethyl)pyrimidine

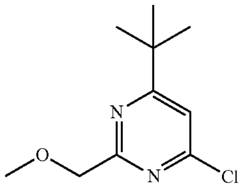

a. 6-(tert-butyl)-2-(methoxymethyl)pyrimidin-4(1H)-one (Intermediate SSa)

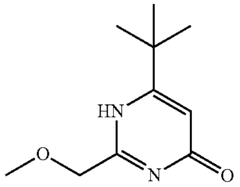

The title compound (2.86 g, 69%) was prepared starting from 2-methoxyacetamidine hydrochloride, (2.62 g, 21.1 mmol) using the procedure described to make Intermediate PPa. The product was purified by FCC eluting with 0-20% MeOH/DCM.

$^1$H NMR (400 MHz, $d_6$-DMSO): 1.19 (9H, s), 3.34 (3H, s, signal partially obscured by solvent signal), 4.25 (2H, s), 6.10 (1H, s), 12.21 (1H, br s).

b. Intermediate SS

The title compound (2.98 g, 96%) was prepared starting from Intermediate SSa (2.85 g, 14.5 mmol) using the procedure described to make Intermediate PP.

$^1$H NMR (400 MHz, $d_6$-DMSO): 1.30 (9H, s), 3.40 (3H, s), 4.55 (2H, s), 7.60 (1H, s).

Intermediate TT. 1-((1S,4R)-4-((3-((R)-1,2-dimethylpyrrolidin-2-yl)-[1,2,4]triazolo[4,3-a]pyridin-6-yl)oxy)-1,2,3,4-tetrahydronaphthalen-1-yl)urea

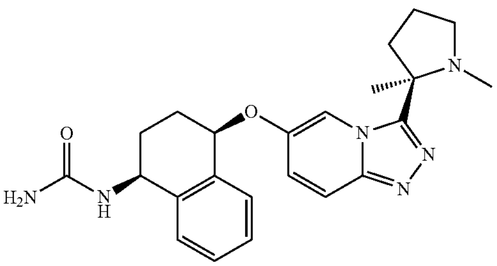 [SMILES: CN1CCC[C@]1(C)c1nnc2ccc(O[C@@H]3CC[C@H](NC(N)=O)c4ccccc43)cn12]

a. (R)-1,2-Dimethyl-pyrrolidine-2-carboxylic Acid Hydrochloride Salt (Intermediate TTa)

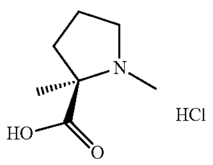

A solution of 2-methyl-D-proline hydrochloride salt (10.0 g, 60.4 mmol) in EtOH (150 ml) was added with formaldehyde (37% in water, 12.0 ml, 148 mmol) and palladium on carbon (10% Pd, 1.5 g). The vessel was evacuated and filled with hydrogen (×3) and the reaction mixture was stirred overnight at RT under hydrogen. The reaction mixture was filtered through a pad of celite and the solvent was removed under reduced pressure. The residue was triturated with ether to give the title compound (10.7 g, 99%).

$^1H$ NMR (300 MHz, $d_6$-DMSO): 1.54 (3H, br s), 1.86-2.14 (3H, m), 2.28 (1H, br s), 2.76 (3H, s), 3.22-3.64 (3H, m).

b. (R)-1,2-Dimethyl-pyrrolidine-2-carboxylic acid N'-(5-Fluoro-pyridine-2-yl)-hydrazide (Intermediate TTb)

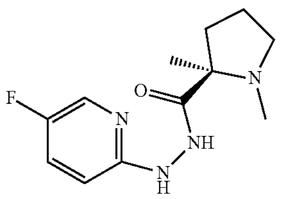 [SMILES: CN1CCC[C@]1(C)C(=O)NNc1ccc(F)cn1]

A solution of Intermediate TTa (10.6 g, 59.1 mmol), (5-fluoro-pyridin-2-yl)-hydrazine (WO 2014/195402, which is incorporated herein by reference in its entirety, 7.50 g, 59.1 mmol), HOBt (0.90 g, 5.91 mmol) and DIPEA (10.1 ml, 59.1 mmol) in DCM (150 ml) was treated with EDC (11.3 g, 59.1 mmol). The reaction mixture was stirred at RT for 2 hours. The volatiles were removed under reduced pressure and the residue was partitioned between EtOAc and $H_2O$. The organic phase was washed with $H_2O$ and brine, dried with $Na_2SO_4$ and the solvent was removed under reduced pressure. The crude was purified by FCC eluting with DCM, followed by 10% acetone/DCM and finally 0-5% 2M $NH_3$ in MeOH/DCM. The resulting solid was triturated with petrol ether to give the title compound (7.60 g, 51%).

$^1H$ NMR (300 MHz, $CDCl_3$): 1.24 (3H, s), 1.73-1.92 (3H, m), 2.12-2.30 (1H, m), 2.38 (3H, s), 2.50-2.63 (1H, m), 3.07-3.18 (1H, m), 6.53 (1H, br s), 6.60 (1H, dd, J=9.0, 3.6 Hz), 7.22-7.33 (1H, m), 8.03 (1H, d, J=2.7 Hz), 9.33 (1H, br s).

c. 3-((R)-1,2-Dimethyl-pyrrolidin-2-yl)-6-fluoro-[1,2,4]triazolo[4,3-a]pyridine (Intermediate TTc)

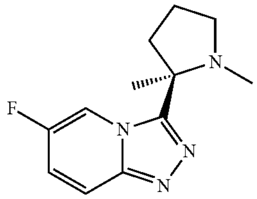 [SMILES: CN1CCC[C@]1(C)c1nnc2ccc(F)cn12]

Hexachloroethane (2.22 g, 9.40 mmol) was portionwise added to a stirred solution of Intermediate TTb (7.50 g, 29.8 mmol), triphenylphosphine (15.6 g, 59.5 mmol) and TEA (16 ml, 118.9 mmol) in 2-methyltetrahydrofuran (150 ml) and the reaction mixture was stirred at 80° C. for 1 h. The reaction mixture was cooled at RT, diluted with $H_2O$ and the two phases were separated. The organic phase was washed with $H_2O$ and extracted with an aqueous 0.5M citric acid solution. The aqueous phase was washed with 2-methyltetrahydrofuran and then basified with solid $K_2CO_3$. The resulting aqueous phase was extracted with DCM (×3). The combined organic phases were dried with $Na_2SO_4$ and the solvent was removed under reduced pressure to afford the title compound (6.74 g, 97%).

$^1H$ NMR (300 MHz, $CDCl_3$): 1.65 (3H, s), 1.85-2.28 (7H, m), 2.74 (1H, q, J=8.7 Hz), 3.20-3.30 (1H, m), 7.17 (1H, ddd, J=9.9, 7.3, 2.1 Hz), 7.73 (1H, dd, J=9.9, 5.0 Hz), 8.82 (1H, m).

d. (1S,4R)-4-[3-((R)-1,2-Dimethyl-pyrrolidin-2-yl)-[1,2,4]triazolo[4,3-a]pyridin-6-yloxy]-1,2,3,4-tetrahydro-naphthalen-1-ylamine (Intermediate TTd)

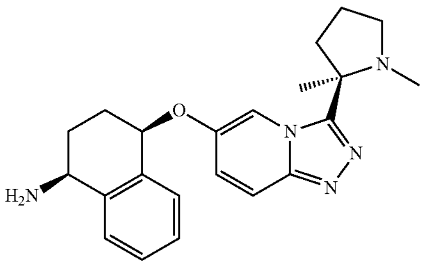 [SMILES: CN1CCC[C@]1(C)c1nnc2ccc(O[C@@H]3CC[C@H](N)c4ccccc43)cn12]

A stirred solution of Intermediate TTc (6.50 g, 27.8 mmol), (1R,4S)-4-amino-1,2,3,4-tetrahydro-naphthalen-1-ol (WO 2014/195402, which is incorporated herein by reference in its entirety, 4.53 g, 27.8 mmol) and 18-crown-6 (750 mg, 2.8 mmol) in 2-methyltetrahydrofuran (100 ml) at 0° C. under nitrogen was added with potassium tert-butoxide (3.58 g, 32.0 mmol). The reaction mixture was warmed at RT, stirred overnight and quenched with $H_2O$. The two phases were separated and the organic phase was washed with $H_2O$ and extracted with an aqueous 0.5M citric acid solution. The aqueous phase was washed with $Et_2O$ and then basified with solid $K_2CO_3$. The resulting aqueous phase was extracted with DCM. The organic phase was dried with $Na_2SO_4$ and the solvent was removed under reduced pressure to afford the title compound (8.32 g, 79%).

$^1H$ NMR (300 MHz, $CDCl_3$): 1.65 (3H, s), 1.84-2.13 (10H, m), 2.18-2.39 (2H, m), 2.73 (1H, q, J=8.9 Hz), 3.11-3.21 (1H, m), 3.98 (1H, dd, J=8.4, 5.1 Hz), 5.17 (1H, t, J=4.5 Hz), 7.11 (1H, dd, J=9.9, 2.3 Hz), 7.29 (1H, d, J=7.2 Hz), 7.33-7.43 (2H, m), 7.60 (1H, d, J=7.7 Hz), 7.68 (1H, dd, J=9.9, 0.8 Hz), 8.57 (1H, d, J=2.2 Hz) plus one proton obscured by water.

e. Intermediate TT

A solution of Intermediate TTd (5 g, 14.3 mmol) in THF (50 ml) was treated with TEA (118 μL, 0.795 mmol) and p-nitro-phenyl chloroformate (128 mg, 0.636 mmol) and the reaction mixture was stirred at RT for 20 min. An aqueous 33% ammonia solution was then added to the RM, which was then left to stir at RT for further 30 minutes. The solvents were removed under reduced pressure and the residue was taken up in saturated aqueous $NaHCO_3$ solution and extracted with DCM. The organic phase was separated with a phase separating cartridge and the solvent was removed under reduced pressure. Purification by FCC, eluting with 100% EtOAc followed by 10% 2M NH3 in MeOH/DCM gave the title compound (170 mg, 70%).

LCMS (Method 4): Rt 0.61 min, m/z 421 [$MH^+$].

Intermediate UU. Phenyl (5-(tert-butyl)-2-methylpyridin-3-yl)carbamate

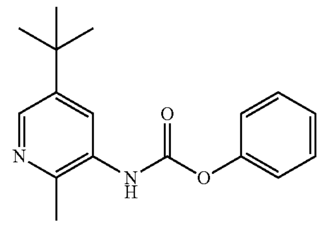 [SMILES: Cc1ncc(C(C)(C)C)cc1NC(=O)Oc1ccccc1]

The title compound (45 mg, 19%) was prepared starting from 5-(tert-butyl)-2-methylpyridin-3-amine (US2005/0245536, 134 mg, 0.82 mmol) using the procedure described to make Intermediate BB.

LCMS (Method 4): Rt 1.01 min, m/z 285 [$MH^+$].

Intermediate VV. 5-(tert-Butyl)-3-isocyanato-2-methoxypyridine

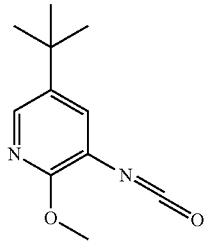

A solution of 5-(tert-butyl)-2-methoxypyridin-3-amine (WO2000/055139, which is incorporated herein by reference in its entirety, 151 mg, 0.84 mmol) in DCM (12 ml) was treated with saturated aqueous $NaHCO_3$ solution (8 ml) and the mixture cooled in ice. A 15% solution of phosgene in toluene (2.4 ml, 3.4 mmol) was added and the mixture was stirred at 0° C. for 1 hour. The two phases were separated and the aqueous phase extracted with DCM. The combined organic phases were dried with $MgSO_4$ and the solvent was removed under reduced pressure to afford the title compound (168 mg, 97%).

$^1$H NMR (400 MHz, $CDCl_3$): 1.29 (9H, s), 4.03 (3H, s), 7.26 (1H, d, J=2.5 Hz), 7.97 (1H, d, J=2.5 Hz).

Intermediate WW. Lithium 6-(tert-butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)picolinate

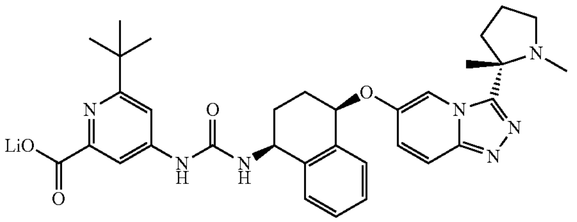

A solution of Intermediate OO (200 mg, 0.32 mmol) in MeOH (2.4 ml)/THF (0.3 ml)/$H_2O$ (0.8 ml) was treated with $LiOH.H_2O$ (28 mg, 0.67 mmol) and the mixture stirred at RT for 90 minutes. The reaction mixture was diluted with water, filtered and the solid washed with water, $Et_2O$ and dried at 50° C. under vacuum to afford the title compound (173 mg, 90%).

LCMS (Method 1): Rt 2.30 min, m/z 596 [$M-H^+$].

Intermediate XX. (4-(tert-Butyl)-6-chloropyrimidin-2-yl)methyl acetate

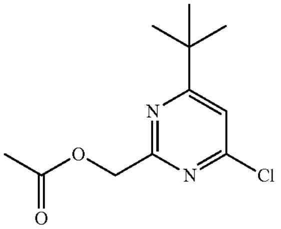 [SMILES: CC(=O)OCc1nc(Cl)cc(C(C)(C)C)n1]

a. (4-(tert-Butyl)-6-chloropyrimidin-2-yl)methanol (Intermediate XXa)

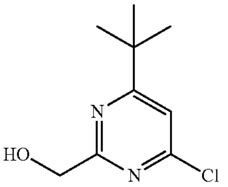

A solution of with Intermediate 1d (1 g, 4.12 mmol) in THF (10 ml) and IMS (5 ml) was treated with $NaBH_4$ (234 mg, 6.18 mmol) at 0° C. under argon. The reaction mixture was stirred at RT overnight. The reaction mixture was quenched with $H_2O$ and extracted with EtOAc. The organic phase was washed with brine, dried with $MgSO_4$ and the solvent was removed under reduced pressure. The residue was applied to a plug of silica, eluting with 0-100% EtOAc/Cyclohexane to afford the title compound (623 mg, 75%).

$^1$H NMR (300 MHz, $CDCl_3$): 1.35 (9H, s), 3.61 (1H, t, J=4.9 Hz), 4.78 (1H, dd, J=4.9, 0.7 Hz), 7.23 (1H, s).

b. Intermediate XX

A solution of Intermediate XXa (300 mg, 1.49 mmol) in pyridine (3 ml) was treated with acetic anhydride (283 μl, 2.99 mmol). The reaction mixture was stirred at RT for 2 hours. The reaction mixture was diluted with EtOAc and washed with aqueous HCl 1M solution. The aqueous phase was extracted with EtOAc and the combined organic phases were washed with aqueous HCl 1M solution and brine, dried with $MgSO_4$ and the solvent was removed under reduced pressure to afford the title compound (333 mg, 92%).

$^1$H NMR (300 MHz, $CDCl_3$): 1.32 (9H, s), 2.21 (3H, s), 5.25 (2H, s), 7.21 (1H, s).

Intermediate YY. 4-(tert-Butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylic Acid

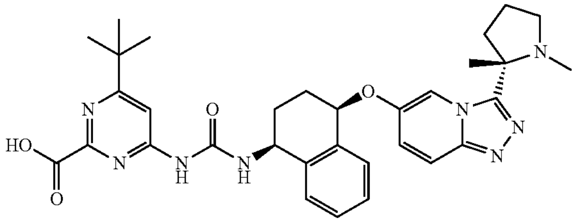 [SMILES: CN1CCC[C@@]1(C)c1nnc2ccc(O[C@@H]3CC[C@H](NC(=O)Nc4cc(C(C)(C)C)nc(C(=O)O)n4)c4ccccc43)cn12]

a. Ethyl 4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylate (Intermediate YYa)

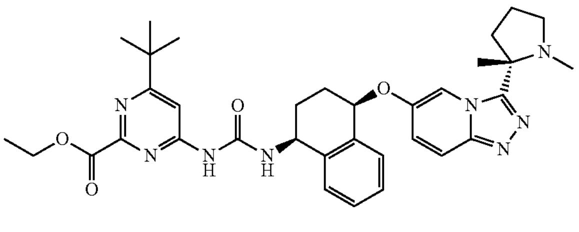 [SMILES: CCOC(=O)c1nc(NC(=O)N[C@H]2CC[C@@H](Oc3ccc4nnc([C@]5(C)CCCN5C)n4c3)c3ccccc32)cc(C(C)(C)C)n1]

A solution of Intermediate OOa (1.04 g, 2.47 mmol) in dioxane (50 ml) was treated with Intermediate 1d (0.5 g, 2.06 mmol), $Pd(OAc)_2$ (23.1 mg, 0.10 mmol), XantPhos (119 mg, 0.20 mmol) and $Cs_2CO_3$ (940 mg, 2.88 mmol). The reaction mixture was evacuated and purged with argon (×3) and then heated at 90° C. for 1.25 h. The reaction mixture was cooled to RT and filtered through a pad of Celite®. The filtrate was partitioned between EtOAc and $H_2O$ and the two phases were separated. The organic phase was washed with brine, dried with $MgSO_4$ and the solvent was removed under reduced pressure. The residue was applied to a plug of silica, eluting with 0-5% 2N $NH_3$ in MeOH/DCM to afford the title compound (548 mg, 42%).

$^1$H NMR (300 MHz, $CDCl_3$): 1.09 (3H, t, J=7.1 Hz), 1.35 (9H, s), 1.87-2.42 (11H, m), 2.73 (1H, q, J=9.0 Hz), 3.13-3.20 (1H, m), 4.11-4.32 (2H, m), 5.18-5.28 (2H, m), 7.05-7.09 (2H, m), 7.29-7.41 (3H, m), 7.55 (1H, d, J=7.2 Hz), 7.74 (1H, d, J=9.8 Hz), 8.58 (1H, d, J=1.6 Hz), 9.05 (1H, s), 9.77 (1H, br s), plus three protons not observed.

b. Intermediate YY

A solution of Intermediate YYa (300 mg, 0.48 mmol) in THF (3 ml) and $H_2O$ (0.3 ml) was treated with LiOH (12.6 mg, 0.53 mmol) and the reaction mixture was stirred at RT overnight. The reaction mixture was acidified to pH 1 with aqueous 1M HCl solution, diluted with EtOAc and the two phases were separated. The organic phase was washed with brine and the combined aqueous phases were extracted with DCM and DCM with a few drops of methanol. The combined organic phases were dried with $MgSO_4$ and the solvent was removed under reduced pressure to afford the title compound (198 mg, 69%).

$^1$H NMR (300 MHz, d-$_6$-DMSO): 1.29 (9H, s), 1.75-2.28 (12H, br s), 2.59 (1H, br s), 3.05 (3H, br s), 3.66-3.92 (1H, m), 4.93-5.03 (1H, m), 5.71 (1H, br s), 7.27-7.49 (6H, m), 7.79 (1H, br s), 7.89 (1H, d, J=9.9 Hz), 8.12-8.27 (1H, m), 9.84-9.94 (1H, m).

Intermediate ZZ. N-(4-(tert-Butyl)-6-chloropyrimidin-2-yl)methanesulfonamide

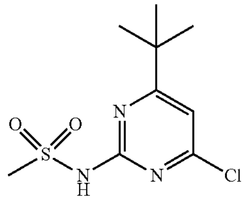 [SMILES: CC(C)(C)c1cc(Cl)nc(NS(C)(=O)=O)n1]

a. 6-(tert-Butyl)-2-(methylthio)pyrimidin-4-ol (Intermediate ZZa)

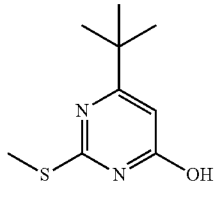

A solution of S-methylisothiourea hemisulfate salt (CAS: 867-44-7, 5.25 g, 37.7 mmol) in $H_2O$ (89 ml) was treated with $Na_2CO_3$ (7.27 g, 68.6 mmol) and methyl 4,4-dimethyl-3-oxo-pentanoate (CAS: 55107-14-7, 5.42 g, 34.3 mmol) and the reaction mixture was stirred at RT for 4 days. The reaction mixture was neutralised to pH 7-8 with aqueous 1M HCl solution and the reaction mixture was filtered. The solid was washed with $H_2O$ followed by $Et_2O$. The $Et_2O$ filtrate was diluted with EtOAc and $H_2O$ and the two phases were separated. The aqueous phase was extracted with EtOAc and the combined organics were washed with brine, dried with $NaSO_4$ and the solvent was removed under reduced pressure to afford the title compound (1.24 g, 18%).

$^1H$ NMR (300 MHz, $CDCl_3$): 1.25 (9H, s), 2.58 (3H, s), 6.17 (1H, s) plus one proton not observed.

b. 4-(tert-Butyl)-6-chloro-2-(methylthio)pyrimidine (ZZb)

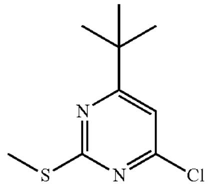

Intermediate ZZa (1.24 g, 6.3 mmol) was treated with $POCl_3$ (2.9 ml, 31.3 mmol) and the reaction mixture was stirred at 80° C. for 2.5 h. The volatiles were evaporated under reduced pressure and the residue was azeotroped with toluene. The residue was partitioned between EtOAc and saturated aqueous $NaHCO_3$ solution and the two phases were separated. The aqueous phase was extracted with EtOAc and the combined organic phases were washed with saturated $NaHCO_3$ solution. The organic phase was washed with brine, dried with $NaSO_4$ and the solvent was removed under reduced pressure to afford the title compound (1.09 g, 81%).

$^1H$ NMR (300 MHz, $CDCl_3$): 1.31 (9H, s), 2.56 (3H, s), 6.96 (1H, s).

c. 4-(tert-Butyl)-6-chloro-2-(methylsulfonyl)pyrimidine (Intermediate ZZc)

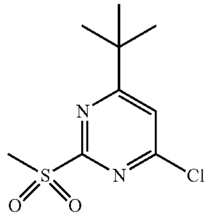

A solution of Intermediate ZZb (550 mg, 2.5 mmol) in DCM (10 ml) was treated with mCPBA (1.32 g, 7.6 mmol) and the reaction mixture was stirred at RT for 1 h. The reaction mixture was diluted with DCM and saturated aqueous $NaHCO_3$ solution and the two phases were separated. The aqueous phase was extracted with DCM and the combined organic phases were washed with saturated $NaHCO_3$ solution, dried with $NaSO_4$ and the solvent was removed under reduced pressure. Purification by FCC, eluting with 0-25% EtOAc/cyclohexane afforded the title compound (440 mg, 70%).

$^1H$ NMR (300 MHz, $CDCl_3$): 1.39 (9H, s), 3.37 (3H, s), 7.51 (1H, s).

d. Intermediate ZZ

A suspension of NaH (60% dispersion, 85 mg, 2.1 mmol) in dry DMF (5 ml) under nitrogen was treated with $MeSO_2NH_2$ (200 mg, 2.1 mmol) and the reaction mixture was stirred at RT for 30 min. A solution of Intermediate ZZc (440 mg, 1.8 mmol) in DMF (3 ml) was added to the reaction mixture and the reaction mixture was stirred at RT overnight. The reaction mixture was diluted with EtOAc and $H_2O$ and the two phases were separated. The aqueous phase was acidified to pH 4 with aqueous 1M HCl solution, extracted with EtOAc and the combined organic phases were washed with brine, dried with $NaSO_4$ and the solvent was removed under reduced pressure. Purification by FCC, eluting with 0-100% EtOAc/cyclohexane afforded the title compound (55 mg, 12%).

$^1H$ NMR (300 MHz, $CDCl_3$): 1.32 (9H, s), 1.57 (1H, br s), 3.47 (3H, s), 7.02 (1H, s).

Intermediate AB. 4-(tert-Butyl)-6-chloro-2-(4-methylpiperazin-1-yl)pyrimidine

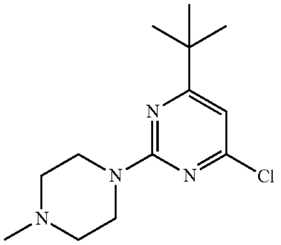 [SMILES: CN1CCN(c2nc(Cl)cc(C(C)(C)C)n2)CC1]

a. 6-(tert-Butyl)-2-(4-methylpiperazin-1-yl)pyrimidin-4(1H)-one (ABa)

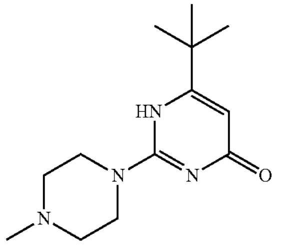 [SMILES: CN1CCN(c2nc(=O)cc(C(C)(C)C)[nH]2)CC1]

A solution of 4-methylpiperazine-1-carboximidamide (CAS: 45798-01-4, 5.00 g, 35.2 mmol) and ethyl pivaloylacetate (CAS: 17094-34-7, 5.30 ml, 30.2 mmol) in methanol (150 ml) was treated with tBuOK (17.0 g, 150.0 mmol) and the reaction mixture was stirred at RT overnight. The reaction mixture was filtered and the filtrate was concentrated under reduced pressure. $H_2O$ was added and the reaction mixture was acidified to pH 5 with 6M HCl solution and washed with EtOAc. The aqueous phase was applied to a SCX cartridge, eluting with methanol followed by 2N $NH_3$ in MeOH. The organic was dried with $MgSO_4$ and the solvent was removed under reduced pressure to afford the title compound (548 mg, 7%).

LCMS (Method 1): Rt 1.96 min, m/z 251 [$MH^+$].

b. Intermediate AB

Intermediate ABa (548 mg, 2.2 mmol) was treated with $POCl_3$ (2 ml, 22.0 mmol) and the reaction mixture was stirred at reflux for 3 h. The reaction mixture was cooled to RT, quenched by slow addition of methanol and the volatiles were evaporated under reduced pressure. Purification by FCC, eluting with 0-10% 2N $NH_3$ in MeOH/DCM, followed by a further FCC, eluting with 0-10% 2N $NH_3$ in MeOH/DCM afforded the title compound (143 mg, 24%).

$^1$H NMR (300 MHz, $CDCl_3$): 1.25 (9H, s), 2.49 (3H, s), 2.68 (4H, br s), 3.99 (4H, br s), 6.56 (1H, s), plus one proton not observed.

Intermediate AC. Ethyl 4-(tert-butyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxylate

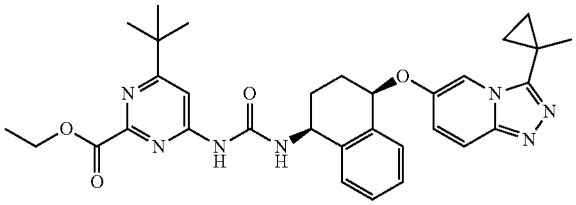 [SMILES: CCOC(=O)c1nc(NC(=O)N[C@H]2CC[C@@H](Oc3ccc4nnc(C5(C)CC5)n4c3)c3ccccc32)cc(C(C)(C)C)n1]

a. N'-(5-Fluoropyridin-2-yl)-1-methylcyclopropane-1-carbohydrazide (Intermediate ACa)

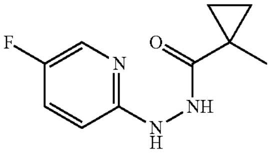

A solution of 1-methylcyclopropane-1-carboxylic acid (CAS: 6914-76-7, 5 g, 50.0 mmol), (5-fluoro-2-pyridyl) hydrazine (WO 2014/195402, which is incorporated herein by reference in its entirety, 6.35 g, 50.0 mmol) and HOBt hydrate (0.77 g, 5.0 mmol) in DCM (75 ml) was cooled in ice and treated with EDC.HCl (9.60 g, 50.0 mmol). The ice bath was removed and the reaction mixture was stirred at RT for 1 h. The volatiles were removed under reduced pressure and the residue was partitioned between 2-methyltetrahydrofuran and $H_2O$. The two phases were separated and the organic phase was extracted with aqueous 1M HCl solution. The aqueous phase was washed with $Et_2O$ and basified with solid $K_2CO_3$. The resulting aqueous phase was extracted with DCM, the organic phase was dried with $NaSO_4$ and the solvent was removed under reduced pressure. Trituration with 20% $Et_2O$/Petrol afforded the title compound (6.1 g, 58%).

$^1$H NMR (300 MHz, $CDCl_3$): 0.66 (2H, dd, J=6.6, 4.0 Hz), 1.24 (2H, dd, J=6.6, 4.0 Hz), 1.43 (3H, s), 6.66 (1H, dd, J=9.0, 3.5 Hz), 6.81 (1H, d, J=3.8 Hz), 7.24-7.31 (1H, m), 7.97 (1H, d, J=2.8 Hz), 8.02 (1H, d, J=2.8 Hz).

b. 6-Fluoro-3-(1-methylcyclopropyl)-[1,2,4]triazolo[4,3-a]pyridine (Intermediate ACb)

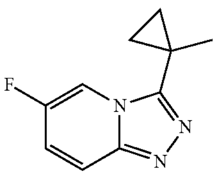

A solution of Intermediate ACa (6.0 g, 28.7 mmol), triphenylphosphine (15.0 g, 57.2 mmol) and TEA (11.6 g, 114.8 mmol) in 2-methyltetrahydrofuran (120 ml) was treated with hexachloroethane (13.6 g, 57.3 mmol). The reaction mixture was stirred at RT for 1 h. The reaction mixture was partitioned between 2-methyltetrahydrofuran and $H_2O$ and the two phases were separated. The organic phase was extracted with an aqueous 1M HCl solution. The aqueous phase was washed with $Et_2O$ and then basified with solid $K_2CO_3$. The resulting aqueous phase was extracted with DCM, the organic phase was dried with $Na_2SO_4$ and the solvent was removed under reduced pressure. Trituration with 10% $Et_2O$/petrol (v/v 1:1) afforded the title compound (4.35 g, 79%).

$^1$H NMR (300 MHz, $CDCl_3$): 0.98 (2H, dd, J=6.6, 4.0 Hz), 1.18 (2H, dd, J=6.6, 4.0 Hz), 1.50 (3H, s), 7.20 (1H, ddd, J=9.8, 7.6, 2.2 Hz), 7.74 (1H, ddd, J=10.0, 5.0, 0.8 Hz), 8.07 (1H, ddd, J=3.1, 2.2, 0.8 Hz)

c. (1S,4R)-4-((3-(1-Methylcyclopropyl)-[1,2,4]triazolo[4,3-a]pyridin-6-yl)oxy)-1,2,3,4-tetrahydronaphthalen-1-amine (Intermediate ACc)

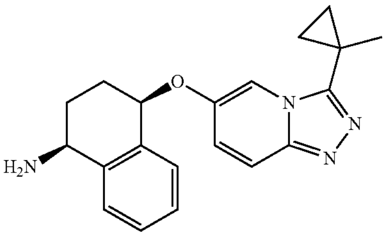 [SMILES: CC1(c2nnc3ccc(O[C@@H]4CC[C@H](N)c5ccccc54)cn23)CC1]

A stirred solution of Intermediate ACb (4.35 g, 22.8 mmol), (1R,4S)-4-amino-1,2,3,4-tetrahydro-naphthalen-1-ol (WO 2014/195402, which is incorporated herein by reference in its entirety, 3.70 g, 23.0 mmol) and 18-crown-6 (0.6 g, 2.3 mmol) in 2-methyltetrahydrofuran (100 ml) at 0° C. under nitrogen was added with potassium tert-butoxide (2.93 g, 26.2 mmol). The reaction mixture was evacuated and purged with nitrogen (×3), warmed to RT and stirred for 2 h. The reaction mixture was partitioned between 2-methyltetrahydrofuran and $H_2O$ and the two phases were separated. The organic phase was extracted with aqueous 10% citric acid solution. The aqueous phase was washed with $Et_2O$ and then basified with solid $K_2CO_3$. The resulting aqueous phase was extracted with DCM. The organic phase was dried with $Na_2SO_4$ and the solvent was removed under reduced pressure. The residue was applied to a plug of silica, eluting with DCM followed by 5% 2N $NH_3$ in MeOH/DCM to afford the title compound (6.6 g, 87%).

$^1$H NMR (300 MHz, $CDCl_3$): 0.90-0.94 (2H, m), 1.13-1.16 (2H, m), 1.46 (3H, s), 1.88-2.15 (3H, m), 2.35-2.45 (1H, m), 3.99-4.03 (1H, m), 5.27 (1H, t, J=4.5 Hz), 7.15 (1H, dd, J=9.6, 2.3 Hz), 7.25-7.34 (3H, m), 7.37-7.44 (1H, m), 7.61 (1H, d, J=7.7 Hz), 8.27 (1H, dd, J=8.1, 0.8 Hz) plus two protons not observed.

d. 1-((1S,4R)-4-((3-(1-Methylcyclopropyl)-[1,2,4]triazolo[4,3-a]pyridin-6-yl)oxy)-1,2,3,4-tetrahydronaphthalen-1-yl)urea (Intermediate ACd)

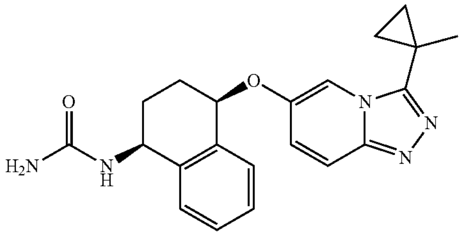 [SMILES: CC1(c2nnc3ccc(O[C@@H]4CC[C@H](NC(N)=O)c5ccccc54)cn23)CC1]

A solution of Intermediate ACc (1.00 g, 3.00 mmol) in DCM (10 ml) was treated with (trimethylsilyl)isocyanate (0.5 ml, 3.6 mmol) at 0° C. The reaction mixture was warmed at RT and stirred overnight. The reaction mixture was cooled and treated with methanol and the solvents were removed under reduced pressure. Purification by FCC, eluting with 0-10% 2N $NH_3$ in MeOH/DCM afforded the title compound (798 mg, 70%).

$^1$H NMR (300 MHz, $CDCl_3$): 0.93-0.95 (2H, m), 1.14-1.17 (2H, m), 1.47 (3H, s), 1.99-2.21 (3H, m), 2.29-2.37 (1H, m), 4.46 (2H, s), 5.03-5.10 (1H, m), 5.25 (1H, t, J=3.4 Hz), 7.10 (1H, dd, J=7.4, 1.5 Hz), 7.26-7.40 (4H, m), 7.51 (1H, d, J=5.7), 7.66 (1H, d, J=7.4), 7.71 (1H, d, J=1.5 Hz).

e. Intermediate AC

A solution of Intermediate ACd (798 mg, 2.11 mmol) in dioxane (20 ml) was treated with Intermediate 1d (513 mg, 2.11 mmol), $Pd(OAc)_2$ (25 mg g, 0.11 mmol), XantPhos (121 mg, 0.21 mmol) and $Cs_2CO_3$ (1.08 g, 3.00 mmol). The reaction mixture was evacuated and purged with nitrogen (×3) and then heated at 90° C. overnight. The reaction mixture was cooled to RT, filtered and washed with ETOAc and the filtrate was evaporated under reduced pressure. The residue was applied to a plug of silica, eluting with EtOAc followed by 10% IMS/EtOAc to afford the title compound (580 mg, 47%).

$^1$H NMR (300 MHz, $CDCl_3$): 0.94-0.96 (2H, m), 1.08 (3H, t, J=5.3 Hz), 1.16-1.19 (2H, m), 1.36 (9H, s), 1.49 (3H, s), 2.13-2.43 (4H, m), 4.15-4.28 (2H, m), 5.20-5.30 (2H, m), 6.78 (1H, s), 7.11 (1H, dd, J=7.4, 1.5 Hz), 7.26-7.39 (5H, m), 7.51-7.56 (1H, m), 7.70 (1H, d, J=7.3 Hz), 7.74 (1H, d, J=1.1 Hz).

Intermediate AD. Ethyl 4-(tert-butyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxylate

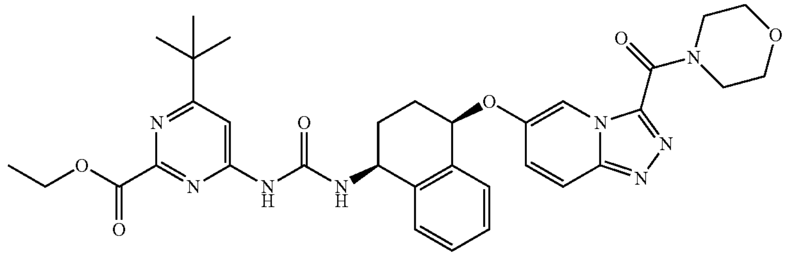 [SMILES: CCOC(=O)c1nc(NC(=O)N[C@H]2CC[C@@H](Oc3ccc4nnc(C(=O)N5CCOCC5)n4c3)c3ccccc32)cc(C(C)(C)C)n1]

a. Ethyl 6-fluoro-[1,2,4]triazolo[4,3-a]pyridine-3-carboxylate (Intermediate ADa)

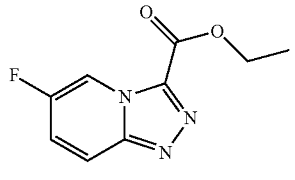

A solution of (5-fluoro-2-pyridyl)hydrazine (WO 2014/195402, which is incorporated herein by reference in its entirety, 12.7 g, 100.0 mmol) in methanol (300 ml) was treated with ethyl 2-oxoacetate 50% in toluene (CAS: 924-44-7, 20.5 g, 100.0 mmol) and the reaction mixture was heated to 60° C. for 1 h. The reaction mixture was cooled to RT and the solvent was evaporated under reduced pressure. The residue was dissolved in DCM (300 ml) and treated with $PhI(OAc)_2$ and the reaction mixture was stirred at RT for 1 hour. The solvent was removed under reduced pressure. Trituration with MeCN afforded the title compound (15.5 g, 74%).

$^1$H NMR (300 MHz, $CDCl_3$): 1.51 (3H, t, J=7.1 Hz), 4.59 (2H, q, J=7.1 Hz), 7.43 (1H, ddd, J=9.8, 7.4, 2.2 Hz), 7.96 (1H, ddd, J=10.0, 4.8, 0.8 Hz), 9.14 (1H, ddd, J=3.4, 2.2, 0.8 Hz)

b. (6-Fluoro-[1,2,4]triazolo[4,3-a]pyridin-3-yl)(morpholino)methanone (Intermediate ADb)

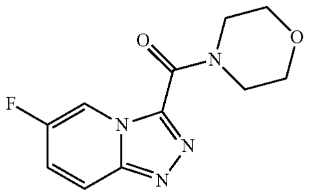 [SMILES: O=C(c1nnc2ccc(F)cn12)N1CCOCC1]

A solution of morpholine (3.6 g, 41.3 mmol) in THF (100 ml) was cooled to −78° C. and treated with n-BuLi (16 M, 27.5 ml, 44 mmol). The reaction mixture was stirred for 10 min. A solution of Intermediate ADa in THF was added to the reaction mixture and the reaction mixture was stirred for 1 h. The reaction mixture was quenched with $H_2O$ and extracted with EtOAc. The organic phase was dried with $MgSO_4$ and the solvent was removed under reduced pressure. Purification by FCC, eluting with 0-100% EtOAc/cyclohexane afforded the title compound (1.99 g, 25%).

$^1$H NMR (300 MHz, $CDCl_3$): 3.82 (6H, m), 4.58 (2H, t, J=4.7 Hz), 7.38 (1H, ddd, J=9.8, 7.3, 2.3 Hz), 7.87 (1H, ddd, J=10.0, 5.0, 0.8 Hz), 9.14 (1H, ddd, J=4.2, 2.3, 0.8 Hz)

c. (6-(((1R,4S)-4-Amino-1,2,3,4-tetrahydronaphthalen-1-yl)oxy)-[1,2,4]triazolo[4,3-a]pyridin-3-yl)(morpholino)methanone (Intermediate ADc)

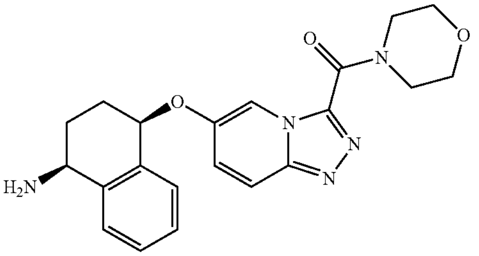 [SMILES: N[C@H]1CC[C@@H](Oc2ccc3nnc(C(=O)N4CCOCC4)n3c2)c2ccccc21]

A solution of Intermediate ADb (125 mg, 0.5 mmol), (1R,4S)-4-amino-1,2,3,4-tetrahydro-naphthalen-1-ol (WO 2014/195402, which is incorporated herein by reference in its entirety, 81.5 mg, 0.5 mmol) and 18-crown-6 (66 mg, 0.25 mmol) in 2-methyltetrahydrofuran (3 ml) at 0° C. under nitrogen was added with potassium tert-butoxide (67.2 mg, 0.6 mmol). The reaction mixture was evacuated and purged with argon (×3), warmed to RT and stirred for 1 h. The reaction mixture was partitioned between 2-methyltetrahydrofuran and $H_2O$ and the two phases were separated. The aqueous phase was extracted with EtOAc and DCM. The combined organic phases were dried with $MgSO_4$ and the solvent was removed under reduced pressure. Purification by FCC, eluting with 0-10% 2N $NH_3$ in MeOH/DCM afforded the title compound (238 mg, 61%).

$^1$H NMR (400 MHz, $CDCl_3$): 1.85-1.95 (2H, m), 2.04-2.14 (1H, m), 2.34-2.41 (1H, m), 3.84-3.88 (6H, m), 3.96-4.00 (1H, m), 4.60 (2H, t, J=4.5 Hz), 5.35 (1H, t, J=3.3 Hz), 7.25-7.41 (4H, m), 7.61 (1H, d, J=7.7 Hz), 7.79 (1H, dd, J=9.8, 0.8 Hz), 8.94 (1H, d, J=2.0 Hz) plus two protons not observed.

d. 1-((1S,4R)-4-((3-(Morpholine-4-carbonyl)-[1,2,4]triazolo[4,3-a]pyridin-6-yl)oxy)-1,2,3,4-tetrahydronaphthalen-1-yl)urea (Intermediate ADd)

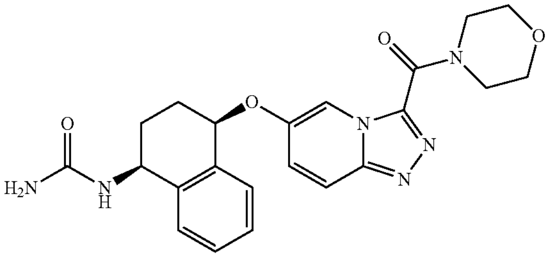 [SMILES: NC(=O)N[C@H]1CC[C@@H](Oc2ccc3nnc(C(=O)N4CCOCC4)n3c2)c2ccccc21]

A solution of triphosgene (176 mg, 0.6 mmol) in DCM (20 ml) was cooled to −10° C. A solution of Intermediate ADc (212 mg, 0.5 mmol) in DCM (20 ml) was cooled to −10° C. and added to the reaction mixture. The reaction mixture was stirred for 1 h, treated with 2N $NH_3$ in MeOH and stirred for a further 2 h. The solvents were removed under reduced pressure. The residue was diluted with EtOAc and washed with saturated aqueous $NaHCO_3$ solution. The organic phase was dried with $MgSO_4$ and the solvent was evaporated under reduced pressure to afford the title compound. (Crude taken forward assuming quantitative yield: 235 mg, 100%).

$^1$H NMR (400 MHz, $CDCl_3$): 2.02-2.22 (3H, m), 2.47-2.56 (1H, m), 3.74-3.89 (6H, m), 4.47-4.62 (4H, m), 4.98-5.06 (1H, m), 5.45-5.48 (1H, m), 5.57 (1H, d, J=7.8 Hz), 7.32-7.37 (2H, m), 7.48 (1H, d, J=7.6 Hz), 7.78 (1H, dd, J=9.8, 0.7 Hz), 8.48 (1H, d, J=1.5 Hz), plus two protons obscured by solvent peak.

e. Intermediate AD

A solution of Intermediate ADd (235 mg, 0.54 mmol) in dioxane (20 ml) was treated with Intermediate 1d (131 mg, 0.54 mmol), $Pd(OAc)_2$ (6 mg, 0.03 mmol), XantPhos (31 mg, 0.05 mmol) and $Cs_2CO_3$ (247 mg, 0.75 mmol). The reaction mixture was evacuated and purged with nitrogen (×3) and then heated at 95° C. overnight. The reaction mixture was diluted with $H_2O$ and extracted with EtOAc. The organic phase was dried with $MgSO_4$ and the solvent was removed under reduced pressure. Purification by FCC, eluting with 0-100% EtOAc/cyclohexane followed by further purification by FCC, eluting with 0-10% 2N $NH_3$ in MeOH/DCM afforded the title compound (195 mg, 56%).

$^1$H NMR (400 MHz, $CDCl_3$): 1.12 (3H, t, J=7.0 Hz), 1.36 (9H, s), 2.11-2.24 (3H, m), 2.45-2.54 (1H, m), 3.77-3.97 (6H, m), 4.17-4.33 (2H, m), 4.52-4.68 (2H, m), 5.16-5.23 (1H, m), 5.42-5.47 (1H, m), 7.14 (1H, br s), 7.22-7.40 (4H, m), 7.50-7.53 (1H, m), 7.80 (1H, dd, J=9.8, 0.6 Hz), 8.16 (1H, br s), 8.77 (1H, br s), 9.21 (1H, br s).

Intermediate AE. Ethyl 4-(tert-butyl)-6-(3-((1S,4R)-4-((3-((S)-2-methylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylate

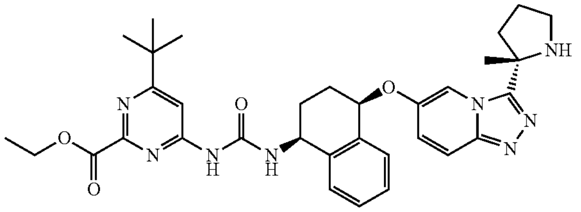 [SMILES: CCOC(=O)c1nc(NC(=O)N[C@H]2CC[C@@H](Oc3ccc4nnc([C@]5(C)CCCN5)n4c3)c3ccccc32)cc(C(C)(C)C)n1]

a. tert-Butyl (S)-2-(2-(5-fluoropyridin-2-yl)hydrazine-1-carbonyl)-2-methylpyrrolidine-1-carboxylate (Intermediate AEa)

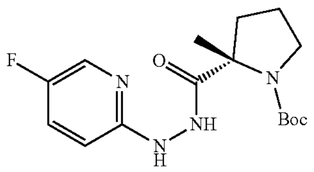 [SMILES: CC(C)(C)OC(=O)N1CCC[C@@]1(C)C(=O)NNc1ccc(F)cn1]

A solution of N-Boc-2-methyl-L-proline (CAS: 103336-06-7, 5.9 g, 38.7 mmol), (5-fluoro-2-pyridyl)hydrazine (WO 2014/195402, which is incorporated herein by reference in its entirety, 5.8 g, 46.4 mmol) and HOBt hydrate (0.63 g, 4.6 mmol) in DCM (100 ml) was treated with EDC.HCl (9.60 g, 50.3 mmol). The reaction mixture was stirred at RT overnight. The reaction mixture was partitioned between 2-methyltetrahydrofuran and $H_2O$. The aqueous phase was extracted with 2-methyltetrahydrofuran, the combined organic phases were dried with $MgSO_4$ and the solvent was removed under reduced pressure to afford the title compound (Crude taken forward assuming quantitative yield: 13.0 g, 100%).

LCMS (Method 4): Rt 1.28 min, m/z 339 [$MH^+$].

b. tert-Butyl (S)-2-(6-fluoro-[1,2,4]triazolo[4,3-a]pyridin-3-yl)-2-methylpyrrolidine-1-carboxylate (Intermediate AEb)

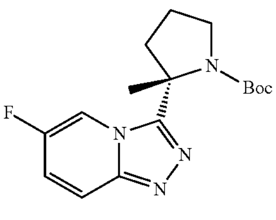 [SMILES: CC(C)(C)OC(=O)N1CCC[C@@]1(C)c1nnc2ccc(F)cn12]

A solution of Intermediate AEa (13 g, 38.7 mmol), triphenylphosphine (20.3 g, 77.4 mmol) and TEA (22 ml, 155.0 mmol) in 2-methyltetrahydrofuran (150 ml) was treated with hexachloroethane (18.1 g, 77.4 mmol). The reaction mixture was stirred at RT overnight. The reaction mixture was partitioned between 2-methyltetrahydrofuran and $H_2O$ and the two phases were separated. The aqueous phase was extracted with 2-methyltetrahydrofuran and the combined organic phases was dried with $MgSO_4$. The solvent was removed under reduced pressure and the residue was purified by FCC, eluting with 0-100% EtOAc/Cyclohexane to afford the title compound (15 g, >100%). LCMS (Method 4): Rt 1.11 min, m/z 321 [$MH^+$].

c. (S)-6-Fluoro-3-(2-methylpyrrolidin-2-yl)-[1,2,4]triazolo[4,3-a]pyridine (Intermediate AEc)

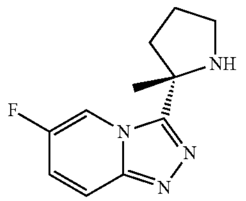 [SMILES: C[C@@]1(c2nnc3ccc(F)cn23)CCCN1]

A solution of Intermediate AEb (15 g, 38.7 mmol) in DCM (50 ml) was treated with TFA (50 ml) and the reaction mixture was stirred at RT overnight. The solvent was evaporated. The residue was purified by FCC, eluting with 0-10% 2N $NH_3$ in MeOH/DCM. The resulting solid was triturated with MeCN and the mother liquors were evaporated and triturated with MeCN (×3) to afford the title compound (2.5 g, 30%).

LCMS (Method 4): Rt 1.18 min, m/z 221 [$MH^+$].

d. (1S,4R)-4-((3-((S)-2-Methylpyrrolidin-2-yl)-[1,2,4]triazolo[4,3-a]pyridin-6-yl)oxy)-1,2,3,4-tetrahydronaphthalen-1-amine (Intermediate AEd)

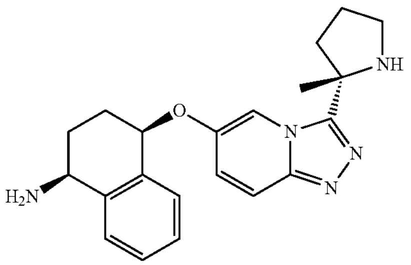 [SMILES: C[C@@]1(c2nnc3ccc(O[C@@H]4CC[C@H](N)c5ccccc54)cn23)CCCN1]

A stirred solution of Intermediate AEc (1.1 g, 5 mmol), (1R,4S)-4-amino-1,2,3,4-tetrahydro-naphthalen-1-ol (WO 2014/195402, which is incorporated herein by reference in its entirety, 0.82 g, 5 mmol) in dry DMF (15 ml) was treated with NaH (60% dispersion in oil, 0.6 g, 15.0 mmol) and the reaction mixture was heated to 60° C. overnight. The reaction mixture was cooled at RT, quenched with MeOH and $H_2O$. The aqueous phase was extracted with DCM and the solvent was removed under reduced pressure. Purification by FCC, eluting with 0-10% 2N $NH_3$ in MeOH/DCM followed by further purification, eluting with 0-10% 2N $NH_3$ afforded the title compound (590 mg, 32%).

LCMS (Method 4): Rt 1.40 min, m/z 364 [$MH^+$].

e. 1-((1S,4R)-4-((3-((S)-2-Methylpyrrolidin-2-yl)-[1,2,4]triazolo[4,3-a]pyridin-6-yl)oxy)-1,2,3,4-tetrahydronaphthalen-1-yl)urea (Intermediate AEe)

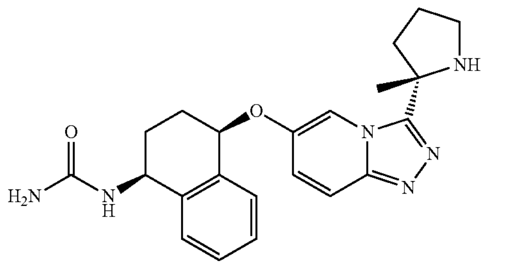 [SMILES: C[C@@]1(c2nnc3ccc(O[C@@H]4CC[C@H](NC(N)=O)c5ccccc54)cn23)CCCN1]

A solution of Intermediate AEd (278 mg, 0.76 mmol) in THF (10 ml) was treated with (trimethylsilyl)isocyanate (71 μl, 0.84 mmol) and the reaction mixture was stirred at RT for 2 h. A further aliquot of (trimethylsilyl)isocyanate (6 μl, 0.08 mmol) was added and the reaction mixture was stirred at RT overnight. The reaction mixture was quenched with methanol and stirred for 3 h and the solvents were removed under reduced pressure. Purification by FCC, eluting with 0-10% 2N $NH_3$ in MeOH/DCM afforded the title compound (202 mg, 65%).

LCMS (Method 4): Rt 1.29 min, m/z 407 [$MH^+$].

f. Intermediate AE

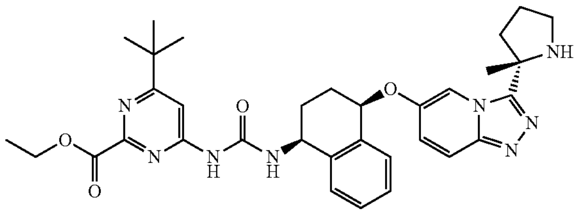 [SMILES: CCOC(=O)c1nc(NC(=O)N[C@H]2CC[C@@H](Oc3ccc4nnc([C@]5(C)CCCN5)n4c3)c3ccccc32)cc(C(C)(C)C)n1]

A solution of Intermediate AEe (202 mg, 0.5 mmol) in dioxane (10 ml) was treated with Intermediate 1d (121 mg, 0.5 mmol), $Pd(OAc)_2$ (5.6 mg, 0.03 mmol), XantPhos (29 mg, 0.05 mmol) and $Cs_2CO_3$ (228 mg, 0.7 mmol). The reaction mixture was evacuated and purged with argon (×3) and then heated at 95° C. for 5.5 h. The reaction mixture was cooled to RT and the solvent was removed under reduced pressure. The residue was partitioned between $H_2O$ and DCM and the two phases were separated. The aqueous phase was extracted with DCM and the combined organic phases were evaporated under reduced pressure. Purification by FCC, eluting with 0-10% 2N $NH_3$ in MeOH/DCM afforded the title compound (37 mg, 12%).

LCMS (Method 4): Rt 1.90 min, m/z 613 [$MH^+$].

Intermediate AF. 2,2,2-Trichloethyl(6-(tert-butyl)-2-(methylthio)pyrimidin-4-yl)carbamate (Intermediate AF)

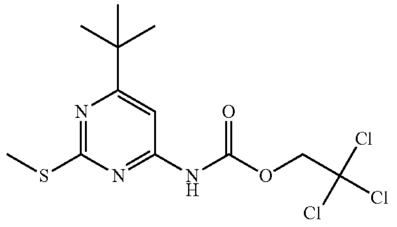 [SMILES: CSc1nc(NC(=O)OCC(Cl)(Cl)Cl)cc(C(C)(C)C)n1]

a. 6-(tert-Butyl)-2-(methylthio)pyrimidin-4-amine (Intermediate AFa)

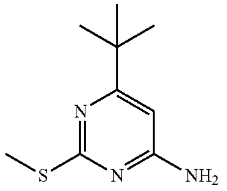

A partial suspension of Intermediate ZZb (50 mg, 0.23 mmol) in IPA (0.7 mL) was added with ammonia solution (0.14 mL, 33% in $H_2O$) and the reaction mixture was warmed under microwave irradiation at 150° C. for 10 hours. Another aliquot of ammonia solution (0.30 mL, 33% in $H_2O$) was added and the reaction mixture was warmed under microwave irradiation at 180° C. for a further 1 hour. The solvent was removed under reduced pressure and the resulting gum was eluted onto SCX-2 ion exchange resin in MeOH followed by 2N ammonia in MeOH. The methanolic ammonia fraction was evaporated under reduced pressure to afford the title compound (33 mg, 72%).

$^1H$ NMR (300 MHz, $CDCl_3$): 1.26 (9H, s), 2.51 (3H, s), 4.70 (2H, br s), 6.09 (1H, s).

b. Intermediate AF

A stirred solution of Intermediate AFa (28 mg, 0.14 mmol) in dioxan (1.4 mL) was added with triethylamine (30 μL, 0.21 mmol) and phenylchloroformate (20 μL, 0.16 mmol), then warmed to 150° C. for 0.5 hours under microwave irradiation. 2,2,2-trichloroethylchloroformate (22 μL, 0.16 mmol) was added and the reaction mixture was warmed for 1 hour to 150° C. under microwave irradiation. The resulting mixture was allowed to cool to 20° C. and filtered, washing with dioxan. The liquors were partitioned with EtOAc and water and the two phases were separated. The aqueous phase was extracted with EtOAc (×2) and the combined organic layers were washed with 10% citric acid solution, saturated $NaHCO_3$ solution and brine, dried with $Na_2SO_4$ and the solvent was removed under reduced pressure. Purification by FCC eluting 0-5% EtOAc in cyclohexane afforded the title compound (25 mg, 56%).

$^1H$ NMR (300 MHz, $CDCl_3$): 1.33 (9H, s), 2.54 (3H, s), 4.83 (2H, s), 7.50 (1H, br s), 7.59 (1H, s).

Intermediate AG. Ethyl 4-(tert-butyl)-6-(3-((1S,4R)-4-((3-isobutyl-[1,2,4]triazolo[4,3-a]pyridine-6-yl)oxy)-1,2,3,4-tetrahydronaphthalen-1-yl)ureido)pyrimidine-2-carboxylate

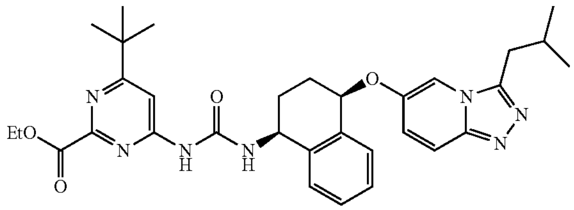 [SMILES: CCOC(=O)c1nc(NC(=O)N[C@H]2CC[C@@H](Oc3ccc4nnc(CC(C)C)n4c3)c3ccccc32)cc(C(C)(C)C)n1]

a. N'-(5-Fluoropyridin-2-yl)-3-methylbutanehydrazine (Intermediate AGa)

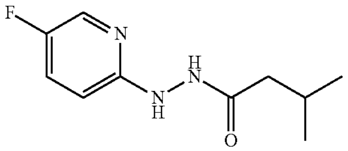

A solution of isovaleric acid (8.02 g, 78.62 mmol) in DCM (120 ml) was treated with EDC (16.62 g, 86.56 mmol), HOBt hydrate (1.06 g, 7.85 mmol) and (5-fluoro-2-pyridyl)hydrazine (10.0 g, 78.74 mmol). The reaction mixture was stirred at 20° C. for 18 hours and then diluted with DCM and water. The two layers were separated and the organic phase was dried with $MgSO_4$. The solvent was removed under reduced pressure. Purification by FCC, eluting 0-100% EtOAc in cyclohexane, followed by trituration with diethyl ether afforded the title compound (3.49 g, 21%).

LCMS (Method 4): Rt=0.94 min, m/z 212 [$M+H^+$], m/z 234 [$M+Na^+$].

b. 6-Fluoro-3-isobutyl-[1,2,4]triazolo[4,3-a]pyridine (Intermediate AGb)

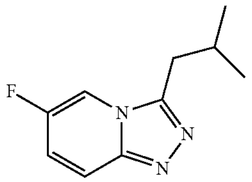

A solution of Intermediate AGa (3.39 g, 16.5 mmol) in 2-methyltetrahydrofuran (70 mL) was treated with triphenylphosphine (4.33 g, 33.08 mmol), triethylamine (6.67 g, 66.0 mmol) and cooled to 0° C. before hexachloroethane (7.84 g, 33.08 mmol) was added. The reaction mixture was allowed to warm to 20° C. overnight. The reaction mixture was filtered, washing the precipitate with diethyl ether. The liquors were washed with water, dried over solid $MgSO_4$ and the solvent was removed under reduced pressure. Purification by FCC eluting with 0-10% MeOH/DCM followed by trituration with diethyl ether afforded the title compound (2.60 g, 81%).

$^1$H NMR (300 MHz, $CDCl_3$): 1.05 (6H, d, J=6.64 Hz), 2.22-2.37 (1H, m), 2.94 (2H, d, J=7.23 Hz), 7.17 (1H, dt, J=2.2, 7.5 Hz), 7.75 (1H, q, J=4.9 Hz), 7.81 (1H, t, J=2.4 Hz). LCMS (Method 4): Rt=0.96 min, m/z 194 [$M+H^+$], m/z 216 [$M+Na^+$].

c. (1S,4R)-4-((3-Isobutyl-[1,2,4]triazolo[4,3-a]pyridine-6-yl)oxy)-1,2,3,4-tetrahydronaphthalen-1-amine (Intermediate AGc)

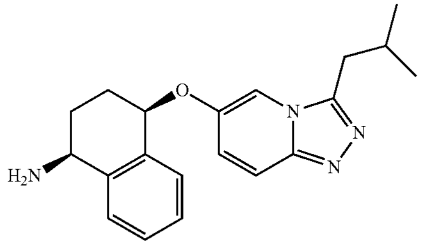 [SMILES: CC(C)Cc1nnc2ccc(O[C@@H]3CC[C@H](N)c4ccccc43)cn12]

A solution of Intermediate AGb (2.60 g, 13.47 mmol), (1R,4S)-4-amino-1,2,3,4-tetrahydronaphthalen-1-ol (2.20 g, 13.47 mmol) and 18-crown-6 ether (1.77 g, 6.73 mmol) in 2-methyltetrahydrofuran (30 mL) was degassed for 10 minutes under sonication bubbling argon through the mixture. The reaction mixture was cooled at 0° C. and potassium tert-butoxide (1.81 g, 16.16 mmol) was added. The reaction mixture was allowed to warm to 20° C. overnight, diluted with EtOAc and washed with water. The organic phase was dried with $MgSO_4$. The solvent removed under reduced pressure. Purification by FCC eluting with 0-10% 2N $NH_3$ in MeOH/DCM afforded the title compound (3.47 g, 76%).

$^1$H NMR (300 MHz, $CDCl_3$): 1.02 (6H, dd, J=6.6, 0.8 Hz), 1.87-1.99 (2H, m), 2.00-2.15 (3H, m), 2.18-2.31 (1H, m), 2.32-2.44 (1H, m), 2.90 (2H, dd, J=3.2, 7.3 Hz), 4.00 (1H, dd, J=5.0, 8.1 Hz), 5.25 (1H, t, J=4.6 Hz), 7.11 (1H, dd, J=2.1, 9.9 Hz), 7.22-7.34 (2H, m), 7.35-7.44 (1H, m), 7.46 (1H, d, J=1.4 Hz), 7.60 (1H, d, J=7.8 Hz), 7.68 (1H, d, J=9.9 Hz). LCMS (Method 4): Rt=0.76 min, m/z 337 [$M+H^+$], m/z 359 [$M+Na^+$].

d. 1-((1S,4R)-4-((3-Isobutyl-[1,2,4]triazolo[4,3-a]pyridine-6-yl)oxy)-1,2,3,4-tetrahydronaphthalen-1-yl)urea (Intermediate AGd)

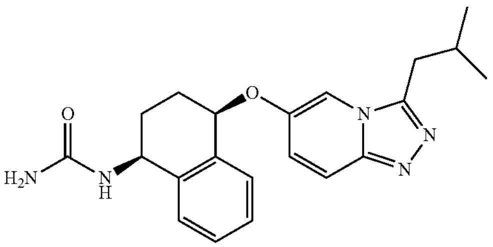 [SMILES: CC(C)Cc1nnc2ccc(O[C@@H]3CC[C@H](NC(N)=O)c4ccccc43)cn12]

A solution of triphosgene (970 mg, 3.27 mmol) in DCM (15 mL) under nitrogen was cooled to −10° C. and a solution of Intermediate AGc (1.0 g, 2.97 mmol) and triethylamine (1.20 g, 11.88 mmol) in DCM (15 mL) was dropwise added keeping the temperature <−10° C. This solution was stirred at 0° C. for one hour before a solution of $NH_3$ in MeOH (2N, 18 mL, 35.64 mmol) pre-cooled to 0° C. was added. The reaction mixture was allowed to warm to 20° C. The mixture was partitioned between water and DCM and the two phases were separated. The aqueous phase was extracted with DCM (×2) and the combined organic layers were dried over solid $MgSO_4$. The solvent removed under reduced pressure. Purification by FCC eluting with 0-10% 2N $NH_3$ in MeOH/DCM afforded the title compound (970 mg, 86%).

$^1$H NMR (300 MHz, $CDCl_3$): 0.98 (6H, dd, J=4.7 Hz), 1.98-2.20 (4H, m), 2.29-2.39 (1H, m), 2.81 (2H, t, J=6.2 Hz), 4.86 (2H, br s), 5.03-5.12 (1H, m), 5.25 (1H, t, J=4.3 Hz), 5.84 (1H, d, J=8.7 Hz), 7.00 (1H, dd, J=2.1, 9.9 Hz), 7.22-7.38 (4H, m), 7.47-7.56 (2H, m). LCMS (Method 4): Rt=1.00 min, m/z 380.3 [M+H$^+$], m/z 402.2 [M+Na$^+$].

e. Intermediate AG

A solution of intermediate AGd (950 mg, 2.50 mmol), Intermediate 1d (610 mg, 2.50 mmol), $Pd(Ac)_2$ (30 mg, 0.125 mmol), Xantphos (150 mg, 0.25 mmol) and cesium carbonate (1.14 g, 0.35 mmol) in dioxan (15 mL) was degassed by bubbling argon through the mixture for 5 minutes under sonication. The reaction mixture was heated at 90° C. for 20 hours. The reaction mixture was cooled at RT, filtered through a pad of Celite®, washing the precipitate with DCM and MeOH. The liquor was evaporated under reduced pressure. Purification by FCC eluting 0 to 10% MeOH in DCM afforded the title compound (1.14 g, 78%).

$^1$H NMR (300 MHz, $CDCl_3$): 1.02 (6H, dd, J=2.1, 6.7 Hz), 1.12 (3H, t, J=7.1 Hz), 1.36 (9H, s), 2.11-2.32 (4H, m), 2.33-2.46 (1H, m), 2.90 (2H, q, J=3.9 Hz), 4.12-4.34 (2H, m), 5.19-5.35 (2H, m), 6.90-6.98 (1H, m), 7.11 (1H, dd, J=2.1, 9.9 Hz), 7.14-7.42 (5H, m), 7.50 (1H, d, J=1.3 Hz), 7.57 (1H, d, J=7.7 Hz), 7.79 (1H, d, J=9.9 Hz). LCMS (Method 4): Rt=1.48 min, m/z 586 [M+H$^+$], m/z 608 [M+Na$^+$].

Intermediate AH. Ethyl 4-(tert-butyl)-6-(3-((1S,4R)-4-((3-(1-methyloxetan-3-yl)-[1,2,4]triazolo[4,3-a]pyridine-6-yl)oxy)-1,2,3,4-tetrahydronaphthalen-1-yl)ureido)pyrimidine-2-carboxylate

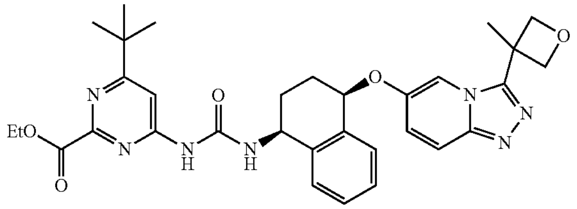 [SMILES: CCOC(=O)c1nc(NC(=O)N[C@H]2CC[C@@H](Oc3ccc4nnc(C5(C)COC5)n4c3)c3ccccc32)cc(C(C)(C)C)n1]

a. N'-(5-Fluoropyridin-2-yl)-3-methyloxetene-3-carbohydrazide (Intermediate AHa)

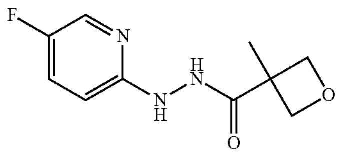 [SMILES: CC1(C(=O)NNc2ccc(F)cn2)COC1]

A solution of 3-methoxy-2,2-dimethylpropionic acid (5.00 g, 43.10 mmol) and (5-fluoro-2-pyridyl)hydrazine (5.47 g, 43.10 mmol) in DCM (100 ml) was treated with HOBt hydrate (0.66 g, 4.30 mmol), and cooled in an ice bath before adding EDC (8.25 g, 43.1 mmol). The reaction mixture was stirred at 0° C. for 5 minutes and at RT for 1 hour and then the solvent was removed under reduced pressure. The residue was partitioned between water and 2-methyltetrahydrofuran. The two phases were separated and the organic layer was washed with water, brine and dried with $Na_2SO_4$. The solvent was removed under reduced pressure. The residue was dissolved in DCM, stirred with flash silica and filtered washing the silica with DCM. The solvent was removed under reduced pressure and the resulting brown solid was triturated with diethyl ether to afford the title compound (5.60 g, 58%).

$^1$H NMR (300 MHz, $CDCl_3$): 1.67 (3H, s), 4.51 (2H, d, J=6.1 Hz), 4.97 (2H, d, J=6.1), 6.67 (1H, dd, J=3.5, 9.0 Hz), 6.78 (1H, d, J=3.9 Hz), 7.31 (1H, dt, J=2.9, 7.8 Hz), 8.03 (1H, d, J=2.9 Hz), 8.09 (1H, s).

b. 6-Fluoro-3-(1-methyloxetan-3-yl)-[1,2,4]triazolo[4,3-a]pyridine (Intermediate AHb)

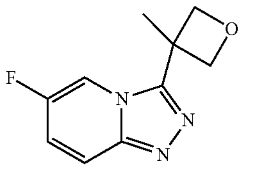

A solution of Intermediate AHa (5.60 g, 24.90 mmol) in 2-methyltetrahydrofuran (100 mL) was treated with triphenylphosphine (13.00 g, 49.60 mmol), triethylamine (10.10 g, 100.0 mmol) and finally hexachloroethane (14.1 g, 59.50 mmol) was added. The reaction mixture was stirred for 1 hour and then washed with water, 10% citric acid solution and aqueous 1N HCl solution. The HCl layer was basified with solid potassium carbonate and extracted into DCM (×3). The combined DCM layers were dried with $Na_2SO_4$ and the solvent was removed under reduced pressure to afford the title compound (1.00 g, 19%).

$^1$H NMR (300 MHz, $CDCl_3$): 1.98 (3H, s), 4.90 (2H, d, J=6.4 Hz), 5.17 (2H, d, J=6.4 Hz), 7.21-7.25 (1H, m), 7.82 (1H, dq, J=0.8, 5.0 Hz), 8.23 (1H, dt, J=0.8, 2.2 Hz).

c. (1S,4R)-4-((3-Methyloxetan-3-yl)-[1,2,4]triazolo[4,3-a]pyridine-6-yl)oxy)-1,2,3,4-tetrahydronaphthalen-1-amine (Intermediate AHc)

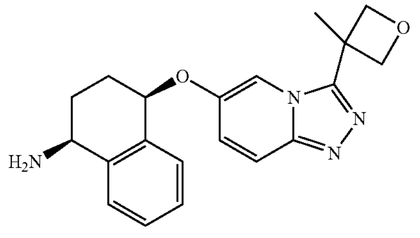 [SMILES: CC1(c2nnc3ccc(O[C@@H]4CC[C@H](N)c5ccccc54)cn23)COC1]

A solution of Intermediate AHb (1.00 g, 4.83 mmol), (1R,4S)-4-amino-1,2,3,4-tetrahydronaphthalen-1-ol (790 mg, 4.83 mmol) and 18-crown-6 ether (130 mg, 0.50 mmol) in 2-methyltetrahydrofuran (50 mL) was degassed for 10 minutes under sonication bubbling argon through the mixture. The mixture was then cooled to 0° C. and potassium tert-butoxide (620 mg, 5.54 mmol) was added. The reaction mixture was allowed to warm to 20° C. overnight with stirring. This mixture was washed with water and 10% citric acid solution. The citric acid solution was washed with diethyl ether, then basified with solid potassium carbonate and extracted with DCM (×2). The combined organic layers were dried with $Na_2SO_4$ to afford the title compound (970 mg, 57%).

$^1$H NMR (300 MHz, $CDCl_3$): 1.88-2.11 (6H, m), 2.34-2.43 (1H, m), 3.98-4.02 (1H, m), 4.82 (2H, q, J=6.3 Hz), 5.15 (2H, q, J=3.0 Hz), 5.26 (1H, t, J=4.7 Hz), 7.17 (1H, dd, J=2.1, 9.9 Hz), 7.22-7.31 (2H, m), 7.38 (1H, dt, J=1.9, 6.8 Hz), 7.59 (1H, d, J=7.8 Hz), 7.75 (1H, dd, J=0.8, 9.9 Hz), 7.79 (1H, d, J=1.3 Hz), plus two protons not observed.

d. 1-((1S,4R)-4-((3-(1-Methyloxetan-3-yl)-[1,2,4]triazolo[4,3-a]pyridine-6-yl)oxy)-1,2,3,4-tetrahydronaphthalen-1-yl)urea (Intermediate AHd)

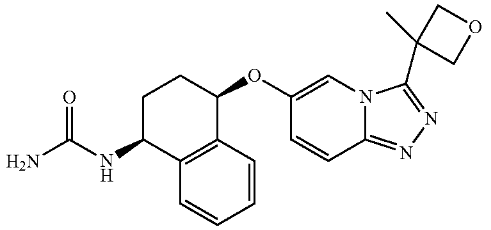 [SMILES: CC1(c2nnc3ccc(O[C@@H]4CC[C@H](NC(N)=O)c5ccccc54)cn23)COC1]

A solution of triphosgene (470 mg, 1.58 mmol) in DCM (8 mL) under nitrogen was cooled to −10° C. and a solution of Intermediate AHc (500 mg, 1.43 mmol) and triethylamine (580 mg, 5.72 mmol) in DCM (8 mL) was dropwise added keeping the temperature <−10° C. This solution was stirred at 0° C. for one hour before a solution of $NH_3$ in MeOH (2N, 8.6 mL, 17.10 mmol) pre-cooled to 0° C. was added. The reaction mixture was allowed to warm to 20° C. The mixture was partitioned between water and DCM and the two phases were separated. The aqueous phase was extracted with DCM (×2) and the combined organic layers were dried over solid $MgSO_4$. The solvent removed under reduced pressure and purification by FCC eluting 0 to 10% (2N $NH_3$ in MeOH) in DCM afforded the title compound (480 mg, 85%).

$^1$H NMR (300 MHz, $CDCl_3$): 1.97 (3H, s), 2.05-2.21 (3H, m), 2.33-2.45 (1H, m), 4.53 (2H, s), 4.71 (2H, q, J=6.7 Hz), 4.82 (1H, d, J=6.8 Hz), 4.97-5.05 (1H, m), 5.09 (1H, d, J=6.6 Hz), 5.32-5.38 (1H, m), 5.78 (1H, d, J=8.2 Hz), 7.16 (1H, dd, J=2.1, 9.9 Hz), 7.19-7.24 (2H, m), 7.28-7.34 (1H, m), 7.46 (11H, d, J=8.0 Hz), 7.72 (1H, d, J=9.9 Hz), 7.75 (1H, d, J=1.3 Hz).

e. Intermediate AH

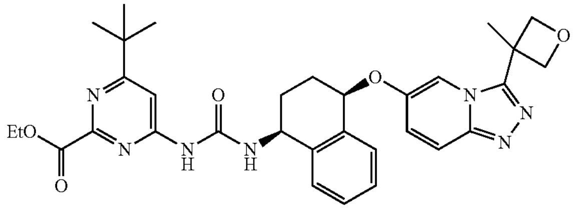 [SMILES: CCOC(=O)c1nc(NC(=O)N[C@H]2CC[C@@H](Oc3ccc4nnc(C5(C)COC5)n4c3)c3ccccc32)cc(C(C)(C)C)n1]

A solution of Intermediate AHd (480 mg, 1.22 mmol), Intermediate 1d (300 mg, 1.22 mmol), palladium(II)acetate (14 mg, 0.06 mmol), Xantphos (70 mg, 0.120 mmol) and cesium carbonate (560 mg, 1.70 mmol) in dioxan (8 mL) was degassed by bubbling argon through the mixture for 5 minutes under sonication. The reaction mixture was warmed to 90° C. for 20 hours. The reaction mixture was filtered through a pad of Celite® washing the precipitate with DCM and EtOH. The solvents were removed under reduced pressure and the residue was purified by FCC eluting 0 to 10% EtOH in DCM to afford the title compound (520 mg, 71%).

LCMS (Method 4): Rt=1.39 min, m/z 600 [M+H$^+$], m/z 622 [M+Na$^+$].

Intermediate AI. Ethyl 4-(tert-butyl)-6-(3-((1S,4R)-4-((3-neopentyl)-[1,2,4]triazolo[4,3-a]pyridine-6-yl)oxy)-1,2,3,4-tetrahydronaphthalen-1-yl)ureido)pyrimidine-2-carboxylate

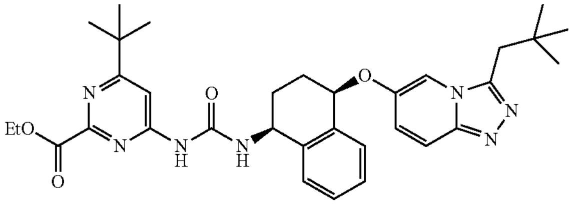 [SMILES: CCOC(=O)c1nc(NC(=O)N[C@H]2CC[C@@H](Oc3ccc4nnc(CC(C)(C)C)n4c3)c3ccccc32)cc(C(C)(C)C)n1]

a. N'-(5-Fluoropyridin-2-yl)-3,3-dimethylbutanehydrazide (Intermediate AIa)

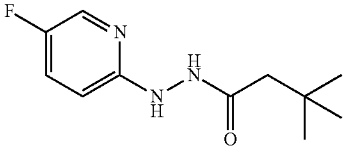 [SMILES: CC(C)(C)CC(=O)NNc1ccc(F)cn1]

A solution of 3,3-dimethylbutanoic acid (5.00 g, 43.10 mmol) and (5-fluoro-2-pyridyl)hydrazine (5.47 g, 43.10 mmol) in DCM (100 ml) was treated with HOBt hydrate (0.66 g, 4.30 mmol), and cooled in an ice bath before adding EDC (8.25 g, 43.1 mmol). The reaction mixture was warmed at RT and stirred for 1 hour and then the solvent was removed under reduced pressure. The residue was partitioned between water and 2-methyltetrahydrofuran and the two phases were separated. The organic layer was extracted with 1N HCl solution. The combined aqueous layers were washed with diethyl ether and basified with solid potassium carbonate and then extracted with DCM (×3). The combined organic layers were dried over solid sodium sulphate and the solvent was removed under reduced pressure. The resulting solid was triturated with diethyl ether to afford the title compound (6.60 g, 68%).

$^1$H NMR (300 MHz, $CDCl_3$): 1.07 (9H, s), 2.14 (2H, s), 6.67 (1H, dd, J=3.5, 9.0), 6.84 (1H, d, J=3.6 Hz), 7.28 (1H, dt, J=2.9, 7.8 Hz), 7.65 (1H, s), 8.02 (1H, d, J=2.9 Hz).

b. 6-Fluoro-3-neopentyl-[1,2,4]triazolo[4,3-a]pyridine (Intermediate AIb)

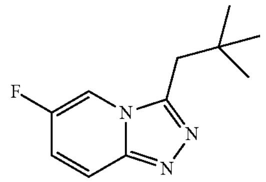

A solution of Intermediate AIa (6.60 g, 29.30 mmol) in 2-methyltetrahydrofuran (300 mL) was treated with triphenylphosphine (15.40 g, 58.80 mmol), triethylamine (11.90 g, 117.8 mmol) and finally hexachloroethane (13.9 g, 58.60 mmol) was added. The reaction mixture was stirred for 1 hour and then it was washed with water and 10% citric acid solution. The organic phase was extracted with 1N HCl aqueous solution and this layer was washed with diethyl ether, basified with solid $K_2CO_3$ and extracted into DCM (×3). The combined organic layers were dried with $Na_2SO_4$ and the solvent was removed under reduced pressure to afford the title compound (5.23 g, 86%).

$^1H$ NMR (300 MHz, $CDCl_3$): 1.08 (9H, s), 2.97 (2H, s), 7.16 (1H, dq, J=2.2, 7.5 Hz), 7.8 (1H, dq, J=0.8, 4.8 Hz), 7.88 (1H, dq, J=0.8, 2.2 Hz).

c. (1S,4R)-4-((3-Neopentyl)-[1,2,4]triazolo[4,3-a]pyridine-6-yl)oxy)-1,2,3,4-tetrahydronaphthalen-1-amine (Intermediate AIc)

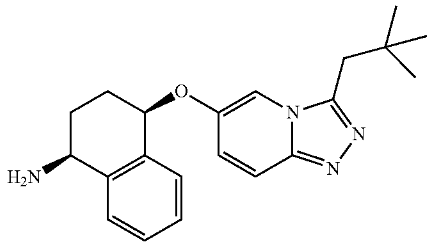 [SMILES: CC(C)(C)Cc1nnc2ccc(O[C@@H]3CC[C@H](N)c4ccccc43)cn12]

A solution of Intermediate AIb (5.00 g, 24.20 mmol), (1R,4S)-4-amino-1,2,3,4-tetrahydronaphthalen-1-ol (3.94 g, 24.2 mmol) and 18-crown-6 ether (640 mg, 2.40 mmol) in 2-methyltetrahydrofuran (150 mL) was degassed for 10 minutes under sonication bubbling argon through the mixture. The mixture was then cooled to 0° C. and potassium tert-butoxide (3.10 g, 27.70 mmol) was added. The reaction mixture was allowed to warm to 20° C. overnight. This mixture was washed with water and extracted with 10% citric acid solution. The aqueous phase was washed with diethyl ether, then basified with $K_2CO_3$ and extracted with DCM (×3). The combined organic layers were dried over $Na_2SO_4$ and the solvent was removed under reduced pressure. This product was triturated with diethyl ether to afford the title compound (7.18 g, 85%).

$^1H$ NMR (300 MHz, $CDCl_3$): 1.04 (9H, s), 1.87-1.99 (1H, m), 1.99-2.13 (2H, m), 2.32-2.43 (1H, m), 2.93 (2H, d, J=5.8 Hz), 4.00 (1H, q, J=5.0 Hz), 5.24 (1H, t, J=4.6 Hz), 7.11 (1H, dd, J=2.1, 9.9 Hz), 7.22-7.33 (2H, m), 7.38 (1H, dt, J=1.7, 7.2 Hz), 7.53 (1H, d, J=1.4 Hz), 7.59 (1H, d, J=7.8 Hz), 7.69 (1H, dd, J=0.8, 9.9 Hz), two protons were not seen.

d. 1-((1S,4R)-4-((3-(3-Neopentyl)-[1,2,4]triazolo[4,3-a]pyridine-6-yl)oxy)-1,2,3,4-tetrahydronaphthalen-1-yl)urea (Intermediate AId)

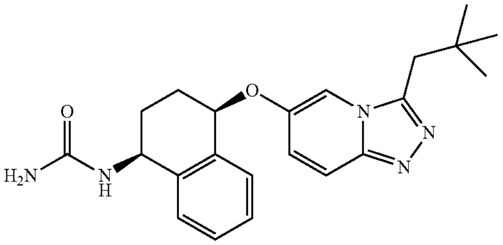 [SMILES: CC(C)(C)Cc1nnc2ccc(O[C@@H]3CC[C@H](NC(N)=O)c4ccccc43)cn12]

A solution of triphosgene (470 mg, 1.58 mmol) in DCM (8 mL) under nitrogen was cooled to −10° C. and a solution of Intermediate AIc (500 mg, 1.43 mmol) and triethylamine (580 mg, 5.72 mmol) in DCM (8 mL) was dropwise added keeping the temperature <−10° C. This solution was stirred at 0° C. for one hour before 2N $NH_3$ in MeOH (8.6 mL, 17.10 mmol, pre-cooled to 0° C.) was added and the reaction mixture was allowed to warm to 20° C. The mixture was partitioned between water and DCM and the two phases were separated. The aqueous phase was extracted with DCM (×2) and the combined organic layers were dried over solid $MgSO_4$. The solvent was removed under reduced pressure and purification by FCC eluting 0 to 10% (2N $NH_3$ in MeOH) in DCM afforded the title compound (540 mg, 96%).

LCMS (Method 4): Rt=1.06 min, m/z 394 [$M+H^+$], m/z 416 [$M+Na^+$].

e. Intermediate AI

A solution of Intermediate AId (540 mg, 1.37 mmol), Intermediate 1d (330 mg, 1.37 mmol), palladium(II)acetate (15 mg, 0.07 mmol), Xantphos (80 mg, 0.140 mmol) and cesium carbonate (625 mg, 1.92 mmol) in dioxan (8 mL) was degassed by bubbling argon through the mixture for 5 minutes under sonication. The reaction mixture was warmed to 90° C. for 20 hours, cooled at RT and filtered through a pad of Celite® washing the precipitate with DCM and EtOH. The solvents were removed under reduced pressure. Purification by FCC eluting 0 to 10% EtOH in DCM afforded the title compound (440 mg, 53%).

LCMS (Method 4): Rt=1.51 min, m/z 600 [$M+H^+$], m/z 622 [$M+Na^+$].

Intermediate AJ. Ethyl 4-(tert-butyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)pyrimidine-2-carboxylate

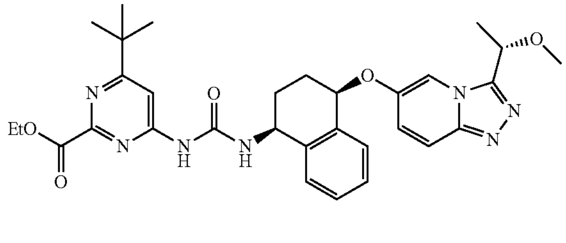 [SMILES: CCOC(=O)c1nc(NC(=O)N[C@H]2CC[C@@H](Oc3ccc4nnc([C@H](C)OC)n4c3)c3ccccc32)cc(C(C)(C)C)n1]

a. (S)—N'-(5-Fluoropyridin-2-yl)-2-methoxypropanehydrazide (Intermediate AJa)

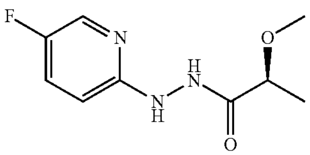

A stirred solution of (R)-2-methoxypropanoic acid (1.0 g, 9.6 mmol), in DCM (50 ml) was treated with EDC (2.4 g, 12.5 mmol), HOBt hydrate (400 mg, 1.15 mmol) and (5-fluoro-2-pyridyl)hydrazine (1.2 g, 11.5 mmol). After 2 hours the reaction mixture was washed with water and the organic layer was dried over solid magnesium sulphate. The solvent was removed under reduced pressure to afford the title compound which was used in the next step as crude.

LCMS (Method 4): Rt 0.80 min, m/z 214 [M+H$^+$], m/z 236 [M+Na$^+$].

b. (S)-6-Fluoro-3-(1-methoxyethyl)-[1,2,4]triazolo[4,3-a]pyridine (Intermediate AJb)

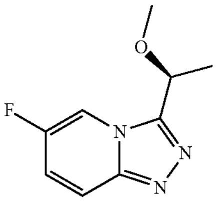

A solution of Intermediate AJa (2.04 g, 9.6 mmol mmol) in 2-methyltetrahydrofuran (150 mL) was treated with triphenylphosphine (5.03 g, 19.2 mmol), triethylamine (3.88 g, 38.4 mmol) and hexachloroethane (4.49 g, 19.2 mmol) stirring for 1 hour at RT. The reaction mixture was partitioned between water and 2-methyltetrahydrofuran and the two phases were separated. The aqueous phase was extracted with 2-methyltetrahydrofuran (×2). The combined organic layers were washed with 1N HCl solution (×3). The combined acidic layers were basified with solid sodium hydrogen carbonate and partitioned with DCM (×3). The combined DCM were passed through a phase separator and the solvent was removed under reduced pressure to afford the title compound (1.43 g, 76%).

LCMS (Method 4): Rt 1.15 min, m/z 196 [M+H$^+$].

c. (1S,4R)-4-((3-((S)-1-Methoxyethyl)-[1,2,4]triazolo[4,3-a]pyridin-6-yl)oxy)-1,2,3,4-tetrahydronaphthalen-1-amine (Intermediate AJc)

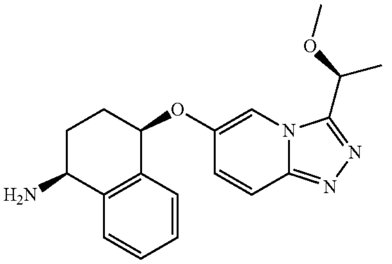 [SMILES: CO[C@@H](C)c1nnc2ccc(O[C@@H]3CC[C@H](N)c4ccccc43)cn12]

A solution of Intermediate AJb (1.43 g, 7.3 mmol), (1R,4S)-4-amino-1,2,3,4-tetrahydronaphthalen-1-ol (1.2 g, 7.3 mmol) and 18-crown-6 ether (482 mg, 1.8 mmol) in 2-methyltetrahydrofuran (160 mL) was added with potassium tert-butoxide (981 mg, 8.76 mmol). The reaction mixture was left overnight and washed with water, dried over solid $MgSO_4$ and the solvent removed under reduced pressure. Purification by FCC eluting 0 to 10% (2N $NH_3$ in MeOH) in DCM afforded the title compound (1.34 g, 55%).

LCMS (Method 4): Rt 1.43 min, m/z 339 [M+H$^+$].

d. 1-((1S,4R)-4-((3-((S)-1-Methoxyethyl)-[1,2,4]triazolo[4,3-a]pyridin-6-yl)oxy)-1,2,3,4-tetrahydronaphthalen-1-yl)urea (Intermediate AJd)

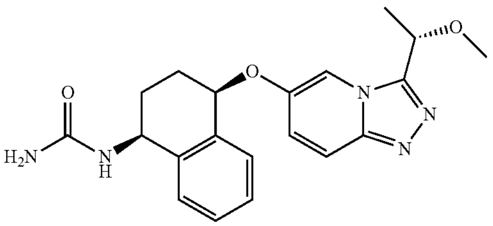 [SMILES: CO[C@@H](C)c1nnc2ccc(O[C@@H]3CC[C@H](NC(N)=O)c4ccccc43)cn12]

A stirred solution of Intermediate AJc (676 mg, 2.0 mmol) in THF (5 mL) was added with trimethylsilylisocyanate (255 mg, 2.2 mmol) and DCM to break up the solid formed. The reaction mixture was stirred for 18 hours and the solvent was removed under reduced pressure. Purification by FCC eluting 0 to 5% (2M $NH_3$ in MeOH) in DCM afforded the title compound (639 mg, 84%).

LCMS (Method 4): Rt 1.26 min, m/z 382 [M+H$^+$], m/z 404 [M+Na$^+$].

e. Intermediate AJ

A solution of Intermediate AJd (639 mg, 1.68 mmol), Intermediate 1d (406 mg, 1.68 mmol), palladium(II)acetate (38 mg, 0.168 mmol), Xantphos (194 mg, 0.34 mmol) and cesium carbonate (767 mg, 2.35 mmol) in dioxan (20 mL) was degassed by bubbling argon through the mixture for 5 minutes under sonication. The reaction mixture was warmed to 55° C. for 24 hours, cooled at RT and partitioned between water and DCM. The two phases were separated and the aqueous phase was extracted with DCM (×2). The combined organic phases were passed through a phase separator and the solvent was removed under reduced pressure. Purification by FCC eluting 0 to 8% (2M $NH_3$ in MeOH) in DCM afforded the title compound (651 mg, 65%), isolated as a mixture of ethyl and methyl esters (ratio ethyl/methyl 1:4)).

LCMS (Method 4): Ethyl ester: Rt 1.79 min, m/z 588 [$M+H^+$]; methyl ester: Rt 1.85 min, m/z 574 [$M+H^+$].

Intermediate AK. Ethyl 4-(tert-butyl)-6-(3-((1S,4R)-4-((3-(1-methylcyclobutyl)-[1,2,4]triazolo[4,3-a]pyridine-6-yl)oxy)-1,2,3,4-tetrahydronaphthalen-1-yl)ureido)pyrimidine-2-carboxylate

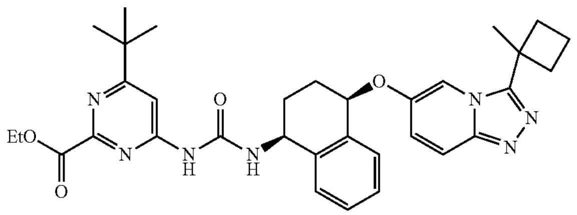 [SMILES: CCOC(=O)c1nc(NC(=O)N[C@H]2CC[C@@H](Oc3ccc4nnc(C5(C)CCC5)n4c3)c3ccccc32)cc(C(C)(C)C)n1]

a. N'-(5-Fluoropyridin-2-yl)-1-methylcyclobutane-1-carbohydrazide (Intermediate AKa)

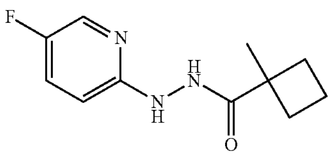 [SMILES: CC1(C(=O)NNc2ccc(F)cn2)CCC1]

A solution of 3-methoxy-2,2-dimethylpropionic acid (5.00 g, 43.90 mmol) and (5-fluoro-2-pyridyl)hydrazine (5.57 g, 43.90 mmol) in DCM (100 ml) was treated with HOBt hydrate (0.67 g, 4.40 mmol), and cooled in an ice bath before adding EDC (8.40 g, 43.90 mmol). The reaction mixture was warmed at RT and stirred for 1 hour. The solvent was removed under reduced pressure and the residue was partitioned between water and 2-methyltetrahydrofuran. The organic layer was washed with water and extracted with aqueous 1N HCl solution. The acidic layer was washed with diethyl ether, then basified with solid potassium carbonate and extracted with DCM (×3). The combined organic layers were dried over solid sodium sulphate and the solvent was removed under reduced pressure. This residue was triturated with diethyl ether to afford the title compound as a light purple solid (6.10 g, 62%).

$^1$H NMR (300 MHz, $CDCl_3$): 1.51 (3H, s), 1.80-1.94 (2H, m), 1.97-2.12 (1H, m), 2.44-2.56 (2H, m), 6.64 (1H, dd, J=3.5, 9.0 Hz), 6.71 (1H, d, J=3.9 Hz), 7.29 (1H, dt, J=2.9, 7.9 Hz), 7.65 (1H, d, J=3.1 Hz), 8.04 (1H, d, J=2.9 Hz).

b. 6-Fluoro-3-(1-methylcyclobutyl)-[1,2,4]triazolo[4,3-a]pyridine (Intermediate AKb)

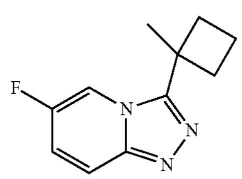

A solution of Intermediate AKa (5.60 g, 24.90 mmol) in 2-methyltetrahydrofuran (100 mL) was treated with triphenylphosphine (13.00 g, 49.60 mmol), triethylamine (10.10 g, 100.0 mmol) and hexachloroethane (14.1 g, 59.50 mmol). The reaction mixture was stirred for 1 hour and then it was washed with water, 10% citric acid solution and extracted with aqueous 1N HCl solution. The HCl layer was basified with solid potassium carbonate and extracted into DCM (×3). The combined organic layers were dried over solid sodium sulphate and the solvent was removed under reduced pressure to afford the title compound (1.00 g, 19%).

$^1$H NMR (300 MHz, $CDCl_3$): 1.98 (3H, s), 4.90 (2H, d, J=6.4 Hz), 5.17 (2H, d, J=6.4 Hz), 7.20-7.26 (1H, m), 7.82 (1H, dq, J=0.8, 5.0 Hz), 8.23 (1H, dt, J=0.8, 2.2 Hz), plus two protons not observed.

c. (1S,4R)-4-((1-Methylcyclobutyl)-[1,2,4]triazolo[4,3-a]pyridine-6-yl)oxy)-1,2,3,4-tetrahydronaphthalen-1-amine (Intermediate AKc)

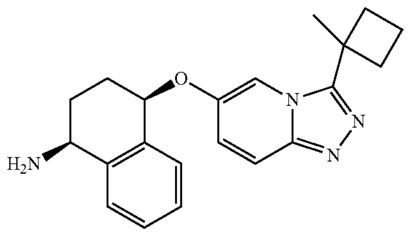 [SMILES: CC1(c2nnc3ccc(O[C@@H]4CC[C@H](N)c5ccccc54)cn23)CCC1]

A solution of Intermediate AKb (4.70 g, 22.90 mmol), (1R,4S)-4-amino-1,2,3,4-tetrahydronaphthalen-1-ol (3.74 g mg, 22.90 mmol) and 18-crown-6 ether (610 mg, 2.30 mmol) in 2-methyltetrahydrofuran (100 mL) was degassed for 10 minutes under sonication bubbling argon through the mixture. The mixture was then cooled to 0° C. and potassium tert-butoxide (2.95 g, 26.30 mmol) was added. The reaction mixture was allowed to warm to 20° C. overnight. This mixture was washed with water (×2) and extracted with 10% citric acid solution. The citric acid solution was washed with diethyl ether, then basified with solid potassium carbonate and extracted with DCM (×2). The combined organic layers were dried over solid sodium sulphate and the solvent was removed under reduced pressure to afford the title compound (7.98 g, 99%).

$^1$H NMR (300 MHz, $CDCl_3$): 1.61 (3H, s), 1.80-2.14 (4H, m), 2.14-2.42 (4H, m), 2.74-2.92 (2H, m), 3.99 (1H, q, J=5.1 Hz), 5.19 (1H, t, J=4.5 Hz), 7.12 (1H, dd, J=2.1, 6.9 Hz), 7.2-7.4 (4H, m), 7.60 (1H, d, J=7.8 Hz), 7.71 (1H, dd, J=0.8, 9.9 Hz), plus three protons not observed.

d. 1-((1S,4R)-4-((3-(1-Methylcyclobutyl)-[1,2,4]triazolo[4,3-a]pyridine-6-yl)oxy)-1,2,3,4-tetrahydronaphthalen-1-yl)urea (Intermediate AKd)

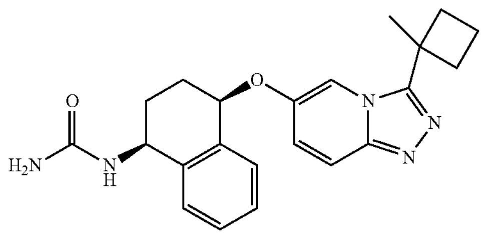 [SMILES: CC1(c2nnc3ccc(O[C@@H]4CC[C@H](NC(N)=O)c5ccccc54)cn23)CCC1]

A solution of triphosgene (470 mg, 1.58 mmol) in DCM (8 mL) under nitrogen was cooled to −10° C. and a solution of Intermediate AKc (500 mg, 1.43 mmol) and triethylamine (580 mg, 5.72 mmol) in DCM (8 mL) was dropwise added keeping the temperature <−10° C. This solution was stirred at 0° C. for one hour before 2N $NH_3$ in MeOH (8.6 mL, 17.10 mmol, pre-cooled to 0° C.) was added and the reaction mixture was allowed to warm to 20° C. The mixture was partitioned between water and DCM and the two phases were separated. The aqueous phase was extracted with DCM (×2) and the combined organic layers were dried over solid $MgSO_4$. The solvent was removed under reduced pressure and purification by FCC eluting 0 to 10% (2N $NH_3$ in MeOH) in DCM afforded the title compound (450 mg, 80%).

LCMS (Method 4): Rt=1.02 min, m/z 392 [$M+H^+$], m/z 414 [$M+Na^+$].

e. Intermediate AK

A solution of Intermediate AKd (450 mg, 1.15 mmol), Intermediate 1d (280 mg, 1.15 mmol), palladium(II)acetate (13 mg, 0.058 mmol), Xantphos (70 mg, 0.120 mmol) and cesium carbonate (530 mg, 1.61 mmol) in dioxan (8 mL) was degassed by bubbling argon through the mixture for 5 minutes under sonication. The reaction mixture was warmed to 90° C. for 20 hours, cooled at RT and filtered through a pad of Celite® washing the precipitate with DCM and EtOH. The solvents were removed under reduced pressure and purification by FCC eluting 0 to 10% EtOH in DCM afforded the title compound (520 mg, 75%).

LCMS (Method 4): Rt=1.46 min, m/z 598 [$M+H^+$], m/z 620 [$M+Na^+$].

Example 13. 1-(6-(tert-Butyl)-2-(hydroxymethyl)pyrimidin-4-yl)-3-((1S,4R)-4-((3-(2-methoxypropan-2-yl)-[1,2,4]triazolo[4,3-a]pyridine-6-yl)oxy)-1,2,3,4-tetrahydronaphthalene-1-yl)urea

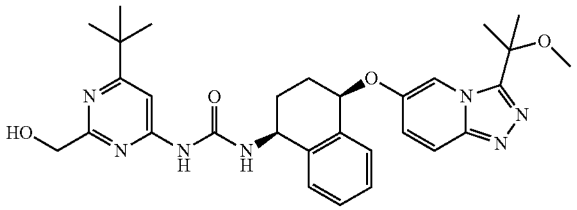 [SMILES: COC(C)(C)c1nnc2ccc(O[C@@H]3CC[C@H](NC(=O)Nc4cc(C(C)(C)C)nc(CO)n4)c4ccccc43)cn12]

a. (4-(tert-Butyl)-6-(3-((1S,4R)-4-((3-(2-methoxy-propan-2-yl)-[1,2,4]triazolo[4,3-a]pyridine-6-yl)oxy)-1,2,3,4-tetrahydronaphthalene-1-yl)ureido)pyrimidin-2-yl)methyl acetate (Example 13a)

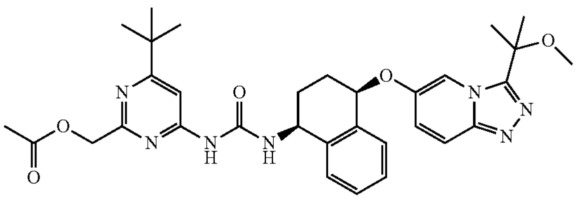 [SMILES: COC(C)(C)c1nnc2ccc(O[C@@H]3CC[C@H](NC(=O)Nc4cc(C(C)(C)C)nc(COC(C)=O)n4)c4ccccc43)cn12]

Intermediate XX (190 mg, 0.79 mmol), Intermediate 12d (310 mg, 0.79 mmol), Palladium acetate (10%, 20 mg, 0.08 mmol), Xantphos (20%, 93 mg, 0.16 mmol) and cesium carbonate (390 mg, 1.19 mmol) in 1,4-dioxan (10 ml) were warmed to 100° C. for 2 hours. The resulting reaction mixture was filtered through a pad of Celite® and the solvent was removed under reduced pressure. Purification by FCC eluting 0-10% (2N $NH_3$ in MeOH)/DCM afforded the title compound (320 mg, 67%).

LCMS (Method 4): Rt 1.71 min, m/z 611 [$M+H^+$].

b. Example 13

A stirred solution of Intermediate 13a (320 mg, 0.53 mmol) in THF/MeOH (8 ml, 5:3) was added with 1N sodium hydroxide solution (0.586 mmol, 0.586 mL). The mixture was stirred at 20° C. for 5 hours. The resulting reaction mixture was acidified to pH ~4 with 10% citric acid solution and diluted with water. This aqueous solution was extracted with EtOAc (×3), the combined organic phases were dried over $MgSO_4$ and the solvent was removed under reduced pressure. Purification by MDAP afforded the title compound (270 mg, 90%).

LCMS (Method 3): Rt 4.09 min, m/z 560 [$M+H^+$], sample assessed as ca. 99.65%. $^1H$ NMR (400 MHz, $d_6$DMSO): 1.27 (9H, s), 1.69 (6H, s), 1.87-2.30 (4H, m), 2.98 (3H, s), 4.42 (2H, d, J=4.1 Hz), 4.93-5.07 (2H, m), 5.49 (1H, t, J=3.8 Hz), 7.26-7.33 (1H, m), 7.33-7.46 (5H, m), 7.80 (1H, dd, J=0.6, 9.9 Hz), 8.13 (1H, d, J=1.4 Hz), 8.51 (1H, br s), 9.58 (1H, s).

Intermediate AL. (4-(tert-Butyl)-6-(3-((1S,4R)-4-((3-(2-methoxypropan-2-yl)-[1,2,4]triazolo[4,3-a]pyridine-6-yl)oxy)-1,2,3,4-tetrahydronaphthalen-1-yl)ureido)pyrimidin-2-yl)methyl methanesulphonate

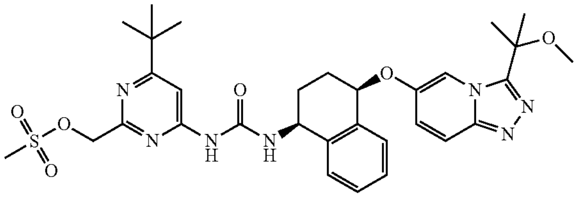

A solution of Example 13 (210 mg, 0.37 mmol), in DCM (5 mL) at 0° C. was added with a solution of methylsulphonyl methanesulfonate (113 mg, 0.66 mmol) and triethyl amine (95 mg, 0.93 mmol) in DCM (5 mL). The reaction mixture was allowed to warm to RT, diluted with saturated sodium bicarbonate solution and extracted with EtOAc (×2). The combined organic layers were dried over solid magnesium sulphate and the solvent was removed under reduced pressure. Purification by FCC eluting 0 to 10% (2M $NH_3$ in MeOH) in DCM afforded the title compound (140 mg, ~29%) as a 1:1 mixture with the ether dimer of Intermediate AL. This mixture was used as crude in the next step.

LCMS (Method 4): Rt=1.48 min, m/z 638 [$M+H^+$], m/z 660 [$M+Na^+$].

Intermediate AM. Ethyl 6-(tert-butyl)-4-(3-((1S,4R)-4-((3-(2-methoxypropan-2-yl)-[1,2,4]triazolo[4,3-a]pyradin-6-yl)oxy)-1,2,3,4-tetrahydronaphthalen-1-yl)ureido)picolinate

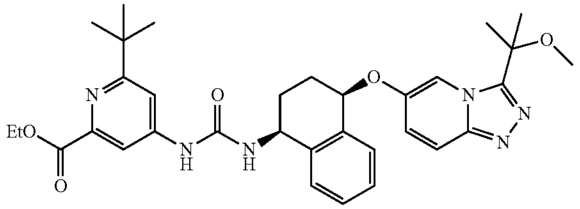 [SMILES: CCOC(=O)c1cc(NC(=O)N[C@H]2CC[C@@H](Oc3ccc4nnc(C(C)(C)OC)n4c3)c3ccccc32)cc(C(C)(C)C)n1]

A solution of Intermediate 12d (200 mg, 0.568 mmol), Intermediate 9d (137 mg, 0.568 mmol), palladium(II)acetate (6 mg, 0.03 mmol), xantphos (32 mg. 0.057 mmol) and cesium carbonate (280 mg, 0.852 mmol) in dioxan (3 mL) was degassed by bubbling argon through the mixture under sonication for 10 minutes. The reaction mixture was stirred at 90° C. for 20 hours, cooled at RT and filtered through a pad of Celite® washing the precipitate with DCM and EtOH. The solvents were evaporated under reduced pressure and the crude mixture was purified by FCC eluting with 0-10% EtOH/DCM to afford the title compound (220 mg, 64%).

LCMS (Method 4): Rt=1.48 min, m/z 601 [M+H$^+$], m/z 623 [M+Na$^+$].

Intermediate AN. Ethyl 6-(tert-butyl)-4-(3-((1S,4R)-4-((3-(1-methoxy-2-methylpropan-2-yl)-[1,2,4]triazolo[4,3-a]pyradin-6-yl)oxy)-1,2,3,4-tetrahydronaphthalen-1-yl)ureido)picolinate

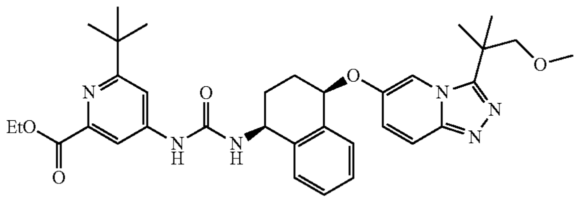 [SMILES: CCOC(=O)c1cc(NC(=O)N[C@H]2CC[C@@H](Oc3ccc4nnc(C(C)(C)COC)n4c3)c3ccccc32)cc(C(C)(C)C)n1]

A solution of Intermediate 7d (200 mg, 0.50 mmol), Intermediate 9d (130 mg, 0.55 mmol), palladium(II)acetate (11 mg, 0.05 mmol), xantphos (58 mg. 0.10 mmol) and cesium carbonate (250 mg, 0.75 mmol) in dioxan (4 mL) was degassed by bubbling argon through the mixture under sonication for 10 minutes. The reaction mixture was stirred at 100° C. for 18 hours, cooled at RT and filtered through a pad of Celite® washing the precipitate with DCM and EtOH. The solvents were evaporated under reduced pressure and the crude mixture was purified by FCC eluting with 0-10% EtOH/DCM to afford the title compound (160 mg, 52%).

LCMS (Method 4): Rt=1.43 min, m/z 615 [M+H$^+$], m/z 637 [M+Na$^+$].

Intermediate AO. (6-(tert-Butyl)-4-chloropyridin-2-yl)methyl Methanesulphonate

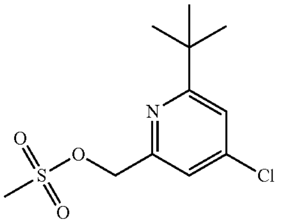 [SMILES: CC(C)(C)c1cc(Cl)cc(COS(C)(=O)=O)n1]

a. (6-(tert-Butyl)-4-chloropyridin-2-yl)methanol (Intermediate AOa)

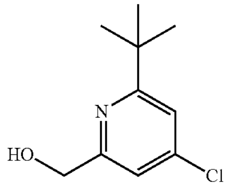

A stirred solution of Intermediate 9d (1.0 g, 4.14 mmol) in THF/IMS (24 mL, 5:1) at 0° C. was added with sodium borohydride (240 mg, 6.22 mmol) portionwise keeping the temperature <0° C. The reaction mixture was left at 0° C. for 30 minutes before allowing it to warm to RT for 30 minutes. A second portion of sodium borohydride (240 mg, 6.22 mmol) was added and the reaction mixture was stirred at RT overnight. The reaction mixture was then partitioned between saturated sodium bicarbonate solution and DCM and the two phases were separated. The aqueous phase was extracted with DCM (×2), the combined organic layers were dried over solid $MgSO_4$ and the solvent was removed under reduced pressure. Purification by FCC eluting 0-40% EtOAc/cyclohexane afforded the title compound (630 mg, 76%).

LCMS (Method 4): Rt=1.40 min, m/z 200 [M+H$^+$].

b. Intermediate AO

A solution of methylsulphonic anhydride (950 mg, 5.53 mmol) and trimethylamine (730 mg, 7.27 mmol) in DCM (10 mL) was added to Intermediate AOa (630 mg, 3.16 mmol) in DCM (10 mL) keeping the temperature <−10° C. The reaction was stirred at −10° C. for 1 hour then quenched with saturated sodium bicarbonate solution and the two phases were separated. The aqueous layer was extracted with EtOAc (×2) and the combined organic layers were dried over solid $MgSO_4$. The solvent was removed under reduced pressure and purification by FCC 0-40% EtOAc/cyclohexane afforded the title compound (800 mg, 91%).

LCMS (Method 4): Rt=1.59 min, m/z 278 [M+H$^+$].

Intermediate AP. 4-(2-((tert-Butyl)-4-chloropyridin-2-yl)methoxy)ethyl)morpholine

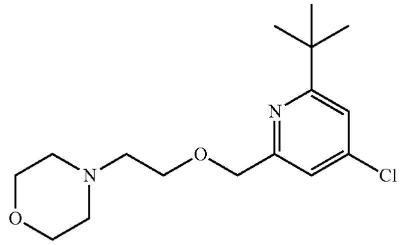 [SMILES: CC(C)(C)c1cc(Cl)cc(COCCN2CCOCC2)n1]

A solution of 4-(2-hydroxyethyl)morpholine (310 mg, 2.38 mmol) in THF (30 mL) was treated with sodium hydride (40% in oil, 170 mg, 4.32 mmol) and stirred at RT for 1 hour before Intermediate AO (600 mg, 2.16 mmol) in THF (30 mL) was added. The reaction mixture was warmed to reflux for 1 hour, allowed to cool to RT, diluted with brine and extracted with EtOAc (×3). The combined organic layers were dried over solid $MgSO_4$ and the solvent was removed under reduced pressure. Purification by FCC eluting with 0-10% EtOAc/cyclohexane afforded the title compound (490 mg, 72%).

$^1$H NMR (300 MHz, $CDCl_3$): 1.32 (9H, s), 2.53 (4H, t, J=4.6 Hz), 2.65 (2H, t, J=5.6 Hz), 3.70 (2H, t, J=5.6 Hz), 3.75 (4H, t, J=4.7 Hz), 4.61 (2H, s), 7.18 (1H, d, J=1.8 Hz), 7.28 (1H, J=1.8 Hz).

Intermediate AQ. (6-(tert-Butyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyridin-2-yl)methyl Acetate

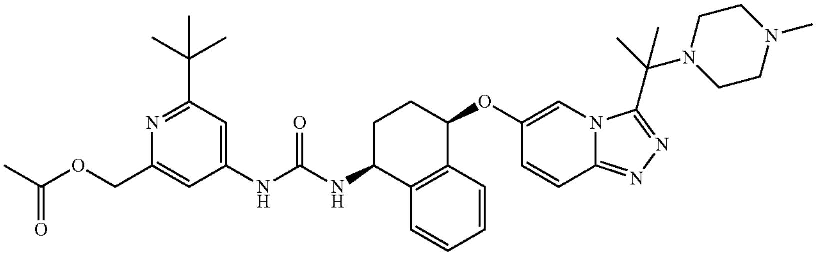 [SMILES: CC(=O)OCc1cc(NC(=O)N[C@H]2CC[C@@H](Oc3ccc4nnc(C(C)(C)N5CCN(C)CC5)n4c3)c3ccccc32)cc(C(C)(C)C)n1]

a. (6-(tert-Butyl)-4-chloropyridin-2-yl)methyl acetate (Intermediate AQa)

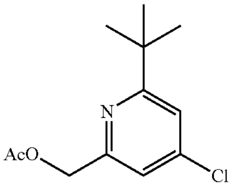 [SMILES: CC(=O)OCc1cc(Cl)cc(C(C)(C)C)n1]

A solution of Intermediate AOa (148 mg, 0.74 mmol, purity ~60%) in pyridine (2.5 ml) was treated with acetic anhydride (140 μl, 1.48 mmol). The reaction mixture was stirred at RT for 5 hours and left standing overnight. The reaction mixture was partitioned between EtOAc and an aqueous 1M HCl solution. The two phases were separated and the aqueous phase was extracted with EtOAc (×3). The combined organic phases were washed with brine, passed through a phase separator and the solvent was removed under reduced pressure. Purification by FCC, eluting with 0-10% EtOAc/cyclohexane afforded the title compound (142 mg, 79%).

$^1$H NMR (300 MHz, $CDCl_3$): 1.33 (9H, s), 2.19 (3H, s), 5.19 (2H, s), 7.13 (1H, d, J=1.7 Hz), 7.23 (1H, d, J=1.7 Hz).

b. Intermediate AQ

A solution of Intermediate FFd (110 mg, 0.24 mmol), Intermediate AOa (75 mg, 0.31 mmol), XantPhos (28 mg, 0.05 mmol) in dioxane (3 ml) was treated with $Cs_2CO_3$ (110 mg, 0.34 mmol) and $Pd(OAc)_2$ (6 mg, 0.025 mmol). The reaction mixture was degassed for a few minutes with argon and then evacuated and purged with argon (×3). The reaction mixture was heated at 95° C. for 24 hours. The reaction mixture was cooled at RT, diluted with DCM and filtered through a pad of Celite®. The solvents were removed under reduced pressure. Purification by FCC, eluting with 0-6% 2N $NH_3$ in MeOH/DCM afforded the title compound (106 mg, 66%).

LCMS (Method 4): Rt 0.86 min, m/z 669 [$MH^+$].

Intermediate AR. Ethyl 6-(tert-butyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinate

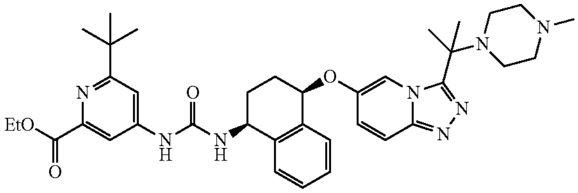 [SMILES: CCOC(=O)c1cc(NC(=O)N[C@H]2CC[C@@H](Oc3ccc4nnc(C(C)(C)N5CCN(C)CC5)n4c3)c3ccccc32)cc(C(C)(C)C)n1]

A solution of Intermediate FFd (130 mg, 0.28 mmol), Intermediate 9d (88 mg, 0.36 mmol), XantPhos (33 mg, 0.06 mmol) in dioxane (3 ml) was treated with $Cs_2CO_3$ (128 mg, 0.39 mmol) and $Pd(OAc)_2$ (6.7 mg, 0.03 mmol). The reaction mixture was degassed for a few minutes with argon and then evacuated and purged with argon (×3). The reaction mixture was heated at 95° C. for 24 hours. The reaction mixture was cooled at RT, diluted with DCM and filtered through a pad of Celite®. The solvents were removed under reduced pressure. Purification by FCC, eluting with 0-8% 2N $NH_3$ in MeOH/DCM afforded the title compound (168 mg, 90%).

LCMS (Method 4): Rt 1.08 min, m/z 669 [$MH^+$].

Intermediate AS. Ethyl 6-(tert-butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)picolinate

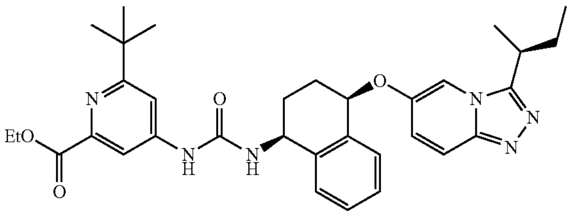

A solution of Intermediate 8d (350 mg, 0.92 mmol), Intermediate 9d (290 mg, 1.2 mmol), XantPhos (106 mg, 0.18 mmol) in dioxane (9 ml) was treated with $Cs_2CO_3$ (420 mg, 1.29 mmol) and $Pd(OAc)_2$ (20 mg, 0.09 mmol). The reaction mixture was degassed for a few minutes with argon, evacuated and purged with argon (×3) and then heated at 95° C. for 18 hours. Other aliquots of $Pd(OAc)_2$ (7 mg, 0.03 mmol) and XantPhos (32 mg, 0.06 mmol) were added and the reaction mixture was stirred at 95° C. for 24 hours. The reaction mixture was cooled at RT, diluted with DCM and filtered through a pad of Celite®. The solvents were removed under reduced pressure. Purification by FCC, eluting with 0-5% 2N $NH_3$ in MeOH/DCM afforded the title compound (294 mg, 55%).

$^1$H NMR (300 MHz, $CDCl_3$): 0.92 (3H, t, J=7.4 Hz), 1.37-1.45 (15H, m), 1.80 (1H, heptet, J=6.9 Hz), 1.99 (1H, heptet, J=7.2 Hz), 2.11-2.40 (4H, m), 3.12 (1H, sextet, J=9.2 Hz), 4.39 (2H, q, J=7.1 Hz), 5.21-5.30 (2H, m), 6.95 (1H, dd, J=9.9, 2.0 Hz), 7.28-7.35 (4H, m), 7.48 (1H, br s), 7.55-7.59 (1H, m), 7.82 (1H, br s), 7.97 (1H, d, J=1.8 Hz), 8.10 (1H, d, J=1.8 Hz), 9.11 (1H, s).

Intermediate AT. N-(6-(tert-Butyl)-4-chloropyridin-2-yl)methanesulfonamide

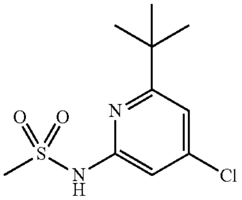 [SMILES: CC(C)(C)c1cc(Cl)cc(NS(C)(=O)=O)n1]

a. 2-(tert-Butyl)-4,6-dichloropyridine (Intermediate ATa)

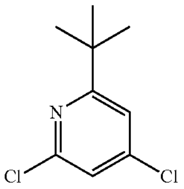

A solution of 6-tert-butyl-4-hydroxy-1,2-dihydropyridin-2-one (CAS: 857428-73-0, 3.47 g, 17.2 mmol) in phosphoryl chloride (20 ml) was stirred at RT for 10 minutes and then treated with DMF (5 ml). The reaction mixture was stirred at RT for 30 minutes and cooled at 0° C. Another aliquot of DMF (11 ml) was added and the reaction mixture was heated at 100° C. for 2 hours. The reaction mixture was cooled at RT, quenched with $H_2O$ and extracted with cyclohexane. The organic phase was dried with $MgSO_4$ and the solvent was removed under reduced pressure. Purification by FCC, eluting with cyclohexane afforded the title compound (3.45 g, 98%).

$^1$H NMR (300 MHz, $CDCl_3$): 1.34 (9H, s), 7.16 (1H, d, J=2.0 Hz), 7.22 (1H, d, J=2.0 Hz).

b. Intermediate AT

A solution of Intermediate ATa (204 mg, 1.0 mmol), methanesulfonamide (124 mg, 1.3 mmol), XantPhos (58 mg, 0.1 mmol) in NMP (15 ml) was treated with $K_3PO_4$ (276 mg, 1.3 mmol) and $Pd(OAc)_2$ (11 mg, 0.05 mmol). The reaction mixture was degassed for a few minutes with argon and then heated at 110° C. for 16 hours. The reaction mixture was cooled at RT, diluted with $H_2O$ and extracted with EtOAc. The organic phase was dried with $MgSO_4$ and the solvent was removed under reduced pressure. Purification by FCC, eluting with 0-40% EtOAc/cyclohexane afforded the title compound (60 mg, 23%).

LCMS (Method 4): Rt 1.15 min, m/z 263 [$MH^+$].

Intermediate AU. N-(6-(tert-Butyl)-4-chloropyridin-2-yl)ethanesulfonamide

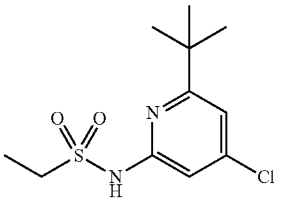 [SMILES: CCS(=O)(=O)Nc1cc(Cl)cc(C(C)(C)C)n1]

A solution of Intermediate ATa (200 mg, 0.98 mmol), XantPhos (58 mg, 0.1 mmol), $Cs_2CO_3$ (424 mg, 1.3 mmol) and $Pd(OAc)_2$ (11 mg, 0.05 mmol) in dioxane (15 ml) was treated with ethanesulfonamide (164 mg, 1.5 mmol). The reaction mixture was degassed for a few minutes with argon and then subjected to microwave conditions (140° C. for 1 hour). The reaction mixture was cooled at RT, diluted with $H_2O$ and extracted with EtOAc. The organic phase was dried with $MgSO_4$ and the solvent was removed under reduced pressure. Purification by FCC, eluting with 0-30% EtOAc/cyclohexane afforded the title compound (126 mg, 46%).

LCMS (Method 4): Rt 1.21 min, m/z 277 [MH+].

Intermediate AV. Ethyl 6-(tert-butyl)-4-(3-((1S,4R)-4-((3-(tert-pentyl)-[1,2,4]triazolo[4,3-a]pyridin-6-yl)oxy)-1,2,3,4-tetrahydronaphthalen-1-yl)ureido)picolinate

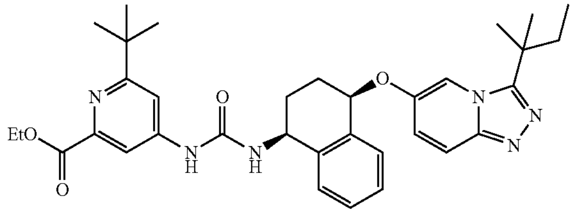 [SMILES: CCOC(=O)c1cc(NC(=O)N[C@H]2CC[C@@H](Oc3ccc4nnc(C(C)(C)CC)n4c3)c3ccccc32)cc(C(C)(C)C)n1]

A solution of Intermediate 2d (500 mg, 1.27 mmol), Intermediate 9d (307 mg, 1.27 mmol), XantPhos (74 mg, 0.13 mmol) in dioxane (10 ml) was treated with $Cs_2CO_3$ (646 mg, 1.78 mmol) and $Pd(OAc)_2$ (14 mg, 0.06 mmol). The reaction mixture was degassed for a few minutes with argon, evacuated and purged with argon (×3) and then heated at 90° C. for 72 hours. The reaction mixture was cooled at RT, diluted with EtOAc and filtered through a pad of Celite®. The solvents were removed under reduced pressure. Purification by FCC, eluting with 0-10% IMS/EtOAc afforded the title compound (312 mg, 41%).

$^1$H NMR (400 MHz, $CDCl_3$): 0.71 (3H, t, J=7.4 Hz), 1.38-1.42 (12H, m), 1.52-1.53 (6H, m), 1.85-1.91 (2H, m), 2.09-2.35 (4H, m), 4.39 (2H, q, J=7.0 Hz), 5.20-5.27 (2H, m), 6.88 (1H, dd, J=10.0, 2.0 Hz), 7.08 (1H, br s), 7.24-7.36 (4H, m), 7.57 (1H, d, J=7.6 Hz), 7.72-7.74 (1H, m), 7.92 (1H, d, J=1.9 Hz), 8.05 (1H, d, J=1.9 Hz), 8.56 (1H, br s).

Intermediate AW. Ethyl 6-(tert-butyl)-4-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)picolinate

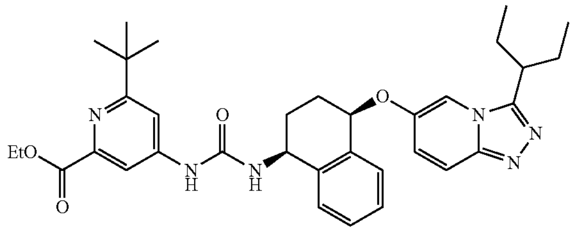 [SMILES: CCOC(=O)c1cc(NC(=O)N[C@H]2CC[C@@H](Oc3ccc4nnc(C(CC)CC)n4c3)c3ccccc32)cc(C(C)(C)C)n1]

A solution of Intermediate 5d (500 mg, 1.27 mmol), Intermediate 9d (307 mg, 1.27 mmol), XantPhos (74 mg, 0.13 mmol) in dioxane (10 ml) was treated with $Cs_2CO_3$ (644 mg, 1.78 mmol) and $Pd(OAc)_2$ (14 mg, 0.06 mmol). The reaction mixture was degassed for a few minutes with argon, evacuated and purged with argon (×3) and then heated at 90° C. for 72 hours. The reaction mixture was cooled at RT, diluted with EtOAc and filtered through a pad of Celite®. The solvents were removed under reduced pressure. Purification by FCC, eluting with 0-10% IMS/EtOAc afforded the title compound (87 mg, 11%).

$^1$H NMR (400 MHz, $CDCl_3$): 0.83 (3H, t, J=7.3 Hz), 0.86 (3H, t, J=7.5 Hz), 1.38-1.42 (12H, m), 1.82-2.00 (4H, m), 2.11-2.36 (4H, m), 2.92-2.99 (1H, m), 4.40 (2H, q, J=7.2 Hz), 5.22-5.26 (2H, m), 6.93-6.96 (1H, m), 7.17-7.71 (7H, m), 7.95-7.96 (1H, m), 8.03-8.04 (1H, m), 8.70 (1H, br s).

Intermediate AX. 4-(tert-Butyl)-6-chloropicolinonitrile

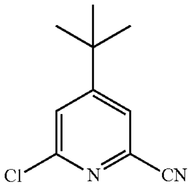

a. 4-(tert-Butyl)picolinonitrile (Intermediate AXa)

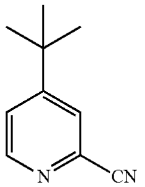

A solution of 4-tert-butylpyridine 1-oxide (CAS: 23569-17-7, 830 mg, 5.44 mmol) in DCM (6 ml) was added to trimethyl silyl cyanide (674 mg, 6.8 mmol). A solution of dimethyl carbamoyl chloride (626 µl, 6.8 mmol) in DCM (2 ml) was added to the mixture and the reaction mixture was stirred at RT overnight. The RM was quenched with the slow addition of 10% $K_2CO_3$ solution and the reaction mixture was stirred at RT for 30 min. The two phases were separated and the organic was evaporated under reduced pressure to afford the title compound (871 mg, 100%—quantitative).

LCMS (Method 1): Rt 3.53 min, m/z 161 [MH+].

b. Intermediate AX

A solution of Intermediate AXa (871 mg, 5.44 mmol) in acetic acid (6 ml) and $H_2O_2$ (30% in $H_2O$, 4.5 ml) was refluxed for 4 h and more $H_2O_2$ (30% in $H_2O$, 4.5 ml) was added. The reaction mixture was quenched with sodium thiosulfate until no more peroxide was detected. The solvent was removed under reduced pressure and $H_2O$ was added and evaporated again. The residue was treated with $Na_2CO_3$ and was extracted with DCM. The phases were separated with a phase separating cartridge, and the organic was removed under reduced pressure to afford 4-(tert-butyl)-2-cyanopyridine 1-oxide (958 mg, 100%—quantitative). This intermediate (561 mg, 3.03 mmol) was dissolved in toluene (40 ml) and treated with $POCl_3$ (1 ml, 10.9 mmol). The reaction mixture was heated at 100° C. for 8 h, cooled at RT and the solvent was evaporated under reduced pressure. Saturated $NaHCO_3$ solution was added to the residue and extracted with EtOAc (×3). The combined organic phases were dried with $Na_2SO_4$ and the solvent was removed under reduced pressure. Purification by FCC, eluting with 0-100% EtOAc/DCM afforded the title compound (118 mg, 20%).

$^1$H NMR (300 MHz, $CDCl_3$): 1.34 (9H, s), 7.50 (1H, d, J=1.5 Hz), 7.61 (1H, d, J=1.5 Hz).

Intermediate AY. Ethyl 4-(tert-butyl)-6-(3-((1S,4R)-4-((3-(tert-butyl)-[1,2,4]triazolo[4,3-a]pyridine-6-yl)oxy)-1,2,3,4-tetrahydronaphthalen-1-yl)ureido)picolinate (NSJ4226-095-01)

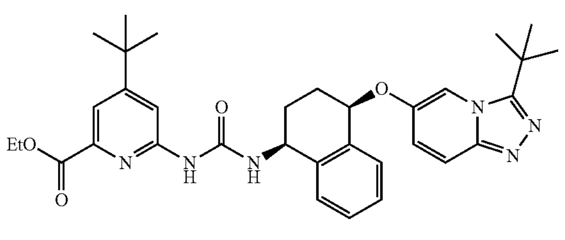 [SMILES: CCOC(=O)c1cc(C(C)(C)C)cc(NC(=O)N[C@H]2CC[C@@H](Oc3ccc4nnc(C(C)(C)C)n4c3)c3ccccc32)n1]

a. 4-(tert-Butyl)-2-chloropyridine 1-oxide (Intermediate AYa)

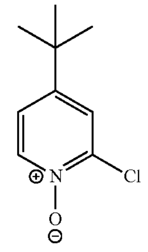

A stirred solution of 2-chloro-4-(1,1-dimethylethyl)-pyridine (8.92 g, 52.7 mmol) in DCM (500 mL) was added with meta-chloroperbenzoic acid (27.4 g, 158.3 mmol). After 1 hour the reaction mixture was washed with saturated sodium bicarbonate solution (×3). The organic layer was dried over solid $MgSO_4$ and the solvent was removed under reduced pressure to afford the title compound (7.89 g, 80%).

LCMS (Method 4): Rt=1.04 min, m/z 186 [$M+H^+$], m/z 208 [$M+Na^+$].

b. 4-(tert-Butyl)-6-chloropicolinonitrile (Intermediate AX-Second Synthetic Route)

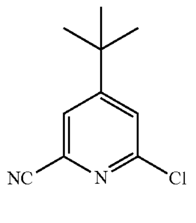

A solution of intermediate AYa (7.50 g, 40.5 mmol) and trimethylsilylcyanide (8.03 g, 81.1 mmol) in MeCN (110 mL) was added with dimethylcarbamylchloride (8.75 g, 81.1 mmol) and warmed to 60° C. for 4 hours. The solvent was removed under reduced pressure and the residue was partitioned with saturated sodium bicarbonate solution and $Et_2O$. The two phases were separated and the aqueous phase was extracted with $Et_2O$ (×2). The combined organic layers were dried over solid $MgSO_4$ and the solvent was removed under reduced pressure. Purification by FCC eluting with 0-100% $Et_2O$/cyclohexane afforded the title compound (5.0 g, 63%).

LCMS (Method 4): Rt=1.55 min, m/z 195 [$M+H^+$].

c. Ethyl 4-(tert-butyl)-6-chloropicolinate (Intermediate AYc)

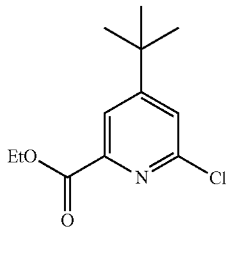 [SMILES: CCOC(=O)c1cc(C(C)(C)C)cc(Cl)n1]

A solution of Intermediate AX (5.88 g, 30.3 mmol) was dissolved in $H_2SO_4$ (21 mL, 95-97%) and warmed to 130° C. for 0.5 hours, then allowed to cool to RT and EtOH (250 mL) was cautiously added. This reaction mixture was warmed to reflux for 3.5 hours and cooled to RT before the solvent was removed under reduced pressure. The residue was partitioned between brine and $Et_2O$. The two phases were separated and the aqueous phase was extracted with $Et_2O$ (×2). The combined organic layers were washed with saturated $NaHCO_3$ solution and dried over solid $MgSO_4$. The solvent was removed under reduced pressure to afford the title compound (6.0 g, 82%).

LCMS (Method 4): Rt=1.57 min, m/z 242 [$M+H^+$], m/z 264 [$M+Na^+$].

d. Intermediate AY

A solution of Intermediate 1h (2.07 g, 5.46 mmol), Intermediate AYc (1.0 g, 4.15 mmol), palladium(II)acetate (50 mg, 0.21 mmol), xantphos (250 mg. 0.42 mmol) and cesium carbonate (2.0 g, 6.23 mmol) in dioxan (30 mL) was degassed by bubbling argon through the mixture under sonication for 10 minutes. The reaction mixture was stirred at 100° C. for 1.5 hours then filtered through a pad of Celite® washing the precipitate with DCM and EtOH. The solvents were evaporated under reduced pressure and the crude mixture was purified by FCC eluting with 0-10% EtOH/DCM to afford the title compound (2.49 g, quant.).

LCMS (Method 4): Rt=1.59 min, m/z 585.4 [$M+H^+$], m/z 607.4 [$M+Na^+$].

Example 14. 1-(6-(tert-Butyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

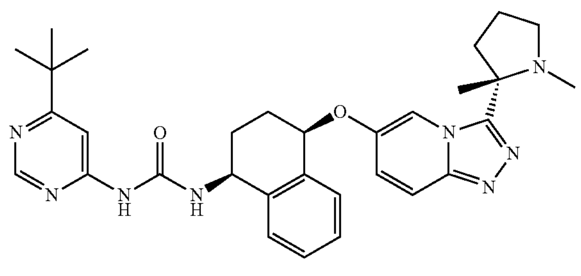 [SMILES: CN1CCC[C@@]1(C)c1nnc2ccc(O[C@@H]3CC[C@H](NC(=O)Nc4cc(C(C)(C)C)ncn4)c4ccccc43)cn12]

A solution of Intermediate BB (125 mg, 0.46 mmol) and (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 158 mg, 0.42 mmol) in dioxane (4.5 ml) under argon was treated with DIPEA (91 μl, 0.52 mmol). The reaction mixture was heated at 60° C. for 48 hours. The reaction mixture was cooled at RT and partitioned between EtOAc and $H_2O$. The two phases were separated and the aqueous phase was extracted with EtOAc. The combined organic phases were washed with an aqueous 1M NaOH solution, $H_2O$ and brine, passed through a phase separator and the solvent was removed under reduced pressure. Purification by MDAP (basic) afforded the title compound (80 mg, 34%).

LCMS (Method 3): Rt 3.33 min, m/z 555 $[MH^+]$. $^1H$ NMR (400 MHz, $d_6$-DMSO): 1.27 (9H, s), 1.51 (3H, s), 1.79-2.23 (11H, m), 2.65 (1H, q, J=8.6 Hz), 3.13-3.18 (1H, m), 4.96-5.02 (1H, m), 5.36 (1H, t, J=4.0 Hz), 7.28-7.43 (5H, m), 7.65 (1H, d, J=0.8 Hz), 7.76 (1H, dd, J=9.8, 0.6 Hz), 8.20 (1H, d, J=8.2 Hz), 8.45 (1H, d, J=1.5 Hz), 8.64 (1H, d, J=1.2 Hz), 9.52 (1H, br s).

Example 15. 1-(6-(tert-Butyl)-2-((dimethylamino)methyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea

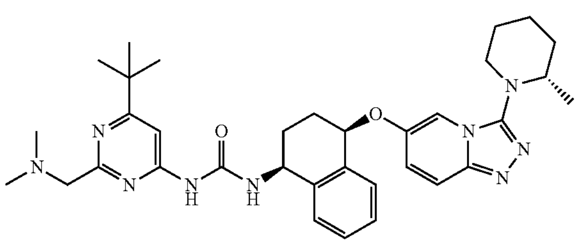

A solution of Intermediate AA (100 mg, 0.15 mmol) in tetrahydrofuran (4 ml) was treated with $K_2CO_3$ (28 mg, 0.2 mmol) and a solution of dimethylamine in tetrahydrofuran (2.0M, 0.75 ml, 1.5 mmol). The reaction mixture was heated at reflux overnight. The reaction mixture was cooled at RT and the solvent was removed under reduced pressure. The residue was partitioned between DCM and $H_2O$ and the two phases were separated. The aqueous phase was extracted with DCM (×2) and the combined organic phases were washed with brine, dried with $Na_2SO_4$ and the solvent was removed under reduced pressure. Purification by HPLC (Gemini C18, 10-50% MeCN in $H_2O$, 0.1% $HCO_2H$, 18 ml/min) afforded the title compound as formate salt. The residue was partitioned between DCM and a saturated aqueous $NaHCO_3$ solution and the two phases were separated. The aqueous phase was extracted with DCM (×2), the combined organic phases were dried with $Na_2SO_4$ and the solvent was removed under reduced pressure. The obtained solid was dissolved in MeCN (1 ml) and $H_2O$ (1 ml) and the mixture was lyophilized to afford the title compound as a free base (2.5 mg, 3%).

LCMS (Method 3): Rt 3.53 min, m/z 612 $[MH^+]$. $^1H$ NMR (400 MHz, $d_6$-DMSO): 0.89 (3H, d, J=6.3 Hz), 1.25 (9H, s), 1.44-1.82 (6H, m), 1.91-2.25 (9H, m), 2.84-2.91 (1H, m), 3.10-3.16 (1H, m), 3.26-3.30 (2H, m), 3.42 (2H, d, J=3.2 Hz), 4.98-5.04 (1H, m), 5.56 (1H, t, J=4.4 Hz), 7.22-7.43 (6H, m), 7.65-7.67 (2H, m), 8.99 (1H, br s), 9.69 (1H, br s).

Example 16. 4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide

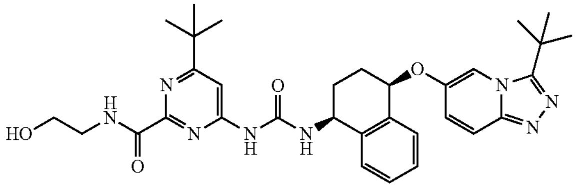 [SMILES: CC(C)(C)c1cc(NC(=O)N[C@H]2CC[C@@H](Oc3ccc4nnc(C(C)(C)C)n4c3)c3ccccc32)nc(C(=O)NCCO)n1]

A solution of Intermediate 1i (100 mg, 0.17 mmol) in methanol (2 ml) was treated with $Na_2CO_3$ (22 mg, 0.20 mmol) and ethanolamine (123 μl, 2.04 mmol). The reaction mixture was heated at 55° C. for 18 hours. The reaction mixture was cooled at RT and diluted with DCM and $H_2O$. The two phases were separated and the aqueous phase was extracted with DCM (×4). The combined organic phases were passed through a phase separator and the solvent was removed under reduced pressure. Purification by MDAP (basic) afforded the title compound (70 mg, 69%).

LCMS (Method 3): Rt 3.87 min, m/z 601 $[MH^+]$. $^1H$ NMR (400 MHz, $d_6$-DMSO): 1.32 (9H, s), 1.53 (9H, s), 1.93-2.26 (4H, m), 3.32-3.38 (2H, m, partially obscured by water peak), 3.50-3.54 (2H, m), 4.81 (1H, br s), 4.96-5.03 (1H, m), 5.63 (1H, t, J=3.8 Hz), 7.28-7.45 (5H, m), 7.74-7.76 (2H, m), 8.15 (1H, d, J=1.4 Hz), 8.24 (1H, br s), 8.57 (1H, t, J=5.9 Hz), 9.92 (1H, s).

Example 17. 4-(tert-Butyl)-N-(2-(dimethylamino)ethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide

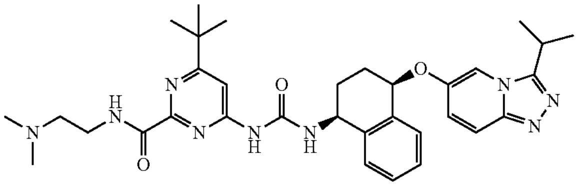 [SMILES: CC(C)c1nnc2ccc(O[C@@H]3CC[C@H](NC(=O)Nc4cc(C(C)(C)C)nc(C(=O)NCCN(C)C)n4)c4ccccc43)cn12]

A solution of Intermediate CC (130 mg, 0.23 mmol) in methanol (2.5 ml) was treated with N,N-dimethylethylenediamine (100 μl, 2.04 mmol). The reaction mixture was heated at 55° C. for 18 hours. The reaction mixture was cooled at RT and the solvent was removed under reduced pressure. The residue was partitioned between DCM and $H_2O$. The two phases were separated and the aqueous phase was extracted with DCM (×2). The combined organic phases were dried with $Na_2SO_4$ and the solvent was removed under reduced pressure. Purification by FCC, eluting with 0-10% 2N $NH_3$ in MeOH/DCM followed by a titration with $Et_2O$ afforded the title compound (123 mg, 87%).

LCMS (Method 3): Rt 3.13 min, m/z 614 $[MH^+]$. $^1H$ NMR (400 MHz, $d_6$-DMSO): 1.31 (9H, s), 1.36-1.40 (6H, m), 1.91-2.27 (10H, m), 2.39 (2H, t, J=6.6 Hz), 3.33-3.39 (2H, m, partially obscured by water peak), 3.57 (1H, quintet, J=6.8 Hz), 4.98-5.03 (1H, m), 5.57 (1H, t, J=3.9 Hz), 7.27 (1H, dd, J=9.8, 2.1 Hz), 7.29-7.43 (4H, m), 7.70 (1H, dd, J=9.8, 0.6 Hz), 7.74 (1H, br s), 8.23 (1H, d, J=1.3 Hz), 8.26 (1H, br s), 8.58 (1H, t, J=5.8 Hz), 9.88 (1H, s).

Example 18. 4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide

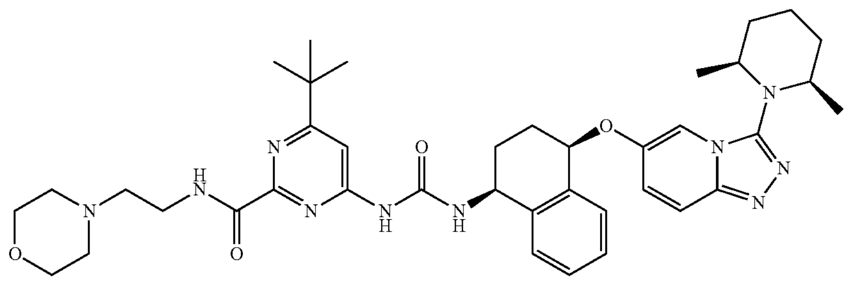 [SMILES: C[C@@H]1CCC[C@H](C)N1c1nnc2ccc(O[C@@H]3CC[C@H](NC(=O)Nc4cc(C(C)(C)C)nc(C(=O)NCCN5CCOCC5)n4)c4ccccc43)cn12]

A solution of Intermediate DD (110 mg, 0.17 mmol) in methanol (2.5 ml) was treated with 4-(2-aminoethyl)morpholine (82 μl, 0.62 mmol). The reaction mixture was heated at 55° C. for 18 hours. The reaction mixture was cooled at RT and the solvent was removed under reduced pressure. The residue was partitioned between DCM and $H_2O$. The two phases were separated and the aqueous phase was extracted with DCM (×3). The combined organic phases were dried with $Na_2SO_4$ and the solvent was removed under reduced pressure. Purification by FCC, eluting with 0-10% 2N $NH_3$ in MeOH/DCM afforded the title compound (88 mg, 71%).

LCMS (Method 3): Rt 3.68 min, m/z 725 [$MH^+$]. $^1H$ NMR (400 MHz, d-$_6$-DMSO): 0.60 (3H, d, J=6.2 Hz), 0.63 (3H, d, J=6.2 Hz), 1.33 (9H, s), 1.41-1.60 (3H, m), 1.67-1.82 (3H, m), 1.92-2.25 (4H, m), 2.42 (4H, br s), 3.13-3.23 (2H, m), 3.39 (2H, q, J=5.9 Hz), 3.58 (4H, t, J=4.4 Hz), 4.97-5.04 (1H, m), 5.57 (1H, t, J=3.8 Hz), 7.26-7.43 (5H, m), 7.67 (1H, dd, J=9.8, 0.6 Hz), 7.71 (1H, br s), 7.92 (1H, d, J=1.4 Hz), 8.32 (1H, br s), 8.69 (1H, t, J=5.7 Hz), 9.93 (1H, s), plus two protons obscured by the solvent peak.

Example 19. 4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide

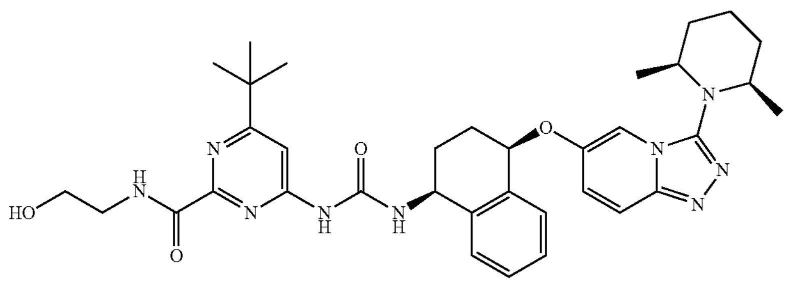 [SMILES: C[C@@H]1CCC[C@H](C)N1c1nnc2ccc(O[C@@H]3CC[C@H](NC(=O)Nc4cc(C(C)(C)C)nc(C(=O)NCCO)n4)c4ccccc43)cn12]

A solution of Intermediate DD (110 mg, 0.17 mmol) in methanol (2.5 ml) was treated with ethanolamine (51 μl, 0.85 mmol). The reaction mixture was heated at 55° C. for 18 hours. The reaction mixture was cooled at RT and the solvent was removed under reduced pressure. The residue was partitioned between DCM and $H_2O$. The two phases were separated and the aqueous phase was extracted with DCM (×3). The combined organic phases were dried with $Na_2SO_4$ and the solvent was removed under reduced pressure. Purification by FCC, eluting with 0-8% 2N $NH_3$ in MeOH/DCM afforded the title compound (96 mg, 86%).

LCMS (Method 3): Rt 4.43 min, m/z 656 [$MH^+$]. $^1H$ NMR (400 MHz, d-$_6$-DMSO): 0.60 (3H, d, J=6.2 Hz), 0.63 (3H, d, J=6.2 Hz), 1.32 (9H, s), 1.38-1.60 (3H, m), 1.68-1.82 (3H, m), 1.91-2.23 (4H, m), 3.13-3.22 (2H, m), 3.36 (2H, q, J=5.8 Hz, partially obscured by water peak), 3.52 (2H, q, J=5.6 Hz), 4.80 (1H, t, J=5.4 Hz), 4.97-5.03 (1H, m), 5.57 (1H, t, J=3.8 Hz), 7.26-7.43 (5H, m), 7.67 (1H, dd, J=9.8, 0.6 Hz), 7.74 (1H, br s), 7.93 (1H, d, J=1.4 Hz), 8.24 (1H, br s), 8.57 (1H, t, J=6.0 Hz), 9.90 (1H, s).

Example 20. 4-(tert-Butyl)-N-(2-(dimethylamino) ethyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido) pyrimidine-2-carboxamide

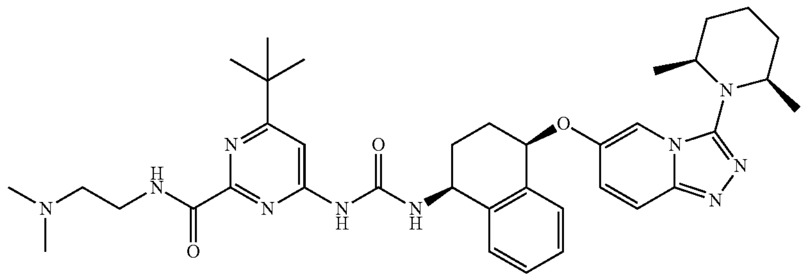

A solution of Intermediate DD (110 mg, 0.17 mmol) in methanol (2.5 ml) was treated with N,N-dimethylethylenediamine (93 µl, 0.85 mmol). The reaction mixture was heated at 55° C. for 18 hours. The reaction mixture was cooled at RT and the solvent was removed under reduced pressure. The residue was partitioned between DCM and $H_2O$. The two phases were separated and the aqueous phase was extracted with DCM (x3). The combined organic phases were dried with $Na_2SO_4$ and the solvent was removed under reduced pressure. Purification by MDAP (basic) afforded the title compound (91 mg, 78%).

LCMS (Method 3): Rt 3.71 min, m/z 683 [$MH^+$]. $^1H$ NMR (400 MHz, d-$_6$-DMSO): 0.60 (3H, d, J=6.2 Hz), 0.63 (3H, d, J=6.2 Hz), 1.31 (9H, s), 1.39-1.58 (3H, m), 1.69-1.81 (3H, m), 1.91-2.23 (10H, m), 2.39 (2H, t, J=6.6 Hz), 3.12-3.22 (2H, m), 4.97-5.03 (1H, m), 5.57 (1H, t, J=3.8 Hz), 7.26-7.43 (5H, m), 7.67 (1H, dd, J=9.8, 0.6 Hz), 7.73 (1H, br s), 7.92 (1H, d, J=1.4 Hz), 8.28 (1H, br s), 8.58 (1H, t, J=5.7 Hz), 9.88 (1H, s), plus two protons obscured by the solvent peak.

Example 21. 1-(6-(tert-Butyl)-2-(morpholinomethyl) pyrimidin-4-yl)-3-((1S,4R)-4-((3-(tert-butyl)-[1,2,4] triazolo[4,3-a]pyridin-6-yl)oxy)-1,2,3,4-tetrahydronaphthalen-1-yl)urea

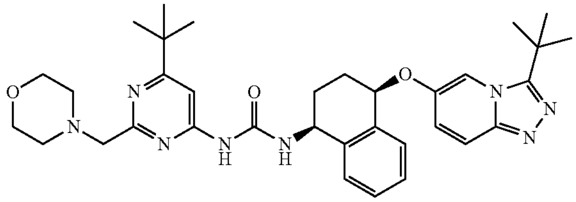 [SMILES: CC(C)(C)c1cc(NC(=O)N[C@H]2CC[C@@H](Oc3ccc4nnc(C(C)(C)C)n4c3)c3ccccc32)nc(CN2CCOCC2)n1]

A solution of Intermediate EE (145 mg, 0.23 mmol) in tetrahydrofuran (2.5 ml) was treated with morpholine (102 µl, 1.17 mmol). The reaction mixture was heated at 55° C. for 18 hours. The reaction mixture was cooled at RT and diluted with DCM and $H_2O$. The two phases were separated and the aqueous phase was extracted with DCM (x2). The combined organic phases were dried with $Na_2SO_4$ and the solvent was removed under reduced pressure. Purification by MDAP (basic) afforded the title compound (66 mg, 47%).

LCMS (Method 3): Rt 3.37 min, m/z 613 [$MH^+$]. $^1H$ NMR (400 MHz, d-$_6$-DMSO): 1.25 (9H, s), 1.52 (9H, s), 1.96-2.25 (4H, m), 2.34 (4H, t, J=4.5 Hz), 3.34-3.40 (4H, m, partially obscured by water peak), 3.48 (1H, d, J=14.2 Hz, AB system), 3.53 (1H, d, J=14.2 Hz, AB system), 4.99-5.05 (1H, m), 5.64 (1H, t, J=3.7 Hz), 7.21-7.42 (6H, m), 7.77 (1H, d, J=9.8 Hz), 8.11 (1H, d, J=1.2 Hz), 9.03 (1H, br s), 9.75 (1H, s).

Example 22. 4-(tert-Butyl)-N-(2-(dimethylamino)ethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide

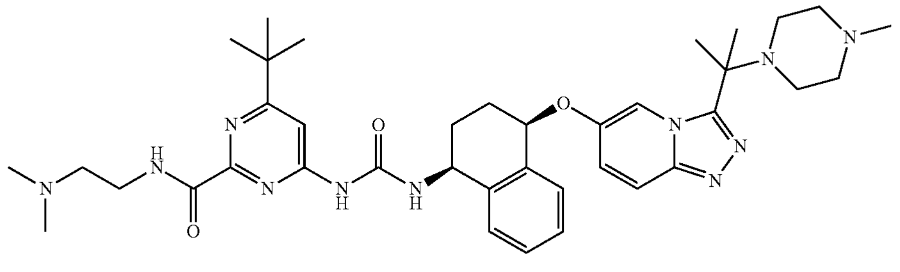

A solution of Intermediate FF (125 mg, 0.19 mmol) in methanol (2.5 ml) was treated with N,N-dimethylethylenediamine (207 μl, 1.9 mmol). The reaction mixture was heated at 55° C. for 18 hours. The reaction mixture was cooled at RT and the solvent was removed under reduced pressure. Purification by FCC, eluting with 0-10% 2N $NH_3$ in MeOH/DCM afforded the title compound (113 mg, 84%).

LCMS (Method 3): Rt 2.63 min, m/z 712 [$MH^+$]. $^1H$ NMR (400 MHz, d-$_6$-DMSO): 1.31 (9H, s), 1.54 (3H, s), 1.55 (3H, s), 2.07-2.46 (19H, m), 3.33-3.37 (2H, m, partially obscured by water peak), 4.99-5.05 (1H, m), 5.48 (1H, t, J=4.0 Hz), 7.31-7.48 (5H, m), 7.73-7.75 (2H, m), 8.23 (1H, br s), 8.57 (1H, t, J=5.7 Hz), 8.72 (1H, d, J=1.8 Hz), 9.87 (1H, s), plus four protons obscured by the solvent peak.

Example 23. 1-(6-(tert-Butyl)-2-(hydroxymethyl)pyrimidin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea

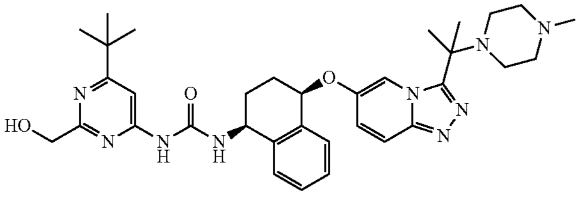 [SMILES: CN1CCN(C(C)(C)c2nnc3ccc(O[C@@H]4CC[C@H](NC(=O)Nc5cc(C(C)(C)C)nc(CO)n5)c5ccccc54)cn23)CC1]

A solution of Intermediate GG (113 mg, 0.17 mmol) in methanol (3 ml) and $H_2O$ (0.5 ml) was treated with $K_2CO_3$ (47 mg, 0.34 mmol). The reaction mixture was stirred at RT for 2 hours. The reaction mixture was diluted with DCM and $H_2O$ and the two phases were separated. The aqueous phase was extracted with DCM (×3) and the combined organic phases were passed through a phase separator. The solvent was removed under reduced pressure. Purification by HPLC (Kinetex C18, 10-45% MeCN in $H_2O$, 0.1% $HCO_2H$, 18 ml/min) afforded the title compound as formate salt. The residue was partitioned between DCM and a saturated aqueous $NaHCO_3$ solution and the two phases were separated. The aqueous phase was extracted with DCM (×4), the combined organic phases were passed through a phase separator and the solvent was removed under reduced pressure. The obtained solid was dissolved in MeCN (1 ml) and $H_2O$ (1 ml) and the mixture was lyophilized to afford the title compound as a free base (30 mg, 28%).

LCMS (Method 2): Rt 3.09 min, m/z 628 [$MH^+$]. $^1H$ NMR (400 MHz, d-$_6$-DMSO): 1.26 (9H, s), 1.54 (3H, s), 1.55 (3H, s), 1.93-2.48 (15H, m), 4.42 (2H, d, J=6.0 Hz), 4.97-5.03 (2H, m), 5.48 (1H, t, J=4.0 Hz), 7.31-7.47 (5H, m), 7.74 (2H, d, J=9.8 Hz), 8.15 (1H, br s), 8.72 (1H, d, J=1.7 Hz), 9.58 (1H, s).

Example 24. N-((4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-2-(dimethylamino)acetamide

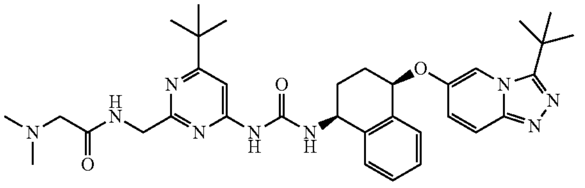 [SMILES: CN(C)CC(=O)NCc1nc(NC(=O)N[C@H]2CC[C@@H](Oc3ccc4nnc(C(C)(C)C)n4c3)c3ccccc32)cc(C(C)(C)C)n1]

A solution of Intermediate II (37 mg, 0.07 mmol), HOBt (1 mg, 0.007 mmol) and 2-(dimethylamino)acetic acid (11 mg, 0.1 mmol) in DCM (3 ml) was treated with EDC (19 mg, 0.1 mmol). The reaction mixture was stirred at RT for 2 hours, partitioned between DCM and $H_2O$ and the two phases were separated. The aqueous phase was extracted with DCM (×4) and the combined organic phases were passed through a phase separator and the solvent was removed under reduced pressure. Purification by MDAP (basic) afforded the title compound (28 mg, 64%).

LCMS (Method 3): Rt 3.21 min, m/z 628 [$MH^+$]. $^1H$ NMR (400 MHz, d-$_6$-DMSO): 1.26 (9H, s), 1.52 (9H, s), 2.00-2.18 (4H, m), 2.20 (6H, s), 2.79 (1H, d, J=15.6 Hz, AB system), 2.85 (1H, d, J=15.6 Hz, AB system), 4.27 (1H, dd, J=17.0, 5.4 Hz, AB system), 4.37 (1H, dd, J=17.0, 5.8 Hz, AB system), 4.97 (1H, q, J=8.1 Hz), 5.61-5.65 (1H, m), 7.29-7.49 (6H, m), 7.75 (1H, d, J=9.9 Hz), 8.18-8.22 (3H, m), 9.51 (1H, s).

Example 25. 4-(tert-Butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide

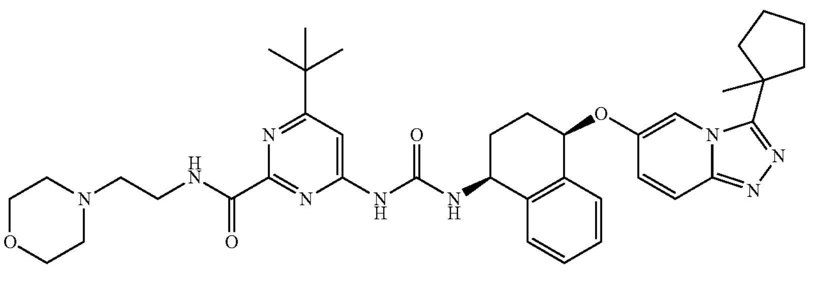 [SMILES: CC(C)(C)c1cc(NC(=O)N[C@H]2CC[C@@H](Oc3ccc4nnc(C5(C)CCCC5)n4c3)c3ccccc32)nc(C(=O)NCCN2CCOCC2)n1]

A solution of Intermediate JJ (60 mg, 0.1 mmol) in methanol (2 ml) was treated with 4-(2-aminoethyl)morpholine (40 μl, 0.3 mmol). The reaction mixture was heated at 55° C. for 18 hours. The reaction mixture was cooled at RT and the solvent was removed under reduced pressure. Purification by MDAP (basic) afforded the title compound (25 mg, 40%).

LCMS (Method 3): Rt 3.51 min, m/z 696 [$MH^+$]. $^1H$ NMR (400 MHz, d-$_6$-DMSO): 1.32 (9H, s), 1.43 (3H, s), 1.62-1.81 (4H, m), 1.90-2.13 (5H, m), 2.21-2.29 (1H, m), 2.32-2.42 (6H, m), 2.46-2.48 (2H, m, partially obscured by the solvent peak), 3.38 (2H, q, J=6.4 Hz), 3.58 (4H, t, J=4.4 Hz), 4.97-5.03 (1H, m), 5.60 (1H, t, J=3.9 Hz), 7.28-7.44 (5H, m), 7.71 (1H, br s), 7.74 (1H, dd, J=9.8, 0.5 Hz), 7.98 (1H, d, J=1.2 Hz), 8.31 (1H, br s), 8.68 (1H, t, J=5.6 Hz), 9.95 (1H, s).

Example 26. (4-(tert-Butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methyl acetate

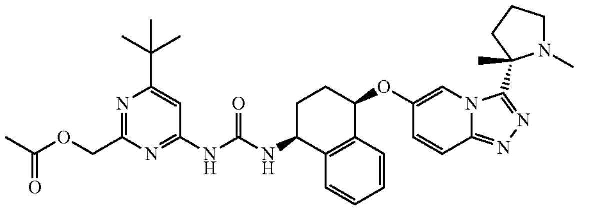 [SMILES: CC(=O)OCc1nc(NC(=O)N[C@H]2CC[C@@H](Oc3ccc4nnc([C@]5(C)CCCN5C)n4c3)c3ccccc32)cc(C(C)(C)C)n1]

A solution of Intermediate XX (50 mg, 0.21 mmol) in dioxane (2 ml) was treated with Intermediate OOa (104 mg, 0.25 mmol), $Pd(dba)_3$ (9.4 mg, 0.01 mmol), Xantphos (11.9 mg, 0.02 mmol) and $K_3PO_4.H_2O$ (66.7 mg, 0.29 mmol). The reaction mixture was purged with argon and treated with microwave irradiation at 150° C. for 30 mins. The reaction mixture was cooled at RT, filtered and concentrated under reduced pressure. The residue was passed through a plug of silica, eluting with 0-10% 2N $NH_3$ in MeOH/DCM followed by further purification by prep HPLC, eluting with 10-98% $MeCN/H_2O$, 0.1% $HCO_2H$ in 2 injections. The residue was dissolved in DCM, washed with saturated $NaHCO_3$ and the solvent was removed under reduced pressure to afford the title compound (52 mg, 40%).

LCMS (Method 3): Rt 3.68 min, m/z 627 [$MH^+$]. $^1H$ NMR (400 MHz, d-$_6$-DMSO): 1.25 (9H, s), 1.51 (3H, s), 1.78-2.33 (14H, m), 2.65 (1H, q, J=8.6 Hz), 3.12-3.17 (1H, m), 4.97-5.08 (3H, m), 5.36 (1H, t, J=4.0 Hz), 7.27-7.45 (6H, m), 7.76 (1H, dd, J=9.8, 0.6 Hz), 8.32 (1H, br s), 8.44 (1H, d, J=1.5 Hz), 9.64 (1H, s).

Example 27. 1-(6-(tert-Butyl)-2-(hydroxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

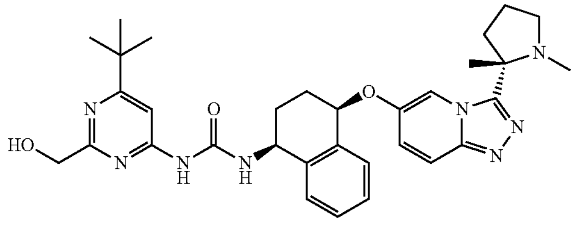

A solution of Example 26 (160 mg, 0.26 mmol) in MeOH (3 ml) and $H_2O$ (0.5 ml) was treated with $K_2CO_3$ (70.6 mg, 0.51 mmol) and the reaction mixture was stirred at RT. The reaction mixture was partitioned between DCM and $H_2O$ and the two phases were separated. The organic phase was washed with brine and the solvent was evaporated under reduced pressure. Purification by prep HPLC, eluting with 10-98% $MeCN/H_2O$, 0.1% $HCO_2H$ in 3 injections followed by another prep HPLC, eluting with 10-98% $MeCN/H_2O$, 0.1% $NH_4OH$ in 2 injections afforded the title compound (66 mg, 44%).

LCMS (Method 3): Rt 3.17 min, m/z 585 [$MH^+$]. $^1H$ NMR (400 MHz, d-$_6$-DMSO): 1.26 (9H, s), 1.51 (3H, s), 1.78-2.33 (11H, m), 2.64 (1H, q, J=8.6 Hz), 3.13-3.19 (1H, m), 4.41 (2H, d, J=6.0 Hz), 4.95-5.03 (2H, m), 5.35 (1H, t, J=4.0 Hz), 7.26-7.45 (6H, m), 7.75 (1H, dd, J=9.8, 0.6 Hz), 8.45 (1H, d, J=1.5 Hz), 8.51 (1H, br s), 9.59 (1H, s).

Example 28. 4-(tert-Butyl)-N-(2-(dimethylamino)ethyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide

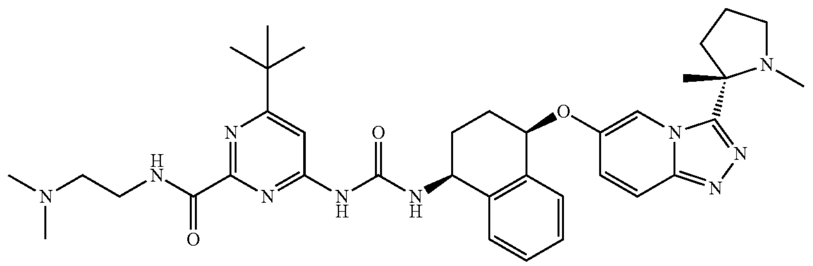

A solution of Intermediate YYa (100 mg, 0.17 mmol) and N',N'-dimethylethane-1,2-diamine (CAS: 108-00-9, 18 μl, 0.17 mmol) in DCM (2 ml) was treated with EDC.HCl (32 mg, 0.17 mmol) and HOBt Hydrate (23 mg, 0.17 mmol). The reaction mixture was stirred at RT for 5 days. The reaction mixture was diluted with DCM and washed with $H_2O$ and brine and the solvent was evaporated under reduced pressure. The residue was passed through a plug of silica, eluting with 0-5% 2N $NH_3$ in MeOH/DCM followed by further purification by prep HPLC, eluting with 10-98% $MeCN/H_2O$, 0.1% $NH_4OH$ to afford the title compound (41 mg, 38%).

LCMS (Method 3): Rt 2.62 min, m/z 669 [$MH^+$]. $^1H$ NMR (400 MHz, d-$_6$-DMSO): 1.31 (9H, s), 1.51 (3H, s), 1.79-2.29 (17H, m), 2.39 (2H, t, J=6.0 Hz), 2.65 (1H, q, J=8.5 Hz), 3.14-3.19 (1H, m), 3.35 (2H, q, J=6.0 Hz), 4.96-5.02 (1H, m), 5.35 (1H, t, J=4.0 Hz), 7.27-7.43 (5H, m), 7.72-7.77 (2H, m), 8.19 (1H, br s), 8.46 (1H, d, J=1.5 Hz), 8.57 (1H, t, J=5.8 Hz), 9.88 (1H, s).

Example 29. 4-(tert-Butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide

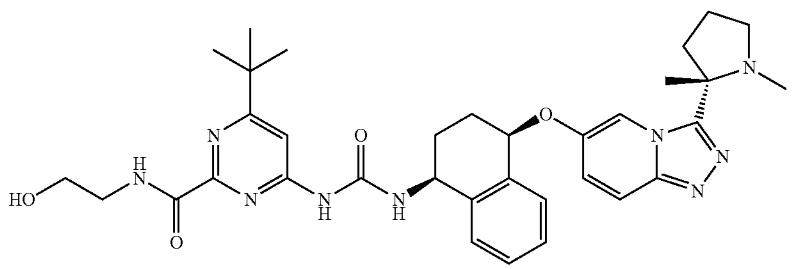 [SMILES: CN1CCC[C@@]1(C)c1nnc2ccc(O[C@@H]3CC[C@H](NC(=O)Nc4cc(C(C)(C)C)nc(C(=O)NCCO)n4)c4ccccc43)cn12]

A solution of Intermediate YY (98 mg, 0.16 mmol) and 2-aminoethan-1-ol (CAS: 141-43-5, 9.9 μl, 0.16 mmol) in DCM (2 ml) was treated with EDC.HCl (31.4 mg, 0.16 mmol) and HOBt Hydrate (22.1 mg, 0.16 mmol). The reaction mixture was stirred at RT overnight. The reaction mixture was diluted with DCM and washed with $H_2O$. The aqueous phase was extracted with DCM and the combined organic phases were washed with brine and the solvent was evaporated under reduced pressure. The residue was passed through a plug of silica, eluting with 0-10% 2N $NH_3$ in MeOH/DCM followed by further purification by prep HPLC, eluting with 10-98% $MeCN/H_2O$, 0.1% $NH_4OH$ to afford the title compound (44 mg, 42%).

LCMS (Method 3): Rt 3.09 min, m/z 642 [$MH^+$]. $^1H$ NMR (400 MHz, d-$_6$-DMSO): 1.31 (9H, s), 1.51 (3H, s), 1.79-2.33 (11H, m), 2.65 (1H, q, J=8.5 Hz), 3.14-3.19 (1H, m), 3.35 (2H, q, J=6.0 Hz), 3.51 (2H, q, J=6.0 Hz), 4.80 (1H, t, J=5.3 Hz), 4.96-5.02 (1H, m), 5.35 (1H, t, J=4.0 Hz), 7.27-7.43 (5H, m), 7.72-7.76 (2H, m), 8.18 (1H, br s), 8.46 (1H, d, J=1.5 Hz), 8.57 (1H, t, J=6.0 Hz), 9.89 (1H, s).

Example 30. N-(4-(tert-Butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methanesulfonamide

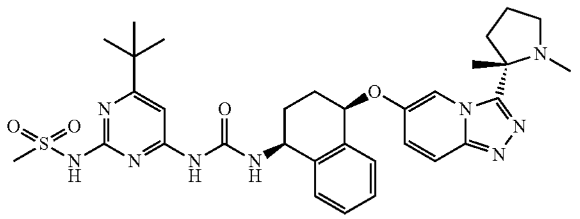

A solution of Intermediate ZZ (51 mg, 0.19 mmol), in dioxane (2 ml) was treated with Intermediate OOa (81 mg, 0.19 mmol), $Pd(OAc)_2$ (2.2 mg, 0.01 mmol), XantPhos (8.4 mg, 0.02 mmol) and $Cs_2CO_3$ (95 mg, 0.29 mmol). The reaction mixture was evacuated and purged with nitrogen (×3) and then heated at 90° C. overnight. The reaction mixture was cooled to RT and the solvent was removed under reduced pressure. The residue was partitioned between DCM and $H_2O$ and the two phases were separated. The aqueous phase was extracted with DCM and the combined organic phases were washed with $H_2O$ and brine, dried with $NaSO_4$ and the solvent was removed under reduced pressure. Purification by MDAP afforded the title compound (55 mg, 44%).

LCMS (Method 3): Rt 2.92 min, m/z 648 [$MH^+$]. $^1H$ NMR (400 MHz, d-$_6$-DMSO): 1.25 (9H, s), 1.53 (3H, s), 1.79-2.31 (11H, m), 2.66 (1H, q, J=8.5 Hz), 3.13-3.19 (1H, m), 4.99-5.05 (1H, m), 5.29 (1H, t, J=3.8 Hz), 6.92 (1H, s), 7.21-7.37 (5H, m), 7.76 (1H, dd, J=9.8, 0.8 Hz), 8.47-8.48 (1H, m), 8.59 (1H, br s), 9.38 (1H, br s), 10.76 (1H, br s) plus three protons not observed.

Example 31. 1-(6-(tert-Butyl)-2-(4-methylpiperazin-1-yl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

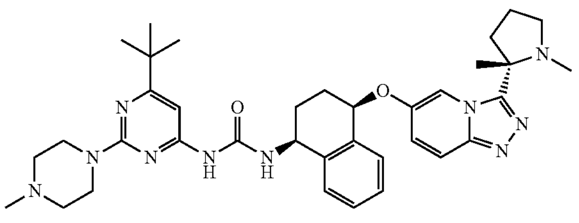

A solution of Intermediate AB (50.0 mg, 0.19 mmol), in dioxane (4 ml) was treated with Intermediate OOa (62.0 mg, 0.15 mmol), $Pd(dba)_3$ (6.8 mg, 0.01 mmol), XantPhos (5.7 mg, 0.02 mmol) and $Cs_2CO_3$ (84.8 mg, 0.26 mmol). The reaction mixture was evacuated and purged with argon (×3) and then heated at 100° C. for 6 h. The reaction mixture was cooled at RT, diluted with $H_2O$ and extracted with EtOAc (×2). The combined organic phases were washed with brine, dried with $MgSO_4$ and the solvent was removed under reduced pressure. The residue was purified by FCC, eluting with 0-10% 2N $NH_3$ in MeOH/DCM. This was further purified by prep HPLC (Gemini C18, 10-95% MeCN in $H_2O$, 0.1% $HCO_2H$, 18 ml/min) and the fractions collected were basified with saturated $NaHCO_3$ solution. This was extracted with DCM and the organic phase was washed with brine, dried with $MgSO_4$ and the solvent was removed under reduced pressure to afford the title compound (19 mg, 20%).

LCMS (Method 3): Rt 2.70 min, m/z 653 [$MH^+$]. $^1H$ NMR (400 MHz, d-$_6$-DMSO): 1.18 (9H, s), 1.50 (3H, s), 1.78-2.33 (18H, m), 2.63 (1H, q, J=8.5 Hz), 3.07-3.13 (1H, m), 4.93-4.98 (1H, m), 5.38 (1H, t, J=4.8 Hz), 6.48 (1H, s), 7.30-7.45 (5H, m), 7.76 (1H, dd, J=9.8, 0.6 Hz), 8.46 (1H, d, J=1.6 Hz), 9.05 (1H, br s), 9.41 (1H, s), plus four protons not observed.

Example 32. 4-(tert-Butyl)-N-(2-(dimethylamino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide

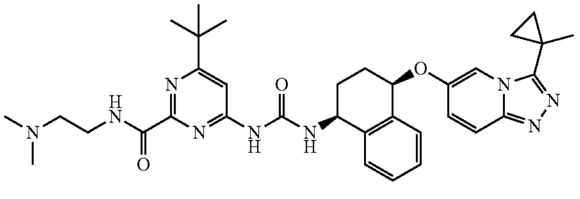

A solution of Intermediate AC (100 mg, 0.17 mmol) in methanol (2 ml) was treated with N',N'-dimethylethane-1,2-diamine (CAS: 108-00-9, 60 mg, 0.68 mmol). The reaction mixture was heated at 60° C. for 2 days. The reaction mixture was cooled to RT and the solvent was removed under reduced pressure. The residue was partitioned between DCM and $H_2O$ and the two phases were separated. The aqueous phase was extracted with DCM and organic was evaporated under reduced pressure. Purification by MDAP (Basic) afforded the title compound (44 mg, 41%).

LCMS (Method 3): Rt 3.23 min, m/z 626 [$MH^+$]. $^1H$ NMR (400 MHz, d-$_6$-DMSO): 0.93-0.95 (2H, m), 1.04-1.05 (2H, m), 1.31 (9H, s), 1.43 (3H, s), 1.92-2.33 (10H, m), 2.39 (2H, t, J=6.6 Hz), 3.32-3.38 (2H, m, partially obscured by the water peak), 4.97-5.03 (1H, m), 5.63 (1H, t, J=4.0 Hz), 7.29-7.45 (5H, m), 7.72-7.74 (2H, m), 8.10 (1H, d, J=1.3 Hz), 8.25 (1H, br s), 8.57 (1H, t, J=5.8 Hz), 9.89 (1H, s).

Example 33. 4-(tert-Butyl)-N-(2-hydroxyethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide

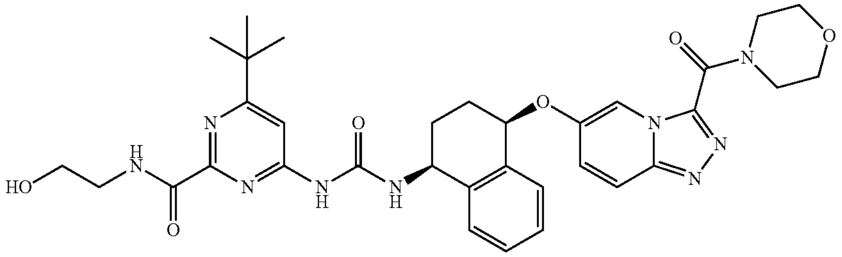 [SMILES: CC(C)(C)c1cc(NC(=O)N[C@H]2CC[C@@H](Oc3ccc4nnc(C(=O)N5CCOCC5)n4c3)c3ccccc32)nc(C(=O)NCCO)n1]

A solution of Intermediate AD (90 mg, 0.14 mmol) in methanol (10 ml) was treated with 2-aminoethanol (CAS: 141-43-5, 0.04 ml, 0.7 mmol). The reaction mixture was stirred at RT overnight. The solvent was removed under reduced pressure and purification by MDAP (Basic) afforded the title compound (44 mg, 47%).

LCMS (Method 3): Rt 3.75 min, m/z 658 [$MH^+$]. $^1H$ NMR (400 MHz, d-$_6$-DMSO): 1.31 (9H, s), 1.88-2.33 (4H, m), 3.51 (2H, q, J=5.6 Hz), 3.73 (6H, br s), 4.27 (2H, br s), 4.80 (1H, t, J=5.2 Hz), 4.97-5.03 (1H, m), 5.50 (1H, t, J=4.0 Hz), 7.29-7.43 (4H, m), 7.55 (1H, dd, J=9.8, 2.2 Hz), 7.75 (1H, br s), 7.96 (1H, dd, J=9.8, 0.7 Hz), 8.21 (1H, br s), 8.57 (1H, t, J=5.9 Hz), 8.75 (1H, d, J=1.6 Hz), 9.88 (1H, s), plus two protons obscured by solvent peak.

Example 34. 4-(tert-Butyl)-N-(2-(dimethylamino) ethyl)-6-(3-((1S,4R)-4-((3-((S)-2-methylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide

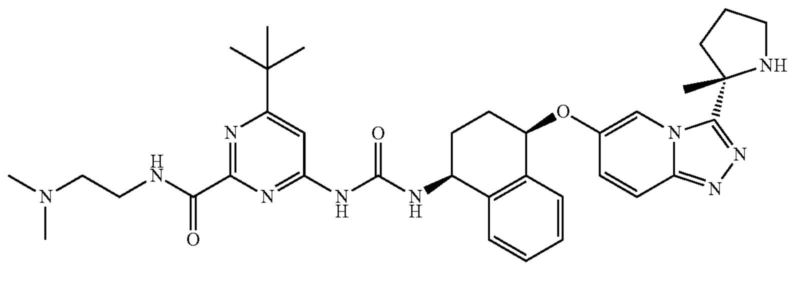 [SMILES: CN(C)CCNC(=O)c1nc(NC(=O)N[C@H]2CC[C@@H](Oc3ccc4nnc([C@]5(C)CCCN5)n4c3)c3ccccc32)cc(C(C)(C)C)n1]

A solution of Intermediate AE (37 mg, 0.06 mmol) in DCM (2 ml) was treated with N',N'-dimethylethane-1,2-diamine (CAS: 108-00-9, 0.5 ml). The reaction mixture was stirred at RT overnight. The solvent was evaporated under reduced pressure. Purification by FCC, eluting with 0-8% 2N $NH_3$ in MeOH/DCM, followed by further purification by reverse phase prep HPLC, eluting with 10-80% MeCN/$H_2O$, 0.1% $NH_4OH$ afforded the title compound (43 mg, >100%).

LCMS (Method 3): Rt 2.57 min, m/z 655 [$MH^+$]. $^1H$ NMR (400 MHz, d-$_6$-DMSO): 1.31 (9H, s), 1.58 (3H, s), 1.65-2.12 (5H, m), 2.17 (6H, s), 2.22-2.33 (2H, m), 2.39 (2H, t, J=6.6 Hz), 2.52-2.59 (1H, m), 2.78-2.85 (2H, m), 3.05-3.11 (1H, m), 4.96-5.02 (1H, m), 5.43 (1H, t, J=4.0 Hz), 7.28-7.44 (5H, m), 7.70 (1H, dd, J=9.9, 0.5 Hz), 7.76 (1H, s), 8.18 (1H, br s), 8.57 (1H, t, J=5.8 Hz), 8.65 (1H, d, J=1.5 Hz), 9.85 (1H, s), plus two protons obscured by solvent peak.

Example 35. 1-(5-(tert-Butyl)-2-methoxypyridin-3-yl)-3-((1S,4R)-4-((3-((S)-1-methylpyrrolidin-2-yl)-[1,2,4]triazolo[4,3-a]pyridin-6-yl)oxy)-1,2,3,4-tetrahydronaphthalen-1-yl)urea hydrochloride Salt

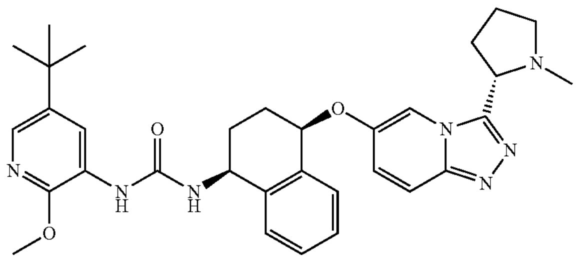

HCl

A stirred solution of (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference inits entirety, 203 mg, 0.56 mmol) and DIPEA (0.29 ml, 0.67 mmol) in 2-methyltetrahydrofuran (2 ml) at 0° C. was dropwise added with a solution of Intermediate VV (60 mg, 0.1 mmol) in 2-methyltetrahydrofuran (4 ml). The reaction mixture was warmed at RT, stirred for 3 hours and then quenched with $H_2O$. The two phases were stirred for 3 hours and then the mixture was diluted with EtOAc and $H_2O$. The two phases were separated and then the aqueous phase was extracted with EtOAc (×2). The combined organic phases were washed with brine, dried with $Na_2SO_4$ and the solvent was removed under reduced pressure. Purification by FCC, eluting with 0-10% MeOH/DCM afforded the title compound as a free base. The obtained solid was dissolved in MeCN (5 ml) and $H_2O$ (5 ml) and aqueous 1M HCl solution (0.435 ml, 1 eq) was added. The mixture was lyophilised to afford the title compound as a hydrochloride salt (258 mg, 80%).

LCMS (Method 3): Rt 3.61 min, m/z 570 [$MH^+$]. $^1H$ NMR (400 MHz, d-$_6$-DMSO): 1.25 (9H, s), 1.81-2.04 (3H, m), 2.10-2.21 (4H, m), 2.30-2.43 (2H, br s), 2.65-2.86 (3H, m), 3.87 (3H, s), 4.87-4.94 (1H, m), 5.33 (0.2H, br s), 5.56 (0.8H, br s), 7.27-7.45 (6H, m), 7.68 (1H, d, J=2.5 Hz), 7.84 (1H, d, J=9.9 Hz), 8.05 (1H, s), 8.48 (1H, br s), 8.54 (1H, d, J=2.3 Hz), plus two protons obscured by the solvent peak.

Example 36. Ethyl 4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylate

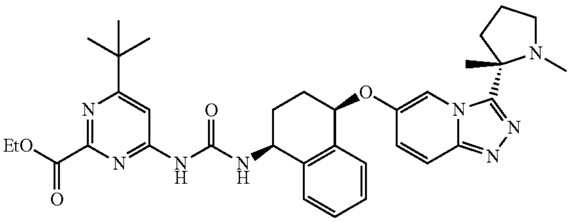 [SMILES: CCOC(=O)c1nc(NC(=O)N[C@H]2CC[C@@H](Oc3ccc4nnc([C@]5(C)CCCN5C)n4c3)c3ccccc32)cc(C(C)(C)C)n1]

A mixture of Intermediate OOa (104 mg, 0.25 mmol), Intermediate 1d (50 mg, 0.43 mmol), Xantphos (12 mg, 0.021 mmol), $Pd_2(dba)_3$ (9.4 mg, 0.01 mmol) and $Cs_2CO_3$ (94 mg, 0.29 mmol) in dioxan (4.0 ml) was purged with argon and heated at 150° C. in the microwave for 30 mins. The mixture was diluted with DCM and washed with water, brine, passed through a phase separator and the filtrate evaporated. The residue was purified by FCC eluting with 0-5% 2M $NH_3$ in MeOH/DCM followed by MDAP (basic) and by HPLC (X-Bridge C18, 10-98% MeCN in water, 0.1% $NH_4OH$). Lyophilization of the fractions containing the desired product afforded the title compound (26 mg).

LCMS (Method 3): Rt 3.69 min, m/z 627 [$MH^+$]. $^1H$ NMR (400 MHz, $d_6$-DMSO): 1.18 (3H, t, J=7.1 Hz), 1.29 (9H, s), 1.51 (3H, s), 1.77-2.28 (11H, m), 2.65 (1H, q, J=68.8 Hz), 3.13 (1H, dt, J=8.8, 4.0 Hz), 4.17-4.31 (2H, m), 4.96-5.04 (1H, m), 5.36 (1H, t, J=4.0 Hz), 7.26-7.45 (5H, m), 7.71-7.79 (2H, m), 8.22 (1H, br s), 8.44 (1H, d, J=1.5 Hz), 10.0 (1H, s).

Example 37. 4-(tert-Butyl)-N-(2-(dimethylamino)ethyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidine-2-carboxamide

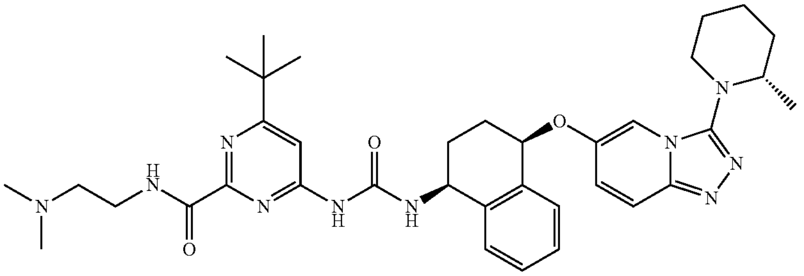

A solution of Intermediate LL (165 mg, 0.28 mmol) and N,N-dimethylethylenediamine (30 μl, 0.28 mmol) in DCM (5 ml) was treated with HOBt.x$H_2O$ (37.2 mg, 0.28 mmol) and EDC (52.8 mg, 0.28 mmol) and the mixture stirred at RT for 18 h. The RM was diluted with DCM and washed with water and brine, passed through a phase separator and evaporated. The residue was purified by HPLC (Kinetex C18, 10-98% MeCN in $H_2O$, 0.1% $HCO_2H$, 18 ml/min) and the relevant fractions lyophilized to afford the title compound (118 mg, 64%).

LCMS (Method 3): Rt 3.53 min, m/z 669 [$MH^+$]. $^1H$ NMR (400 MHz, $d_6$-DMSO): 0.90 (3H, d, J=6.3 Hz), 1.31 (9H, s), 1.40-2.30 (17H, m), 2.38 (2H, t, J=6.6 Hz), 2.84-2.93 (1H, m), 3.10-3.18 (1H, m), 4.96-5.04 (1H, m), 5.55 (1H, t, J=3.9 Hz), 7.24-7.45 (5H, m), 7.64 (1H, d, J=9.8 Hz), 7.69 (1H, d, J=1.4 Hz), 7.72 (1H, br s), 8.32 (1H, br s), 8.57 (1H, t, H=5.7 Hz), 9.90 (1H, s), plus two protons obscured by solvent peak.

Example 38. 4-(tert-Butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpyrimidine-2-carboxamide

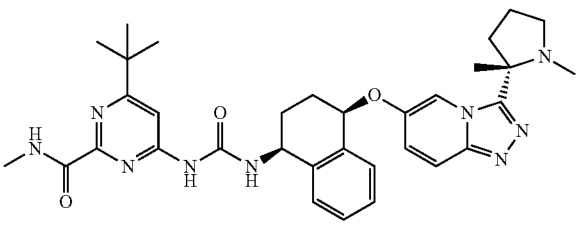

A solution of Intermediate NN (80 mg, 0.21 mmol) and (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference inits entirety, 79 mg, 0.21 mmol) in dioxane (1 ml) was heated at 100° C. for 18 hours. The reaction mixture was cooled at RT, diluted with DCM and washed with $H_2O$ (×2). The organic phase was passed through a phase separator and the solvent was removed under reduced pressure. Purification by HPLC (Kinetex C18, 10-98% MeCN/$H_2O$, 0.1% $HCO_2H$, 18 ml/min) afforded the title compound (51 mg, 40%).

LCMS (Method 3): Rt 3.40 min, m/z 612 [$MH^+$]. $^1H$ NMR (400 MHz, $d_6$-DMSO): 1.32 (9H, s), 1.51 (3H, s), 1.77-2.31 (11H, m), 2.65 (1H, q, J=8.8 Hz), 2.80 (3H, d, J=4.8 Hz), 3.13-3.21 (1H, m), 4.95-5.04 (1H, m), 5.36 (1H, t, J=3.8 Hz), 7.26-7.33 (1H, m), 7.34-7.45 (4H, m), 7.70 (1H, br s), 7.76 (1H, dd, J=9.8, 0.5 Hz), 8.30 (1H, br s), 8.47 (1H, d, J=1.6 Hz), 8.62 (1H, q, J=4.8 Hz), 9.91 (1H, s).

Example 39. 1-(4-(tert-Butyl)-6-cyanopyridin-2-yl)-3-((1S,4R)-4-((3-((R)-1,2-dimethylpyrrolidin-2-yl)-[1,2,4]triazolo[4,3-a]pyridin-6-yl)oxy)-1,2,3,4-tetrahydronaphthalen-1-yl)urea

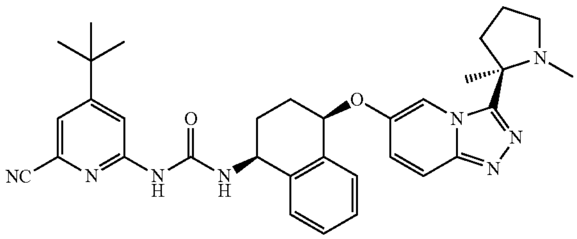 [SMILES: CN1CCC[C@]1(C)c1nnc2ccc(O[C@@H]3CC[C@H](NC(=O)Nc4cc(C(C)(C)C)cc(C#N)n4)c4ccccc43)cn12]

A solution of Intermediate TT (170 mg, 0.40 mmol) in dioxane (5 ml) was treated with Intermediate AX (118 mg, 0.60 mmol), $Pd(OAc)_2$ (18 mg, 0.10 mmol), XPhos (58 mg, 0.12 mmol) and $Cs_2CO_3$ (197 mg, 0.60 mmol). The reaction mixture was evacuated and purged with argon (×3) and then heated at 70° C. under argon for 3 h. The reaction mixture was cooled to RT and the solvent was evaporated under reduced pressure. The residue was partitioned between H2O and DCM and the two phases were separated and the organic was evaporated under reduced pressure. The residue was purified by HPLC (Gemini C18, 20-60% MeCN in $H_2O$, 0.1% $HCO_2H$, 18 ml/min). The collected fractions were applied to an SCX-2 cartridge, eluting with MeOH followed by 2M $NH_3$ in MeOH and the solvent was evaporated under reduced pressure to afford the title compound (35 mg, 30%).

LCMS (Method 3): Rt 3.76 min, m/z 579 [$MH^+$]. $^1H$ NMR (300 MHz, $CDCl_3$): 1.27 (9H, s), 1.50 (3H, s), 1.75-2.33 (13H, m), 4.94-4.99 (1H, m), 5.35 (1H, t, J=4.0 Hz), 7.28-7.43 (5H, m), 7.69 (1H, d, J=1.6 Hz), 7.73-7.77 (2H, m), 8.09 (1H, d, J=1.5 Hz), 8.44 (1H, d, J=1.6 Hz), 9.50 (1H, s).

Example 40. 1-(6-(tert-Butyl)-2-methylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

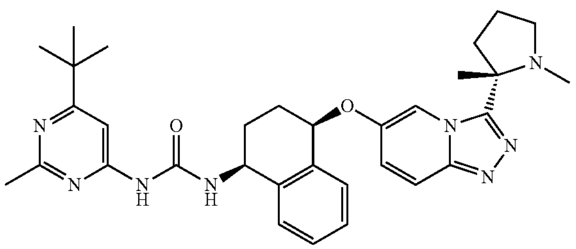

A mixture of Intermediate OOa (120 mg, 0.29 mmol), Intermediate PP (79 mg, 0.43 mmol), Xphos (41 mg, 0.086 mmol), $Pd(OAc)_2$ (13 mg, 0.058 mmol) and $Cs_2CO_3$ (139 mg, 0.43 mmol) in dioxan (3.0 ml) was purged with argon. The mixture was heated at 90° C. for 5 h and stood overnight at RT. The mixture was filtered and the filtrate loaded onto a pre-conditioned 5 g SCX-2 cartridge and eluted with DCM/MeOH (1:1) and MeOH and the basic components were then eluted with 2M $NH_3$ in MeOH, MeOH and then DCM/MeOH (1:1). The eluate was evaporated and the residue purified by HPLC (X-Bridge C18, 40-70% MeCN in water, 0.1% $NH_4OH$) to afford the title compound (15.4 mg, 9%).

LCMS (Method 3): Rt 3.27 min, m/z 569 [$MH^+$]. $^1H$ NMR (400 MHz, $d_6$-DMSO): 1.24 (9H, s), 1.50 (3H, s), 1.76-2.24 (11H, m), 2.39 (3H, s), 2.64 (1H, q, J=8.8 Hz), 3.12 (1H, dt, J=8.8, 3.8 Hz), 4.93-5.02 (1H, m), 5.36 (1H, t, J=4.0 Hz), 7.27-7.46 (6H, m), 7.76 (1H, d, J=9.8 Hz), 8.36 (1H, br s), 8.43 (1H, d, J=1.6 Hz), 9.48 (1H, s).

Example 41. 1-(6-(tert-Butyl)-2-ethylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

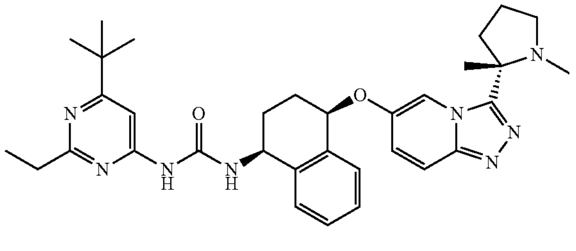 [SMILES: CCc1nc(NC(=O)N[C@H]2CC[C@@H](Oc3ccc4nnc([C@]5(C)CCCN5C)n4c3)c3ccccc32)cc(C(C)(C)C)n1]

The title compound (37.7 mg, 23%) was prepared starting from Intermediate OOa (120 mg, 0.29 mmol) and Intermediate QQ (85 mg, 0.43 mmol) using the procedure described to make Example 40.

LCMS (Method 3): Rt 3.62 min, m/z 583 [$MH^+$]. $^1H$ NMR (400 MHz, $d_6$-DMSO): 1.10 (3H, t, J=7.6 Hz), 1.24 (9H, s), 1.50 (3H, s), 1.76-2.24 (11H, m), 2.59-2.71 (3H, m), 3.11 (1H, dt, J=8.5, 3.5 Hz), 4.95-5.05 (1H, m), 5.36 (1H, t, J=4.2 Hz), 7.24-7.45 (6H, m), 7.76 (1H, dd, J=9.8, 0.6 Hz), 8.42 (1H, d, J=1.5 Hz), 8.71 (1H, br s), 9.57 (1H, s).

Example 42. 1-(6-(tert-Butyl)-2-isopropylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

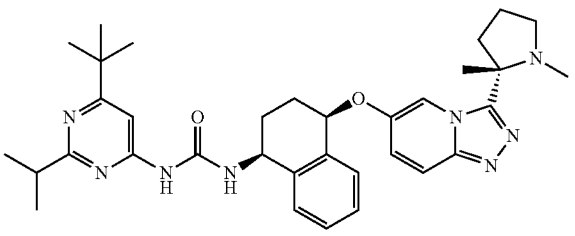 [SMILES: CC(C)c1nc(NC(=O)N[C@H]2CC[C@@H](Oc3ccc4nnc([C@]5(C)CCCN5C)n4c3)c3ccccc32)cc(C(C)(C)C)n1]

The title compound (52.2 mg, 31%) was prepared starting from Intermediate OOa (120 mg, 0.29 mmol) and Intermediate RR (91 mg, 0.43 mmol) using the procedure described to make Example 40.

LCMS (Method 3): Rt 4.00 min, m/z 597 [$MH^+$]. $^1H$ NMR (400 MHz, $d_6$-DMSO): 1.06 (3H, d, J=6.9 Hz), 1.11 (3H, d, J=6.9 Hz), 1.24 (9H, s), 1.51 (3H, s), 1.76-2.23 (11H, m), 2.64 (1H, q, J=8.7 Hz), 2.87 (1H, septet, J=6.9 Hz), 3.11 (1H, dt, J=8.7, 3.4 Hz), 4.95-5.05 (1H, m), 5.37 (1H, t, J=4.3 Hz), 7.18 (1H, br s), 7.25-7.45 (5H, m), 7.77 (1H, dd, J=9.8, 0.5 Hz), 8.42 (1H, d, J=1.5 Hz), 8.97 (1H, br s), 9.62 (1H, s).

Example 43. 1-(6-(tert-Butyl)-2-(methoxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

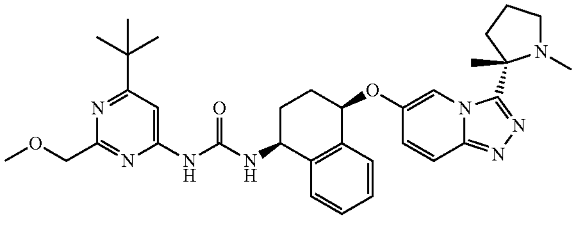

The title compound (71.5 mg, 42%) was prepared starting from Intermediate OOa (120 mg, 0.29 mmol) and Intermediate SS (92 mg, 0.43 mmol) using the procedure described to make Example 40.

LCMS (Method 3): Rt 3.59 min, m/z 599 [$MH^+$]. $^1H$ NMR (400 MHz, $d_6$-DMSO): 1.25 (9H, s), 1.51 (3H, s), 1.77-2.26 (11H, m), 2.64 (1H, q, J=8.8 Hz), 3.09-3.17 (1H, m), 3.25 (3H, s), 4.35 (1H, d, J=14.3, Hz, AB system), 4.39 (1H, d, J=14.3 Hz, AB system), 4.96-5.05 (1H, m), 5.36 (1H, t, J=4.1 Hz), 7.25-7.46 (6H, m), 7.76 (1H, dd, J=9.9, 0.5 Hz), 8.44 (1H, d, J=1.5 Hz), 8.68 (1H, br s), 9.70 (1H, s).

Example 44. 1-(4-(tert-Butyl)pyridin-2-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

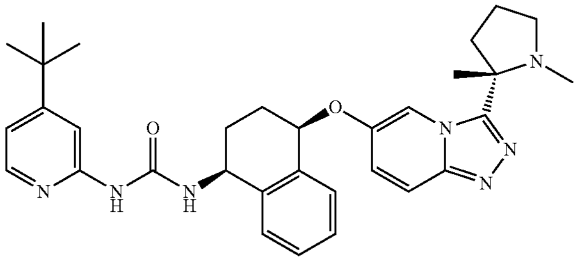 [SMILES: CN1CCC[C@@]1(C)c1nnc2ccc(O[C@@H]3CC[C@H](NC(=O)Nc4cc(C(C)(C)C)ccn4)c4ccccc43)cn12]

The title compound (54 mg, 34%) was prepared starting from Intermediate OOa (120 mg, 0.29 mmol) and 4-(tert-butyl)-2-chloropyridine (73 mg, 0.43 mmol) using the procedure described to make Example 40.

LCMS (Method 3): Rt 3.27 min, m/z 554 [$MH^+$]. $^1H$ NMR (400 MHz, $d_6$-DMSO): 1.25 (9H, s), 1.51 (3H, s), 1.77-2.26 (11H, m), 2.64 (1H, q, J=8.8 Hz), 3.11-3.18 (1H, m), 4.96-5.05 (1H, m), 5.36 (1H, t, J=3.8 Hz), 6.97 (1H, dd, J=5.5, 1.7 Hz), 7.25-7.47 (7H, m), 7.76 (1H, dd, J=9.9, 0.5 Hz), 8.02 (1H, d, J=5.5 Hz), 8.44 (1H, d, J=1.5 Hz), 8.76 (1H, br d, J=7.2 Hz), 9.18 (1H, br s).

Example 45. 1-(6-(tert-Butyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea

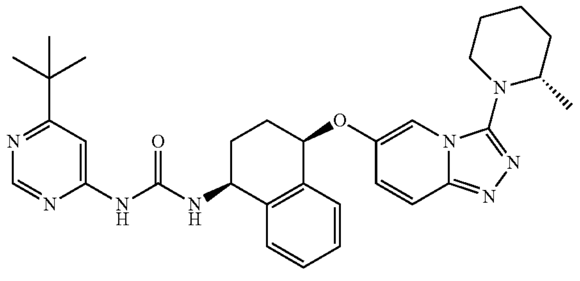 [SMILES: C[C@H]1CCCCN1c1nnc2ccc(O[C@@H]3CC[C@H](NC(=O)Nc4cc(C(C)(C)C)ncn4)c4ccccc43)cn12]

A solution of Intermediate BB (110 mg, 0.41 mmol) and (1S,4R)-4-[3-((S)-2-methyl-piperidin-1-yl)-[1,2,4]triazolo[4,3-a]pyridin-6-yloxy]-1,2,3,4-tetrahydro-naphthalen-1-ylamine (WO2014/194956, which is incorporated herein by reference inits entirety, 153 mg, 0.41 mmol) in dioxan (3 ml) in a reaction tube was treated with (88 µl, 0.51 mmol) DIPEA and purged with argon. The tube was sealed and heated at 50° C. for 72 h. The RM was cooled at RT, diluted with EtOAc and washed with 1M NaOH solution, saturated $NaHCO_3$ solution, brine, dried with $MgSO_4$ and evaporated. The residue was purified by MDAP (basic) to afford the title compound as a cream solid (159 mg, 98%).

LCMS (Method 3): Rt 4.52 min, m/z 555 [$MH^+$]. $^1H$ NMR (400 MHz, $d_6$-DMSO): 0.91 (3H, d, J=6.3 Hz), 1.27 (9H, s), 1.44-2.24 (10H, m), 2.85-2.94 (1H, m), 3.12-3.20 (1H, m), 4.94-5.03 (1H, m), 5.56 (1H, t, J=3.9 Hz), 7.22-7.45 (5H, m), 7.63-7.69 (2H, m), 7.72 (1H, d, J=1.4 Hz), 8.19 (1H, br d, J=8.3 Hz), 8.65 (1H, d, H=1.2 Hz), 9.52 (1H, s) plus one proton obscured by solvent peak.

Example 46. 1-(6-(tert-Butyl)pyrimidin-4-yl)-3-((1S,4R)-4-((3-((S)-1-methylpyrrolidin-2-yl)-[1,2,4]triazolo[4,3-a]pyridine-6-yl)oxy)-1,2,3,4-tetrahydronaphthalene-1-yl)urea Hydrochloride

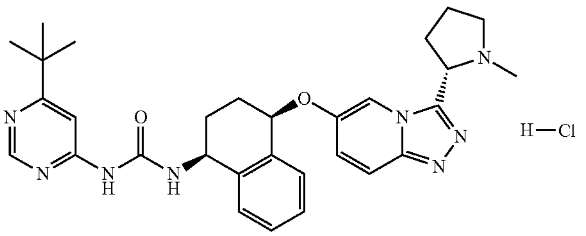 [SMILES: CN1CCC[C@H]1c1nnc2ccc(O[C@@H]3CC[C@H](NC(=O)Nc4cc(C(C)(C)C)ncn4)c4ccccc43)cn12 ; Cl]

A stirred solution of Intermediate BB (90.6 mg, 0.334 mmol) in 2-methyltetrahydrofuran (3.5 mL) under argon was added with diisopropylamine (49.1 mg, 0.38 mmol) and the (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entiery, 110 mg, 0.304 mmol) which gradually dissolved and a cream precipitate was formed overnight. The reaction mixture was stirred at 20° C. for 5 days then heated to 45° C. overnight. The reaction mixture was quenched with water and partitioned with EtOAc (×2). The combined organic layers were washed with 1N NaOH, water and brine. The solvent was removed at reduced pressure to give a pale brown glassy material purified by FCC eluting 0-20% MeOH in EtOAc. This product was dissolved in MeCN (~5 mL) and 1N HCl (0.15 mL) was added followed by water (5.5 mL) and lyophilised to afford the title compound (76.7 mg).

LCMS (Method 3): Rt 3.30 min, m/z 541 [$M+H^+$], sample assessed as ca. 98.8%. $^1H$ NMR (400 MHz, $d_6$DMSO): 1.27 (9H, s), 1.86-2.00 (1H, m), 2.01-2.31 (5H, m), 2.42 (2H, br s), 2.67-2.82 (2H, m), 2.91 (2H, s), 3.76 (1H, br s), 5.01 (1H, q, J=8.4 Hz), 5.42 (0.7H, br s), 5.59-5.70 (1.3H, m), 7.29-7.36 (1H, m), 7.36-7.45 (4H, m), 7.68 (1H, s), 7.81 (1H, d, J=9.9 Hz), 8.20-8.32 (1H, m), 8.53 (0.6H, br s), 8.66 (1H, d, J=1.1 Hz), 8.87 (0.4H, br s), 9.51-9.65 (1H, m), 10.72 (1H, br s).

Example 47. 1-(6-(tert-Butyl)pyrimidin-4-yl)-3-((1S,4R)-4-((3-((S)-1-isopropylpyrrolidin-2-yl)-[1,2,4]triazolo[4,3-a]pyridine-6-yl)oxy)-1,2,3,4-tetrahydronaphthalene-1-yl)urea Hydrochloride

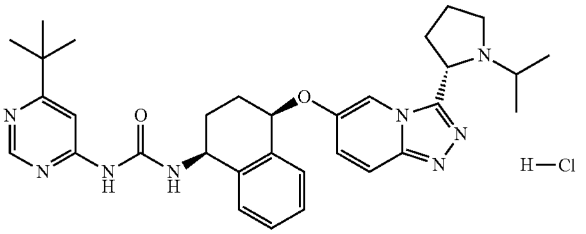 [SMILES: CC(C)N1CCC[C@H]1c1nnc2ccc(O[C@@H]3CC[C@H](NC(=O)Nc4cc(C(C)(C)C)ncn4)c4ccccc43)cn12 ; Cl]

A stirred solution of Intermediate BB (200 mg, 0.737 mmol) in dioxan (7 mL) under argon was added with diisopropylamine (108 mg, 0.838 mmol) and (1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) (262 mg, 0.67 mmol) and the reaction mixture was heated to 60° C. for 2 days. The reaction mixture was quenched with water and partitioned with EtOAc (x3). The combined organic layers were washed with 1N NaOH, water and brine. The solvent was removed at reduced pressure and the residue was purified by FCC eluting with 0-20% MeOH/EtOAc, followed by a further purification by MDAP (acidic). The residue was dissolved in MeCN (6 mL), aqueous 1N HCl solution (0.13 mL) and water (7 mL) and the solution was lyophilised to afford the title compound (54 mg, 13%).

LCMS (Method 3): Rt 3.43 min, m/z 569.4 [$M+H^+$], sample assessed as >99%. $^1H$ NMR (400 MHz, $d_6$DMSO): 1.14 (1H, d, J=6.4 Hz), 1.20-1.26 (5H, m), 1.27 (9H, s), 1.84-1.99 (1H, m), 2.00-2.41 (4H, m), 2.60-2.75 (1H, m), 3.04-3.16 (0.5H, m), 3.39-3.51 (2H, m), 3.65 (2H, br s), 4.95-5.06 (1H, m), 5.52-5.67 (1.5H, m), 5.92 (0.5H, br s), 7.29-7.36 (1H, m), 7.36-7.47 (3H, m), 7.67 (1H, s), 7.87 (1H, d, J=9.9 Hz), 8.20-8.32 (1H, m), 8.55 (1H, br s), 8.66 (1H, s), 8.92 (0.5H, s), 9.50-9.65 (1H, m), 10.43 (1H, br s), 12.02 (0.5H, s), plus 0.5 protons not observed.

Example 48. 1-(6-(tert-Butyl)-2-(methylthio)pyrimidin-4-yl)-3-((1S,4R)-4-((3-((S)-1-[1,2,4]triazolo[4,3-a]pyridine-6-yl)oxy)-1,2,3,4-tetrahydronaphthalen-1-yl)urea

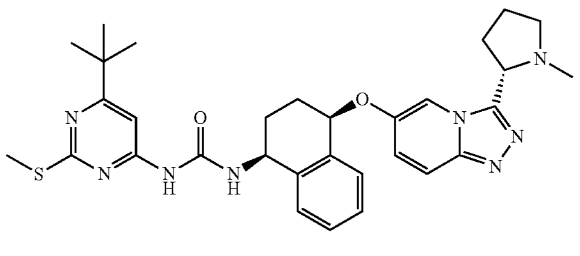

A stirred solution of Intermediate AF (21 mg, 0.057 mmol) in dioxane (0.6 ml) was added diisopropylethylamine (13 μL, 0.077 mmol) followed by (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety, 19 mg, 0.051 mmol). The mixture was stirred at 100° C. for 18 hours before adding (1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-ylamine (WO 2014/195402, which is incorporated herein by reference in its entirety, 5 mg) and dioxane (0.3 mL). The heating was continued for 24 hours at 100° C. The resulting reaction mixture was cooled at RT, partitioned between DCM/MeOH (19:1) and water and the two phases were separated. The aqueous layer was extracted with DCM (x2). The combined organic layers were washed with brine, dried with $Na_2SO_4$ and the solvent was removed under reduced pressure. Purification by FCC eluting with 0-5% (2N $NH_3$ in MeOH) in DCM gave a colourless glass which was taken up in MeCN/water and lyophilized to afford the title compound (7 mg).

LCMS (Method 3): Rt=3.95 min, m/z 587 [$M+H^+$], sample assessed as ca. 97.8%. $^1H$ NMR (400 MHz, $d_6$DMSO): 1.24 (9H, s), 1.83-2.26 (11H, m), 2.27-2.41 (4H, m), 3.08-3.14 (1H, m), 3.98 (1H, t, J=8.0 Hz), 4.93-5.02 (1H, m), 5.43 (1H, t, J=4.1 Hz), 7.22-7.45 (6H, m), 7.76 (1H, d, J=9.9 Hz), 8.15-8.23 (2H, m), 9.59 (1H, s).

Example 49. 1-(6-(tert-Butyl)-2-(methylthio)pyrimidin-4-yl)-3-((1S,4R)-4-((3-((S)-1,2-dimethylpyrrolidin-2-yl)-[1,2,4]triazolo[4,3-a]pyridine-6-yl)oxy)-1,2,3,4-tetrahydronaphthalen-1-yl)urea

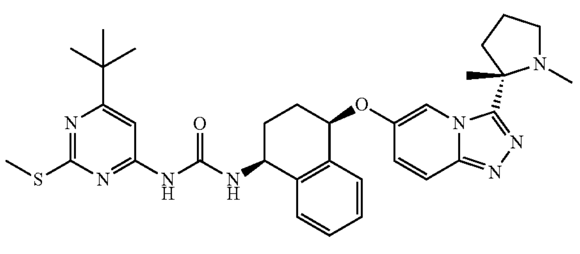

A stirred solution of Intermediate AF (390 mg, 1.10 mmol) in dioxan (1.1 ml) was added with diisopropylethylamine (0.28 mL, 1.60 mmol) followed by (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 440 mg, 1.20 mmol) and the mixture was stirred at 100° C. for 24 hours. The resulting reaction mixture was partitioned with water/DCM and the two phases were separated. The aqueous phase was extracted with DCM (x2) and the combined organic layers were washed with brine and dried with $Na_2SO_4$. The solvent was removed under reduced pressure. Purification by FCC eluting 0-3.5% (2N $NH_3$ in MeOH) in DCM, followed by a further purification by HPLC (Gemini C18 column, 18 mL/min eluting 10-98% MeCN/water+0.1% HCOOH over 30 minutes) afforded the title compound as a formate salt. The residue was partitioned between saturated sodium bicarbonate solution and DCM. The two phases were separated and the aqueous phase was extracted with DCM (x2). The combined DCM layers were evaporated under reduced pressure. The residue was dissolved in MeCN/water and lyophilized to afford the title compound (43 mg, 68%).

LCMS (Method 3): Rt=4.04 min, m/z 601 [$M+H^+$], sample assessed as >99%. $^1H$ NMR (400 MHz, $d_6$DMSO): 1.24 (9H, s), 1.50 (3H, s), 1.76-2.32 (11H, m), 2.31 (3H, s), 2.64 (1H, q, J=8.7 Hz), 3.13 (1H, dt, J=3.7, 8.5 Hz), 4.98 (1H, q, J=5.5, 13.9 Hz), 5.36 (1H, t, J=4.1 Hz), 7.23-7.46 (6H, m), 7.76 (1H, d, J=9.9 Hz), 8.21 (1H, s), 8.43 (1H, d, J=1.6 Hz), 9.59 (1H, s).

Example 50. 1-(5-(tert-Butyl)-2-methylpyridin-3-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

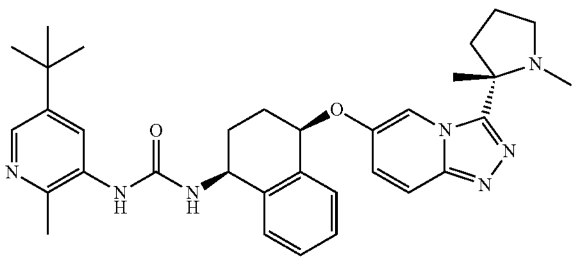 [SMILES: Cc1ncc(C(C)(C)C)cc1NC(=O)N[C@H]1CC[C@@H](Oc2ccc3nnc([C@]4(C)CCCN4C)n3c2)c2ccccc21]

The title compound (34 mg, 38%) was prepared from (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 60 mg, 0.16 mmol) and Intermediate UU (45 mg, 0.16 mmol) using the procedure described to make Example 45.

LCMS (Method 3): Rt 2.60 min, m/z 568 [$MH^+$]. $^1H$ NMR (400 MHz, $d_6$-DMSO): 1.29 (9H, s), 1.52 (3H, s), 1.78-2.24 (11H, m), 2.36 (3H, s), 2.66 (1H, q, J=8.5 Hz), 3.13-3.20 (1H, m), 4.88-4.96 (1H, m), 5.36 (1H, t, J=4.4 Hz), 7.22 (1H, d, J=8.5 Hz), 7.27-7.46 (5H, m), 7.73-7.79 (2H, m), 8.12 (1H d, J=2.2 Hz), 8.38 (1H, d, J=2.2 Hz), 8.47 (1H, d, J=1.6 Hz).

Example 51. 1-(2-(tert-Butyl)-6-(hydroxymethyl)pyridin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

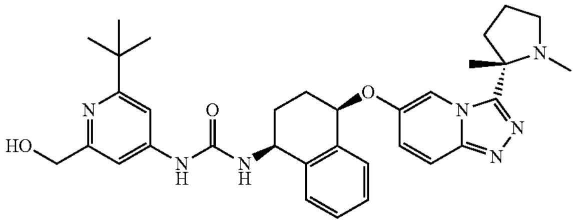 [SMILES: CN1CCC[C@@]1(C)c1nnc2ccc(O[C@@H]3CC[C@H](NC(=O)Nc4cc(CO)nc(C(C)(C)C)c4)c4ccccc43)cn12]

A solution of Intermediate OO (48 mg, 0.077 mmol) in dry THF (0.7 ml) was cooled in ice and treated with 2M $LiAlH_4$ in THF (19 μl, 0.038 mmol). After 45 min stirring at 0-5° C. a further aliquot of 2M $LiAlH_4$ in THF (38 μl, 0.076 mmol) was added and stirring continued at RT. After 2.25 h the RM was cooled in ice and quenched cautiously with water. The mixture was partitioned between water and EtOAc and the two phases were separated. The aqueous phase was extracted with EtOAc (×2) and the combined organic layers extracted with 10% citric acid solution. The citric acid layer was basified with aqueous $NaHCO_3$ solution and extracted with DCM (×3). The combined DCM layers were dried ($Na_2SO_4$) and evaporated. Purification by FCC eluting with 0-6% 2M $NH_3$ in MeOH/DCM afforded the title compound (13 mg, 29%).

LCMS (Method 3): Rt 2.45 min, m/z 584 [$MH^+$]. $^1H$ NMR (400 MHz, $d_6$-DMSO): 1.27 (9H, s), 1.51 (3H, s), 1.78-2.25 (11H, m), 2.66 (1H, q, J=8.6 Hz), 3.12-3.20 (1H, m), 4.45 (2H, d, J=5.8 Hz), 4.87-4.96 (1H, m), 5.24 (1H, t, J=5.8 Hz), 5.35 (1H, t, J=4.0 Hz), 6.81 (1H, br d, J=8.6 Hz), 7.26-7.43 (7H, m), 7.76 (1H, dd, J=9.9, 0.6 Hz), 8.46 (1H, d, J=1.5 Hz), 8.80 (1H, s).

Example 52. 1-(5-(tert-Butyl)-2-methoxypyridin-3-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea

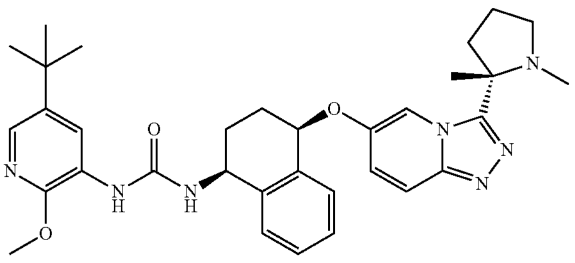 [SMILES: COc1ncc(C(C)(C)C)cc1NC(=O)N[C@H]1CC[C@@H](Oc2ccc3nnc([C@]4(C)CCCN4C)n3c2)c2ccccc21]

A solution of Intermediate VV (166 mg, 0.80 mmol) in 2-methyl THF (3 ml) was added to a solution of (1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-amine (WO 2013/083604, which is incorporated herein by reference in its entirety, 304 mg, 0.80 mmol) in 2-methyl THF (3 ml) and the reaction mixture was stirred at RT for 1 hour. The solvent was removed under reduced pressure and the residue was crystallised from DMSO to afford the title compound (115 mg, 24%).

LCMS (Method 3): Rt 3.80 min, m/z 584 [$MH^+$]. $^1H$ NMR (400 MHz, $d_6$-DMSO): 1.28 (9H, s), 1.52 (3H, s), 1.78-2.25 (11H, m), 2.66 (1H, q, J=8.5 Hz), 3.13-3.21 (1H, m), 3.90 (3H, s), 4.87-4.95 (1H, m), 5.35 (1H, t, J=4.4 Hz), 7.26-7.46 (6H, m), 7.71 (1H, d, J=2.4 Hz), 7.76 (1H, dd, J=9.8, 0.5 Hz), 8.05 (1H br s), 8.47 (1H, d, J=1.6 Hz), 8.57 (1H, d, J=2.4 Hz).

Example 53. 6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpicolinamide

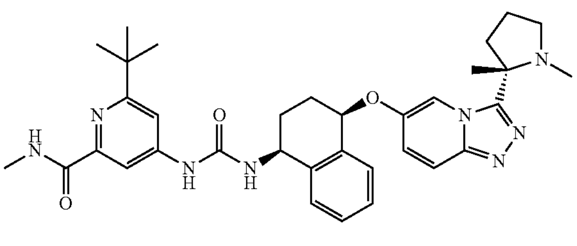

A solution of Intermediate WW (60 mg, 0.10 mmol) in DCM (1 ml) was treated with methylamine hydrochloride (10 mg, 0.15 mmol), HOBt.x$H_2O$ (27 mg, 0.20 mmol), DIPEA (70 μl, 0.40 mmol) and finally with EDC (39 mg, 0.20 mmol) and the mixture stirred at RT for 18 h. The reaction mixture was partitioned between DCM and water and the two phases were separated. The aqueous layer extracted with DCM (×2) and the combined organic layers were washed with $NaHCO_3$ solution, brine, dried with $Na_2SO_4$ and the solvent was removed under reduced pressure. Purification by MDAP (basic) afforded the title compound (27 mg, 44%).

LCMS (Method 3): Rt 3.52 min, m/z 611 [$MH^+$]. $^1H$ NMR (400 MHz, $d_6$-DMSO): 1.33 (9H, s), 1.51 (3H, s), 1.78-2.26 (11H, m), 2.65 (1H, q, J=8.7 Hz), 2.84 (3H, d, J=4.9 Hz), 3.13-3.20 (1H, m), 4.89-4.97 (1H, m), 5.35 (1H, t, J=4.0 Hz), 6.99 (1H, br d, J=8.5 Hz), 7.26-7.43 (5H, m), 7.66 (1H, d, J=1.9 Hz), 7.76 (1H, dd, J=9.9, 0.5 Hz), 7.90 (1H, d, J=1.9 Hz), 8.46 (1H, d, J=1.6 Hz), 8.49 (1H, q, J=4.9 Hz) 9.11 (1H, br s).

Example 54. 4-(tert-Butyl)-N-(2-(dimethylamino)ethyl)-6-(3-((1S,4R)-4-((3-(methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide

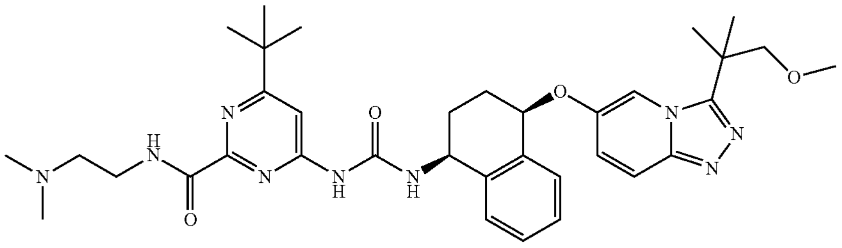

A solution of Intermediate 7e (100 mg, 0.162 mmol) in MeOH (3 mL) was added to N,N-dimethylethylenediamine (72 mg, 0.813 mmol) and warmed to 50° C. for 18 hours. The reaction mixture was partitioned between water and DCM and the two phases were separated. The aqueous phase was extracted with DCM (×2), the combined DCM phases were dried with $MgSO_4$ and the solvent was removed under reduced pressure. Purification by MDAP (basic) afforded the title compound (63 mg, 59%).

LCMS (Method 3): Rt=3.33 min, m/z 658 [$M+H^+$], sample assessed as ca. 99.1%. $^1H$ NMR (400 MHz, $d_6$DMSO): 1.31 (9H, s), 1.53 (6H, s), 1.89-2.28 (4H, m), 2.17 (6H, s), 2.40 (2H, t, J=6.6 Hz), 3.23 (3H, s), 3.36 (2H, q, J=6.5 Hz), 3.67 (2H, s), 5.00 (1H, q, J=8.4, 5.6 Hz), 5.54 (1H, t, J=3.9 Hz), 7.27-7.47 (5H, m), 7.69-7.79 (2H, m), 8.22 (1H, br s), 8.28 (1H, s), 8.58 (1H, t, J=5.8 Hz), 9.89 (1H, s).

Example 55. 4-(tert-Butyl)-N-(2-(dimethylamino)ethyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)pyrimidine-2-carboxamide

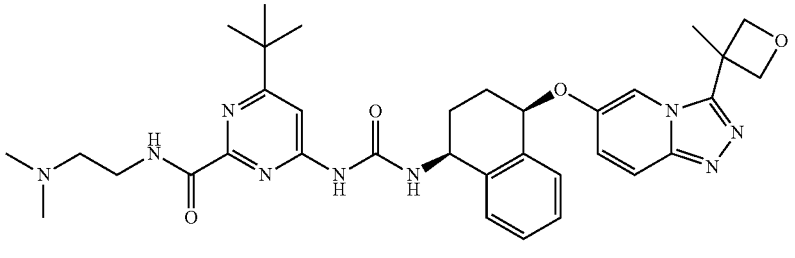 [SMILES: CN(C)CCNC(=O)c1nc(NC(=O)N[C@H]2CC[C@@H](Oc3ccc4nnc(C5(C)COC5)n4c3)c3ccccc32)cc(C(C)(C)C)n1]

A solution of Intermediate AH (100 mg, 0.167 mmol) in MeOH (3 mL) was added with N,N-dimethylethylenediamine (74 mg, 0.835 mmol) and warmed to 50° C. for 18 hours. The reaction mixture was partitioned between saturated sodium bicarbonate solution and DCM and the two phases were separated. The aqueous phase was extracted with DCM (×2) and the combined DCM phases were dried over solid $MgSO_4$ and purified by MDAP to afford the title compound (67 mg, 62%).

LCMS (Method 3): Rt=3.07 min, m/z 642.3 [M+H$^+$], sample assessed as ca. 99.5%. $^1$H NMR (400 MHz, $d_6$DMSO): 1.31 (9H, s), 1.78 (3H, s), 1.87-2.13 (3H, m), 2.17 (6H, s), 2.19-2.29 (1H, m), 2.50 (2H, t, J=1.8 Hz), 3.35 (2H, q, J=6.1 Hz), 4.82 (2H, d, J=6.1 Hz), 4.99 (1H, q, J=5.6 Hz), 5.12 (2H, q, J=4.2 Hz), 5.58 (1H, t, J=3.8 Hz), 7.27-7.45 (5H, m), 7.74 (1H, s), 7.79 (1H, d, J=9.9 Hz), 7.91 (1H, s), 8.21 (1H, br s), 8.53 (1H, t, J=5.8 Hz), 9.86 (1H, br s).

Example 56. 4-(tert-Butyl)-N-(2-(dimethylamino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalene-1-yl)ureido)pyrimidin-2-carboxamide

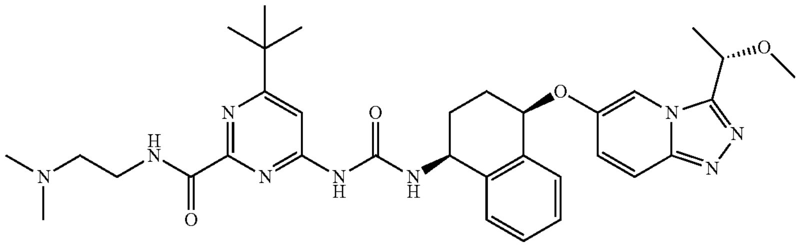

A stirred solution of Intermediate AJ (98 mg, 0.167 mmol) and N,N-dimethylamine ethanediamine (146 mg, 1.67 mmol) in DCM (3 mL) was stirred for 24 hours at RT and then the solvent was removed under reduced pressure. This residue was purified by MDAP to afford the title compound (82 mg, 77%).

LCMS (Method 3): Rt 3.18 min, m/z 630 [M+H$^+$], sample assessed as ca. 98.7%. $^1$H NMR (400 MHz, $d_6$DMSO): 1.31 (9H, s), 1.66 (3H, d, J=6.6 Hz), 1.87-2.31 (4H, m), 2.17 (6H, s), 2.39 (2H, t, J=6.6 Hz), 3.23 (3H, s), 3.36 (2H, q, J=6.2 Hz), 5.00 (1H, q, J=8.5 Hz), 5.17 (1H, q, J=6.6 Hz), 5.53 (1H, t, J=3.9 Hz), 7.27-7.49 (5H, m), 7.74 (1H, s), 7.78 (1H, d, J=9.9 Hz), 8.17 (1H, s), 8.24 (1H, br s), 8.58 (1H, t, J=5.7 Hz), 9.87 (1H, br s).

Example 57. 1-(2-(tert-Butyl)-6-((2-morpholinoethoxy)methyl)pyrimidin-4-yl)-3-((1S,4R)-4-((3-(2-methoxypropan-2-yl)-[1,2,4]triazolo[4,3-a]pyridin-6-yl)oxy)-1,2,3,4-tetrahydronaphthalen-1-yl)urea

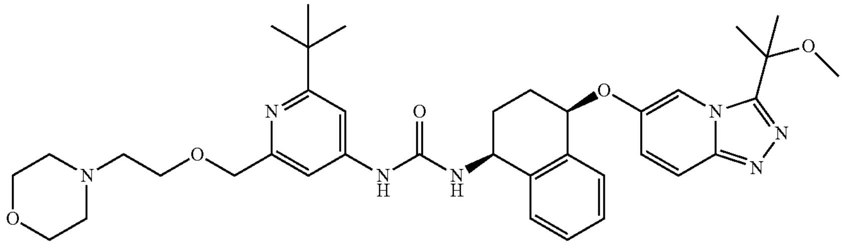 [SMILES: COC(C)(C)c1nnc2ccc(O[C@@H]3CC[C@H](NC(=O)Nc4cc(COCCN5CCOCC5)nc(C(C)(C)C)c4)c4ccccc43)cn12]

A solution of Intermediate 12d (250 mg, 0.71 mmol), Intermediate AP (250 mg, 0.78 mmol), palladium(II)acetate (17 mg, 0.07 mmol), xantphos (81 mg. 0.14 mmol) and cesium carbonate (350 mg, 1.06 mmol) in dioxan (10 mL) was degassed by bubbling argon through the mixture under sonication for 10 minutes. The reaction mixture was stirred at 100° C. for 90 minutes then filtered through a pad of Celite®. The precipitate was washed with DCM and MeOH. The solvents were removed under reduced pressure and the crude mixture was purified by FCC eluting with 0-10% (2M $NH_3$ in MeOH)/DCM followed by MDAP (basic) to afford the title compound (270 mg, 64%).

LCMS (Method 2): Rt=2.73 min, m/z 672 [M+H$^+$], sample assessed as ca. 99%. $^1$H-NMR (400 MHz, DMSO): 1.27 (9H, s), 1.69 (6H, s), 1.85-2.26 (4H, m), 2.42 (4H, t, J=4.4 Hz), 2.54 (2H, t, J=5.8 Hz), 2.98 (3H, s), 3.56 (4H, t, J=4.6 Hz), 3.63 (2H, t, J=5.8 Hz), 4.45 (2H, s), 4.92 (1H, q, J=8.7 Hz), 5.48 (1H, t, J=4.1 Hz), 6.86 (1H, d, J=8.6 Hz), 7.26-7.44 (7H, m), 7.82 (1H, d, J=9.9 Hz), 8.12 (1H, s), 8.84 (1H, s).

Example 58. 4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide

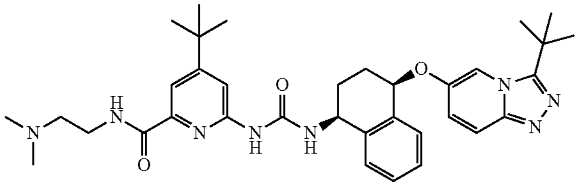 [SMILES: CN(C)CCNC(=O)c1cc(C(C)(C)C)cc(NC(=O)N[C@H]2CC[C@@H](Oc3ccc4nnc(C(C)(C)C)n4c3)c3ccccc32)n1]

A solution of Intermediate AY (150 mg, 0.25 mmol) and N,N-dimethylethylene diamine (226 mg, 2.50 mmol) in ethanol (4 mL) was warmed to 80° C. for 2 days. The solvent was removed under reduced pressure and purification by FCC eluting with 0-10% (2M $NH_3$ in MeOH)/DCM followed by MDAP (basic) afforded the title compound (75 mg, 48%).

LCMS (Method 3): Rt=3.33 min, m/z 627 [M+H$^+$], sample assessed as ca. 99.5%. $^1$H-NMR (400 MHz, DMSO): 1.29 (9H, s), 1.53 (9H, s), 1.84-2.25 (4H, m), 2.14 (6H, s), 2.34 (2H, t, J=6.3 Hz), 3.35 (2H, dd, J=1.8, 6.1 Hz, partially obscured by the water peak), 4.96 (1H, q, J=8.7 Hz), 5.64 (1H, t, J=4.1 Hz), 7.25-7.48 (5H, m), 7.58 (1H, d, J=8.5 Hz), 7.62 (1H, d, J=1.7 Hz), 7.75 (1H, d, J=9.9 Hz), 8.05 (1H, t, J=5.6 Hz), 8.10 (1H, d, J=1.6 Hz), 8.14 (1H, s), 9.08 (1H, s).

Example 59. 4-(tert-Butyl)-N-(2-(dimethylamino)ethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide

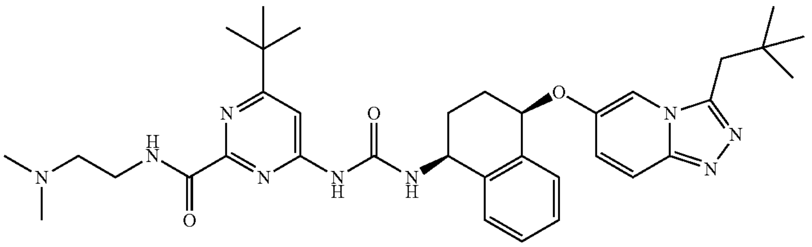 [SMILES: CN(C)CCNC(=O)c1nc(NC(=O)N[C@H]2CC[C@@H](Oc3ccc4nnc(CC(C)(C)C)n4c3)c3ccccc32)cc(C(C)(C)C)n1]

A solution of Intermediate AI (100 mg, 0.167 mmol) in MeOH (3 mL) was added to N,N-dimethylethylenediamine (74 mg, 0.835 mmol) and warmed to 50° C. for 18 hours. The reaction mixture was partitioned between saturated sodium bicarbonate solution and DCM and the two phases were separated. The aqueous phase was extracted with DCM (×2) and the combined DCM phases were dried over solid $MgSO_4$ and the solvent was removed under reduced pressure. Purification by MDAP (basic) afforded the title compound (67 mg, 62%).

LCMS (Method 3): Rt=3.44 min, m/z 642 [MH$^+$], sample assessed as ca. 99.5%. $^1$H NMR (400 MHz, $d_6$DMSO): 1.98 (9H, s), 1.31 (9H, s), 1.89-2.29 (4H, m), 2.17 (6H, s), 2.38 (2H, t, J=6.6 Hz), 3.03 (2H, q, J=14.55 Hz), 3.39 (2H, q, J=6.1 Hz, partially obscured by the water peak), 5.01 (1H, q, J=8.7 Hz), 5.57 (1H, t, J=3.9 Hz), 7.23-7.32 (2H, m), 7.32-7.46 (3H, m), 7.70 (1H, d, J=9.8 Hz), 7.72 (1H, s), 8.31 (2H, br d, J=1.3 Hz), 8.59 (1H, t, J=7.5 Hz), 9.88 (1H, br s).

Example 60. 4-(tert-Butyl)-N-(2-hydroxyethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide

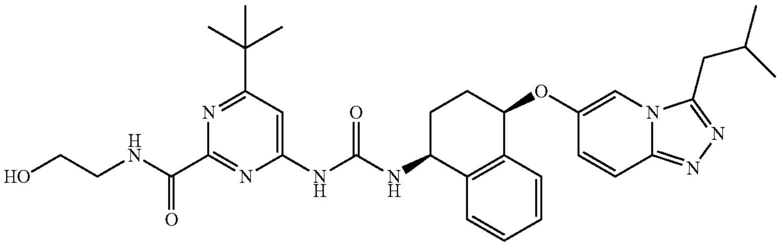 [SMILES: CC(C)Cc1nnc2ccc(O[C@@H]3CC[C@H](NC(=O)Nc4cc(C(C)(C)C)nc(C(=O)NCCO)n4)c4ccccc43)cn12]

A solution of Intermediate AG (100 mg, 0.17 mmol) in MeOH (3 mL) was added with ethanolamine (52 mg, 0.85 mmol) and warmed to 55° C. for 8 hours. The reaction mixture was partitioned between water and DCM and the two phases were separated. The aqueous phase was extracted with DCM (×2) and the combined DCM phases were dried with $MgSO_4$ and the solvent was removed under reduced pressure. Purification by MDAP (basic) afforded the title compound (56 mg, 55%).

LCMS (Method 3): Rt=3.91 min, m/z 601 [$M+H^+$], sample assessed as ca. 98.8%. $^1H$ NMR (400 MHz, $d_6$DMSO): 0.96 (6H, d, J=6.6 Hz), 1.31 (9H, s), 1.88-2.31 (5H, m), 2.98 (2H, d, J=6.8 Hz), 3.35 (2H, q, J=5.8 Hz), 3.51 (2H, t, J=5.8 Hz), 4.81 (1H, s), 5.00 (1H, q, J=8.7 Hz), 5.57 (1H, t, J=3.9 Hz), 7.23-7.45 (5H, m), 7.66-7.95 (2H, m), 8.23 (2H, s), 8.58 (1H, t, J=5.9 Hz), 9.91 (1H, s).

Example 61. 6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)picolinamide

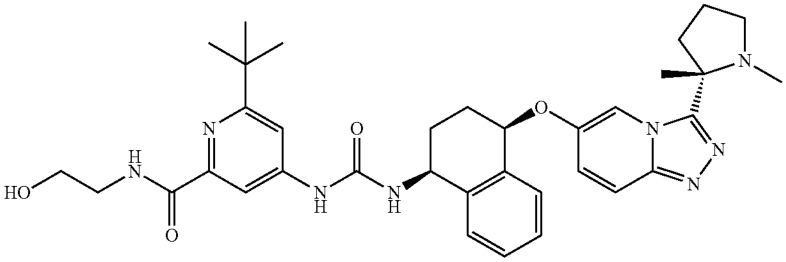 [SMILES: CN1CCC[C@@]1(C)c1nnc2ccc(O[C@@H]3CC[C@H](NC(=O)Nc4cc(C(=O)NCCO)nc(C(C)(C)C)c4)c4ccccc43)cn12]

A solution of Intermediate 00 (55 mg, 0.09 mmol) in DCM (0.9 ml) was treated with ethanolamine (6.6 μl, 0.14 mmol), $HOBt.xH_2O$ (18 mg, 0.14 mmol), DIPEA (40 μl, 0.23 mmol) and finally with EDC (26 mg, 0.14 mmol) and the mixture stirred at RT for 2 h. Further aliquots of ethanolamine (6.6 μl, 0.14 mmol) and EDC (26 mg, 0.14 mmol) were added along with DMF (0.5 ml) and the RM was warmed to 50° C. for 18 hours. Further aliquots of ethanolamine (6.6 μl, 0.14 mmol) and EDC (26 mg, 0.14 mmol) were added and stirring continued at 50° C. for 5 h. The RM was partitioned between DCM and water and the two phases were separated. The aqueous layer was extracted with DCM (×2) and the combined organic layers were washed with $NaHCO_3$ solution, brine, dried with $Na_2SO_4$ and the solvent was removed under reduced pressure. Purification by MDAP (basic) afforded the title compound (19 mg, 33%).

LCMS (Method 3): Rt 3.22 min, m/z 641 [$MH^+$]. $^1H$ NMR (400 MHz, $d_6$-DMSO): 1.33 (9H, s), 1.51 (3H, s), 1.78-2.26 (11H, m), 2.65 (1H, q, J=8.7 Hz), 3.13-3.20 (1H, m), 3.39 (2H, q, J=5.8 Hz), 3.54 (2H t, J=5.8 Hz), 4.83 (1H, br s), 4.89-4.97 (1H, m), 5.35 (1H, t, J=4.0 Hz), 7.11 (1H, br d, J=8.5 Hz), 7.26-7.43 (5H, m), 7.69 (1H, d, J=1.9 Hz), 7.76 (1H, dd, J=9.9, 0.5 Hz), 7.93 (1H, d, J=1.9 Hz), 8.46 (1H, d, J=1.6 Hz), 8.53 (1H, t, J=5.8 Hz) 9.24 (1H, br s).

Example 62. 6-(tert-Butyl)-N-(2-(dimethylamino)ethyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)picolinamide

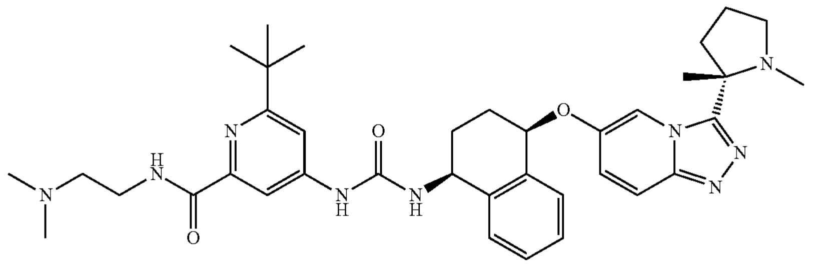

The title compound (9 mg, 15%) was prepared from N,N-dimethylethylenediamine (36 μl, 0.33 mmol) and Intermediate 00 (55 mg, 0.09 mmol) using the procedure described to make Example 61.

LCMS (Method 3): Rt 2.72 min, m/z 668 [$MH^+$]. $^1H$ NMR (400 MHz, $d_6$-DMSO): 1.33 (9H, s), 1.51 (3H, s), 1.78-2.26 (17H, m), 2.42 (2H, t, J=6.5 Hz), 2.65 (1H, q, J=8.7 Hz), 3.13-3.20 (1H, m), 3.38 (2H, q, J=5.8 Hz), 4.89-4.97 (1H, m), 5.35 (1H, t, J=4.0 Hz), 6.96 (1H, br d, J=8.5 Hz), 7.26-7.43 (5H, m), 7.67 (1H, d, J=1.9 Hz), 7.76 (1H, dd, J=9.9, 0.5 Hz), 7.90 (1H, d, J=1.9 Hz), 8.46 (1H, d, J=1.6 Hz), 8.58 (1H, t, J=5.8 Hz), 9.07 (1H, br s).

Example 63. 1-(6-(tert-Butyl)-2-((2-morpholinoethoxy)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea

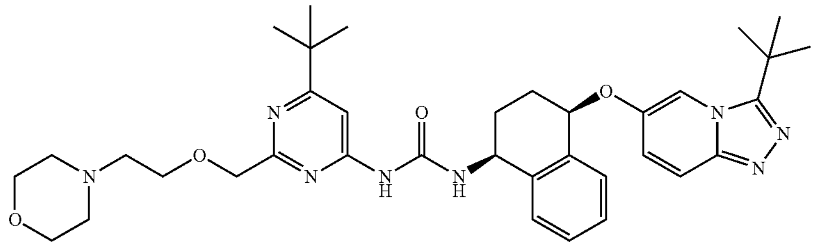 [SMILES: CC(C)(C)c1cc(NC(=O)N[C@H]2CC[C@@H](Oc3ccc4nnc(C(C)(C)C)n4c3)c3ccccc32)nc(COCCN2CCOCC2)n1]

A solution of Intermediate EE (136 mg, 0.22 mmol) in 2-methyltetrahydrofuran (5 ml) was treated with $K_2CO_3$ (91 mg, 0.66 mmol) and 2-morpholinoethanol (CAS: 622-40-2, 80 μl, 0.66 mmol). The reaction mixture was heated at 70° C. for 5 hours and then another aliquot of morpholinoethanol (80 μl, 0.66 mmol) was added. The reaction mixture was heated at 90° C. for 5 days. The reaction mixture was cooled at RT and then treated with sodium hydride (60% in mineral oil, 10 mg, 0.26 mmol). The resulting mixture was heated at 80° C. for 18 hours. The reaction mixture was cooled at RT and then treated another aliquot of sodium hydride (60% in mineral oil, 10 mg, 0.26 mmol). The resulting mixture was heated at 80° C. for 18 hours, cooled at RT and quenched with $H_2O$. The product was extracted with EtOAc and the solvent was removed under reduced pressure. Purification by MDAP (basic), followed by HPLC (Kinetex C18, 5-50% MeCN in $H_2O$, 0.1% $HCO_2H$, 18 ml/min) afforded the title compound as formate salt. The residue was partitioned between 2-methyltetrahydrofuran and saturated aqueous $NaHCO_3$ solution and the two phases were separated. The solvent was removed under reduced pressure. The residue was partitioned between DCM and an aqueous 1M NaOH solution and the two phases were separated. The solvent was removed under reduced pressure to afford the title compound as a free base (8 mg, 5%).

LCMS (Method 3): Rt 3.27 min, m/z 657 [$MH^+$]. $^1H$ NMR (400 MHz, $CDCl_3$): 1.29 (9H, s), 1.59 (9H, s), 2.12-2.27 (3H, m), 2.34-2.42 (7H, m), 3.59-3.64 (6H, m), 4.50 (1H, d, J=14.6 Hz, AB system), 4.55 (1H, d, J=14.6 Hz, AB system), 5.19-5.25 (2H, m), 6.73 (1H, s), 7.16 (1H, dd, J=9.9, 2.0 Hz), 7.28-7.38 (3H, m), 7.54-7.57 (1H, m), 7.77 (1H, d, J=9.9 Hz), 7.82 (1H, d, J=1.3 Hz), 8.38 (1H, br s), 9.83 (1H, br s).

Example 64. 4-(tert-Butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide

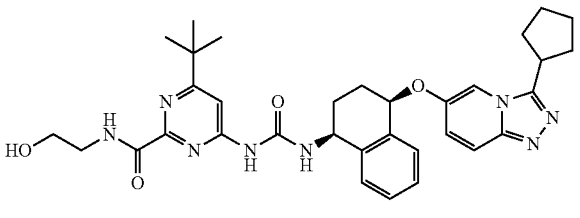 [SMILES: CC(C)(C)c1cc(NC(=O)N[C@H]2CC[C@@H](Oc3ccc4nnc(C5CCCC5)n4c3)c3ccccc32)nc(C(=O)NCCO)n1]

A solution of Intermediate KK (90 mg, 0.15 mmol) in methanol (2 ml) was treated with N,N-dimethylethylenediamine (91 μl, 1.5 mmol). The reaction mixture was heated at 55° C. for 18 hours, cooled at RT and the solvent was removed under reduced pressure. Purification by MDAP (basic) afforded the title compound (70 mg, 60%).

LCMS (Method 3): Rt 3.92 min, m/z 613 [$MH^+$]. $^1H$ NMR (400 MHz, d-$_6$-DMSO): 1.39 (9H, s), 1.66-2.22 (12H, m), 3.30-3.37 (2H, m), 3.51 (2H, br s), 3.62 (1H, quintet, J=7.9 Hz), 4.80 (1H, br s), 4.98-5.04 (1H, m), 5.57 (1H, t, J=4.0 Hz), 7.25-7.43 (5H, m), 7.69 (1H, dd, J=9.8, 0.6 Hz), 7.74 (1H, br s), 8.20 (1H, d, J=1.3 Hz), 8.25 (1H, br s), 8.57 (1H, t, J=5.8 Hz), 9.84 (1H, br s).

Examples 65-211 a. Procedure I (Examples 65-85, 89-102, 104-109, 111-112, 114-125, 128-134, 136-143, 145-197 and 199-211)

A solution of Intermediate (Table 1, 1 eq) and the relevant amine (Reagent, Table 1, 2-15 eq) in suitable solvent such as MeOH (3-5 ml) or EtOH (3-5 ml) was heated to a range of temperature, usually between 50° C. and 80° C. for 18 h. After cooling the mixture was evaporated and the residue was purified by FCC eluting with 0-10% (2M NH3 in MeOH)/DCM to afford the title compound (10%-90%). Where necessary, further purification by, for example, trituration, crystallisation, HPLC, MDAP or SFC could be undertaken.

b. Procedure II (Examples 86-88, 113 and 135)

A solution of Intermediate (Table 1, 1 eq) in tetrahydrofuran was treated with the relevant amine (Reagent, Table 1, 1-10 eq). The reaction mixture was heated at 60° C. for 18 hours. The reaction mixture was cooled at RT and diluted with DCM and $H_2O$. The two phases were separated and the aqueous phase was extracted with DCM (×2). The combined organic phases were dried with $Na_2SO_4$ and the solvent was removed under reduced pressure. Purification by FCC eluting with 0-10% (2M NH3 in MeOH)/DCM or MDAP (basic) afforded the title compound (40%-50%). Where necessary, further purification by, for example, trituration, crystallisation, HPLC, MDAP or SFC could be undertaken.

c. Procedure III (Examples 103, 110 and 126-127)

A solution of Intermediate (Table 1, 1 eq), HOBt (1.2 eq) and EDC (1.2 eq) in DCM (3-5 ml) was treated with the relevant acid (Reagent, Table 1, 1.2 eq). The reaction mixture was stirred at RT for 1 hour. The reaction mixture was diluted with DCM and $H_2O$ and the two phases were separated. The aqueous phase was extracted with DCM (×3) and the combined organic phases were passed through a phase separator and the solvent was removed under reduced pressure. Purification by FCC, eluting with 0-10% 2N $NH_3$ in MeOH/DCM afforded the title compound (10%-50%). Where necessary, further purification by, for example, trituration, crystallization, HPLC, MDAP or SFC could be undertaken.

d. Procedure IV (Example 144)

A solution of the relevant alcohol (Reagent, Table 1, 2 eq) in tetrahydrofuran (4 ml) under nitrogen was treated with NaH (60% in mineral oil, 2 eq). The reaction mixture was stirred for 1 hour and a solution of Intermediate (Table 1, 1 eq) in tetrahydrofuran (2 ml) was added. The reaction mixture was stirred at RT for 1 hour and partitioned between $H_2O$ and EtOAc. The two phases were separated and the aqueous phase was extracted with EtOAc. The combined organic phases were dried with $MgSO_4$ and the solvent was removed under reduced pressure. Purification by FCC eluting with 0-10% (2M NH3 in MeOH)/DCM afforded the title compound (3%).

e. Procedure V (Example 198)

A solution of Intermediate (Table 1, 1 eq) in MeOH (3 ml) and $H_2O$ (0.5 ml) was treated with $K_2CO_3$. The reaction mixture was stirred at RT for 2 hours and diluted with $H_2O$ and DCM. The two phases were separated and the aqueous phase was extracted with DCM (×3). The combined organic phases were passed through a phase separator and the solvent was removed under reduced pressure. Purification by MDAP (basic) afforded the title compound (69%).

TABLE 1

| Structure | Ex. | Chemical Name | NMR | LCMS | Interm. | Reagent |
|---|---|---|---|---|---|---|
| 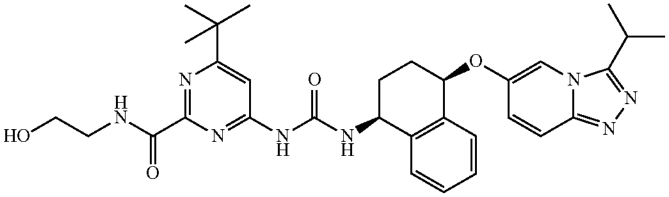 [SMILES: CC(C)c1nnc2ccc(O[C@@H]3CC[C@H](NC(=O)Nc4cc(C(C)(C)C)nc(C(=O)NCCO)n4)c4ccccc43)cn12] | 65 | 4-(tert-butyl)-N-(2-hydroxyethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.32 (9H, s), 1.37 (3H, d, J = 7.2 Hz), 1.39 (3H, d, J = 7.2 Hz), 1.91-2.28 (4H, m), 3.35 (2H, q, J = 6.0 Hz), 3.50-3.60 (3H, m), 4.78 (1H, t, J = 4.9 Hz), 4.97-5.03 (1H, m), 5.57 (1H, t, J = 4.0 Hz), 7.26-7.44 (5H, m), 7.70 (1H, dd, J = 9.8, 0.6 Hz), 7.74 (1H, br s), 8.20-8.25 (2H, m), 8.56 (1H, t, J = 5.8 Hz), 9.89 (1H, s). | (Method 2): Rt 3.66 min, m/z 587 [MH$^+$]. | CC | Ethanolamine CAS: 141-43-5 |
| 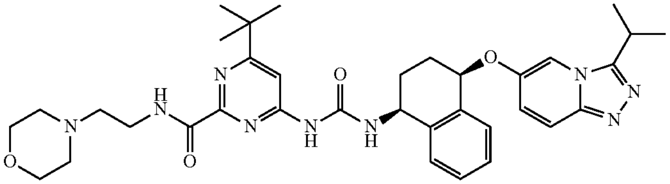 [SMILES: CC(C)c1nnc2ccc(O[C@@H]3CC[C@H](NC(=O)Nc4cc(C(C)(C)C)nc(C(=O)NCCN5CCOCC5)n4)c4ccccc43)cn12] | 66 | 4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-morpholinoethyl) pyrimidine-2-carboxamide | $^1$H NMR (400 MHz, d-6-DMSO): 1.33 (9H, s), 1.37 (3H, d, J = 6.8 Hz), 1.39 (3H, d, J = 6.8 Hz), 1.93-2.28 (4H, m), 2.42 (4H, t, J = 4.1 Hz), 3.38 (2H, q, J = 6.4 Hz), 3.55-3.60 (5H, m), 4.98-5.04 (1H, m), 5.57 (1H, t, J = 4.0 Hz), 7.25-7.44 (5H, m), 7.70 (1H, dd, J = 9.9, 0.7 Hz), 7.72 (1H, br s), 8.22 (1H, d, J = 1.4 Hz), 8.31 (1H, br s), 8.67 (1H, t, J = 5.5 Hz), 9.92 (1H, s), plus two protons obscured by the solvent peak. | (Method 2): Rt 3.19 min, m/z 656 [MH$^+$]. | CC | 4-(2-aminoethyl) morpholine CAS: 2038-03-1 |
| 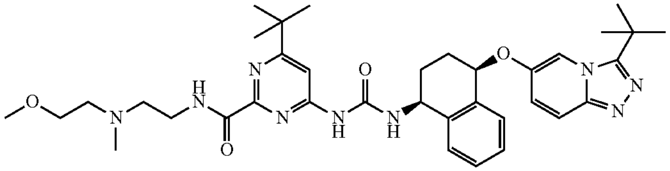 [SMILES: COCCN(C)CCNC(=O)c1nc(NC(=O)N[C@H]2CC[C@@H](Oc3ccc4nnc(C(C)(C)C)n4c3)c3ccccc32)cc(C(C)(C)C)n1] | 67 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl) amino)ethyl)pyrimidine-2-carboxamide | $^1$H NMR (400 MHz, d-6-DMSO): 1.31 (9H, s), 1.52 (9H, s), 1.92-2.33 (9H, m), 3.19 (3H, s), 3.40 (2H, t, J = 6.0 Hz), 4.97-5.03 (1H, m), 5.63 (1H, t, J = 3.8 Hz), 7.28-7.44 (5H, m), 7.71 (1H, br s), 7.74 (1H, dd, J = 9.8, 0.6 Hz), 8.15 (1H, d, J = 1.2 Hz), 8.29 (1H, br s), 8.58 (1H, t, J = 5.6 Hz), 9.92 (1H, s), plus four protons obscured by the solvent peak. | (Method 3): Rt 3.35 min, m/z 672 [MH$^+$]. | 1i | N'-(2-methoxyethyl)-N'-methyl-ethane-1,2-diamine CAS: 14165-17-4 |

TABLE 1-continued

| Structure | Ex. | Chemical Name | NMR | LCMS | Interm. | Reagent |
|---|---|---|---|---|---|---|
| 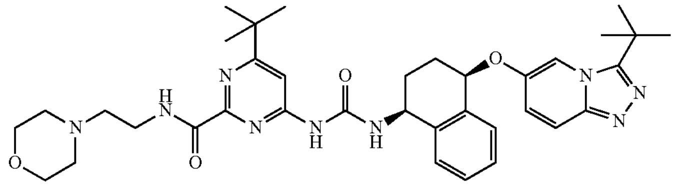 [SMILES: CC(C)(C)c1cc(NC(=O)N[C@H]2CC[C@@H](Oc3ccc4nnc(C(C)(C)C)n4c3)c3ccccc32)nc(C(=O)NCCN2CCOCC2)n1] | 68 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-morpholinoethyl) pyrimidine-2-carboxamide | $^1$H NMR (400 MHz, d-6-DMSO): 1.33 (9H, s), 1.53 (9H, s), 1.92-2.27 (4H, m), 2.42 (4H, br s), 3.39 (2H, q, J = 6.4 Hz), 3.58 (4H, t, J = 4.4 Hz), 4.97-5.03 (1H, m), 5.63 (1H, t, J = 3.8 Hz), 7.28-7.45 (5H, m), 7.72 (1H, br s), 7.75 (1H, dd, J = 9.8, 0.6 Hz), 8.15 (1H, d, J = 1.2 Hz), 8.30 (1H, br s), 8.69 (1H, t, J = 5.6 Hz), 9.95 (1H, s), plus two protons obscured by the solvent peak. | (Method 3): Rt 3.34 min, m/z 670 [MH+]. | 1i | 4-(2-aminoethyl) morpholine CAS: 2038-03-1 |
| 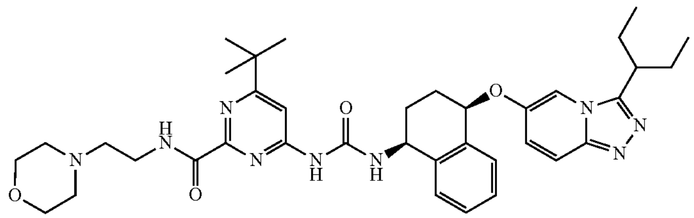 [SMILES: CCC(CC)c1nnc2ccc(O[C@@H]3CC[C@H](NC(=O)Nc4cc(C(C)(C)C)nc(C(=O)NCCN5CCOCC5)n4)c4ccccc43)cn12] | 69 | 4-(tert-butyl)-N-(2-morpholinoethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.77 (3H, t, J = 7.4 Hz), 0.80 (3H, t, J = 7.4 Hz), 1.33 (9H, s), 1.76-2.26 (8H, m), 2.42 (4H, br s), 3.38 (2H, q, J = 6.0 Hz), 3.57 (4H, t, J = 4.4 Hz), 4.98-5.04 (1H, m), 5.57 (1H, t, J = 4.0 Hz), 7.25-7.43 (5H, m), 7.69-7.72 (2H, m), 8.27 (1H, d, J = 1.4 Hz), 8.30 (1H, br s), 8.69 (1H, t, J = 5.6 Hz), 9.93 (1H, s), plus three protons obscured by the solvent peak. | (Method 3): Rt 3.43 min, m/z 684 [MH$^+$]. | 5e | 4-(2-aminoethyl) morpholine CAS: 2038-03-1 |
| 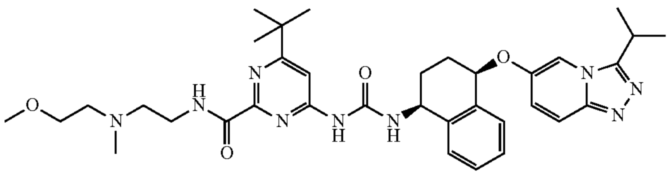 [SMILES: COCCN(C)CCNC(=O)c1nc(NC(=O)N[C@H]2CC[C@@H](Oc3ccc4nnc(C(C)C)n4c3)c3ccccc32)cc(C(C)(C)C)n1] | 70 | 4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-((2-methoxyethyl)(methyl) amino)ethyl)pyrimidine-2-carboxamide | $^1$H NMR (400 MHz, d-6-DMSO): 1.32 (9H, s), 1.37 (3H, d, J = 6.8 Hz), 1.39 (3H, d, J = 6.8 Hz), 1.91-2.27 (7H, m), 2.53 (2H, q, J = 5.9 Hz, partially obscured by the solvent peak), 3.20 (3H, s), 3.41 (2H, t, J = 6.0 Hz), 3.57 (1H, heptet, J = 6.8 Hz), 4.98-5.04 (1H, m), 5.57 (1H, t, J = 4.0 Hz), 7.26-7.44 (5H, m), 7.70 (1H, dd, J = 9.8, 0.6 Hz), 7.72 (1H, br s), 8.23 (1H, d, J = 1.3 Hz), 8.30 (1H, br s), 8.58 (1H, t, J = 5.6 Hz), 9.80 (1H, s), plus four protons obscured by the solvent peak. | (Method 3): Rt 3.25 min, m/z 658 [MH$^+$]. | CC | (2-aminoethyl)(2-methoxyethyl) methylamine CAS: 14165-17-4 |

TABLE 1-continued

| Structure | Ex. | Chemical Name | NMR | LCMS | Interm. | Reagent |
|---|---|---|---|---|---|---|
| 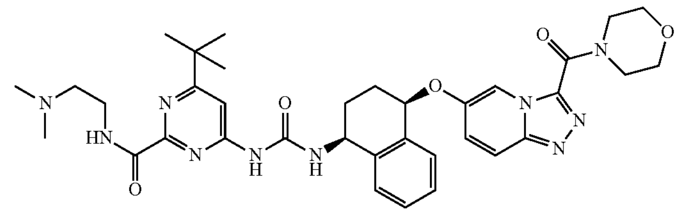 [SMILES: CN(C)CCNC(=O)c1nc(NC(=O)N[C@H]2CC[C@@H](Oc3ccc4nnc(C(=O)N5CCOCC5)n4c3)c3ccccc32)cc(C(C)(C)C)n1] | 71 | 4-(tert-butyl)-N-(2-(dimethylamino)ethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.31 (9H, s), 1.88-2.32 (10H, m), 2.39 (2H, t, J = 6.6 Hz), 3.35 (2H, q, J = 6.2 Hz, partially covered by the solvent peak), 3.74 (6H, br s), 4.28 (2H, br s), 4.97-5.03 (1H, m), 5.50 (1H, t, J = 3.8 Hz), 7.30-7.45 (4H, m), 7.55 (1H, dd, J = 9.8, 2.2 Hz), 7.75 (1H, s), 7.96 (1H, dd, J = 9.8, 0.6 Hz), 8.22 (1H, br s), 8.58 (1H, t, J = 5.7 Hz), 8.75 (1H, d, J = 1.6 Hz), 9.87 (1H, s). | (Method 3): Rt 3.20 min, m/z 685 [MH$^+$]. | AD | N,N-dimethyl-ethylene diamine CAS: 108-00-9 |
| 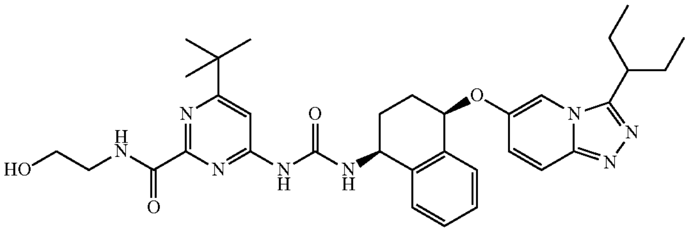 [SMILES: CCC(CC)c1nnc2ccc(O[C@@H]3CC[C@H](NC(=O)Nc4cc(C(C)(C)C)nc(C(=O)NCCO)n4)c4ccccc43)cn12] | 72 | 4-(tert-butyl)-N-(2-hydroxyethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.78 (3H, t, J = 7.4 Hz), 0.80 (3H, t, J = 7.4 Hz), 1.32 (9H, s), 1.76-2.24 (8H, m), 3.52 (2H, br s), 4.81 (1H, br s), 4.98-5.03 (1H, m), 5.57 (1H, t, J = 4.0 Hz), 7.25-7.43 (5H, m), 7.70 (1H, dd, J = 9.8, 0.6 Hz), 7.74 (1H, br s), 8.24 (1H, br s), 8.28 (1H, d, J = 1.3 Hz), 8.58 (1H, t, J = 5.8 Hz), 9.91 (1H, s), plus three protons obscured by the solvent peak. | (Method 3): Rt 4.03 min, m/z 615 [MH$^+$]. | 5e | Ethanolamine CAS: 141-43-5 |
| 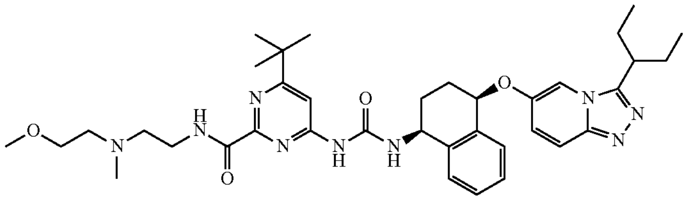 [SMILES: CCC(CC)c1nnc2ccc(O[C@@H]3CC[C@H](NC(=O)Nc4cc(C(C)(C)C)nc(C(=O)NCCN(C)CCOC)n4)c4ccccc43)cn12] | 73 | 4-(tert-butyl)-N-(2-((2-methoxyethyl)(methyl)amino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.77 (3H, t, J = 7.4 Hz), 0.80 (3H, t, J = 7.4 Hz), 1.32 (9H, s), 1.76-2.26 (11H, m), 2.53 (4H, q, J = 6.0 Hz, partially obscured by the solvent peak), 3.20 (3H, s), 3.41 (2H, t, J = 6.0 Hz), 4.98-5.04 (1H, m), 5.57 (1H, t, J = 4.0 Hz), 7.25-7.43 (5H, m), 7.69-7.72 (2H, m), 8.27 (1H, d, J = 1.3 Hz), 8.31 (1H, br s), 8.58 (1H, t, J = 5.6 Hz), 9.91 (1H, s), plus three protons obscured by the solvent peak. | (Method 2): Rt 3.54 min, m/z 686 [MH$^+$]. | 5e | (2-aminoethyl)(2-methoxyethyl) methylamine CAS: 14165-17-4 |

TABLE 1-continued

| Structure | Ex. | Chemical Name | NMR | LCMS | Interm. | Reagent |
|---|---|---|---|---|---|---|
| 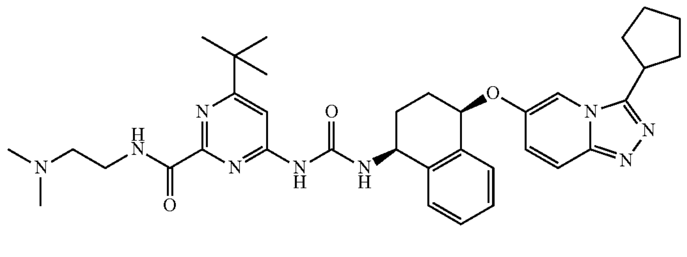 [SMILES: CN(C)CCNC(=O)c1nc(NC(=O)N[C@H]2CC[C@@H](Oc3ccc4nnc(C5CCCC5)n4c3)c3ccccc32)cc(C(C)(C)C)n1] | 74 | 4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)-pyrimidine-2-carboxamide | $^1$H NMR (400 MHz, d-6-DMSO): 1.31 (9H, s), 1.66-2.29 (18H, m), 2.39 (2H, t, J = 6.6 Hz), 3.30-3.37 (2H, m, partially obscured by the water peak), 3.62 (1H, quintet, J = 7.8 Hz), 4.98-5.04 (1H, m), 5.57 (1H, t, J = 4.0 Hz), 7.25-7.44 (5H, m), 7.68 (1H, dd, J = 9.8, 0.6 Hz), 7.73 (1H, br s), 8.19 (1H, d, J = 1.3 Hz), 8.28 (1H, br s), 8.58 (1H, t, J = 5.7 Hz), 9.89 (1H, s). | (Method 3): Rt 3.37 min, m/z 640 [MH$^+$]. | KK | N,N-dimethyl-ethylene diamine CAS: 108-00-9 |
| 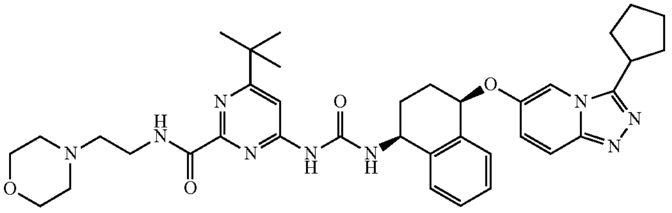 [SMILES: CC(C)(C)c1cc(NC(=O)N[C@H]2CC[C@@H](Oc3ccc4nnc(C5CCCC5)n4c3)c3ccccc32)nc(C(=O)NCCN2CCOCC2)n1] | 75 | 4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, d-6-DMSO): 1.33 (9H, s), 1.66-2.30 (12H, m), 2.42 (4H, br s), 2.46-2.50 (2H, m), 3.38 (2H, q, J = 6.4 Hz), 3.56-3.63 (5H, m), 4.99-5.04 (1H, m), 5.57 (1H, t, J = 4.0 Hz), 7.25-7.43 (5H, m), 7.69 (1H, dd, J = 9.8, 0.6 Hz), 7.71 (1H, br s), 8.18 (1H, d, J = 1.4 Hz), 8.33 (1H, br s), 8.69 (1H, t, J = 5.6 Hz), 9.94 (1H, s). | (Method 3): Rt 3.37 min, m/z 682 [MH$^+$]. | KK | 4-(2-aminoethyl) morpholine CAS: 2038-03-1 |
| 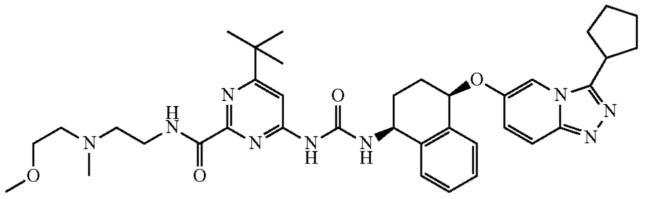 [SMILES: COCCN(C)CCNC(=O)c1nc(NC(=O)N[C@H]2CC[C@@H](Oc3ccc4nnc(C5CCCC5)n4c3)c3ccccc32)cc(C(C)(C)C)n1] | 76 | 4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-((2-methoxyethyl)(methyl)-amino)ethyl)pyrimidine-2-carboxamide | $^1$H NMR (400 MHz, d-6-DMSO): 1.32 (9H, s), 1.64-2.28 (15H, m), 2.50-2.55 (2H, m, partially obscured by the solvent peak), 3.20 (3H, s), 3.30-3.36 (2H, m), 3.41 (2H, t, J = 6.0 Hz), 3.61 (1H, quintet, J = 7.8 Hz), 4.98-5.04 (1H, m), 5.57 (1H, t, J = 4.0 Hz), 7.25-7.43 (5H, m), 7.69 (1H, dd, J = 9.8, 0.6 Hz), 7.71 (1H, s), 8.18 (1H, d, J = 1.3 Hz), 8.32 (1H, br s), 8.58 (1H, t, J = 5.6 Hz), 9.92 (1H, s), plus two protons obscured by the solvent peak. | (Method 3): Rt 3.45 min, m/z 684 [MH$^+$]. | KK | (2-aminoethyl)(2-methoxyethyl) Methylamine CAS: 14165-17-4 |
| 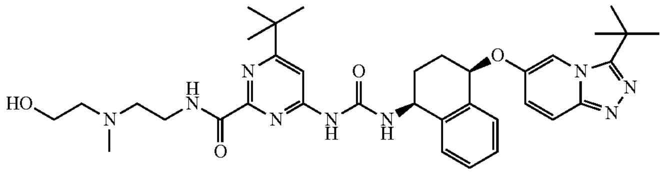 [SMILES: CN(CCO)CCNC(=O)c1nc(NC(=O)N[C@H]2CC[C@@H](Oc3ccc4nnc(C(C)(C)C)n4c3)c3ccccc32)cc(C(C)(C)C)n1] | 77 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)-amino)ethyl)pyrimidine- | $^1$H NMR (400 MHz, d-6-DMSO): 1.31 (9H, s), 1.53 (9H, s), 1.92-2.13 (3H, m), 2.20-2.24 (4H, m), 2.46 (2H, t, J = 6.5 Hz), 3.48 (2H, q, J = 5.3 Hz), 4.36 (1H, t, J = 5.3 Hz), 4.96-5.03 (1H, m), 5.63 (1H, t, J = 3.7 Hz), 7.28-7.45 (5H, m), 7.73 (1H, br s), 7.75 (1H, d, J = 10.0 Hz), 8.15 (1H, d, J = 1.2 Hz), | (Method 3): Rt 3.33 min, m/z 658 [MH$^+$]. | 1i | 2-[(2-aminoethyl)-(methyl) amino]ethanol CAS: 5753-50-4 |

TABLE 1-continued

| Structure | Ex. | Chemical Name | NMR | LCMS | Interm. | Reagent |
|---|---|---|---|---|---|---|
| | | 2-carboxamide | 8.28 (1H, br s), 8.61 (1H, t, J = 5.6 Hz), 9.93 (1H, s), plus four protons obscured by the solvent peak. | | | |
| 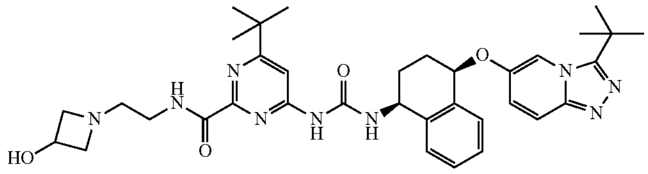 [SMILES: CC(C)(C)c1cc(NC(=O)N[C@H]2CC[C@@H](Oc3ccc4nnc(C(C)(C)C)n4c3)c3ccccc32)nc(C(=O)NCCN2CC(O)C2)n1] | 78 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)pyrimidine-2-carboxamide | $^1$H NMR (400 MHz, d-6-DMSO): 1.31 (9H, s), 1.53 (9H, s), 1.94-2.13 (3H, m), 2.20-2.25 (1H, m), 2.69-2.73 (2H, m), 3.22 (2H, q, J = 6.2 Hz), 3.52-3.55 (2H, m), 4.14 (1H, sextet, J = 6.3 Hz), 4.97-5.03 (1H, m), 5.25 (1H, d, J = 6.6 Hz), 5.64 (1H, t, J = 3.9 Hz), 7.28-7.45 (5H, m), 7.72 (1H, br s), 7.74 (1H, d, J = 9.9 Hz), 8.16 (1H, d, J = 1.2 Hz), 8.26 (1H, br s), 8.55 (1H, t, J = 5.9 Hz), 9.89 (1H, s), plus two protons obscured by the solvent peak. | (Method 3): Rt 3.26 min, m/z 656 [MH+]. | 1i | 1-(2-aminoethyl) azetidin-3-ol CAS: 1260773-28-1 |
| 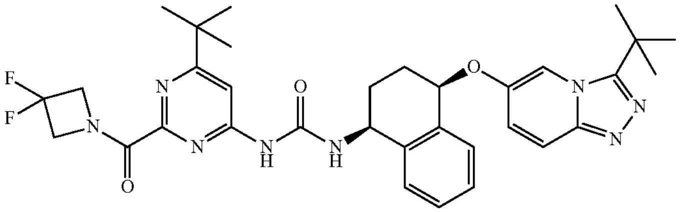 [SMILES: CC(C)(C)c1cc(NC(=O)N[C@H]2CC[C@@H](Oc3ccc4nnc(C(C)(C)C)n4c3)c3ccccc32)nc(C(=O)N2CC(F)(F)C2)n1] | 79 | 1-(6-(tert-butyl)-2-(3,3-difluoroazetidine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.29 (9H, s), 1.52 (9H, s), 1.91-2.33 (4H, m), 4.48 (2H, t, J = 12.3 Hz), 4.92-5.02 (3H, m), 5.63 (1H, t, J = 4.0 Hz), 7.28-7.45 (5H, m), 7.72 (1H, br s), 7.75 (1H, dd, J = 9.8, 0.6 Hz), 8.15 (1H, d, J = 1.2 Hz), 8.22 (1H, br s), 9.91 (1H, s). | (Method 3): Rt 4.72 min, m/z 33 [MH$^+$]. | 1i | 3,3-difluoro-azetidine hydrochloride CAS: 288315-03-7 |
| 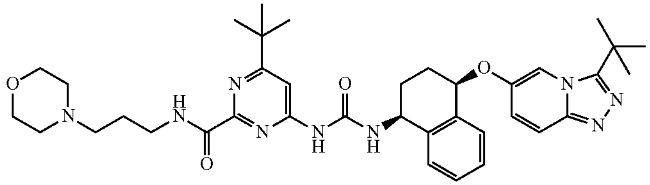 [SMILES: CC(C)(C)c1cc(NC(=O)N[C@H]2CC[C@@H](Oc3ccc4nnc(C(C)(C)C)n4c3)c3ccccc32)nc(C(=O)NCCCN2CCOCC2)n1] | 80 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)-pyrimidine-2-carboxamide | $^1$H NMR (400 MHz, d-6-DMSO): 1.32 (9H, s), 1.53 (9H, s), 1.66 (2H, quintet, J = 5.3 Hz), 1.95-2.31 (10H, m), 4.96-5.02 (1H, m), 5.63 (1H, t, J = 4.0 Hz), 7.28-7.44 (5H, m), 7.69 (1H, br s), 7.74 (1H, d, J = 9.8 Hz), 8.15 (1H, d, J = 1.2 Hz), 8.33 (1H, br s), 8.61 (1H, t, J = 6.0 Hz), 9.90 (1H, s), plus six protons obscured by the solvent peak. | (Method 3): Rt 3.37 min, m/z 684 [MH$^+$]. | 1i | 3-morpholino-propan-1-amine CAS: 123-00-2 |

TABLE 1-continued

| Structure | Ex. | Chemical Name | NMR | LCMS | Interm. | Reagent |
|---|---|---|---|---|---|---|
| 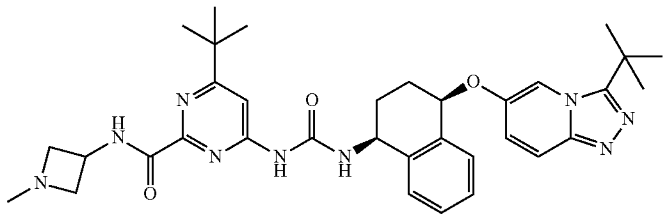 [SMILES: CN1CC(NC(=O)c2nc(NC(=O)N[C@H]3CC[C@@H](Oc4ccc5nnc(C(C)(C)C)n5c4)c4ccccc43)cc(C(C)(C)C)n2)C1] | 81 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylazetidin-3-yl)pyrimidine-2-carboxamide | $^1$H NMR (400 MHz, d-6-DMSO): 1.32 (9H, s), 1.52 (9H, s), 1.91-2.33 (7H, m), 2.95-3.00 (2H, m), 3.49-3.53 (2H, m), 4.33-4.40 (1H, m), 4.95-5.01 (1H, m), 5.63 (1H, t, J = 4.0 Hz), 7.28-7.44 (5H, m), 7.72-7.75 (2H, m), 8.14 (2H, d, J = 1.2 Hz), 8.74 (1H, d, J = 7.6 Hz), 9.89 (1H, s). | (Method 3): Rt 3.34 min, m/z 626 [MH$^+$]. | 1i | 1-methylazetidine-3-amine CAS: 959957-92-7 |
| 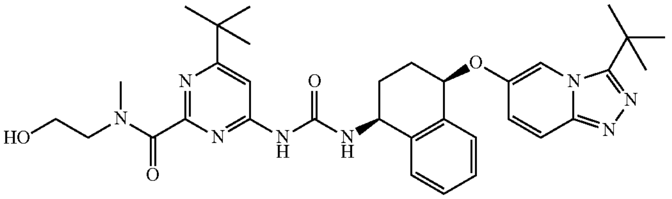 [SMILES: CN(CCO)C(=O)c1nc(NC(=O)N[C@H]2CC[C@@H](Oc3ccc4nnc(C(C)(C)C)n4c3)c3ccccc32)cc(C(C)(C)C)n1] | 82 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)-N-methylpyrimidine-2-carboxamide | $^1$H NMR (400 MHz, d-6-DMSO): 1.27 (9H, s), 1.52 (9H, s), 1.87-2.33 (4H, m), 2.81 (1H, s), 2.98 (2H, s), 3.14 (1H, t, J = 6.5 Hz), 3.44-3.50 (2H, m), 3.54-3.59 (1H, m), 4.67 (0.33H, br s, rotamer), 4.76 (0.66H, br s, rotamer), 4.91-4.98 (1H, m), 5.63 (1H, t, J = 4.0 Hz), 7.27-7.46 (5H, m), 7.72-7.86 (3H, m), 8.15 (1H, s), 9.66 (1H, br s). | (Method 3): Rt 3.76 min, m/z 615 [MH$^+$]. | 1i | 2-(methyl-amino) ethanol CAS: 109-83-1 |
| 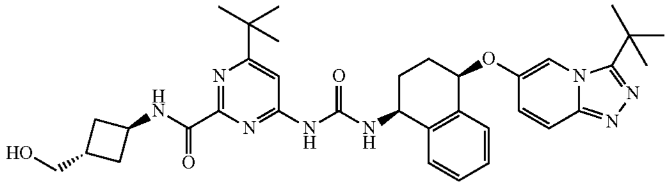 [SMILES: CC(C)(C)c1cc(NC(=O)N[C@H]2CC[C@@H](Oc3ccc4nnc(C(C)(C)C)n4c3)c3ccccc32)nc(C(=O)N[C@H]2C[C@H](CO)C2)n1] | 83 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1s,3R)-3-(hydroxymethyl)-cyclobutyl)pyrimidine-2-carboxamide | $^1$H NMR (400 MHz, d-6-DMSO): 1.32 (9H, s), 1.52 (9H, s), 1.91-2.33 (9H, m), 3.45 (2H, t, J = 5.6 Hz), 4.43 (1H, sextet, J = 8.0 Hz), 4.60 (1H, t, J = 5.2 Hz), 4.96-5.02 (1H, m), 5.63 (1H, t, J = 4.0 Hz), 7.28-7.45 (5H, m), 7.71 (1H, br s), 7.74 (1H, dd, J = 9.9, 0.6 Hz), 8.15 (1H, d, J = 1.2 Hz), 8.22 (1H, br s), 8.65 (1H, d, J = 8.1 Hz), 9.89 (1H, s). | (Method 3): Rt 4.13 min, m/z 641 [MH$^+$]. | 1i | trans-3-amino-cyclobutane methanol hydrochloride CAS: 1284250-10-7 |
| 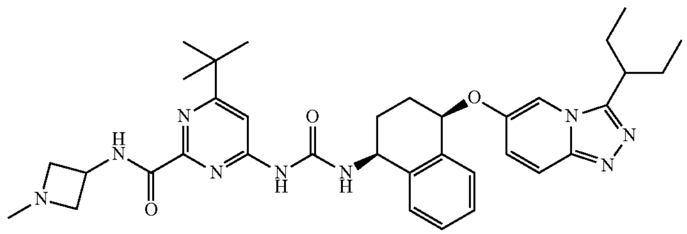 [SMILES: CCC(CC)c1nnc2ccc(O[C@@H]3CC[C@H](NC(=O)Nc4cc(C(C)(C)C)nc(C(=O)NC5CN(C)C5)n4)c4ccccc43)cn12] | 84 | 4-(tert-butyl)-N-(1-methylazetidin-3-yl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.78 (3H, t, J = 7.4 Hz), 0.80 (3H, t, J = 7.4 Hz), 1.32 (9H, s), 1.77-2.22 (11H, m), 2.98 (2H, t, J = 6.7 Hz), 3.51 (2H, t, J = 6.8 Hz), 4.37 (1H, sextet, J = 7.1 Hz), 4.97-5.03 (1H, m), 5.57 (1H, t, J = 3.9 Hz), 7.23-7.43 (5H, m), 7.69-7.75 (2H, m), 8.17 (1H, br s), 8.27 (1H, br s), 8.75 (1H, d, J = 7.5 Hz), 9.87 (1H, s), plus one proton obscured by the | (Method 3): Rt 3.44 min, m/z 640 [MH+]. | 5e | 1-methylazetidin-3-amine CAS: 959957-92-7 |

TABLE 1-continued

| Structure | Ex. | Chemical Name | NMR | LCMS | Interm. | Reagent |
|---|---|---|---|---|---|---|
| | | | solvent peak. | | | |
| 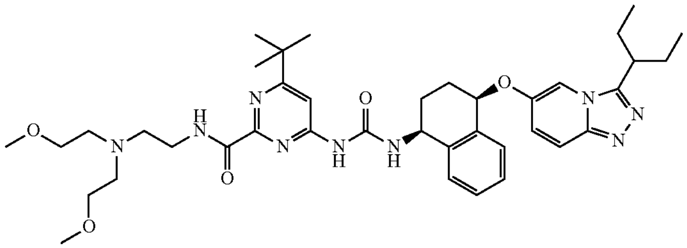 [SMILES: CCC(CC)c1nnc2ccc(O[C@@H]3CC[C@H](NC(=O)Nc4cc(C(C)(C)C)nc(C(=O)NCCN(CCOC)CCOC)n4)c4ccccc43)cn12] | 85 | N-(2-(bis(2-methoxyethyl)amino)ethyl)-4-(tert-butyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.77 (3H, t, J = 7.4 Hz), 0.80 (3H, t, J = 7.4 Hz), 1.32 (9H, s), 1.76-2.26 (8H, m), 2.64-2.69 (6H, m), 3.18 (6H, s), 3.38 (4H, t, J = 6.1 Hz), 4.98-5.04 (1H, m), 5.57 (1H, t, J = 3.9 Hz), 7.25-7.43 (5H, m), 7.69-7.71 (2H, m), 8.27 (1H, d, J = 1.3 Hz), 8.35 (1 H, br s), 8.59 (1H, t, J = 5.6 Hz), 9.93 (1H, s), plus three protons obscured by the solvent peak. | (Method 3): Rt 3.64 min, m/z 730 [MH+]. | 5e | (2-aminoethyl) bis(2-methoxyethyl) amine CAS: 116763-69-0 |
| 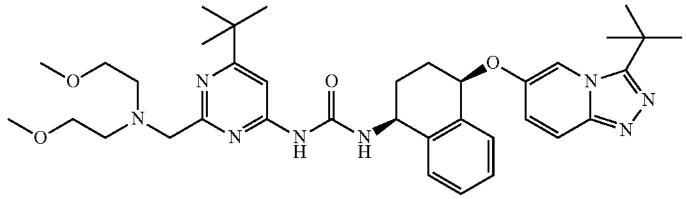 [SMILES: COCCN(CCOC)Cc1nc(NC(=O)N[C@H]2CC[C@@H](Oc3ccc4nnc(C(C)(C)C)n4c3)c3ccccc32)cc(C(C)(C)C)n1] | 86 | 1-(2-((bis(2-methoxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.25 (9H, s), 1.53 (9H, s), 1.92-2.23 (4H, m), 2.70 (4H, t, J = 6.2 Hz), 3.10 (6H, s), 3.24-3.30 (4H, m), 3.72 (2H, s), 4.98-5.04 (1H, m), 5.64 (1H, t, J = 3.9 Hz), 7.25-7.45 (6H, m), 7.76 (1H, dd, J = 9.8, 0.5 Hz), 8.12 (1H, d, J = 1.2 Hz), 8.76 (1H, br s), 9.64 (1H, s). | (Method 3): Rt 3.66 min, m/z 659 [MH$^+$]. | EE | bis(2-methoxyethyl)-amine CAS: 111-95-5 |
| 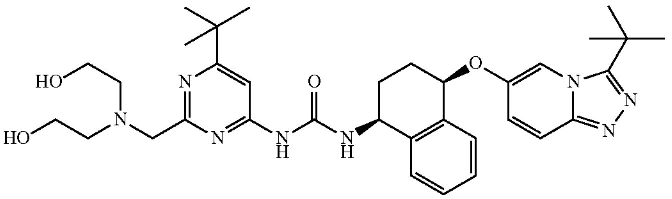 [SMILES: CC(C)(C)c1cc(NC(=O)N[C@H]2CC[C@@H](Oc3ccc4nnc(C(C)(C)C)n4c3)c3ccccc32)nc(CN(CCO)CCO)n1] | 87 | 1-(2-((bis(2-hydroxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.26 (9H, s), 1.53 (9H, s), 1.91-2.21 (4H, m), 2.65 (4H, t, J = 6.1 Hz), 3.35 (4H, br s, partially covered by water peak), 3.75 (2H, s), 4.32 (2H, br s), 4.96-5.02 (1H, m), 5.63 (1H, t, J = 3.9 Hz), 7.29-7.44 (6H, m), 7.75 (1H, dd, J = 9.8, 0.5 Hz), 8.14 (1H, d, J = 1.2 Hz), 8.48 (1H, br s), 9.58 (1H, s). | (Method 3): Rt 3.22 min, m/z 631 [MH+]. | EE | diethanolamine CAS: 111-42-2 |
| 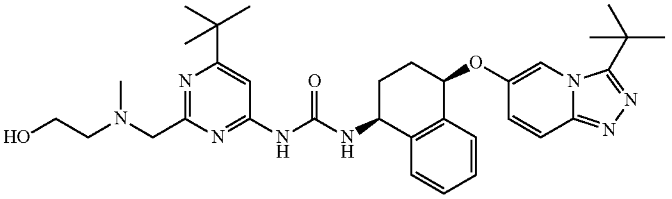 [SMILES: CN(CCO)Cc1nc(NC(=O)N[C@H]2CC[C@@H](Oc3ccc4nnc(C(C)(C)C)n4c3)c3ccccc32)cc(C(C)(C)C)n1] | 88 | 1-(6-(tert-butyl)-2-(((2-hydroxyethyl)(methyl)amino)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.25 (9H, s), 1.52 (9H, s), 1.92-2.20 (7H, m), 3.40 (2H, br s), 3.57 (1H, d, J = 14.6 Hz, AB system), 3.61 (1H, d, J = 14.6 Hz, AB system), 4.28 (1H, br s), 4.96-5.02 (1H, m), 5.64 (1H, t, J = 4.1 Hz), 7.27-7.45 (6H, m), 7.75 (1H, dd, J = 9.9, 0.6 Hz), 8.13 (1H, d, J = 1.3 Hz), | (Method 3): Rt 3.27 min, m/z 601 [MH+]. | EE | 2-(methylamino) ethanol CAS: 109-83-1 |

TABLE 1-continued

| Structure | Ex. | Chemical Name | NMR | LCMS | Interm. | Reagent |
|---|---|---|---|---|---|---|
| | | | 8.69 (1H, br s), 9.62 (1H, s), plus two protons obscured by the solvent peak. | | | |
| 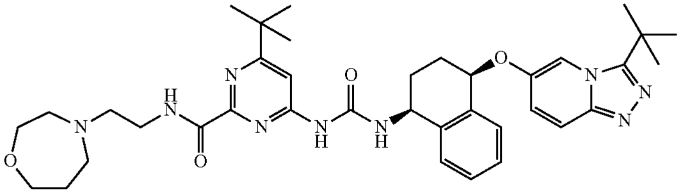 [SMILES: CC(C)(C)c1cc(NC(=O)N[C@H]2CC[C@@H](Oc3ccc4nnc(C(C)(C)C)n4c3)c3ccccc32)nc(C(=O)NCCN2CCCOCC2)n1] | 89 | N-(2-(1,4-oxazepan-4-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.32 (9H, s), 1.52 (9H, s), 1.79 (2H, quintet, J = 5.9), 1.91-2.33 (4H, m), 2.63-2.70 (6H, m), 3.59-3.61 (2H, m), 3.67 (2H, t, J = 6.0 Hz), 5.00 (1H, br s), 5.63 (1H, t, J = 4.0 Hz), 7.27-7.44 (5H, m), 7.70 (1H, br s), 7.74 (1H, dd, J = 9.9, 0.5 Hz), 8.15 (1H, d, J = 1.2 Hz), 8.32 (1H, br s), 8.65 (1H, t, J = 5.6 Hz), 9.97 (1H, s), plus two protons obscured by the solvent peak. | (Method 3): Rt 3.35 min, m/z 684 [MH$^+$]. | 1i | 2-(1,4-oxazepan-4-yl)ethan-1-amine CAS: 878155-50-1 |
| 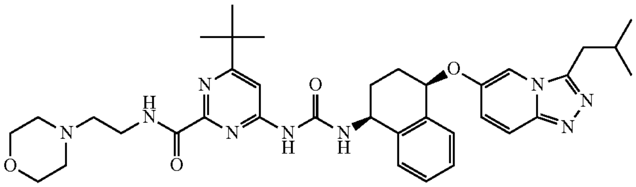 [SMILES: CC(C)Cc1nnc2ccc(O[C@@H]3CC[C@H](NC(=O)Nc4cc(C(C)(C)C)nc(C(=O)NCCN5CCOCC5)n4)c4ccccc43)cn12] | 90 | 4-(tert-butyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, d$_6$DMSO): 0.96 (6H, d, J = 6.6 Hz), 1.33 (9H, s), 1.88-2.02 (1H, m), 2.02-2.13 (2H, m), 2.18 (1H, q, J = 6.8 Hz), 2.21-2.30 (1H, m), 2.42 (4H, s), 2.44-2.50 (2H, m), 2.98 (2H, d, J = 6.6 Hz), 3.38 (2H, q, J = 6.4 Hz), 3.58 (4H, t, J = 4.4 Hz), 5.01 (1H, q, J = 8.3 Hz), 5.57 (1H, t, J = 3.9 Hz), 7.26 (1H, dd, J = 2.1, 9.8 Hz), 7.31 (1H, dd, J = 1.1, 7.3 Hz), 7.37 (1H, dt, J = 1.4, 7.3 Hz), 7.39-7.46 (2H, m), 7.66-7.76 (2H, m), 8.23 (1H, d, J = 1.3 Hz), 8.31 (1H, br s), 8.69 (1H, t, J = 5.6 Hz), 9.94 (1 H, s). | (Method 3): Rt 3.35 min, m/z 670.3 [M + H$^+$], sample assessed as ca. >99.3%. | AG | 4-(2-aminoethyl) morpholine CAS: 2038-03-1 |
| 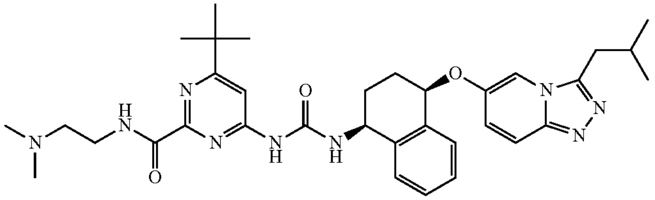 [SMILES: CC(C)Cc1nnc2ccc(O[C@@H]3CC[C@H](NC(=O)Nc4cc(C(C)(C)C)nc(C(=O)NCCN(C)C)n4)c4ccccc43)cn12] | 91 | 4-(tert-butyl)-N-(2-(dimethylamino)ethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz d6DMSO): 0.96 (6H, d, J = 6.6 Hz), 1.31 (9H, s), 1.89-2.30 (5H, m), 2.17 (6H, s), 2.39 (2H, t, J = 6.6 Hz), 2.98 (2H, d, J = 6.7 Hz), 3.35 (2H, q, J = 6.5 Hz), 4.98-5.04 (1H, m), 5.57 (1H, t, J = 3.9 Hz), 7.26 (1H, dd, J = 9.9, 2.1 Hz), 7.31 (1H, dt, J = 7.4, 1.1 Hz), 7.37 (1H, dt, J = 7.2, 1.3 Hz), 7.39-7.45 (2H, m), 7.69 (1H, d, J = 9.8 Hz), 7.73 (1H, s), 8.23 (1H, s), 8.27 (1H, br s), 8.58 (1H, t, J = 5.7 Hz), 9.89 | (Method 3): Rt 3.34 min, m/z 628.3 [M + H$^+$], sample assessed as ca. >98.9%. | AG | N,N-dimethyl-ethylene diamine CAS: 108-00-9 |

TABLE 1-continued

| Structure | Ex. | Chemical Name | NMR | LCMS | Interm. | Reagent |
|---|---|---|---|---|---|---|
| | | | (1H, s). | | | |
| 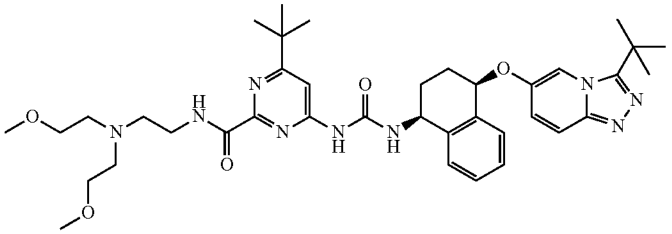 [SMILES: COCCN(CCNC(=O)c1nc(NC(=O)N[C@H]2CC[C@@H](Oc3ccc4nnc(C(C)(C)C)n4c3)c3ccccc32)cc(C(C)(C)C)n1)CCOC] | 92 | N-(2-(bis(2-methoxyethyl)amino)-ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.32 (9H, s), 1.52 (9H, s), 1.92-2.33 (4H, m), 2.64-2.69 (6H, m), 3.18 (6H, s), 3.38 (4H, t, J = 6.0 Hz), 4.97-5.03 (1H, m), 5.63 (1H, t, J = 4.0 Hz), 7.27-7.44 (5H, m), 7.70 (1H, br s), 7.74 (1H, dd, J = 9.9, 0.6 Hz), 8.15 (1H, d, J = 1.2 Hz), 8.33 (1H, br s), 8.58 (1H, t, J = 5.6 Hz), 9.94 (1H, s), plus two protons obscured by the solvent peak. | (Method 3): Rt 2.10 min, m/z 616 [MH$^+$]. | 1i | (2-aminoethyl) bis(2-methoxyethyl) amine CAS: 116763-69-0 |
| 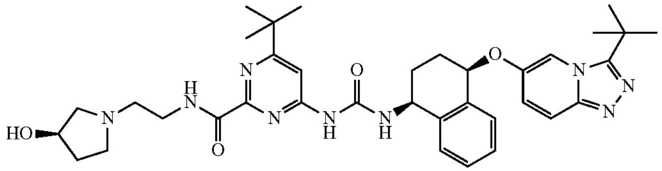 [SMILES: CC(C)(C)c1cc(NC(=O)N[C@H]2CC[C@@H](Oc3ccc4nnc(C(C)(C)C)n4c3)c3ccccc32)nc(C(=O)NCCN2CC[C@@H](O)C2)n1] | 93 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((R)-3-hydroxypyrrolidin-1-yl)ethyl)pyrimidine-2-carboxamide | $^1$H NMR (400 MHz, d-6-DMSO): 1.31 (9H, s), 1.53 (9H, s), 1.90-2.13 (5H, m), 2.19-2.33 (2H, m), 2.52-2.60 (4H, m, partially covered by the solvent peak), 2.77 (1H, dd, J = 9.6, 6.3 Hz), 3.35 (2H, q, J = 6.5 Hz, partially covered by water peak), 4.14-4.21 (1H, m), 4.67 (1H, d, J = 4.4 Hz), 4.97-5.03 (1H, m), 5.64 (1H, t, J = 4.0 Hz), 7.28-7.45 (5H, m), 7.72 (1H, br s), 7.75 (1H, d, J = 9.9 Hz), 8.15 (1H, d, J = 1.2 Hz), 8.27 (1H, br s), 8.65 (1H, t, J = 6.2 Hz), 9.91 (1H, s). | (Method 3): Rt 3.35 min, m/z 670 [MH+]. | 1i | (R)-1-(2-aminoethyl) pyrrolidin-3-ol CAS: 672325-36-9 |
| 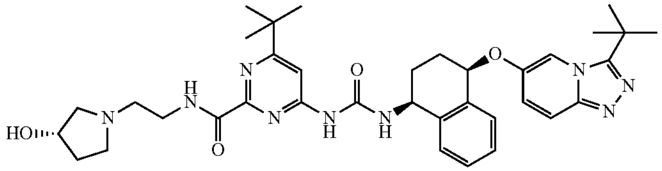 [SMILES: CC(C)(C)c1cc(NC(=O)N[C@H]2CC[C@@H](Oc3ccc4nnc(C(C)(C)C)n4c3)c3ccccc32)nc(C(=O)NCCN2CC[C@H](O)C2)n1] | 94 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)pyrimidine-2-carboxamide | $^1$H NMR (400 MHz, d-6-DMSO): 1.31 (9H, s), 1.53 (9H, s), 1.90-2.13 (5H, m), 2.20-2.33 (2H, m), 2.52-2.61 (4H, m, partially covered by the solvent peak), 2.77 (1H, dd, J = 9.6, 6.3 Hz), 3.35 (2H, q, J = 6.5 Hz, partially covered by water peak), 4.14-4.21 (1H, m), 4.67 (1H, d, J = 4.5 Hz), 4.97-5.03 (1H, m), 5.64 (1H, t, J = 3.8 Hz), 7.28-7.45 (5H, m), 7.72 (1H, br s), 7.75 (1H, d, J = 9.8 Hz), 8.15 (1H, d, J = 1.3 Hz), 8.27 (1H, br s), 8.65 (1H, t, J = 5.8 Hz), 9.91 (1H, s). | (Method 3): Rt 3.27 min, m/z 670 [MH+]. | 1i | (S)-1-(2-aminoethyl) pyrrolidin-3-ol CAS: 540787-75-5 |

TABLE 1-continued

| Structure | Ex. | Chemical Name | NMR | LCMS | Interm. | Reagent |
|---|---|---|---|---|---|---|
| 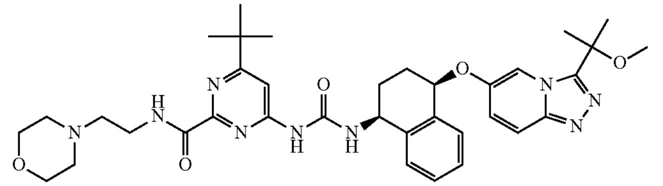 [SMILES: COC(C)(C)c1nnc2ccc(O[C@@H]3CC[C@H](NC(=O)Nc4cc(C(C)(C)C)nc(C(=O)NCCN5CCOCC5)n4)c4ccccc43)cn12] | 95 | 4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H-NMR (400 MHz, d6DMSO): 1.32 (9H, s), 1.69 (6H, s), 1.88-2.01 (1H, m), 2.01-2.18 (2H, m), 2.19-2.31 (1H, m), 2.42 (4H, s), 2.45-2.49 (2H, m), 2.98 (3H, s), 3.39 (2H, q, J = 6.7 Hz), 3.58 (4H, t, J = 4.4 Hz), 5.00 (1H, q, J = 8.7 Hz), 5.49 (1H, t, J = 3.8 Hz), 7.30 (1H, dt, J = 7.3, 1.1 Hz), 7.34-7.45 (4H, m), 7.73 (1H, s), 7.81 (1H, dd, J = 9.9, 0.5 Hz), 8.14 (1H, d, J = 1.4 Hz), 8.28 (1H, br s), 8.68 (1H, t, J = 5.6 Hz), 9.92 (1H, s). | (Method 3): Rt = 3.29 min, m/z 686.4 [M + H$^+$], sample assessed as ca. 99.5%. | 12e | 4-(2-aminoethyl) morpholine CAS: 2038-03-1 |
| 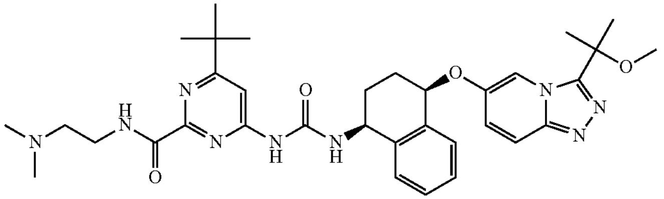 | 96 | 4-(tert-butyl)-N-(2-(dunethylamino)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d6DMSO): 1.31 (9H, s), 1.69 (6H, s), 1.87-2.31 (4H, m), 2.17 (6H, s), 2.39 (2H, t, J = 6.6 Hz), 2.98 (3H, s), 3.36 (2H, q, J = 6.5 Hz), 4.97-5.03 (1H, m), 5.49 (1H, t, J = 3.8 Hz), 7.31 (1H, t, J = 7.3 Hz), 7.37 (1H, dt, J = 8.6, 2.2 Hz), 7.39-7.45 (3H, m), 7.75 (1H, s), 7.80 (1H, dd, J = 9.9, 0.6 Hz), 8.14 (1H, d, J = 1.4 Hz), 8.22 (1H, br s), 8.57 (1H, t, J = 5.7 Hz), 9.87 (1H, s). | (Method 3): Rt 3.29 min, m/z 644.4 [M + H$^+$], sample assessed as ca. >99.4%. | 12e | N,N-dimethyl-ethylene diamine CAS: 108-00-9 |
| 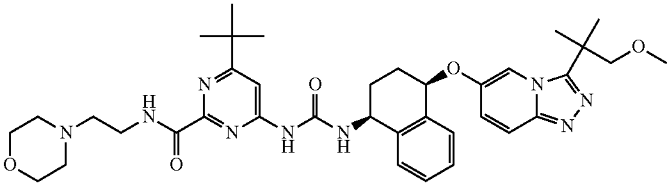 [SMILES: COCC(C)(C)c1nnc2ccc(O[C@@H]3CC[C@H](NC(=O)Nc4cc(C(C)(C)C)nc(C(=O)NCCN5CCOCC5)n4)c4ccccc43)cn12] | 97 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, d6DMSO): 1.32 (9H, s), 1.52 (6H, s), 1.89-2.29 (4H, m), 2.42 (4H, br s), 2.45-2.50 (2H, m, partially obscured by the solvent peak), 3.23 (3H, s), 3.39 (2H, q, J = 6.4 Hz), 3.58 (4H, t, J = 4.4 Hz), 3.67 (2H, s), 5.00 (1H, q, J = 8.6 Hz), 5.54 (1H, t, J = 3.8 Hz), 7.27-7.47 (5H, m), 7.69-7.77 (2H, m), 8.28 (2H, s), 8.69 (1H, t, J = 5.6 Hz), 9.94 (1H, s). | (Method 3): Rt = 3.34 min, m/z 700.4 [M + H$^+$], sample assessed as ca. 99.1%. | 7e | 4-(2-aminoethyl) morpholine CAS: 2038-03-1 |

TABLE 1-continued

| Structure | Ex. | Chemical Name | NMR | LCMS | Interm. | Reagent |
|---|---|---|---|---|---|---|
| 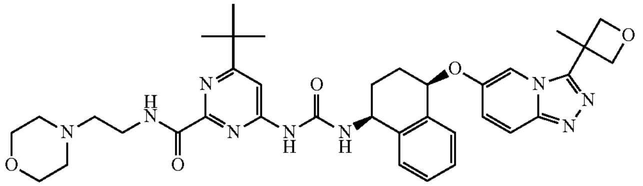 [SMILES: CC(C)(C)c1cc(NC(=O)N[C@H]2CC[C@@H](Oc3ccc4nnc(C5(C)COC5)n4c3)c3ccccc32)nc(C(=O)NCCN2CCOCC2)n1] | 98 | 4-(tert-butyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^{1}$H NMR (400 MHz, $d_6$DMSO): 1.32 (9H, s), 1.78 (3H, m), 1.87-2.15 (3H, m), 2.18-2.30 (1H, m), 2.42 (4H, br s), 2.45-2.50 (2H, m, partially obscured by the solvent peak), 3.39 (2H, q, J = 6.4 Hz), 3.58 (4H, t, J = 4.4 Hz), 4.82 (2H, d, J = 6.0 Hz), 4.99 (1 H, q, J = 8.8 Hz), 5.13 (2H, dd, J = 4.0, 6.0 Hz), 5.58 (1H, t, J = 3.7 Hz), 7.27-7.46 (5H, m), 7.72 (1H, s), 7.80 (1H, d, J = 9.9 Hz), 7.90 (1H, s), 8.26 (1H, br s), 8.69 (1H, t, J = 5.6 Hz), 9.93 (1H, br s). | (Method 3): Rt = 3.08 min, m/z 684.3 [M + H$^+$], sample assessed as ca. 98.4%. | AH | 4-(2-aminoethyl) morpholine CAS: 2038-03-1 |
| 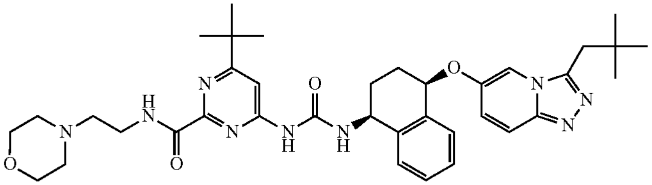 [SMILES: CC(C)(C)Cc1nnc2ccc(O[C@@H]3CC[C@H](NC(=O)Nc4cc(C(C)(C)C)nc(C(=O)NCCN5CCOCC5)n4)c4ccccc43)cn12] | 99 | 4-(tert-butyl)-N-(2-morpholinoethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide | $^{1}$H NMR (400 MHz, $d_6$DMSO): 0.97 (9H, s), 1.32 (9H, s), 1.88-2.16 (3H, m), 2.16-2.30 (1H, m), 2.41 (4H, s), 2.44-2.50 (2H, m), 3.02 (2H, q, J = 14.5 Hz), 3.38 (2H, q, J = 6.4 Hz), 3.57 (4H, t, J = 4.4 Hz), 5.02 (1H, q, J = 8.6 Hz), 5.57 (1H, t, J = 3.8 Hz), 7.27 (1H, dd, J = 2.1, 9.8 Hz), 7.30 (1H, dd, J = 0.9, 7.4 Hz), 7.32-7.46 (3H, m), 7.66-7.75 (2H, m), 8.31 (1H, d, J = 1.3 Hz), 8.36 (1H, br s), 8.69 (1H, t, J = 5.5 Hz), 9.93 (1H, br s). | (Method 3): Rt 3.46 min, m/z 684.4 [M + H$^+$], sample assessed as ca. >99.5%. | AI | 4-(2-aminoethyl) morpholine CAS: 2038-03-1 |
| 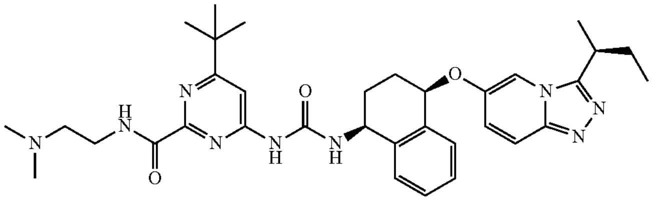 [SMILES: CC[C@H](C)c1nnc2ccc(O[C@@H]3CC[C@H](NC(=O)Nc4cc(C(C)(C)C)nc(C(=O)NCCN(C)C)n4)c4ccccc43)cn12] | 100 | 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)-pyrimidine-2-carboxamide | $^{1}$H NMR (400 MHz, d6DMSO): 0.87 (3H, t, J = 7.4 Hz), 1.31 (9H, s), 1.34 (3H, d, J = 6.9 Hz), 1.75 (1H, q, J = 6.9 Hz), 1.89 (1H, q, J = 6.3 Hz), 1.93-2.31 (5H, m), 2.17 (6H, s), 2.39 (2H, t, J = 6.6 Hz), 3.43 (2H, q, J = 6.9 Hz), 5.01 (1H, q, J = 8.5 Hz), 5.57 (1H, t, J = 4.2 Hz), 7.22-7.47 (5H, m), 7.70 (1H, d, J = 9.9 Hz), 7.73 (1H, s), 8.25 (1H, s), 8.27 (1H, br s), 8.59 (1H, t, J = 5.8 Hz), 9.88 (1H, s). | (Method 3): Rt 3.28 min, m/z 628.6 [M + H$^+$], sample assessed as ca. 98.86%. | 8e | N,N-dimethylamine ethandiamine CAS: 108-00-9 |

TABLE 1-continued

| Structure | Ex. | Chemical Name | NMR | LCMS | Interm. | Reagent |
|---|---|---|---|---|---|---|
| 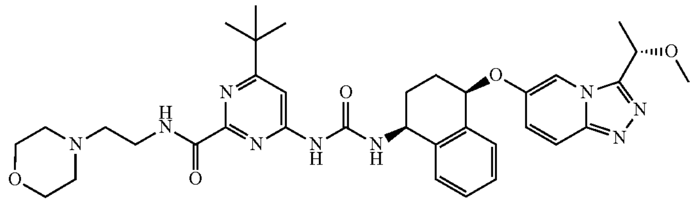 [SMILES: CO[C@@H](C)c1nnc2ccc(O[C@@H]3CC[C@H](NC(=O)Nc4cc(C(C)(C)C)nc(C(=O)NCCN5CCOCC5)n4)c4ccccc43)cn12] | 101 | 4-(tert-butyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, d6DMSO): 1.33 (9H, s), 1.66 (3H, d, J = 6.6 Hz), 1.85-2.31 (4H, m), 2.42 (4H, br s), 2.45-2.50 (2H, m, partially obscured by the solvent peak), 3.23 (3H, s), 3.39 (2H, q, J = 6.4 Hz), 3.58 (4H, t, J = 4.4 Hz), 5.01 (1H, q, J = 8.8 Hz), 5.17 (1H, q, J = 6.6 Hz), 5.53 (1H, t, J = 4.0 Hz), 7.28-7.47 (4H, m), 7.72 (1H, s), 7.79 (1H, dd, J = 0.7, 9.9 Hz), 8.17 (1H, d, J = 1.4 Hz), 8.28 (1H, br s), 8.69 (1H, t, J = 5.6 Hz), 9.87 (1H, br s). | (Method 3): Rt 3.24 min, m/z 672.4 [M + H$^+$], m/z 670.5 [M + H$^-$], sample assessed as ca. 98.9%. | AJ | 4-(2-aminoethyl) morpholine CAS: 2038-03-1 |
| 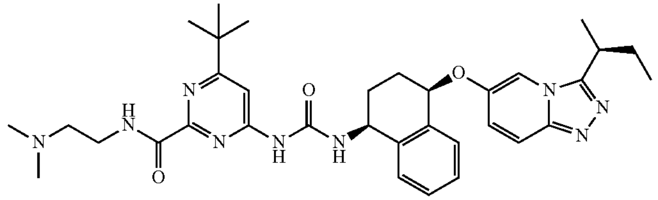 | 102 | 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, d-6-DMSO): 0.87 (3H, t, J = 7.4 Hz), 1.32 (9H, s), 1.34 (3H, s), 1.74 (1H, quintet, J = 7.1 Hz), 1.84-2.28 (5H, m), 2.41 (4H, br s), 3.36-3.47 (3H, m), 3.57 (4H, t, J = 4.4 Hz), 4.98-5.04 (1H, m), 5.56 (1H, t, J = 4.0 Hz), 7.25-7.43 (5H, m), 7.70 (1H, dd, J = 9.8, 0.5 Hz), 7.71 (1H, s), 8.24 (1H, d, J = 1.3 Hz), 8.31 (1H, br s), 8.68 (1H, t, J = 5.5 Hz), 9.93 (1H, s), plus two protons obscured by solvent peak. | (Method 3): Rt 3.33 min, m/z 670 [MH$^+$]. | 8e | 4-(2-aminoethyl) morpholine CAS: 2038-03-1 |
| 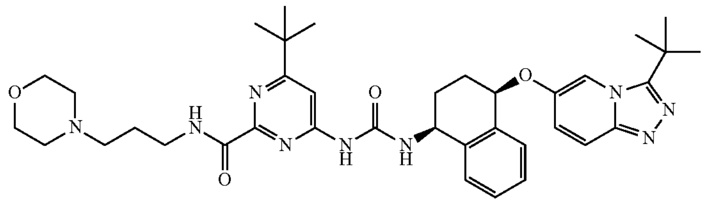 [SMILES: CC(C)(C)c1cc(NC(=O)N[C@H]2CC[C@@H](Oc3ccc4nnc(C(C)(C)C)n4c3)c3ccccc32)nc(C(=O)NCCCN2CCOCC2)n1] | 103 | N-((4-(tert-butyl)-6-(3-((1S,4R)-4-((3-(tert-butyl)-[1,2,4]-triazolo[4,3-a]pyridin-6-yl)oxy)-1,2,3,4-tetrahydronaphthalen-1-yl)ureido)pyrimidin-2-yl)methyl)-3-morpholinopropanamide | $^1$H NMR (400 MHz, d-6-DMSO): 1.26 (9H, s), 1.53 (9H, s), 1.94-2.30 (10H, m), 2.43 (2H, t, J = 6.9 Hz), 3.47 (3H, t, J = 4.6 Hz), 4.22 (1H, dd, J = 16.5, 5.7 Hz, AB system), 4.32 (1H, dd, J = 16.5, 6.1 Hz), 4.94-5.03 (1H, m), 5.61-5.65 (1H, m), 7.26-7.44 (6H, m), 7.76 (1H, dd, J = 9.9, 0.5 Hz), 8.19 (1H, d, J = 1.3 Hz), 8.31 (1H, t, J = 5.8 Hz), 8.43 (1H, br s), 9.58 (1H, br s) plus one proton obscured by the solvent peak. | (Method 3): Rt 3.22 min, m/z 684 [MH$^+$]. | II | 4-Morpholine propanoic acid CAS: 4497-04-5 |

TABLE 1-continued

| Structure | Ex. | Chemical Name | NMR | LCMS | Interm. | Reagent |
|---|---|---|---|---|---|---|
| 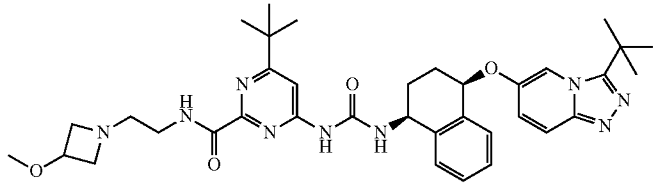 [SMILES: COC1CN(CCNC(=O)c2nc(NC(=O)N[C@H]3CC[C@@H](Oc4ccc5nnc(C(C)(C)C)n5c4)c4ccccc43)cc(C(C)(C)C)n2)C1] | 104 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide | $^{1}$H NMR (400 MHz, d-6-DMSO): 1.31 (9H, s), 1.52 (9H, s), 1.92-2.33 (4H, m), 2.54 (2H, t, J = 6.5 Hz), 2.78-2.82 (2H, m), 3.11 (3H, s), 3.23 (2H, q, J = 6.0 Hz), 3.50-3.53 (2H, m), 3.92 (1H, quintet, J = 5.8 Hz), 4.95-5.02 (1H, m), 5.63 (1H, t, J = 4.0 Hz), 7.27-7.46 (5H, m), 7.71 (1H, br s), 7.74 (1H, dd, J = 9.8, 0.5 Hz), 8.15 (1H, d, J = 1.2 Hz), 8.28 (1H, br s), 8.55 (1H, t, J = 6.0 Hz), 9.91 (1H, s). | (Method 3): Rt 3.39 min, m/z 670 [MH$^{+}$]. | 1i | 2-(3-methoxy-azetidin-1-yl)ethan-1-amine CAS: 911300-65-7 |
| 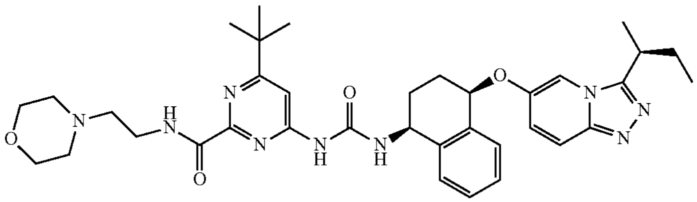 [SMILES: CC[C@H](C)c1nnc2ccc(O[C@@H]3CC[C@H](NC(=O)Nc4cc(C(C)(C)C)nc(C(=O)NCCN5CCOCC5)n4)c4ccccc43)cn12] | 105 | 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)-amino)ethyl)pyrimidine-2-carboxamide | $^{1}$H NMR (400 MHz, d-6-DMSO): 0.87 (3H, t, J = 7.4 Hz), 1.31 (9H, s), 1.34 (3H, d, J = 6.9 Hz), 1.69-1.80 (1H, m), 1.85-2.27 (8H, m), 2.51-2.55 (4H, m, partially covered by the solvent peak), 3.20 (3H, s), 3.33-3.44 (5H, m, partially obscured by water peak), 4.98-5.04 (1H, m), 5.57 (1H, t, J = 4.0 Hz), 7.25-7.44 (5H, m), 7.70 (1H, dd, J = 9.8, 0.6 Hz), 7.72 (1H, br s), 8.24 (1H, d, J = 1.3 Hz), 8.31 (1H, br s), 8.58 (1H, t, J = 5.6 Hz), 9.93 (1H, s). | (Method 3): Rt 3.39 min, m/z 672 [MH+]. | 8e | (2-aminoethyl)(2-methoxyethyl) methylamine CAS: 14165-17-4 |
| 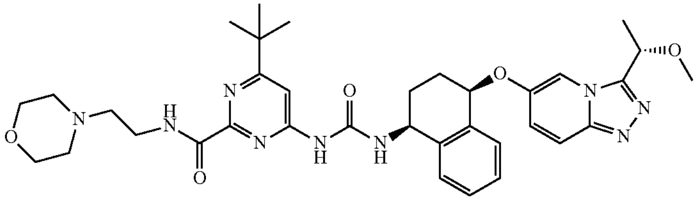 [SMILES: CO[C@@H](C)c1nnc2ccc(O[C@@H]3CC[C@H](NC(=O)Nc4cc(C(C)(C)C)nc(C(=O)NCCN5CCOCC5)n4)c4ccccc43)cn12] | 106 | 4-(tert-butyl)-N-(2-((2-methoxyethyl)(methyl) amino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)pyrimidine-2-carboxamide | $^{1}$H NMR (400 MHz, d-6-DMSO): 1.32 (9H, s), 1.66 (3H, d, J = 6.7 Hz), 1.89-2.30 (9H, m), 2.53 (2H, q, J = 6.0 Hz, partially obscured by solvent peak), 3.20 (3H, s), 3.22 (3H, s), 3.41 (2H, t, J = 6.0 Hz), 4.97-5.05 (1H, m), 5.17 (1H, q, J = 6.6 Hz), 5.53 (1H, t, J = 3.9 Hz), 7.29-7.46 (5H, m), 7.73 (1H, br s), 7.78 (1H, dd, J = 9.8, 0.6 Hz), 8.17 (1H, d, J = 1.3 Hz), 8.28 (1H, br s), 8.58 (1H, t, J = 5.6 Hz), 9.90 (1H, br s), plus two protons obscured by the solvent peak. | (Method 3): Rt 3.27 min, m/z 674 [MH$^{+}$]. | AJ | (2-aminoethyl)(2-methoxyethyl) methylamine CAS: 911300-63-5 |

TABLE 1-continued

| Structure | Ex. | Chemical Name | NMR | LCMS | Interm. | Reagent |
|---|---|---|---|---|---|---|
| 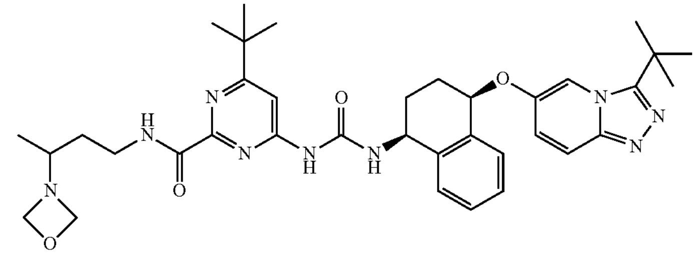 [SMILES: CC(CCNC(=O)c1nc(NC(=O)N[C@H]2CC[C@@H](Oc3ccc4nnc(C(C)(C)C)n4c3)c3ccccc32)cc(C(C)(C)C)n1)N1COC1] | 107 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(methyl(oxetan-3-yl)amino)ethyl)-pyrimidine-2-carboxamide | $^1$H NMR (400 MHz, d-6-DMSO): 1.32 (9H, s), 1.52 (9H, s), 1.92-2.27 (9H, m), 2.37 (2H, t, J = 6.4 Hz), 3.57 (1H, quintet, J = 6.5 Hz), 4.38 (2H, t, J = 6.5Hz), 4.50 (2H, t, J = 6.5 Hz), 4.97-5.02 (1H, m), 5.63 (1H, t, J = 4.0 Hz), 7.28-7.44 (5H, m), 7.72 (1H, br s), 7.74 (1H, dd, J = 9.8, 0.6 Hz), 8.15 (1H, d, J = 1.2 Hz), 8.31 (1H, br s), 8.65 (1H, t, J = 6.0 Hz), 9.94 (1H, s). | (Method 3): Rt 3.32 min, m/z 670 [MH$^+$]. | 1i | N-(2-aminoethyl)-N-methyloxetan-3-amine CAS: 1554560-03-0 |
| 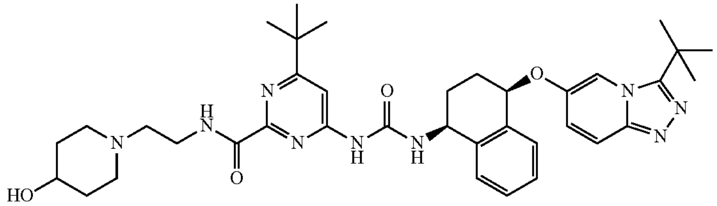 [SMILES: CC(C)(C)c1cc(NC(=O)N[C@H]2CC[C@@H](Oc3ccc4nnc(C(C)(C)C)n4c3)c3ccccc32)nc(C(=O)NCCN2CCC(O)CC2)n1] | 108 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-hydroxypiperidin-1-yl)ethyl)pyrimidine-2-carboxamide | $^1$H NMR (400 MHz, d-6-DMSO): 1.32-1.43 (11H, m), 1.52 (9H, s), 1.69-1.72 (2H, m), 1.95-2.33 (7H, m), 2.44 (2H, t, J = 6.5 Hz), 2.66-2.74 (2H, m), 4.56 (1H, br s), 4.97-5.02 (1H, m), 5.63 (1H, t, J = 4.0 Hz), 7.28-7.44 (5H, m), 7.70 (1H, br s), 7.74 (1H, d, J = 9.8 Hz), 8.15 (1H, d, J = 1.2 Hz), 8.32 (1H, br s), 8.67 (1H, t, J = 5.4 Hz), 9.95 (1H, s), plus two protons obscured by the solvent peak. | (Method 3): Rt 3.27 min, m/z 684 [MH$^+$]. | 1i | 1-(2-aminoethyl) piperidin-4-ol CAS: 129999-60-6 |
| 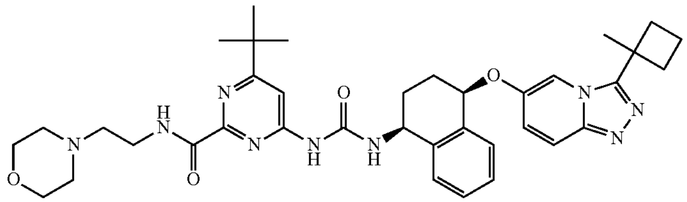 [SMILES: CC(C)(C)c1cc(NC(=O)N[C@H]2CC[C@@H](Oc3ccc4nnc(C5(C)CCC5)n4c3)c3ccccc32)nc(C(=O)NCCN2CCOCC2)n1] | 109 | 4-(tert-butyl)-6-(3-((1S,4R)-4-((3-(1-methylcyclobutyl)-[1,2,4]triazolo[4,3-a]pyridin-6-yl)oxy)-1,2,3,4-tetrahydronaphthalen-1-yl)ureido)-N-(2-morpholinoethyl)-pyrimidine-2-carboxamide | $^1$H NMR (400 MHz, $d_6$DMSO): 1.32 (9H, s), 1.58 (3H, s), 1.80-2.35 (8H, m), 2.42 (4H, br s), 2.44-2.49 (2H, m), 2.62-2.79 (2H, m), 3.38 (2H, q, J = 6.4 Hz), 3.57 (4H, t, J = 4.3 Hz), 4.99 (1H, q, J = 8.4 Hz), 5.57 (1H, t, J = 3.8 Hz), 7.26-7.46 (5H, m), 7.71 (2H, s), 7.74 (1H, d, J = 9.9 Hz), 8.31 (1H, br s), 8.69 (1H, t, J = 5.6 Hz), 9.96 (1H, s). | (Method 3): Rt = 3.34 min, m/z 682 [M + H$^+$], sample assessed as ca. 98.6%. | AK | 4-(2-aminoethyl) morpholine CAS: 2038-05-1 |
| 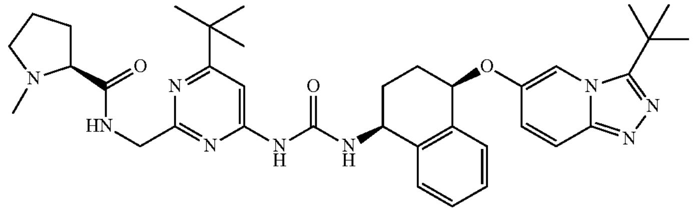 [SMILES: CN1CCC[C@H]1C(=O)NCc1nc(NC(=O)N[C@H]2CC[C@@H](Oc3ccc4nnc(C(C)(C)C)n4c3)c3ccccc32)cc(C(C)(C)C)n1] | 110 | (S)-N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylpyrrolidine-2- | $^1$H NMR (400 MHz, d-6-DMSO): 1.26 (9H, s), 1.52 (9H, s), 1.68-1.74 (3H, m), 1.96-2.19 (5H, m), 2.25-2.33 (1H, m), 2.36 (3H, s), 2.73-2.79 (1H, m), 3.03-3.07 (1H, m), 4.27 (1H, dd, J = 17.1, 5.5 Hz, AB system), 4.33 (1H, dd, J = 17.2, 5.7 Hz, AB system), 4.93-4.99 (1H, m), 5.63 (1H, t, J = 3.8 Hz), | (Method 2): Rt 3.29 min, m/z 654 [MH$^+$]. | II | N-methyl-L-proline CAS: 475-11-6 |

TABLE 1-continued

| Structure | Ex. | Chemical Name | NMR | LCMS | Interm. | Reagent |
|---|---|---|---|---|---|---|
| | | carboxamide | 7.29-7.45 (5H, m), 7.56 (1H, s), 7.75 (1H, dd, J = 9.8, 0.6 Hz), 8.11 (1H, br s), 8.16 (1H, d, J = 1.2 Hz), 8.27 (1H, t, J = 5.7 Hz), 9.48 (1H, s). | | | |
| 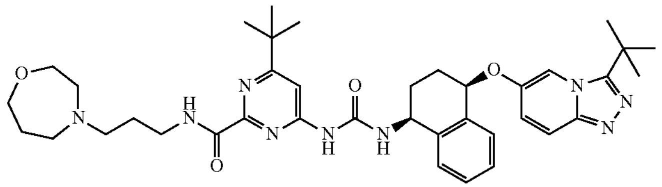 0.57 eq HCOOH | 111 | N-(3-(1,4-Oxazepan-4-yl)propyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide partial formate salt | $^1$H NMR (400 MHz, d-6-DMSO): 1.32 (9H, s), 1.53 (9H, s), 1.65 (2H, quintet, J = 6.8 Hz), 1.76 (2H, quintet, J = 5.8 Hz), 1.93-2.13 (3H, m), 2.19-2.26 (1H, m), 2.58-2.63 (4H, m), 3.56-3.58 (2H, m), 3.63 (2H, t, J = 6.0 Hz), 4.97-5.03 (1H, m), 5.63 (1H, t, J = 3.8 Hz), 7.28-7.45 (5H, m), 7.69 (1H, br s), 7.75 (1H, dd, J = 9.9, 0.6 Hz), 8.15 (1H, d, J = 1.2 Hz), 8.19 (0.57H, s), 8.33 (1H, br s), 8.63 (1H, t, J = 6.0 Hz), 9.90 (1H, s), plus four protons obscured by the solvent peak. | (Method 2): Rt 3.44 min, m/z 698 [MH+]. | 1i | 3-(1,4-oxazepan-4-yl)-1-propanamine CAS: 49809-08-7 |
| 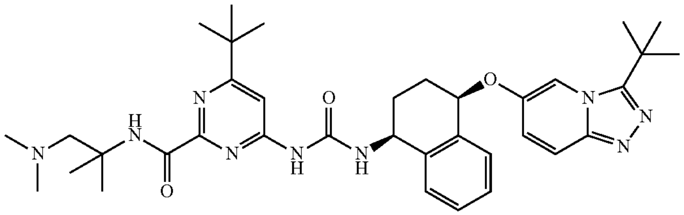 [SMILES: CN(C)CC(C)(C)NC(=O)c1nc(NC(=O)N[C@H]2CC[C@@H](Oc3ccc4nnc(C(C)(C)C)n4c3)c3ccccc32)cc(C(C)(C)C)n1] | 112 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-(dimethylamino)-2-methylpropan-2-yl)pyrimidine-2-carboxamide | $^1$H NMR (400 MHz, d-6-DMSO): 1.30 (9H, s), 1.35 (6H, s), 1.53 (9H, s), 1.96-2.28 (4H, m), 2.32 (6H, s), 2.44 (2H, s), 4.97-5.02 (1H, m), 5.64 (1H, t, J = 4.0 Hz), 7.28-7.44 (5H, m), 7.71-7.73 (2H, m), 8.15 (1H, d, J = 1.2 Hz), 8.31 (1H, br s), 8.63 (1H, s), 9.91 (1H, s). | (Method 2): Rt 3.56 min, m/z 656 [MH$^+$]. | 1i | 1-dimethylamino-2-methyl-2-aminopropane CAS: 89379-40-8 |
| 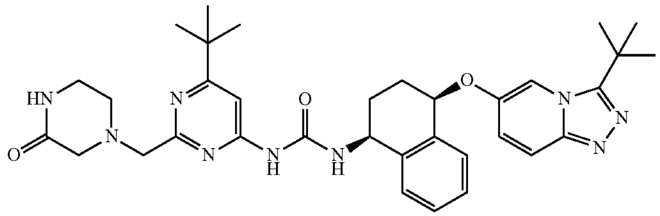 [SMILES: CC(C)(C)c1cc(NC(=O)N[C@H]2CC[C@@H](Oc3ccc4nnc(C(C)(C)C)n4c3)c3ccccc32)nc(CN2CCNC(=O)C2)n1] 0.2 eq HCOOH | 113 | 1-(6-(tert-Butyl)-2-((3-oxopiperazin-1-yl)methyl)pyrimidin-4-yl)-3-((1S,4R)-4-((3-(tert-butyl)-[1,2,4]-triazolo[4,3-a]pyridin-6-yl)oxy)-1,2,3,4-tetrahydronaphthalen-1-yl)urea partial formate salt | $^1$H NMR (400 MHz, d-6-DMSO): 1.26 (9H, s), 1.53 (9H, s), 1.90-2.18 (4H, m), 2.56-2.68 (2H, m), 3.00-3.11 (4H, m), 3.60 (1H, d, J = 14.2 Hz, AB system), 3.65 (1H, d, J = 14.2 Hz, AB system), 4.94-5.00 (1H, m), 5.64 (1H, t, J = 4.1 Hz), 7.29-7.45 (6H, m), 7.65 (1H, br s), 7.74 (1H, d, J = 9.8 Hz), 8.16 (1H, d, J = 1.3 Hz), 8.37 (0.2H, s), 8.48 (1H, br s), 9.66 (1H, s). | (Method 2): Rt 3.42 min, m/z 626 [MH$^+$]. | EE | 2-Piperazinone CAS: 5625-67-2 |

TABLE 1-continued

| Structure | Ex. | Chemical Name | NMR | LCMS | Interm. | Reagent |
|---|---|---|---|---|---|---|
| 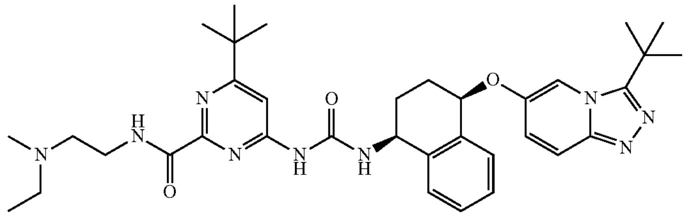 [SMILES: CCN(C)CCNC(=O)c1nc(NC(=O)N[C@H]2CC[C@@H](Oc3ccc4nnc(C(C)(C)C)n4c3)c3ccccc32)cc(C(C)(C)C)n1] | 114 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)-ethyl)pyrimidine-2-carboxamide | $^1$H NMR (400 MHz, d-6-DMSO): 0.98 (3H, t, J = 7.0 Hz), 1.31 (9H, s), 1.52 (9H, s), 1.93-2.25 (7H, m), 2.39 (2H, q, J = 7.0 Hz), 4.97-5.02 (1H, m), 5.63 (1H, t, J = 4.0 Hz), 7.28-7.45 (5H, m), 7.71 (1H, br s), 7.74 (1H, d, J = 9.8 Hz), 8.15 (1H, d, J = 1.2 Hz), 8.29 (1H, br s), 8.60 (1H, t, J = 5.6 Hz), 9.92 (1H, s), plus four protons obscured by the solvent peak. | (Method 2): Rt 3.41 min, m/z 642 [MH$^+$]. | 1i | (2-aminoethyl)-(ethyl)methyl-amine CAS: 70111-47-6 |
| 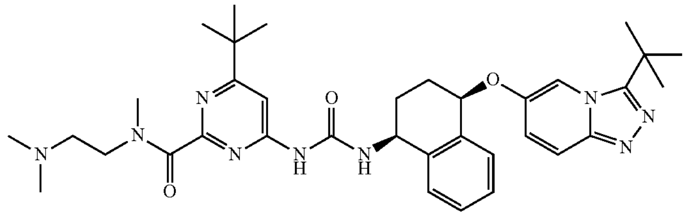 [SMILES: CN(C)CCN(C)C(=O)c1nc(NC(=O)N[C@H]2CC[C@@H](Oc3ccc4nnc(C(C)(C)C)n4c3)c3ccccc32)cc(C(C)(C)C)n1] | 115 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)-N-methylpyrimidine-2-carboxamide | $^1$H NMR (400 MHz, d-6-DMSO): 1.27 (9H, m), 1.52 (9H, s), 1.87-2.17 (10H, m), 2.31-2.39 (2H, m), 2.77 (1H, s), 2.95 (2H, s), 3.14 (1H, t, J = 7.0 Hz), 3.48 (1H, t, J = 7.0 Hz), 4.93-4.99 (1H, m), 5.63 (1H, t, J = 4.0 Hz), 7.27-7.45 (5H, m), 7.74-7.92 (3H, m), 8.15 (1H, br s), 9.66 (0.66H, s, rotamer), 9.74 (0.33H, s, rotamer). | (Method 2): Rt 3.29 min, m/z 642 [MH$^+$]. | 1i | N,N',N'-trimethylethane-1,2-diamine CAS: 142-25-6 |
| 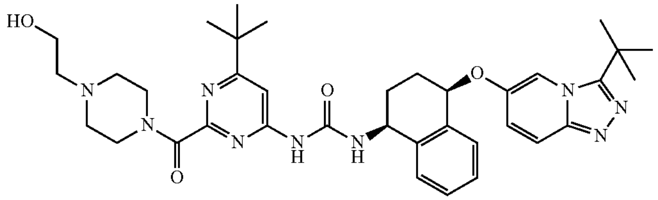 [SMILES: CC(C)(C)c1cc(NC(=O)N[C@H]2CC[C@@H](Oc3ccc4nnc(C(C)(C)C)n4c3)c3ccccc32)nc(C(=O)N2CCN(CCO)CC2)n1] | 116 | 1-(6-(tert-butyl)-2-(4-(2-hydroxyethyl)piperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.27 (9H, m), 1.52 (9H, s), 1.89-2.17 (5H, m), 2.29-2.45 (5H, m), 3.10-3.13 (2H, m), 3.46 (2H, q, J = 6.0 Hz), 3.54-3.58 (2H, m), 4.40 (1H, t, J = 5.3 Hz), 4.94-4.99 (1H, m), 5.63 (1H, t, J = 4.0 Hz), 7.27-7.46 (5H, m), 7.72 (1H, br s), 7.74 (1H, dd, J = 9.9, 0.5 Hz), 7.89 (1H, br s), 8.15 (1H, d, J = 1.2 Hz), 9.71 (1H, s). | (Method 2): Rt 3.20 min, m/z 670 [MH$^+$]. | 1i | 2-piperazin-1-ylethanol CAS: 103-76-4 |
| 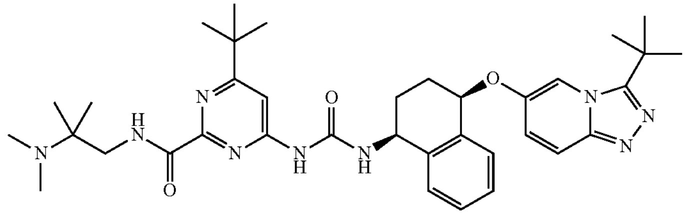 [SMILES: CN(C)C(C)(C)CNC(=O)c1nc(NC(=O)N[C@H]2CC[C@@H](Oc3ccc4nnc(C(C)(C)C)n4c3)c3ccccc32)cc(C(C)(C)C)n1] | 117 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide | $^1$H NMR (400 MHz, d-6-DMSO): 0.98 (6H, s), 1.30 (9H, s), 1.52 (9H, s), 1.90-2.35 (10H, m), 3.23 (2H, d, J = 5.2 Hz), 4.96-5.03 (1H, m), 5.63 (1H, t, J = 4.0 Hz), 7.27-7.47 (5H, m), 7.74 (1H, dd, J = 9.8, 0.6 Hz), 7.77 (1H, br s), 8.15 (1H, d, J = 1.2 Hz), 8.19 (1H, br s), 8.51 (1H, t, J = 5.2 Hz), 9.92 (1H, s). | (Method 2): Rt 3.46 min, m/z 656 [MH$^+$]. | 1i | (2-Amino-1,1-dimethylethyl) dimethylamine CAS: 76936-44-2 |

TABLE 1-continued

| Structure | Ex. | Chemical Name | NMR | LCMS | Interm. | Reagent |
|---|---|---|---|---|---|---|
| 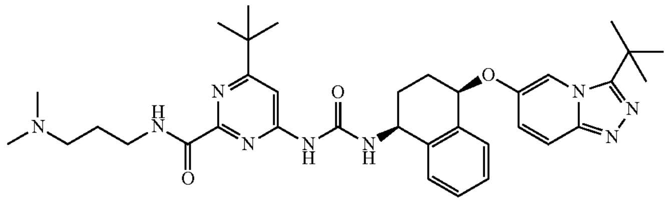 [SMILES: CN(C)CCCNC(=O)c1nc(NC(=O)N[C@H]2CC[C@@H](Oc3ccc4nnc(C(C)(C)C)n4c3)c3ccccc32)cc(C(C)(C)C)n1] | 118 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-(dimethylamino)-propyl)pyrimidine-2-carboxamide | $^1$H NMR (400 MHz, d-6-DMSO): 1.32 (9H, s), 1.53 (9H, s), 1.64 (2H, quintet, J = 6.6 Hz), 1.92-2.10 (3H, m), 2.13 (6H, s), 2.19-2.33 (3H, m), 4.97-5.03 (1H, m), 5.63 (1H, t, J = 4.0 Hz), 7.28-7.44 (5H, m), 7.68 (1 H, br s), 7.74 (1H, d, J = 9.8 Hz), 8.15 (1H, d, J = 1.2 Hz), 8.37 (1H, br s), 8.90 (1H, t, J = 6.0 Hz), 9.92 (1H, s), plus two protons obscured by die solvent peak. | (Method 2): Rt 3.40 min, m/z 642 [MH$^+$]. | 1i | N,N',N'-trimethyl-propane-1,3-diamine CAS: 4543-96-8 |
| 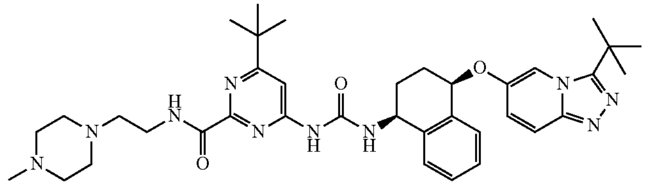 [SMILES: CN1CCN(CCNC(=O)c2nc(NC(=O)N[C@H]3CC[C@@H](Oc4ccc5nnc(C(C)(C)C)n5c4)c4ccccc43)cc(C(C)(C)C)n2)CC1] | 119 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methylpiperazin-1-yl)ethyl)pyrimidine-2-carboxamide | $^1$H NMR (400 MHz, d-6-DMSO): 1.32 (9H, m), 1.52 (9H, s), 1.92-2.11 (3H, m), 2.13 (3H, s), 2 21-2 44 (9H, m), 4.97-5.03 (1H, m), 5.63 (1H, t, J = 4.0 Hz), 7.28-7.44 (5H, m), 7.70 (1H, br s), 7.75 (1H, dd, J = 9.9, 0.5 Hz), 8.15 (1H, d, J = 1.2 Hz), 8.31 (1H, br s), 8.68 (1H, t, J = 5.4 Hz), 9.96 (1H, s), plus four protons obscured by the solvent peak. | (Method 2): Rt 3.30 min, m/z 683 [MH$^+$]. | 1i | 1-(2-Aminoethyl)-4-methyl-piperazine CAS: 934-98-5 |
| 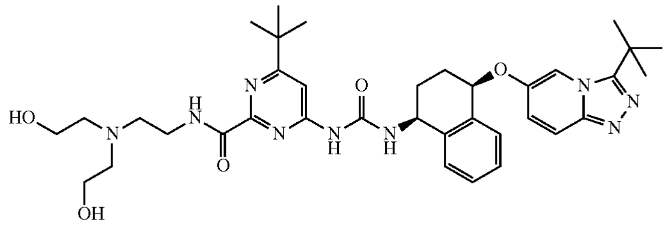 [SMILES: CC(C)(C)c1cc(NC(=O)N[C@H]2CC[C@@H](Oc3ccc4nnc(C(C)(C)C)n4c3)c3ccccc32)nc(C(=O)NCCN(CCO)CCO)n1] | 120 | N-(2-(bis(2-hydroxyethyl)amino) ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.31 (9H, s), 1.52 (9H, s), 1.92-2.33 (4H, m), 2.58 (4H, t, J = 6.4 Hz), 2.65 (2H, t, J = 6.4 Hz), 3.43 (4H, q, J = 6.4 Hz), 4.35 (2H, t, J = 5.4 Hz), 4.97-5.02 (1H, m), 5.63 (1H, t, J = 4.0 Hz), 7.28-7.44 (5H, m), 7.71 (1H, br s), 7.74 (1H, dd, J = 9.8, 0.6 Hz), 8.15 (1H, d, J = 1.2 Hz), 8.29 (1H, br s), 8.64 (1H, t, J = 5.8 Hz), 9.92 (1H, s), plus two protons obscured by the solvent peak. | (Method 2): Rt 3.31 min, m/z 688 [MH$^+$]. | 1i | N,N-Bis(2-hydroxyethyl) ethylene-diamine CAS: 3197-06-6 |
| 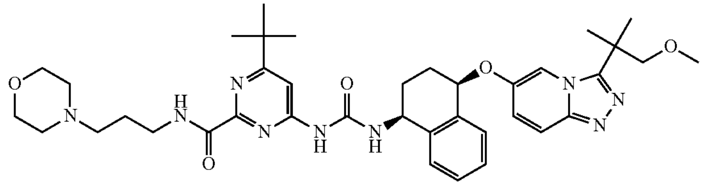 [SMILES: COCC(C)(C)c1nnc2ccc(O[C@@H]3CC[C@H](NC(=O)Nc4cc(C(C)(C)C)nc(C(=O)NCCCN5CCOCC5)n4)c4ccccc43)cn12] | 121 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(3- | $^1$H NMR (400 MHz, d6DMSO): 1.31 (9H, s), 1.52 (6H, s), 1.67 (2H, t, J = 7.1 Hz), 1.88-2.02 (1H, m), 2.02-2.17 (2H, m), 2.17-2.27 (1H, m), 2.27-2.37 (6H, m), 3.23 (3H, s), 3.25-3.32 (2H, m), 3.54 (4H, t = 4.6 Hz), 3.67 (2H, s), 5.00 (1H, q, J = 8.9, 5.5 Hz), 5.54 (1H, t, J = | (Method 3): Rt 3.35 min, m/z 714.5 [M + H$^+$], sample assessed as ca. >98.4%. | 7e | 4-(2-aminoethyl) morpholine CAS: 2038-03-1 |

TABLE 1-continued

| Structure | Ex. | Chemical Name | NMR | LCMS | Interm. | Reagent |
|---|---|---|---|---|---|---|
| | | morpholinopropyl)-pyrimidine-2-carboxamide | 3.8 Hz), 7.26-7.47 (6H, m), 7.67-7.76 (2H, m), 8.29 (1H, s), 8.61 (1H, t, J = 6.0 Hz), 9.89 (1H, s). | | | |
| 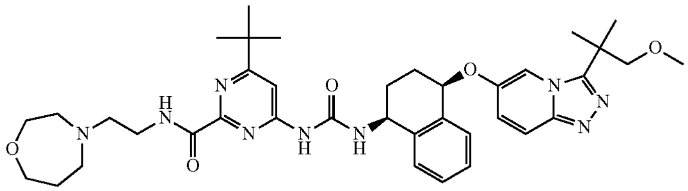 | 122 | N-(2-(1,4-oxazepan-4-yl)ethyl)-4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d6DMSO): 1.32 (9H, s), 1.53 (6H, s), 1.80 (2H, t, J = 5.9 Hz), 1.90-2.02 (1H, m), 2.02-2.17 (2H, m), 2.17-2.28 (1H, m), 2.60-2.72 (6H, m), 3.23 (3H, s), 3.33-3.40 (2H, m), 3.60 (2H, t, J = 4.6 Hz), 3.64-3.71 (4H, m), 5.00 (1H, q, J = 8.8 Hz), 5.54 (1H, t, J = 3.9 Hz), 7.27-7.43 (5H, m), 7.72-7.74 (2H, m), 8.28 (2H, s), 8.65 (1H, t, J = 5.5 Hz), 9.95 (1H, s). | (Method 3): Rt 3.33 min, m/z 7)4.5 [M + H$^+$], sample assessed as ca. >98.2%. | 7e | 2-(1,4-oxazepan-4-yl)ethanamine CAS: 878155-50-1 |
| 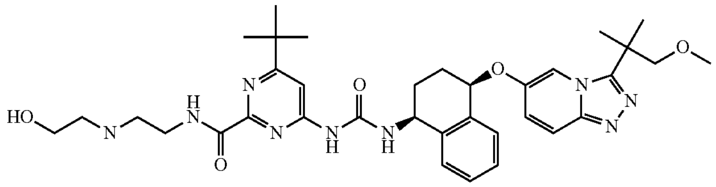 | 123 | 4-(tert-butyl)-N-(2-((2-hydroxyethyl)(methyl)-amino)ethyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d6DMSO): 1.31 (9H, s), 1.53 (6H, s), 1.89-2.16 (3H, m), 2.17-2.28 (1H, m), 7 46 (7H, t, J = 6.4 Hz), 2.49-2.51 (4H, m, partially obscured by the solvent peak), 2.52-2.56 (2H, m), 3.23 (3H, s), 3.30-3.42 (4H, m, partially obscured by the water peak), 3.48 (2H, t, J = 6.4 Hz), 3.67 (2H, s), 5.00 (1H, q, J = 8.8, 5.6 Hz), 5.54 (1H, t, J = 3.8 Hz), 7.27-7.47 (6H, m), 7.69-7.78 (2H, m), 8.28 (1H, s), 8.61 (1H, t, J = 5.6 Hz), 9.92 (1H, br s). | (Method 3): Rt 3.27 min, m/z 688.5 [M + H$^+$], sample assessed as ca. >99.5%. | 7e | 2-[(2-Aminoethyl)-(methyl) amino]ethanol CAS: 5753-50-4 |
| 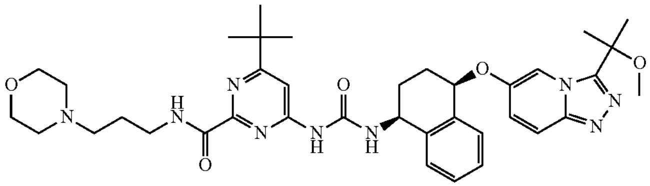 [SMILES: COC(C)(C)c1nnc2ccc(O[C@@H]3CC[C@H](NC(=O)Nc4cc(C(C)(C)C)nc(C(=O)NCCCN5CCOCC5)n4)c4ccccc43)cn12] | 124 | 4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(3-morpholinopropyl)-pyrimidine-2-carboxamide | $^1$H NMR (400 MHz, d6DMSO): 1.31 (9H, s), 1.61-1.69 (2H, m), 1.70 (6H, s), 1.88-2.01 (1H, m), 2.01-2.18 (2H, m), 2.19-2.27 (1H, m), 2.28-2.38 (6H, m), 2.98 (3H, s), 3.27-3.32 (2H, m), 3.54 (4H, t, J = 4.6 Hz), 5.00 (1H, q, 9.0 Hz), 5.49 (1H, t, J = 3.8 Hz), 7.30 (1H, t, 7.3 Hz), 7.36 (1H, dd, J = 1.5, 7.6 Hz), 7.38-7.45 (3H, m), 7.71 (1H, s), 7.80 (1H, d, J = 9.9 Hz), 8.14 (1H, d, J = 1.4 Hz), 8.30 (1H, br s), 8.61 (1H, t, J = 6.1 Hz), 9.87 (1H, br s). | (Method 3): Rt 3.31 min, m/z 700.5 [M + H$^+$], sample assessed as ca. >98.16%. | 12e | 3-morpholino-propan-1-amine CAS: 123-00-2 |

TABLE 1-continued

| Structure | Ex. | Chemical Name | NMR | LCMS | Interm. | Reagent |
|---|---|---|---|---|---|---|
| 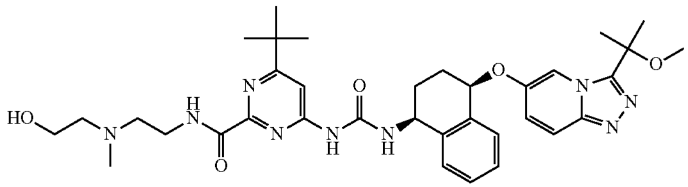 [SMILES: COC(C)(C)c1nnc2ccc(O[C@@H]3CC[C@H](NC(=O)Nc4cc(C(C)(C)C)nc(C(=O)NCCN(C)CCO)n4)c4ccccc43)cn12] | 125 | 4-(tert-butyl)-N-(2-((2-hydroxyethyl)(methyl)-amino)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^{1}$H NMR (400 MHz, d6DMSO): 1.31 (9H, s), 1.69 (6H, s), 1.91-2.17 (4H, m), 2.24 (3H, s), 2.46 (2H, t, J = 6.4 Hz), 2.50-2.54 (2H, m, partially obscured by the solvent peak), 2.98 (3H, s), 3.48 (2H, t, J = 6.4 Hz), 4.36 (1H, br s), 5.00 (1H, q, J = 8.8 Hz), 5.49 (1H, t, J = 3.8 Hz), 7.31 (1H, t, J = 7.3 Hz), 7.34-7.45 (4H, m), 7.74 (1H, s), 7.81 (1H, d, J = 9.9 Hz), 8.14 (1H, d, J = 1.4 Hz), 8.24 (1H, s), 8.60 (1H, t, J = 5.6 Hz), 9.89 (1H, s), plus two protons obscured by the water peak. | (Method 3): Rt 3.24 min, m/z 674.5 [M + H$^{+}$], sample assessed as ca. >99.2%. | 12e | 2-[(2-Aminoethyl)-(methyl) amino]ethanol CAS: 5753-50-4 |
| 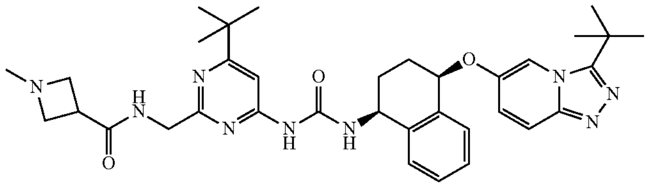 [SMILES: CN1CC(C(=O)NCc2nc(NC(=O)N[C@H]3CC[C@@H](Oc4ccc5nnc(C(C)(C)C)n5c4)c4ccccc43)cc(C(C)(C)C)n2)C1] | 126 | N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylazetidine-3-carboxamide | $^{1}$H NMR (400 MHz, d-6-DMSO): 1.26 (9H, s), 1.52 (9H, s), 1.98-2.22 (7H, m), 2.98-3.05 (3H, m), 3.19-3.29 (2H, m), 4.25-4.27 (2H, m), 4.96 (1H, q, J = 7.6 Hz), 5.63 (1H, t, J = 3.9 Hz), 7.28-7.44 (6H, m), 7.75 (1H, dd, J = 9.9, 0.6 Hz), 8.18 (1H, d, J = 1.2 Hz), 8.21 (1H, t, J = 5.8 Hz), 8.29 (1H, br s), 8.53 (1H, s). | (Method 3): Rt 3.15 min, m/z 640 [MH$^{+}$]. | II | 1-methyl-3-azetidine carboxylic acid CAS: 875629-26-8 |
| 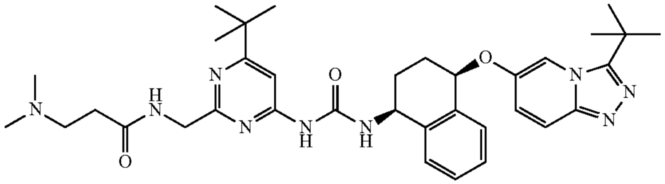 [SMILES: CN(C)CCC(=O)NCc1nc(NC(=O)N[C@H]2CC[C@@H](Oc3ccc4nnc(C(C)(C)C)n4c3)c3ccccc32)cc(C(C)(C)C)n1] | 127 | N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-3-(dimethylamino)-propanamide | $^{1}$H NMR (400 MHz, d-6-DMSO): 1.27 (9H, s), 1.52 (9H, s), 1.98-2.21 (12H, m), 2.36-2.41 (2H, m), 4.23 (1H, dd, J = 16.6, 5.6 Hz), 4.32 (1H, dd, J = 16.7, 5.9 Hz), 4.95-5.01 (1H, m), 5.62-5.64 (1H, m), 7.28-7.44 (6H, m), 7.75 (1H, dd, J = 9.8, 0.5 Hz), 8.18 (1H, d, J = 1.2 Hz), 8.35 (1H, br s), 8.41 (1H, t, J = 5.7 Hz), 8.56 (1H, s). | (Method 3): Rt 3.15 min, m/z 642 [MH$^{+}$]. | II | N,N-dimethyl-β-alanine CAS: 6300-04-5 |

TABLE 1-continued

| Structure | Ex. | Chemical Name | NMR | LCMS | Interm. | Reagent |
|---|---|---|---|---|---|---|
| 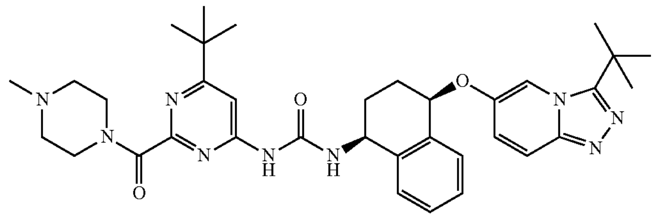 [SMILES: CN1CCN(C(=O)c2nc(NC(=O)N[C@H]3CC[C@@H](Oc4ccc5nnc(C(C)(C)C)n5c4)c4ccccc43)cc(C(C)(C)C)n2)CC1] | 128 | 1-(6-(tert-butyl)-2-(4-methylpiperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.27 (9H, m), 1.52 (9H, s), 1.88-2.34 (11H, m), 3.11-3.13 (2H, m), 3.56 (2H, br s), 4.94-5.00 (1H, m), 5.64 (1H, t, J = 4.0 Hz), 7.26-7.46 (5H, m), 7.71 (1H, br s), 7.75 (1H, dd, J = 9.9, 0.5 Hz), 7.92 (1H, br s), 8.15 (1H, d, J = 1.2 Hz), 9.73 (1H, s). | (Method 2): Rt 3.24 min, m/z 640 [MH$^+$]. | 1i | 1-methyl-piperazine CAS: 109-01-3 |
| 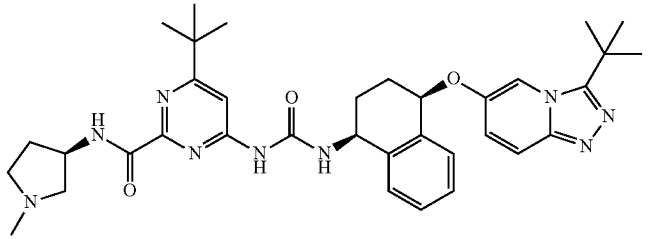 [SMILES: CN1CC[C@@H](NC(=O)c2nc(NC(=O)N[C@H]3CC[C@@H](Oc4ccc5nnc(C(C)(C)C)n5c4)c4ccccc43)cc(C(C)(C)C)n2)C1] | 129 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((R)-1-methylpyrrolidin-3-yl)pyrimidine-2-carboxamide | $^1$H NMR (400 MHz, d-6-DMSO): 1.30 (9H, s), 1.52 (9H, s), 1.64-1.72 (1H, m), 1.90-2.21 (5H, m), 2.24 (3H, s), 2.28-2.34 (1H, m), 2.45 (1H, dd, J = 9.4, 4.4 Hz), 2.58-2.67 (2H, m), 4.31-4.39 (1H, m), 4.95-5.01 (1H, m), 5.63 (1H, t, J = 4.0 Hz), 7.27-7.44 (5H, m), 7.73-7.76 (2H, m), 8.12 (1H, br s), 8.14 (1H, d, J = 1.2 Hz), 8.39 (1H, d, J = 7.9 Hz), 9.88 (1H, s). | (Method 2): Rt 3.38 min, m/z 640 [MH$^+$]. | 1i | (R)-1-methyl-pyrrolidin-3-amine CAS: 83030-08-4 |
| 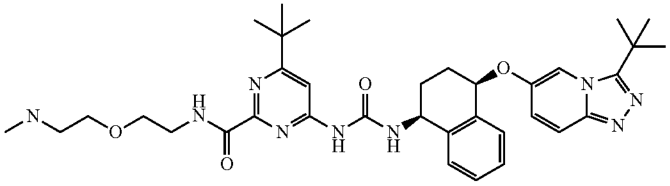 [SMILES: CNCCOCCNC(=O)c1nc(NC(=O)N[C@H]2CC[C@@H](Oc3ccc4nnc(C(C)(C)C)n4c3)c3ccccc32)cc(C(C)(C)C)n1] | 130 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(2-(dimethylamino)ethoxy)-ethyl)pyrimidine-2-carboxamide | $^1$H NMR (400 MHz, d-6-DMSO): 1.31 (9H, s), 1.52 (9H, s), 1.92-2.09 (3H, m), 2.11 (6H, s), 2.21-2.27 (1H, m), 2.38 (2H, t, J = 5.9 Hz), 3.41-3.53 (6H, m), 4.97-5.02 (1H, m), 5.63 (1H, t, J = 4.0 Hz), 7.28-7.44 (5H, m), 7.71 (1H, s), 7.74 (1H, dd, J = 9.8, 0.5 Hz), 8.15 (1H, d, J = 1.2 Hz), 8.28 (1H, br s), 8.57 (1H, t, J = 5.8 Hz), 9.92 (1H, s). | (Method 3): Rt 3.32 min, m/z 640 [MH$^+$]. | 1i | 2-(2-dimethylamino-ethoxy)-ethylamine CAS: 85322-63-0 |
| 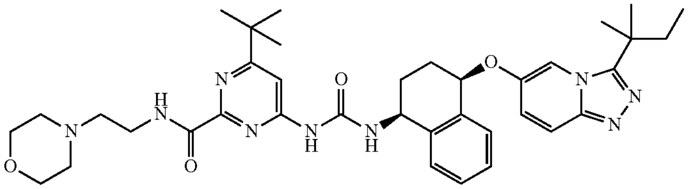 [SMILES: CCC(C)(C)c1nnc2ccc(O[C@@H]3CC[C@H](NC(=O)Nc4cc(C(C)(C)C)nc(C(=O)NCCN5CCOCC5)n4)c4ccccc43)cn12] | 131 | 4-(tert-butyl)-N-(2-morpholinoethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.63 (3H, t, J = 7.4 Hz), 1.33 (9H, s), 1.50 (6H, s), 1.89-2.25 (6H, m), 2.42 (4H, br s), 3.39 (2H, q, J = 5.9 Hz, partially obscured by water peak), 3.58 (4H, t, J = 4.4 Hz), 4.97-5.03 (1H, m), 5.61 (1H, t, J = 3.8 Hz), 7.27-7.43 (5H, m), 7.71 (1H, br s), 7.49 (1H, d, J = 9.9 Hz), 8.10 (1H, d, J = 1.2 Hz), 8.33 (1H, br s), 8.68 (1H, t, J = 5.6 Hz), 9.95 (1H, s), plus | (Method 2): Rt 3.49 min, m/z 684 [MH+]. | 2e | 4-(2-aminoethyl) morpholine CAS: 2038-03-1 |

TABLE 1-continued

| Structure | Ex. | Chemical Name | NMR | LCMS | Interm. | Reagent |
|---|---|---|---|---|---|---|
| | | | two protons obscured by the solvent peak. | | | |
| 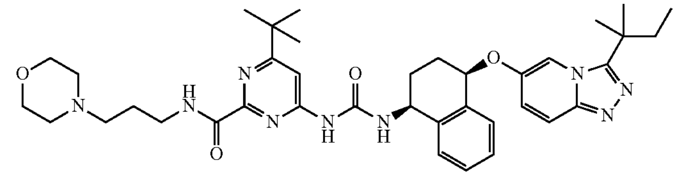 [SMILES: CCC(C)(C)c1nnc2ccc(O[C@@H]3CC[C@H](NC(=O)Nc4cc(C(C)(C)C)nc(C(=O)NCCCN5CCOCC5)n4)c4ccccc43)cn12] | 132 | 4-(tert-butyl)-N-(3-morpholinopropyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.64 (3H, t, J = 7.4 Hz), 1.32 (9H, s), 1.50 (6H, s), 1.67 (2H, quintet, J = 7.0 Hz), 1.89-2.12 (5H, m), 2.19-2.25 (1H, m), 2.28-2.31 (6H, m), 3.54 (4H, t, J = 4.6 Hz), 4.97-5.02 (1H, m), 5.61 (1H, t, J = 3.7 Hz), 7.27-7.43 (5H, m), 7.69 (1H, s), 7.75 (1H, d, J = 9.8 Hz), 8.10 (1H, d, J = 1.2 Hz), 8.34 (1H, br s), 8.60 (1H, t, J = 6.0 Hz), 9.89 (1H, s), plus two protons obscured by the solvent peak. | (Method 2): Rt 3.52 min, m/z 698 [MH+]. | 2e | 3-morpholino-propan-1-amine CAS: 123-00-2 |
| 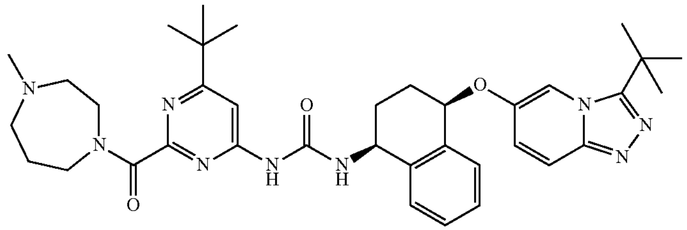 [SMILES: CN1CCCN(C(=O)c2nc(NC(=O)N[C@H]3CC[C@@H](Oc4ccc5nnc(C(C)(C)C)n5c4)c4ccccc43)cc(C(C)(C)C)n2)CC1] | 133 | 1-(6-(tert-butyl)-2-(4-methyl-1,4-diazepane-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.27 (9H, s), 1.53 (9H, s), 1.64-2.10 (9H, m), 2.39-2.47 (2H, m), 2.54-2.67 (2H, m), 3.15-3.24 (2H, m), 3.51-3.61 (2H, m), 4.94-4.99 (1H, m), 5.63 (1H, t, J = 4.0 Hz), 7.26-7.45 (5H, m), 7.71 (1H, br s), 7.75 (1H, d, J = 9.8 Hz), 7.95 (1H, br s), 8.14 (1H, br s), 9.25 (1H, br s). | (Method 3): Rt 3.17 min, m/z 654 [MH$^+$]. | 1i | 1-methyl-1,4-diazepane CAS: 4318-37-0 |
| 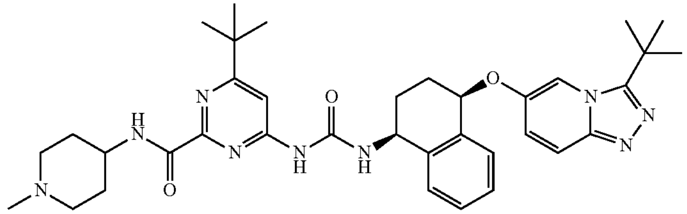 [SMILES: CN1CCC(NC(=O)c2nc(NC(=O)N[C@H]3CC[C@@H](Oc4ccc5nnc(C(C)(C)C)n5c4)c4ccccc43)cc(C(C)(C)C)n2)CC1] | 134 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylpiperidin-4-yl)pyrimidine-2-carboxamide | $^1$H NMR (400 MHz, d-6-DMSO): 1.30 (9H, s), 1.52 (9H, s), 1.57-1.75 (4H, m), 1.89-2.11 (5H, m), 2.14 (3H, s), 2.16-2.27 (1H, m), 2.65-2.69 (2H, m), 3.63-3.73 (1H, m), 4.96-5.01 (1H, m), 5.63 (1H, t, J = 4.0 Hz), 7.28-7.44 (5H, m), 7.72 (1H, br s), 7.74 (1H, dd, J = 9.8, 0.5 Hz), 8.14 (1H, d, J = 1.2 Hz), 8.19 (1H, br s), 8.28 (1H, d, J = 8 Hz), 9.87 (1H, s). | (Method 3): Rt 3.27 min, m/z 654 [MH$^+$]. | 1i | 1-methyl-piperidin-4-amine CAS: 41838-46-4 |

TABLE 1-continued

| Structure | Ex. | Chemical Name | NMR | LCMS | Interm. | Reagent |
|---|---|---|---|---|---|---|
| 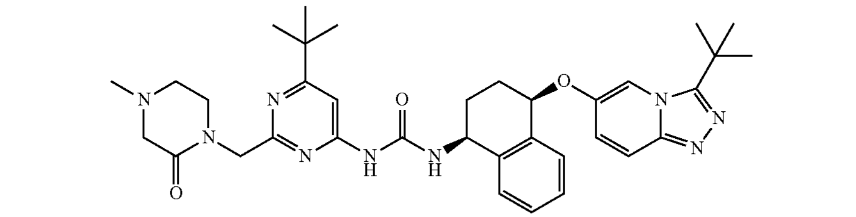 [SMILES: CN1CCN(Cc2nc(NC(=O)N[C@H]3CC[C@@H](Oc4ccc5nnc(C(C)(C)C)n5c4)c4ccccc43)cc(C(C)(C)C)n2)C(=O)C1] 1.0 eq HCOOH | 135 | 1-(6-(tert-Butyl)-2-((4-methyl-2-oxopiperazin-1-yl)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea formate salt | $^1$H NMR (400 MHz, d-6-DMSO): 1.30 (9H, s), 1.52 (9H, s), 1.96-2.23 (4H, m), 3.23 (3H, s), 3.53-3.74 (2H, m), 3.84-3.89 (2H, m), 4.17 (1H, d, J = 16.1 Hz, AB system), 4.41 (1H, d, J = 16.2 Hz, AB system), 4.65 (2H, s), 4.93-4.99 (1H, m), 5.60-5.62 (1H, m), 7.26-7.39 (5H, m), 7.75 (1H, dd, J = 9.8, 0.5 Hz), 8.05 (1H, d, J = 2.3 Hz), 8.16 (1H, br s), 8.44-8.49 (2H, m), 8.66 (1H, s), 10.56 (1H, br s). | (Method 3): Rt 3.20 min, m/z 640 [MH$^+$]. | EE | 1-Methyl-3-oxopiperazine CAS: 34770-60-0 |
| 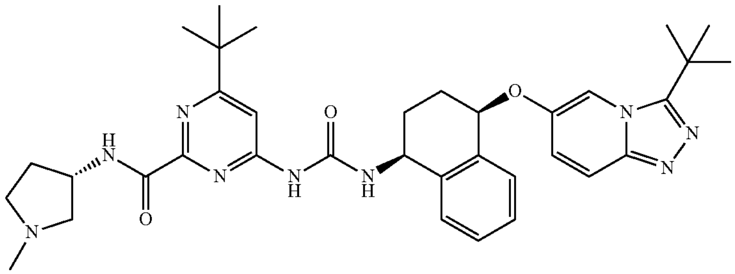 [SMILES: CN1CC[C@H](NC(=O)c2nc(NC(=O)N[C@H]3CC[C@@H](Oc4ccc5nnc(C(C)(C)C)n5c4)c4ccccc43)cc(C(C)(C)C)n2)C1] | 136 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((S)-1-methylpyrrolidin-3-yl)pyrimidine-2-carboxamide | $^1$HNMR (400 MHz, d-6-DMSO): 1.30 (9H, s), 1.52 (9H, s), 1.64-1.72 (1H, m), 1.91-2.21 (5H, m), 2.24 (3H, s), 2.28-2.34 (1H, m), 2.45 (1H, dd, J = 9.4, 4.4 Hz), 2.58-2.67 (2H, m), 4.31-4.39 (1H, m), 4.95-5.01 (1H, m), 5.63 (1H, t, J = 4.0 Hz), 7.27-7.44 (5H, m), 7.73-7.76 (2H, m), 8.12 (1H, br s), 8.14 (1H, d, J = 1.2 Hz), 8.39 (1H, d, J = 7.9 Hz), 9.90 (1H, s). | (Method 3): Rt 3.33 min, m/z 640 [MH$^+$]. | 1i | (3S)-1-methyl-pyrrolidin-3-amine CAS: 214357-95-6 |
| 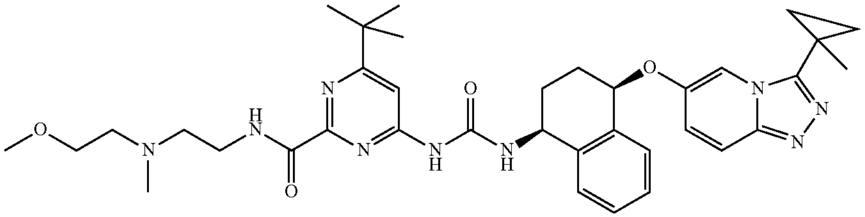 [SMILES: COCCN(C)CCNC(=O)c1nc(NC(=O)N[C@H]2CC[C@@H](Oc3ccc4nnc(C5(C)CC5)n4c3)c3ccccc32)cc(C(C)(C)C)n1] | 137 | 4-(tert-butyl)-N-(2-((2-methoxyethyl)(methyl)-amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.92-0.95 (2H, m), 1.03-1.05 (2H, m), 1.31 (9H, s), 1.43 (3H, s), 1.95-2.16 (3H, m), 2.23 (3H, s), 2.25-2.33 (1H, m), 3.20 (3H, s), 3.40 (2H, t, J = 6.0 Hz), 4.97-5.03 (1H, m), 5.63 (1H, t, J = 4.0 Hz), 7.29-7.45 (5H, m), 7.71-7.74 (2H, m), 8.10 (1H, d, J = 1.3 Hz), 8.29 (1H, br s), 8.58 (1H, t, J = 5.6 Hz), 9.92 (1H, s), plus six protons obscured by solvent peaks. | (Method 3): Rt 3.32 min, m/z 670 [MH$^+$]. | AC | N'-(2-methoxyethyl)-N'-methyl-ethane-1,2-diamine CAS: 14165-17-4 |

TABLE 1-continued

| Structure | Ex. | Chemical Name | NMR | LCMS | Interm. | Reagent |
|---|---|---|---|---|---|---|
| 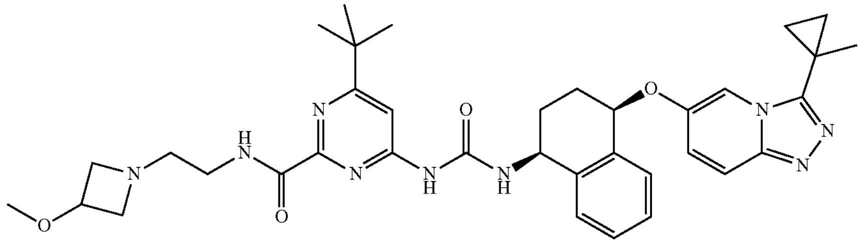 | 138 | 4-(tert-butyl)-N-(2-(3-methoxyazetidin-1-yl)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz. d-6-DMSO): 0.93-0.95 (2H, m), 1.03-1.05 (2H, m), 1.31 (9H, s), 1.44 (3H, s), 1.92-2.16 (3H, m), 2.23-2.33 (1H, m), 2.78-2.82 (2H, m), 3.11 (3H, s), 3.23 (2H, q, J = 6.0 Hz), 3.49-3.53 (2H, m), 3.92 (1H, quintet, J = 5.7 Hz), 4.97-5.03 (1H, m), 5.63 (1H, t, J = 4.0 Hz), 7.29-7.45 (5H, m), 7.71-7.74 (2H, m), 8.10 (1H, d, J = 1.3 Hz), 8.27 (1H, br s), 8.54 (1H, t, J = 6.0 Hz), 9.89 (1H, s), plus two protons obscured by solvent peaks. | (Method 3): Rt 3.29 min, m/z 668 [MH$^+$]. | AC | 2-(3-methoxy-azetidin-1-yl)ethan-1-amine CAS: 911300-65-7 |
| 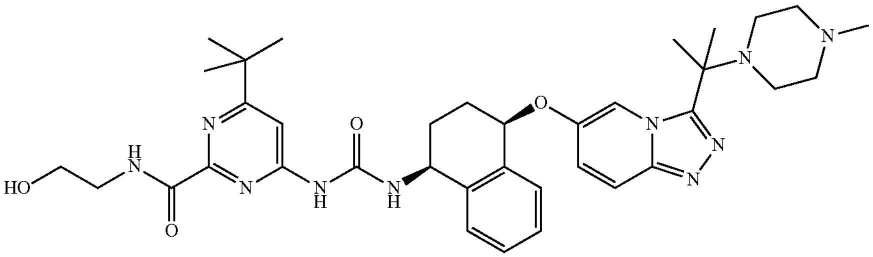 [SMILES: CN1CCN(C(C)(C)c2nnc3ccc(O[C@@H]4CC[C@H](NC(=O)Nc5cc(C(C)(C)C)nc(C(=O)NCCO)n5)c5ccccc54)cn23)CC1] | 139 | 4-(tert-butyl)-N-(2-hydroxyethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.32 (9H, s), 1.54 (3H, s), 1.55 (3H, s), 1.95-2.46 (14H, m), 3.35 (2H, q, J = 6.1 Hz, partially covered by water peak), 3.51 (2H, q, J = 5.6 Hz), 4.80 (1H, t, J = 5.3 Hz), 4.99-5.05 (1H, m), 5.46-5.49 (1H, m), 7.31-7.47 (5H, m), 7.73-7.76 (2H, m), 8.21 (1H, br s), 8.57 (1H, t, J = 5.9 Hz), 8.72 (1H, d, J = 1.6 Hz), 9.89 (1H, s), plus one proton obscured by the solvent peak. | (Method 3): Rt 3.09 min, m/z 685 [MH$^+$]. | FF | Ethanolamine CAS: 141-43-5 |
| 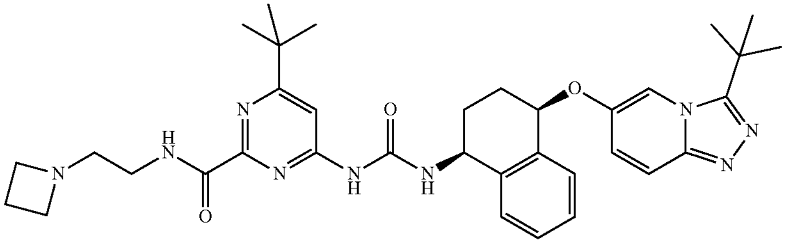 [SMILES: CC(C)(C)c1cc(NC(=O)N[C@H]2CC[C@@H](Oc3ccc4nnc(C(C)(C)C)n4c3)c3ccccc32)nc(C(=O)NCCN2CCC2)n1] | 140 | N-(2-(azetidin-1-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.30 (9H, s), 1.52 (9H, s), 1.93 (2H, quintet, J = 7.0 Hz), 1.98-2.13 (3H, m), 2.10-2.27 (1H, m), 3.11 (4H, t, J = 7.0 Hz), 3.20 (2H, q, J = 6.4 Hz), 4.96-5.02 (1H, m), 5.63 (1H, t, J = 4.0 Hz), 7.28-7.44 (5H, m), 7.72 (1H, s), 7.74 (1H, dd, J = 9.9, 0.5 Hz), 8.14 (1H, d, J = 1.2 Hz), 8.29 (1H, br s), 8.54 (1H, t, J = 5.9 Hz), 9.92 (1H, s), plus two protons obscured by solvent. | (Method 3): Rt 3.42 min, m/z 640 [MH$^+$]. | 1i | 2-(azetidin-1-yl)ethan-1-amine CAS: 795299-77-3 |

TABLE 1-continued

| Structure | Ex. | Chemical Name | NMR | LCMS | Interm. | Reagent |
|---|---|---|---|---|---|---|
| 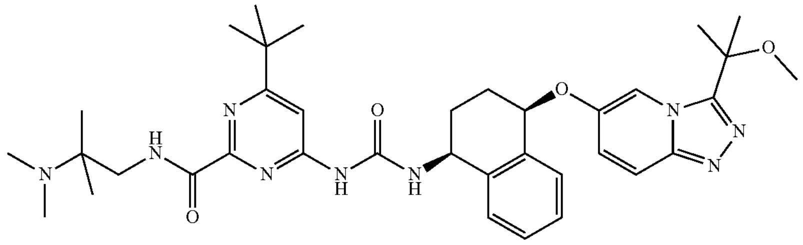 | 141 | 4-(tert-butyl)-N-(2-(dimethylamino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.98 (6H, s), 1.30 (9H, s), 1.69 (6H, s), 1.90-2.16 (3H, m), 2.19 (6H, s), 2.21-2.28 (1H, m), 2.98 (3H, s), 3.23 (2H, d, J = 5.3 Hz), 4.97-5.02 (1H, m), 5.49 (1H, t, J = 4.0 Hz), 7.28-7.43 (5H, m), 7.78 (1H, s), 7.81 (1H, dd, J = 9.8, 0.6 Hz), 8.14 (1H, d, J = 1.4 Hz), 8.20 (1H, br s), 8.50 (1H, t, J = 5.2 Hz), 9.88 (1H, s). | (Method 3): Rt 3.47 min, m/z 672 [MH$^+$]. | 12e | (2-Amino-1,1-dimethylethyl) dimethylamine CAS: 76936-44-2 |
| 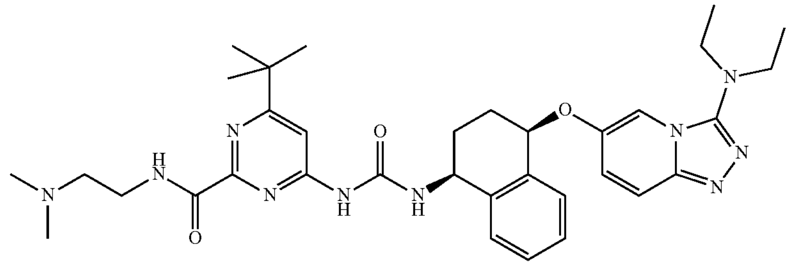 [SMILES: CCN(CC)c1nnc2ccc(O[C@@H]3CC[C@H](NC(=O)Nc4cc(C(C)(C)C)nc(C(=O)NCCN(C)C)n4)c4ccccc43)cn12] | 142 | 4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)-pyrimidine-2-carboxamide | $^1$HNMR (400 MHz, d-6-DMSO): 1.01 (6H, t, J = 7.0 Hz), 1.31 (9H, s), 1.92-2.28 (10H, m), 2.39 (2H, t, J = 6.6 Hz), 3.23 (4H, q, J = 7.1 Hz), 3.35 (2H, q, J = 6.2 Hz, partially obscured by water peak), 4.97-5.02 (1H, m), 5.54 (1H, t, J = 4.4 Hz), 7.22-7.42 (5H, m), 7.63 (1H, dd, J = 9.8, 0.7 Hz), 7.72-7.74 (2H, m), 8.29 (1H, br s), 8.57 (1H, t, J = 5.8 Hz), 9.89 (1H, s). | (Method 3): Rt 3.27 min, m/z 643 [MH+]. | 11a | N,N-dimethylamine ethandiamine CAS: 108-00-9 |
| 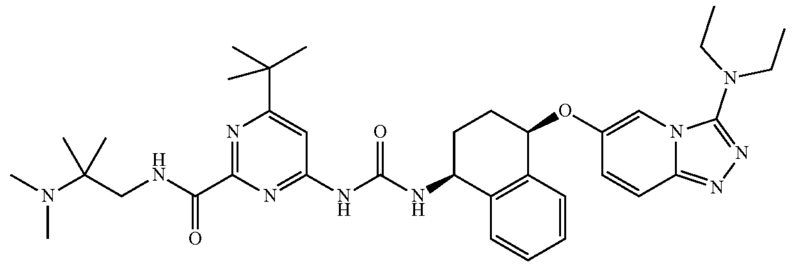 [SMILES: CCN(CC)c1nnc2ccc(O[C@@H]3CC[C@H](NC(=O)Nc4cc(C(C)(C)C)nc(C(=O)NCC(C)(C)N(C)C)n4)c4ccccc43)cn12] | 143 | 4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide | $^1$H NMR (400 MHz, d-6-DMSO): 0.98 (6H, s), 1.02 (6H, t, J = 7.1 Hz), 1.31 (9H, s), 1.89-2.26 (10H, m), 3.20-3.26 (6H, m), 4.96-5.02 (1H, m), 5.54 (1H, t, J = 4.1 Hz), 7.22-7.43 (5H, m), 7.63 (1H, dd, J = 9.8, 0.7 Hz), 7.71 (1H, d, J = 1.4 Hz), 7.78 (1H, br s), 8.20 (1H, br s), 8.51 (1H, t, J = 5.2 Hz), 9.90 (1H, s). | (Method 3): Rt 3.36 min, m/z 671 [MH+]. | 11a | (2-Amino-1,1-dimethylethyl) dimethylamine CAS: 76936-44-2 |

TABLE 1-continued

| Structure | Ex. | Chemical Name | NMR | LCMS | Interm. | Reagent |
|---|---|---|---|---|---|---|
| 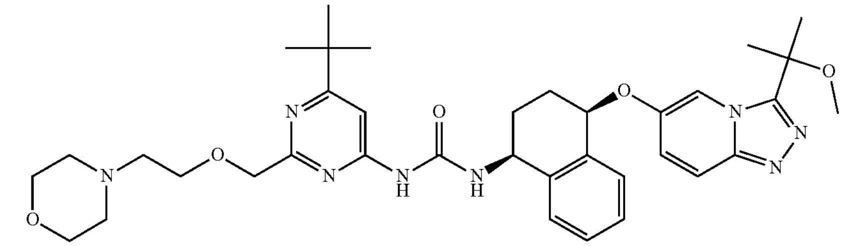 [SMILES: COC(C)(C)c1nnc2ccc(O[C@@H]3CC[C@H](NC(=O)Nc4cc(C(C)(C)C)nc(COCCN5CCOCC5)n4)c4ccccc43)cn12] | 144 | 1-(6-(tert-butyl)-2-((2-morpholinoethoxy)-methyl)pyrimidin-4-yl)-3-((1S,4R)-4-((3-(2-methoxypropan-2-yl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.26 (9H ,s), 1.69 (6H, s), 1.86-2.23 (4H, m), 2.23-2.31 (4H, br s), 2.31-2.42 (2H, m), 2.98 (3H, s), 3.29-3.32 (2H, m, partially obscured by the solvent peak), 3.46 (2H, t, J = 4.6 Hz), 3.55 (2H, t, J = 5.8 Hz), 4.44 (2H, d, J = 1.3 Hz), 4.97-5.03 (1H, m), 5.50 (1H, t, J = 3.9 Hz), 7.27-7.33 (2H, m), 7.34-7.44 (4H, m), 7.82 (1H, dd, J = 0.6, 9.9 Hz), 8.13 (1H, d, J = 1.42 Hz), 8.66 (1H, br s), 9.67 (1H, s). | (Method 3): Rt 3.29 min, m/z 673.6 [M + H$^+$], sample assessed as ca. 99.5%. | EE | 4-(2-hydroxyethyl) morpholine CAS: 622-40-2 |
| 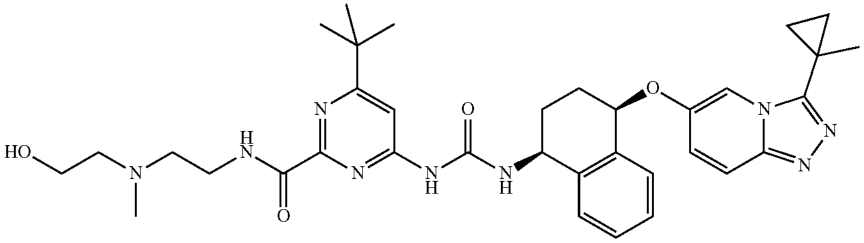 [SMILES: CN(CCO)CCNC(=O)c1nc(NC(=O)N[C@H]2CC[C@@H](Oc3ccc4nnc(C5(C)CC5)n4c3)c3ccccc32)cc(C(C)(C)C)n1] | 145 | 4-(tert-butyl)-N-(2-((2-hydroxyethyl)(methyl)-amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.93-0.95 (2H, m), 1.04-1.05 (2H, m), 1.31 (9H, s), 1.44 (3H, s), 1.92-2.15 (3H, m), 2.23 (3H, s), 2.25-2.33 (1H, m), 3.47 (2H, q, J = 6.0 Hz), 4.35 (1H, t, J = 5.3 Hz), 4.97-5.03 (1H, m), 5.63 (1H, t, J = 4.0 Hz), 7.29-7.45 (5H, m), 7.71-7.74 (2H, m), 8.10 (1H, d, J = 1.3 Hz), 8.27 (1H, br s), 8.60 (1H, t, J = 5.7 Hz), 9.91 (1H, s), plus six protons obscured by solvent peaks. | (Method 3): Rt 3.19 min, m/z 656 [MH$^+$]. | AC | 2-[(2-aminoethyl)-(methyl)amine] ethanol CAS: 5753-50-4 |
| 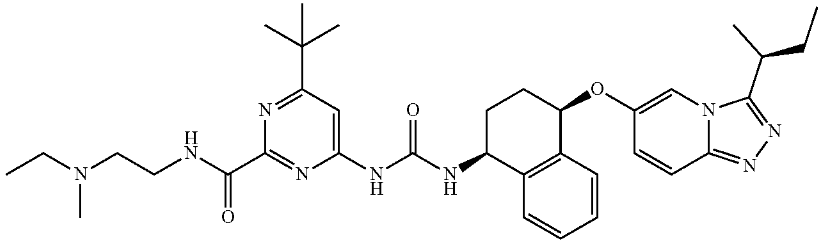 [SMILES: CC[C@H](C)c1nnc2ccc(O[C@@H]3CC[C@H](NC(=O)Nc4cc(C(C)(C)C)nc(C(=O)NCCN(C)CC)n4)c4ccccc43)cn12] | 146 | 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(ethyl(methyl)amino)-ethyl)pyrimidine-2-carboxamide | $^1$H NMR (400 MHz, d-6-DMSO): 0.87 (3H, t, J = 7.4 Hz), 0.98 (3H, t, J = 7.1 Hz), 1.31 (9H, s), 1.34 (3H, d, J = 6.9 Hz), 1.75 (1H, heptet, J = 7.0 Hz), 1.85-2.28 (8H, m), 2.39 (2H, q, J = 7.1 Hz), 2.46-2.50 (2H, m, partially covered by the solvent peak), 3.44 (1H, sextet, J = 6.9 Hz), 4.98-5.04 (1H, m), 5.57 (1H, t, J = 4.1 Hz), 7.25-7.44 (5H, m), 7.70 (1H, d, J = 9.8 Hz), 7.72 (1H, br s), 8.24 (1H, d, J = 1.3 Hz), 8.31 (1H, br s), 8.61 (1H, t, J = 5.6 Hz), 9.92 (1H, s), plus two protons obscured by the solvent peak. | (Method 2): Rt 3.32 min, m/z 642 [MH+]. | 8e | (2-aminoethyl)-(ethyl)-methylamine CAS: 70111-47-6 |

TABLE 1-continued

| Structure | Ex. | Chemical Name | NMR | LCMS | Interm. | Reagent |
|---|---|---|---|---|---|---|
| 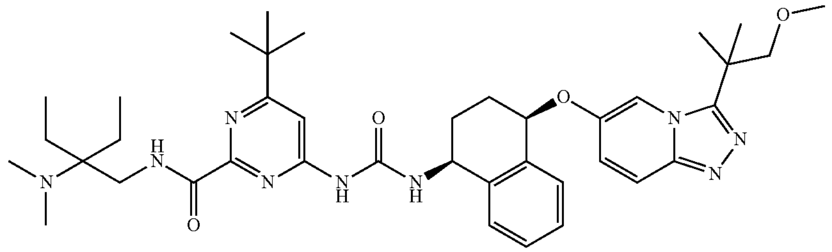 | 147 | 4-(tert-butyl)-N-(2-(dimethylamino)-2-ethylbutyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.83 (6H, t, J = 7.4 Hz), 1.30 (9H, s), 1.39-1.57 (10H, m), 1.92-2.26 (4H, m), 2.31 (6H, s), 3.23 (3H, s), 3.27 (2H, d, J = 5.2 Hz), 3.67 (2H, s), 4.97-5.03 (1H, m), 5.54 (1H, t, J = 3.9 Hz), 7.29-7.45 (5H, m), 7.73 (1H, d, J = 9.9 Hz), 7.76 (1H, br s), 8.21 (1H, br s), 8.28 (1H, d, J = 1.4 Hz), 8.57 (1H, t, J = 5.1 Hz), 9.93 (1H, s). | (Method 2): Rt 3.55 min, m/z 714 [MH+]. | 7e | N-[1-(aminomethyl)-1-ethylpropyl]-N,N-dimethylamine CAS: 891647-25-9 |
| 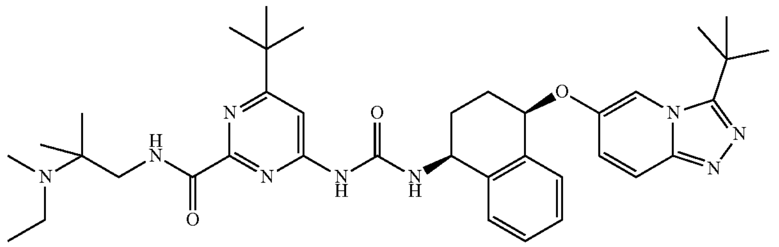 [SMILES: CCN(C)C(C)(C)CNC(=O)c1nc(NC(=O)N[C@H]2CC[C@@H](Oc3ccc4nnc(C(C)(C)C)n4c3)c3ccccc32)cc(C(C)(C)C)n1] | 148 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)-2-methylpropyl)pyrimidine-2-carboxamide | $^1$H NMR (400 MHz, d-6-DMSO): 0.99 (6H, s), 1.03 (3H, t, J = 7.0 Hz), 1.31 (9H, s), 1.52 (9H, s), 1.92-2.13 (3H, m), 2.16 (3H, s), 2.20-2.28 (1H, m), 3.39 (2H, q, J = 7.0 Hz), 3.22 (2H, d, J = 4.9 Hz), 4.97-5.03 (1H, m), 5.63 (1H, t, J = 4.0 Hz), 7.28-7.44 (5R m), 7.73 (1H, s), 7.74 (1H, dd, J = 9.9, 0.6 Hz), 8.14 (1H, d, J = 1.2 Hz), 8.31 (1H, br s), 8.62 (1H, t, J = 4.9 Hz), 9.97 (1H, s). | (Method 3): Rt 3.42 min, m/z 670 [MH$^+$]. | 1i | (2-amino-1,1-dimethylethyl) ethyl(methyl)-amine CAS: 1018289-07-0 |
| 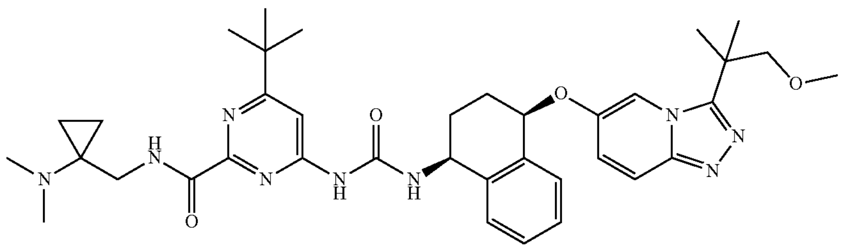 | 149 | 4-(tert-butyl)-N-((1-(dimethylamino) cyclopropyl)methyl)-6-(3-((1S,4R)-4-((3-(l-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.46-0.49 (2H, m), 0.59-0.62 (2H, m), 1.31 (9H, s), 1.53 (6H, s), 1.92-2.24 (4H, m), 2.34 (6H, s), 3.23 (3H, s), 3.43 (2H, d, J = 6.4 Hz), 3.67 (2H, s), 4.97-5.03 (1H, m), 5.54 (1H, t, J = 3.9 Hz), 7.29-7.45 (5H, m), 7.72 (1H, d, J = 9.9 Hz), 7.75 (1H, br s), 8.19 (1H, br s), 8.28 (1H, d, J = 1.3 Hz), 8.45 (1H, t, J = 6.3 Hz), 9.90 (1H, s). | (Method 2): Rt 3.38 min, m/z 684 [MH$^+$]. | 7e | 1-(aminomethyl)-N,N-dimethyl-cyclopropan-1-amine CAS: 176445-82-2 |

TABLE 1-continued

| Structure | Ex. | Chemical Name | NMR | LCMS | Interm. | Reagent |
|---|---|---|---|---|---|---|
| 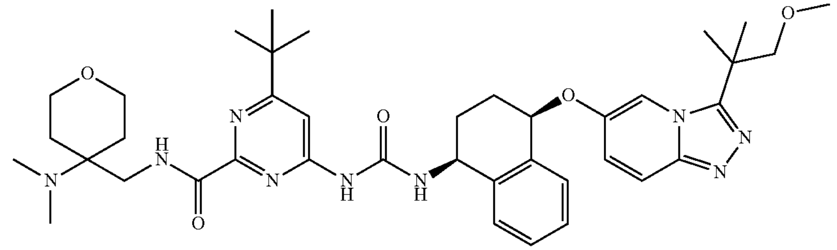 | 150 | 4-(tert-butyl)-N-((4-(dimethylamino)-tetrahydro-2H-pyran-4-yl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.31 (9H, s), 1.39-1.45 (2H, m), 1.53 (6H, s), 1.66-1.73 (2H, m), 1.91-2.25 (4H, m), 2.30 (6H, s), 3.24 (3H, s), 3.45-3.51 (4H, m), 3.63-3.68 (4H, m), 4.96-5.03 (1H, m), 5.54 (1H, t, J = 4.0 Hz), 7.29-7.45 (5H, m), 7.73 (1H, dd, J = 9.8, 0.4 Hz), 7.78 (1H, br s), 8.18 (1H, br s), 8.28 (1H, d, J = 1.3 Hz), 8.45 (1H, t, J = 6.1 Hz), 9.91 (1H, s). | (Method 2): Rt 3.33 min, m/z 728 [MH$^+$]. | 7e | 4-(aminomethyl)-N,N-dimethyl-tetrahydro-2H-pyran-4-amine CAS: 176445-80-0 |
| 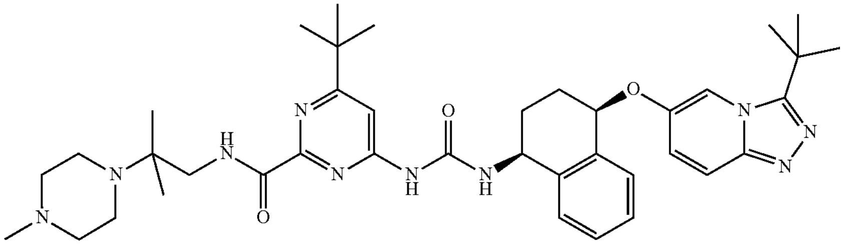 [SMILES: CN1CCN(C(C)(C)CNC(=O)c2nc(NC(=O)N[C@H]3CC[C@@H](Oc4ccc5nnc(C(C)(C)C)n5c4)c4ccccc43)cc(C(C)(C)C)n2)CC1] | 151 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide | $^1$H NMR (400 MHz, d-6-DMSO): 1.00 (6H, s), 1.35 (9H, s), 1.52 (9H, s), 1.91-2.12 (3H, m), 2.14 (3H, s), 2.20-2.43 (5H, m), 3.23 (2H, d, J = 4.7 Hz), 4.97-5.03 (1H, m), 5.62 (1H, t, J = 4.0 Hz), 7.28-7.44 (5H, m), 7.71 (1H, s), 7.74 (1H, dd, J = 9.9, 0.5 Hz), 8.14 (1H, d, J = 1.2 Hz), 8.35 (1H, br s), 8.64 (1H, t, J = 4.6 Hz), 9.94 (1H, br s), plus four protons obscured by solvent peak. | (Method 3): Rt 3.37 min, m/z 711 [MH$^+$]. | 1i | 2-methyl-2-(4-methylpiperazin-1-yl)propan-1-amine CAS: 21404-92-2 |
| 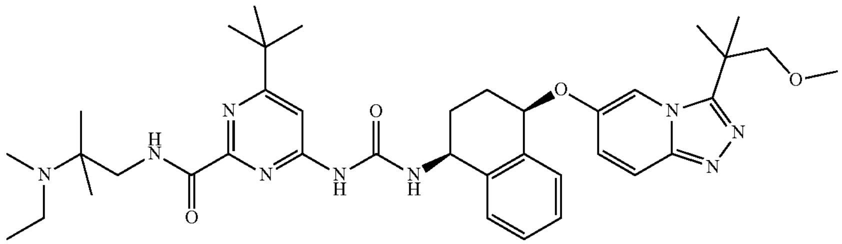 | 152 | 4-(tert-butyl)-N-(2-(ethyl(methyl)amino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.00 (6H, s), 1.03 (3H, t, J = 7.0 Hz), 1.31 (9H, s), 1.52 (6H, s), 1.91-2.14 (3H, m), 2.16 (3H, s), 2.19-2.33 (1H, m), 2.39 (2H, q, J = 7.0 Hz), 3.22 (2H, br s), 3.23 (3H, s), 3.66 (2H, s) 4.97-5.03 (1H, m), 5.54 (1H, t, J = 4.0 Hz), 7.29-7.45 (5H, m), 7.72-7.74 (2H, m), 8.27 (2H, d, J = 1.3 Hz), 8.62 (1H, t, J = 4.9 Hz), 9.96 (1H, s). | (Method 3): Rt 3.45 min, m/z 700 [MH$^+$]. | 7e | (2-amino-1,1-dimethylethyl) ethyl(methyl)-amine CAS: 1018289-07-0 |

TABLE 1-continued

| Structure | Ex. | Chemical Name | NMR | LCMS | Interm. | Reagent |
|---|---|---|---|---|---|---|
| 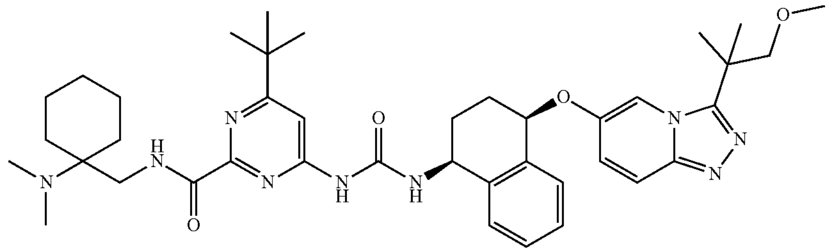 | 153 | 4-(tert-butyl)-N-((1-(dimethylamino) cyclohexyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.29-1.38 (15H, m), 1.52-1.61 (10H, m), 1.92-2.24 (4H, m), 2.27 (6H, s), 3.23 (3H, s), 3.37 (2H, d, J = 5.8 Hz), 3.67 (2H, s), 4.97-5.03 (1H, m), 5.54 (1H, t, J = 4.0 Hz), 7.30-7.45 (5H, m), 7.72 (1H, d, J = 9.8 Hz), 7.77 (1H, br s), 8.17 (1H, br s), 8.28 (1H, d, J = 1.3 Hz), 8.44 (1H, t, J = 5.8 Hz), 9.91 (1H, s). | (Method 2): Rt 3.58 min, m/z 726 [MH$^+$]. | 7e | 1-(amino-methyl)-N,N-dimethyl-cyclohexanamine CAS: 41806-09-1 |
| 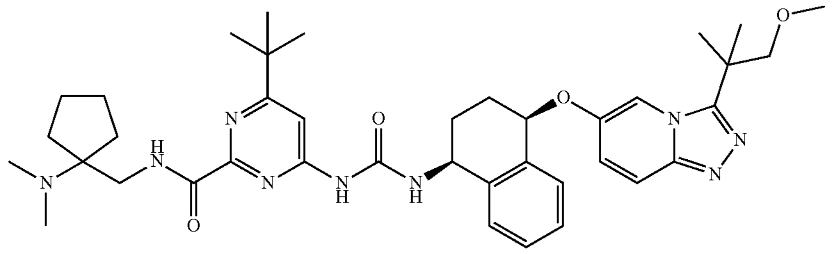 | 154 | 4-(tert-butyl)-N-((1-(dimethylamino) cyclopentyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.30 (9H, s), 1.37-1.43 (2H, m), 1.53 (6H, s), 1.55-1.72 (6H, m), 1.93-2.21 (4H, m), 2.24 (6H, s), 3.23 (3H, s), 3.35 (2H, d, J = 5.6 Hz), 3.67 (2H, s), 4.97-5.03 (1H, m), 5.54 (1H, t, J = 3.9 Hz), 7.29-7.45 (5H, m), 7.73 (1H, dd, J = 9.8, 0.5 Hz), 7.79 (1H, br s), 8.17 (1H, br s), 8.28 (1H, d, J = 1.3 Hz), 8.47 (1H, t, J = 5.5 Hz), 9.91 (1H, s). | (Method 2): Rt 3.49 min, m/z 712 [MH$^+$]. | 7e | N-[1-(aminomethyl)-cyclopentyl]-N,N-dimethylamine CAS: 164642-21-1 |
| 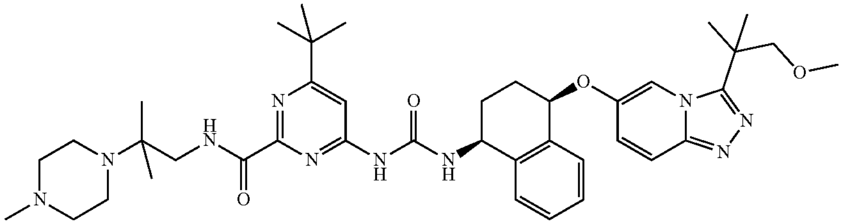 | 155 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide | $^1$H NMR (400 MHz, d-6-DMSO): 1.00 (6H, s), 1.35 (9H, s), 1.52 (6H, s), 1.91-2.12 (6H, m), 2.14 (3H, s), 2.19-2.43 (4H, m), 3.23 (3H, s), 3.24 (2H, br s), 3.66 (2H, s) 4.97-5.03 (1H, m), 5.53 (1H, t, J = 4.0 Hz), 7.29-7.44 (5H, m), 7.72 (1H, br s), 7.74 (1H, br s), 8.27 (1H, d, J = 1.3 Hz), 8.32(1H, br s), 8.64 (1H, t, J = 4.8 Hz), 10.01 (1H, s), plus two protons obscured by solvent peak. | (Method 3): Rt 3.40 min, m/z 741 [MH$^+$]. | 7e | 2-methyl-2-(4-methylpiperazin-1-yl)propan-1-amine CAS: 21404-92-2 |

TABLE 1-continued

| Structure | Ex. | Chemical Name | NMR | LCMS | Interm. | Reagent |
|---|---|---|---|---|---|---|
| 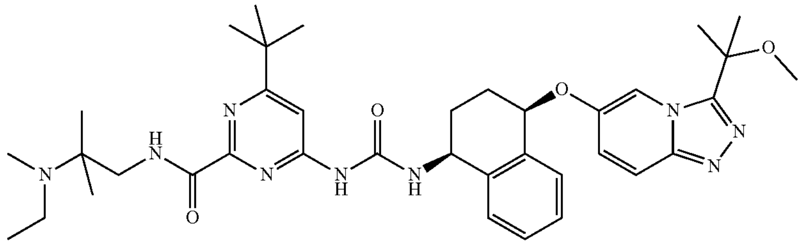 | 156 | 4-(tert-butyl)-N-(2-(ethyl(methyl)amino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.00 (6H, s), 1.03 (3H, t, J = 6.9 Hz), 1.31 (9H, s), 1.69 (6H, s), 1.91-2.14 (3H, m), 2.16 (3H, s), 2.22-2.29 (1H, m), 2.39 (2H, q, J = 6.9 Hz), 2.98 (3H, s), 3.23 (2H, d, J = 4.5 Hz), 4.97-5.03 (1H, m), 5.49 (1H, t, J = 4.0 Hz), 7.28-7.43 (5H, m), 7.73 (1H, s), 7.81 (1H, dd, J = 9.8, 0.6 Hz), 8.14 (1H, d, J = 1.4 Hz), 8.31 (1H, br s), 8.61 (1H, t, J = 4.9 Hz), 9.94 (1H, s). | (Method 3): Rt 3.40 min, m/z 686 [MH$^+$]. | 12e | (2-amino-1,1-dimethylethyl) ethyl(methyl) amine CAS: 1018289-07-0 |
| 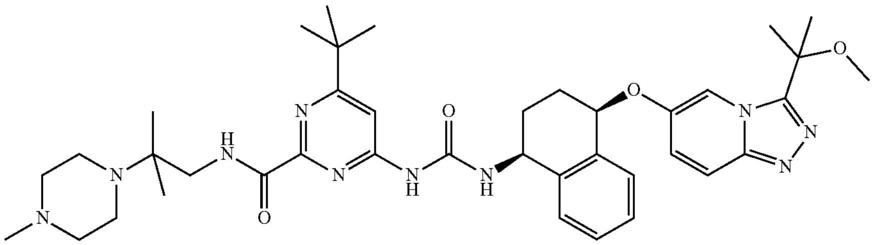 | 157 | 4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide | $^1$H NMR (400 MHz, d-6-DMSO): 1.00 (6H, s), 1.35 (9H, s), 1.69 (6H, s), 1.94-2.13 (6H, m), 2.14 (3H, s), 2.24-2.46 (4H, m), 2.98 (3H, s), 3.24 (2H, d, J = 4.5 Hz), 4.98-5.03 (1H, m), 5.49 (1H, t, J = 4.0 Hz), 7.28-7.43 (5H, m), 7.71 (1H, s), 7.81 (1H, dd, J = 9.9, 0.4 Hz), 8.14 (1H, d, J = 1.5 Hz), 8.36 (1H, br s), 8.64 (1H, t, J = 4.7 Hz), 9.99 (1H, s), plus two protons obscured by solvent peak. | (Method 3): Rt 3.36 min, m/z 727 [MH$^+$]. | 12e | 2-methyl-2-(4-methylpiperazin-1-yl)propan-1-amine CAS: 21404-92-2 |
| 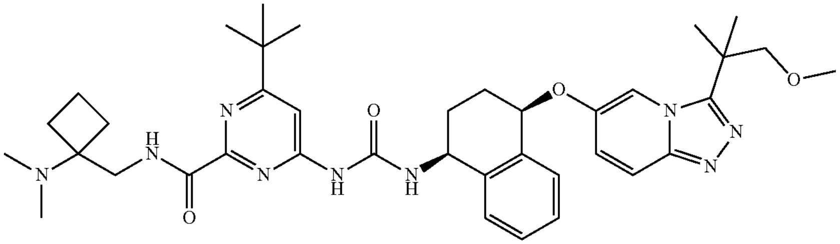 1.0 eq HCOOH | 158 | 4-(tert-Butyl)-N-((1-(dimethylamino)-cyclobutyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide formate salt | $^1$H NMR (400 MHz, d-6-DMSO): 1.30 (9H, s), 1.53 (6H, s), 1.59-1.78 (4H, m), 1.91-2.15 (6H, m), 2.21 (6H, s), 3.24 (3H, s), 3.51 (2H, d, J = 5.9 Hz), 3.67 (2H, s), 4.97-5.03 (1H, m), 5.54 (1H, t, J = 4.0 Hz), 7.30-7.45 (5H, m), 7.73 (1H, dd, J = 9.8, 0.4 Hz), 7.78 (1H, br s), 8.16 (2H, br s), 8.28 (1H, d, J = 1.3 Hz), 8.47 (1H, t, J = 5.8 Hz), 9.89 (1H, s). | (Method 2): Rt 3.43 min, m/z 698 [MH$^+$]. | 7e | 1-(amino-methyl)-N,N-dimethyl-cyclo-butanamine CAS: 176445-78-6 |

TABLE 1-continued

| Structure | Ex. | Chemical Name | NMR | LCMS | Interm. | Reagent |
|---|---|---|---|---|---|---|
| 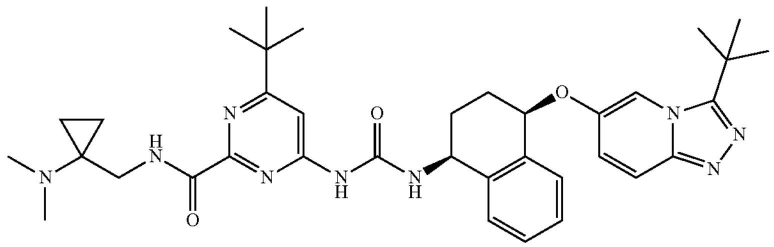 [SMILES: CN(C)C1(CNC(=O)c2nc(NC(=O)N[C@H]3CC[C@@H](Oc4ccc5nnc(C(C)(C)C)n5c4)c4ccccc43)cc(C(C)(C)C)n2)CC1] | 159 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)-cyclopropyl)methyl)-pyrimidine-2-carboxamide | $^1$H NMR (400 MHz, d-6-DMSO): 0.46-0.49 (2H, m), 0.59-0.62 (2H, m), 1.31 (9H, s), 1.53 (9H, s), 1.95-2.25 (4H, m), 2.34 (6H, s), 3.43 (2H, d, J = 6.4 Hz), 4.97-5.03 (1H, m), 5.64 (1H, t, J = 3.8 Hz), 7.29-7.45 (5H, m), 7.73-7.75 (2H, m), 8.15 (1H, d, J = 1.2 Hz), 8.21 (1H, br s), 8.45 (1H, t, J = 6.3 Hz), 9.91 (1H, s). | (Method 2): Rt 3.35 min, m/z 654 [MH$^+$]. | 1i | 1-(aminomethyl)-N,N-dimethyl-cyclopropan-1-amine CAS: 176445-82-2 |
| 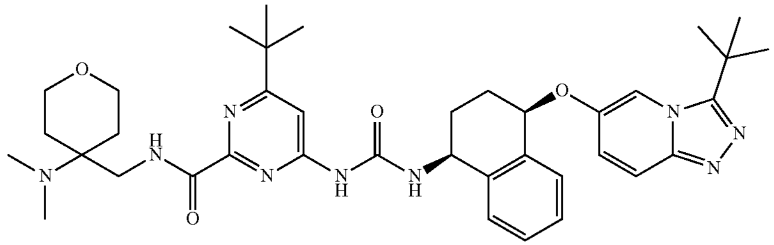 [SMILES: CN(C)C1(CNC(=O)c2nc(NC(=O)N[C@H]3CC[C@@H](Oc4ccc5nnc(C(C)(C)C)n5c4)c4ccccc43)cc(C(C)(C)C)n2)CCOCC1] | 160 | 4-(tert-butyl)-6-(3-((1S,4R)-4-((3-(tert-butyl)-[1,2,4]triazolo[4,3-a]pyridm-6-yl)oxy)-1,2,3,4-tetrahydronaphthalen-1-yl)ureido)-N-((4-(dimethylamino)-tetrahydro-2H-pyran-4-yl)methyl)pyrimidine-2-carboxamide | $^1$H NMR (400 MHz, d-6-DMSO): 1.31 (9H, s), 1.39-1.45 (2H, m), 1.53 (9H, s), 1.66-1.72 (2H, m), 1.93-2.29 (10H, m), 3.45-3.51 (4H, m), 3.63-3.68 (2H, m), 4.96-5.02 (1H, m), 5.64 (1H, t, J = 3.8 Hz), 7.29-7.45 (5H, m), 7.74 (1H, dd, J = 9.9, 0.5 Hz), 7.77 (1H, br s), 8.15 (1H, d, J = 1.3 Hz), 8.20 (1H, br s), 8.45 (1H, t, J = 6.0 Hz), 9.92 (1H, s). | (Method 2): Rt 3.30 min, m/z 698 [MH$^+$]. | 1i | 4-(aminomethyl)-N,N-dimethyl-tetrahydro-2H-pyran-4-amine CAS: 176445-80-0 |
| 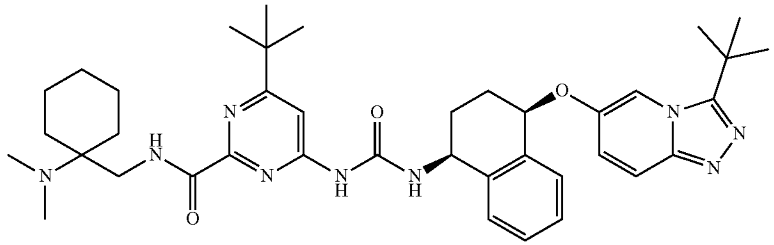 [SMILES: CN(C)C1(CNC(=O)c2nc(NC(=O)N[C@H]3CC[C@@H](Oc4ccc5nnc(C(C)(C)C)n5c4)c4ccccc43)cc(C(C)(C)C)n2)CCCCC1] | 161 | 4-(tert-butyl)-6-(3-((1S,4R)-4-((3-(tert-butyl)-[1,2,4]-triazolo[4,3-a]pyridin-6-yl)oxy)-1,2,3,4-tetrahydronaphthalen-1-yl)ureido)-N-((1-(dimethylamino)-cyclohexyl)methyl) pyrimidine-2-carboxamide | $^1$H NMR (400 MHz, d-6-DMSO): 1.27-1.36 (15H, m), 1.51-1.61 (13H, m), 1.93-2.13 (3H, m), 2.19-2.27 (7H, m), 3.37 (2H, d, J = 5.8 Hz), 4.96-5.03 (1H, m), 5.63 (1H, t, J = 3.8 Hz), 7.29-7.45 (5H, m), 7.74 (1H, d, J = 10.0 Hz), 7.76 (1H, br s), 8.15 (1H, d, J = 1.2 Hz), 8.20 (1H, br s), 8.44 (1H, t, J = 5.7 Hz), 9.92 (1H, s). | (Method 2): Rt 3.55 min, m/z 696 [MH$^+$]. | 1i | 1-(aminomethyl)-N,N-dimethyl-cyclo-hexanamine CAS: 41806-09-1 |
| 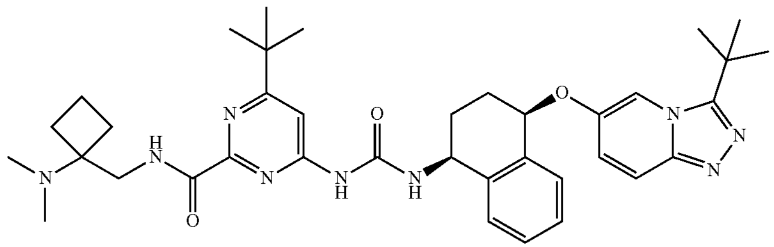 [SMILES: CN(C)C1(CNC(=O)c2nc(NC(=O)N[C@H]3CC[C@@H](Oc4ccc5nnc(C(C)(C)C)n5c4)c4ccccc43)cc(C(C)(C)C)n2)CCC1] | 162 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)-cyclobutyl)methyl) pyrimidine-2-carboxamide | $^1$H NMR (400 MHz, d-6-DMSO): 1.30 (9H, s), 1.53 (9H, s), 1.61-1.77 (4H, m), 1.96-2.10 (6H, m), 2.19 (6H, s), 3.50 (2H, d, J = 6.0 Hz), 4.97-5.03 (1H, m), 5.64 (1H, t, J = 4.0 Hz), 7.29-7.45 (5H, m), 7.74 (1H, dd, J = 9.9, 0.5 Hz), 7.77 (1H, br s), 8.15 (1H, d, J = 1.2 Hz), 8.20 (1H, br s), 8.45 (1H, t, J = 5.9 Hz), 9.91 (1H, s). | (Method 2): Rt 3.40 min, m/z 668 [MH$^+$]. | 1i | 1-(aminomethyl)-N,N-dimethyl-cyclo-butanamine CAS: 176445-78-6 |

TABLE 1-continued

| Structure | Ex. | Chemical Name | NMR | LCMS | Interm. | Reagent |
|---|---|---|---|---|---|---|
| 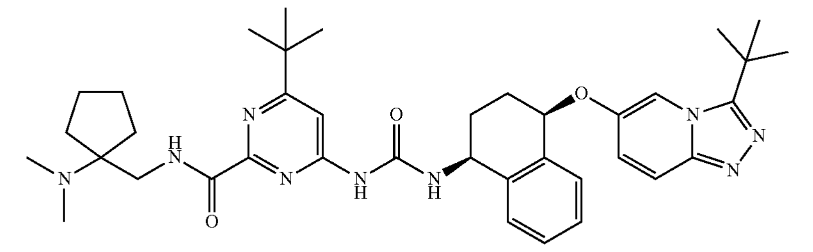 | 163 | 4-(tert-butyl)-6-(3-((1S,4R)-4-((3-(tert-butyl)-[1,2,4]-triazolo[4,3-a]pyridin-6-yl)oxy)-1,2,3,4-tetrahydronaphthalen-1-yl)ureido)-N-((1-(dimethylamino)-cyclopentyl)methyl)-pyrimidine-2-carboxamide | $^1$H NMR (400 MHz, d-6-DMSO): 1.30 (9H, s), 1.37-1.43 (2H, m), 1.53 (9H, s), 1.55-1.60 (4H, m), 1.65-1.72 (2H, m), 1.94-2.22 (4H, m), 2.23 (6H, s), 3.35 (2H, d, J = 5.6 Hz, partially obscured by water peak), 4.96-5.03 (1H, m), 5.63 (1H, t, J = 4.0 Hz), 7.28-7.45 (5H, m), 7.74 (1H, d, J = 9.8 Hz), 7.78 (1H, br s), 8.15 (1H, d, J = 1.3 Hz), 8.19 (1H, br s), 8.47 (1H, t, J = 5.3 Hz), 9.90 (1H, s). | (Method 2): Rt 3.45 min, m/z 662 [MH$^+$]. | 1i | N-[1-(aminomethyl)-cyclopentyl]-N,N-dimethylamine CAS: 164642-21-1 |
| 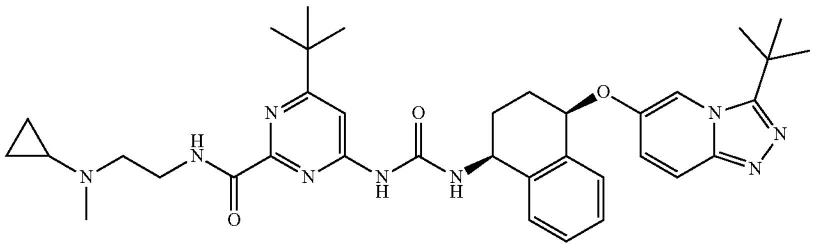 [SMILES: CN(CCNC(=O)c1nc(NC(=O)N[C@H]2CC[C@@H](Oc3ccc4nnc(C(C)(C)C)n4c3)c3ccccc32)cc(C(C)(C)C)n1)C1CC1] | 164 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(cyclopropyl(methyl)-amino)ethyl)pyrimidine-2-carboxamide | $^1$H NMR (400 MHz, d-6-DMSO): 0.28-0.32 (2H, m), 0.43-0.47 (2H, m), 1.30 (9H, s), 1.53 (9H, s), 1.71-1.76 (1H, m), 1.92-2.12 (3H, m), 2.20-2.27 (1H, m), 2.30 (3H, s), 2.67 (2H, t, J = 6.4 Hz), 3.33-3.38 (2H, m, partially obscured by water peak), 4.97-5.03 (1H, m), 5.63 (1H, t, J = 3.8 Hz), 7.28-7.45 (5H, m), 7.71 (1H, br s), 7.74 (1H, d, J = 9.8 Hz), 8.15 (1H, d, J = 1.2 Hz), 8.30 (1H, br s), 8.48 (1H, t, J = 5.5 Hz), 9.94 (1H, s). | (Method 2): Rt 3.36 min, m/z 654 [MH$^+$]. | 1i | N-(2-aminoethyl)-N-methylcyclo propanamine CAS: 126105-24-6 |
| 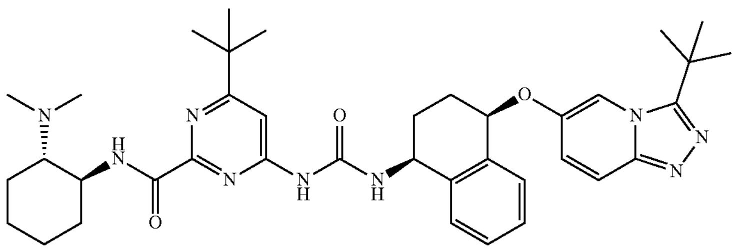 [SMILES: CN(C)[C@H]1CCCC[C@@H]1NC(=O)c1nc(NC(=O)N[C@H]2CC[C@@H](Oc3ccc4nnc(C(C)(C)C)n4c3)c3ccccc32)cc(C(C)(C)C)n1] | 165 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1S,2S)-2-(dimethylamino)-cyclohexyl)pyrimidine-2-carboxamide | $^1$H NMR (400 MHz, d-6-DMSO): 1.18-1.25 (4H, m), 1.31 (9H, s), 1.53 (9H, s), 1.61-1.66 (1H, m), 1.73-1.82 (2H, m), 1.94-2.13 (4H, m), 2.19-2.25 (7H, m), 2.44-2.49 (1H, m, partially obscured by the solvent peak), 3.50-3.58 (1H, m), 4.96-5.02 (1H, m), 5.63 (1H, t, J = 4.1 Hz), 7.28-7.45 (5H, m), 7.72-7.75 (2H, m), 8.15 (1H, d, J = 1.4 Hz), 8.22 (1H, br s), 8.53 (1H, d, J = 6.0 Hz), 9.90 (1H, s). | (Method 2): Rt 3.46 min, m/z 682 [MH$^+$]. | 1i | (1S,2S)-N1,N1-dimethyl-cyclohexane-1,2-diamine CAS: 894493-95-9 |

TABLE 1-continued

| Structure | Ex. | Chemical Name | NMR | LCMS | Interm. | Reagent |
|---|---|---|---|---|---|---|
| 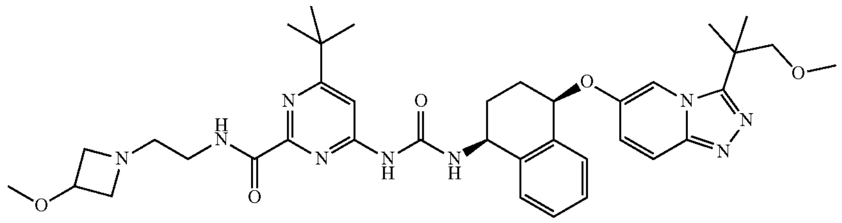 | 166 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2- | $^1$H NMR (400 MHz, d-6-DMSO): 1.31 (9H, s), 1.52 (6H, s), 1.91-2.13 (3H, m), 2.19-2.26 (1H, m), 2.54 (2H, t, J = 6.5 Hz), 2.78-2.83 (2H, m), 3.11 (3H, s), 3.21-3.26 (5H, m), 3.50-3.53 (2H, m), 3.66 (2H, s), 3.92 (1H, quintet, J = 5.8), 4.97-5.02 (1H, m), 5.54 (1H, t, J = 4.0 Hz), 7.28-7.45 (5H, m), 7.71-7.74 (2H, m), 8.25 (1H, br 8.55 (1H, t, J = 6.0 Hz), 9.90 11H, s). | (Method 3): Rt 3.40 min, m/z 700 [MH$^+$]. | 7e | 2-(3-methoxy-azetidin-1-yl)ethan-1-amine CAS: 911300-65-7 |
| 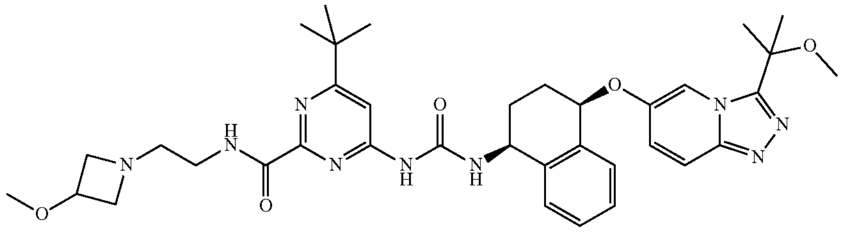 | 167 | 4-(tert-butyl)-N-(2-(3-methoxyazetidin-1-yl)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.31 (9H, s), 1.69 (6H, s), 1.91-2.15 (3H, m), 2.23-2.33 (1H, m), 2.78-2.82 (2H, m), 2.98 (3H, s), 3.11 (3H, s), 3.23 (2H, q, J = 6.0 Hz), 3.50-3.53 (2H, m), 3.92 (1H, quintet, J = 5.7 Hz), 4.97-5.02 (1H, m), 5.49 (1H, t, J = 4.0 Hz), 7.28-7.42 (5H, m), 7.73 (1H, s), 7.80 (1H, dd, J = 9.9, 0.6 Hz), 8.14 (1H, d, J = 1.5 Hz), 8.25 (1H, br (1H, s), plus two protons obscured by solvent peak. | (Method 3): Rt 3.37 min, m/z 686 [MH$^+$]. | 12e | 2-(3-methoxy-azetidin-1-yl)ethan-1-amine CAS: 911300-65-7 |
| 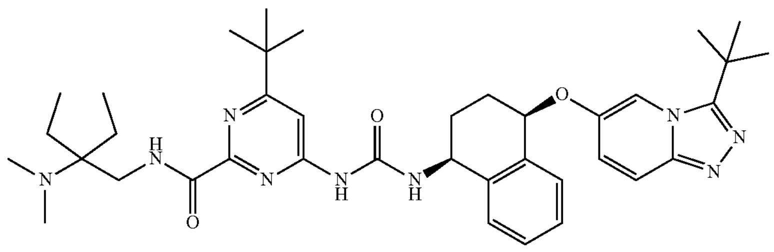 [SMILES: CCC(CC)(CNC(=O)c1nc(NC(=O)N[C@H]2CC[C@@H](Oc3ccc4nnc(C(C)(C)C)n4c3)c3ccccc32)cc(C(C)(C)C)n1)N(C)C] | 168 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-ethylbutyl)pyrimidine-2-carboxamide | $^1$H NMR (400 MHz, d-6-DMSO): 0.83 (6H, t, J = 7.4 Hz), 1.30 (9H, s), 1.39-1.57 (13H, m), 1.92-2.14 (3H, m), 2.20-2.27 (1H, m), 2.31 (6H, s), 3.27 (2H, d, J = 5.2 Hz), 4.97-5.03 (1H, m), 5.63 (1H, t, J = 3.7 Hz), 7.29-7.45 (5H, m), 7.73-7.75 (2H, m), 8.14 (1H, d, J = 1.2 Hz), 8.23 (1H, br s), 8.57 (1H, t, J = 5.0 Hz), 9.94 (1H, s). | (Method 3): Rt 3.61 min, m/z 684 [MH$^+$]. | 1i | N-[1-(aminomethyl)-1-ethylpropyl]-N,N-dimethylamine CAS: 891647-25-9 |

TABLE 1-continued

| Structure | Ex. | Chemical Name | NMR | LCMS | Interm. | Reagent |
|---|---|---|---|---|---|---|
| 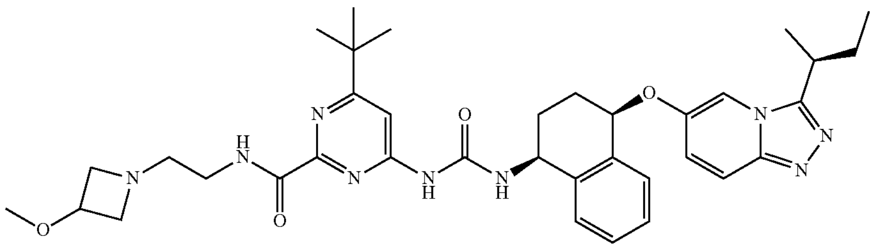 [SMILES: CC[C@H](C)c1nnc2ccc(O[C@@H]3CC[C@H](NC(=O)Nc4cc(C(C)(C)C)nc(C(=O)NCCN5CC(OC)C5)n4)c4ccccc43)cn12] | 169 | 4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide | $^1$H NMR (400 MHz, d-6-DMSO): 0.87 (3H, t, J = 7.4 Hz), 1.32 (9H, s), 1.34 (3H, d, J = 6.9 Hz), 1.75 (1H, heptet, J = 7.0 Hz), 1.85-2.15 (4H, m), 2.20-2.28 (1H, m), 2.54 (2H, t, J = 6.4 Hz, partially obscured by the solvent peak), 2.79-2.82 (2H, m), 3.12 (3H, s), 3.23 (2H, q, J = 6.2 Hz), 3.44 (1H, q, J = 6.8 Hz), 3.50-3.53 (2H, m), 3.92 (1H, quintet, J = 5.8 Hz), 4.98-5.04 (1H, m), 5.57 (1H, t, J = 4.0 Hz), 7.25-7.44 (5H, m), 7.70 (1H, d, J = 9.9 Hz), 7.72 (1H, br s), 8.25 (1H, d, J = 1.3 Hz), 8.29 (1H, br s), 8.56 (1H, t, J = 6.0 Hz), 9.89 (1H, s). | (Method 3): Rt 3.40 min, m/z 670 [MH$^+$]. | 8e | 2-(3-methoxy-azetidin-1-yl)ethan-1-amine CAS: 911300-65-7 |
| 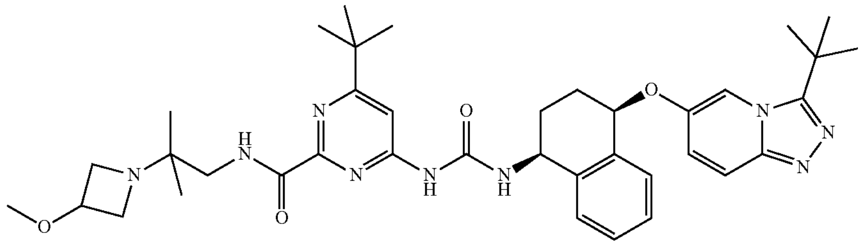 [SMILES: COC1CN(C(C)(C)CNC(=O)c2nc(NC(=O)N[C@H]3CC[C@@H](Oc4ccc5nnc(C(C)(C)C)n5c4)c4ccccc43)cc(C(C)(C)C)n2)C1] | 170 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide | $^1$H NMR (400 MHz, d-6-DMSO): 0.89 (6H, s), 1.32 (9H, s), 1.52 (9H, s), 1.91-2.14 (3H, m), 2.20-2.26 (1H, m), 2.98-3.02 (2H, m), 3.08 (2H, d, J = 5.8 Hz), 3.14 (3H, s), 3.91 (1H, quintet, J = 5.6 Hz), 4.96-5.02 (1H, m), 5.63 (1H, t, J = 4.0 Hz), 7.28-7.44 (5H, m), 7.73-7.76 (2H, m), 8.14 (1H, d, J = 1.2 Hz), 8.20 (1H, br s), 8.47 (1H, t, J = 5.7 Hz), 9.92 (1H, br s), plus two protons obscured by solvent peak. | (Method 3): Rt 3.45 min, m/z 698 [MH$^+$]. | 1i | 2-(3-methoxy-azetidin-1-yl)-2-methylpropan-1-amine CAS: 1849260-84-9 |
| 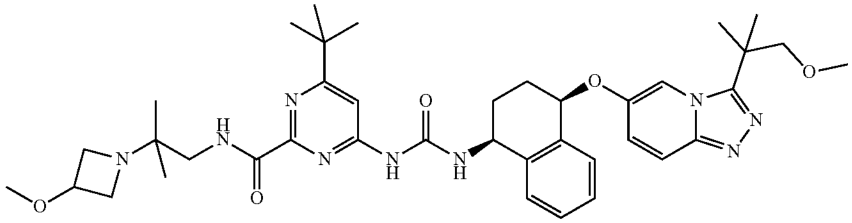 | 171 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide | $^1$H NMR (400 MHz, d-6-DMSO): 0.89 (6H, s), 1.32 (9H, s), 1.52 (6H, s), 1.91-2.14 (3H, m), 2.19-2.33 (1H, m), 2.98-3.02 (2H, m), 3.09 (2H, d, J = 6.0 Hz), 3.14 (3H, s), 3.23 (3H, s), 3.66 (2H, s), 3.91 (1H, quintet, J = 5.7 Hz), 4.97-5.02 (1H, m), 5.54 (1H, t, J = 4.0 Hz), 7.29-7.44 (5H, m), 7.73 (1H, d, J = 9.8 Hz), 7.77 (1H, s), 8.18 (1H, br s), 8.27 (1H, d, J = 1.4 Hz), 8.47 (1H, t, J = 5.7 Hz), 9.91 (1H, s), plus two protons obscured by solvent peak. | (Method 3): Rt 3.46 min, m/z 728 [MH$^+$]. | 7e | 2-(3-methoxy-azetidin-1-yl)-2-methylpropan-1-amine CAS: 1849260-84-9 |

TABLE 1-continued

| Structure | Ex. | Chemical Name | NMR | LCMS | Interm. | Reagent |
|---|---|---|---|---|---|---|
| 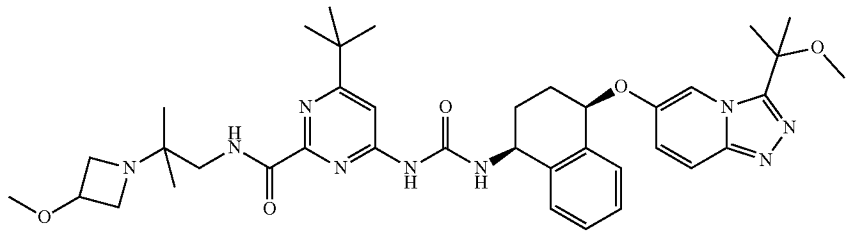 | 172 | 4-(tert-butyl)-N-(2-(3-methoxyazetidin-1-yl)-2-rnethylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz. d-6-DMSO): 0.89 (6H, s), 1.32 (9H, s), 1.69 (6H, s), 1 89-2.15 (3H, m), 2.22-2.33 (1H, m), 2.98-3.02 (5H, m), 3.09 (2H, d, J = 6.0 Hz), 3.14 (3H, s), 3.91 (1H, quintet, J = 5.7 Hz), 4.97-5.02 (1H, m), 5.49 (1H, t, J = 4.0 Hz), 7.28-7.42 (5H, m), 7.77 (1H, s), 7.80 (1H, dd, J = 9.8, 0.6 Hz), 8.14 (1H, d, J = 1.4 Hz), J = 5.7 Hz), 9.89 (1H, s), plus two protons obscured by solvent peak. | (Method 3): Rt 3.44 min, m/z 714 [MH$^+$]. | 12e | 2-(3-methoxyazetidin-1-yl)-2-methylpropan-1-amine CAS: 1849260-84-9 |
| 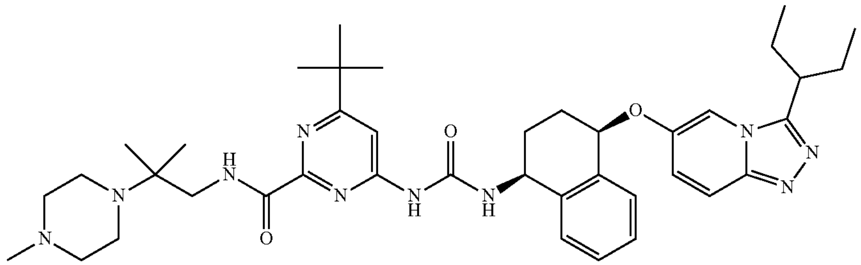 [SMILES: CCC(CC)c1nnc2ccc(O[C@@H]3CC[C@H](NC(=O)Nc4cc(C(C)(C)C)nc(C(=O)NCC(C)(C)N5CCN(C)CC5)n4)c4ccccc43)cn12] 1.0 eq HCOOH | 173 | 4-(tert-butyl)-N-(2-methyl-2-(4-methylpiperazin-1-yl)propyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt | $^1$H NMR (400 MHz, d6DMSO): 0.74-0.83 (6H, m), 1.00 (6H, s), 1.36 (9H, s), 1.75-2.27 (11H, m), 2.39 (4H, br s),3.23 (2H, d, J = 4.8 Hz), 3.28-3.38 (4H, m, partially obscured by the water peak), 5.02 (1H, q, J = 8.7 Hz), 5.56 (1H, t, J = 4.0 Hz), 7.25-7.43 (5H, m), 7.69-7.72 (2H, m), 8.17 (1H, s), 8.26 (1H, s), 8.36 (1H, br s), 8.65 (1H, t, J = 4.7 Hz), 10.01 (1H, s), plus one proton obscured by the solvent peak. | (Method 3): Rt 3.51 min, m/z 725.3 [M + H$^+$], sample assessed as ca. 97.8%. | 5e | 2-methyl-2-(4-methyl-1-piperazin-yl) CAS: 21404-92-2 |
| 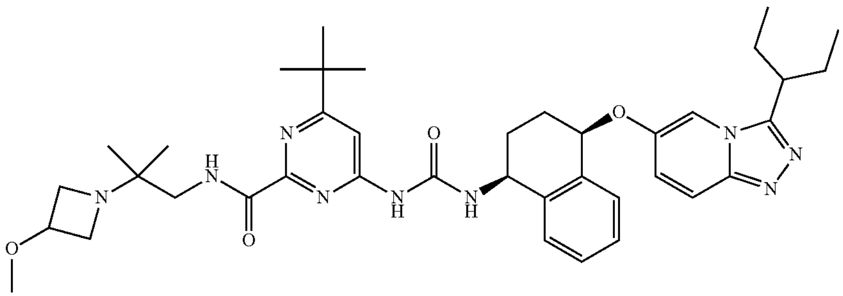 [SMILES: CCC(CC)c1nnc2ccc(O[C@@H]3CC[C@H](NC(=O)Nc4cc(C(C)(C)C)nc(C(=O)NCC(C)(C)N5CC(OC)C5)n4)c4ccccc43)cn12] 1.2 eq HCOOH | 174 | 4-(tert-butyl)-N-(2-(3-methoxyazetidin-1-yl)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt | $^1$H NMR (400 MHz, d6DMSO): 0.77 (3H, t, J = 7.4 Hz), 0.80 (3H, t, J = 7.4 Hz), 0.90 (6H, s), 1.32 (9H, s), 1.76-2.25 (8H, m), 3 01 (2H, t, J = 5.8 Hz), 3.10 (2H, d, J = 5.8 Hz), 3.14 (3H, s), 3.92 (1H, t, J = 5.7 Hz), 5.01 (1H, q, J = 8.9 Hz), 5.56 (1H, t, J = 4.0 Hz), 7.25 (1H, dd, J = 2.0, 9.4 Hz), 7.30 (1H, t, J = 7.3 Hz), 7.37 (1H, dt, J = 1.3, 7.2 Hz), 7.39-7.45 (2H, m), 7.67 (1H, d, J = 9.9 Hz), 7.77 (1H, s), 8.17 (1.2H, s), 8.21 (1H, br s), 8.27 (1H, s), 8.48 (1H, t, J = 5.6 Hz), 9.91 (1H, s), plus three protons obscured by the solvent peak. | (Method 3): Rt 3.56 min, m/z 712.3 [M + H$^+$], sample assessed as ca. >97.9%. | 5e | 2-(3-methoxy-azetidin-1-yl)-2-methylpropan-1-amine CAS: 1849260-84-9 |

TABLE 1-continued

| Structure | Ex. | Chemical Name | NMR | LCMS | Interm. | Reagent |
|---|---|---|---|---|---|---|
| 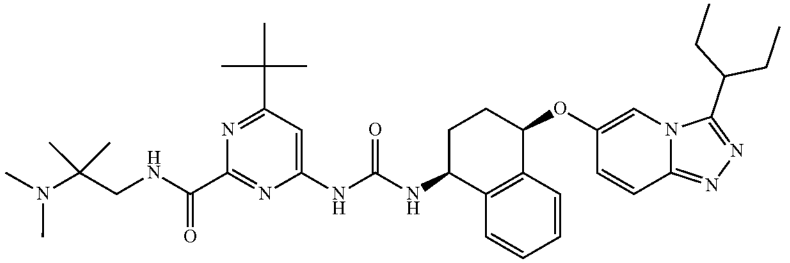 [SMILES: CCC(CC)c1nnc2ccc(O[C@@H]3CC[C@H](NC(=O)Nc4cc(C(C)(C)C)nc(C(=O)NCC(C)(C)N(C)C)n4)c4ccccc43)cn12] 1.0 eq HCOOH | 175 | 4-(tert-butyl)-N-(2-(dimethylamino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt | $^1$H NMR (400 MHz, d6DMSO): 0.75-0.82 (6H, m), 1.00 (6H, s), 1.31 (9H, s), 1.72-1.92 (4H, m), 1.92-2.01 (1H, m), 2.01-2.17 (3H, m), 2.22 (6H, s), 3.25 (2H, d, J = 5.3 Hz), 3.34 (1H, t, J = 7.8 Hz), 4.98-5.04 (1H, m), 5.57 (1H, t, J = 3.94 Hz), 7.26 (1H, dd, J = 2.03, 9.85 Hz), 7.30 (1H, t, J = 7.35 Hz), 7.37 (1H, dt, J = 1.34, 7.23 Hz), 7.39-7.45 (2H, m), 7.71 (1H, d, J = 9.81 Hz), 7.78 (1H, s), 8.19 (1H, s), 8.27 (1H, s), 8.33 (1H, br s), 8.54 (1H, t, J = 5.23 Hz), 9.91 (1H, s). | (Method 3): Rt 3.51 min, m/z 670.3 [M + H$^+$], sample assessed as ca. >98.0%. | 5e | (2-Amino-1,1-dimethylethyl)-dimethylamine CAS: 76936-44-2 |
| 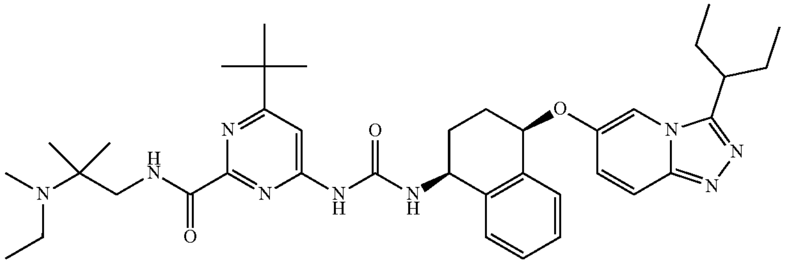 [SMILES: CCC(CC)c1nnc2ccc(O[C@@H]3CC[C@H](NC(=O)Nc4cc(C(C)(C)C)nc(C(=O)NCC(C)(C)N(C)CC)n4)c4ccccc43)cn12] 1.0 eq HCOOH | 176 | 4-(tert-butyl)-N-(2-(ethyl(methyl)amino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d6DMSO): 0.78 (6H, q, J = 7.36, 11.09 Hz), 1.00 (6H, s), 1.04 (3H, t, J = 6.96 Hz), 1.31 (9H, s), 1.71-1.92 (4H, m), 1.92-2.02 (1H, m), 2.02-2.28 (3H, m), 2.18 (3H, s), 2.41 (2H, q, J = 6.94 Hz), 3.23 (2H, d, J = 4.97 Hz), 3.28-3.39 (1H, m, obscured), 5.01 (1H, q, J = 8.48, 5.48 Hz), 5.56 (1H, t, J = 3.98 Hz), 7.27 (1H, dd, J = 1.93, 9.83 Hz), 7.31 (1H, d, J = 7.33 Hz), 7.37 (1H, dt, J = 1.30, 7.24), 7.39-7.45 (2H, m), 7.70 (1H, d, J = 9.85 Hz), 7.73 (1H, s), 8.17 (1H, s), 8.26 (1H, s), 8.31 (1H, br s), 8.63 (1H, t, J = 4.76 Hz), 9.96 (1H, s). | (Method 3): Rt 3.55 min, m/z 684.3 [M + H$^+$], sample assessed as ca. >97.8%. | 5e | (2-amino-1,1,dimethyl-ethyl)methyl-amine CAS: 1018289-07-0 |
| 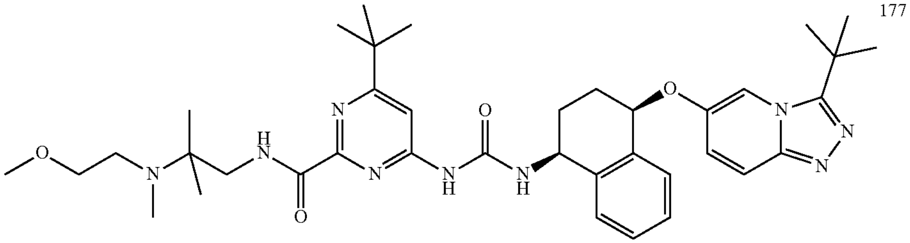 | 177 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)-amino)-2-methylpropyl)pyrimidine-2-carboxamide | $^1$H NMR (400 MHz, d-6-DMSO): 0.99 (6H, s), 1.32 (9H, s), 1.52 (9H, s), 1.95-2.12 (3H, m), 2.21 (3H, s), 2.23-2.25 (1H, m), 3.19 (3H, s), 3.22 (2H, d, J = 5.2 Hz), 3.39 (2H, t, J = 6.2), 4.96-5.02 (1H, m), 5.63 (1H, t, J = 4.0 Hz), 7.28-7.44 (5H, m), 7.73 (1H, br s), 7.76 (1H, br s), 8.14 (1H, d, J = 1.2 Hz), 8.29 (1H, br s), 8.54 (1H, t, J = 5.0 Hz), 9.94 (1H, br s), plus two protons obscured by solvent peak. | (Method 3): Rt 3.47 min, m/z 700 [MH$^+$]. | 1i | (1-amino-2-methylpropan-2-yl)(2-methoxyethyl) methylamine CAS: 1247781-44-7 |

TABLE 1-continued

| Structure | Ex. | Chemical Name | NMR | LCMS | Interm. | Reagent |
|---|---|---|---|---|---|---|
| 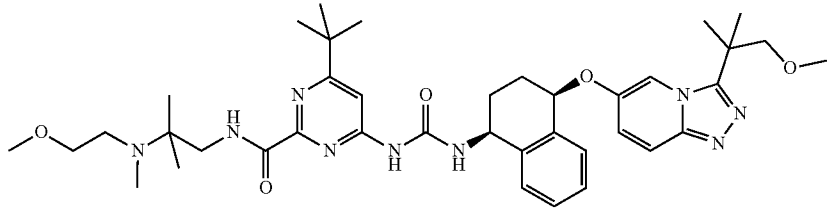 | 178 | 4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-((2-methoxyethyl)(methyl)-amino)-2-methylpropyl)pyrimidine-2-carboxamide | $^1$H NMR (400 MHz, d-6-DMSO): 0.99 (6H, s), 1.32 (9H, s), 1.52 (6H, s), 1.91-2.14 (3H, m), 2.16-2.26 (4H, m), 3.19 (3H, s), 3.21-3.23 (5H, m), 3.39 (2H, t, J = 6.2 Hz), 3.66 (2H, s), 4.97-5.03 (1H, m), 5.54 (1H, t, J = 4.0 Hz), 7.29-7.45 (5H, m), 7.72-7.74 (2H, m), 8.25 (1H, br s), 8.27 (1H, d, J = 1.3 Hz), 8.54 (1H, t, J = 5.0 Hz), 9.92 (1H, s), plus two protons obscured by solvent peak. | (Method 3): Rt 3.49 min, m/z 730 [MH$^+$]. | 7e | (1-amino-2-methylpropan-2-yl)(2-methoxyethyl) methylamine CAS: 1247781-44-7 |
| 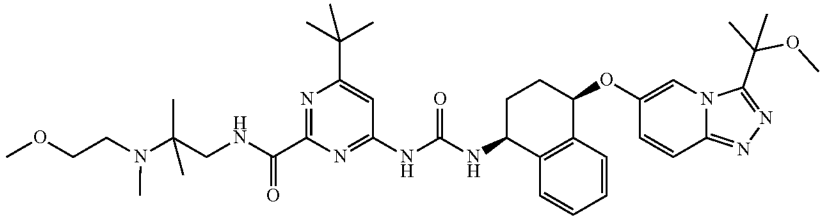 | 179 | 4-(tert-butyl)-N-(2-((2-methoxyethyl)(methyl) amino)-2-methylmpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.99 (6H, s), 1.32 (9H, s), 1.69 (6H, s), 1.90-2.16 (3H, m), 2.21 (3H, s), 2.23-2.33 (1H, m), 2.98 (3H, s), 3.19 (3H, s), 3.23 (2H, d, J = 5.2 Hz), 3.39 (2H, t, J = 6.2 Hz), 4.97-5.03 (1H, m), 5.49 (1H, t, J = 4.0 Hz), 7.28-7.42 (5H, m), 7.74 (1H, s), 7.80 (1H, dd, J = 9.9, 0.6 Hz), 8.14 (1H, d, J = 1.4 Hz), 8.29 (1H, br s), 8.53 (1H, t, J = 5.0 Hz), 9.89 (1H, s), plus two protons obscured by solvent peak. | (Method 3): Rt 3.46 min, m/z 716 [MH$^+$]. | 12e | (1-amino-2-methylpropan-2-yl)(2-methoxyethyl) methylamine CAS: 1247781-44-7 |
| 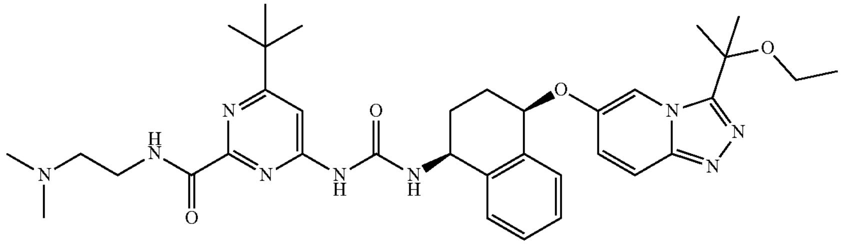 [SMILES: CCOC(C)(C)c1nnc2ccc(O[C@@H]3CC[C@H](NC(=O)Nc4cc(C(C)(C)C)nc(C(=O)NCCN(C)C)n4)c4ccccc43)cn12] 1.0 eq HCOOH | 180 | 4-(tert-Butyl)-N-(2-(dimethylamino)ethyl)-6-(3-((1S,4R)-4-((3-(2-ethoxypropan-2-yl)-[1,2,4]triazolo[4,3-a]pyridin-6-yl)oxy)-1,2,3,4-tetrahydronaphthalen-1-yl)ureido)pyrimidine-2-carboxamide formate salt | $^1$H NMR (400 MHz, d-6-DMSO): 1.07 (3H, t, J = 6.9 Hz), 1.31 (9H, s), 1.71 (3H, s), 1.71 (3H, s), 1.90-2.23 (10H, m), 2.43 (2H, t, J = 6.6 Hz), 3.06-3.20 (2H, m, partially obscured by water peak), 3.37 (2H, q, J = 6.1 Hz, partially obscured by water peak), 4.97-5.03 (1H, m), 5.47 (1H, t, J = 3.9 Hz), 7.29-7.43 (5H, m), 7.75 (1H, s), 7.80 (1H, d, J = 9.9 Hz), 8.18 (1H, s), 8.20 (1H, d, J = 1.5 Hz), 8.22 (1H, br s), 8.59 (1H, t, J = 5.8 Hz), 9.87 (1H, s). | (Method 3): Rt 3.41 min, m/z 658 [MH$^+$]. | HH | N,N-dimethylamine ethandiamine CAS: 108-00-9 |

TABLE 1-continued

| Structure | Ex. | Chemical Name | NMR | LCMS | Interm. | Reagent |
|---|---|---|---|---|---|---|
| 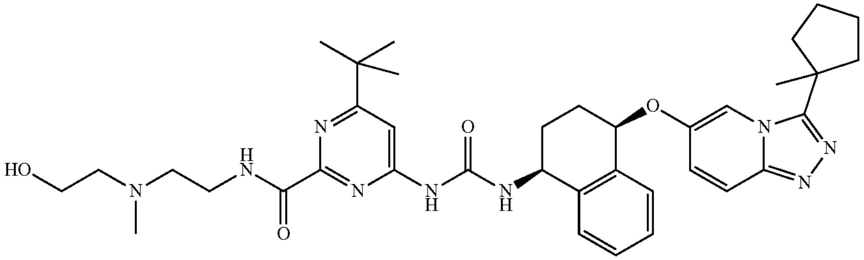 [SMILES: CN(CCO)CCNC(=O)c1nc(NC(=O)N[C@H]2CC[C@@H](Oc3ccc4nnc(C5(C)CCCC5)n4c3)c3ccccc32)cc(C(C)(C)C)n1] | 181 | 4-(tert-butyl)-N-(2-((2-hydroxyethyl)(methyl)amino)ethyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.31 (9H, s), 1.44 (3H, s), 1.60-1.80 (4H, m), 1.91-2.13 (5H, m), 2.22-2.28 (4H, m), 2.33-2.42 (2H, m), 2.46 (2H, t, J = 6.4 Hz), 2.50-2.54 (2H, m, partially obscured by the solvent peak), 3.33-3.37 (2H, m, partially obscured by water peak), 3.46-3.49 (2H, m), 4.36 (1H, br s), 4.97-5.03 (1H, m), 5.60 (1H, t, J = 3.6 Hz), 7.28-7.44 (5H, m), 7.72-7.75 (2H, m), 7.98 (1H, d, J = 1.2 Hz), 8.29 (1H, br s), 8.61 (1H, t, J = 5.6 Hz), 9.93 (1H, s). | (Method 3): Rt 3.41 min, m/z 684 [MH$^+$]. | JJ | 2-[(2-aminoethyl)-(methyl)amino] ethanol CAS: 5753-50-4 |
| 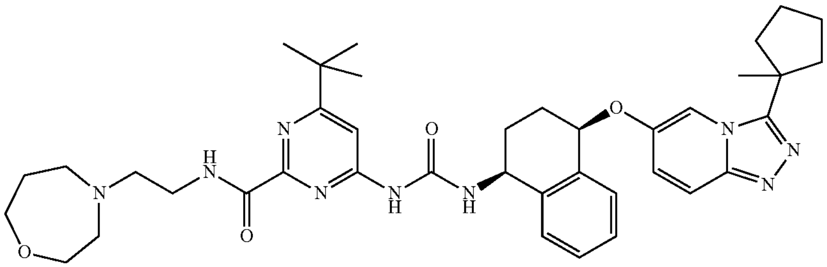 [SMILES: CC(C)(C)c1cc(NC(=O)N[C@H]2CC[C@@H](Oc3ccc4nnc(C5(C)CCCC5)n4c3)c3ccccc32)nc(C(=O)NCCN2CCCOCC2)n1] | 182 | N-(2-(1,4-oxazepan-4-yl)ethyl)-4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 1.32 (9H, s), 1.43 (3H, s), 1.58-1.82 (6H, m), 1.90-2.14 (5H, m), 2.22-2.44 (3H, m), 2.63-2.70 (6H, m), 3.35 (2H, q, J = 5.9 Hz), 3.59-3.61 (2H, m), 3.67 (2H, t, J = 6.0 Hz), 4.97-5.03 (1H, m), 5.60 (1H, t, J = 3.8 Hz), 7.28-7.43 (5H, m), 7.70 (1H, br s), 7.74 (1H, d, J = 9.9 Hz), 7.97 (1H, d, J = 1.3 Hz), 8.34 (1H, br s), 8.65 (1H, t, J = 5.5 Hz), 9.97 (1H, s). | (Method 3): Rt 3.47 min, m/z 710 [MH$^+$]. | JJ | 2-(1,4-oxazepan-4-yl)ethan-1-amine CAS: 878155-50-1 |
| 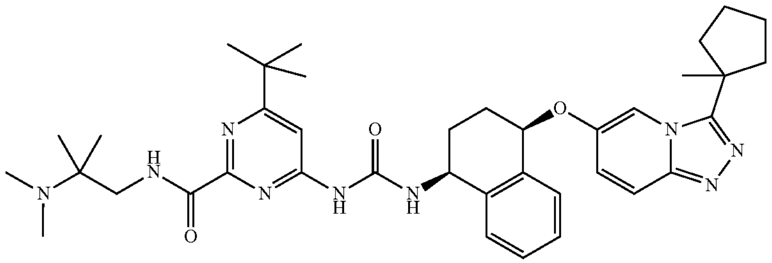 [SMILES: CN(C)C(C)(C)CNC(=O)c1nc(NC(=O)N[C@H]2CC[C@@H](Oc3ccc4nnc(C5(C)CCCC5)n4c3)c3ccccc32)cc(C(C)(C)C)n1] | 183 | 4-(tert-butyl)-N-(2-(dimethylamino)-2-methylpropyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide | $^1$H NMR (400 MHz, d-6-DMSO): 0.98 (6H, s), 1.31 (9H, s), 1.43 (3H, s), 1.61-1.80 (4H, m), 1.90-2.14 (5H, m), 2.19-2.27 (7H, m), 2.32-2.44 (2H, m), 3.23 (2H, d, J = 5.3 Hz), 4.97-5.03 (1H, m), 5.60 (1H, t, J = 3.9 Hz), 7.28-7.44 (5H, m), 7.74 (1H, dd, J = 9.8, 0.4 Hz), 7.77 (1H, s), 7.97 (1H, d, J = 1.2 Hz), 8.22 (1H, br s), 8.51 (1H, t, J = 5.2 Hz), 9.92 (1H, s). | (Method 3): Rt 3.52 min, m/z 682 [MH$^+$]. | JJ | (2-Amino-1,1-dimethylethyl) dimethylamine CAS: 76936-44-2 |

TABLE 1-continued

| Structure | Ex. | Chemical Name | NMR | LCMS | Interm. | Reagent |
|---|---|---|---|---|---|---|
| 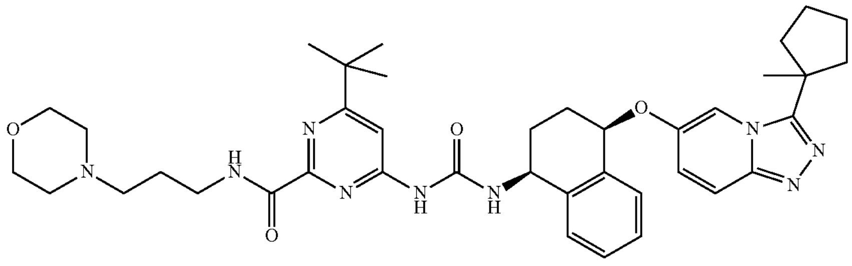 1.3 eq HCOOH | 184 | 4-(tert-Butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(3-morpholinopropyl)-pyrimidine-2-carboxamide formate salt | $^1$H NMR (400 MHz, d-6-DMSO): 1.32 (9H, s), 1.44 (3H, s), 1.63-1.80 (6H, m), 1.90-2.13 (5H, m), 2.22-2.44 (9H, m), 3.30 (2H, q, J = 6.8 Hz), 3.54 (4H, t, J = 4.6 Hz), 4.97-5.03 (1H, m), 5.60 (1H, t, J = 3.9 Hz), 7.28-7.43 (5H, m), 7.69 (1H, s), 7.74 (1H, dd, J = 9.8, 0.4 Hz), 7.98 (1H, d, J = 1.2 Hz), 8.17 (1.3H, s), 8.33 (1H, br s), 8.61 (1H, t, J = 6.1 Hz), 9.90 (1H, s). | (Method 3): Rt 3.51 min, m/z 710 [MH$^+$]. | JJ | 3-morpholino-propan-1-amine CAS: 123-00-2 |
| 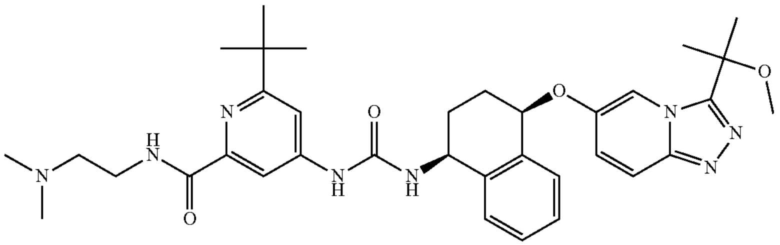 | 185 | 6-(tert-butyl)-N-(2-(dimethylamino)ethyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide | $^1$H NMR (400 MHz, DMSO): 1.32 (9H, s), 1.69 (6H, s), 1.88-2.17 (4H, m), 2.20 (6H, s), 2.42 (2H, t, J = 6.5 Hz), 2.98 (3H, s), 3.39 (2H, q, J = 6.4 Hz), 4.94 (1H, q, J = 8.8, 5.6 Hz), 5.49 (1H, t, J = 3.8 Hz), 6.97 (1H, d, J = 8.7 Hz), 7.30 (1H, dd, J = 1.6, 7.1 Hz), 7.35-7.44 (4H, m), 7.68 (1H, d, J = 1.9 Hz), 7.82 (1H, d, J = 9.9 Hz), 7.90 (1H, d, J = 1.9 Hz), 8.12 (1H, s), 8.58 (1H, t, J = 5.73 Hz), 9.08 (1H, s). | (Method 2): Rt = 3.46 min, m/z 643.6 [M + H$^+$], sample assessed as ca. 99.3%. | AM | N,N-dimethyl-ethylene diamine CAS: 108-00-9 |
| 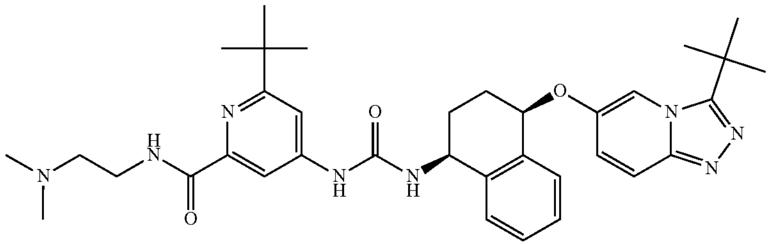 [SMILES: CN(C)CCNC(=O)c1cc(NC(=O)N[C@H]2CC[C@@H](Oc3ccc4nnc(C(C)(C)C)n4c3)c3ccccc32)cc(C(C)(C)C)n1] | 186 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)-picolinamide | $^1$H NMR (400 MHz, DMSO): 1.33 (9H, s), 1.53 (9H, s), 1.90-2.20 (4H, m), 2.21 (6H, s), 2.42 (2H, t, J = 6.5 Hz), 3.39 (2H, q, J - 6.4 Hz), 4.93 (1H, q, J = 8.2 Hz), 5.63 (1H, t, J = 3.8 Hz), 6.96 (1H, d, J = 8.5 Hz), 7.23-7.46 (5H, m), 7.68 (1H, d, J = 1.9 Hz), 7.75 (1H, d, J = 9.9 Hz), 7.90 (1H, d, J = 1.9 Hz), 8.14 (1H, s), 8.58 (1H, t, J = 5.7 Hz), 9.15 (1H, s). | (Method 2): Rt = 3.45 min, m/z 627.5 [M + H$^+$], sample assessed as ca. 95.9%. | 9e | N,N-dimethyl-ethylene diamine CAS: 108-00-9 |

TABLE 1-continued

| Structure | Ex. | Chemical Name | NMR | LCMS | Interm. | Reagent |
|---|---|---|---|---|---|---|
| 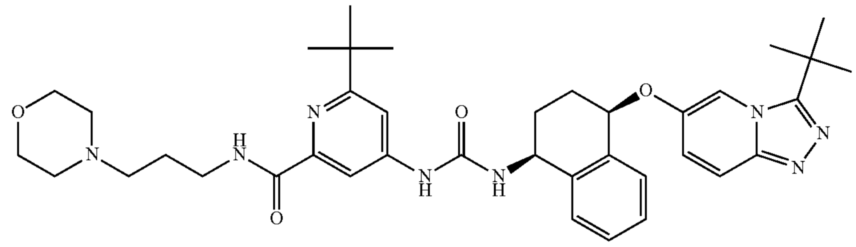 [SMILES: CC(C)(C)c1cc(NC(=O)N[C@H]2CC[C@@H](Oc3ccc4nnc(C(C)(C)C)n4c3)c3ccccc32)cc(C(=O)NCCCN2CCOCC2)n1] | 187 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)-picolinamide | $^1$H NMR (400 MHz, DMSO): 1.34 (9H, s), 1.53 (9H, s), 1.70 (2H, t, J = 7.0 Hz), 1.91-2.24 (4H, m), 2.28-2.40 (6H, m), 3.32-3.40 (2H, m, partially obscured by the solvent peak), 3.57 (4H, t, J = 4.6 Hz), 4.93 (1H, q, J = 8.2 Hz), 5.63 (1H, t, J = 3.9 Hz), 6.93 (1H, d, J = 8.6 Hz), 7.23-7.46 (5H, m), 7.67 (1H, d, J = 1.9 Hz), 7.75 (1H, d, J = 9.8 Hz), 7.90 (1H, d, J = 1.9 Hz), 8.14 (1H, s), 8.51 (1H, t, J = 6.2 Hz), 9.11 (1H, s). | (Method 3): Rt = 3.40 min, m/z 683.5 [M + H$^+$], sample assessed as ca. 98.5%. | 9e | 3-morpholino-propan-1-amine CAS: 123-00-2 |
| 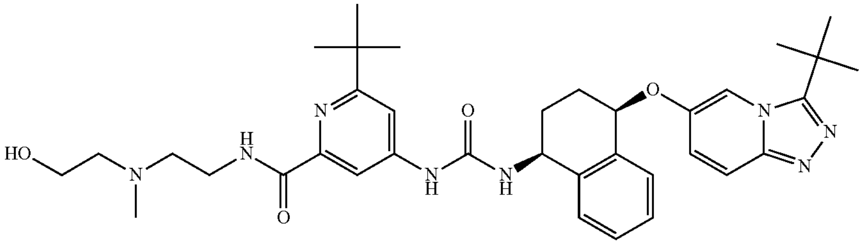 [SMILES: CN(CCO)CCNC(=O)c1cc(NC(=O)N[C@H]2CC[C@@H](Oc3ccc4nnc(C(C)(C)C)n4c3)c3ccccc32)cc(C(C)(C)C)n1] | 188 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)-amino)ethyl)picolinamide | $^1$H NMR (400 MHz, DMSO): 1.33 (9H, s), 1.53 (9H, s), 1.91-2.23 (4H, m), 2.26 (3H, s), 2.47 (2H, t, J = 6.9 Hz, partially obscured by the solvent peak), 2.55 (2H, t, J = 6.4 Hz), 3.38 (2H, q, J = 6.3 Hz), 3.50 (2H, q, J = 6.8 Hz), 4.36 (1H, t, J = 5.4 Hz), 4.93 (1H, q, J = 8.3 Hz), 5.63 (1H, t, J = 3.9 Hz), 6.93 (1H, d, J = 8.5 Hz), 7.24-7.45 (5H, m), 7.67 (1H, d, J = 1.9 Hz), 7.75 (1H, d, J = 9.9 Hz), 7.90 (1H, d, J = 1.9 Hz), 8.14 (1H, s), 8 59 (1H, t, J = 5.6 Hz), 9.11 (1H, s). | (Method 2): Rt = 3.44 min, m/z 657.6 [M + H$^+$], sample assessed as ca. 98.5%. | 9e | 2-[(2-Aminoethyl)-(methyl)amino] ethanol CAS: 5753-50-4 |
| 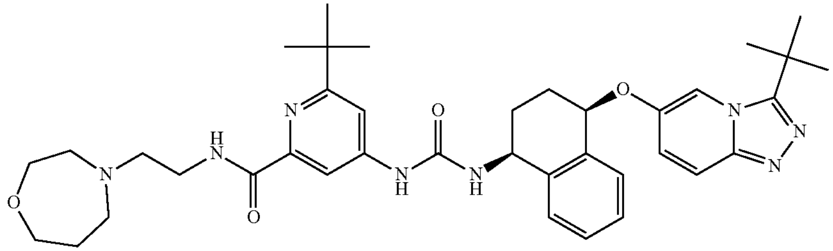 [SMILES: CC(C)(C)c1cc(NC(=O)N[C@H]2CC[C@@H](Oc3ccc4nnc(C(C)(C)C)n4c3)c3ccccc32)cc(C(=O)NCCN2CCCOCC2)n1] | 189 | N-(2-(1,4-oxazepan-4-yl)ethyl)-6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)picolinamide | $^1$H NMR (400 MHz, DMSO): 1.34 (9H, s), 1.52 (9H, s), 1.83 (2H, t, J = 5.9 Hz), 1.91-2.24 (4H, m), 2.63-2.75 (6H, m), 3.39 (2H, q, J = 5.8 Hz, partially obscured by the solvent peak), 3.63 (2H, t, J = 4.6 Hz), 3.70 (2H, t, J = 6.0 Hz), 4.93 (1H, q, J = 7.9 Hz), 5.62 (1H, t, J = 3.8 Hz), 7.07 (1H, d, J = 8.5 Hz), 7.23-7.45 (5H, m), 7.69 (1H, d, J = 1.9 Hz), 7.75 (1H, d, J = 9.9 Hz), 7.92 (1H, d, J = 1.9 Hz), 8.14 (1H, s), 8.67 (1H, t, J = 5.4 Hz), 9.27 (1H, s). | (Method 3): Rt = 3.40 min, m/z 683.5 [M + H$^+$], sample assessed as ca. 99.9%. | 9e | 2-(1,4-oxazepan-4-yl)ethanamine CAS: 878155-50-1 |

TABLE 1-continued

| Structure | Ex. | Chemical Name | NMR | LCMS | Interm. | Reagent |
|---|---|---|---|---|---|---|
| 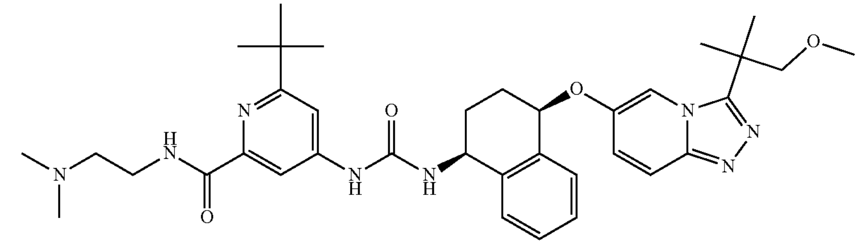 | 190 | 6-(tert-butyl)-N-(2-(dimethylamino)ethyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide | $^1$H NMR (400 MHz, DMSO): 1.33 (9H, s), 1.53 (6H, s), 1.88-2.20 (4H, m), 2.21 (6H, s), 2.43 (2H, t, J = 6.5 Hz), 3.23 (3H, s), 3.39 (2H, q, J = 6.4 Hz), 3.66 (2H, s), 4.93 (1H, q, J = 8.5 Hz), 5.54 (1H, t, J = 3.9 Hz), 6.98 (1H, d, J = 8.6 Hz), 7.24-7.46 (5H, m), 7.68 (1H, d, J = 1.9 Hz), 7.74 (1H, d, J = 9.8 Hz), 7.90 (1H, d, J = 1.2 Hz), 8.27 (1H, s), 8.58 (1H, t, J = 5.7 Hz), 9.14 (1H, s). | (Method 3): Rt = 3.39 min, m/z 657.5 [M + H$^+$], sample assessed as ca. 98%. | AN | N,N-dimethyl-ethylene diamine CAS: 108-00-9 |
| 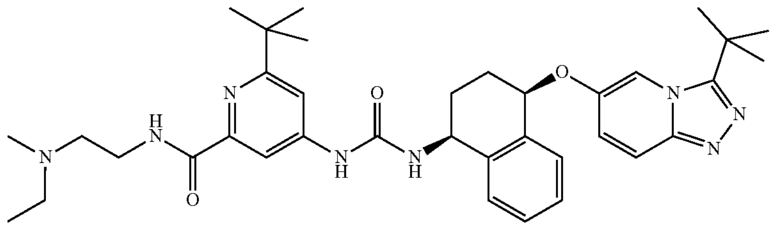 [SMILES: CCN(C)CCNC(=O)c1cc(NC(=O)N[C@H]2CC[C@@H](Oc3ccc4nnc(C(C)(C)C)n4c3)c3ccccc32)cc(C(C)(C)C)n1] | 191 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)-ethyl)picolinamide | $^1$H NMR (400 MHz, DMSO): 1.01 (3H, t, J = 7.1 Hz), 1.32 (9H, s), 1.52 (9H, s), 1.89-2.19 (4H, m), 2.21 (3H, s), 2.42 (2H, q, J = 7.1 Hz), 2.47-2.52 (2H, m, partially obscured by the solvent peak), 3.38 (2H, q, J = 6.2 Hz), 4.92 (1H, q, J = 8.2 Hz), 5.63 (1H, t, J = 3.9 Hz), 6.97 (1H, d, J = 8.5 Hz), 7.24-7.46 (5H, m), 7.68 (1H, d, J = 1.9 Hz), 7.75 (1H, d, J = 9.9 Hz), 7.90 (1H, d, J = 1.9 Hz), 8.14 (1H, s), 8.61 (1H, t, J = 5.5 Hz), 9.15 (1H, s). | (Method 3): Rt 3.49 min, m/z 641.6 [M + H+]. | 9e | (2-aminoethyl)-(ethyl)methyl-amine CAS: 70111-47-6 |
| 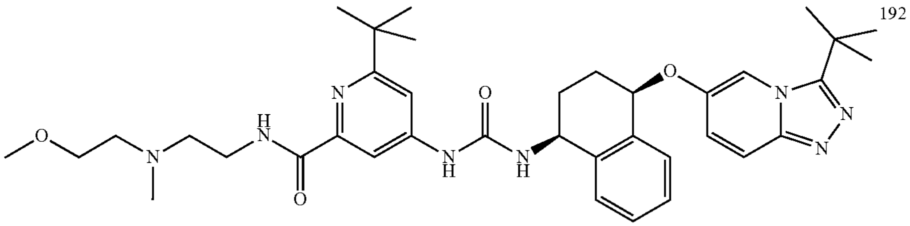 | 192 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)-amino)ethyl)picolinamide | $^1$H NMR (400 MHz, d-6-DMSO): 1.33 (9H, s), 1.53 (9H, s), 1.95-2.21 (4H, m), 2.26 (3H, s), 2.54-2.58 (4H, m), 3.22 (3H, s), 3.37 (2H, q, J = 5.9 Hz), 3.44 (2H, t, J = 6.0 Hz), 4.90-4.96 (1H, m), 5.63 (1H, t, J = 3.8 Hz), 6.94 (1H, d, J = 8.6 Hz), 7.26-7.43 (5H, m), 7.68 (1H, d, J = 1.9 Hz), 7.75 (1H, dd, J = 9.8, 0.6 Hz), 7.90 (1H, d, J = 1.9 Hz), 8.14 (1H, d, J = 1.3 Hz), 8.58 (1H, t, J = 5.5 Hz), 9.12 (1H, s). | (Method 3): Rt 3.48 min, m/z 671 [MH$^+$]. | 9e | N'-(2-methoxyethyl)-N'-methyl-ethane-1,2-diamine CAS: 14165-17-4 |

TABLE 1-continued

| Structure | Ex. | Chemical Name | NMR | LCMS | Interm. | Reagent |
|---|---|---|---|---|---|---|
| 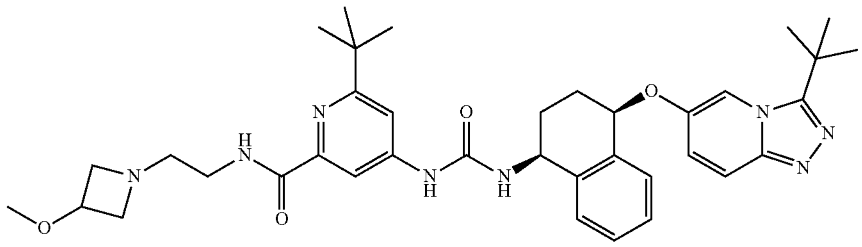 [SMILES: COC1CN(CCNC(=O)c2cc(NC(=O)N[C@H]3CC[C@@H](Oc4ccc5nnc(C(C)(C)C)n5c4)c4ccccc43)cc(C(C)(C)C)n2)C1] | 193 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)picolinainide | $^1$H NMR (400 MHz. d-6-DMSO): 1.33 (9H, s), 1.52 (9H, s), 1.92-2.22 (4H, m), 2.57 (2H, t, J = 6.3 Hz), 2.79-2.85 (2H, m), 3.14 (3H, s), 3.28 (2H, q, J = 6.3 Hz, partially obscured by solvent peak), 3.50-3.57 (2H, m), 3.95 (1H, quintet, J = 5.8 Hz), 4.93 (1H, q, J = 8.1 Hz), 5.63 (1H, t, J = 3.8 Hz), 6.95 (1H, d, J = 8.5 Hz), 7.24-7.45 (5H, m), 7.67 (1H, d, J = 1.9 Hz), 7.75 (1H, dd, J = 9.8, 0.6 Hz), 7.90 (1H, d, J = 1.9 Hz), 8.13 (1H, d, J = 1.2 Hz), 8.51 (1H, t, J = 5.9 Hz), 9.13 (1H, s). | (Method 3): Rt 3.58 min, m/z 669 [MH$^+$]. | 9e | 2-(3-methoxy-azetidin-1-yl)ethan-1-amine CAS: 911300-65-7 |
| 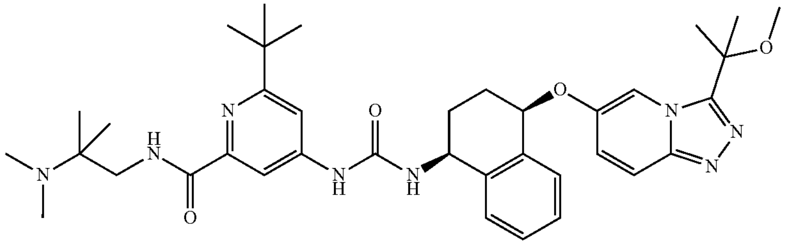 | 194 | 6-(tert-butyl)-N-(2-(dimethylamino)-2-methylpropyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide | $^1$H NMR (400 MHz, d-6-DMSO): 1.00 (6H, s), 1.32 (9H, s), 1.69 (6H, s), 1.93-2.21 (10H, m), 2.98 (3H, s), 3.25 (2H, d, J = 5.3 Hz), 4.91-4.97 (1H, m), 5.49 (1H, t, J = 3.9 Hz), 6.96 (1H, d, J = 8.6 Hz), 7.28-7.43 (5H, m), 7.67 (1H, d, J = 1.9 Hz), 7.82 (1H, dd, J = 9.9, 0.6 Hz), 7.91 (1H, d, J = 1.9 Hz), 8.12 (1H, d, J = 1.4 Hz), 8.66 (1H, t, J = 5.2 Hz), 9.06 (1H, s). | (Method 2): Rt 3.50 min, m/z 671 [MH$^+$]. | AM | (2-Amino-1,1-dimethylethyl) dimethylamine CAS: 76936-44-2 |
| 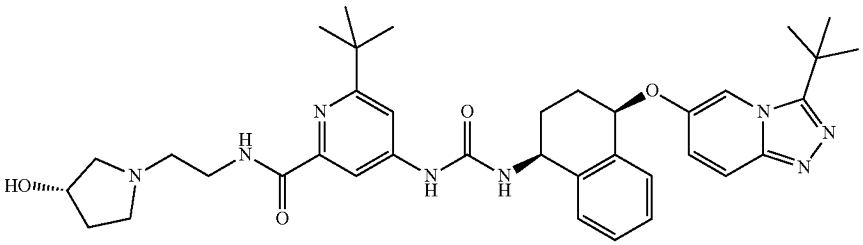 [SMILES: CC(C)(C)c1cc(NC(=O)N[C@H]2CC[C@@H](Oc3ccc4nnc(C(C)(C)C)n4c3)c3ccccc32)cc(C(=O)NCCN2CC[C@H](O)C2)n1] | 195 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)picolinamide | $^1$H NMR (400 MHz, d-6-DMSO): 1.33 (9H, s), 1.53 (9H, s), 1.90-2.22 (5H, m), 2.32 (2H, dd, J = 9.5, 4.1 Hz), 2.49-2.63 (4H, m, partially obscured by solvent peak), 2.82 (1H, dd, J = 9.5, 6.9 Hz), 3.39 (2H, q, J = 6.5 Hz, partially obscured by solvent peak), 4.15-4.23 (1H, m), 4.68 (1H, d, J = 4.4 Hz), 4.93 (1H, q, J = 6.7 Hz), 5.63 (1H, t, J = 4.0 Hz), 6.97 (1H, d, J = 8.5 Hz), 7.25-7.45 (5H, m), 7.67 (1H, d, J = 1.9 Hz), 7.75 (111, dd, J = 9.8, 0.6 Hz), 7.90 (1H, d, J = 1.9 Hz), 8.13 (1H, d, J = 1.2 Hz), 8.64 (1H, t, J = 5.6 Hz), 9.15 (1H, s). | (Method 2): Rt 3.35 min, m/z 669 [MH$^+$]. | 9e | (S)-1-(2-aminoethyl)-pyrrolidin-3-ol CAS: 672325-36-9 |

TABLE 1-continued

| Structure | Ex. | Chemical Name | NMR | LCMS | Interm. | Reagent |
|---|---|---|---|---|---|---|
| 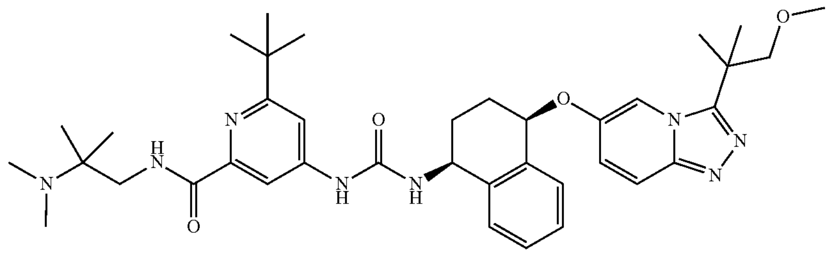 | 196 | 6-(tert-butyl)-N-(2-(dimethylamino)-2-methylpropyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide | $^1$H NMR (400 MHz, d-6-DMSO): 1.00 (6H, s), 1.32 (9H, s), 1.52 (6H, s), 1.94-2.20 (10H, m), 3.23 (3H, s), 3.26 (2H, d, J = 5.3 Hz), 3.66 (2H, s), 4.90-4.96 (1H, m), 5.54 (1H, t, J = 3.9 Hz), 7.07 (1H, d, J = 8.7 Hz), 7.27-7.44 (5H, m), 7.68 (1H, d, J = 1.9 Hz), 7.74 (1H, d, J = 9.9 Hz), 7.92 (1H, d, J = 1.9 Hz), 8.27 (1H, d, J = 1.4 Hz), 8.66 (1H, t, J = 5.2 Hz), 9.23 (1H, s). | (Method 2): Rt 3.51 min, m/z 685 [MH$^+$]. | AN | (2-Amino-1,1-dimethylethyl) dimethylamine CAS: 76936-44-2 |
| 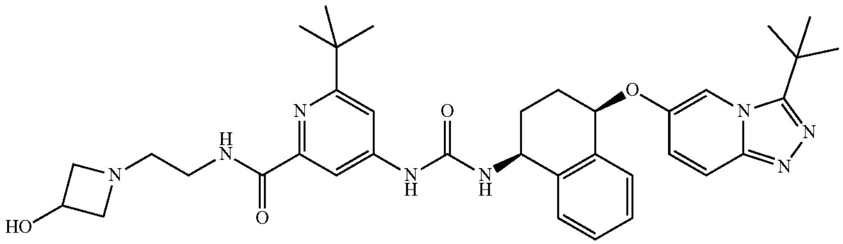 [SMILES: CC(C)(C)c1cc(NC(=O)N[C@H]2CC[C@@H](Oc3ccc4nnc(C(C)(C)C)n4c3)c3ccccc32)cc(C(=O)NCCN2CC(O)C2)n1] | 197 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)picolinamide | $^1$H NMR (400 MHz, d-6-DMSO): 1.33 (9H, s), 1.53 (9H, s), 1.95-2.21 (4H, m), 2.55 (2H, t, J = 6.4 Hz), 2.72-2.75 (2H, m), 3.27 (2H, q, J = 6.2 Hz), 3.53-3.57 (2H, m), 4.16 (1H, sextet, J = 6.3 Hz), 4.90-4.96 (1H, m), 5.26 (1H, d, J = 6.6 Hz), 5.63 (1H, t, J = 3.9 Hz), 6.98 (1H, d, J = 8.5 Hz), 7.26-7.43 (5H, m), 7.67 (1H, d, J = 2.0 Hz), 7.75 (1H, dd, J = 9.9, 0.6 Hz), 7.90 (1H, d, J = 1.9 Hz), 8.14 (1H, d, J = 1.2 Hz), 8.52 (1H, t, J = 6.0 Hz), 9.16 (1H, s). | (Method 2): Rt 3.33 min, m/z 655 [MH$^+$]. | 9e | 1-(2-aminoethyl)-azetidin-3-ol CAS: 1260773-28-1 |
| 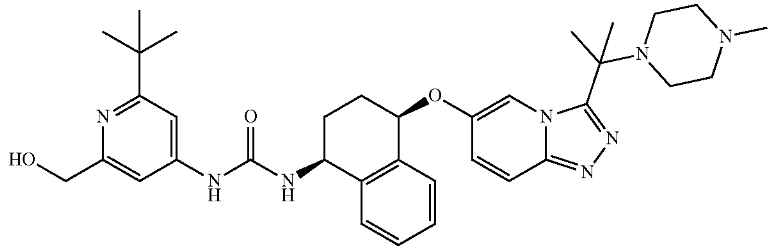 [SMILES: CN1CCN(C(C)(C)c2nnc3ccc(O[C@@H]4CC[C@H](NC(=O)Nc5cc(CO)nc(C(C)(C)C)c5)c5ccccc54)cn23)CC1] | 198 | 1-(2-(tert-butyl)-6-(hydroxymethyl)pyridin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea | $^1$H NMR (400 MHz, d-6-DMSO): 1.26 (9H, s), 1.54 (3H, s), 1.55 (3H, s), 1.93-2.47 (15H, m), 4.45 (2H, s), 4.91-4.97 (1H, m), 5.26(1H, s), 5.48 (1H, t, J = 4.2 Hz), 6.87 (1H, d, J = 8.5 Hz), 7.29-7.41 (6H, m), 7.48 (1H, d, J = 7.4 Hz), 7.75 (1H, d, J = 9.9 Hz), 8.73 (1H, d, J = 1.8 Hz), 8.83 (1H, br s). | (Method 3): Rt 2.40 min, m/z 627 [MH+]. | AQ | |

TABLE 1-continued

| Structure | Ex. | Chemical Name | NMR | LCMS | Interm. | Reagent |
|---|---|---|---|---|---|---|
| 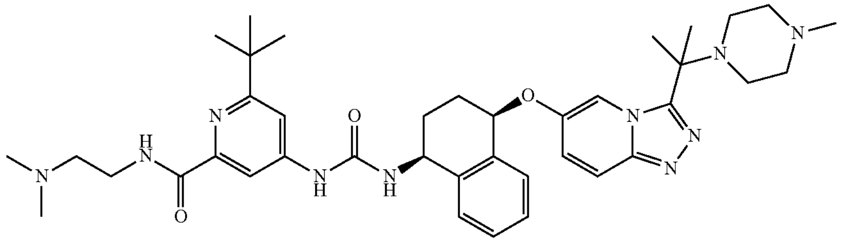 1.5 eq HCOOH | 199 | 6-(tert-Butyl)-N-(2-(dimethylamino)ethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt | $^1$H NMR (400 MHz, d-6-DMSO): 1.33 (9H, s), 1.54 (3H, s), 1.55 (3H, s), 1.93-2.37 (20H, m), 2.43-2.49 (3H, m, partially obscured by the solvent peak), 3.41 (2H, q, J = 6.1 Hz, partially obscured by water peak), 4.92-4.98 (1H, m), 5.48 (1H, t, J = 4.2 Hz), 7.10 (1H, d, J = 8.4 Hz), 7.29-7.43 (4H, m), 7.48 (1H, d, J = 7.3 Hz), 7.68 (1H, d, J = 1.9 Hz), 7.74 (1H, d, J = 9.8 Hz), 7.91 (1H, d, J = 1.9 Hz), 8.18 (1.5H, br s), 8.59 (1H, t, J = 5.8 Hz), 8.72 (1H, d, J = 1.6 Hz), 9.20 (1H, s). | (Method 3): Rt 2.67 min, m/z 711 [MH$^+$]. | AR | N,N-dimethyl-ethylene diamine CAS: 108-00-9 |
| 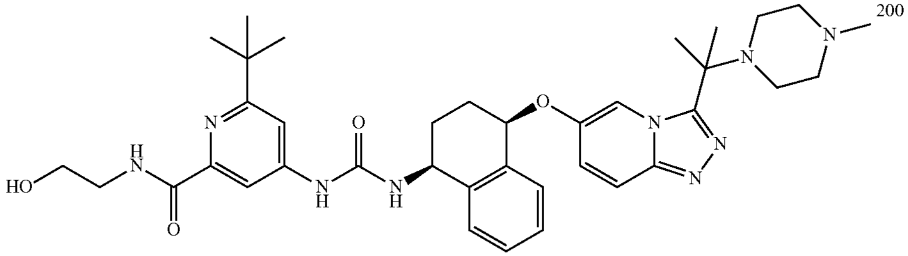 1.0 eq HCOOH | 200 | 6-(tert-Butyl)-N-(2-hydroxyethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt | $^1$H NMR (400 MHz, d-6-DMSO): 1.33 (9H, s), 1.54 (3H, s), 1.55 (3H, s), 1.93-2.11 (6H, m), 2.18-2.48 (9H, m), 3.39 (2H, q, J = 5.6 Hz, partially obscured by water peak), 3.54 (2H, t, J = 5.8 Hz, partially obscured by water peak), 4.82 (1H, br s), 4.92-4.98 (1H, m), 5.48 (1H, t, J = 4.2 Hz), 7.04 (1H, d, J = 8.5 Hz), 7.29-7.43 (4H, m), 7.48 (1H, d, J = 7.5 Hz), 7.68 (1H, d, J = 1.9 Hz), 7.74 (1H, d, J = 9.6 Hz), 7.92 (1H, d, J = 1.9 Hz), 8.17 (1H, s), 8.53 (1H, t, J = 5.9 Hz), 8.73 (1H, d, J = 1.6 Hz), 9.14 (1H, s). | (Method 3): Rt 3.14 min, m/z 684 [MH$^+$]. | AR | Ethanolamine CAS: 141-43-5 |
| 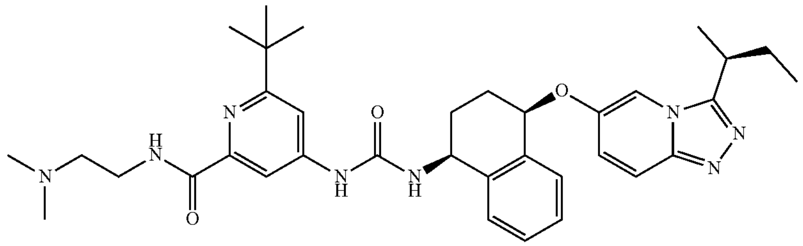 1.0 eq HCOOH | 201 | 6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)-picolinamide formate salt | $^1$H NMR (400 MHz, d-6-DMSO): 0.88 (3H, t, J = 7.4 Hz), 1.33 (9H, s), 1.35 (3H, d, J = 6.9 Hz), 1.75 (1H, heptet, J = 7.0 Hz), 1.85-2.04 (3H, m), 2.06-2.23 (8H, m), 2.46 (2H, q, J = 6.6 Hz, partially obscured by the solvent peak), 3.38-3.48 (3H, m, partially obscured by water peak), 4.91-4.96 (1H, m), 5.56 (1H, t, J = 4.1 Hz), 7.06 (1H, d, J = 9.6 Hz), 7.20 (1H, dd, J = 9.8, 2.0 Hz), 7.29-7.43 (4H, m), 7.68 (1H, d, J = 1.9 Hz), 7.70 (1H, d, J = 10.0 Hz), | (Method 3): Rt 3.39 min, m/z 627 [MH$^+$]. | AS | N,N-dimethyl-ethylene diamine CAS: 108-00-9 |

TABLE 1-continued

| Structure | Ex. | Chemical Name | NMR | LCMS | Interm. | Reagent |
|---|---|---|---|---|---|---|
| | | | 7.91 (1H, d, J = 1.9 Hz), 8.19 (1H, s), 8.25 (1H, d, J = 1.3 Hz), 8.59 (1H, t, J = 5.7 Hz), 9.19 (1H, s). | | | |
| 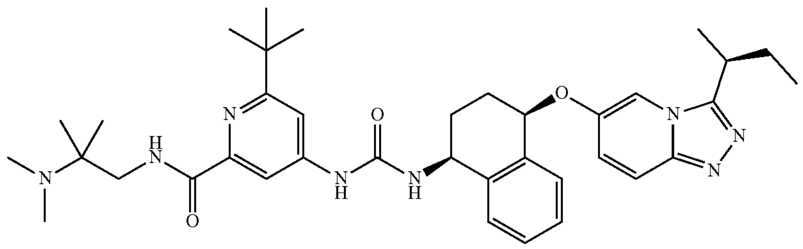 1.0 eq HCOOH | 202 | 6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)-picolinamide formate salt | $^1$H NMR (400 MHz. d-6-DMSO): 0.88 (3H, t, J = 7.4 Hz), 1.02 (6H, s), 1.32 (9H, s), 1.35 (3H, d, J = 6.9 Hz), 1.75 (1H, hept, J = 6.9 Hz), 1.86-2.04 (3H, m), 2.07-2.25 (8H, m), 3.28 (2H, d, J = 5.4 Hz, partially obscured by water peak), 3.40-3.49 (1H, m, partially obscured by water peak), 4.91-4.97 (1H, m), 5.56 (1H, t, J = 4.0 Hz), 7.05 (1H, d, J = 8.6 Hz), 7.20 (1H, dd, J = 9.8, 2.0 Hz), 7.29-7.43 (4H, m), 7.67 (1H, d, J = 1.9 Hz), 7.70 (1H, d, J = 9.9 Hz), 7.92 (1H, d, J = 1.9 Hz), 8.17 (1H, s), 8.25 (1H, d, J = 1.3 Hz), 8.67 (1H, t, J = 5.4 Hz), 9.18 (1H, s). | (Method 3): Rt 3.49 min, m/z 655 [MH$^+$]. | AS | (2-Amino-1,1-dimethylethyl) dimethylamine CAS: 76936-44-2 |
| 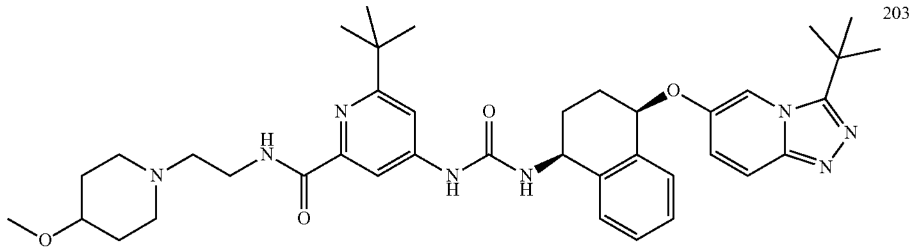 | 203 | 6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methoxypiperidin-1-yl)ethyl)picolinamide | $^1$H NMR (400 MHz, d-6-DMSO): 1.33 (9H, s), 1.38-1.50 (2H, m), 1.53 (9H, s), 1.80-2.21 (9H, m), 2.71-2.29 (2H, m), 3.14-3.21 (2H, m, partially obscured by solvent peak), 3.23 (3H, s), 4.93 (1H, q, J = 8.0 Hz), 5.63 (1H, t, J = 3.9 Hz), 7.01 (1H, d, J = 8.5 Hz), 7.25-7.44 (5H, m), 7.68 (1H, d, J = 1.9 Hz), 7.75 (1H, dd, J = 9.8, 0.6 Hz), 7.91 (1H, d, J = 1.9 Hz), 8.14 (1H, d, J = 1.2 Hz), 8.70 (1H, t, J = 5.3 Hz), 9.20 (1H, s), plus two protons obscured by the solvent peak. | (Method 3): Rt 3.49 min, m/z 697 [MH$^+$]. | 9d | 2-(4-methoxy-piperidin-1-yl)ethan-1-amine CAS: 911300-69-1 |

TABLE 1-continued

| Structure | Ex. | Chemical Name | NMR | LCMS | Interm. | Reagent |
|---|---|---|---|---|---|---|
| 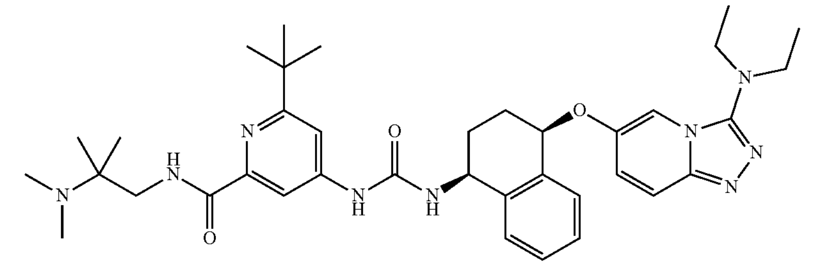 1.0 eq HCOOH | 204 | 6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)-picolinamide formate salt | $^1$H NMR (400 MHz, d-6-DMSO): 1.00-1.04 (12H, m), 1.32 (9H, s), 1.89-2.24 (10H, m), 3.21-3.29 (6H, m, partially obscured by water peak), 4.89-4.95 (1H, m), 5.54 (1H, t, J = 3.9 Hz), 7.07 (1H, d, J = 8.4 Hz), 7.19 (1H, dd, J = 9.9, 2.0 Hz), 7.28-7.41 (4H, m), 7.64 (1H, dd, J = 9.8, 0.6 Hz), 7.68 (1H, d, J = 1.9 Hz), 7.71 (1H, d, J = 1.4 Hz), 7.92 (1H, d, J = 1.9 Hz), 8.18 (1H, s), 8.67 (1H, t, J = 5.4 Hz), 9.20 (1H, s). | (Method 3): Rt 3.48 min, m/z 670 [MH$^+$]. | 10e | (2-Amino-1,1-dimethylethyl) dimethylamine CAS: 76936-44-2 |
| 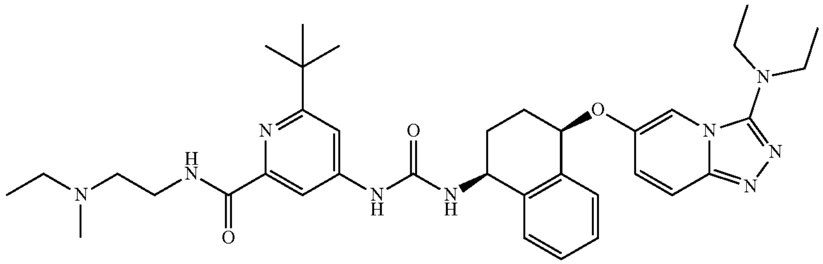 1.0 eq HCOOH | 205 | 6-(tert-Butyl)-4-(3-((1S,4R)-4-((3-(diethylamino)-[1,2,4]triazolo[4,3-a]pyridin-6-yl)oxy)-1,2,3,4-tetra-hydronaphthalen-1-yl)ureido)-N-(2-(ethyl(methyl)amino)-ethyl)picolinamide formate salt | $^1$H NMR (400 MHz, d-6-DMSO): 1.00-1.05 (9H, m), 1.33 (9H, s), 1.92-2.22 (4H, m), 2.26 (3H, s), 2.45-2.50 (2H, m, partially obscured by the solvent peak), 2.56 (2H, t, J = 6.3 Hz), 3.24 (4H, q, J = 7.1 Hz, partially obscured by water signal), 3.40 (2H, q, J = 5.8 Hz, partially obscured by water peak), 4.89-4.95 (1H, m), 5.54 (1H, t, J = 4.0 Hz), 7.04 (1H, d, J = 8.6 Hz), 7.19 (1H, dd, J = 9.8, 2.1 Hz), 7.28-7.41 (4H, m), 7.63 (1H, dd, J = 9.8, 0.4 Hz), 7.68 (1H, d, J = 1.9 Hz), 7.71 (1H, d, J = 1.4 Hz), 7.91 (1H, d, J = 1.9 Hz), 8.18 (1H, s), 8.63 (1H, t, J = 5.5 Hz), 9.17 (1H, s). | (Method 3): Rt 3.42 min, m/z 656 [MH$^+$]. | 10e | (2-aminoethyl)-(ethyl)methyl-amine CAS: 70111-47-6 |
| 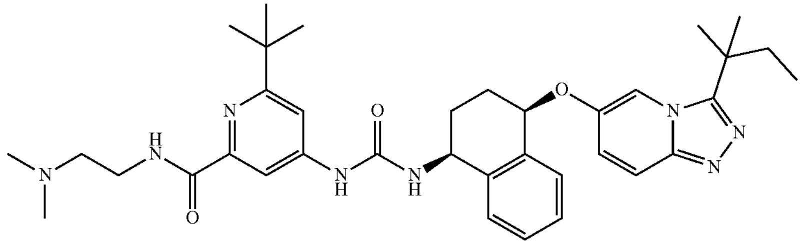 [SMILES: CCC(C)(C)c1nnc2ccc(O[C@@H]3CC[C@H](NC(=O)Nc4cc(C(=O)NCCN(C)C)nc(C(C)(C)C)c4)c4ccccc43)cn12] | 206 | 6-(tert-butyl)-N-(2-(dimethylamino)ethyl)-4-(3-((1S,4R)-4-((3-(tert-pentyl)-[1,2,4]triazolo[4,3-a]pyridin-6-yl)oxy)-1,2,3,4-tetrahydronaphthalen-1-yl)ureido)picolinamide | $^1$H NMR (400 MHz, d-6-DMSO): 0.64 (3H, t, J = 7.5 Hz), 1.33 (9H, s), 1.49 (3H, s), 1.50 (3H, s), 1.89-2.20 (12H, m), 2.42 (2H, t, J = 6.5 Hz), 3.39 (2H, q, J = 6.0 Hz), 4.90-4.95 (1H, m), 5.61 (1H, t, J = 3.8 Hz), 6.97 (1H, d, J = 8.4 Hz), 7.27-7.42 (5H, m), 7.68 (1H, d, J = 1.9 Hz), 7.75 (1H, d, J = 9.9 Hz), 7.90 (1H, d, J = 1.9 Hz), 8.08 (1H, d, J = 1.1 Hz), 8.58 (1H, t, J = 5.8 Hz), 9.16 (1H, s). | (Method 3): Rt 3.48 min, m/z 641 [MH$^+$]. | AV | N,N-dimethyl-ethylene diamine CAS: 108-00-9 |

TABLE 1-continued

| Structure | Ex. | Chemical Name | NMR | LCMS | Interm. | Reagent |
|---|---|---|---|---|---|---|
| 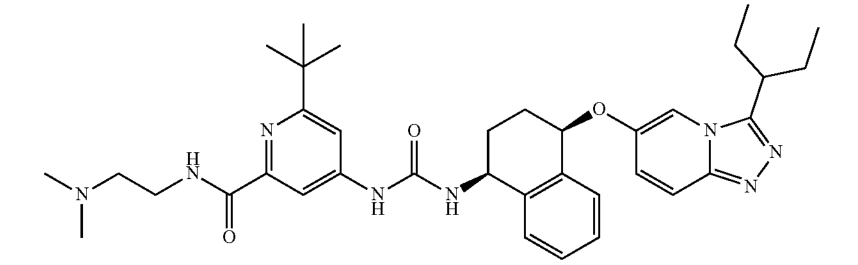 [SMILES: CCC(CC)c1nnc2ccc(O[C@@H]3CC[C@H](NC(=O)Nc4cc(C(=O)NCCN(C)C)nc(C(C)(C)C)c4)c4ccccc43)cn12] | 207 | 6-(tert-butyl)-N-(2-(dimethylamino)ethyl)-4-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)picolinamide | $^1$H NMR (400 MHz, d-6-DMSO): 0.78 (3H, t, J = 7.4 Hz), 0.81 (3H, t, J = 7.4 Hz), 1.33 (9H, s), 1.77-2.20 (14H, m), 2.42 (2H, t, J = 6.5 Hz), 3.34-3.41 (3H, m, partially obscured by water peak), 4.90-4.97 (1H, m), 5.56 (1H, t, J = 4.2 Hz), 7.01 (1H, d, J = 8.4 Hz), 7.20 (1H, dd, J = 9.8, 2.0 Hz), 7.28-7.42 (4H, m), 7.68 (1H, d, J = 1.9 Hz), 7.70 (1H, d, J = 9.8 Hz), 7.90 (1H, d, J = 1.9 Hz), 8.28 (1H, d, J = 1.3 Hz), 8.58 (1H, t, J = 5.7 Hz), 9.13 (1H, s). | (Method 3): Rt 3.47 min, m/z 641 [MH$^+$]. | AW | N,N-dimethyl-ethylene diamine CAS: 108-00-9 |
| 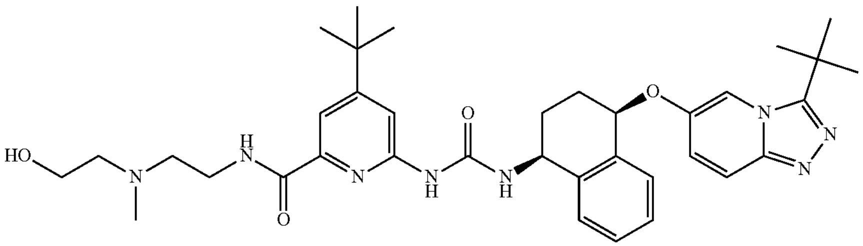<br>1.2 eq HCOOH | 208 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)-amino)ethyl) picolinamide formate salt | $^1$H NMR (400 MHz, DMSO): 1.29 (9H, s), 1.53 (9H, s), 1.88-2.20 (4H, m), 2.21 (3H, s), 2.44 (2H, t, J = 6.4 Hz), 2.46-2.49 (2H, m, partially obscured by the solvent peak), 3.35 (2H, dd, J = 2.4, 5.9 Hz), 3.46 (2H, t, J = 6.4 Hz), 4.96 (1H, q, J = 8.6 Hz), 5.64 (1H, t, J = 3.9 Hz), 7.24-7.49 (5H, m), 7.61 (1H, d, J = 1.7 Hz), 7.64 (1H, d, J = 8.4 Hz), 7.75 (1H, d, J = 9.9 Hz), 8.09 (1H, d, J = 1.6 Hz), 8.12 (1H, t, J = 6.0 Hz), 8.14 (1H, d, J = 1.3 Hz), 8.18 (1.2H, s), 9.06 (1H, s), plus one proton obscured by the solvent peak. | (Method 2): Rt = 3.28 min, m/z 657.5 [M + H$^+$], sample assessed as ca. 97.2%. | AY | 2-[(2-Aminoethyl)-(methyl)amino] ethanol CAS: 5753-50-4 |
| 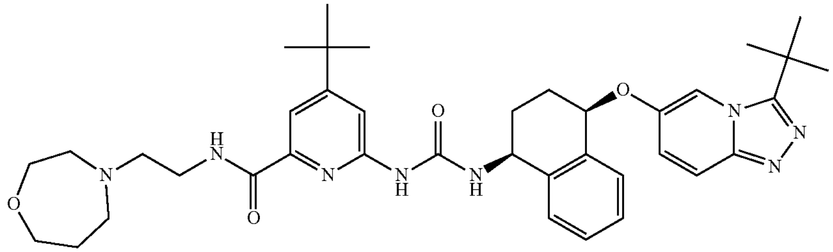 [SMILES: CC(C)(C)c1cc(NC(=O)N[C@H]2CC[C@@H](Oc3ccc4nnc(C(C)(C)C)n4c3)c3ccccc32)nc(C(=O)NCCN2CCCOCC2)c1]<br>1.2 eq HCOOH | 209 | N-(2-(1,4-oxazepan-4-yl)ethyl)-4-(tert-butyl)-6-(3-((1S,4R)-4-((3-(tert-butyl)-[1,2,4]triazolo[4,3-a] pyridin-6-yl)oxy)-1,2,3,4-tetrahydronaphthalen-1-yl)ureido)picolinamide formate salt | $^1$H NMR (400 MHz, DMSO): 1.29 (9H, s), 1.53 (9H, s), 1.74 (2H, t, J = 5.8 Hz), 1.88-2.25 (4H, m), 2.58 (2H, t, J = 6.7 Hz), 2.62-2.70 (4H, m), 3.31-3.39 (2H, m obscured), 3.56 (2H, t, J = 4.7 Hz), 3.62 (2H, t, J = 5.9 Hz), 4.97 (1H, q, J = 8.5 Hz), 5.64 (1H, t, J = 3.8 Hz), 7.24-7.48 (5H, m), 7.60 (1H, d, J = 1.6 Hz), 7.69-7.78 (2H, m), 8.04 (1H, d, J = 1.6 Hz), 8.09 (1H, t, J = 5.7 Hz), 8.14 (1H, s), 8.16 (1.2H, s), 9.05 (1H, s). | (Method 3): Rt = 3.39 min, m/z 683.3 [M + H$^+$], sample assessed as ca. 99.5%. | AY | 2-(1,4-oxazepan-4-yl)ethanamine CAS: 878155-50-1 |

TABLE 1-continued

| Structure | Ex. | Chemical Name | NMR | LCMS | Interm. | Reagent |
|---|---|---|---|---|---|---|
| 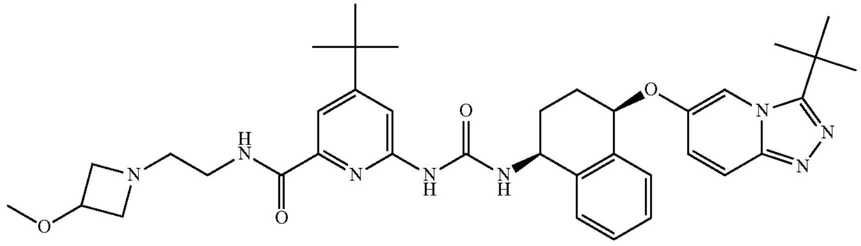 1.0 eq HCOOH | 210 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)picolinamide formate salt | $^1$H NMR (400 MHz, DMSO): 1.29 (9H, s), 1.53 (9H, s), 1.87-2.27 (4H, m), 2.78 (2H, t, J = 6.0 Hz), 3.10 (3H, s), 3.16-3.26 (2H, m, partially obscured by the water peak), 3.45-3.51 (2H, m, partially obscured by the water peak), 3.91 (1H, t, J = 5.8 Hz), 4.96 (1H, q, J = 8.9 Hz), 5.64 (1H, t, J = 3.9 Hz), 7.25-7.48 (5H, m), 7.60 (1H, d, J = 1.7 Hz), 7.63 (1H, d, J = 8.4 Hz), 7.76 (1H, d, J = 9.9 Hz), 8.03 (1H, t, J = 5.8 Hz), 8.07 (1H, d, J = 1.6 Hz), 8.15 (1H, s), 8.17 (1H, s), 9.10 (1H, s), plus two protons obscured by the solvent peak. | (Method 3): Rt = 3.39 min, m/z 669.3 [M + H$^+$], sample assessed as ca. 97.5%. | AY | 2-(3-methoxyazetidin-1-yl)ethan-1-amine CAS: 911300-65-7 |
| 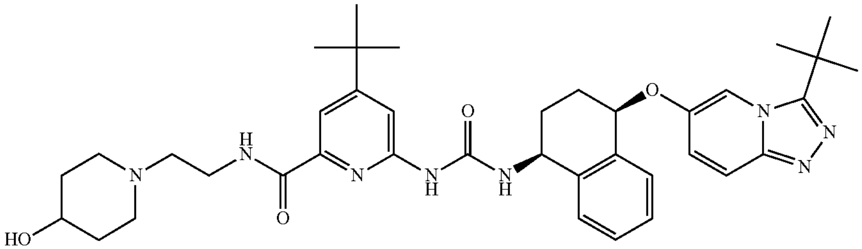 1.0 eq HCOOH | 211 | 4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(-(2-(4-hydroxypiperidin-1-yl)ethyl)picolinamide formate salt | $^1$H NMR (400 MHz. DMSO): 1.29 (9H, s), 1.35 (2H, d, J = 9.6 Hz), 1.53 (9H, s), 1.63 (2H, d, J = 13.5 Hz), 1.88-2.24 (6H, m), 2.39 (2H, t, J = 6.7 Hz), 2.64-2.75 (2H, m), 4.52 (1H, br s), 4.97 (1H, q, J = 8.51 Hz), 5.64 (1H, t, J = 3.86 Hz), 7.24-7.48 (5H, m), 7.60 (1H, d, J = 1.7 Hz), 7.70 (1H, d, J = 8.4 Hz), 7.75 (1H, d, J = 9.8 Hz), 8.05 (1H, d, J = 1.6 Hz), 8.07 (1H, t, J = 5.8 Hz), 8.14 (1H, s), 8.17 (1H, s), 9.06 (1H, s), plus three protons obscured by the solvent peak. | (Method 3): Rt = 3.30 min, m/z 683.3 [M + H$^+$], sample assessed as ca. 99.5%. | AY | 1-(2-aminoethyl) piperidin-4-ol CAS: 129999-60-6 |

Example 212. N-(6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)methanesulfonamide

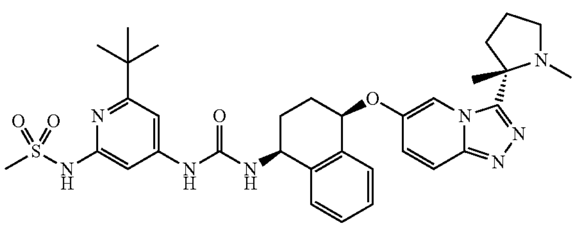

A solution of Intermediate AT (322 mg, 1.23 mmol), Intermediate OOa (520 mg, 1.23 mmol), XPhos (59 mg, 0.123 mmol) in previously degassed dioxane (5 ml) was treated with $Cs_2CO_3$ (601 mg, 1.85 mmol) and $Pd(OAc)_2$ (14 mg, 0.062 mmol). The reaction mixture was degassed for a few minutes with argon and heated at 110° C. for 24 hours. The reaction mixture was cooled at RT, diluted with DCM and filtered through a pad of Celite®. The solvent was removed under reduced pressure and the residue was dissolved in dioxane (5 ml). This solution was added with Intermediate AT (322 mg, 1.23 mmol), XPhos (59 mg, 0.123 mmol), $Cs_2CO_3$ (601 mg, 1.85 mmol) and $Pd(OAc)_2$ (14 mg, 0.062 mmol) and the reaction mixture was heated at 95° C. for 1 hour. Other aliquots of XPhos (59 mg, 0.123 mmol) and $Pd(OAc)_2$ (14 mg, 0.062 mmol) were added and the reaction mixture was stirred at 95° C. for 1 hour. The reaction mixture was partitioned between DCM and $H_2O$ and the two phases were separated. The organic phases was dried with $Na_2SO_4$ and the solvent was removed under reduced pressure. Purification by FCC, eluting with 0-10% 2N $NH_3$ in MeOH/DCM, followed by a further purification by HPLC (Waters C18, 15-80% MeCN in $H_2O$, 0.1% $NH_4OH$, 18 ml/min) afforded the title compound (191 mg, 23%).

LCMS (Method 3): Rt 3.10 min, m/z 646 [$MH^+$]. $^1H$ NMR (400 MHz, d-$_6$-DMSO): 1.28 (9H, s), 1.53 (3H, s), 1.80-2.23 (11H, m), 2.68 (1H, q, J=8.8 Hz), 3.12-3.17 (1H, m), 3.24 (3H, br s), 4.89-4.95 (1H, m), 5.35 (1H, t, J=4.4 Hz), 6.66 (1H, d, J=8.2 Hz), 6.95 (1H, s), 7.04 (1H, s), 7.25-7.42 (6H, m), 7.70 (1H, dd, J=9.8, 0.8 Hz), 8.46-8.47 (1H, m), 8.75 (1H, br s).

Example 213. N-(6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)ethanesulfonamide

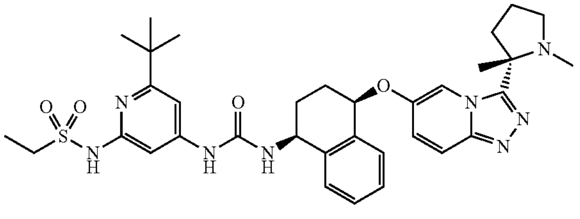 [SMILES: CCS(=O)(=O)Nc1cc(NC(=O)N[C@H]2CC[C@@H](Oc3ccc4nnc([C@]5(C)CCCN5C)n4c3)c3ccccc32)cc(C(C)(C)C)n1]

A solution of Intermediate AU (126 mg, 0.46 mmol), Intermediate OOa (193 mg, 0.46 mmol), XPhos (22 mg, 0.46 mmol) in previously degassed dioxane (4 ml) was treated with $Cs_2CO_3$ (225 mg, 0.69 mmol) and $Pd(OAc)_2$ (5 mg, 0.023 mmol). The reaction mixture was degassed for a few minutes with argon and heated at 110° C. for 1 hour. The reaction mixture was cooled at RT, diluted with $H_2O$ and extracted with DCM (×3). The combined organic phases were dried with $MgSO_4$ and the solvent was removed under reduced pressure. Purification by FCC, eluting with 0-10% 2N $NH_3$ in MeOH/DCM afforded the title compound (120 mg, 40%).

LCMS (Method 3): Rt 3.19 min, m/z 661 [$MH^+$]. $^1H$ NMR (400 MHz, d-$_6$-DMSO): 1.21-1.25 (12H, m), 1.51 (3H, s), 1.79-2.22 (11H, m), 2.66 (1H, q, J=8.8 Hz), 3.14-3.19 (1H, m), 3.55 (2H, br s), 4.88-4.93 (1H, m), 5.35 (1H, t, J=4.1 Hz), 6.80 (1H, br s), 6.91 (1H, br s), 7.05 (1H, br s), 7.27-7.40 (5H, m), 7.76 (1H, dd, J=9.9, 0.6 Hz), 8.46 (1H, d, J=1.5 Hz), 8.87 (1H, br s), 10.2 (1H, br s).

Example 214. 4-(tert-Butyl)-N-(2-(dimethylamino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide

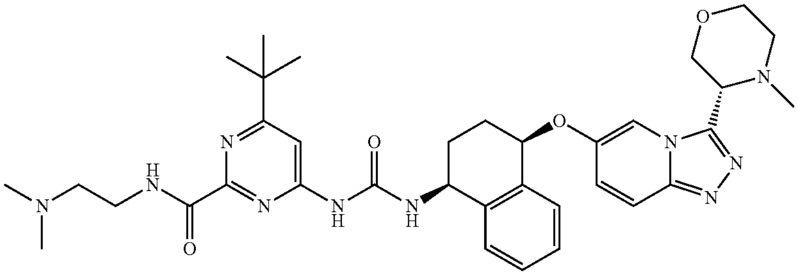

a. (S)—N'-(5-Fluoropyridin-2-yl)-4-methylmorpholine-3-carbohydrazide (Intermediate 214a)

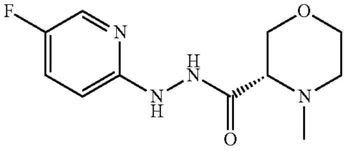 [SMILES: CN1CCOC[C@H]1C(=O)NNc1ccc(F)cn1]

A solution of (S)-4-methylmorpholine-3-carboxylic acid (16.2 g, 111.7 mmol) in DCM (250 ml) was treated with N-(3-dimethylaminopropyl)-N'-ethylcarbodiimide hydrochloride (17.2 g, 89.6 mmol), hydroxybenzotriazole (1.37 g, 10.1 mmol) and (5-fluoro-2-pyridyl)hydrazine (11.4 g, 89.7 mmol). The reaction mixture was stirred at 20° C. for 4 hours then diluted with 2-methyltetrahyrofuran. The organic layer was washed with 2N citric acid solution (×2) and water. The combined citric acid layers were washed with $Et_2O$, basified with solid $K_2CO_3$ and extracted with DCM (×2). The combined DCM layers were dried over solid $Na_2SO_4$ and the solvent was removed under reduced pressure. Purification by FCC, eluting 10% acetone in DCM followed 10% (2M $NH_3$ in MeOH)/DCM to afford the title compound (7.6 g, 33%).

$^1H$ NMR (300 MHz, $CDCl_3$): 2.17 (3H, s), 2.38 (1H, dt, J=11.4, 3.5 Hz), 2.82 (1H, dt, J=11.9, 2.3 Hz), 2.96 (1H, dd, J=3.9, 9.9 Hz), 3.54 (1H, dd, J=9.9, 11.3 Hz), 3.65 (1H, dt, J=2.4, 11.3 Hz), 3.88 (1H, d, J=11.5 Hz), 4.04 (1H, dq, J=0.9, 3.9, 11.34 Hz), 6.62 (1H, dd, J=3.4, 9.0 Hz), 6.67 (1H, s), 7.29 (1H, quintet, J=2.9, 7.8, 8.97 Hz), 8.03 (1H, d, J=2.9 Hz), 8.64 (1H, br s).

b. (R)-3-(6-Fluoro-[1,2,4]triazolo[4,3-a]pyridin-3-yl)-4-methylmorpholine (Intermediate 214b)

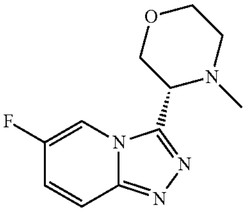 [SMILES: CN1CCOC[C@H]1c1nnc2ccc(F)cn12]

A solution of Intermediate 214a (6.5 g, 25.6 mmol) in 2-methyltetrahydrofuran (100 mL) was treated with triphenylphosphine (13.4 g, 51.2 mmol), triethylamine (10.3 g, 102.4 mmol) and cooled to 0° C. before hexachloroethane (12.1 g, 51.2 mmol) was slowly added. The reaction mixture was allowed to warm to rt over 1 hour, exotherming to 32° C. The reaction mixture was washed with water, then extracted into 1N HCl solution. The acidic layer was washed with $Et_2O$, basified with solid $Na_2SO_4$ and extracted with DCM (×2). The combined DCM phases were dried over $Na_2SO_4$ and the solvent was removed under reduced pressure to afford the title compound (4.20 g, 70%).

$^1H$ NMR (300 MHz, $CDCl_3$): 2.11 (3H, s), 2.52 (1H, dt, J=3.4, 11.7 Hz), 2.94 (1H, dt, J=1.9, 11.8 Hz), 3.66 (1H, t, J=11.1 Hz), 3.81 (1H, dt, J=2.4, 11.6 Hz), 3.92-4.01 (2H, m), 4.14 (1H, dd, J=3.8, 10.8 Hz), 7.21 (1H, ddd, J=2.3, 7.5 Hz), 7.75 (1H, dq, J=0.7, 5.0 Hz), 8.89 (1H, t, J=2.7 Hz).

c. (1S,4R)-4-((3-((R)-4-Methylmorpholin-3-yl)-[1,2,4]triazolo[4,3-a]pyridin-6-yl)oxy)-1,2,3,4-tetrahydronaphthalen-1-amine (Intermediate 214c)

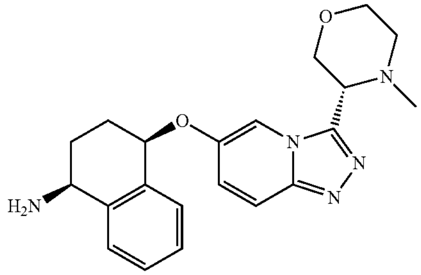 [SMILES: CN1CCOC[C@H]1c1nnc2ccc(O[C@@H]3CC[C@H](N)c4ccccc43)cn12]

A solution of Intermediate 214b (4.25 g, 18.0 mmol), (1R,4S)-4-amino-1,2,3,4-tetrahydronaphthalen-1-ol (2.93 g, 18.0 mmol) and 18-crown-6 ether (2.36 g, 9.0 mmol) in 2-methyltetrahydrofuran (30 mL) was degassed for 10 minutes under sonication bubbling argon through the mixture, then cooled to 0° C. and potassium tert-butoxide (2.4 g, 21.6 mmol) was added. The reaction mixture was allowed to warm to 20° C. over 3 hours with stirring. The reaction mixture was diluted with 2-methyltetrahydrofuran and washed with water, then dried over solid $Na_2SO_4$. The solvent removed under reduced pressure and purification by FCC, eluting with 0-10% 2N $NH_3$ in MeOH/DCM afforded the title compound (5.2 g, 70%).

$^1H$ NMR (300 MHz, $CDCl_3$): 1.88-2.00 (1H, m), 2.02-2.11 (2H, m), 2.12 (3H, s), 2.33-2.43 (1H, m), 2.50 (1H, dt, J=3.4, 11.8 Hz), 2.89 (1H, d, J=11.9 Hz), 3.62 (1H, t, J=11.1 Hz), 3.68 (1H, dt, J=2.3, 11.4 Hz), 3.92 (1H, dd, J=3.7, 7.3 Hz), 3.97 (1H, s), 4.00 (1H, dd, J=5.2, 8.1 Hz), 4.09 (1H, dd, J=3.8, 10.8 Hz), 5.24 (1H, t, J=4.4 Hz), 7.14 (1H, dd, J=2.2, 9.9 Hz), 7.28 (1H, d, J=7.3 Hz), 7.34 (1H, d, J=6.5 Hz), 7.40 (1H, dt, J=1.4, 7.5 Hz), 7.61 (1H, d, J=7.7 Hz), 7.68 (1H, d, J=9.9 Hz), 8.44 (1H, s).

d. 1-((1S,4R)-4-((3-((R)-4-Methylmorpholin-3-yl)-[1,2,4]triazolo[4,3-a]pyridin-6-yl)oxy)-1,2,3,4-tetrahydronaphthalen-1-yl)urea (Intermediate 214d)

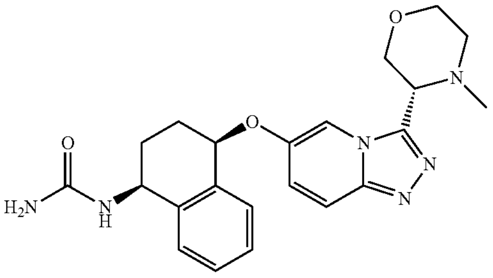 [SMILES: CN1CCOC[C@H]1c1nnc2ccc(O[C@@H]3CC[C@H](NC(N)=O)c4ccccc43)cn12]

A solution of triphosgene (1.72 g, 5.79 mmol) in DCM (25 mL) under nitrogen was cooled to −10° C. and a solution of Intermediate 214c (2.0 g, 5.27 mmol) and triethylamine (3.0 mL, 21.1 mmol) in DCM (25 mL) was dropwise added at or below −10° C. This solution was stirred at 0° C. for one hour before a solution of $NH_3$ in MeOH (2N, 80 mL, 158 mmol) pre-cooled to 0° C. was added and the reaction mixture was allowed to warm to 20° C. The mixture was partitioned between water and DCM and the two phases were separated. The aqueous phase was extracted with DCM (×2), the combined DCM layers were dried over solid $MgSO_4$ and the solvent was removed under reduced pressure. Purification by FCC eluting 0 to 10% (2N $NH_3$ in MeOH) in DCM afforded the title compound (1.42 g, 60%).

$^1H$ NMR (300 MHz, $CDCl_3$): 1.99-2.32 (3H, m), 2.14 (3H, s), 2.28-2.40 (1H, m), 2.51 (1H, dt, J=3.3, 11.8 Hz), 2.91 (1H, d, J=11.7 Hz), 3.64 (1H, t, J=11.1 Hz), 3.70 (1H. dt, J=2.0, 11.7 Hz), 3.88-4.01 (2H, m), 4.08 (1H, dd, J=3.7, 10.7 Hz), 4.53 (2H, s), 5.07 (2H, s), 5.21 (1H, t, J=4.4 Hz), 7.09 (1H, dd, J=2.2, 9.9 Hz), 7.27-7.41 (3H, m), 7.51 (1H, d, J=7.4 Hz), 7.64 (1H, d, J=9.9 Hz), 8.48 (1H, s).

e. Ethyl 4-(tert-butyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido) pyrimidine-2-carboxylate (Intermediate 214e)

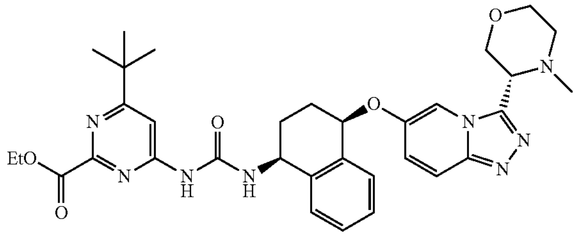 [SMILES: CCOC(=O)c1nc(NC(=O)N[C@H]2CC[C@@H](Oc3ccc4nnc([C@@H]5COCCN5C)n4c3)c3ccccc32)cc(C(C)(C)C)n1]

A solution of Intermediate 214d (710 mg, 1.70 mmol), Intermediate 1d (408 mg, 1.70 mmol), palladium(II)acetate (190 mg, 0.85 mmol), Xantphos (98 mg, 0.17 mmol) and cesium carbonate (776 mg, 0.17 mmol) in dioxan (20 mL) was degassed by bubbling argon through the mixture for 5 minutes under sonication and the reaction mixture was heated to 90° C. for 20 hours. The reaction mixture was filtered through a pad of Celite® washing the precipitate with EtOAc. The solvents were removed under reduced pressure. Purification by FCC eluting with 0-10% IMS in EtOAc afforded the title compound (610 mg, 57%).

$^1H$ NMR (300 MHz, $CDCl_3$): 1.26 (3H, t, J=7.2 Hz), 1.36 (9H, s), 1.39-1.44 (1H, m), 2.05 (3H, s), 2.07-2.59 (5H, m), 2.91 (1H, d, J=11.7 Hz), 3.63-3.78 (2H, m), 3.89-4.01 (1H, m), 4.08-4.32 (2H, m), 4.12 (2H, q, J=7.2 Hz), 5.17-5.28 (1H, m), 6.87 (1H, br s), 7.11 (1H, dd, J=2.0, 9.9 Hz), 7.28-7.42 (2H, m), 7.55 (1H, d, J=7.8 Hz), 7.70 (1H, d, J=7.8 Hz), 8.06 (1H, s), 8.53 (1H, s), 9.77 (1H, br s).

f. 4-(tert-Butyl)-N-(2-(dimethylamino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide (Example 214)

A solution of Intermediate 214e (100 mg, 0.17 mmol) in MeOH (3 mL) was added with ethanolamine (52 mg, 0.85 mmol) and warmed to 55° C. for 18 hours. The solvent was removed under reduced pressure and purified by MDAP followed by FCC eluting 0-10% (2M $NH_3$ in MeOH)/DCM afforded the title compound (16 mg, 14%).

LCMS (Method 3): Rt 4.20 min, m/z 671 [$MH^+$]. $^1H$ NMR (400 MHz, $d_6DMSO$): 1.31 (9H, s), 1.88-2.45 (7H, m), 1.99 (3H, s), 2.17 (6H, s), 2.90 (1H, d, J=11.8 Hz), 3.34-3.39 (2H, m, partially obscured by the water peak), 3.69 (1H, dt, J=11.9, 2.2 Hz), 3.74-3.82 (2H, m), 3.86 (1H, d, J=11.2 Hz), 3.98 (1H, dd, J=4.4, 9.4 Hz), 5.01 (1H, q, J=4.8 Hz), 5.51 (1H, t, J=3.7 Hz), 7.26-7.45 (5H, m), 7.70-7.79 (2H, m), 8.25 (1H, br s), 8.53 (1H, d, J=1.5 Hz), 8.58 (1H, t, J=5.7 Hz), 9.87 (1H, br s).

Example 215. 4-(tert-Butyl)-N-(2-((2-hydroxyethyl)(methyl)amino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido) pyrimidine-2-carboxamide

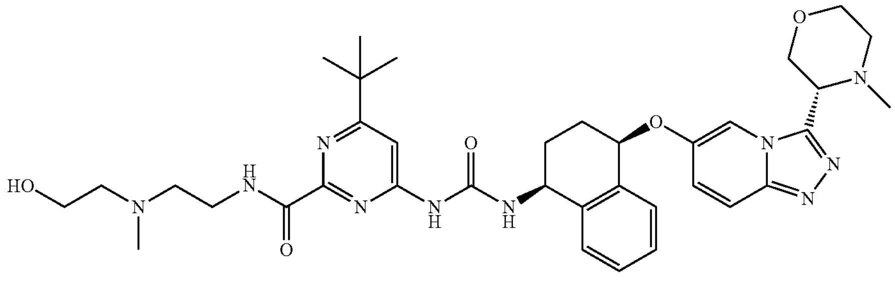 [SMILES: CN(CCO)CCNC(=O)c1nc(NC(=O)N[C@H]2CC[C@@H](Oc3ccc4nnc([C@@H]5COCCN5C)n4c3)c3ccccc32)cc(C(C)(C)C)n1]

A solution of Intermediate 214e (102 mg, 0.162 mmol) in IMS (3 mL) was added with 2-[(2-aminoethyl)(methyl)amino]ethanol (190 mg, 0.50 mmol) and warmed to 55° C. for 18 hours. The solvent was removed under reduced pressure and purified by HPLC (Kinetex C18, 10-95% MeCN in $H_2O$, 0.1% $HCO_2H$, 18 ml/min). The required fractions were evaporated under reduced pressure and the residue was dissolved in saturated bicarbonate solution. The aqueous phase was extracted with DCM (×2) and the combined organic layers were evaporated under reduced pressure. Final purification by MDAP (basic) afforded the title compound (16 mg, 14%).

LCMS (Method 3): Rt 2.69 min, m/z 701 [$MH^+$]. $^1H$ NMR (400 MHz, $d_6DMSO$): 1.32 (9H, s), 2.00 (3H, s), 2.03-2.19 (2H, m), 2.21-2.34 (4H, m), 2.40 (1H, dt, J=11.5, 3.2 Hz), 2.47 (2H, t, J=7.0 Hz), 2.52-2.56 (2H, m), 2.90 (1H, d, J=11.7 Hz), 3.35 (4H, q, J=6.3 Hz), 3.48 (2H, t, J=6.5 Hz), 3.69 (1H, dt, J=2.2, 11.1 Hz), 3.74-3.82 (2H, m), 3.86 (1H, d, J=10.9 Hz), 3.98 (1H, dd, J=4.3, 9.3 Hz), 5.01 (1H, q, J=8.9 Hz), 5.51 (1H, t, J=3.8 Hz), 7.26-7.46 (4H, m), 7.69-7.80 (2H, m), 8.19 (1H, s), 8.27 (1H, br s), 8.53 (1H, d, J=1.4 Hz), 8.61 (1H, t, J=5.6 Hz), 9.90 (1H, s).

Biological Assays

P38 Alpha Enzyme Inhibition Assay

The inhibitory activity of compounds was determined using an Alphascreen® (Perkin Elmer) based kinase activity assay. Kinase reactions consisted of 25 mM HEPES pH 7.5, 10 mM $MgCl_2$, 100 μM $Na_3VO_4$, 2 mM DTT, 0.05 mg/ml Tween 20, 100 pM p38 alpha (Invitrogen, PV3304), 1% DMSO and 0.3 μg/ml ATF-2 fusion protein (New England Biolabs, 9224). Compounds were incubated under these conditions for 2 hours, at 25° C., prior to the initiation of the kinase activity by the addition of the 250 μM ATP. Reaction volumes were 20 μL. After 1 hr at 25° C. reactions were stopped by the adding 10 μL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. $IC_{50}$ values were determined from concentration-response curves. Results are shown in the following Table.

| Example numbers | p38α inhibition |
|---|---|
| 12, 17, 21, 22, 23, 26, 30, 34, 36, 39, 41, 42, 43, 48, 49, 52, 53, 55, 56, 57, 59, 61, 63, 66, 67, 70, 71, 74, 75, 76, 79, 80, 82, 86, 88, 89, 90, 91, 92, 95, 96, 98, 99, 101, 103, 104, 106, 110, 112, 113, 115, 116, 118, 124, 125, 133, 134, 135, 137, 139, 141, 144, 147, 148, 150, 153, 156, 157, 159, 160, 161, 162, 163, 164, 165, 167, 168, 170, 171, 172, 177, 178, 179, 180, 185, 187, 189, 191, 192, 193, 194, 196, 199, 202, 203, 214, 215 | + |
| 1, 2, 3, 4, 5, 6, 7, 8, 9, 10, 11, 13, 14, 15, 16, 18, 19, 20, 24, 25, 27, 28, 29, 32, 35, 37, 38, 40, 44, 45, 46, 47, 50, 51, 54, 58, 60, 62, 64, 65, 68, 69, 72, 73, 77, 78, 81, 83, 84, 85, 87, 93, 94, 97, 100, 102, 105, 107, 108, 109, 111, 114, 117, 119, 120, 121, 122, 123, 126, 127, 128, 129, 130, 131, 132, 136, 138, 140, 142, 143, 145, 146, 149, 151, 152, 154, 155, 158, 166, 169, 173, 174, 175, 176, 181, 182, 183, 184, 186, 188, 190, 195, 197, 198, 200, 201, 204, 205, 206, 207, 208, 209, 210, 211, 212, 213 | ++ |

In the table above, p38α potencies ($IC_{50}$ values) are indicated as follows:

1-10 nM '+';

<1 nM '++'

LPS-Stimulated PBMC TNFα Release Assay

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using MSD plates on the Sector Imager 6000 (MesoScale).

A dose response curve to each test compound was performed and the effect of compound in each experiment was expressed as a percentage inhibition of the control TNFα release. Dose response curves were plotted and compound potency ($IC_{50}$) was determined. Compounds were tested in at least three separate experiments. Results are shown in the following Table.

| Example numbers | LPS-stimulated PBMC TNFα release inhibition |
|---|---|
| 15, 21, 23, 24, 31, 32, 34, 37, 47, 49, 55, 56, 57, 59, 62, 64, 65, 66, 70, 74, 75, 76, 78, 81, 82, 84, 85, 86, 87, 88, 91, 92, 93, 94, 95, 97, 99, 102, 103, 107, 108, 109, 111, 113, 119, 120, 125, 126, 127, 128, 129, 130, 134, 136, 137, 138, 139, 140, 145, 151, 152, 154, 155, 159, 166, 195, 196, 197, 198, 199, 200, 208, 211, 214, 215 | + |
| 1, 2, 3, 4, 5, 6, 7, 8, 9, 10, 11, 12, 13, 18, 20, 26, 28, 30, 40, 43, 44, 45, 46, 53, 54, 58, 60, 61, 67, 68, 69, 72, 73, 77, 80, 83, 89, 96, 100, 105, 110, 112, 118, 121, 122, 123, 124, 131, 132, 142, 143, 146, 149, 158, 169, 171, 173, 174, 175, 176, 178, 181, 183, 187, 188, 189, 190, 191, 192, 193, 201, 202, 204, 205, 206, 210, 212, 213 | ++ |
| 14, 16, 19, 25, 27, 29, 35, 36, 38, 39, 50, 51, 52, 104, 114, 117, 182, 184, 186, 207, 209 | +++ |

In the table above, human PBMC potencies ($IC_{50}$ values) are indicated as follows:

>5 nM '+';

1-5 nM '++';

<1 nM '+++'

Anti-Inflammatory Activity of P38 Alpha Inhibitors in a LPS-Challenge Model in Rat Twelve hours after compound/vehicle administration, rats are challenged intratracheally with LPS. Four hours later, rats are sacrificed, bronchoalveolar lavage fluid (BALF) collected and the total cell number and neutrophil numbers determined. Anti-inflammatory activity is represented by a reduction in the number of neutrophils as compared to a vehicle-treated control group.

Solubility Assays

Kinetic Solubility

Using a 10 μM stock solution of each test and control compound (hydrocortisone, reserpine) in 100% DMSO, dilutions were prepared to a theoretical concentration of 200 μM in both 0.1 M potassium phosphate buffer containing 0.8% NaCl (PBS), pH 7.4 (2% DMSO final), and in 100% DMSO. An aliquot of the 200 μM DMSO solution was then further diluted to 10 μM and all dilutions (n=2, in 96-well plates) allowed to equilibrate at RT on an orbital shaker for two hours. The PBS dilutions were filtered using a Multiscreen HTS solubility filter plate (Millipore) and filtrate was analysed by LC-UV with confirmation of the peak of interest by mass spectrometry. The concentration of compound in PBS filtrate was determined by comparing the UV absorbance peak with that of the two DMSO dilutions as calibration standards.

The effective range of the assay is 10 to 200 μM and compounds returning values close to the upper limit may have much higher solubilities.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

(I)

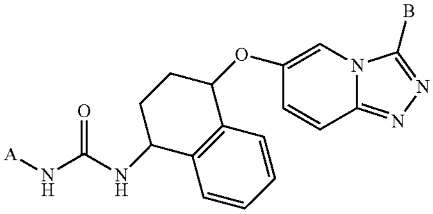

wherein:

A is a group of formula (Ia), (Ib), (Ic), or (Id):

(Ia)

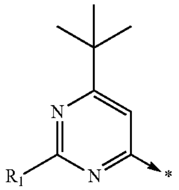

(Ib)

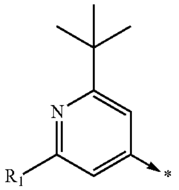

(Ic)

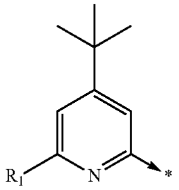

(Id)

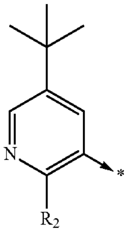

B is a group of formula (IIa), (IIb), (IIc), (IId), (IIe), (IIf), (IIg), (II h), or (Iii):

(IIa)

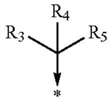

(IIb)

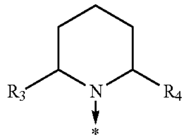

(IIc)

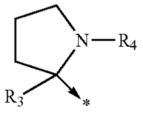

(IId)

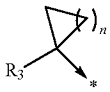

(IIe)

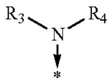

(IIf)

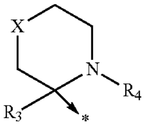

(IIg)

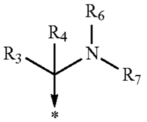

(IIh)

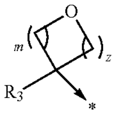

(IIi)

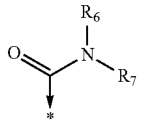

$R_1$ is H, —CN, linear or branched $(C_1\text{-}C_4)$alkyl-, $(R_8)(R_9)$NC(O)—, $R_{12}$O—$(C_1\text{-}C_4)$alkylene-, $(R_8)(R_9)$N—$(C_1\text{-}C_4)$alkylene-, $(C_1\text{-}C_4)$alkyl-C(O)O—$(C_1\text{-}C_4)$alkylene-, $(R_8)$C(O)O—; $(C_1\text{-}C_4)$alkyl-S$(O)_2$NH—, $(C_1\text{-}C_4)$alkyl-S—, $(R_8)(R_9)$N—, $(R_8)(R_9)$N—$(C_1\text{-}C_4)$alkylene-C(O)NH—$(C_1\text{-}C_4)$alkylene-, optionally substituted $(C_3\text{-}C_7)$heterocycloalkyl-C(O)NH—$(C_1\text{-}C_4)$alkylene-, $(C_1\text{-}C_4)$alkyl-OC(O)—, or $(R_8)(R_9)$N—$(C_1\text{-}C_4)$alkylene-O—$(C_1\text{-}C_4)$alkylene-;

$R_2$ is H, linear or branched $(C_1\text{-}C_4)$alkyl-, or $(C_1\text{-}C_4)$alkyl-O—;

$R_3$ is H or linear or branched $(C_1\text{-}C_4)$alkyl-;

$R_4$ is H or linear or branched $(C_1\text{-}C_4)$alkyl-;

$R_5$ is H, linear or branched $(C_1\text{-}C_4)$alkyl-, $R_{12}$O—$(C_1\text{-}C_4)$alkylene-, or $R_{12}$O—;

$R_6$ is H or linear or branched $(C_1\text{-}C_4)$alkyl-;

$R_7$ is H or linear or branched $(C_1\text{-}C_4)$alkyl-; or $R^6$ and $R^7$ may form, together with the nitrogen atom to which they are attached, an optionally substituted 4-7 membered saturated heterocyclic monocyclic ring system, optionally containing a further oxygen or nitrogen heteroatom;

X is —$CH_2$—, —($R_3$)N—, or —O—;

$R_8$ is H, linear or branched —($C_1$-$C_4$)alkyl-, or $R_{12}$O—($C_1$-$C_4$)alkylene-;

$R_9$ is H, linear or branched ($C_1$-$C_4$)alkyl-, optionally substituted ($C_3$-$C_7$)heterocycloalkyl-, optionally substituted ($C_3$-$C_7$)cycloalkyl-, $R_{12}$O—($C_1$-$C_4$)alkylene-, ($R_{10}$)($R_{11}$)N—($C_1$-$C_4$)alkylene-, or ($R_{10}$)($R_{11}$)N—($C_1$-$C_4$)alkylene-O—($C_1$-$C_4$)alkylene-, wherein said ($C_1$-$C_4$)alkylene- in ($C_3$-$C_7$)cycloalkyle-, $R_{12}$O—($C_1$-$C_4$)alkylene-, ($R_{10}$)($R_{11}$)N—($C_1$-$C_4$)alkylene-, and ($R_{10}$)($R_{11}$)N—($C_1$-$C_4$)alkylene-O—($C_1$-$C_4$)alkylene may be optionally substituted with one or more groups selected from the group consisting of linear or branched ($C_1$-$C_4$)alkyl-, spiro-($C_1$-$C_6$)cycloalkyl, and spiro-($C_1$-$C_6$)heterocycloalkyl;

or $R^8$ and $R^9$ may form, together with the nitrogen atom to which they are attached, an optionally substituted 4-7 membered saturated heterocyclic monocyclic ring system, optionally containing a further oxygen or nitrogen heteroatom;

$R_{10}$ is H, linear or branched ($C_1$-$C_4$)alkyl-, $R_{12}$O—($C_1$-$C_4$)alkylene-, ($C_3$-$C_7$)cycloalkyl-, or ($C_3$-$C_7$)heterocycloalkyl-;

$R_{11}$ is H, linear or branched ($C_1$-$C_4$)alkyl-, or $R_{12}$O—($C_1$-$C_4$)alkylene-;

or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom;

n is an integer from 1 to 4;

m is an integer from 1 to 2;

z is an integer from 1 to 2;

wherein "optionally substituted" means substitution by one or more groups selected from the group consisting of linear or branched ($C_1$-$C_4$)alkyl-, halo, $R_{12}$O—($C_1$-$C_4$)alkylene-, $R_{12}$O—, oxo, and ($C_1$-$C_4$)alkyl($C_1$-$C_4$)alkyl)N—;

$R_{12}$ is H or linear or branched ($C_1$-$C_4$)alkyl-; and the symbol * indicates the point of attachment to the rest of the molecule;

with the proviso that when A is (Ib) then $R_1$ is not H, $CH_3$ or CN;

or a pharmaceutically acceptable salt thereof.

2. A compound or pharmaceutically acceptable salt according to claim 1, wherein B is a group of formula (IIa), (IIb), (IIc), (IId), (IIe), (IIg), (IIh), or (IIi):

(IIa)

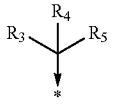

(IIb)

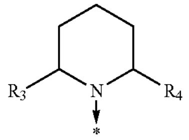

(IIc)

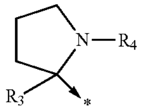

-continued (IId)

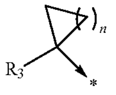

(IIe)

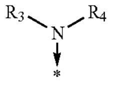

(IIg)

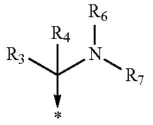

(IIh)

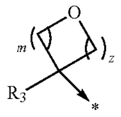

(IIi)

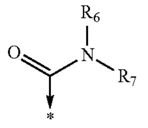

$R_1$ is H, —CN, linear or branched ($C_1$-$C_4$)alkyl, ($R_8$)($R_9$)NC(O)—, $R_{12}$O—($C_1$-$C_4$)alkylene-, ($R_8$)($R_9$)N—($C_1$-$C_4$)alkylene-, ($C_1$-$C_4$)alkyl-S(O)$_2$NH—, ($C_1$-$C_4$)alkyl-S—, ($C_1$-$C_4$)alkyl-OC(O)—, or ($R_8$)($R_9$)N—($C_1$-$C_4$)alkylene-O—($C_1$-$C_4$)alkylene-;

$R^6$ and $R^7$ form, together with the nitrogen atom to which they are attached, an optionally substituted 4-7 membered saturated heterocyclic monocyclic ring system, optionally containing a further oxygen or nitrogen heteroatom;

$R_8$ is H, linear or branched —($C_1$-$C_4$)alkyl-;

$R_9$ is linear or branched ($C_1$-$C_4$)alkyl-, optionally substituted ($C_3$-$C_7$)cycloalkyl-, $R_{12}$O—($C_1$-$C_4$)alkylene-, or ($R_{10}$)($R_{11}$)N—($C_1$-$C_4$)alkylene-, wherein said ($C_1$-$C_4$)alkylene- in ($R_{10}$)($R_{11}$)N—($C_1$-$C_4$)alkylene- may be optionally substituted with one or more groups selected from the group consisting of linear or branched ($C_1$-$C_4$)alkyl-, spiro-($C_1$-$C_6$)cycloalkyl, and spiro-($C_1$-$C_6$)heterocycloalkyl;

or $R^8$ and $R^9$ may form, together with the nitrogen atom to which they are attached, an optionally substituted 4-7 membered saturated heterocyclic monocyclic ring system, optionally containing a further oxygen or nitrogen heteroatom;

$R_{10}$ is linear or branched ($C_1$-$C_4$)alkyl- or ($C_3$-$C_7$)cycloalkyl-;

$R_{11}$ is linear or branched ($C_1$-$C_4$)alkyl- or $R_{12}$O—($C_1$-$C_4$)alkylene-;

or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom;

n is 3;

m is 1; and z is 1.

3. A compound or pharmaceutically acceptable salt according to claim 1, wherein A is group of formula (Ia):

(Ia)

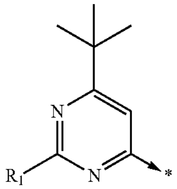

B is a group of formula (IIa) or (IIe):

(IIa)

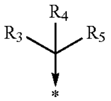

(IIe)

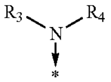

$R_1$ is H or $(R_8)(R_9)NC(O)$—;

$R_3$ is linear or branched $(C_1$-$C_4)$alkyl-;

$R_5$ is linear or branched $(C_1$-$C_4)$alkyl-, $R_{12}O$—$(C_1$-$C_4)$ alkylene-, or $R_{12}O$—;

$R_8$ is H;

$R_9$ is $(R_{10})(R_{11})N$—$(C_1$-$C_4)$alkylene-, wherein said $(C_1$-$C_4)$alkylene- in $(R_{10})(R_{11})N$—$(C_1$-$C_4)$alkylene- may be optionally substituted with one or more linear or branched $(C_1$-$C_4)$ alkyl- groups;

$R_{10}$ is linear or branched $(C_1$-$C_4)$alkyl-;

$R_{11}$ is linear or branched $(C_1$-$C_4)$alkyl- or and $R_{12}O$—$(C_1$-$C_4)$alkylene-;

or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom.

4. A compound or pharmaceutically acceptable salt according to claim 1, wherein A is group of formula (Ib):

(Ib)

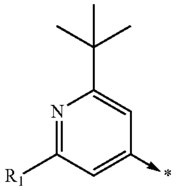

B is a group of formula (IIa) or (IIe):

(IIa)

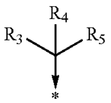

(IIe)

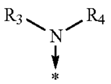

$R_1$ is H or $(R_8)(R_9)NC(O)$—;

$R_3$ is linear or branched $(C_1$-$C_4)$alkyl-;

$R_5$ is linear or branched $(C_1$-$C_4)$alkyl-, $R_{12}O$—$(C_1$-$C_4)$ alkylene-, or $R_{12}O$—;

$R_8$ is H;

$R_9$ is $(R_{10})(R_{11})N$—$(C_1$-$C_4)$alkylene-, wherein said $(C_1$-$C_4)$alkylene- in $(R_{10})(R_{11})N$—$(C_1$-$C_4)$alkylene-may be optionally substituted with one or more linear or branched $(C_1$-$C_4)$alkyl- groups;

$R_{10}$ is linear or branched $(C_1$-$C_4)$alkyl-;

$R_{11}$ is linear or branched $(C_1$-$C_4)$alkyl- or $R_{12}O$—$(C_1$-$C_4)$alkylene-;

or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom.

5. A compound or pharmaceutically acceptable salt according to claim 1, wherein A is group of formula (Ia):

(Ia)

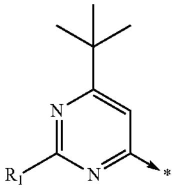

B is a group of formula (IIa), (IIb), (IIc), (IId), (IIe), (IIg), or (IIi):

(IIa)

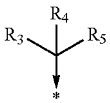

(IIb)

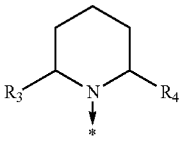

(IIc)

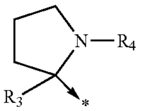

(IId)

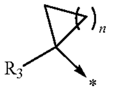

(IIe)

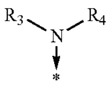

(IIg)

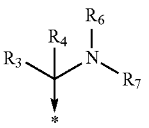

-continued (IIh)

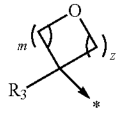

(IIi)

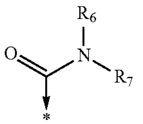

- $R_1$ is H, linear or branched ($C_1$-$C_4$)alkyl, ($R_8$)($R_9$)NC(O)—, $R_{12}$O—($C_1$-$C_4$)alkylene-, ($R_8$)($R_9$)N—($C_1$-$C_4$)alkylene-, ($C_1$-$C_4$)alkyl-S(O)$_2$NH—, ($C_1$-$C_4$)alkyl-S—, ($C_1$-$C_4$)alkyl-OC(O)—, or ($R_8$)($R_9$)N—($C_1$-$C_4$)alkylene-O—($C_1$-$C_4$)alkylene-;
- $R^6$ and $R^7$ form, together with the nitrogen atom to which they are attached an optionally substituted 4-7 membered saturated heterocyclic monocyclic ring system, optionally containing a further oxygen or nitrogen heteroatom;
- $R_8$ is H or linear or branched —($C_1$-$C_4$)alkyl-;
- $R_9$ is linear or branched ($C_1$-$C_4$)alkyl-, optionally substituted ($C_3$-$C_7$)cycloalkyl-, $R_{12}$O—($C_1$-$C_4$)alkylene-, or ($R_{10}$)($R_{11}$)N—($C_1$-$C_4$)alkylene-, wherein said ($C_1$-$C_4$)alkylene- in ($R_{10}$)($R_{11}$)N—($C_1$-$C_4$)alkylene- may be optionally substituted with one or more groups selected from the group consisting of linear or branched ($C_1$-$C_4$)alkyl-, spiro-($C_1$-$C_6$)cycloalkyl, and spiro-($C_1$-$C_6$)heterocycloalkyl;
- or $R^8$ and $R^9$ may form, together with the nitrogen atom to which they are attached, an optionally substituted 4-7 membered saturated heterocyclic monocyclic ring system, optionally containing a further oxygen or nitrogen heteroatom;
- $R_{10}$ is linear or branched ($C_1$-$C_4$)alkyl- or ($C_3$-$C_7$)cycloalkyl-;
- $R_{11}$ is linear or branched ($C_1$-$C_4$)alkyl- or $R_{12}$O—($C_1$-$C_4$)alkylene-;
- or $R^{10}$ and $R^{11}$ may form together with the nitrogen atom to which they are attached an optionally substituted 4-7 membered saturated heterocyclic monocyclic ring system, optionally containing a further oxygen or nitrogen heteroatom;
- n is 3;
- m is 1; and
- z is 1.

6. A compound or pharmaceutically acceptable salt according to claim 1, wherein A is group of formula (Ib):

(Ib)

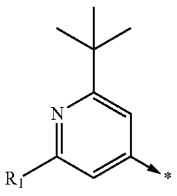

B is a group of (IIa), (IIc), or (IIe):

(IIa)

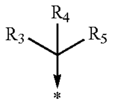

(IIc)

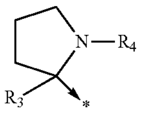

(IIe)

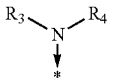

- $R_1$ is H, ($R_8$)($R_9$)NC(O)—, $R_{12}$O—($C_1$-$C_4$)alkylene-, or ($C_1$-$C_4$)alkyl-S(O)$_2$NH—;
- $R_3$ is linear or branched ($C_1$-$C_4$)alkyl-;
- $R_5$ is linear or branched ($C_1$-$C_4$)alkyl-, $R_{12}$O—($C_1$-$C_4$)alkylene-, or $R_{12}$O—;
- $R_8$ is H;
- $R_9$ is $R_{12}$O—($C_1$-$C_4$)alkylene- or ($R_{10}$)($R_{11}$)N—($C_1$-$C_4$)alkylene-, wherein said ($C_1$-$C_4$)alkylene- in ($R_{10}$)($R_{11}$)N—($C_1$-$C_4$)alkylene- may be optionally substituted with one or more linear or branched ($C_1$-$C_4$)alkyl- groups;
- $R_{10}$ is linear or branched ($C_1$-$C_4$)alkyl-;
- $R_{11}$ is linear or branched ($C_1$-$C_4$)alkyl- or $R_{12}$O—($C_1$-$C_4$)alkylene-;
- or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom;
- wherein "optionally substituted" means substitution by one or more $R_{12}$O groups.

7. A compound or pharmaceutically acceptable salt according to claim 1, wherein A is a group of formula (Ic) or (Id):

(Ic)

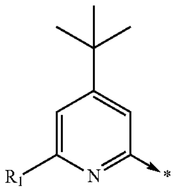

(Id)

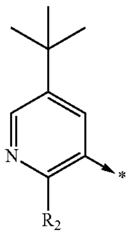

B is a group of formula (IIa) or (IIc):

(IIa)

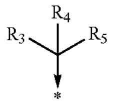

(IIc)

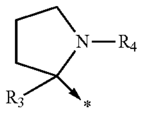

$R_1$ is H or CN, $(R_8)(R_9)NC(O)$—;

$R_2$ is linear or branched $(C_1$-$C_4)$alkyl-, or $(C_1$-$C_4)$alkyl-O—;

$R_4$ is linear or branched $(C_1$-$C_4)$alkyl-;

$R_5$ is linear or branched $(C_1$-$C_4)$alkyl-, $R_8$ is H;

$R_9$ is $(R_{10})(R_{11})N$—$(C_1$-$C_4)$alkylene-;

$R_{10}$ is linear or branched $(C_1$-$C_4)$alkyl-;

$R_{11}$ is linear or branched $(C_1$-$C_4)$alkyl-;

or $R^{10}$ and $R^{11}$ may form, together with the nitrogen atom to which they are attached, an optionally substituted 4-7 membered saturated heterocyclic monocyclic ring system, optionally containing a further oxygen or nitrogen heteroatom.

8. A compound or pharmaceutically acceptable salt according to claim 1, which is selected from the group consisting of 4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-hydroxyethyl)(methyl)amino)ethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(dimethylamino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(3-methoxyazetidin-1-yl)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

6-(tert-butyl)-4-(3-((1S,4R)-4-((3-(tert-butyl)-[1,2,4]triazolo[4,3-a]pyridin-6-yl)oxy]-1,2,3,4-tetrahydronaphthalen-1-yl}ureido)-N-(2-(4-hydroxypiperidin-1-yl)ethyl)picolinamide;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

4-(tert-Butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy]-1,2,3,4-tetrahydronaphthalen-1-yl)ureido)-N-(2-morpholinoethyl)pyrimidine-2-carboxamide;

1-(6-(tert-butyl)-2-(hydroxymethyl)pyrimidin-4-yl)-3-((1S,4R)-4-((3-(2-methoxypropan-2-yl)-[1,2,4]triazolo[4,3-a]pyridine-6-yl)oxy)-1,2,3,4-tetrahydronaphthalene-1-yl)urea;

1-(6-(tert-Butyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-((dimethylamino)methyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

4-(tert-Butyl)-N-(2-(dimethylamino)ethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-Butyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

4-(tert-Butyl)-N-(2-(dimethylamino)ethyl)-6-(3-((1S,4R)-4-((3-((2R,6S)-2,6-dimethylpiperidin-1-yl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-Butyl)-2-(morpholinomethyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-Butyl)-N-(2-(dimethylamino)ethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-Butyl)-2-(hydroxymethyl)pyrimidin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea;

N-((4-(tert-Butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-2-(dimethylamino)acetamide;

4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

(4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methyl acetate;

1-(6-(tert-butyl)-2-(hydroxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

4-(tert-butyl)-N-(2-(dimethylamino)ethyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)pyrimidine-2-carboxamide;

N-(4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidin-2-yl)methanesulfonamide;

1-(6-(tert-butyl)-2-(4-methylpiperazin-1-yl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

4-(tert-butyl)-N-(2-(dimethylamino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-((S)-2-methylpyrrolidin-2-yl)-[1,2,4]triazolo[4,3-a]pyridin-6-yl)oxy)-1,2,3,4-tetrahydronaphthalen-1-yl)ureido)pyrimidine-2-carboxamide;

1-(5-(tert-butyl)-2-methoxypyridin-3-yl)-3-((1S,4R)-4-((3-((S)-1-methylpyrrolidin-2-yl)-[1,2,4]triazolo[4,3-a]pyridin-6-yl)oxy)-1,2,3,4-tetrahydronaphthalen-1-yl)urea hydrochloride salt;

Ethyl 4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyrimidine-2-carboxylate;

4-(tert-butyl)-N-(2-(dimethylamino)ethyl)-6-(3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpyrimidine-2-carboxamide;

1-(4-(tert-butyl)-6-cyanopyridin-2-yl)-3-((1S,4R)-4-((3-((R)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-methylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-ethylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-isopropylpyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-Butyl)-2-(methoxymethyl)pyrimidin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(4-(tert-butyl)pyridin-2-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(6-(tert-butyl)pyrimidin-4-yl)-3-((1S,4R)-4-((3-((S)-2-methylpiperidin-1-yl)-[1,2,4]triazolo[4,3-a]pyridin-6-yl)oxy)-1,2,3,4-tetrahydronaphthalen-1-yl)urea;

1-(6-(tert-butyl)pyrimidin-4-yl)-3-((1S,4R)-4-((3-((S)-1-methylpyrrolidin-2-yl)-[1,2,4]triazolo[4,3-a]pyridine-6-yl)oxy)-1,2,3,4-tetrahydronaphthalene-1-yl)urea hydrochloride;

1-(6-(tert-butyl)pyrimidin-4-yl)-3-((1S,4R)-4-((3-((S)-1-isopropylpyrrolidin-2-yl)-[1,2,4]triazolo[4,3-a]pyridine-6-yl)oxy)-1,2,3,4-tetrahydronaphthalene-1-yl)urea hydrochloride;

1-(6-(tert-butyl)-2-(methylthio)pyrimidin-4-yl)-3-((1S,4R)-4-((3-((S)-1-[1,2,4]triazolo[4,3-a]pyridine-6-yl)oxy)-1,2,3,4-tetrahydronaphthalen-1-yl)urea;

1-(6-(tert-butyl)-2-(methylthio)pyrimidin-4-yl)-3-((1S,4R)-4-((3-((S)-1,2-dimethylpyrrolidin-2-yl)-[1,2,4]triazolo[4,3-a]pyridine-6-yl)oxy)-1,2,3,4-tetrahydronaphthalen-1-yl)urea;

1-(2-(tert-Butyl)-5-methylpyridin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(2-(tert-Butyl)-6-(hydroxymethyl)pyridin-4-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

1-(5-(tert-butyl)-2-methoxypyridin-3-yl)-3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)urea;

6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-methylpicolinamide;

4-(tert-butyl)-N-(2-(dimethylamino)ethyl)-6-(3-((1S,4R)-4-((3-(methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalene-1-yl)ureido)pyrimidin-2-carboxamide;

1-(2-(tert-butyl)-6-((2-morpholinoethoxy)methyl)pyrimidin-4-yl)-3-((1S,4R)-4-((3-(2-methoxypropan-2-yl)-[1,2,4]triazolo[4,3-a] pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

4-(tert-butyl)-N-(2-(dimethylamino)ethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide;

6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)-N-(2-hydroxyethyl)picolinamide;

6-(tert-Butyl)-N-(2-(dimethylamino)ethyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)picolinamide;

1-(6-(tert-Butyl)-2-((2-morpholinoethoxy)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-N-(2-hydroxyethyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-morpholinoethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isopropyl-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-N-(2-(dimethylamino)ethyl)-6-(3-((1S,4R)-4-((3-(morpholine-4-carbonyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-methoxyethyl)(methyl)amino)ethyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-cyclopentyl-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)pyrimidine-2-carboxamide;

1-(6-(tert-butyl)-2-(3,3-difluoroazetidine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylazetidin-3-yl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-hydroxyethyl)-N-methylpyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1s,3R)-3-(hydroxymethyl)cyclobutyl)pyrimidine-2-carboxamide;

4-(tert-butyl)-N-(1-methylazetidin-3-yl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

N-(2-(bis(2-methoxyethyl)amino)ethyl)-4-(tert-butyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

1-(2-((bis(2-methoxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

1-(2-((bis(2-hydroxyethyl)amino)methyl)-6-(tert-butyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

1-(6-(tert-butyl)-2-(((2-hydroxyethyl)(methyl)amino)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

N-(2-(1,4-oxazepan-4-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-(dimethylamino)ethyl)-6-(3-((1S,4R)-4-((3-isobutyl-[1,2,4]triazolo[4,3-a]pyridin-6-yl)oxy)-1,2,3,4-tetrahydronaphthalen-1-yl)ureido)pyrimidine-2-carboxamide;

N-(2-(bis(2-methoxyethyl)amino)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((R)-3-hydroxypyrrolidin-1-yl)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-(dimethylamino)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-(3-methyloxetan-3-yl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-N-(2-morpholinoethyl)-6-(3-((1S,4R)-4-((3-neopentyl-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-3-morpholinopropanamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)pyrimidine-2-carboxamide;

4-(tert-butyl)-N-(2-((2-methoxyethyl)(methyl)amino)ethyl)-6-(3-((1S,4R)-4-((3-((S)-1-methoxyethyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(methyl(oxetan-3-yl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-hydroxypiperidin-1-yl)ethyl)pyrimidine-2-carboxamide;

4-(tert-butyl)-6-(3-((1S,4R)-4-((3-(1-methylcyclobutyl)-[1,2,4]triazolo[4,3-a]pyridin-6-yl)oxy)-1,2,3,4-tetrahydronaphthalen-1-yl)ureido)-N-(2-morpholinoethyl)pyrimidine-2-carboxamide;

(S)—N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylpyrrolidine-2-carboxamide;

N-(3-(1,4-Oxazepan-4-yl)propyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide partial formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-(dimethylamino)-2-methylpropan-2-yl)pyrimidine-2-carboxamide;

1-(6-(tert-Butyl)-2-((3-oxopiperazin-1-yl)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea partial formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)-N-methylpyrimidine-2-carboxamide;

1-(6-(tert-butyl)-2-(4-(2-hydroxyethyl)piperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-(dimethylamino)propyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methylpiperazin-1-yl)ethyl)pyrimidine-2-carboxamide;

N-(2-(bis(2-hydroxyethyl)amino)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

N-(2-(1,4-oxazepan-4-yl)ethyl)-4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-((2-hydroxyethyl)(methyl)amino)ethyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide;

4-(tert-butyl)-N-(2-((2-hydroxyethyl)(methyl)amino)ethyl)-6-(3-((1S,4R)-4-((3-(2-methoxypropan-2-yl)-[1, 2,4]triazolo[4,3-a]pyridin-6-yl)oxy)-1,2,3,4-tetrahydronaphthalen-1-yl)ureido)pyrimidine-2-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-1-methylazetidine-3-carboxamide;

N-((4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidin-2-yl)methyl)-3-(dimethylamino)propanamide;

1-(6-(tert-butyl)-2-(4-methylpiperazine-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N—((R)-1-methylpyrrolidin-3-yl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(2-(dimethylamino)ethoxy)ethyl)pyrimidine-2-carboxamide;

4-(tert-butyl)-N-(2-morpholinoethyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(3-morpholinopropyl)-6-(3-((1S,4R)-4-((3-(tert-pentyl)-[1,2,4]triazolo[4,3-a]pyridin-6-yl)oxy)-1,2,3,4-tetrahydronaphthalen-1-yl)ureido)pyrimidine-2-carboxamide;

1-(6-(tert-butyl)-2-(4-methyl-1,4-diazepane-1-carbonyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(1-methylpiperidin-4-yl)pyrimidine-2-carboxamide;

1-(6-(tert-Butyl)-2-((4-methyl-2-oxopiperazin-1-yl)methyl)pyrimidin-4-yl)-3-((1S,4R)-4-((3-(tert-butyl)-[1,2,4]triazolo[4,3-a]pyridin-6-yl)oxy)-1,2,3,4-tetrahydronaphthalen-1-yl)urea formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N—((S)-1-methylpyrrolidin-3-yl)pyrimidine-2-carboxamide;

4-(tert-butyl)-N-(2-((2-methoxyethyl)(methyl)amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(3-methoxyazetidin-1-yl)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-hydroxyethyl)-6-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)pyrimidine-2-carboxamide;

N-(2-(azetidin-1-yl)ethyl)-4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)ethyl)pyrimidine-2-carboxamide;

4-(tert-butyl)-6-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)pyrimidine-2-carboxamide;

1-(6-(tert-butyl)-2-((2-morpholinoethoxy)methyl)pyrimidin-4-yl)-3-((1S,4R)-4-((3-(2-methoxypropan-2-yl)-[1,2,4]triazolo[4,3-a]pyridin-6-yl)oxy)-1,2,3,4-tetrahydronaphthalen-1-yl)urea;

4-(tert-butyl)-N-(2-((2-hydroxyethyl)(methyl)amino)ethyl)-6-(3-((1S,4R)-4-((3-(1-methylcyclopropyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)pyrimidine-2-carboxamide;

4-(tert-butyl)-N-(2-(dimethylamino)-2-ethylbutyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)-2-methylpropyl)pyrimidine-2-carboxamide;

4-(tert-butyl)-N-(1-(dimethylamino)cyclopropyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((4-(dimethylamino)tetrahydro-2H-pyran-4-yl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-butyl)-N-(2-(ethyl(methyl)amino)-2-methylpropyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((1-(dimethylamino)cyclohexyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-((1-(dimethylamino)cyclopentyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-butyl)-N-(2-(ethyl(methyl)amino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)-N-(2-methyl-2-(4-methylpiperazin-1-yl)propyl)pyrimidine-2-carboxamide;

4-(tert-Butyl)-N-((1-(dimethylamino)cyclobutyl)methyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclopropyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((4-(dimethylamino)tetrahydro-2H-pyran-4-yl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclohexyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclobutyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1-(dimethylamino)cyclopentyl)methyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(cyclopropyl(methyl)amino)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-((1S,2S)-2-(dimethylamino)cyclohexyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-N-(2-(3-methoxyazetidin-1-yl)ethyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)-2-ethylbutyl)pyrimidine-2-carboxamide;

4-(tert-butyl)-6-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-(3-methoxyazetidin-1-yl)-2-methylpropyl)pyrimidine-2-carboxamide;

4-(tert-butyl)-N-(2-(3-methoxyazetidin-1-yl)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-methyl-2-(4-methylpiperazin-1-yl)propyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(3-methoxyazetidin-1-yl)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(dimethylamino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-(ethyl(methyl)amino)-2-methylpropyl)-6-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)-2-methylpropyl)pyrimidine-2-carboxamide;

4-(tert-butyl)-6-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)-2-methylpropyl)pyrimidine-2-carboxamide;

4-(tert-butyl)-N-(2-((2-methoxyethyl)(methyl)amino)-2-methylpropyl)-6-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-N-(2-(dimethylamino)ethyl)-6-(3-((1S,4R)-4-((3-(2-ethoxypropan-2-yl)-[1,2,4]triazolo[4,3-a]pyridin-6-yl)oxy)-1,2,3,4-tetrahydronaphthalen-1-yl)ureido)pyrimidine-2-carboxamide formate salt;

4-(tert-butyl)-N-(2-((2-hydroxyethyl)(methyl)amino)ethyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

N-(2-(1,4-oxazepan-4-yl)ethyl)-4-(tert-butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

4-(tert-butyl)-N-(2-(dimethylamino)-2-methylpropyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)pyrimidine-2-carboxamide;

4-(tert-Butyl)-6-(3-((1S,4R)-4-((3-(1-methylcyclopentyl)-[1,2,4]triazolo[4,3-a]pyridin-6-yl)oxy)-1,2,3,4-tetrahydronaphthalen-1-yl)ureido)-N-(3-morpholinopropyl)pyrimidine-2-carboxamide formate salt;

6-(tert-butyl)-N-(2-(dimethylamino)ethyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(3-morpholinopropyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)picolinamide;

N-(2-(1,4-oxazepan-4-yl)ethyl)-6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)picolinamide;

6-(tert-butyl)-N-(2-(dimethylamino)ethyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(ethyl(methyl)amino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-methoxyethyl)(methyl)amino)ethyl)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-methoxyazetidin-1-yl)ethyl)picolinamide;

6-(tert-butyl)-N-(2-(dimethylamino)-2-methylpropyl)-4-(3-((1S,4R)-4-((3-(2-methoxypropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((S)-3-hydroxypyrrolidin-1-yl)ethyl)picolinamide;

6-(tert-butyl)-N-(2-(dimethylamino)-2-methylpropyl)-4-(3-((1S,4R)-4-((3-(1-methoxy-2-methylpropan-2-yl)-[1,2,4]triazolo[4,3-a]pyridin-6-yl)oxy)-1,2,3,4-tetrahydronaphthalen-1-yl)ureido)picolinamide;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(3-hydroxyazetidin-1-yl)ethyl)picolinamide;

1-(2-(tert-butyl)-6-(hydroxymethyl)pyridin-4-yl)-3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)urea;

6-(tert-Butyl)-N-(2-(dimethylamino)ethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt;

6-(tert-Butyl)-N-(2-hydroxyethyl)-4-(3-((1S,4R)-4-((3-(2-(4-methylpiperazin-1-yl)propan-2-yl)-[1,2,4]triazolo[4,3-a]pyridin-6-yl)oxy)-1,2,3,4-tetrahydronaphthalen-1-yl)ureido)picolinamide formate salt;

6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)ethyl)picolinamide formate salt;

6-(tert-Butyl)-4-(3-((1S,4R)-4-((3-((S)-sec-butyl)-[1,2,4]triazolo[4,3-a]pyridin-6-yl)oxy)-1,2,3,4-tetrahydronaphthalen-1-yl)ureido)-N-(2-(dimethylamino)-2-methylpropyl)picolinamide formate salt;

6-(tert-butyl)-4-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-(4-methoxypiperidin-1-yl)ethyl)picolinamide;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(dimethylamino)-2-methylpropyl)picolinamide formate salt;

6-(tert-Butyl)-4-(3-((1S,4R)-4-((3-(diethylamino)-[1,2,4]triazolo[4,3-a]pyridin-6-yl)oxy)-1,2,3,4-tetrahydronaphthalen-1-yl)ureido)-N-(2-(ethyl(methyl)amino)ethyl)picolinamide formate salt;

6-(tert-butyl)-N-(2-(dimethylamino)ethyl)-4-(3-((1S,4R)-4-((3-(tert-pentyl)-[1,2,4]triazolo[4,3-a]pyridin-6-yl)oxy)-1,2,3,4-tetrahydronaphthalen-1-yl)ureido)picolinamide;

6-(tert-butyl)-N-(2-(dimethylamino)ethyl)-4-(3-((1S,4R)-4-((3-(pentan-3-yl)-[1,2,4]triazolo[4,3-a]pyridin-6-yl)oxy)-1,2,3,4-tetrahydronaphthalen-1-yl)ureido)picolinamide;

4-(tert-butyl)-6-(3-((1S,4R)-4-((3-(tert-butyl)-[1,2,4]triazolo[4,3-a]pyridin-6-yl)oxy)-1,2,3,4-tetrahydronaphthalen-1-yl)ureido)-N-(2-((2-hydroxyethyl)(methyl)amino)ethyl)picolinamide formate salt;

N-(2-(1,4-oxazepan-4-yl)ethyl)-4-(tert-butyl)-6-(3-((1S,4R)-4-((3-(tert-butyl)-[1,2,4]triazolo[4,3-a] pyridin-6-yl)oxy)-1,2,3,4-tetrahydronaphthalen-1-yl)ureido)picolinamide formate salt;

4-(tert-butyl)-6-(3-((1S,4R)-4-((3-(tert-butyl)-[1,2,4]triazolo[4,3-a] pyridin-6-yl)oxy)-1,2,3,4-tetrahydronaphthalen-1-yl)ureido)-N-(2-(3-methoxyazetidin-1-yl)ethyl)picolinamide formate salt;

4-(tert-butyl)-6-(3-((1S,4R)-4-((3-(tert-butyl)-[1,2,4]triazolo[4,3-a] pyridin-6-yl)oxy)-1,2,3,4-tetrahydronaphthalen-1-yl)ureido)-N-(-(2-(4-hydroxypiperidin-1-yl)ethyl)picolinamide formate salt;

N-(6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)methanesulfonamide;

N-(6-(tert-Butyl)-4-(3-((1S,4R)-4-((3-((S)-1,2-dimethylpyrrolidin-2-yl)-[1,2,4]triazolo[4,3-a]pyridin-6-yl)oxy)-1,2,3,4-tetrahydronaphthalen-1-yl)ureido)pyridin-2-yl)ethanesulfonamide;

4-(tert-Butyl)-N-(2-(dimethylamino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide; and 4-(tert-Butyl)-N-(2-((2-hydroxyethyl)(methyl)amino)ethyl)-6-(3-((1S,4R)-4-((3-((R)-4-methylmorpholin-3-yl)-[1,2,4]triazolo[4,3-a]pyridin-6-yl)oxy)-1,2,3,4-tetrahydronaphthalen-1-yl)ureido)pyrimidine-2-carboxamide.

9. A pharmaceutical composition, comprising a compound or pharmaceutically acceptable salt according to claim 1 and one or more pharmaceutically acceptable carriers.

10. A method of treating a disease or condition selected from the group consisting of chronic eosinophilic pneumonia, asthma, COPD, and adult respiratory distress syndrome (ARDS), said method comprising administering to a subject in need thereof and effective amount of a compound or pharmaceutically acceptable salt according to claim 1.

11. A method according to claim 10, wherein said disease or condition is chronic eosinophilic pneumonia.

12. A method according to claim 10, wherein said disease or condition is asthma.

13. A method according to claim 10, wherein said disease or condition is COPD.

14. A method according to claim 10, wherein said disease or condition is adult respiratory distress syndrome (ARDS).

15. A method of treating a disease or condition selected from the group consisting of chronic eosinophilic pneumonia, asthma, COPD, and adult respiratory distress syndrome (ARDS), said method comprising administering to a subject in need thereof and effective amount of a compound or pharmaceutically acceptable salt according to claim 8.

16. A method according to claim 15, wherein said disease or condition is chronic eosinophilic pneumonia.

17. A method according to claim 15, wherein said disease or condition is asthma.

18. A method according to claim 15, wherein said disease or condition is COPD.

19. A method according to claim 15, wherein said disease or condition is adult respiratory distress syndrome (ARDS).

* * * * *